(12) United States Patent
Buzard et al.

(10) Patent No.: US 10,781,211 B2
(45) Date of Patent: *Sep. 22, 2020

(54) SPIROCYCLE COMPOUNDS AND METHODS OF MAKING AND USING SAME

(71) Applicant: Lundbeck La Jolla Research Center, Inc., San Diego, CA (US)

(72) Inventors: Daniel J. Buzard, San Diego, CA (US); Michael B. Shaghafi, San Diego, CA (US); Justin S. Cisar, San Diego, CA (US); Cheryl A. Grice, Encinitas, CA (US); Todd K. Jones, Solana Beach, CA (US); Olivia D. Weber, San Diego, CA (US)

(73) Assignee: LUNDBECK LA JOLLA RESEARCH CENTER, INC., San Diego, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/300,501

(22) PCT Filed: May 11, 2017

(86) PCT No.: PCT/US2017/032276
§ 371 (c)(1),
(2) Date: Nov. 9, 2018

(87) PCT Pub. No.: WO2017/197192
PCT Pub. Date: Nov. 16, 2017

(65) Prior Publication Data
US 2020/0022977 A1    Jan. 23, 2020

Related U.S. Application Data

(60) Provisional application No. 62/335,597, filed on May 12, 2016.

(51) Int. Cl.
| | | |
|---|---|---|
| *C07D 471/10* | (2006.01) | |
| *C07D 519/00* | (2006.01) | |
| *A61K 31/499* | (2006.01) | |
| *A61K 31/5377* | (2006.01) | |
| *A61K 31/55* | (2006.01) | |
| *A61P 25/28* | (2006.01) | |
| *A61P 29/00* | (2006.01) | |
| *A61P 25/08* | (2006.01) | |
| *A61K 31/538* | (2006.01) | |
| *A61K 31/541* | (2006.01) | |

(52) U.S. Cl.
CPC .......... *C07D 471/10* (2013.01); *A61K 31/499* (2013.01); *A61K 31/538* (2013.01); *A61K 31/5377* (2013.01); *A61K 31/541* (2013.01); *A61K 31/55* (2013.01); *C07D 519/00* (2013.01)

(58) Field of Classification Search
CPC .. C07D 471/10; C07D 519/00; A61K 31/499; A61K 31/5377; A61K 31/55; A61P 25/08; A61P 25/28; A61P 29/00
See application file for complete search history.

(56) References Cited

U.S. PATENT DOCUMENTS

| | | | |
|---|---|---|---|
| 9,133,148 | B2 | 9/2015 | Cisar et al. |
| 9,487,495 | B2 | 11/2016 | Cisar et al. |
| 9,828,379 | B2 | 11/2017 | Jones et al. |
| 9,957,242 | B2 | 5/2018 | Cisar et al. |
| 1,003,002 | A1 | 7/2018 | Cisar et al. |
| 2005/0234090 | A1 | 10/2005 | Colon-Cruz et al. |
| 2011/0071180 | A1 | 3/2011 | Akireddy et al. |
| 2012/0208812 | A1 | 8/2012 | Chai et al. |
| 2013/0165422 | A1 | 6/2013 | Bartsch et al. |
| 2016/0137649 | A1 | 5/2016 | Jones et al. |

FOREIGN PATENT DOCUMENTS

| | | |
|---|---|---|
| WO | WO-2010141817 A1 | 12/2010 |
| WO | WO-2011109277 A1 | 9/2011 |
| WO | WO-2012052730 A1 | 4/2012 |
| WO | WO-2014048865 A1 | 4/2014 |
| WO | WO-2015003002 A1 | 1/2015 |
| WO | WO-2016149401 A2 | 9/2016 |
| WO | WO-2017021805 A1 | 2/2017 |
| WO | WO-2017197192 A1 | 11/2017 |
| WO | WO-2018093949 A1 | 5/2018 |
| WO | WO-2019046318 A1 | 3/2019 |
| WO | WO-2019046330 A1 | 3/2019 |

OTHER PUBLICATIONS

Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Brun et al. Drug sensitivity of Chinese Trypanosoma evansi and Trypanosoma equiperdum isolates. Vet. Parasitol. 52:37-46 (1994).
Chang et al. Highly Selective Inhibitors of Monoacylglycerol Lipase Bearing a Reactive Group that is Bioisosteric with Endocannabinoid Substrates. ChemBiol 19(5):579-588 (2012).
Changsen et al. Improved green fluorescent protein reporter gene-based microplate screening for antituberculosis compounds by utilizing an acctamidasc promoter. Antimicrob AgentsChemother 47:3682-3687 (2003).
Chen et al. SAP102 mediates synaptic clearance of NMDA receptors. Cell Rep. 2(5):1120-1128 (2012).
Cho et al. Low-oxygen-recovery assay for high-throughput screening of compounds against nonreplicating *Mycobacterium tuberculosis*. Antimicrobl AgentsChemother 51:1380-1385 (2007).

(Continued)

*Primary Examiner* — Sahar Javanmard
(74) *Attorney, Agent, or Firm* — Wilson Sonsini Goodrich & Rosati

(57) ABSTRACT

Provided herein are spirocycle compounds and pharmaceutical compositions comprising said compounds. The subject compounds and compositions are useful as modulators of MAGL and/or ABHD6. Furthermore, the subject compounds and compositions are useful for the treatment of pain.

16 Claims, No Drawings

(56) References Cited

OTHER PUBLICATIONS

Collins et al. Microplate alamar blue assay versus BACTEC 460 system for high-throughput screening of compounds against *Mycobacterium tuberculosis* and *Mycobacterium avium*. Antimicrobl Agents Chemother 41:1004-1009 (1997).
Long et al. Selective blockade of 2-arachidonoylglycerol hydrolysis produces cannabinoid behavioral effects. Nat Chem Biol. 5(1):37-44 (2009).
Niphakis et al. Evaluation of NHS carbamates as a potent and selective class of endocannabinoid hydrolase inhibitors. ACS Chem Neurosci 4(9):1322-1332 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Activation of the endocannabinoid system by organophosphorus nerve agents. Nat Chem Biol. 4(6):373-378 (2008).
Nomura et al. Endocannabinoid hydrolysis generates brain prostaglandins that promote neuroinflammation. Science 334(6057):809-813 (2011).
Nomura et al. Monoacylglycerol lipase regulates 2-arachidonoylglycerol action and arachidonic acid levels. Bioorg Med Chem Lett. 18(22):5875-5878 (2008).
PCT/US2014045145 International Preliminary Report on Patentability dated Jan. 14, 2016.
PCT/US2014045145 International Search Report and Written Opinion dated Dec. 10, 2014.
PCT/US2017/032276 International Search Report and Written Opinion dated Sep. 26, 2017.
PCT/US2017/061870 International Search Report and Written Opinion dated Mar. 26, 2018.
PCT/US2017/061870 Invitation to Pay Additional Fees dated Jan. 22, 2018.
Piro et al. A dysregulated endocannabinoid-eicosanoid network supports pathogenesis in a mouse model of Alzheimer's disease. Cell Rep. 1(6):617-623 (2012).
PUBCHEM, Substance Database, SID 239803465. Retrieved from Internet:< URL: https://pubchem.ncbi.nlm.nih.gov/substance/239803465> (7pgs.) (Available Date Feb. 13, 2015) (retrieved Jun. 27, 2017).
Raz et al. The Alamar Blue® assay to determine drug sensitivity of African trypanosomes (T.b. rhodesiense and T.b. gambiense) in vitro. Acta Tropica 68:139-147 (1997).
Snewin et al. Assessment of immunity to mycobacterial infection with luciferase reporter constructs. Infection and Immunity 67:4586-4593 (1999).
U.S. Appl. No. 14/902,324 Office Action dated Dec. 30, 2016.
Fleisher et al. Improved oral drug delivery: solubility limitations overcome by the use of prodrugs. Advanced Drug Delivery Reviews 19:115-130 (1996).
PCT/US2018/048372 International Search Report and Written Opinion dated Dec. 4, 2018.
PCT/US2018/048372 Invitation to Pay Additional Fees dated Oct. 4, 2018.
PCT/US2018/048388 International Search Report and Written Opinion dated Dec. 4, 2018.
PCT/US2018/048388 Invitation to Pay Additional Fees dated Oct. 4, 2018.

SPIROCYCLE COMPOUNDS AND METHODS OF MAKING AND USING SAME

CROSS-REFERENCE

This application is a U.S. National Entry of International Application No. PCT/US2017/032276, filed May 11, 2017, which claims benefit of U.S. Provisional Application No. 62/335,597, filed on May 12, 2016, both of which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. The serine hydrolase ca-3-hydrolase domain 6 (ABHD6) is another lipid mediator.

BRIEF SUMMARY OF THE INVENTION

This disclosure provides, for example, compounds and compositions which are modulators of MAGL and/or ABHD6, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL and/or ABHD6 activity in warm-blooded animals such as humans.

In one aspect is a compound having the structure of Formula (I):

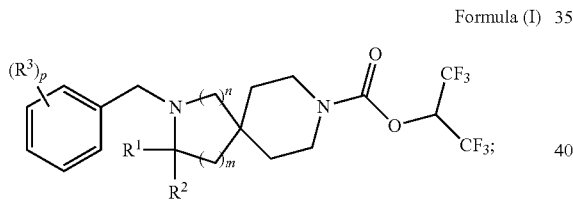

Formula (I)

wherein:
$R^1$ is H or optionally substituted $C_{1-6}$alkyl;
$R^2$ is H or optionally substituted $C_{1-6}$alkyl;
each $R^3$ is independently selected from $C_{1-6}$alkyl, halogen, —CN, $C_{1-6}$haloalkyl, aminoalkyl, —$C_{1-6}$alkyl(heterocycloalkyl), —$NR^5R^6$, —$OR^7$, —$CO_2R^8$, —$C(O)R^8$, and —$C(O)NR^8R^9$; or two adjacent $R^3$ form a heterocycloalkyl ring optionally substituted with one, two, or three $R^4$;
each $R^4$ is selected from $C_{1-6}$alkyl, cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;
each $R^5$ and $R^6$ is independently selected from H, $C_{1-6}$alkyl, $C_{1-6}$haloalkyl, aminoalkyl, cycloalkyl, —$C_{1-6}$ alkyl(heterocycloalkyl), —$C_{1-6}$alkyl-C(O)(heterocycloalkyl), optionally substituted heterocycloalkyl, optionally substituted aryl, and optionally substituted heteroaryl; or $R^5$ and $R^6$, together with the nitrogen to which they are attached, form a heterocycloalkyl ring optionally substituted with one, two, or three $R^{10}$;
each $R^7$ is independently selected from H, $C_{1-6}$alkyl, $C_{1-6}$haloalkyl, aminoalkyl, cycloalkyl, —$C_{1-6}$alkyl (heterocycloalkyl), —$C_{1-6}$alkyl-C(O)(heterocycloalkyl), optionally substituted heterocycloalkyl, optionally substituted aryl, and optionally substituted heteroaryl;
each $R^8$ and $R^9$ is independently selected from H, $C_{1-6}$alkyl, $C_{1-6}$haloalkyl, cycloalkyl, aryl, and heteroaryl;
each $R^{10}$ is selected from $C_{1-6}$alkyl, cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;
p is 0, 1, 2, 3, 4, or 5;
n is 0 or 1; and
m is 1 or 2; provided that when n is 0, then m is 2; and when n is 1, then m is 1;
or a solvate, hydrate, tautomer, N-oxide, stereoisomer, or pharmaceutically acceptable salt thereof.

In some embodiments is a compound having the structure of Formula (Ia):

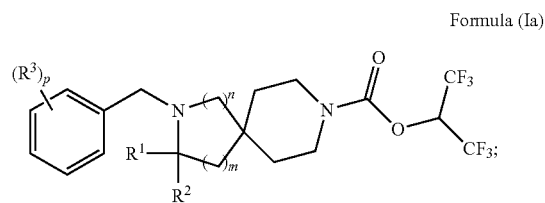

Formula (Ia)

wherein:
$R^1$ is H or $C_{1-6}$alkyl;
$R^2$ is H or $C_{1-6}$alkyl;
each $R^3$ is independently selected from $C_{1-6}$alkyl, $C_{1-6}$alkenyl, $C_{1-6}$alkynyl, halogen, —CN, $C_{1-6}$ haloalkyl, $C_{1-6}$aminoalkyl, heterocycloalkyl, —$C_{1-6}$alkyl(heterocycloalkyl), heteroaryl, —$SF_5$, —$NR^5R^6$, —$OR^7$, —$CO_2R^8$, —$C(O)R^8$, and —$C(O)NR^8R^9$, wherein heterocycloalkyl and —$C_{1-6}$ alkyl(heterocycloalkyl) are optionally substituted with one or two $R^4$; or two adjacent $R^3$ form a heterocycloalkyl ring, wherein the heterocycloalkyl ring and the heteroaryl ring are optionally substituted with one, two, or three $R^4$;
each $R^4$ is independently selected from $C_{1-6}$alkyl, $C_{1-6}$haloalkyl, $C_{3-8}$cycloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;
each $R^5$ and $R^6$ is independently selected from H, $C_{1-6}$alkyl, $C_{1-6}$haloalkyl, $C_{1-6}$aminoalkyl, $C_{3-8}$cycloalkyl, —$C_{1-6}$alkyl(heterocycloalkyl), —$C_{1-6}$ alkyl-C(O)(heterocycloalkyl), heterocycloalkyl, aryl, and heteroaryl; or $R^5$ and $R^6$, together with the nitrogen to which they are attached, form a heterocycloalkyl ring optionally substituted with one, two, or three $R^{10}$;
each $R^7$ is independently selected from H, $C_{1-6}$alkyl, $C_{1-6}$haloalkyl, $C_{1-6}$aminoalkyl, $C_{3-8}$cycloalkyl, —$C_{1-6}$alkyl(heterocycloalkyl), —$C_{1-6}$alkyl-C(O)(heterocycloalkyl), heterocycloalkyl, aryl, and heteroaryl, wherein heterocycloalkyl, aryl, and heteroaryl are optionally substituted with one or two groups selected from oxo, $C_{1-6}$alkyl, $C_{1-6}$haloalkyl, $CO_2H$, and $C(O)NH_2$;
each $R^8$ and $R^9$ is independently selected from H, $C_{1-6}$alkyl, $C_{1-6}$haloalkyl, $C_{3-8}$cycloalkyl, aryl, and heteroaryl; or $R^8$ and $R^9$, together with the nitrogen to which they are attached, form a heterocycloalkyl ring optionally substituted with one or two groups selected from $C_{1-6}$alkyl, $C_{1-6}$ haloalkyl, $CO_2H$, and $C(O)NH_2$;

each $R^{10}$ is independently selected from $C_{1-6}$alkyl, $C_{3-8}$cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

p is 0, 1, 2, 3, 4, or 5;

n is 0 or 1; and m is 1 or 2; provided that when n is 0, then m is 2; and when n is 1, then m is 1;

or a solvate, hydrate, tautomer, N-oxide, stereoisomer, or pharmaceutically acceptable salt thereof.

In another embodiment is a compound of Formula (Ia), or a solvate, hydrate, tautomer, N-oxide, stereoisomer, or a pharmaceutically acceptable salt thereof, wherein each $R^3$ is independently selected from $C_{1-6}$alkyl, $C_{2-6}$alkynyl, halogen, —CN, $C_{1-6}$haloalkyl, heterocycloalkyl, —$C_{1-6}$alkyl (heterocycloalkyl), heteroaryl, —$SF_5$, —$NR^5R^6$, —$OR^7$, —$CO_2R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein each $R^3$ is independently selected from $C_{1-6}$alkyl, $C_{2-6}$alkynyl, halogen, $C_{1-6}$haloalkyl, —$C_{1-6}$alkyl (heterocycloalkyl), —$NR^5R^6$, —$OR^7$, —$CO_2R^8$, and —$C(O)NR^8R^9$. In another embodiment is a compound of Formula (I) or (Ia), or a solvate, hydrate, tautomer, N-oxide, stereoisomer, or a pharmaceutically acceptable salt thereof, wherein $R^1$ is H. In another embodiment is a compound of Formula (I) or (Ia), or a solvate, hydrate, tautomer, N-oxide, stereoisomer, or a pharmaceutically acceptable salt thereof, wherein $R^2$ is H. In another embodiment is a compound of Formula (I) or (Ia), or a solvate, hydrate, tautomer, N-oxide, stereoisomer, or a pharmaceutically acceptable salt thereof, wherein $R^1$ and $R^2$ are both H. In another embodiment is a compound of Formula (I) or (Ia), or a solvate, hydrate, tautomer, N-oxide, stereoisomer, or a pharmaceutically acceptable salt thereof, wherein $R^1$ is $C_{1-6}$alkyl. In another embodiment is a compound of Formula (I) or (Ia), or a solvate, hydrate, tautomer, N-oxide, stereoisomer, or a pharmaceutically acceptable salt thereof, wherein $R^1$ is —$CH_3$. In another embodiment is a compound of Formula (I) or (Ia), or a solvate, hydrate, tautomer, N-oxide, stereoisomer, or a pharmaceutically acceptable salt thereof, wherein $R^1$ and $R^2$ are both —$CH_3$. In another embodiment is a compound of Formula (I) or (Ia), or a solvate, hydrate, tautomer, N-oxide, stereoisomer, or a pharmaceutically acceptable salt thereof, wherein each $R^3$ is independently selected from $C_{1-6}$alkyl, $C_{2-6}$alkynyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (I) or (Ia), or a solvate, hydrate, tautomer, N-oxide, stereoisomer, or a pharmaceutically acceptable salt thereof, wherein each $R^3$ is independently selected from halogen, $C_{1-6}$haloalkyl, —$NR^5R^6$, and —$OR^7$. In another embodiment is a compound of Formula (I) or (Ia), or a solvate, hydrate, tautomer, N-oxide, stereoisomer, or a pharmaceutically acceptable salt thereof, wherein $R^5$ and $R^6$, together with the nitrogen to which they are attached, form a heterocycloalkyl ring optionally substituted with one, two, or three $R^{10}$. In another embodiment is a compound of Formula (I) or (Ia), or a solvate, hydrate, tautomer, N-oxide, stereoisomer, or a pharmaceutically acceptable salt thereof, wherein $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (I) or (Ia), or a solvate, hydrate, tautomer, N-oxide, stereoisomer, or a phar-maceutically acceptable salt thereof, wherein $R^5$ and $R^6$, together with the nitrogen to which they are attached, form a heterocycloalkyl ring substituted with one or two $R^{10}$ independently selected from $C_{1-6}$alkyl and —$CO_2H$. In another embodiment is a compound of Formula (I) or (Ia), or a solvate, hydrate, tautomer, N-oxide, stereoisomer, or a pharmaceutically acceptable salt thereof, wherein $R^5$ and $R^6$, together with the nitrogen to which they are attached, form an unsubstituted heterocycloalkyl ring. In another embodiment is a compound of Formula (I) or (Ia), or a solvate, hydrate, tautomer, N-oxide, stereoisomer, or a pharmaceutically acceptable salt thereof, wherein $R^5$ and $R^6$, together with the nitrogen to which they are attached, form a heterocycloalkyl ring selected from:

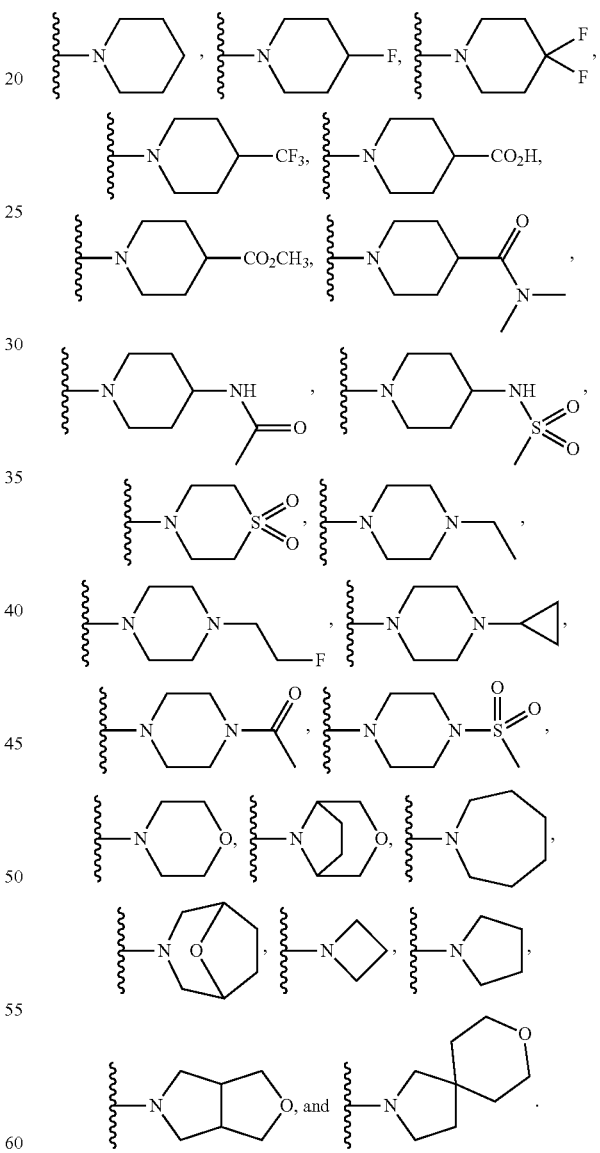

In another embodiment is a compound of Formula (I) or (Ia), or a solvate, hydrate, tautomer, N-oxide, stereoisomer, or a pharmaceutically acceptable salt thereof, wherein $R^5$ and $R^6$, together with the nitrogen to which they are attached, form a heterocycloalkyl ring selected from:

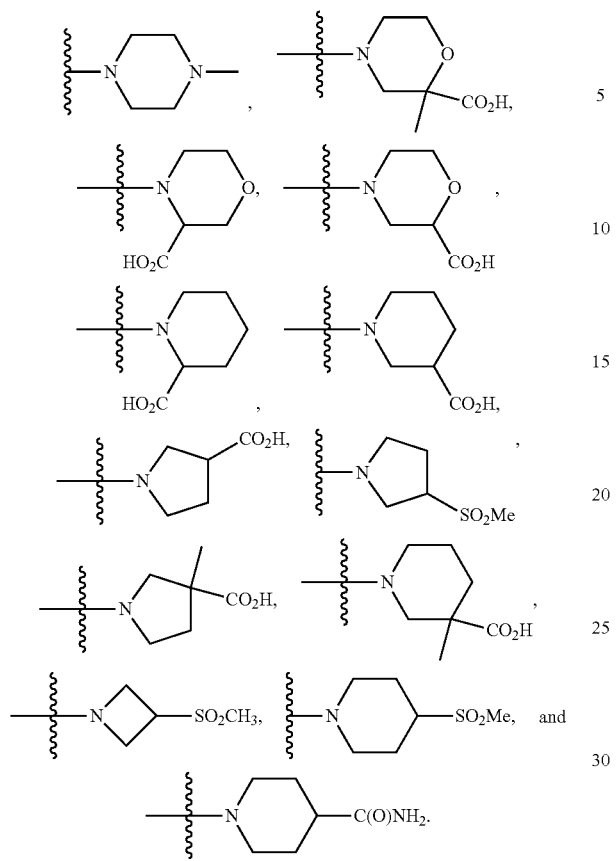

In another embodiment is a compound of Formula (I) or (Ia), or a solvate, hydrate, tautomer, N-oxide, stereoisomer, or a pharmaceutically acceptable salt thereof, wherein $R^7$ is independently selected from $C_{1-6}$alkyl, $C_{1-6}$haloalkyl, $C_{1-6}$aminoalkyl, —$C_{1-6}$alkyl(heterocycloalkyl), —$C_{1-6}$alkyl-C(O)(heterocycloalkyl), heterocycloalkyl, and heteroaryl. In another embodiment is a compound of Formula (I) or (Ia), or a solvate, hydrate, tautomer, N-oxide, stereoisomer, or a pharmaceutically acceptable salt thereof, wherein two adjacent $R^3$ form a heterocycloalkyl ring optionally substituted with one, two, or three $R^4$. In another embodiment is a compound of Formula (I) or (Ia), or a solvate, hydrate, tautomer, N-oxide, stereoisomer, or a pharmaceutically acceptable salt thereof, wherein two adjacent $R^3$ form a heterocycloalkyl ring substituted with one or two $R^4$. In another embodiment is a compound of Formula (I) or (Ia), or a solvate, hydrate, tautomer, N-oxide, stereoisomer, or a pharmaceutically acceptable salt thereof, wherein each $R^4$ is selected from $C_{1-6}$alkyl, $C_{3-8}$cycloalkyl, —C(O)$R^8$, and —SO$_2R^8$. In another embodiment is a compound of Formula (I) or (Ia), or a solvate, hydrate, tautomer, N-oxide, stereoisomer, or a pharmaceutically acceptable salt thereof, wherein two adjacent $R^3$ form an unsubstituted heterocycloalkyl ring. In another embodiment is a compound of Formula (I) or (Ia), or a solvate, hydrate, tautomer, N-oxide, stereoisomer, or a pharmaceutically acceptable salt thereof, wherein two adjacent $R^3$ form a heterocycloalkyl ring selected from:

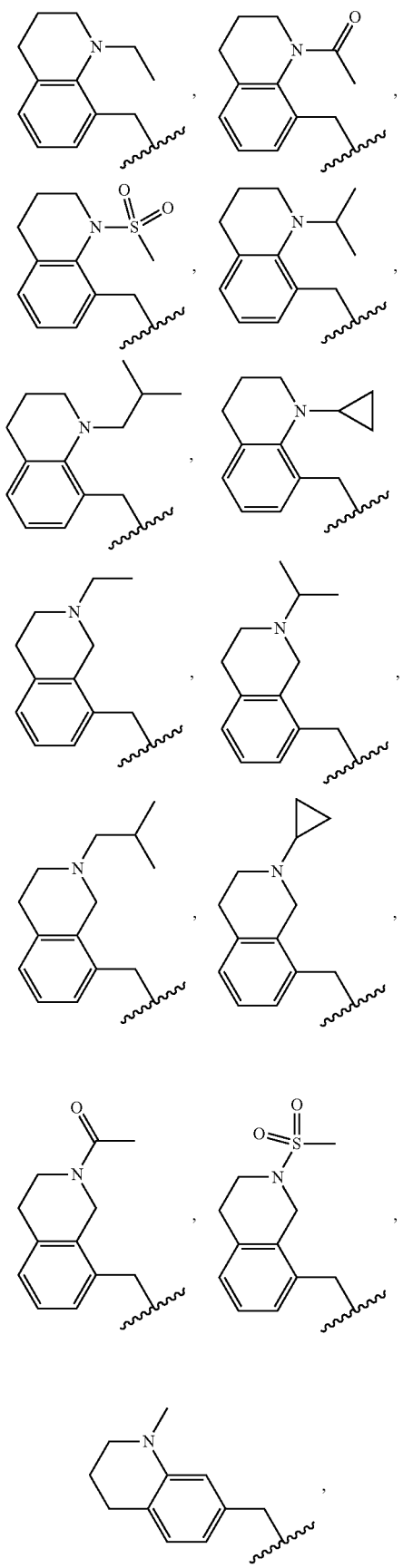

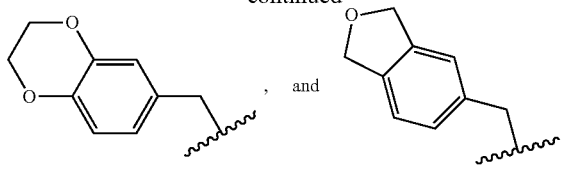
, and

In another embodiment is a compound of Formula (I) or (Ia), or a solvate, hydrate, tautomer, N-oxide, stereoisomer, or a pharmaceutically acceptable salt thereof, wherein p is 2. In another embodiment is a compound of Formula (I) or (Ia), or a solvate, hydrate, tautomer, N-oxide, stereoisomer, or a pharmaceutically acceptable salt thereof, wherein p is 1. In another embodiment is a compound of Formula (I) or (Ia), or a solvate, hydrate, tautomer, N-oxide, stereoisomer, or a pharmaceutically acceptable salt thereof, wherein p is 0. In another embodiment is a compound of (I) or (Ia), or a solvate, hydrate, tautomer, N-oxide, stereoisomer, or a pharmaceutically acceptable salt thereof, wherein n is 0 and m is 2. In another embodiment is a compound of Formula (I) or (Ia), or a solvate, hydrate, tautomer, N-oxide, stereoisomer, or a pharmaceutically acceptable salt thereof, wherein n is 1 and m is 1.

In another aspect is a pharmaceutical composition comprising a compound of Formula (I) or (Ia), or a solvate, hydrate, tautomer, N-oxide, stereoisomer, or a pharmaceutically acceptable salt thereof, and at least one pharmaceutically acceptable excipient.

In another aspect is a method of treating pain in a patient, comprising administering a therapeutically effective amount of a compound of Formula (I) or (Ia), or a solvate, hydrate, tautomer, N-oxide, stereoisomer, or a pharmaceutically acceptable salt thereof, to a patient in need thereof to treat said pain. In some embodiments is a method of treating pain in a patient, comprising administering a therapeutically effective amount of a compound of Formula (I) or (Ia), or a solvate, hydrate, tautomer, N-oxide, stereoisomer, or a pharmaceutically acceptable salt thereof, to a patient in need thereof to treat said pain, wherein the pain is neuropathic pain. In some embodiments is a method of treating pain in a patient, comprising administering a therapeutically effective amount of a compound of Formula (I) or (Ia), or a solvate, hydrate, tautomer, N-oxide, stereoisomer, or a pharmaceutically acceptable salt thereof, to a patient in need thereof to treat said pain, wherein the pain is inflammatory pain.

In another embodiment is a method of treating a disease or disorder in a patient in need thereof comprising administering to the patient a therapeutically effective amount of a compound of Formula (I) or (Ia) described herein, or a pharmaceutically acceptable salt or solvate thereof, wherein the disease or disorder is selected from the group consisting of epilepsy/seizure disorder, multiple sclerosis, neuromyelitis optica (NMO), Tourette syndrome, Alzheimer's disease, and abdominal pain associated with irritable bowel syndrome. In some embodiments, the disease or disorder is epilepsy/seizure disorder. In some embodiments, the disease or disorder is multiple sclerosis. In some embodiments, the disease or disorder is neuromyelitis optica (NMO). In some embodiments, the disease or disorder is Tourette syndrome. In some embodiments, the disease or disorder is Alzheimer's disease. In some embodiments, the disease or disorder is abdominal pain associated with irritable bowel syndrome.

In another embodiment is a compound having the structure:

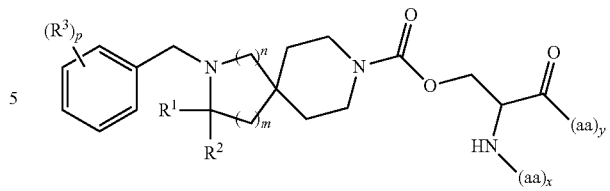

wherein:

$R^1$ is H or $C_{1-6}$alkyl;

$R^2$ is H or $C_{1-6}$alkyl;

each $R^3$ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, heterocycloalkyl, —$C_{1-6}$alkyl(heterocycloalkyl), heteroaryl, —$SF_5$, —$NR^5R^6$, —$OR^7$, —$CO_2R^8$, —$C(O)R^8$, and —$C(O)NR^8R^9$, wherein heterocycloalkyl and —$C_{1-6}$ alkyl(heterocycloalkyl) are optionally substituted with one or two $R^4$; or two adjacent $R^3$ form a heterocycloalkyl ring, wherein the heterocycloalkyl ring and the heteroaryl ring are optionally substituted with one, two, or three $R^4$;

each $R^4$ is independently selected from $C_{1-6}$alkyl, $C_{1-6}$haloalkyl, $C_{3-8}$cycloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

each $R^5$ and $R^6$ is independently selected from H, $C_{1-6}$alkyl, $C_{1-6}$haloalkyl, $C_{1-6}$aminoalkyl, $C_{3-8}$cycloalkyl, —$C_{1-6}$alkyl(heterocycloalkyl), —$C_{1-6}$alkyl-C(O)(heterocycloalkyl), heterocycloalkyl, aryl, and heteroaryl; or $R^5$ and $R^6$, together with the nitrogen to which they are attached, form a heterocycloalkyl ring optionally substituted with one, two, or three $R^{10}$;

each $R^7$ is independently selected from H, $C_{1-6}$alkyl, $C_{1-6}$haloalkyl, $C_{1-6}$aminoalkyl, $C_{3-8}$cycloalkyl, —$C_{1-6}$alkyl(heterocycloalkyl), —$C_{1-6}$alkyl-C(O)(heterocycloalkyl), heterocycloalkyl, aryl, and heteroaryl, wherein heterocycloalkyl, aryl, and heteroaryl are optionally substituted with one or two groups selected from oxo, $C_{1-6}$alkyl, $C_{1-6}$haloalkyl, $CO_2H$, and $C(O)NH_2$;

each $R^8$ and $R^9$ is independently selected from H, $C_{1-6}$alkyl, $C_{1-6}$haloalkyl, $C_{3-8}$cycloalkyl, aryl, and heteroaryl; or $R^8$ and $R^9$, together with the nitrogen to which they are attached, form a heterocycloalkyl ring optionally substituted with one or two groups selected from $C_{1-6}$alkyl, $C_{1-6}$ haloalkyl, $CO_2H$, and $C(O)NH_2$;

each $R^{10}$ is independently selected from $C_{1-6}$alkyl, $C_{3-8}$cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

p is 0, 1, 2, 3, 4, or 5;

n is 0 or 1;

m is 1 or 2; provided that when n is 0, then m is 2; and when n is 1, then m is 1; and x and y are each at least one amino acid (aa).

In another embodiment is a compound having the structure:

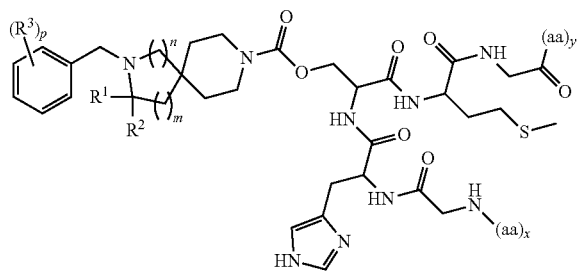

wherein:

R¹ is H or $C_{1-6}$alkyl;

R² is H or $C_{1-6}$alkyl;

each R³ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, heterocycloalkyl, —$C_{1-6}$alkyl(heterocycloalkyl), heteroaryl, —$SF_5$, —$NR^5R^6$, —$OR^7$, —$CO_2R^8$, —$C(O)R^8$, and —$C(O)NR^8R^9$, wherein heterocycloalkyl and —$C_{1-6}$alkyl(heterocycloalkyl) are optionally substituted with one or two R⁴; or two adjacent R³ form a heterocycloalkyl ring, wherein the heterocycloalkyl ring and the heteroaryl ring are optionally substituted with one, two, or three R⁴;

each R⁴ is independently selected from $C_{1-6}$alkyl, $C_{1-6}$haloalkyl, $C_{3-8}$cycloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

each R⁵ and R⁶ is independently selected from H, $C_{1-6}$alkyl, $C_{1-6}$haloalkyl, $C_{1-6}$aminoalkyl, $C_{3-8}$cycloalkyl, —$C_{1-6}$alkyl(heterocycloalkyl), —$C_{1-6}$alkyl-C(O)(heterocycloalkyl), heterocycloalkyl, aryl, and heteroaryl; or R⁵ and R⁶, together with the nitrogen to which they are attached, form a heterocycloalkyl ring optionally substituted with one, two, or three R¹⁰;

each R⁷ is independently selected from H, $C_{1-6}$alkyl, $C_{1-6}$haloalkyl, $C_{1-6}$aminoalkyl, $C_{3-8}$cycloalkyl, —$C_{1-6}$alkyl(heterocycloalkyl), —$C_{1-6}$alkyl-C(O)(heterocycloalkyl), heterocycloalkyl, aryl, and heteroaryl, wherein heterocycloalkyl, aryl, and heteroaryl are optionally substituted with one or two groups selected from oxo, $C_{1-6}$alkyl, $C_{1-6}$haloalkyl, $CO_2H$, and $C(O)NH_2$;

each R⁸ and R⁹ is independently selected from H, $C_{1-6}$alkyl, $C_{1-6}$haloalkyl, $C_{3-8}$cycloalkyl, aryl, and heteroaryl; or R⁸ and R⁹, together with the nitrogen to which they are attached, form a heterocycloalkyl ring optionally substituted with one or two groups selected from $C_{1-6}$alkyl, $C_{1-6}$ haloalkyl, $CO_2H$, and $C(O)NH_2$;

each R¹⁰ is independently selected from $C_{1-6}$alkyl, $C_{3-8}$cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

p is 0, 1, 2, 3, 4, or 5;

n is 0 or 1;

m is 1 or 2; provided that when n is 0, then m is 2; and when n is 1, then m is 1; and x and y are each at least one amino acid (aa).

In another embodiment is a compound having the structure:

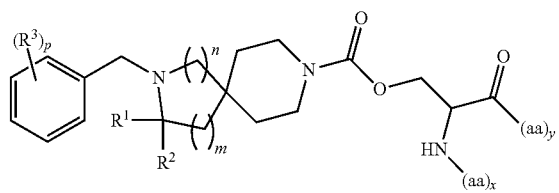

wherein:

R¹ is H or optionally substituted $C_{1-6}$alkyl;

R² is H or optionally substituted $C_{1-6}$alkyl;

each R³ is independently selected from $C_{1-6}$alkyl, halogen, —CN, $C_{1-6}$haloalkyl, aminoalkyl, —$C_{1-6}$alkyl (heterocycloalkyl), —$NR^5R^6$, —$OR^7$, —$CO_2R^8$, —$C(O)R^8$, and —$C(O)NR^8R^9$; or two adjacent R³ form a heterocycloalkyl ring optionally substituted with one, two, or three R⁴;

each R⁴ is selected from $C_{1-6}$alkyl, cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

each R⁵ and R⁶ is independently selected from H, $C_{1-6}$alkyl, $C_{1-6}$haloalkyl, aminoalkyl, cycloalkyl, —$C_{1-6}$alkyl(heterocycloalkyl), —$C_{1-6}$alkyl-C(O)(heterocycloalkyl), optionally substituted heterocycloalkyl, optionally substituted aryl, and optionally substituted heteroaryl; or R⁵ and R⁶, together with the nitrogen to which they are attached, form a heterocycloalkyl ring optionally substituted with one, two, or three R¹⁰;

each R⁷ is independently selected from H, $C_{1-6}$alkyl, $C_{1-6}$haloalkyl, aminoalkyl, cycloalkyl, —$C_{1-6}$alkyl (heterocycloalkyl), —$C_{1-6}$alkyl-C(O)(heterocycloalkyl), optionally substituted heterocycloalkyl, optionally substituted aryl, and optionally substituted heteroaryl;

each R⁸ and R⁹ is independently selected from H, $C_{1-6}$alkyl, $C_{1-6}$haloalkyl, cycloalkyl, aryl, and heteroaryl;

each R¹⁰ is selected from $C_{1-6}$alkyl, cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;

p is 0, 1, 2, 3, 4, or 5;

n is 0 or 1;

m is 1 or 2; provided that when n is 0, then m is 2; and when n is 1, then m is 1; and x and y are each at least one amino acid (aa).

In another embodiment is a compound having the structure:

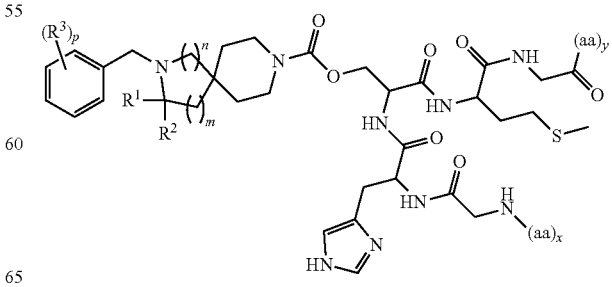

wherein:

R$^1$ is H or optionally substituted C$_{1-6}$alkyl;

R$^2$ is H or optionally substituted C$_{1-6}$alkyl;

each R$^3$ is independently selected from C$_{1-6}$alkyl, halogen, —CN, C$_{1-6}$haloalkyl, aminoalkyl, —C$_{1-6}$alkyl (heterocycloalkyl), —NR$^5$R$^6$, —OR$^7$, —CO$_2$R$^8$, —C(O)R$^8$, and —C(O)NR$^8$R$^9$; or two adjacent R$^3$ form a heterocycloalkyl ring optionally substituted with one, two, or three R$^4$;

each R$^4$ is selected from C$_{1-6}$alkyl, cycloalkyl, C$_{1-6}$haloalkyl, halogen, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;

each R$^5$ and R$^6$ is independently selected from H, C$_{1-6}$alkyl, C$_{1-6}$haloalkyl, aminoalkyl, cycloalkyl, —C$_{1-6}$alkyl(heterocycloalkyl), —C$_{1-6}$alkyl-C(O)(heterocycloalkyl), optionally substituted heterocycloalkyl, optionally substituted aryl, and optionally substituted heteroaryl; or R$^5$ and R$^6$, together with the nitrogen to which they are attached, form a heterocycloalkyl ring optionally substituted with one, two, or three R$^{10}$;

each R$^7$ is independently selected from H, C$_{1-6}$alkyl, C$_{1-6}$haloalkyl, aminoalkyl, cycloalkyl, —C$_{1-6}$alkyl (heterocycloalkyl), —C$_{1-6}$alkyl-C(O)(heterocycloalkyl), optionally substituted heterocycloalkyl, optionally substituted aryl, and optionally substituted heteroaryl;

each R$^8$ and R$^9$ is independently selected from H, C$_{1-6}$alkyl, C$_{1-6}$haloalkyl, cycloalkyl, aryl, and heteroaryl;

each R$^{10}$ is selected from C$_{1-6}$alkyl, cycloalkyl, C$_{1-6}$haloalkyl, halogen, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;

p is 0, 1, 2, 3, 4, or 5;

n is 0 or 1;

m is 1 or 2; provided that when n is 0, then m is 2; and when n is 1, then m is 1; and x and y are each at least one amino acid (aa).

DETAILED DESCRIPTION OF THE INVENTION

This disclosure is directed, at least in part, to MAGL and/or ABHD6 modulators or inhibitors. For example, provided herein are compounds capable of inhibiting MAGL and/or ABHD6.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.

"Cyano" refers to the —CN radical.

"Nitro" refers to the —NO$_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises one to five carbon atoms (e.g., C$_1$-C$_5$ alkyl). In other embodiments, an alkyl comprises one to four carbon atoms (e.g., C$_1$-C$_4$ alkyl). In other embodiments, an alkyl comprises one to three carbon atoms (e.g., C$_1$-C$_3$ alkyl). In other embodiments, an alkyl comprises one to two carbon atoms (e.g., C$_1$-C$_2$ alkyl). In other embodiments, an alkyl comprises one carbon atom (e.g., C$_1$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). In other embodiments, an alkyl comprises two to five carbon atoms (e.g., C$_2$-C$_5$ alkyl). In other embodiments, an alkyl comprises three to five carbon atoms (e.g., C$_3$-C$_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, or heteroaryl, and each R$^f$ is independently alkyl, fluoroalkyl, cycloalkyl, aryl, aralkyl, heterocycloalkyl, or heteroaryl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In certain embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, or heteroaryl, and each R$^f$ is independently alkyl, fluoroalkyl, cycloalkyl, aryl, aralkyl, heterocycloalkyl, or heteroaryl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, or heteroaryl, and each R$^f$ is independently alkyl, fluoroalkyl, cycloalkyl, aryl, aralkyl, heterocycloalkyl, or heteroaryl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, cycloalkyl, aryl, aralkyl, heterocycloalkyl, or heteroaryl, and each R$^f$ is independently alkyl, fluoroalkyl, cycloalkyl, aryl, aralkyl, heterocycloalkyl, or heteroaryl.

"Aminoalkyl" refers to a radical of the formula —R$^c$—N(R$^a$)$_2$ or —R$^c$—N(R$^a$)—R$^c$, where each R$^c$ is independently an alkylene chain as defined above, for example, methylene, ethylene, and the like; and each R$^a$ is independently hydrogen, alkyl, fluoroalkyl, cycloalkyl, aryl, aralkyl, heterocycloalkyl, or heteroaryl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted heterocycloalkyl, optionally substituted heteroaryl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocycloalkyl, or heteroaryl, each R$^b$ is independently a direct bond or a straight or branched alkylene or alkenylene chain, and R$^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl is fully saturated, (i.e., containing single C—C bonds only) or partially unsaturated (i.e., containing one or more double bonds). Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals as defined above that are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted heterocycloalkyl, optionally substituted heteroaryl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N(R$^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, or heteroaryl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Haloalkyl" refers to an alkyl radical, as defined above, that is substituted by one or more halogen radicals, as defined above, for example, trifluoromethyl, chloroethyl, and the like. The alkyl part of the haloalkyl radical is optionally substituted as defined above for an alkyl group.

"Heteroalkyl" refers to a straight or branched hydrocarbon chain alkyl radical containing no unsaturation, having from one to fifteen carbon atoms (e.g., $C_1$-$C_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, —$OR^a$, —$SR^a$, —OC(O)$R^a$, —N($R^a$)$_2$, —C(O)$R^a$, —C(O)$OR^a$, —C(O)N($R^a$)$_2$, —N($R^a$)C(O)$OR^f$, —OC(O)—NR$^a$R$^f$, —N($R^a$)C(O)$R^f$, —N($R^a$)S(O)$_t$$R^f$ (where t is 1 or 2), —S(O)$_t$$OR^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, or heteroaryl, and each $R^f$ is independently alkyl, fluoroalkyl, cycloalkyl, aryl, aralkyl, heterocycloalkyl, or heteroaryl.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which includes fused, bridged, or spirocyclic ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted heterocycloalkyl, optionally substituted heteroaryl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$) C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, or heteroaryl, each $R^b$ is independently a direct bond or a straight or branched alkylene or alkenylene chain, and $R^c$ is a straight or branched alkylene or alkenylene chain.

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) t-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above that are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted heterocycloalkyl, optionally substituted heteroaryl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, or heteroaryl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula $-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula $-O-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

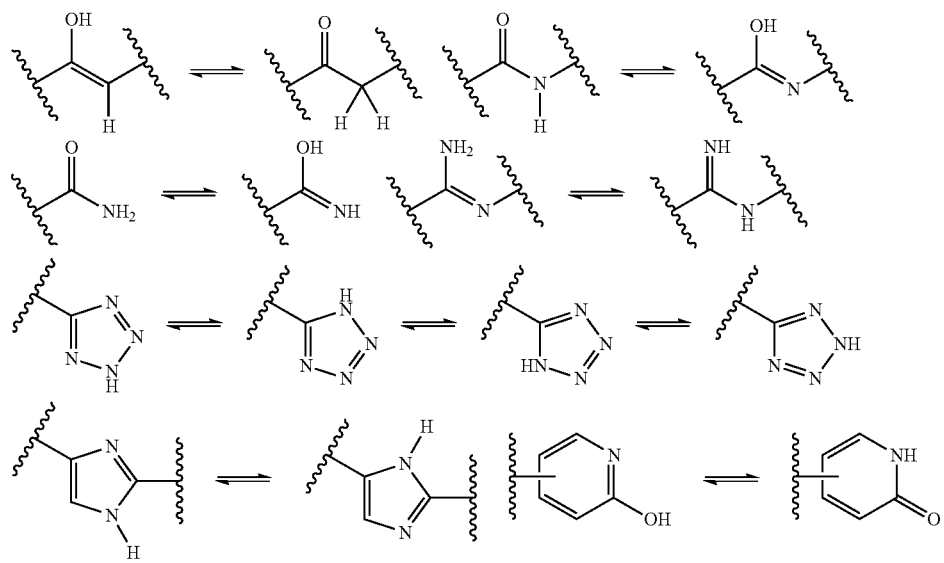

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution. "Optionally substituted" and "substituted or unsubstituted" and "unsubstituted or substituted" are used interchangeably herein.

"Pharmaceutically acceptable salt" includes both acid and base addition salts. A pharmaceutically acceptable salt of any one of the spirocycle compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has been made.

Compounds

Spirocycle compounds are described herein which are modulators of MAGL and/or ABHD6. These compounds, and compositions comprising these compounds, are useful for the treatment of pain. In some embodiments, the compounds described herein are useful for treating epilepsy/seizure disorder, multiple sclerosis, neuromyelitis optica (NMO), Tourette syndrome, Alzheimer's disease, or abdominal pain associated with irritable bowel syndrome.

In some embodiments is a compound having the structure of Formula (I):

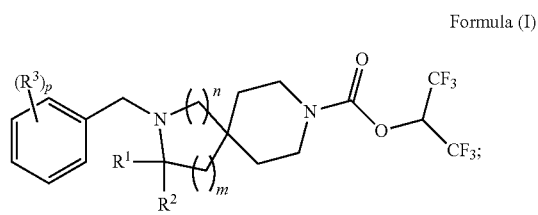

Formula (I)

wherein:
$R^1$ is H or optionally substituted $C_{1-6}$alkyl;
$R^2$ is H or optionally substituted $C_{1-6}$alkyl;
each $R^3$ is independently selected from $C_{1-6}$alkyl, halogen, —CN, $C_{1-6}$haloalkyl, aminoalkyl, —$C_{1-6}$ alkyl (heterocycloalkyl), —$NR^5R^6$, —$OR^7$, —$CO_2R^8$, —$C(O)R^8$, and —$C(O)NR^8R^9$; or two adjacent $R^3$ form a heterocycloalkyl ring optionally substituted with one, two, or three $R^4$;
each $R^4$ is selected from $C_{1-6}$alkyl, cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;
each $R^5$ and $R^6$ is independently selected from H, $C_{1-6}$alkyl, $C_{1-6}$haloalkyl, aminoalkyl, cycloalkyl, —$C_{1-6}$alkyl(heterocycloalkyl), —$C_{1-6}$alkyl-C(O)(heterocycloalkyl), optionally substituted heterocycloalkyl, optionally substituted aryl, and optionally substituted heteroaryl; or $R^5$ and $R^6$, together with the nitrogen to which they are attached, form a heterocycloalkyl ring optionally substituted with one, two, or three $R^{10}$;
each $R^7$ is independently selected from H, $C_{1-6}$alkyl, $C_{1-6}$haloalkyl, aminoalkyl, cycloalkyl, —$C_{1-6}$alkyl (heterocycloalkyl), —$C_{1-6}$alkyl-C(O)(heterocycloalkyl), optionally substituted heterocycloalkyl, optionally substituted aryl, and optionally substituted heteroaryl;
each $R^8$ and $R^9$ is independently selected from H, $C_{1-6}$alkyl, $C_{1-6}$haloalkyl, cycloalkyl, aryl, and heteroaryl;
each $R^{10}$ is selected from $C_{1-6}$alkyl, cycloalkyl, $C_{1-6}$haloalkyl, halogen, oxo, —CN, —$CO_2R^8$, —$C(O)R^8$, —$C(O)NR^8R^9$, —$SO_2R^8$, —$NR^9C(O)R^8$, and —$NR^9SO_2R^8$;
p is 0, 1, 2, 3, 4, or 5;
n is 0 or 1; and
m is 1 or 2; provided that when n is 0, then m is 2; and when n is 1, then m is 1;
or a solvate, hydrate, tautomer, N-oxide, stereoisomer, or pharmaceutically acceptable salt thereof.

In some embodiments is a compound of Formula (I), or a solvate, hydrate, tautomer, N-oxide, stereoisomer, or a pharmaceutically acceptable salt thereof, wherein n is 0 and m is 2. In some embodiments is a compound of Formula (I), or a solvate, hydrate, tautomer, N-oxide, stereoisomer, or a pharmaceutically acceptable salt thereof, wherein n is 1 and m is 1.

In some embodiments is a compound of Formula (I), or a solvate, hydrate, tautomer, N-oxide, stereoisomer, or a pharmaceutically acceptable salt thereof, wherein $R^1$ is H. In some embodiments is a compound of Formula (I), or a solvate, hydrate, tautomer, N-oxide, stereoisomer, or a pharmaceutically acceptable salt thereof, wherein $R^2$ is H. In some embodiments is a compound of Formula (I), or a solvate, hydrate, tautomer, N-oxide, stereoisomer, or a pharmaceutically acceptable salt thereof, wherein $R^1$ and $R^2$ are both H. In some embodiments is a compound of Formula (I), or a solvate, hydrate, tautomer, N-oxide, stereoisomer, or a pharmaceutically acceptable salt thereof, wherein $R^1$ is $C_{1-6}$alkyl. In some embodiments is a compound of Formula (I), or a solvate, hydrate, tautomer, N-oxide, stereoisomer, or a pharmaceutically acceptable salt thereof, wherein $R^1$ is —$CH_3$. In some embodiments is a compound of Formula (I), or a solvate, hydrate, tautomer, N-oxide, stereoisomer, or a pharmaceutically acceptable salt thereof, wherein $R^2$ is $C_{1-6}$alkyl. In some embodiments is a compound of Formula (I), or a solvate, hydrate, tautomer, N-oxide, stereoisomer, or a pharmaceutically acceptable salt thereof, wherein $R^2$ is —$CH_3$. In some embodiments is a compound of Formula (I), or a solvate, hydrate, tautomer, N-oxide, stereoisomer, or a pharmaceutically acceptable salt thereof, wherein $R^1$ and $R^2$ are both $C_{1-6}$alkyl. In some embodiments is a compound of Formula (I), or a solvate, hydrate, tautomer, N-oxide, stereoisomer, or a pharmaceutically acceptable salt thereof, wherein $R^1$ and $R^2$ are both —$CH_3$.

In another embodiment is a compound of Formula (I), or a solvate, hydrate, tautomer, N-oxide, stereoisomer, or a pharmaceutically acceptable salt thereof, wherein p is 0, 1, 2, or 3. In another embodiment is a compound of Formula (I), or a solvate, hydrate, tautomer, N-oxide, stereoisomer, or a pharmaceutically acceptable salt thereof, wherein p is 0. In another embodiment is a compound of Formula (I), or a solvate, hydrate, tautomer, N-oxide, stereoisomer, or a pharmaceutically acceptable salt thereof, wherein p is 1. In another embodiment is a compound of Formula (I), or a solvate, hydrate, tautomer, N-oxide, stereoisomer, or a pharmaceutically acceptable salt thereof, wherein p is 2. In another embodiment is a compound of Formula (I), or a solvate, hydrate, tautomer, N-oxide, stereoisomer, or a pharmaceutically acceptable salt thereof, wherein p is 3. In another embodiment is a compound of Formula (I), or a solvate, hydrate, tautomer, N-oxide, stereoisomer, or a pharmaceutically acceptable salt thereof, wherein p is 4. In another embodiment is a compound of Formula (I), or a solvate, hydrate, tautomer, N-oxide, stereoisomer, or a pharmaceutically acceptable salt thereof, wherein p is 5.

In another embodiment is a compound of Formula (I), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (I), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (I), or a solvate, hydrate, tautomer, N-oxide, stereoisomer, or a pharmaceutically acceptable salt thereof, wherein p is 1 and $R^3$ is halogen. In another embodiment is a compound of Formula (I), or a solvate, hydrate, tautomer, N-oxide, stereoisomer, or a pharmaceutically acceptable salt thereof, wherein p is 1 and $R^3$ is —Cl. In another embodiment is a compound of Formula (I), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (I), or a solvate, hydrate, tautomer, N-oxide, stereoisomer, or a pharmaceutically acceptable salt thereof, wherein p is 1 and $R^3$ is —CF$_3$. In another embodiment is a compound of Formula (I), or a solvate, hydrate, tautomer, N-oxide, stereoisomer, or a pharmaceutically acceptable salt thereof, wherein p is 1 and $R^3$ is —$C_{1-6}$alkyl(heterocycloalkyl).

In another embodiment is a compound of Formula (I), or a solvate, hydrate, tautomer, N-oxide, stereoisomer, or a pharmaceutically acceptable salt thereof, wherein p is 1 and $R^3$ is —NR$^5$R$^6$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring optionally substituted with one, two, or three $R^{10}$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form an unsubstituted heterocycloalkyl ring. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with two $R^{10}$ independently selected from $C_{1-6}$alkyl, cycloalkyl, $C_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, $R^5$ and $R^6$, together with the nitrogen to which they are attached, form a heterocycloalkyl ring substituted with two $R^{10}$, and $R^0$ is halogen. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, $R^5$ and $R^6$, together with the nitrogen to which they are attached, form a heterocycloalkyl ring substituted with two $R^{10}$, and $R^{10}$ is oxo. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$ selected from $C_{1-6}$alkyl, cycloalkyl, $C_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is $C_{1-6}$alkyl. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is cycloalkyl. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is $C_{1-6}$haloalkyl. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is halogen. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —CO$_2$R$^8$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —CO$_2$H. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —C(O)R$^8$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —C(O)CH$_3$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —C(O)NR$^8$R$^9$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —C(O)NH$_2$. In another embodiment is a compound of Formula (I), or a solvate, hydrate, tautomer, N-oxide, stereoisomer, or a pharmaceutically acceptable salt thereof, wherein p is 1, $R^3$ is —NR$^5$R$^6$, and $R^5$ and $R^6$, together with the nitrogen to which they are attached, form a heterocycloalkyl ring substituted with one $R^{10}$, and $R^{10}$ is —SO$_2$R$^8$. In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$SO_2CH_3$. In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NR^9C(O)R^8$. In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NHC(O)CH_3$. In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NR^9SO_2R^8$. In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NHSO_2CH_3$. In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

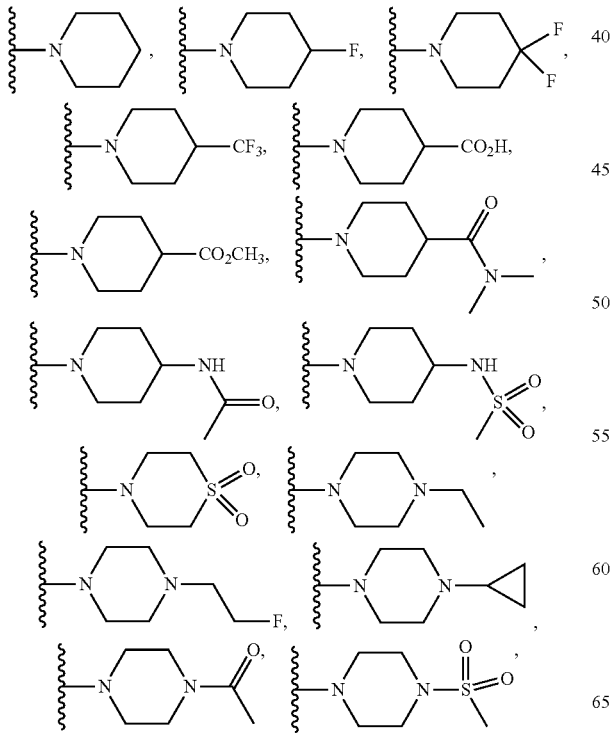

In another embodiment is a compound of Formula (I), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

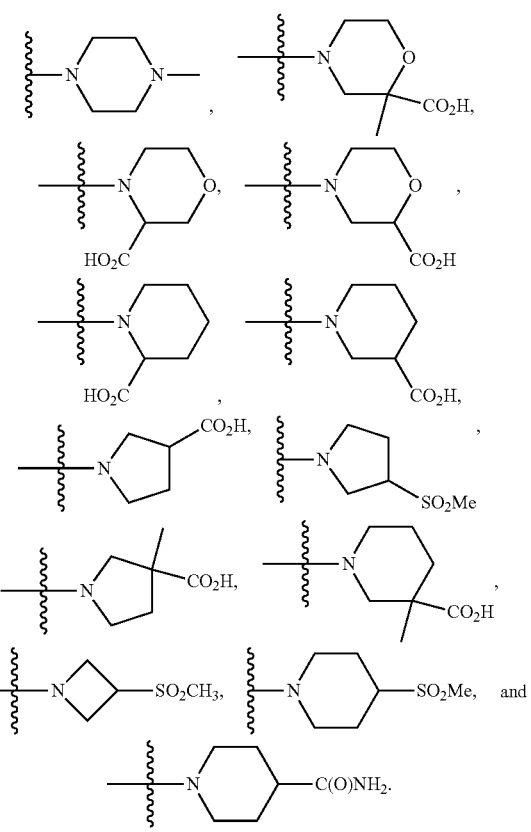

In another embodiment is a compound of Formula (I), or a solvate, hydrate, tautomer, N-oxide, stereoisomer, or a pharmaceutically acceptable salt thereof, wherein p is 1 and $R^3$ is —$OR^7$. In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is independently selected from $C_{1-6}$alkyl, $C_{1-6}$haloalkyl, aminoalkyl, —$C_{1-6}$alkyl(heterocycloalkyl), —$C_{1-6}$alkyl-C(O)(heterocycloalkyl), optionally substituted heterocycloalkyl, and optionally substituted heteroaryl. In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$alkyl. In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$haloalkyl. In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is aminoalkyl. In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl(heterocycloalkyl). In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl-C(O)(heterocycloalkyl). In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is optionally substituted heterocycloalkyl. In another embodiment is a compound of Formula (I), or a solvate, hydrate, tautomer, N-oxide, stereoisomer, or a pharmaceutically acceptable salt thereof, wherein p is 1 and $R^3$ is —$OR^7$, and $R^7$ is optionally substituted heteroaryl.

In another embodiment is a compound of Formula (I), or a solvate, hydrate, tautomer, N-oxide, stereoisomer, or a pharmaceutically acceptable salt thereof, wherein p is 1 and $R^3$ is —$CO_2R^8$. In another embodiment is a compound of Formula (I), or a solvate, hydrate, tautomer, N-oxide, stereoisomer, or a pharmaceutically acceptable salt thereof, wherein p is 1 and $R^3$ is —$CO_2H$. In another embodiment is a compound of Formula (I), or a solvate, hydrate, tautomer, N-oxide, stereoisomer, or a pharmaceutically acceptable salt thereof, wherein p is 1 and $R^3$ is —$C(O)NR^8R^9$. In another embodiment is a compound of Formula (I), or a solvate, hydrate, tautomer, N-oxide, stereoisomer, or a pharmaceutically acceptable salt thereof, wherein p is 1 and $R^3$ is —$C(O)NH_2$.

In another embodiment is a compound of Formula (I), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (I), or a solvate, hydrate, tautomer, N-oxide, stereoisomer, or a pharmaceutically acceptable salt thereof, wherein p is 2, one $R^3$ is halogen, and one $R^3$ is —$OR^7$. In another embodiment is a compound of Formula (I), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is $C_{1-6}$alkyl. In another embodiment is a compound of Formula (I), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is —$C_{1-6}$alkyl(heterocycloalkyl). In another embodiment is a compound of Formula (I), or a solvate, hydrate, tautomer, N-oxide, stereoisomer, or a pharmaceutically acceptable salt thereof, wherein p is 2, one $R^3$ is halogen, and one $R^3$ is —$NR^5R^6$. In another embodiment is a compound of Formula (I), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form an unsubstituted heterocycloalkyl ring. In another embodiment is a compound of Formula (I), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (I), or a solvate, hydrate, tautomer, N-oxide, stereoisomer, or a pharmaceutically acceptable salt thereof, wherein p is 2, one $R^3$ is —Cl, and one $R^3$ is —$NR^5R^6$. In another embodiment is a compound of Formula (I), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form an unsubstituted heterocycloalkyl ring. In another embodiment is a compound of Formula (I), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (I), or a solvate, hydrate, tautomer, N-oxide, stereoisomer, or a pharmaceutically acceptable salt thereof, wherein p is 2, one $R^3$ is $C_{1-6}$haloalkyl, and one $R^3$ is —$NR^5R^6$. In another embodiment is a compound of Formula (I), or a solvate, hydrate, tautomer, N-oxide, stereoisomer, or a pharmaceutically acceptable salt thereof, wherein p is 2, one $R^3$ is $C_{1-6}$haloalkyl, one $R^3$ is —$NR^5R^6$, and $R^5$ and $R^6$, together with the nitrogen to which they are attached, form an unsubstituted heterocycloalkyl ring. In another embodiment is a compound of Formula (I), or a solvate, hydrate, tautomer, N-oxide, stereoisomer, or a pharmaceutically acceptable salt thereof, wherein p is 2, one $R^3$ is $C_{1-6}$haloalkyl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (I), or a solvate, hydrate, tautomer, N-oxide, stereoisomer, or a pharmaceutically acceptable salt thereof, wherein p is 2, one $R^3$ is —$CF_3$, and one $R^3$ is —$NR^5R^6$. In another embodiment is a compound of Formula (I), or a solvate, hydrate, tautomer, N-oxide, stereoisomer, or a pharmaceutically acceptable salt thereof, wherein p is 2, one $R^3$ is —$CF_3$, one $R^3$ is —$NR^5R^6$, and $R^5$ and $R^6$, together with the nitrogen to which they are attached, form an unsubstituted heterocycloalkyl ring. In another embodiment is a compound of Formula (I), or a solvate, hydrate, tautomer, N-oxide, stereoisomer, or a pharmaceutically acceptable salt thereof, wherein p is 2, one $R^3$ is —$CF_3$, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$.

In another embodiment is a compound of Formula (I), or a solvate, hydrate, tautomer, N-oxide, stereoisomer, or a pharmaceutically acceptable salt thereof, wherein p is 2, one $R^3$ is $C_{1-6}$alkyl, halogen, $C_{1-6}$haloalkyl, —$C_{1-6}$alkyl(heterocycloalkyl), —OR⁷, —CO₂R⁸, or —C(O)NR⁸R⁹, and one R³ is —NR⁵R⁶, wherein R⁵ and R⁶, together with the nitrogen to which they are attached, form a heterocycloalkyl ring selected from:

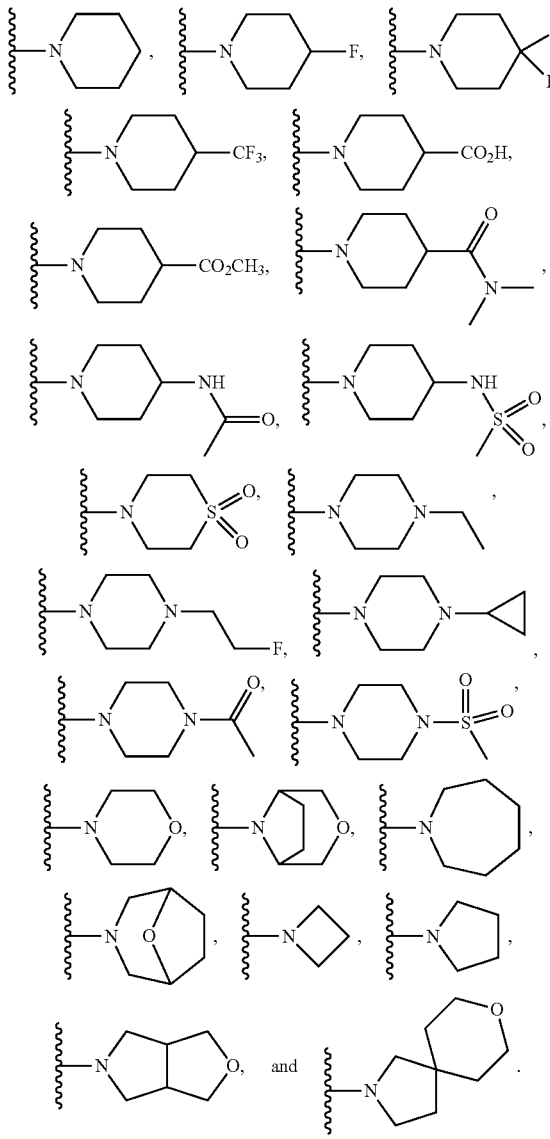

In another embodiment is a compound of Formula (I), or a solvate, hydrate, tautomer, N-oxide, stereoisomer, or a pharmaceutically acceptable salt thereof, wherein p is 2, one R³ is $C_{1-6}$alkyl, halogen, $C_{1-6}$haloalkyl, —$C_{1-6}$alkyl(heterocycloalkyl), —OR⁷, —CO₂R⁸, or —C(O)NR⁸R⁹, and one R³ is —NR⁵R⁶, wherein R⁵ and R⁶, together with the nitrogen to which they are attached, form a heterocycloalkyl ring selected from:

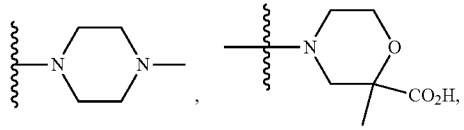

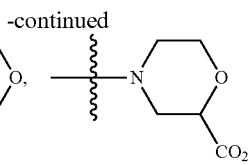

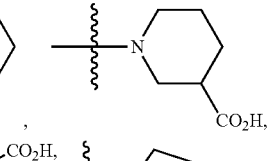

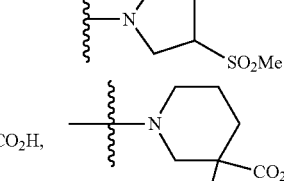

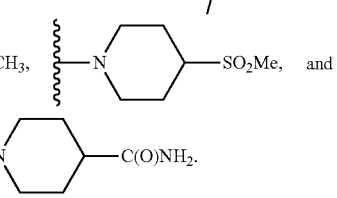

In another embodiment is a compound of Formula (I), or a solvate, hydrate, tautomer, N-oxide, stereoisomer, or a pharmaceutically acceptable salt thereof, wherein two adjacent R³ form a heterocycloalkyl ring optionally substituted with one, two, or three R⁴. In another embodiment is a compound of Formula (I), or a solvate, hydrate, tautomer, N-oxide, stereoisomer, or a pharmaceutically acceptable salt thereof, wherein two adjacent R³ form an unsubstituted heterocycloalkyl ring. In another embodiment is a compound of Formula (I), or a solvate, hydrate, tautomer, N-oxide, stereoisomer, or a pharmaceutically acceptable salt thereof, wherein two adjacent R³ form a heterocycloalkyl ring substituted with one, two, or three R⁴. In another embodiment is a compound of Formula (I), or a solvate, hydrate, tautomer, N-oxide, stereoisomer, or a pharmaceutically acceptable salt thereof, wherein two adjacent R³ form a heterocycloalkyl ring substituted with one or two R⁴. In another embodiment is a compound of Formula (I), or a solvate, hydrate, tautomer, N-oxide, stereoisomer, or a pharmaceutically acceptable salt thereof, wherein two adjacent R³ form a heterocycloalkyl ring substituted with one or two R⁴ independently selected from $C_{1-6}$alkyl, cycloalkyl, —C(O)R⁸, and —SO₂R⁸. In another embodiment is a compound of Formula (I), or a solvate, hydrate, tautomer, N-oxide, stereoisomer, or a pharmaceutically acceptable salt thereof, wherein two adjacent R³ form a heterocycloalkyl ring selected from:

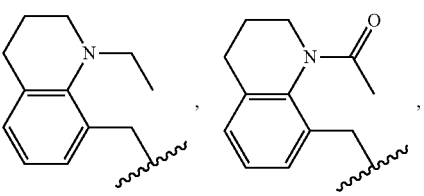

-continued

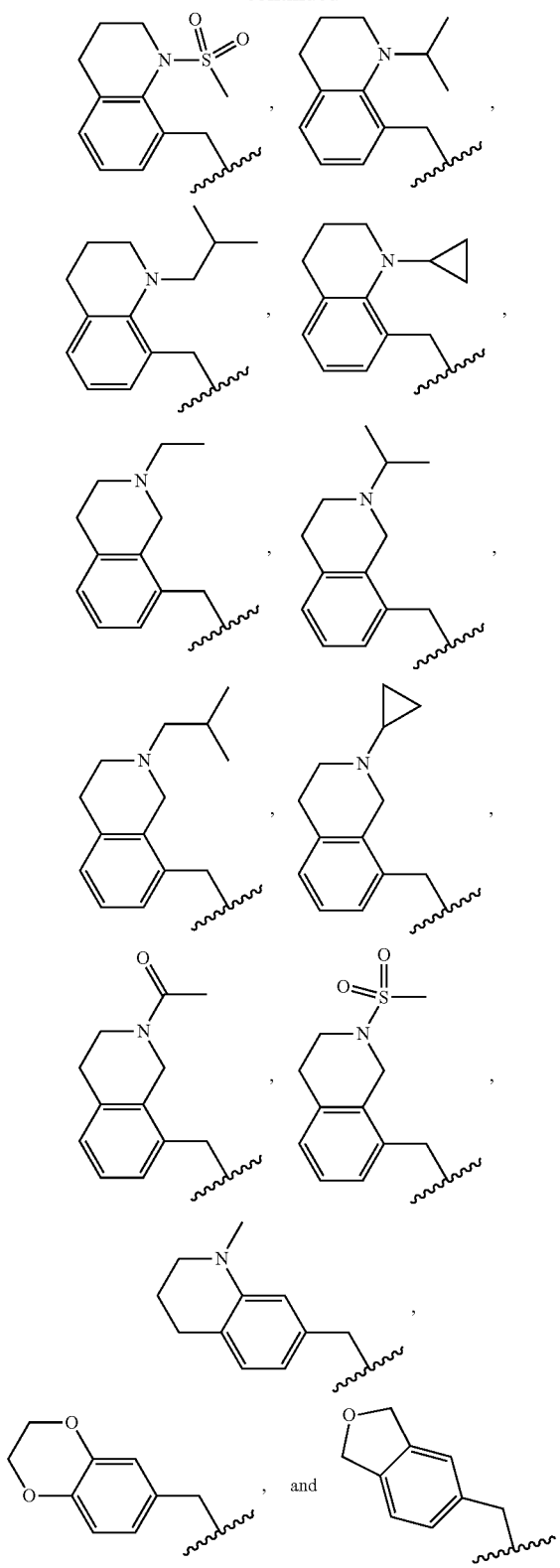

In some embodiments is a compound having the structure of Formula (Ia):

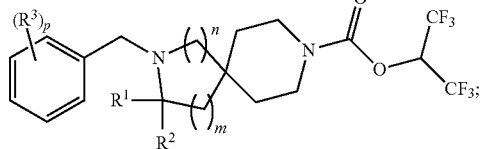

Formula (Ia)

wherein:
R$^1$ is H or C$_{1-6}$alkyl;
R$^2$ is H or C$_{1-6}$alkyl;
each R$^3$ is independently selected from C$_{1-6}$alkyl, C$_{1-6}$alkenyl, C$_{1-6}$alkynyl, halogen, —CN, C$_{1-6}$haloalkyl, C$_{1-6}$aminoalkyl, heterocycloalkyl, —C$_{1-6}$alkyl(heterocycloalkyl), heteroaryl, —SF$_5$, —NR$^5$R$^6$, —OR$^7$, —CO$_2$R$^8$, —C(O)R$^8$, and —C(O)NR$^8$R$^9$, wherein heterocycloalkyl and —C$_{1-6}$alkyl(heterocycloalkyl) are optionally substituted with one or two R$^4$; or two adjacent R$^3$ form a heterocycloalkyl ring, wherein the heterocycloalkyl ring and the heteroaryl ring are optionally substituted with one, two, or three R$^4$;
each R$^4$ is independently selected from C$_{1-6}$alkyl, C$_{1-6}$haloalkyl, C$_{3-8}$cycloalkyl, halogen, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
each R$^5$ and R$^6$ is independently selected from H, C$_{1-6}$alkyl, C$_{1-6}$haloalkyl, C$_{1-6}$aminoalkyl, C$_{3-8}$cycloalkyl, —C$_{1-6}$alkyl(heterocycloalkyl), —C$_{1-6}$alkyl-C(O)(heterocycloalkyl), heterocycloalkyl, aryl, and heteroaryl; or R$^5$ and R$^6$, together with the nitrogen to which they are attached, form a heterocycloalkyl ring optionally substituted with one, two, or three R$^{10}$;
each R$^7$ is independently selected from H, C$_{1-6}$alkyl, C$_{1-6}$haloalkyl, C$_{1-6}$aminoalkyl, C$_{3-8}$cycloalkyl, —C$_{1-6}$alkyl(heterocycloalkyl), —C$_{1-6}$alkyl-C(O)(heterocycloalkyl), heterocycloalkyl, aryl, and heteroaryl, wherein heterocycloalkyl, aryl, and heteroaryl are optionally substituted with one or two groups selected from oxo, C$_{1-6}$alkyl, C$_{1-6}$haloalkyl, CO$_2$H, and C(O)NH$_2$;
each R$^8$ and R$^9$ is independently selected from H, C$_{1-6}$alkyl, C$_{1-6}$haloalkyl, C$_{3-8}$cycloalkyl, aryl, and heteroaryl; or R$^8$ and R$^9$, together with the nitrogen to which they are attached, form a heterocycloalkyl ring optionally substituted with one or two groups selected from C$_{1-6}$alkyl, C$_{1-6}$ haloalkyl, CO$_2$H, and C(O)NH$_2$;
each R$^{10}$ is independently selected from C$_{1-6}$alkyl, C$_{3-8}$cycloalkyl, C$_{1-6}$haloalkyl, halogen, oxo, —CN, —CO$_2$R$^8$, —C(O)R$^8$, —C(O)NR$^8$R$^9$, —SO$_2$R$^8$, —NR$^5$C(O)R$^8$, and —NR$^9$SO$_2$R$^8$;
p is 0, 1, 2, 3, 4, or 5;
n is 0 or 1; and
m is 1 or 2; provided that when n is 0, then m is 2; and when n is 1, then m is 1;
or a solvate, hydrate, tautomer, N-oxide, stereoisomer, or pharmaceutically acceptable salt thereof.

In some embodiments is a compound of Formula (Ia), or a solvate, hydrate, tautomer, N-oxide, stereoisomer, or pharmaceutically acceptable salt thereof, wherein n is 0 and m is 2. In some embodiments is a compound of Formula (Ia), or a solvate, hydrate, tautomer, N-oxide, stereoisomer, or pharmaceutically acceptable salt thereof, wherein n is 1 and m is 1.

In some embodiments is a compound of Formula (Ia), or a solvate, hydrate, tautomer, N-oxide, stereoisomer, or a pharmaceutically acceptable salt thereof, wherein $R^1$ is H. In some embodiments is a compound of Formula (Ia), or a solvate, hydrate, tautomer, N-oxide, stereoisomer, or a pharmaceutically acceptable salt thereof, wherein $R^2$ is H. In some embodiments is a compound of Formula (Ia), or a solvate, hydrate, tautomer, N-oxide, stereoisomer, or a pharmaceutically acceptable salt thereof, wherein $R^1$ and $R^2$ are both H. In some embodiments is a compound of Formula (Ia), or a solvate, hydrate, tautomer, N-oxide, stereoisomer, or a pharmaceutically acceptable salt thereof, wherein $R^1$ is $C_{1-6}$alkyl. In some embodiments is a compound of Formula (Ia), or a solvate, hydrate, tautomer, N-oxide, stereoisomer, or a pharmaceutically acceptable salt thereof, wherein $R^1$ is —$CH_3$. In some embodiments is a compound of Formula (Ia), or a solvate, hydrate, tautomer, N-oxide, stereoisomer, or a pharmaceutically acceptable salt thereof, wherein $R^2$ is $C_{1-6}$alkyl. In some embodiments is a compound of Formula (Ia), or a solvate, hydrate, tautomer, N-oxide, stereoisomer, or a pharmaceutically acceptable salt thereof, wherein $R^2$ is —$CH_3$. In some embodiments is a compound of Formula (Ia), or a solvate, hydrate, tautomer, N-oxide, stereoisomer, or a pharmaceutically acceptable salt thereof, wherein $R^1$ and $R^2$ are both $C_{1-6}$alkyl. In some embodiments is a compound of Formula (Ia), or a solvate, hydrate, tautomer, N-oxide, stereoisomer, or a pharmaceutically acceptable salt thereof, wherein $R^1$ and $R^2$ are both —$CH_3$.

In another embodiment is a compound of Formula (Ia), or a solvate, hydrate, tautomer, N-oxide, stereoisomer, or a pharmaceutically acceptable salt thereof, wherein p is 0, 1, 2, or 3. In another embodiment is a compound of Formula (Ia), or a solvate, hydrate, tautomer, N-oxide, stereoisomer, or a pharmaceutically acceptable salt thereof, wherein p is 0. In another embodiment is a compound of Formula (Ia), or a solvate, hydrate, tautomer, N-oxide, stereoisomer, or a pharmaceutically acceptable salt thereof, wherein p is 1. In another embodiment is a compound of Formula (Ia), or a solvate, hydrate, tautomer, N-oxide, stereoisomer, or a pharmaceutically acceptable salt thereof, wherein p is 2. In another embodiment is a compound of Formula (Ia), or a solvate, hydrate, tautomer, N-oxide, stereoisomer, or a pharmaceutically acceptable salt thereof, wherein p is 3. In another embodiment is a compound of Formula (Ia), or a solvate, hydrate, tautomer, N-oxide, stereoisomer, or a pharmaceutically acceptable salt thereof, wherein p is 4. In another embodiment is a compound of Formula (Ia), or a solvate, hydrate, tautomer, N-oxide, stereoisomer, or a pharmaceutically acceptable salt thereof, wherein p is 5.

In another embodiment is a compound of Formula (Ia), or a solvate, hydrate, tautomer, N-oxide, stereoisomer, or a pharmaceutically acceptable salt thereof, wherein p is 1 and $R^3$ is selected from $C_{1-6}$alkyl, $C_{2-6}$alkynyl, halogen, —CN, $C_{1-6}$haloalkyl, heterocycloalkyl, —$C_{1-6}$alkyl(heterocycloalkyl), heteroaryl, —$SF_5$, —$NR^5R^6$, —$OR^7$, —$CO_2R^8$, —$C(O)R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein p is 1 and $R^3$ is selected from $C_{1-6}$alkyl, $C_{2-6}$alkynyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (Ia), or a solvate, hydrate, tautomer, N-oxide, stereoisomer, or a pharmaceutically acceptable salt thereof, wherein p is 1 and $R^3$ is $C_{2-6}$alkenyl. In another embodiment is a compound of Formula (Ia), or a solvate, hydrate, tautomer, N-oxide, stereoisomer, or a pharmaceutically acceptable salt thereof, wherein p is 1 and $R^3$ is $C_{2-6}$alkynyl. In another embodiment is a compound of Formula (Ia), or a solvate, hydrate, tautomer, N-oxide, stereoisomer, or a pharmaceutically acceptable salt thereof, wherein p is 1 and $R^3$ is halogen. In another embodiment is a compound of Formula (Ia), or a solvate, hydrate, tautomer, N-oxide, stereoisomer, or a pharmaceutically acceptable salt thereof, wherein p is 1 and $R^3$ is —Cl. In another embodiment is a compound of Formula (Ia), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (Ia), or a solvate, hydrate, tautomer, N-oxide, stereoisomer, or a pharmaceutically acceptable salt thereof, wherein p is 1 and $R^3$ is —$CF_3$. In another embodiment is a compound of Formula (Ia), or a solvate, hydrate, tautomer, N-oxide, stereoisomer, or a pharmaceutically acceptable salt thereof, wherein p is 1 and $R^3$ is —$C_{1-6}$alkyl (heterocycloalkyl).

In another embodiment is a compound of Formula (Ia), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring optionally substituted with one, two, or three $R^{10}$. In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form an unsubstituted heterocycloalkyl ring. In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, $C_{3-8}$cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with two $R^{10}$ independently selected from $C_{1-6}$alkyl, $C_{3-8}$cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, $R^5$ and $R^6$, together with the nitrogen to which they are attached, form a heterocycloalkyl ring substituted with two $R^{10}$, and $R^{10}$ is halogen. In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, $R^5$ and $R^6$, together with the nitrogen to which they are attached, form a heterocycloalkyl ring substituted with two R$^{10}$, and R$^{10}$ is oxo. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$ selected from C$_{1-6}$alkyl, C$_{3-8}$cycloalkyl, C$_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is C$_{1-6}$alkyl. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is C$_{3-8}$cycloalkyl. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is C$_{1-6}$haloalkyl. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is halogen. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —CO$_2$R$^8$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —CO$_2$H. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)R$^8$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)CH$_3$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)NR$^8$R$^9$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)NH$_2$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —SO$_2$R$^8$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —SO$_2$CH$_3$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —NR$^9$C(O)R$^8$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —NHC(O)CH$_3$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —NR$^9$SO$_2$R$^8$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —NHSO$_2$CH$_3$. In another embodiment is a compound of Formula (Ia), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring selected from:

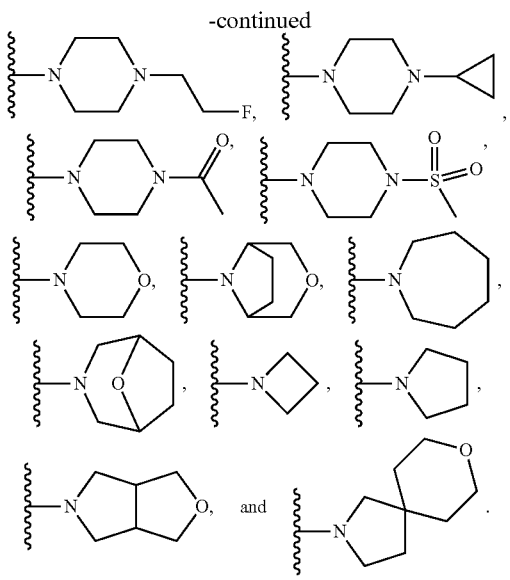

In another embodiment is a compound of Formula (Ia), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

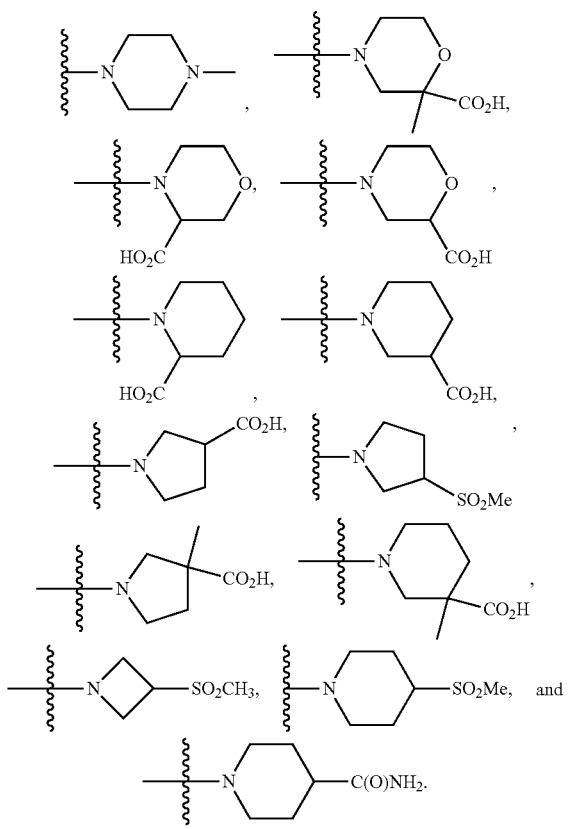

In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$. In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is independently selected from $C_{1-6}$alkyl, $C_{1-6}$haloalkyl, $C_{1-6}$aminoalkyl, —$C_{1-6}$alkyl(heterocycloalkyl), —$C_{1-6}$alkyl-C(O)(heterocycloalkyl), heterocycloalkyl, aryl, and heteroaryl, wherein heterocycloalkyl, aryl, and heteroaryl are optionally substituted with one or two groups selected from oxo, $C_{1-6}$alkyl, $C_{1-6}$haloalkyl, $CO_2H$, and $C(O)NH_2$. In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$alkyl. In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$haloalkyl. In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$aminoalkyl. In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl(heterocycloalkyl). In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl-C(O)(heterocycloalkyl). In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is heterocycloalkyl optionally substituted with one or two groups selected from oxo, $C_{1-6}$alkyl, $C_{1-6}$haloalkyl, $CO_2H$, and $C(O)NH_2$. In another embodiment is a compound of Formula (Ia), or a solvate, hydrate, tautomer, N-oxide, stereoisomer, or a pharmaceutically acceptable salt thereof, wherein p is 1 and $R^3$ is —$OR^7$, and $R^7$ is heteroaryl optionally substituted with one or two groups selected from oxo, $C_{1-6}$alkyl, $C_{1-6}$haloalkyl, $CO_2H$, and $C(O)NH_2$.

In another embodiment is a compound of Formula (Ia), or a solvate, hydrate, tautomer, N-oxide, stereoisomer, or a pharmaceutically acceptable salt thereof, wherein p is 1 and $R^3$ is —$CO_2R^8$. In another embodiment is a compound of Formula (Ia), or a solvate, hydrate, tautomer, N-oxide, stereoisomer, or a pharmaceutically acceptable salt thereof, wherein p is 1 and $R^3$ is —$CO_2H$. In another embodiment is a compound of Formula (Ia), or a solvate, hydrate, tautomer, N-oxide, stereoisomer, or a pharmaceutically acceptable salt thereof, wherein p is 1 and $R^3$ is —$C(O)NR^8R^9$. In another embodiment is a compound of Formula (Ia), or a solvate, hydrate, tautomer, N-oxide, stereoisomer, or a pharmaceutically acceptable salt thereof, wherein p is 1 and $R^3$ is —$C(O)NH_2$.

In another embodiment is a compound of Formula (Ia), or a solvate, hydrate, tautomer, N-oxide, stereoisomer, or a pharmaceutically acceptable salt thereof, wherein p is 2 and each $R^3$ is independently selected from $C_{1-6}$alkyl, $C_{2-6}$alkynyl, halogen, —CN, $C_{1-6}$haloalkyl, heterocycloalkyl, —$C_{1-6}$alkyl(heterocycloalkyl), heteroaryl, —$SF_5$, —$NR^5R^6$, —$OR^7$, —$CO_2R^8$, —$C(O)R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein p is 2 and each $R^3$ is independently selected from $C_{1-6}$alkyl, $C_{2-6}$alkynyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (Ia), or a solvate, hydrate, tautomer, N-oxide, stereoisomer, or a pharmaceutically acceptable salt thereof, wherein p is 2, one $R^3$ is halogen, and one $R^3$ is —$OR^7$. In another embodiment is a compound of Formula (Ia), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is $C_{1-6}$alkyl. In another embodiment is a compound of Formula (Ia), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is —$C_{1-6}$alkyl(heterocycloalkyl). In another embodiment is a compound of Formula (Ia), or a solvate, hydrate, tautomer, N-oxide, stereoisomer, or a pharmaceutically acceptable salt thereof, wherein p is 2, one $R^3$ is halogen, and one $R^3$ is —$NR^5R^6$. In another embodiment is a compound of Formula (Ia), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form an unsubstituted heterocycloalkyl ring. In another embodiment is a compound of Formula (Ia), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, $C_{3-8}$cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (Ia), or a solvate, hydrate, tautomer, N-oxide, stereoisomer, or a pharmaceutically acceptable salt thereof, wherein p is 2, one $R^3$ is —Cl, and one $R^3$ is —$NR^5R^6$. In another embodiment is a compound of Formula (Ia), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form an unsubstituted heterocycloalkyl ring. In another embodiment is a compound of Formula (Ia), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, $C_{3-8}$cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (Ia), or a solvate, hydrate, tautomer, N-oxide, stereoisomer, or a pharmaceutically acceptable salt thereof, wherein p is 2, one $R^3$ is $C_{1-6}$haloalkyl, and one $R^3$ is —$NR^5R^6$. In another embodiment is a compound of Formula (Ia), or a solvate, hydrate, tautomer, N-oxide, stereoisomer, or a pharmaceutically acceptable salt thereof, wherein p is 2, one $R^3$ is $C_{1-6}$haloalkyl, one $R^3$ is —$NR^5R^6$, and $R^5$ and $R^6$, together with the nitrogen to which they are attached, form an unsubstituted heterocycloalkyl ring. In another embodiment is a compound of Formula (Ia), or a solvate, hydrate, tautomer, N-oxide, stereoisomer, or a pharmaceutically acceptable salt thereof, wherein p is 2, one $R^3$ is $C_{1-6}$haloalkyl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, $C_{3-8}$cycloalkyl, $C_{1-6}$haloalkyl, halogen, —$CO_2R^8$, —$C(O)R^8$, —$C(O)$ $NR^8R^9$, —$SO_2R^8$, —$NR^9C(O)R^8$, and —$NR^9SO_2R^8$. In another embodiment is a compound of Formula (Ia), or a solvate, hydrate, tautomer, N-oxide, stereoisomer, or a pharmaceutically acceptable salt thereof, wherein p is 2, one $R^3$ is —$CF_3$, and one $R^3$ is —$NR^5R^6$. In another embodiment is a compound of Formula (Ia), or a solvate, hydrate, tautomer, N-oxide, stereoisomer, or a pharmaceutically acceptable salt thereof, wherein p is 2, one $R^3$ is —$CF_3$, one $R^3$ is —$NR^5R^6$, and $R^5$ and $R^6$, together with the nitrogen to which they are attached, form an unsubstituted heterocycloalkyl ring. In another embodiment is a compound of Formula (Ia), or a solvate, hydrate, tautomer, N-oxide, stereoisomer, or a pharmaceutically acceptable salt thereof, wherein p is 2, one $R^3$ is —$CF_3$, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, $C_{3-8}$cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$.

In another embodiment is a compound of Formula (Ia), or a solvate, hydrate, tautomer, N-oxide, stereoisomer, or a pharmaceutically acceptable salt thereof, wherein p is 2, one $R^3$ is $C_{1-6}$alkyl, halogen, $C_{1-6}$haloalkyl, —$C_{1-6}$alkyl(heterocycloalkyl), —$OR^7$, —$CO_2R^8$, or —$C(O)NR^8R^9$, and one $R^3$ is —$NR^5R^6$, wherein $R^5$ and $R^6$, together with the nitrogen to which they are attached, form a heterocycloalkyl ring selected from:

-continued

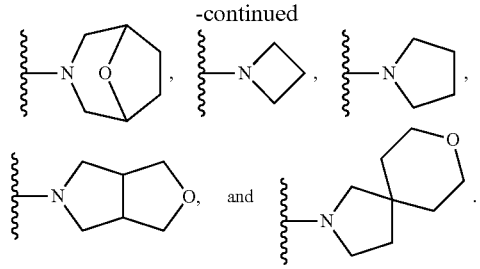

In another embodiment is a compound of Formula (Ia), or a solvate, hydrate, tautomer, N-oxide, stereoisomer, or a pharmaceutically acceptable salt thereof, wherein p is 2, one $R^3$ is $C_{1-6}$alkyl, halogen, $C_{1-6}$haloalkyl, —$C_{1-6}$alkyl(heterocycloalkyl), —$OR^7$, —$CO_2R^8$, or —$C(O)NR^8R^9$, and one $R^3$ is —$NR^5R^6$, wherein $R^5$ and $R^6$, together with the nitrogen to which they are attached, form a heterocycloalkyl ring selected from:

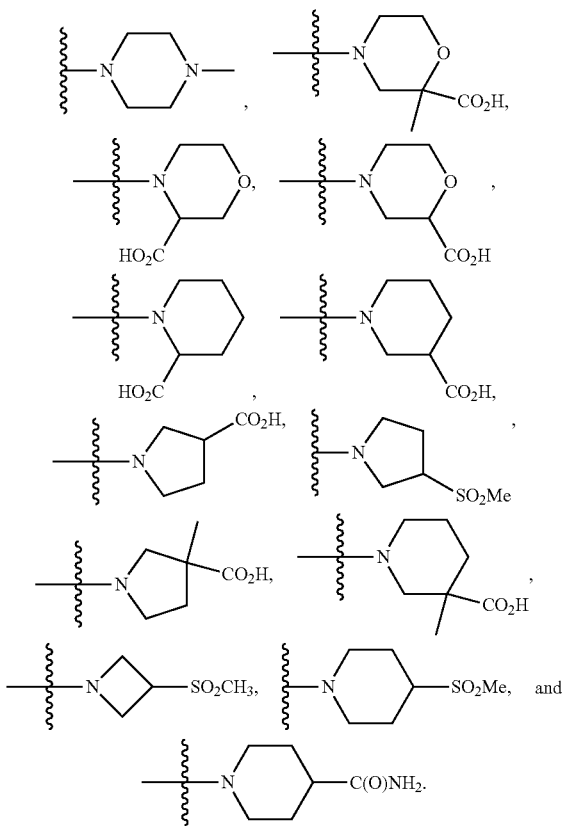

In another embodiment is a compound of Formula (Ia), or a solvate, hydrate, tautomer, N-oxide, stereoisomer, or a pharmaceutically acceptable salt thereof, wherein two adjacent $R^3$ form a heterocycloalkyl ring optionally substituted with one, two, or three $R^4$. In another embodiment is a compound of Formula (Ia), or a solvate, hydrate, tautomer, N-oxide, stereoisomer, or a pharmaceutically acceptable salt thereof, wherein two adjacent $R^3$ form an unsubstituted heterocycloalkyl ring. In another embodiment is a compound of Formula (Ia), or a solvate, hydrate, tautomer, N-oxide, stereoisomer, or a pharmaceutically acceptable salt thereof, wherein two adjacent $R^3$ form a heterocycloalkyl ring substituted with one, two, or three $R^4$. In another embodiment is a compound of Formula (Ia), or a solvate, hydrate, tautomer, N-oxide, stereoisomer, or a pharmaceutically acceptable salt thereof, wherein two adjacent $R^3$ form a heterocycloalkyl ring substituted with one or two $R^4$. In another embodiment is a compound of Formula (Ia), or a solvate, hydrate, tautomer, N-oxide, stereoisomer, or a pharmaceutically acceptable salt thereof, wherein two adjacent $R^3$ form a heterocycloalkyl ring substituted with one or two $R^4$ independently selected from $C_{1-6}$alkyl, $C_{3-8}$cycloalkyl, —$C(O)R^8$, and —$SO_2R^8$. In another embodiment is a compound of Formula (Ia), or a solvate, hydrate, tautomer, N-oxide, stereoisomer, or a pharmaceutically acceptable salt thereof, wherein two adjacent $R^3$ form a heterocycloalkyl ring selected from:

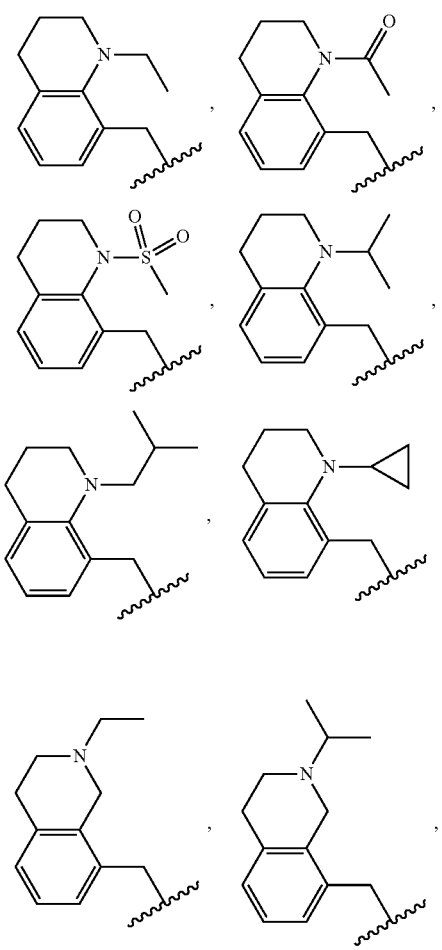

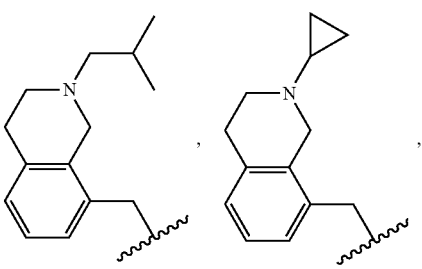

-continued

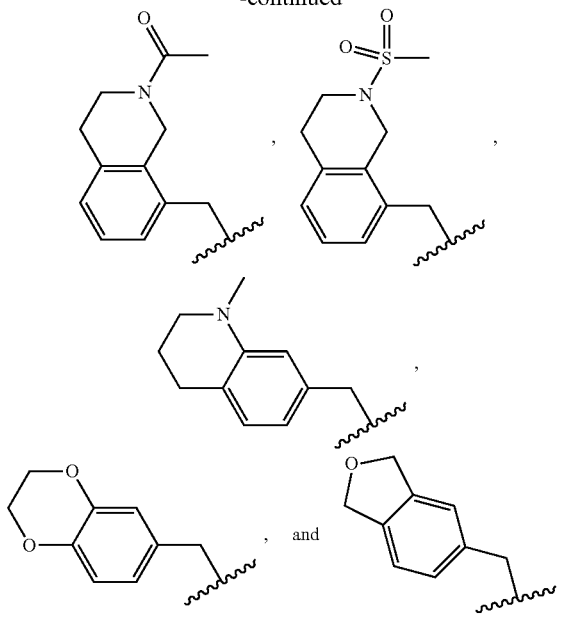

In some embodiments is a compound having the structure of Formula (II):

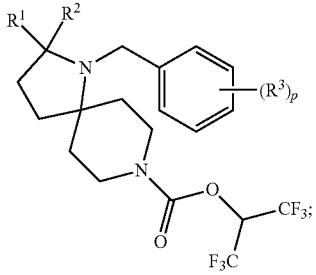

Formula (II)

wherein:
R¹ is H or optionally substituted $C_{1-6}$alkyl;
R² is H or optionally substituted $C_{1-6}$alkyl;
each R³ is independently selected from $C_{1-6}$alkyl, halogen, —CN, $C_{1-6}$haloalkyl, aminoalkyl, —$C_{1-6}$alkyl(heterocycloalkyl), —NR⁵R⁶, —OR⁷, —CO₂R⁸, —C(O)R⁸, and —C(O)NR⁸R⁹; or two adjacent R³ form a heterocycloalkyl ring optionally substituted with one, two, or three R⁴;
each R⁴ is selected from $C_{1-6}$alkyl, cycloalkyl, $C_{1-6}$haloalkyl, halogen, oxo, —CN, —CO₂R⁸, —C(O)R⁸, —C(O)NR⁸R⁹, —SO₂R⁸, —NR⁹C(O)R⁸, and —NR⁹SO₂R⁸;
each R⁵ and R⁶ is independently selected from H, $C_{1-6}$alkyl, $C_{1-6}$haloalkyl, aminoalkyl, cycloalkyl, —$C_{1-6}$ alkyl(heterocycloalkyl), —$C_{1-6}$alkyl-C(O)(heterocycloalkyl), optionally substituted heterocycloalkyl, optionally substituted aryl, and optionally substituted heteroaryl; or R⁵ and R⁶, together with the nitrogen to which they are attached, form a heterocycloalkyl ring optionally substituted with one, two, or three R¹⁰;
each R⁷ is independently selected from H, $C_{1-6}$alkyl, $C_{1-6}$haloalkyl, aminoalkyl, cycloalkyl, —$C_{1-6}$alkyl(heterocycloalkyl), —$C_{1-6}$alkyl-C(O)(heterocycloalkyl), optionally substituted heterocycloalkyl, optionally substituted aryl, and optionally substituted heteroaryl;
each R⁸ and R⁹ is independently selected from H, $C_{1-6}$alkyl, $C_{1-6}$haloalkyl, cycloalkyl, aryl, and heteroaryl;
each R¹⁰ is selected from $C_{1-6}$alkyl, cycloalkyl, $C_{1-6}$haloalkyl, halogen, oxo, —CN, —CO₂R⁸, —C(O)R⁸, —C(O)NR⁸R⁹, —SO₂R⁸, —NR⁹C(O)R⁸, and —NR⁹SO₂R⁸; and
p is 0, 1, 2, 3, 4, or 5;
or a solvate, hydrate, tautomer, N-oxide, stereoisomer, or pharmaceutically acceptable salt thereof.

In some embodiments is a compound of Formula (II), or a solvate, hydrate, tautomer, N-oxide, stereoisomer, or a pharmaceutically acceptable salt thereof, wherein R¹ is H. In some embodiments is a compound of Formula (II), or a solvate, hydrate, tautomer, N-oxide, stereoisomer, or a pharmaceutically acceptable salt thereof, wherein R² is H. In some embodiments is a compound of Formula (II), or a solvate, hydrate, tautomer, N-oxide, stereoisomer, or a pharmaceutically acceptable salt thereof, wherein R¹ and R² are both H. In some embodiments is a compound of Formula (II), or a solvate, hydrate, tautomer, N-oxide, stereoisomer, or a pharmaceutically acceptable salt thereof, wherein R¹ is $C_{1-6}$alkyl. In some embodiments is a compound of Formula (II), or a solvate, hydrate, tautomer, N-oxide, stereoisomer, or a pharmaceutically acceptable salt thereof, wherein R¹ is —CH₃. In some embodiments is a compound of Formula (II), or a solvate, hydrate, tautomer, N-oxide, stereoisomer, or a pharmaceutically acceptable salt thereof, wherein R² is $C_{1-6}$alkyl. In some embodiments is a compound of Formula (II), or a solvate, hydrate, tautomer, N-oxide, stereoisomer, or a pharmaceutically acceptable salt thereof, wherein R² is —CH₃. In some embodiments is a compound of Formula (II), or a solvate, hydrate, tautomer, N-oxide, stereoisomer, or a pharmaceutically acceptable salt thereof, wherein R¹ and R² are both $C_{1-6}$alkyl. In some embodiments is a compound of Formula (II), or a solvate, hydrate, tautomer, N-oxide, stereoisomer, or a pharmaceutically acceptable salt thereof, wherein R¹ and R² are both —CH₃.

In another embodiment is a compound of Formula (II), or a solvate, hydrate, tautomer, N-oxide, stereoisomer, or a pharmaceutically acceptable salt thereof, wherein p is 0, 1, 2, or 3. In another embodiment is a compound of Formula (II), or a solvate, hydrate, tautomer, N-oxide, stereoisomer, or a pharmaceutically acceptable salt thereof, wherein p is 0. In another embodiment is a compound of Formula (II), or a solvate, hydrate, tautomer, N-oxide, stereoisomer, or a pharmaceutically acceptable salt thereof, wherein p is 1. In another embodiment is a compound of Formula (II), or a solvate, hydrate, tautomer, N-oxide, stereoisomer, or a pharmaceutically acceptable salt thereof, wherein p is 2. In another embodiment is a compound of Formula (II), or a solvate, hydrate, tautomer, N-oxide, stereoisomer, or a pharmaceutically acceptable salt thereof, wherein p is 3. In another embodiment is a compound of Formula (II), or a solvate, hydrate, tautomer, N-oxide, stereoisomer, or a pharmaceutically acceptable salt thereof, wherein p is 4. In another embodiment is a compound of Formula (II), or a solvate, hydrate, tautomer, N-oxide, stereoisomer, or a pharmaceutically acceptable salt thereof, wherein p is 5.

In another embodiment is a compound of Formula (II), or a solvate, hydrate, tautomer, N-oxide, stereoisomer, or a pharmaceutically acceptable salt thereof, wherein p is 1 and R³ is selected from $C_{1-6}$alkyl, halogen, $C_{1-6}$haloalkyl, —$C_{1-6}$alkyl(heterocycloalkyl), —NR⁵R⁶, —OR⁷, —CO₂R⁸, and —C(O)NR$^8$R$^9$. In another embodiment is a compound of Formula (II), or a solvate, hydrate, tautomer, N-oxide, stereoisomer, or a pharmaceutically acceptable salt thereof, wherein p is 1 and R$^3$ is C$_{1-6}$alkyl. In another embodiment is a compound of Formula (II), or a solvate, hydrate, tautomer, N-oxide, stereoisomer, or a pharmaceutically acceptable salt thereof, wherein p is 1 and R$^3$ is halogen. In another embodiment is a compound of Formula (II), or a solvate, hydrate, tautomer, N-oxide, stereoisomer, or a pharmaceutically acceptable salt thereof, wherein p is 1 and R$^3$ is —Cl. In another embodiment is a compound of Formula (II), or a solvate, hydrate, tautomer, N-oxide, stereoisomer, or a pharmaceutically acceptable salt thereof, wherein p is 1 and R$^3$ is C$_{1-6}$haloalkyl. In another embodiment is a compound of Formula (II), or a solvate, hydrate, tautomer, N-oxide, stereoisomer, or a pharmaceutically acceptable salt thereof, wherein p is 1 and R$^3$ is —CF$_3$. In another embodiment is a compound of Formula (II), or a solvate, hydrate, tautomer, N-oxide, stereoisomer, or a pharmaceutically acceptable salt thereof, wherein p is 1 and R$^3$ is —C$_{1-6}$alkyl(heterocycloalkyl).

In another embodiment is a compound of Formula (II), or a solvate, hydrate, tautomer, N-oxide, stereoisomer, or a pharmaceutically acceptable salt thereof, wherein p is 1 and R$^3$ is —NR$^5$R$^6$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring optionally substituted with one, two, or three R$^{10}$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form an unsubstituted heterocycloalkyl ring. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one or two R$^{10}$ independently selected from C$_{1-6}$alkyl, cycloalkyl, C$_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with two R$^{10}$ independently selected from C$_{1-6}$alkyl, cycloalkyl, C$_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, R$^5$ and R$^6$, together with the nitrogen to which they are attached, form a heterocycloalkyl ring substituted with two R$^{10}$, and R$^{10}$ is halogen. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, R$^5$ and R$^6$, together with the nitrogen to which they are attached, form a heterocycloalkyl ring substituted with two R$^{10}$, and R$^{10}$ is oxo. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$ selected from C$_{1-6}$alkyl, cycloalkyl, C$_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is C$_{1-6}$alkyl. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is cycloalkyl. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is C$_{1-6}$haloalkyl. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is halogen. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —CO$_2$R$^8$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —CO$_2$H. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)R$^8$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^0$ is —C(O)CH$_3$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)NR$^8$R$^9$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one R$^{10}$, and R$^{10}$ is —C(O)NH$_2$. In another embodiment is a compound of Formula (II), or a solvate, hydrate, tautomer, N-oxide, stereoisomer, or a pharmaceutically acceptable salt thereof, wherein p is 1, R$^3$ is —NR$^5$R$^6$, and R$^5$ and R$^6$, together with the nitrogen to which they are attached, form a heterocycloalkyl ring substituted with one $R^{10}$, and $R^{10}$ is —$SO_2R^8$. In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$SO_2CH_3$. In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NR^9C(O)R^8$. In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NHC(O)CH_3$. In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NR^9SO_2R^8$. In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NHSO_2CH_3$. In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

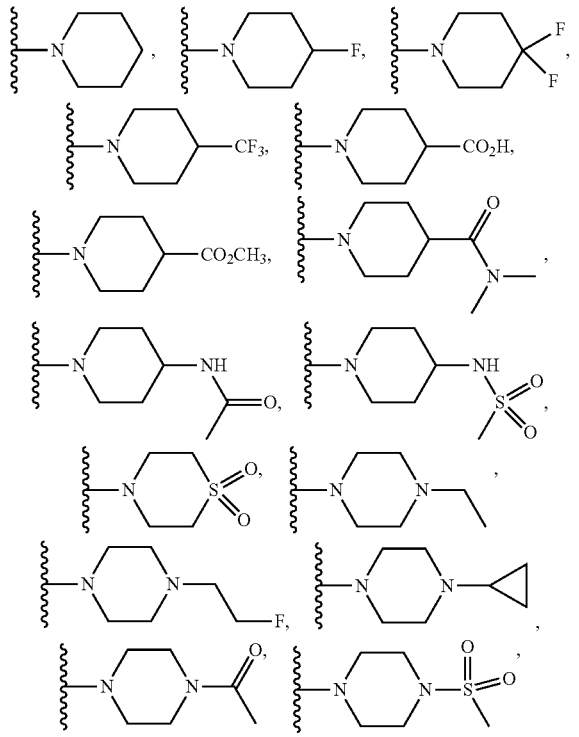

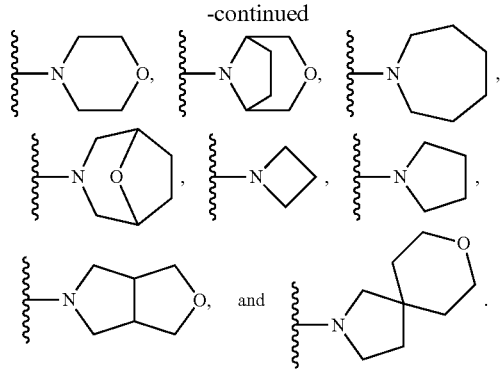

In another embodiment is a compound of Formula (II), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

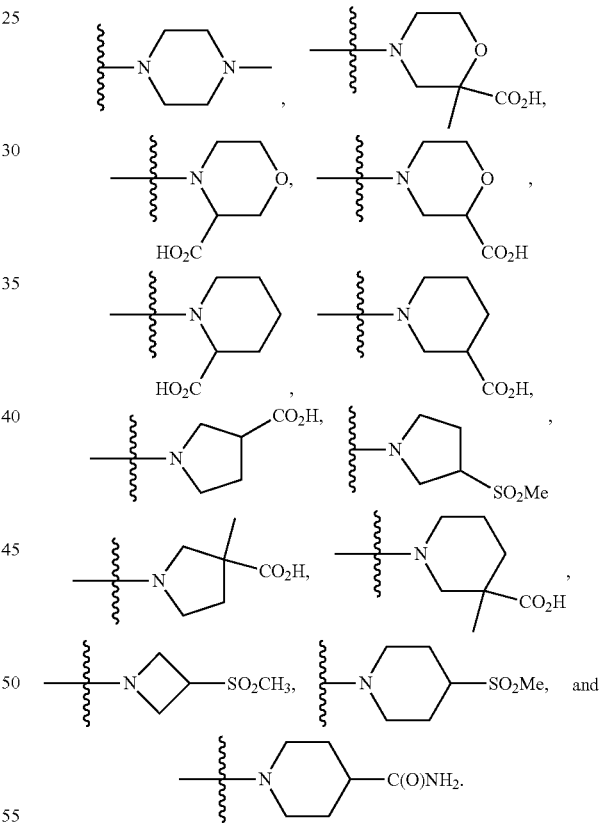

In another embodiment is a compound of Formula (II), or a solvate, hydrate, tautomer, N-oxide, stereoisomer, or a pharmaceutically acceptable salt thereof, wherein p is 1 and $R^3$ is —$OR^7$. In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is independently selected from $C_{1-6}$alkyl, $C_{1-6}$haloalkyl, aminoalkyl, —$C_{1-6}$alkyl(heterocycloalkyl), —$C_{1-6}$alkyl-C(O)(heterocycloalkyl), optionally substituted heterocycloalkyl, and optionally substituted heteroaryl. In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$alkyl. In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$haloalkyl. In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is aminoalkyl. In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl(heterocycloalkyl). In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl-C(O)(heterocycloalkyl). In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is optionally substituted heterocycloalkyl. In another embodiment is a compound of Formula (II), or a solvate, hydrate, tautomer, N-oxide, stereoisomer, or a pharmaceutically acceptable salt thereof, wherein p is 1 and $R^3$ is —$OR^7$, and $R^7$ is optionally substituted heteroaryl.

In another embodiment is a compound of Formula (II), or a solvate, hydrate, tautomer, N-oxide, stereoisomer, or a pharmaceutically acceptable salt thereof, wherein p is 1 and $R^3$ is —$CO_2R^8$. In another embodiment is a compound of Formula (II), or a solvate, hydrate, tautomer, N-oxide, stereoisomer, or a pharmaceutically acceptable salt thereof, wherein p is 1 and $R^3$ is —$CO_2H$. In another embodiment is a compound of Formula (II), or a solvate, hydrate, tautomer, N-oxide, stereoisomer, or a pharmaceutically acceptable salt thereof, wherein p is 1 and $R^3$ is —$C(O)NR^8R^9$. In another embodiment is a compound of Formula (II), or a solvate, hydrate, tautomer, N-oxide, stereoisomer, or a pharmaceutically acceptable salt thereof, wherein p is 1 and $R^3$ is —$C(O)NH_2$.

In another embodiment is a compound of Formula (II), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (II), or a solvate, hydrate, tautomer, N-oxide, stereoisomer, or a pharmaceutically acceptable salt thereof, wherein p is 2, one $R^3$ is halogen, and one $R^3$ is —$OR^7$. In another embodiment is a compound of Formula (II), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is $C_{1-6}$alkyl. In another embodiment is a compound of Formula (II), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is —$C_{1-6}$alkyl(heterocycloalkyl). In another embodiment is a compound of Formula (II), or a solvate, hydrate, tautomer, N-oxide, stereoisomer, or a pharmaceutically acceptable salt thereof, wherein p is 2, one $R^3$ is halogen, and one $R^3$ is —$NR^5R^6$. In another embodiment is a compound of Formula (II), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form an unsubstituted heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (II), or a solvate, hydrate, tautomer, N-oxide, stereoisomer, or a pharmaceutically acceptable salt thereof, wherein p is 2, one $R^3$ is —Cl, and one $R^3$ is —$NR^5R^6$. In another embodiment is a compound of Formula (II), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form an unsubstituted heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl, and one $R^3$ is —$NR^5R^6$. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl, one $R^3$ is —$NR^5R^6$, and $R^5$ and $R^6$, together with the nitrogen to which they are attached, form an unsubstituted heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$, and one $R^3$ is —$NR^5R^6$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$, one $R^3$ is —$NR^5R^6$, and $R^5$ and $R^6$, together with the nitrogen to which they are attached, form an unsubstituted heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is —$CF_3$, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$.

In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$alkyl, halogen, $C_{1-6}$haloalkyl, —$C_{1-6}$alkyl(heterocycloalkyl), —$OR^7$, —$CO_2R^8$, or —$C(O)NR^8R^9$, and one $R^3$ is —$NR^5R^6$, wherein $R^5$ and $R^6$, together with the nitrogen to which they are attached, form a heterocycloalkyl ring selected from:

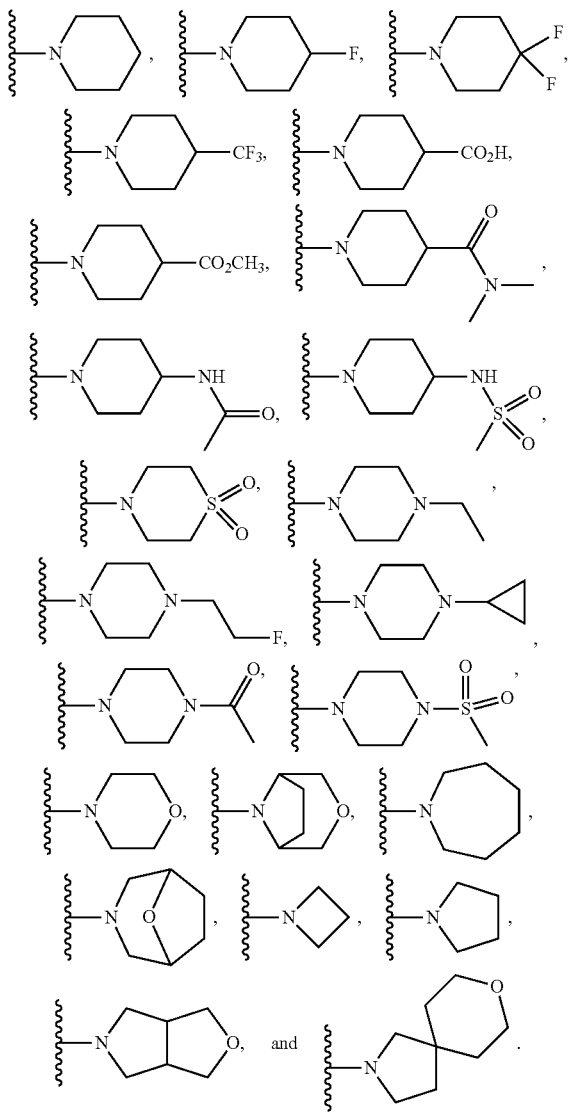

In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$alkyl, halogen, $C_{1-6}$haloalkyl, —$C_{1-6}$alkyl(heterocycloalkyl), —$OR^7$, —$CO_2R^8$, or —$C(O)NR^8R^9$, and one $R^3$ is —$NR^5R^6$, wherein $R^5$ and $R^6$, together with the nitrogen to which they are attached, form a heterocycloalkyl ring selected from:

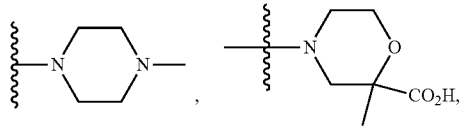

-continued

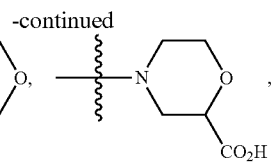

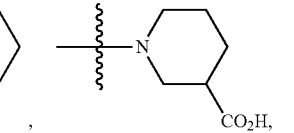

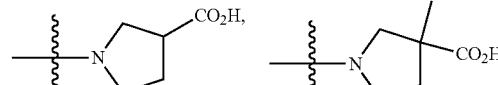

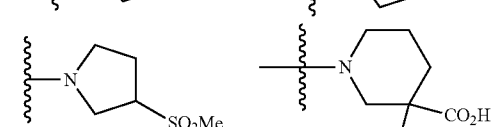

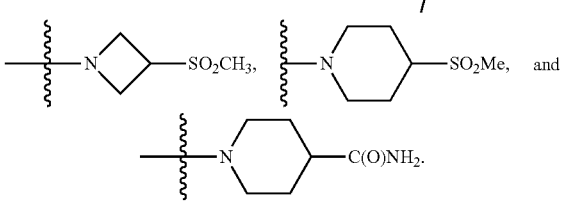

In another embodiment is a compound of Formula (II), or a solvate, hydrate, tautomer, N-oxide, stereoisomer, or a pharmaceutically acceptable salt thereof, wherein two adjacent $R^3$ form a heterocycloalkyl ring optionally substituted with one, two, or three $R^4$. In another embodiment is a compound of Formula (II), or a solvate, hydrate, tautomer, N-oxide, stereoisomer, or a pharmaceutically acceptable salt thereof, wherein two adjacent $R^3$ form an unsubstituted heterocycloalkyl ring. In another embodiment is a compound of Formula (II), or a solvate, hydrate, tautomer, N-oxide, stereoisomer, or a pharmaceutically acceptable salt thereof, wherein two adjacent $R^3$ form a heterocycloalkyl ring substituted with one, two, or three $R^4$. In another embodiment is a compound of Formula (II), or a solvate, hydrate, tautomer, N-oxide, stereoisomer, or a pharmaceutically acceptable salt thereof, wherein two adjacent $R^3$ form a heterocycloalkyl ring substituted with one or two $R^4$. In another embodiment is a compound of Formula (II), or a solvate, hydrate, tautomer, N-oxide, stereoisomer, or a pharmaceutically acceptable salt thereof, wherein two adjacent $R^3$ form a heterocycloalkyl ring substituted with one or two $R^4$ independently selected from $C_{1-6}$alkyl, cycloalkyl, —$C(O)R^8$, and —$SO_2R^8$. In another embodiment is a compound of Formula (II), or a solvate, hydrate, tautomer, N-oxide, stereoisomer, or a pharmaceutically acceptable salt thereof, wherein two adjacent $R^3$ form a heterocycloalkyl ring selected from:

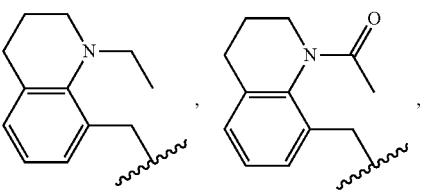

-continued

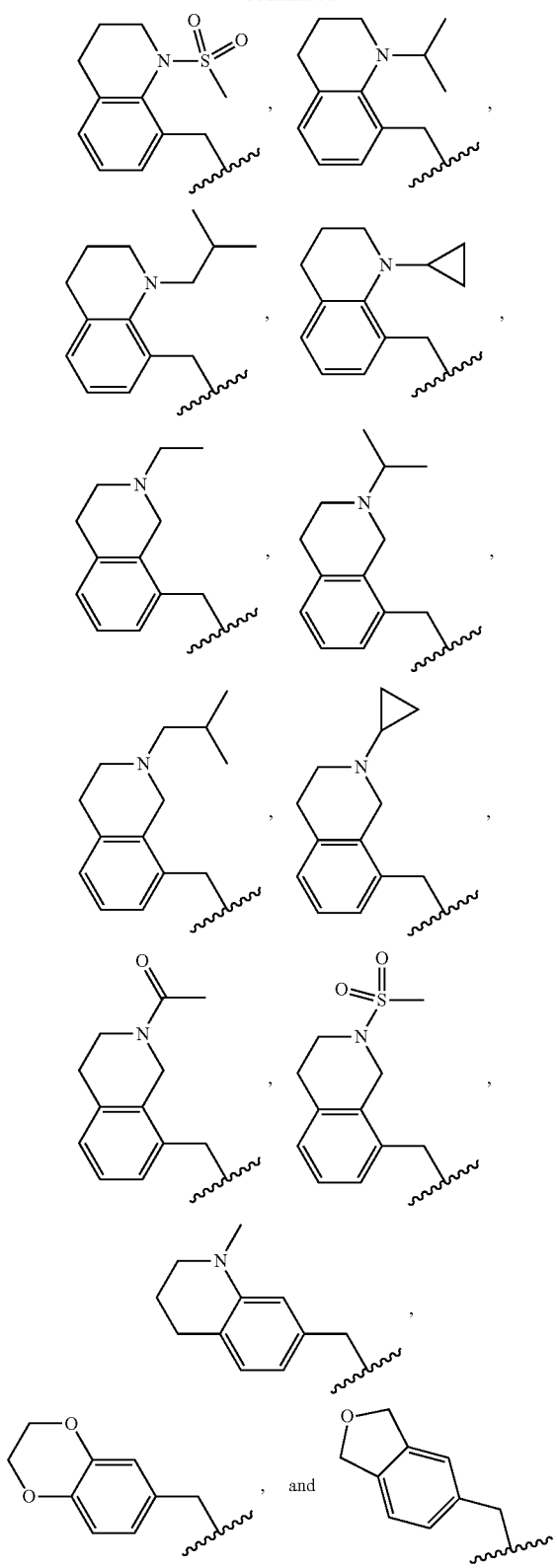

In some embodiments is a compound having the structure of Formula (III):

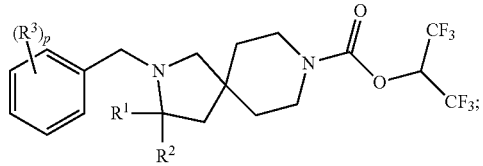

Formula (III)

wherein:
R¹ is H or optionally substituted $C_{1-6}$alkyl;
R² is H or optionally substituted $C_{1-6}$alkyl;
each R³ is independently selected from $C_{1-6}$alkyl, halogen, —CN, $C_{1-6}$haloalkyl, aminoalkyl, —$C_{1-6}$alkyl(heterocycloalkyl), —NR⁵R⁶, —OR⁷, —CO₂R⁸, —C(O)R⁸, and —C(O)NR⁸R⁹; or two adjacent R³ form a heterocycloalkyl ring optionally substituted with one, two, or three R⁴;
each R⁴ is selected from $C_{1-6}$alkyl, cycloalkyl, $C_{1-6}$haloalkyl, halogen, oxo, —CN, —CO₂R⁸, —C(O)R⁸, —C(O)NR⁸R⁹, —SO₂R⁸, —NR⁹C(O)R⁸, and —NR⁹SO₂R⁸;
each R⁵ and R⁶ is independently selected from H, $C_{1-6}$alkyl, $C_{1-6}$haloalkyl, aminoalkyl, cycloalkyl, —$C_{1-6}$ alkyl(heterocycloalkyl), —$C_{1-6}$alkyl-C(O)(heterocycloalkyl), optionally substituted heterocycloalkyl, optionally substituted aryl, and optionally substituted heteroaryl; or R⁵ and R⁶, together with the nitrogen to which they are attached, form a heterocycloalkyl ring optionally substituted with one, two, or three R¹⁰;
each R⁷ is independently selected from H, $C_{1-6}$alkyl, $C_{1-6}$haloalkyl, aminoalkyl, cycloalkyl, —$C_{1-6}$alkyl(heterocycloalkyl), —$C_{1-6}$alkyl-C(O)(heterocycloalkyl), optionally substituted heterocycloalkyl, optionally substituted aryl, and optionally substituted heteroaryl;
each R⁸ and R⁹ is independently selected from H, $C_{1-6}$alkyl, $C_{1-6}$haloalkyl, cycloalkyl, aryl, and heteroaryl;
each R¹⁰ is selected from $C_{1-6}$alkyl, cycloalkyl, $C_{1-6}$haloalkyl, halogen, oxo, —CN, —CO₂R⁸, —C(O)R⁸, —C(O)NR⁸R⁹, —SO₂R⁸, —NR⁹C(O)R⁸, and —NR⁹SO₂R⁸; and
p is 0, 1, 2, 3, 4, or 5;
or a solvate, hydrate, tautomer, N-oxide, stereoisomer, or pharmaceutically acceptable salt thereof.

In some embodiments is a compound of Formula (III), or a solvate, hydrate, tautomer, N-oxide, stereoisomer, or a pharmaceutically acceptable salt thereof, wherein R¹ is H. In some embodiments is a compound of Formula (III), or a solvate, hydrate, tautomer, N-oxide, stereoisomer, or a pharmaceutically acceptable salt thereof, wherein R² is H. In some embodiments is a compound of Formula (III), or a solvate, hydrate, tautomer, N-oxide, stereoisomer, or a pharmaceutically acceptable salt thereof, wherein R¹ and R² are both H. In some embodiments is a compound of Formula (III), or a solvate, hydrate, tautomer, N-oxide, stereoisomer, or a pharmaceutically acceptable salt thereof, wherein R¹ is $C_{1-6}$alkyl. In some embodiments is a compound of Formula (III), or a solvate, hydrate, tautomer, N-oxide, stereoisomer, or a pharmaceutically acceptable salt thereof, wherein R¹ is —CH₃. In some embodiments is a compound of Formula (III), or a solvate, hydrate, tautomer, N-oxide, stereoisomer, or a pharmaceutically acceptable salt thereof, wherein R² is $C_{1-6}$alkyl. In some embodiments is a compound of Formula (III), or a solvate, hydrate, tautomer, N-oxide, stereoisomer, or a pharmaceutically acceptable salt thereof, wherein $R^2$ is —$CH_3$. In some embodiments is a compound of Formula (III), or a solvate, hydrate, tautomer, N-oxide, stereoisomer, or a pharmaceutically acceptable salt thereof, wherein $R^1$ and $R^2$ are both $C_{1-6}$alkyl. In some embodiments is a compound of Formula (III), or a solvate, hydrate, tautomer, N-oxide, stereoisomer, or a pharmaceutically acceptable salt thereof, wherein $R^1$ and $R^2$ are both —$CH_3$.

In another embodiment is a compound of Formula (III), or a solvate, hydrate, tautomer, N-oxide, stereoisomer, or a pharmaceutically acceptable salt thereof, wherein p is 0, 1, 2, or 3. In another embodiment is a compound of Formula (III), or a solvate, hydrate, tautomer, N-oxide, stereoisomer, or a pharmaceutically acceptable salt thereof, wherein p is 0. In another embodiment is a compound of Formula (III), or a solvate, hydrate, tautomer, N-oxide, stereoisomer, or a pharmaceutically acceptable salt thereof, wherein p is 1. In another embodiment is a compound of Formula (III), or a solvate, hydrate, tautomer, N-oxide, stereoisomer, or a pharmaceutically acceptable salt thereof, wherein p is 2. In another embodiment is a compound of Formula (III), or a solvate, hydrate, tautomer, N-oxide, stereoisomer, or a pharmaceutically acceptable salt thereof, wherein p is 3. In another embodiment is a compound of Formula (III), or a solvate, hydrate, tautomer, N-oxide, stereoisomer, or a pharmaceutically acceptable salt thereof, wherein p is 4. In another embodiment is a compound of Formula (III), or a solvate, hydrate, tautomer, N-oxide, stereoisomer, or a pharmaceutically acceptable salt thereof, wherein p is 5.

In another embodiment is a compound of Formula (III), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (III), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (III), or a solvate, hydrate, tautomer, N-oxide, stereoisomer, or a pharmaceutically acceptable salt thereof, wherein p is 1 and $R^3$ is halogen. In another embodiment is a compound of Formula (III), or a solvate, hydrate, tautomer, N-oxide, stereoisomer, or a pharmaceutically acceptable salt thereof, wherein p is 1 and $R^3$ is —Cl. In another embodiment is a compound of Formula (III), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (III), or a solvate, hydrate, tautomer, N-oxide, stereoisomer, or a pharmaceutically acceptable salt thereof, wherein p is 1 and $R^3$ is —$CF_3$. In another embodiment is a compound of Formula (III), or a solvate, hydrate, tautomer, N-oxide, stereoisomer, or a pharmaceutically acceptable salt thereof, wherein p is 1 and $R^3$ is —$C_{1-6}$alkyl(heterocycloalkyl).

In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring optionally substituted with one, two, or three $R^{10}$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form an unsubstituted heterocycloalkyl ring. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, $R^5$ and $R^6$, together with the nitrogen to which they are attached, form a heterocycloalkyl ring substituted with two $R^{10}$, and $R^{10}$ is halogen. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, $R^5$ and $R^6$, together with the nitrogen to which they are attached, form a heterocycloalkyl ring substituted with two $R^{10}$, and $R^{10}$ is oxo. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$ selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is $C_{1-6}$alkyl. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is cycloalkyl. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is $C_{1-6}$haloalkyl. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is halogen. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$CO_2R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$CO_2H$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$C(O)R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$C(O)CH_3$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$C(O)NR^8R^9$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$C(O)NH_2$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$SO_2R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$SO_2CH_3$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NR^9C(O)R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^{10}$ is —$NHC(O)CH_3$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^0$ is —$NR^9SO_2R^8$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring substituted with one $R^{10}$, and $R^0$ is —$NHSO_2CH_3$. In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

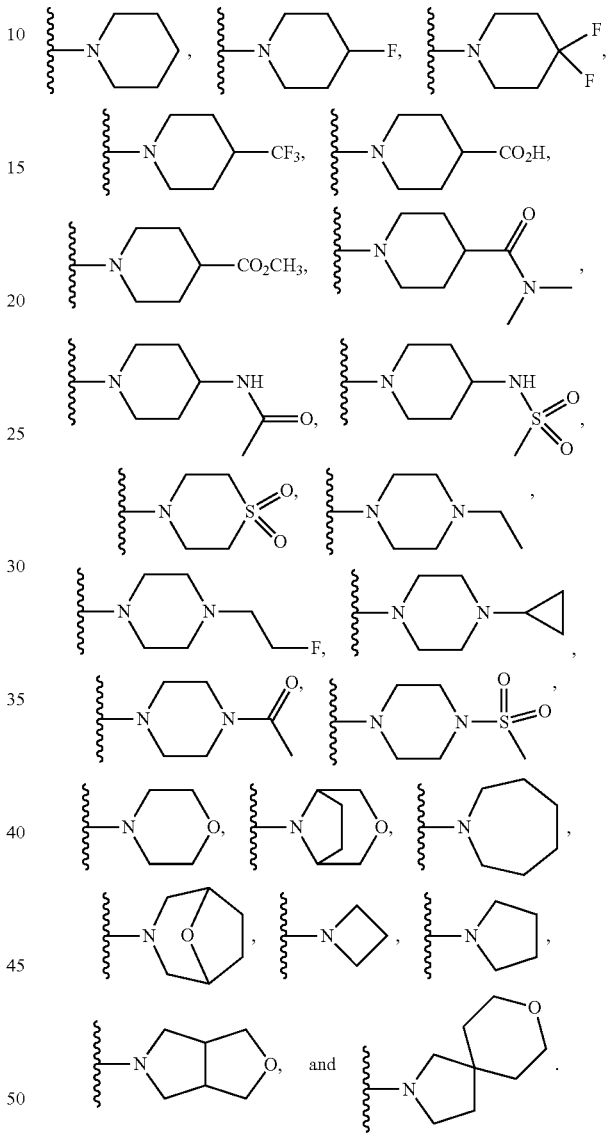

In another embodiment is a compound of Formula (III), or a solvate, hydrate, tautomer, N-oxide, stereoisomer, or a pharmaceutically acceptable salt thereof, wherein p is 1, $R^3$ is —$NR^5R^6$, and $R^5$ and $R^6$, together with the nitrogen to which they are attached, form a heterocycloalkyl ring selected from:

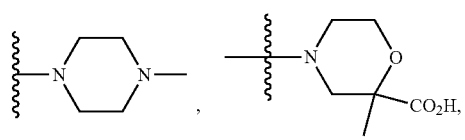

-continued

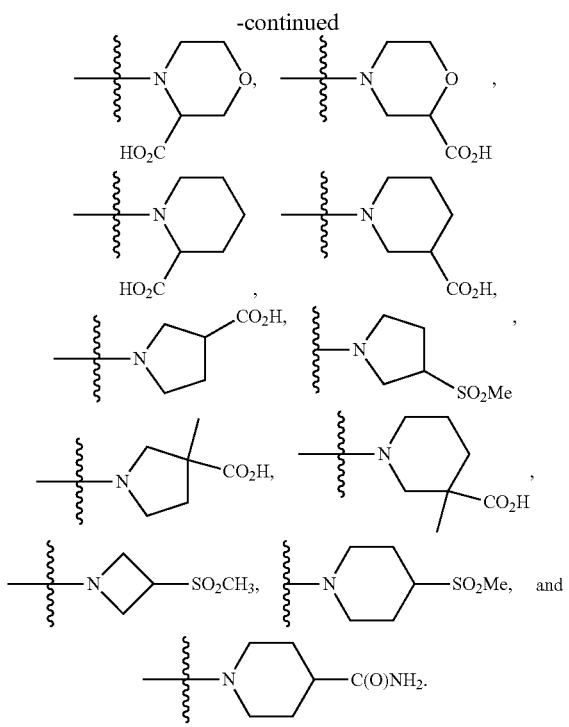

In another embodiment is a compound of Formula (III), or a solvate, hydrate, tautomer, N-oxide, stereoisomer, or a pharmaceutically acceptable salt thereof, wherein p is 1 and $R^3$ is —$OR^7$. In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is independently selected from $C_{1-6}$alkyl, $C_{1-6}$haloalkyl, aminoalkyl, —$C_{1-6}$alkyl(heterocycloalkyl), —$C_{1-6}$alkyl-C(O)(heterocycloalkyl), optionally substituted heterocycloalkyl, and optionally substituted heteroaryl. In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$alkyl. In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is $C_{1-6}$haloalkyl. In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is aminoalkyl. In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl (heterocycloalkyl). In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is —$C_{1-6}$alkyl-C(O)(heterocycloalkyl). In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is optionally substituted heterocycloalkyl. In another embodiment is a compound of Formula (III), or a solvate, hydrate, tautomer, N-oxide, stereoisomer, or a pharmaceutically acceptable salt thereof, wherein p is 1 and $R^3$ is —$OR^7$, and $R^7$ is optionally substituted heteroaryl.

In another embodiment is a compound of Formula (III), or a solvate, hydrate, tautomer, N-oxide, stereoisomer, or a pharmaceutically acceptable salt thereof, wherein p is 1 and $R^3$ is —$CO_2R^8$. In another embodiment is a compound of Formula (III), or a solvate, hydrate, tautomer, N-oxide, stereoisomer, or a pharmaceutically acceptable salt thereof, wherein p is 1 and $R^3$ is —$CO_2H$. In another embodiment is a compound of Formula (III), or a solvate, hydrate, tautomer, N-oxide, stereoisomer, or a pharmaceutically acceptable salt thereof, wherein p is 1 and $R^3$ is —$C(O)NR^8R^9$. In another embodiment is a compound of Formula (III), or a solvate, hydrate, tautomer, N-oxide, stereoisomer, or a pharmaceutically acceptable salt thereof, wherein p is 1 and $R^3$ is —$C(O)NH_2$.

In another embodiment is a compound of Formula (III), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$C_{1-6}$alkyl(heterocycloalkyl), —$NR^5R^6$, —$OR^7$, —$CO_2R^8$, and —$C(O)NR^8R^9$. In another embodiment is a compound of Formula (III), or a solvate, hydrate, tautomer, N-oxide, stereoisomer, or a pharmaceutically acceptable salt thereof, wherein p is 2, one $R^3$ is halogen, and one $R^3$ is —$OR^7$. In another embodiment is a compound of Formula (III), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is $C_{1-6}$alkyl. In another embodiment is a compound of Formula (III), or a solvate, hydrate, tautomer, N-oxide, stereoisomer, or a pharmaceutically acceptable salt thereof, wherein p is 2, one $R^3$ is —Cl, one $R^3$ is —$OR^7$, and $R^7$ is —$C_{1-6}$alkyl(heterocycloalkyl). In another embodiment is a compound of Formula (III), or a solvate, hydrate, tautomer, N-oxide, stereoisomer, or a pharmaceutically acceptable salt thereof, wherein p is 2, one $R^3$ is halogen, and one $R^3$ is —$NR^5R^6$. In another embodiment is a compound of Formula (III), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form an unsubstituted heterocycloalkyl ring. In another embodiment is a compound of Formula (III), or a solvate, hydrate, tautomer, N-oxide, stereoisomer, or a pharmaceutically acceptable salt thereof, wherein p is 2, one $R^3$ is halogen, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —$NR^9SO_2R^8$. In another embodiment is a compound of Formula (III), or a solvate, hydrate, tautomer, N-oxide, stereoisomer, or a pharmaceutically acceptable salt thereof, wherein p is 2, one $R^3$ is —Cl, and one $R^3$ is —$NR^5R^6$. In another embodiment is a compound of Formula (III), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form an unsubstituted heterocycloalkyl ring. In another embodiment is a compound of Formula (III), or a solvate, hydrate, tautomer, N-oxide, stereoisomer, or a pharmaceutically acceptable salt thereof, wherein p is 2, one $R^3$ is —Cl, one $R^3$ is —$NR^5R^6$, and $R^5$ and $R^6$, together with the nitrogen to which they are attached, form a heterocycloalkyl ring substituted with one or two $R^{10}$ independently selected from $C_{1-6}$alkyl, cycloalkyl, $C_{1-6}$haloalkyl, halogen, —$CO_2R^8$, —$C(O)R^8$, —$C(O)NR^8R^9$, —$SO_2R^8$, —$NR^9C(O)R^8$, and —NR⁹SO₂R⁸. In another embodiment is a compound of Formula (III), or a solvate, hydrate, tautomer, N-oxide, stereoisomer, or a pharmaceutically acceptable salt thereof, wherein p is 2, one R³ is C₁₋₆haloalkyl, and one R³ is —NR⁵R⁶. In another embodiment is a compound of Formula (III), or a solvate, hydrate, tautomer, N-oxide, stereoisomer, or a pharmaceutically acceptable salt thereof, wherein p is 2, one R³ is C₁₋₆haloalkyl, one R³ is —NR⁵R⁶, and R⁵ and R⁶, together with the nitrogen to which they are attached, form an unsubstituted heterocycloalkyl ring. In another embodiment is a compound of Formula (III), or a solvate, hydrate, tautomer, N-oxide, stereoisomer, or a pharmaceutically acceptable salt thereof, wherein p is 2, one R³ is C₁₋₆haloalkyl, one R³ is —NR⁵R⁶, and R⁵ and R⁶, together with the nitrogen to which they are attached, form a heterocycloalkyl ring substituted with one or two R¹⁰ independently selected from C₁₋₆alkyl, cycloalkyl, C₁₋₆haloalkyl, halogen, —CO₂R⁸, —C(O)R⁸, —C(O)NR⁸R⁹, —SO₂R⁸, —NR⁹C(O)R⁸, and —NR⁹SO₂R⁸. In another embodiment is a compound of Formula (III), or a solvate, hydrate, tautomer, N-oxide, stereoisomer, or a pharmaceutically acceptable salt thereof, wherein p is 2, one R³ is —CF₃, and one R³ is —NR⁵R⁶. In another embodiment is a compound of Formula (III), or a solvate, hydrate, tautomer, N-oxide, stereoisomer, or a pharmaceutically acceptable salt thereof, wherein p is 2, one R³ is —CF₃, one R³ is —NR⁵R⁶, and R⁵ and R⁶, together with the nitrogen to which they are attached, form an unsubstituted heterocycloalkyl ring. In another embodiment is a compound of Formula (III), or a solvate, hydrate, tautomer, N-oxide, stereoisomer, or a pharmaceutically acceptable salt thereof, wherein p is 2, one R³ is —CF₃, one R³ is —NR⁵R⁶, and R⁵ and R⁶, together with the nitrogen to which they are attached, form a heterocycloalkyl ring substituted with one or two R¹⁰ independently selected from C₁₋₆alkyl, cycloalkyl, C₁₋₆haloalkyl, halogen, —CO₂R⁸, —C(O)R⁸, —C(O)NR⁸R⁹, —SO₂R⁸, —NR⁹C(O)R⁸, and —NR⁹SO₂R⁸.

In another embodiment is a compound of Formula (III), or a solvate, hydrate, tautomer, N-oxide, stereoisomer, or a pharmaceutically acceptable salt thereof, wherein p is 2, one R³ is C₁₋₆alkyl, halogen, C₁₋₆haloalkyl, —C₁₋₆alkyl(heterocycloalkyl), —OR⁷, —CO₂R⁸, or —C(O)NR⁸R⁹, and one R³ is —NR⁵R⁶, wherein R⁵ and R⁶, together with the nitrogen to which they are attached, form a heterocycloalkyl ring selected from:

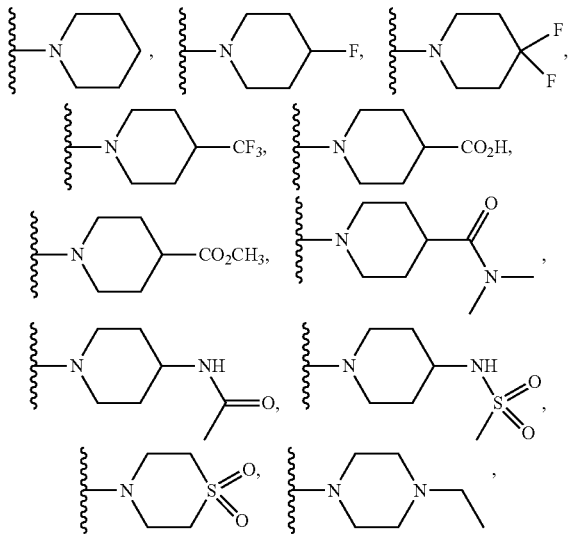

-continued

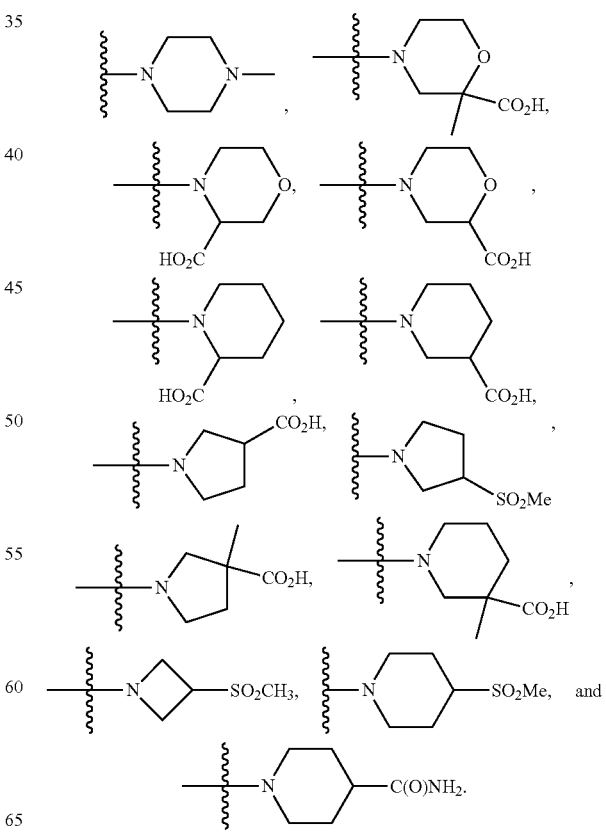

In another embodiment is a compound of Formula (III), or a solvate, hydrate, tautomer, N-oxide, stereoisomer, or a pharmaceutically acceptable salt thereof, wherein p is 2, one R³ is C₁₋₆alkyl, halogen, C₁₋₆haloalkyl, —C₁₋₆alkyl(heterocycloalkyl), —OR⁷, —CO₂R⁸, or —C(O)NR⁸R⁹, and one R³ is —NR⁵R⁶, wherein R⁵ and R⁶, together with the nitrogen to which they are attached, form a heterocycloalkyl ring selected from:

In another embodiment is a compound of Formula (III), or a solvate, hydrate, tautomer, N-oxide, stereoisomer, or a pharmaceutically acceptable salt thereof, wherein two adjacent $R^3$ form a heterocycloalkyl ring optionally substituted with one, two, or three $R^4$. In another embodiment is a compound of Formula (III), or a solvate, hydrate, tautomer, N-oxide, stereoisomer, or a pharmaceutically acceptable salt thereof, wherein two adjacent $R^3$ form an unsubstituted heterocycloalkyl ring. In another embodiment is a compound of Formula (III), or a solvate, hydrate, tautomer, N-oxide, stereoisomer, or a pharmaceutically acceptable salt thereof, wherein two adjacent $R^3$ form a heterocycloalkyl ring substituted with one, two, or three $R^4$. In another embodiment is a compound of Formula (III), or a solvate, hydrate, tautomer, N-oxide, stereoisomer, or a pharmaceutically acceptable salt thereof, wherein two adjacent $R^3$ form a heterocycloalkyl ring substituted with one or two $R^4$. In another embodiment is a compound of Formula (III), or a solvate, hydrate, tautomer, N-oxide, stereoisomer, or a pharmaceutically acceptable salt thereof, wherein two adjacent $R^3$ form a heterocycloalkyl ring substituted with one or two $R^4$ independently selected from $C_{1-6}$alkyl, cycloalkyl, —C(O)$R^8$, and —SO$_2R^8$. In another embodiment is a compound of Formula (III), or a solvate, hydrate, tautomer, N-oxide, stereoisomer, or a pharmaceutically acceptable salt thereof, wherein two adjacent $R^3$ form a heterocycloalkyl ring selected from:

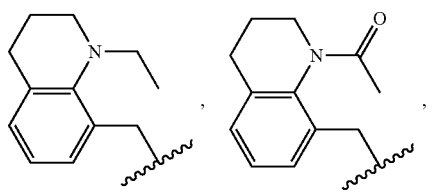

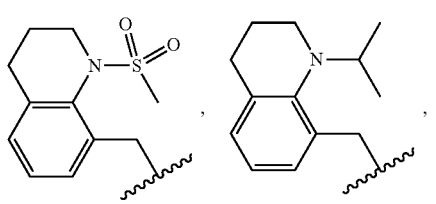

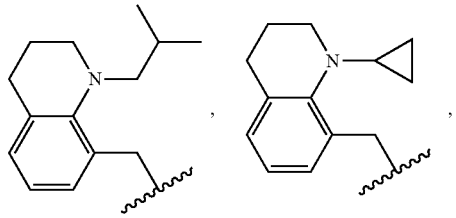

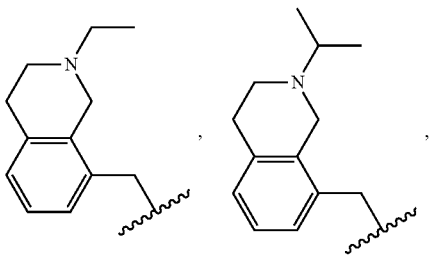

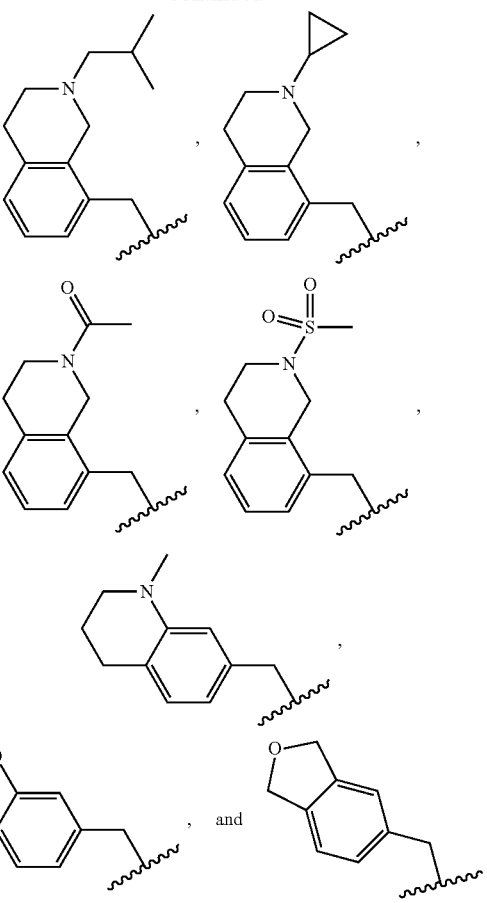

Further embodiments provided herein include combinations of one or more of the particular embodiments set forth above.

In some embodiments, the compound disclosed herein has the structure provided in Examples 1-281.

In another embodiment is a compound having the structure:

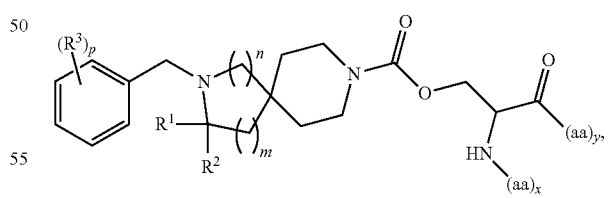

wherein $R^1$, $R^2$, $R^3$, m, n, and p are defined as in Formula (I) described herein, and x and y are at least one amino acid (aa).

In another embodiment is a compound having the structure:

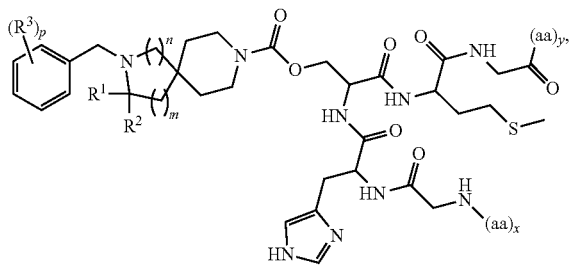

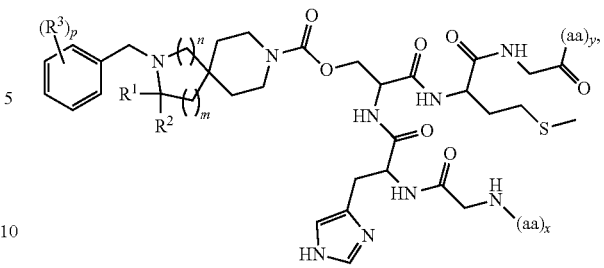

wherein R¹, R², R³, m, n, and p are defined as in Formula (I) described herein, and x and y are at least one amino acid (aa).

Described herein are inhibitors of monoacylglycerol lipase (MAGL) having the structure of Formula (I). In one embodiment, the inhibitors of MAGL are covalent inhibitors of MAGL, that is, the compounds of Formula (I) react with a serine residue of MAGL to form a modified serine residue, comprising the staying group of Formula (I); in such an embodiment, the leaving group of Formula (I) is removed from the compound of Formula (I). In a further embodiment, the covalent inhibitors of MAGL react irreversibly with a serine residue of MAGL to form the modified serine residue.

The staying group portion of the compounds of Formula (I) is:

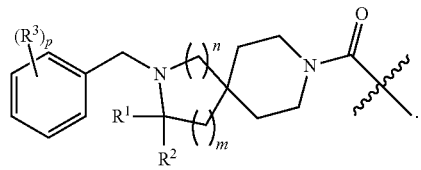

The leaving group portion of the compounds of Formula (I) is:

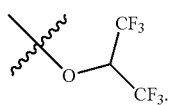

In another embodiment is a compound having the structure:

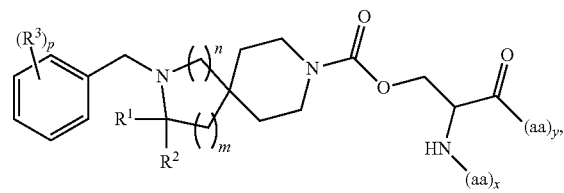

wherein R¹, R², R³, m, n, and p are defined as in Formula (I) described herein, and x and y are at least one amino acid (aa).

In another embodiment is a compound having the structure:

wherein R¹, R², R³, m, n, and p are defined as in Formula (Ia) described herein, and x and y are at least one amino acid (aa).

Described herein are inhibitors of monoacylglycerol lipase (MAGL) having the structure of Formula (Ia). In one embodiment, the inhibitors of MAGL are covalent inhibitors of MAGL, that is, the compounds of Formula (Ia) react with a serine residue of MAGL to form a modified serine residue, comprising the staying group of Formula (Ia); in such an embodiment, the leaving group of Formula (Ia) is removed from the compound of Formula (Ia). In a further embodiment, the covalent inhibitors of MAGL react irreversibly with a serine residue of MAGL to form the modified serine residue.

The staying group portion of the compounds of Formula (Ia) is:

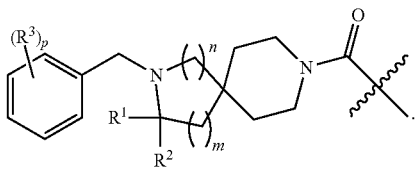

The leaving group portion of the compounds of Formula (Ia) is:

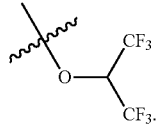

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the spirocycle compounds described herein is P. H. Stahl & C. G. Wermuth "Handbook of Pharmaceutical Salts", Verlag Helvetica Chimica Acta, Zurich, 2002.

The compounds of Formula (I), (Ia), (II), or (III) described herein are prepared by the general synthetic routes described below in Schemes 1-3.

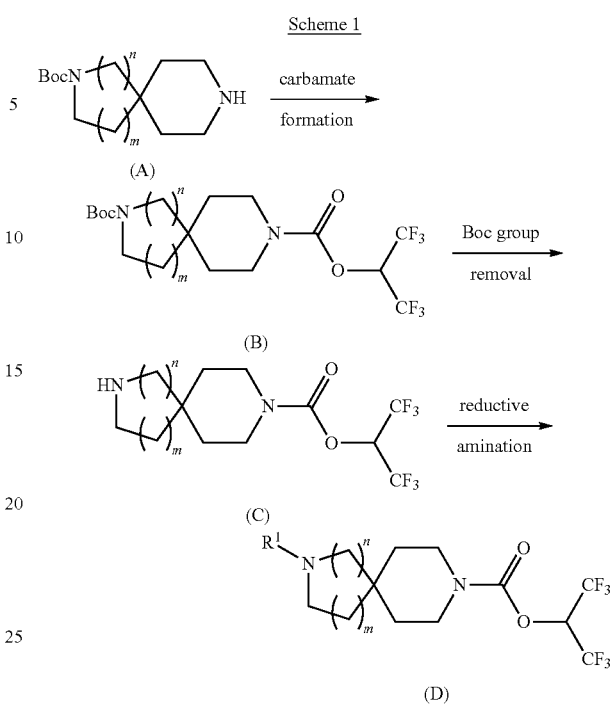

A method for preparing compounds of formula D is provided in Scheme 1. Reaction of spirocyclic amine A with appropriate reagents, such as triphosgene and HFIP, provides intermediate carbamate B. Removal of the Boc group with an acid such as trifluoroacetic acid or HCl leads to amine intermediate C. Reductive amination affords a spirocycle compound D. In some embodiments, $R^1$ of compound D contains a protecting group. In further embodiments, the protecting group is removed and additional functionalization of the compound is performed (e.g., N-alkylation, O-alkylation, acylation, or sulfonylation) to provide another spirocycle compound of formula D. In some embodiments, N-alkylation of intermediate C using the appropriate electrophile provides a spirocycle compound of formula D. In some embodiments, acylation of intermediate C followed by amide reduction, using a reagent such as borane, provides a spirocycle compound of formula D.

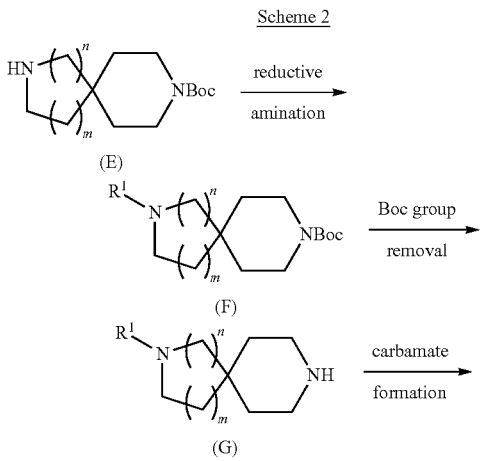

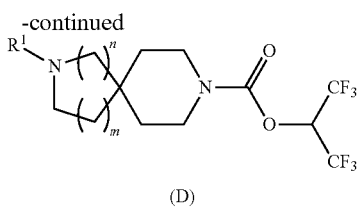

(D)

Another method for preparing compounds of formula D is provided in Scheme 2. Reduction amination of spirocyclic amine E provides intermediate compound F. Removal of the Boc group with an acid, such as trifluoroacetic acid or HCl, affords intermediate G. Subsequent coupling with a reagent such as hexafluoropropan-2-yl chloroformate affords a spirocycle compound of formula D. In some embodiments, N-alkylation of spirocyclic amine E using the appropriate electrophile provides intermediate F.

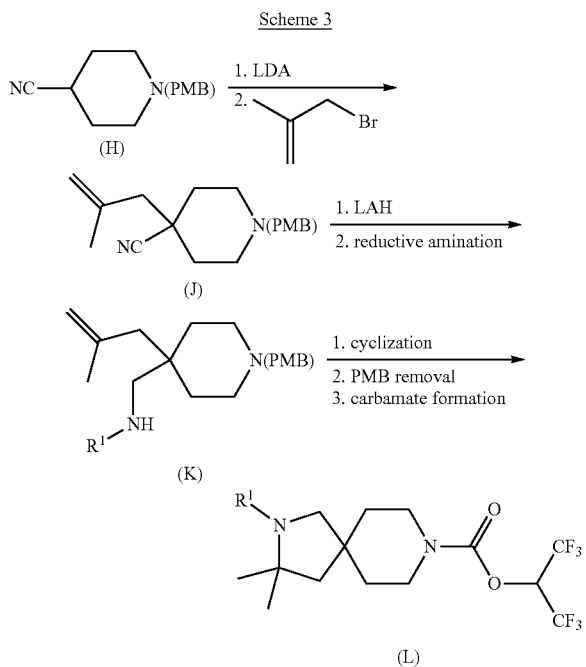

A method of preparing compounds of formula L is provided in Scheme 3. Starting material H is alkylated under strongly basic conditions to form intermediate J. Reduction of the nitrile to the amine followed by reductive amination affords intermediate K. Cyclization to the spirocycle using appropriate reagents, such as a Pt(II) catalyst, followed by PMB group removal, and carbamate formation provides a spirocycle compound of formula L.

Further Forms of Compounds

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, the compounds described herein are prepared as optically pure enantiomers by chiral chromatographic resolution of the racemic mixture. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, solvate, hydrates or derivatives thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. The disclosure described herein provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the spirocycle compound as described herein is administered as a pure chemical. In other embodiments, the spirocycle compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one spirocycle compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (Ia), or a pharmaceutically acceptable salt thereof.

One embodiment provides a pharmaceutical composition comprising a pharmaceutically acceptable carrier and a compound of Formula (II), or a pharmaceutically acceptable salt thereof.

One embodiment provides a pharmaceutical composition comprising a pharmaceutically acceptable carrier and a compound of Formula (III), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof. Another embodiment provides a pharmaceutical composition consisting essentially of a pharmaceutically acceptable carrier and a compound of Formula (Ia), or a pharmaceutically acceptable salt thereof. Another embodiment provides a pharmaceutical composition consisting essentially of a pharmaceutically acceptable carrier and a compound of Formula (II), or a pharmaceutically acceptable salt thereof. Another embodiment provides a pharmaceutical composition consisting essentially of a pharmaceutically acceptable carrier and a compound of Formula (III), or a pharmaceutically acceptable salt thereof.

In certain embodiments, the spirocycle compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration.

Methods

Disclosed herein are methods of modulating the activity of MAGL and/or ABHD6. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (II), or (III). The ability of compounds described herein to modulate or inhibit MAGL and/or ABHD6 is evaluated by procedures known in the art and/or described herein. Another aspect of this disclosure provides methods of treating a disease associated with expression or activity of MAGL and/or ABHD6 in a patient. For example, provided herein are compounds that are selective in inhibiting MAGL or ABHD6, or both, as compared to inhibition of other serine hydrolases e.g., FAAH, e.g., 10, 100, 1000 or more fold inhibition of MAGL over FAAH. In other embodiments, disclosed compounds are more selective in inhibition of MAGL as compared to ABHD6.

In some embodiments is a method of treating pain in a patient, comprising administering a therapeutically effective amount of a compound of Formula (I), (Ia), (II), or (III), or a solvate, hydrate, tautomer, N-oxide, stereoisomer, or a pharmaceutically acceptable salt thereof, to a patient in need thereof to treat said pain. In some embodiments is a method of treating pain in a patient, comprising administering a therapeutically effective amount of a compound of Formula (I), (Ia), (II), or (III), or a solvate, hydrate, tautomer, N-oxide, stereoisomer, or a pharmaceutically acceptable salt thereof, to a patient in need thereof to treat said pain, wherein the pain is neuropathic pain.

Also disclosed herein are methods of treating and/or preventing in a patient in need thereof a disorder such as one or more of acute or chronic pain and neuropathy. Disclosed methods include administering a pharmaceutically effective amount of a compound described herein.

In another embodiment is a method of treating a disease or disorder in a patient comprising administering to the patient in need thereof a therapeutically effective amount of a compound of Formula described herein, or a pharmaceutically acceptable salt or solvate thereof, wherein the disease or disorder is selected from the group consisting of epilepsy/seizure disorder, multiple sclerosis, neuromyelitis optica (NMO), Tourette syndrome, Alzheimer's disease, and abdominal pain associated with irritable bowel syndrome. In another embodiment is a method of treating epilepsy/seizure disorder in a patient comprising administering to the patient in need thereof a therapeutically effective amount of a compound of Formula (I), (Ia), (II), or (III) described herein, or a pharmaceutically acceptable salt or solvate thereof. In another embodiment is a method of treating multiple sclerosis in a patient comprising administering to the patient in need thereof a therapeutically effective amount of a compound of Formula (I), (Ia), (II), or (III) described herein, or a pharmaceutically acceptable salt or solvate thereof. In another embodiment is a method of treating neuromyelitis optica (NMO) in a patient comprising administering to the patient in need thereof a therapeutically effective amount of a compound of Formula (I), (Ia), (II), or (III) described herein, or a pharmaceutically acceptable salt or solvate thereof. In another embodiment is a method of treating Tourette syndrome in a patient comprising administering to the patient in need thereof a therapeutically effective amount of a compound of Formula (I), (Ia), (II), or (III) described herein, or a pharmaceutically acceptable salt or solvate thereof. In another embodiment is a method of treating Alzheimer's disease in a patient comprising administering to the patient in need thereof a therapeutically effective amount of a compound of Formula (I), (Ia), (II), or (III) described herein, or a pharmaceutically acceptable salt or solvate thereof. In another embodiment is a method of treating abdominal pain associated with irritable bowel syndrome in a patient comprising administering to the patient in need thereof a therapeutically effective amount of a compound of Formula (I), (Ia), (II), or (III) described herein, or a pharmaceutically acceptable salt or solvate thereof.

In another embodiment is a method of treating acute pain, inflammatory pain, cancer pain, pain caused by peripheral neuropathy, central pain, fibromyalgia, migraine, vasoocclusive painful crises in sickle cell disease, spasticity or pain associated with multiple sclerosis, functional chest pain, rheumatoid arthritis, osteoarthritis, or functional dyspepsia in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating acute pain in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating inflammatory pain in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating central pain in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating migraine in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating spasticity or pain associated with multiple sclerosis in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), (II), or (III) described herein, or a pharmaceutically acceptable salt or solvate thereof.

In some embodiments, disclosed herein is a method of treating Persistent Motor Tic Disorder in a patient in need thereof, comprising administering to the patient a therapeutically effective amount of a compound of Formula (I), (Ia), (II), or (III) described herein, or a pharmaceutically acceptable salt or solvate thereof. In some embodiments, disclosed herein is a method of treating Persistent Vocal Tic Disorder in a patient in need thereof, comprising administering to the patient a therapeutically effective amount of a compound of Formula (I), (Ia), (II), or (III) described herein, or a pharmaceutically acceptable salt or solvate thereof.

In some embodiments, disclosed herein is a method of treating Persistent Motor Tic Disorder in a patient in need thereof, comprising administering to the patient a therapeutically effective amount of a compound of Formula (I), (Ia), (II), or (III) described herein, or a pharmaceutically acceptable salt or solvate thereof. In some embodiments, disclosed herein is a method of treating Persistent Vocal Tic Disorder in a patient in need thereof, comprising administering to the patient a therapeutically effective amount of a compound of Formula (I), (Ia), (II), or (III) described herein, or a pharmaceutically acceptable salt or solvate thereof.

In another embodiment is a method of treating attention deficit hyperactivity disorder (ADHD) in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating obsessive-compulsive disorder (OCD) in a patient in need thereof, comprising administering to the patient a therapeutically effective amount of a compound of Formula (I), (Ia), (II), or (III) described herein, or a pharmaceutically acceptable salt or solvate thereof.

In another embodiment is a method of lowering intraocular eye pressure (IOP) in a patient in need thereof, comprising administering to the patient a therapeutically effective amount of a compound of Formula (I), (Ia), (II), or (III) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), (II), or (III) described herein, or a pharmaceutically acceptable salt or solvate thereof.

In another embodiment is a method of treating atopic dermatitis in a patient in need thereof, comprising administering to the patient a therapeutically effective amount of a compound of Formula (I), (Ia), (II), or (III) described herein, or a pharmaceutically acceptable salt or solvate thereof.

In another embodiment is a method of treating pruritis in a patient in need thereof, comprising administering to the patient a therapeutically effective amount of a compound of Formula (I), (Ia), (II), or (III) described herein, or a pharmaceutically acceptable salt or solvate thereof.

In another embodiment is a method of treating Down's syndrome in a patient in need thereof, comprising administering to the patient a therapeutically effective amount of a compound of Formula (I), (Ia), (II), or (III) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), (II), or (III) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), (II), or (III) described herein, or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), (II), or (III).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule) having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the disclosure in any way.

EXAMPLES

List of Abbreviations

As used above, and throughout the description, the following abbreviations, unless otherwise indicated, shall be understood to have the following meanings:
ACN or MeCN acetonitrile
Bn benzyl
BOC or Boc tert-butyl carbamate
CDI 1,1'-carbonyldiimidazole
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HFIP 1,1,1,3,3,3-hexafluoropropan-2-ol
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1: 1,1,1,3,3,3-Hexafluoropropan-2-yl 1-(4-methoxybenzyl)-1,8-diazaspiro[4.5]decane-8-carboxylate

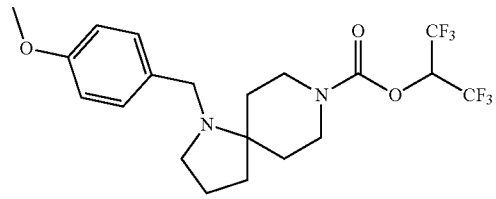 [SMILES: COc1ccc(CN2CCCC23CCN(C(=O)OC(C(F)(F)F)C(F)(F)F)CC3)cc1]

Step 1: Preparation of bis(1,1,1,3,3,3-hexafluoropropan-2-yl) carbonate

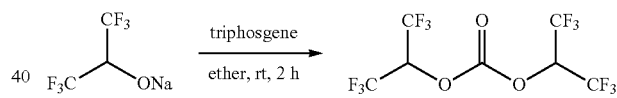

A flask was charged with sodium hydride (60% dispersion, 8.16 g, 204 mmol). Ether (100 mL) was added and the reaction was cooled to 0° C. A solution of 1,1,1,3,3,3-hexafluoro-2-propanol (21 mL, 204 mmol) in 40 mL ether was added via addition funnel over 10 min. The solution became clear by the end of the addition. The reaction was stirred at 0° C. for 20 min and then allowed to warm to rt and stirred for 20 min. The solution was transferred via cannula (~10 mL/min) to a 0 OC solution of triphosgene (10 g, 33.7 mmol) in ether (40 mL) resulting in an exothermic reaction and precipitate formation. The solution was stirred at rt for 2 h. The reaction was filtered and solids were washed with 50 mL ether. The filtrate was carefully concentrated (bath 36° C., 500 Torr) via rotary evaporation and yielded a cloudy solution, which partitioned into a top (organic) and bottom (fluorous) layer. The bottom layer was retained and found to be bis(1,1,1,3,3,3-hexafluoropropan-2-yl) carbonate (8.00 g, 78% by weight solution in ether, 51% yield) solution and stored and used as a solution without further purification. $^1$H NMR (400 MHz, Chloroform-d) δ 5.50 (hept, J=5.7 Hz, 1H). $^{13}$C NMR (101 MHz, CDCl$_3$) δ 151.6, 123.9, 121.0, 118.2, 115.4, 72.5, 72.2, 71.8, 71.5, 71.1.

Step 2: Preparation of 1,1,1,3,3,3-hexafluoropropan-2-yl 1,8-diazaspiro[4.5]decane-8-carboxylate

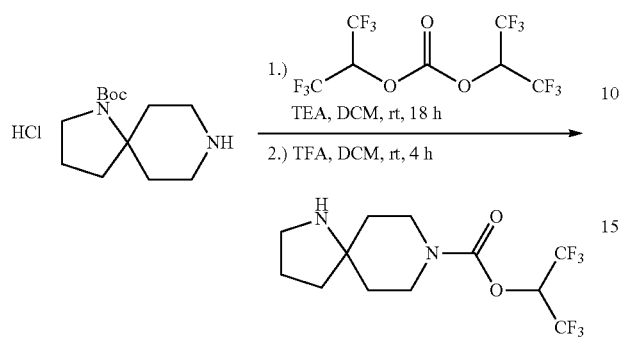

A flask was charged with tert-butyl 1,8-diazaspiro[4.5]decane-1-carboxylate hydrochloride (3000 mg, 10.8 mmol), DCM (20 mL), and TEA (1.88 mL, 13.0 mmol). The flask was cooled to 0° C. and bis(1,1,1,3,3,3-hexafluoropropan-2-yl) carbonate (4.34 mL, 10.84 mmol) was added via syringe. The reaction was stirred at rt for 18 h and concentrated. MeOH (50 mL) was added and the solution was concentrated to yield crude 1-(tert-butyl) 8-(1,1,1,3,3,3-hexafluoropropan-2-yl) 1,8-diazaspiro[4.5]decane-1,8-dicarboxylate as a white solid. The crude material was resuspended in DCM (20 mL). TFA (6 mL) was added and the reaction was stirred at rt for 4 h. The reaction was concentrated and diluted in DCM (100 mL) and 1 N NaOH (100 mL, final pH>10). The aqueous phase was extracted with DCM (2×100 mL). The combined organic layers were dried over anhydrous Na$_2$SO$_4$, filtered, and concentrated to yield 1,1,1,3,3,3-hexafluoropropan-2-yl 1,8-diazaspiro[4.5]decane-8-carboxylate (3000 mg, 8.97 mmol, 82% yield) as an orange oil, which was carried on without further purification. $^1$H NMR (400 MHz, Chloroform-d) δ 5.77 (hept, J=6.2 Hz, 1H), 3.67-3.51 (m, 4H), 3.00 (t, J=6.9 Hz, 2H), 1.83 (p, J=7.2 Hz, 2H), 1.71-1.52 (m, 6H). LCMS (ESI, m/z): 335.1 [M+H]$^+$.

Step 3: Preparation of 1,1,1,3,3,3-hexafluoropropan-2-yl 1-(4-methoxybenzyl)-1,8-diazaspiro[4.5]decane-8-carboxylate

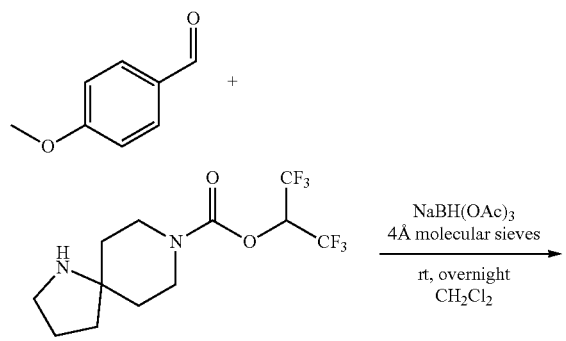

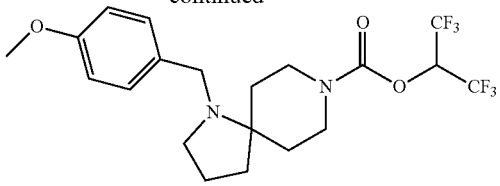

A vial was charged with 1,1,1,3,3,3-hexafluoropropan-2-yl 1,8-diazaspiro[4.5]decane-8-carboxylate (13 mg, 0.040 mmol) and DCM (2 mL). 4-Methoxybenzaldehyde (5.3 mg, 0.040 mmol) and molecular sieves (100 mg) were added and the reaction was stirred at rt for 30 min. NaBH(OAc)$_3$ (16 mg, 0.080 mmol) was added and the reaction was stirred at rt for 18 h. The reaction was poured into brine (20 mL) and extracted DCM (3×40 mL). The combined organic layers were dried over anhydrous Na$_2$SO$_4$, filtered, and concentrated. The resulting oil was purified on a silica column (0 to 30% EtOAc in hexane) to yield 1,1,1,3,3,3-hexafluoropropan-2-yl 1-(4-methoxybenzyl)-1,8-diazaspiro[4.5]decane-8-carboxylate (18 mg, 0.039 mmol, 99% yield) as a yellow oil. $^1$H NMR (400 MHz, Chloroform-d) δ 7.14 (d, J=8.5 Hz, 2H), 6.80-6.73 (m, 2H), 5.69 (hept, J=6.3 Hz, 1H), 4.20-4.07 (m, 2H), 3.72 (s, 3H), 3.44 (d, J=2.1 Hz, 2H), 2.91 (dtd, J=22.4, 13.3, 2.5 Hz, 2H), 2.59 (t, J=6.0 Hz, 2H), 1.80-1.58 (m, 6H), 1.45-1.36 (m, 2H). LCMS (ESI, m/z): 455.2 [M+H]$^+$.

Example 2: 1,1,1,3,3,3-Hexafluoropropan-2-yl 1-(3-methoxybenzyl)-1,8-diazaspiro[4.5]decane-8-carboxylate

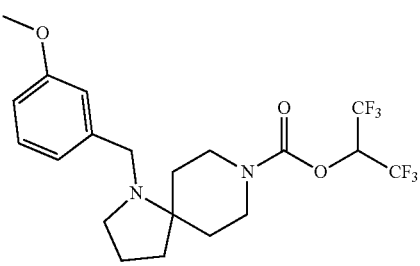 [SMILES: COc1cccc(CN2CCCC23CCN(C(=O)OC(C(F)(F)F)C(F)(F)F)CC3)c1]

The title compound was synthesized directly from commercially available 3-methoxybenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(3-methoxybenzyl)-1,8-diazaspiro[4.5]decane-8-carboxylate as a white solid. $^1$H NMR (400 MHz, Chloroform-d) δ 7.24 (td, J=8.1, 1.5 Hz, 1H), 6.96-6.89 (m, 2H), 6.83-6.76 (m, 1H), 5.80 (hept, J=6.3 Hz, 1H), 4.30-4.16 (m, 2H), 3.83 (d, J=1.5 Hz, 3H), 3.59 (s, 2H), 3.00 (dt, J=23.8, 12.9 Hz, 2H), 2.78-2.67 (m, 2H), 1.90-1.67 (m, 6H), 1.58-1.45 (m, 2H). LCMS (ESI, m/z): 455.1 [M+H]$^+$.

Example 3: 1,1,1,3,3,3-Hexafluoropropan-2-yl 1-(2-methoxybenzyl)-1,8-diazaspiro[4.5]decane-8-carboxylate

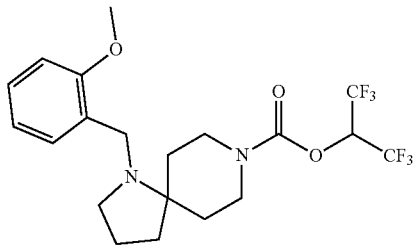 [SMILES: COc1ccccc1CN1CCCC12CCN(C(=O)OC(C(F)(F)F)C(F)(F)F)CC2]

The title compound was synthesized directly from commercially available 2-methoxybenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(2-methoxybenzyl)-1,8-diazaspiro[4.5]decane-8-carboxylate as a white solid. $^1$H NMR (400 MHz, Chloroform-d) δ 7.40-7.33 (m, 1H), 7.24 (td, J=8.1, 1.6 Hz, 1H), 6.95 (t, J=7.4 Hz, 1H), 6.88 (d, J=8.2 Hz, 1H), 5.81 (hept, J=6.2 Hz, 1H), 4.31-4.15 (m, 2H), 3.85 (s, 3H), 3.64 (s, 2H), 3.00 (dtd, J=21.4, 13.3, 2.6 Hz, 2H), 2.84-2.74 (m, 2H), 1.92-1.74 (m, 6H), 1.55-1.45 (m, 2H). LCMS (ESI, m/z): 455.1 [M+H]$^+$.

Example 4: 1,1,1,3,3,3-Hexafluoropropan-2-yl 1-(4-ethoxybenzyl)-1,8-diazaspiro[4.5]decane-8-carboxylate

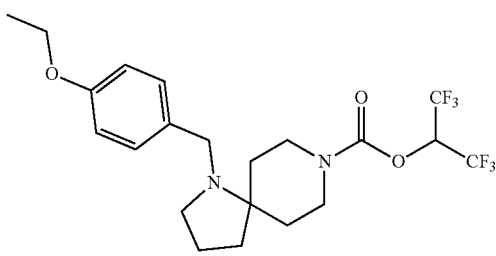 [SMILES: CCOc1ccc(CN2CCCC23CCN(C(=O)OC(C(F)(F)F)C(F)(F)F)CC3)cc1]

The title compound was synthesized directly from commercially available 4-ethoxybenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(4-ethoxybenzyl)-1,8-diazaspiro[4.5]decane-8-carboxylate as a white solid. $^1$H NMR (400 MHz, Chloroform-d) δ 7.22 (d, J=8.5 Hz, 2H), 6.85 (d, J=8.6 Hz, 2H), 5.79 (hept, J=6.3 Hz, 1H), 4.30-4.16 (m, 2H), 4.04 (q, J=7.0 Hz, 2H), 3.59-3.46 (m, 2H), 3.08-2.91 (m, 2H), 2.72-2.64 (m, 2H), 1.79 (ddt, J=22.8, 13.5, 8.2 Hz, 6H), 1.50 (td, J=8.3, 7.8, 3.9 Hz, 2H), 1.43 (t, J=7.0 Hz, 3H). LCMS (ESI, m/z): 469.1 [M+H]$^+$.

Example 5: 1,1,1,3,3,3-Hexafluoropropan-2-yl 1-(3-ethoxybenzyl)-1,8-diazaspiro[4.5]decane-8-carboxylate

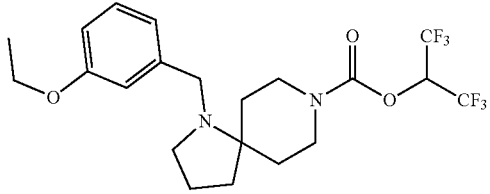 [SMILES: CCOc1cccc(CN2CCCC23CCN(C(=O)OC(C(F)(F)F)C(F)(F)F)CC3)c1]

The title compound was synthesized directly from commercially available 3-ethoxybenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(3-ethoxybenzyl)-1,8-diazaspiro[4.5]decane-8-carboxylate as a white solid. H NMR (400 MHz, Chloroform-d) δ 7.22 (t, J=7.8 Hz, 1H), 6.90 (d, J=7.4 Hz, 2H), 6.81-6.74 (m, 1H), 5.79 (hept, J=6.2 Hz, 1H), 4.30-4.16 (m, 2H), 4.05 (q, J=7.0 Hz, 2H), 3.64-3.51 (m, 2H), 3.00 (dtd, J=22.5, 13.3, 2.5 Hz, 2H), 2.78-2.67 (m, 2H), 1.90-1.66 (m, 6H), 1.55-1.39 (m, 5H). LCMS (ESI, m/z): 469.2 [M+H]$^+$.

Example 6: 1,1,1,3,3,3-Hexafluoropropan-2-yl 1-(2-ethoxybenzyl)-1,8-diazaspiro[4.5]decane-8-carboxylate The title compound was synthesized directly from commercially available 2-ethoxybenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(2-ethoxybenzyl)-1,8-diazaspiro[4.5]decane-8-carboxylate as a white solid. $^1$H NMR (400 MHz, Chloroform-d) δ 7.35-7.29 (m, 1H), 7.25-7.17 (m, 1H), 6.99-6.88 (m, 1H), 6.86 (d, J=8.2 Hz, 1H), 5.81 (hept, J=6.2 Hz, 1H), 4.30-4.17 (m, 2H), 4.12-4.01 (m, 2H), 3.63 (q, J=13.4 Hz, 2H), 3.00 (dtd, J=20.7, 13.3, 2.5 Hz, 2H), 2.86-2.74 (m, 2H), 1.93-1.78 (m, 6H), 1.56-1.40 (m, 5H). LCMS (ESI, m/z): 469.2 [M+H]$^+$.

Example 7: 1,1,1,3,3,3-Hexafluoropropan-2-yl 1-(2-chloro-3-methoxybenzyl)-1,8-diazaspiro[4.5]decane-8-carboxylate

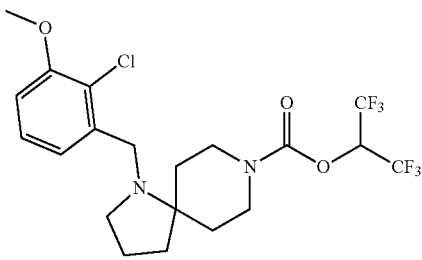 [SMILES: COc1cccc(CN2CCCC23CCN(C(=O)OC(C(F)(F)F)C(F)(F)F)CC3)c1Cl]

The title compound was synthesized directly from commercially available 2-chloro-3-methoxybenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(2-chloro-3-methoxybenzyl)-1,8-diazaspiro[4.5]decane-8-carboxylate as a white solid. $^1$H NMR (400 MHz, Chloroform-d) δ 7.20 (t, J=7.9 Hz, 1H), 7.10 (d, J=7.5 Hz, 1H), 6.85 (d, J=7.9 Hz, 1H), 5.79 (hept, J=6.3 Hz, 1H), 4.30-4.17 (m, 2H), 3.91 (s, 3H), 3.74 (s, 2H), 3.09-2.91 (m, 2H), 2.76 (t, J=6.1 Hz, 2H), 1.80 (dd, J=20.8, 4.9 Hz, 6H), 1.57-1.47 (m, 2H). LCMS (ESI, m/z): 489.1 [M+H]$^+$.

Example 8: 1,1,1,3,3,3-Hexafluoropropan-2-yl 1-(5-fluoro-2-methoxybenzyl)-1,8-diazaspiro[4.5]decane-8-carboxylate

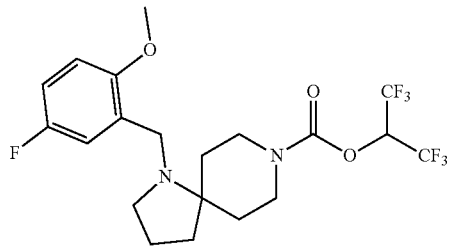 [SMILES: COc1ccc(F)cc1CN1CCCC12CCN(C(=O)OC(C(F)(F)F)C(F)(F)F)CC2]

The title compound was synthesized directly from commercially available 2-methoxy-5-fluorobenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(2-methoxy-5-fluorobenzyl)-1,8-diazaspiro[4.5]decane-8-carboxylate as a white solid. $^1$H NMR (400 MHz, Chloroform-d) δ 7.06 (dd, J=9.3, 2.6 Hz, 1H), 6.79 (td, J=8.5, 3.1 Hz, 1H), 6.68 (dd, J=8.9, 4.4 Hz, 1H), 5.69 (hept, J=6.3 Hz, 1H), 4.19-4.06 (m, 2H), 3.72 (s, 3H), 3.51 (s, 2H), 2.90 (dtd, J=22.3, 13.3, 2.5 Hz, 2H), 2.72-2.66 (m, 2H), 1.87-1.57 (m, 6H), 1.45-1.35 (m, 2H). LCMS (ESI, m/z): 473.1 [M+H]$^+$.

Example 9: 1,1,1,3,3,3-Hexafluoropropan-2-yl 1-(4-chloro-2-methoxybenzyl)-1,8-diazaspiro[4.5]decane-8-carboxylate

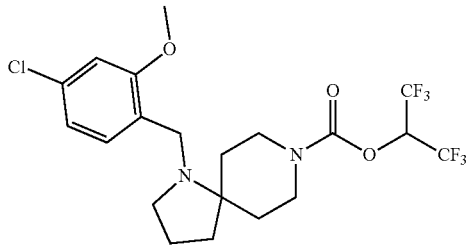 [SMILES: COc1cc(Cl)ccc1CN1CCCC12CCN(C(=O)OC(C(F)(F)F)C(F)(F)F)CC2]

The title compound was synthesized directly from commercially available 2-methoxy-4-chlorobenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(4-chloro-2-methoxybenzyl)-1,8-diazaspiro[4.5]decane-8-carboxylate as a white solid. $^1$H NMR (400 MHz, Chloroform-d) δ 7.28 (d, J=8.0 Hz, 1H), 6.92 (dd, J=8.0, 1.9 Hz, 1H), 6.84 (d, J=1.9 Hz, 1H), 5.79 (hept, J=6.3 Hz, 1H), 4.29-4.16 (m, 2H), 3.83 (s, 3H), 3.57 (s, 2H), 2.99 (dtd, J=22.3, 13.3, 2.5 Hz, 2H), 2.76 (s, 2H), 1.99-1.69 (m, 6H), 1.53-1.43 (m, 2H). LCMS (ESI, m/z): 489.1 [M+H]$^+$.

Example 10: 1,1,1,3,3,3-Hexafluoropropan-2-yl 1-(3-chloro-2-methoxybenzyl)-1,8-diazaspiro[4.5]decane-8-carboxylate

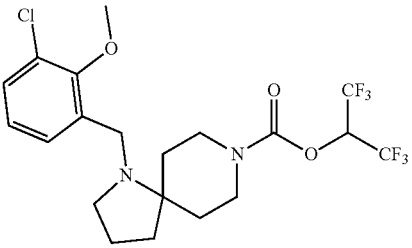 [SMILES: COc1c(Cl)cccc1CN1CCCC12CCN(C(=O)OC(C(F)(F)F)C(F)(F)F)CC2]

The title compound was synthesized directly from commercially available 2-methoxy-3-chlorobenzaldehyde and 1,1,1,3,3,3-hexafluoropropan-2-yl 1,8-diazaspiro[4.5]decane-8-carboxylate according to the representative procedure of Example 1, Steps 1-3 to provide 1,1,1,3,3,3-hexafluoropropan-2-yl 1-(3-chloro-2-methoxybenzyl)-1,8-diazaspiro[4.5]decane-8-carboxylate as a white solid. $^1$H NMR (400 MHz, Chloroform-d) δ 7.34-7.25 (m, 2H), 7.03 (t, J=7.8 Hz, 1H), 5.79 (hept, J=6.2 Hz, 1H), 4.31-4.18 (m, 2H), 3.87 (s, 3H), 3.74-3.59 (m, 2H), 3.09-2.91 (m, 2H), 2.75-2.68 (m, 2H), 1.90-1.73 (m, 6H), 1.56-1.47 (m, 2H). LCMS (ESI, m/z): 489.1 [M+H]$^+$.

Example 11: 1,1,1,3,3,3-Hexafluoropropan-2-yl 1-(3-(2-(piperidin-1-yl)ethoxy)benzyl)-1,8-diazaspiro[4.5]decane-8-carboxylate

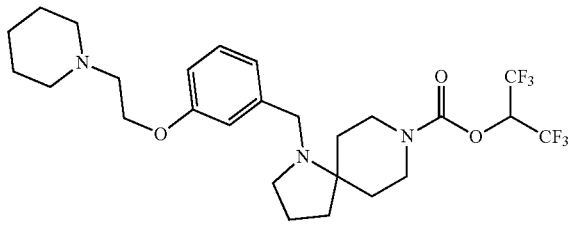 [SMILES: O=C(OC(C(F)(F)F)C(F)(F)F)N1CCC2(CCCN2Cc2cccc(OCCN3CCCCC3)c2)CC1]

The title compound was synthesized directly from commercially available 3-(2-(piperidin-1-yl)ethoxy)benzaldehyde and 1,1,1,3,3,3-hexafluoropropan-2-yl 1,8-diazaspiro[4.5]decane-8-carboxylate according to the representative procedure of Example 1, Steps 1-3. The compound was purified by preparative HPLC to give 1,1,1,3,3,3-hexafluoropropan-2-yl 1-(3-(2-(piperidin-1-yl)ethoxy)benzyl)-1,8-diazaspiro[4.5]decane-8-carboxylate formate salt as a clear oil. $^1$H NMR (400 MHz, Chloroform-d) δ 8.54 (s, 1H), 7.22 (t, J=7.8 Hz, 1H), 6.94 (d, J=7.6 Hz, 1H), 6.88 (s, 1H), 6.77 (d, J=8.2 Hz, 1H), 5.77 (hept, J=6.3 Hz, 1H), 4.31-4.25 (m, 2H), 4.25-4.16 (m, 2H), 3.57 (d, J=3.1 Hz, 2H), 3.22 (t, J=4.9 Hz, 2H), 3.00 (p, J=13.4 Hz, 6H), 2.70 (d, J=6.5 Hz, 2H), 1.78 (dtd, J=46.9, 13.2, 12.6, 5.3 Hz, 10H), 1.58 (d, J=4.3 Hz, 4H). LCMS (ESI, m/z): 552.3 [M+H]$^+$.

Example 12: 1,1,1,3,3,3-Hexafluoropropan-2-yl 1-(3-(2-(pyrrolidin-1-yl)ethoxy)benzyl)-1,8-diazaspiro[4.5]decane-8-carboxylate

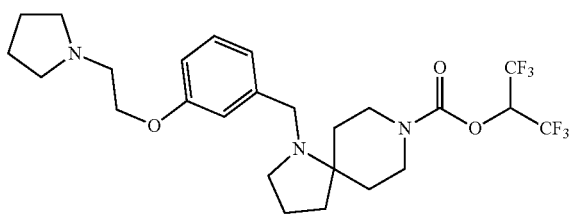 [SMILES: O=C(OC(C(F)(F)F)C(F)(F)F)N1CCC2(CCCN2Cc2cccc(OCCN3CCCC3)c2)CC1]

The title compound was synthesized directly from commercially available 3-(2-(pyrrolidin-1-yl)ethoxy)benzaldehyde and 1,1,1,3,3,3-hexafluoropropan-2-yl 1,8-diazaspiro[4.5]decane-8-carboxylate according to the representative procedure of Example 1, Steps 1-3. The compound was purified by preparative HPLC to give 1,1,1,3,3,3-hexafluoropropan-2-yl 1-(3-(2-(pyrrolidin-1-yl)ethoxy)benzyl)-1,8-diazaspiro[4.5]decane-8-carboxylate formate salt as a clear oil. $^1$H NMR (400 MHz, Chloroform-d) δ 8.44 (br s, 1H), 7.26-7.14 (m, 1H), 7.02-6.85 (m, 2H), 6.81-6.63 (m, 1H), 5.89-5.61 (m, 1H), 4.48-4.06 (m, 4H), 3.61 (s, 2H), 3.51-3.20 (m, 6H), 3.10-2.86 (m, 2H), 2.73 (s, 2H), 2.06 (s, 4H), 1.94-1.67 (m, 6H), 1.63-1.46 (m, 2H). LCMS (ESI, m/z): 538.3 [M+H]$^+$.

Example 13: 1,1,1,3,3,3-Hexafluoropropan-2-yl 1-(3-(2-morpholinoethoxy)benzyl)-1,8-diazaspiro[4.5]decane-8-carboxylate

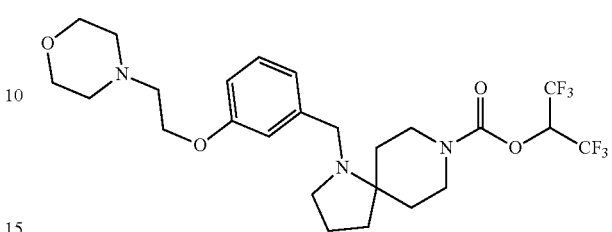

The title compound was synthesized directly from commercially available 3-(2-morpholinoethoxy)benzaldehyde and 1,1,1,3,3,3-hexafluoropropan-2-yl 1,8-diazaspiro[4.5]decane-8-carboxylate according to the representative procedure of Example 1, Steps 1-3. The compound was purified by preparative HPLC to give 1,1,1,3,3,3-hexafluoropropan-2-yl 1-(3-(2-morpholinoethoxy)benzyl)-1,8-di azaspiro[4.5]decane-8-carboxylate formate salt as a clear oil. $^1$H NMR (400 MHz, Chloroform-d) δ 8.5 (m, 1H), 7.23 (t, J=7.8 Hz, 1H), 7.01-6.87 (m, 2H), 6.80 (dd, J=8.2, 2.2 Hz, 1H), 5.77 (hept, J=6.2 Hz, 1H), 4.37-4.05 (m, 4H), 3.91-3.75 (m, 4H), 3.72-3.59 (m, 2H), 3.11-2.90 (m, 4H), 2.88-2.63 (m, 6H), 2.03-1.69 (m, 6H), 1.67-1.47 (m, 2H). LCMS (ESI, m/z): 554.1 [M+H]$^+$.

Example 14: 1,1,1,3,3,3-Hexafluoropropan-2-yl 1-(4-(2-morpholinoethoxy)benzyl)-1,8-diazaspiro[4.5]decane-8-carboxylate

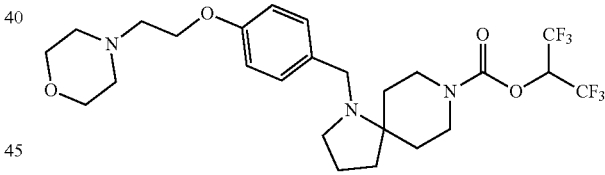

The title compound was synthesized directly from commercially available 4-(2-morpholinoethoxy)benzaldehyde and 1,1,1,3,3,3-hexafluoropropan-2-yl 1,8-diazaspiro[4.5]decane-8-carboxylate according to the representative procedure of Example 1, Steps 1-3. The compound was purified by preparative HPLC to give 1,1,1,3,3,3-hexafluoropropan-2-yl 1-(4-(2-morpholinoethoxy)benzyl)-1,8-di azaspiro[4.5]decane-8-carboxylate formate salt as a clear oil. $^1$H NMR (400 MHz, Chloroform-d) δ 8.45 (s, 1H), 7.33 (d, J=2.0 Hz, 1H), 7.14 (dd, J=8.4, 1.9 Hz, 1H), 6.85 (d, J=8.4 Hz, 1H), 5.76 (hept, J=6.2 Hz, 1H), 4.48-4.33 (m, 2H), 4.30-4.12 (m, 2H), 3.51 (d, J=2.8 Hz, 2H), 3.45-3.37 (m, 2H), 3.21 (br s, 4H), 3.07-2.88 (m, 2H), 2.73-2.59 (m, 2H), 1.96-1.56 (m, 12H), 1.50 (d, J=11.1 Hz, 2H). LCMS (ESI, m/z): 586.2 [M+H]$^+$.

Example 15: 1,1,1,3,3,3-Hexafluoropropan-2-yl 1-(3-chloro-4-(2-(piperidin-1-yl)ethoxy)benzyl)-1,8-diazaspiro[4.5]decane-8-carboxylate

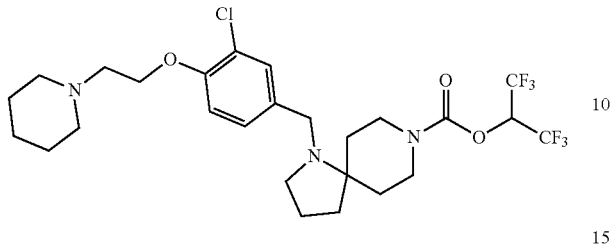

The title compound was synthesized directly from commercially available 3-chloro-4-(2-(piperidin-1-yl)ethoxy)benzaldehyde and 1,1,1,3,3,3-hexafluoropropan-2-yl 1,8-diazaspiro[4.5]decane-8-carboxylate according to the representative procedure of Example 1, Steps 1-3. The compound was purified by preparative HPLC to give 1,1,1,3,3,3-hexafluoropropan-2-yl 1-(3-chloro-4-(2-(piperidin-1-yl)ethoxy)benzyl)-1,8-diazaspiro[4.5]decane-8-carboxylate formate salt as a clear oil. $^1$H NMR (400 MHz, Chloroform-d) δ 8.45 (s, 1H), 7.33 (d, J=2.0 Hz, 1H), 7.14 (dd, J=8.4, 1.9 Hz, 1H), 6.85 (d, J=8.4 Hz, 1H), 5.76 (hept, J=6.2 Hz, 1H), 4.48-4.33 (m, 2H), 4.30-4.12 (m, 2H), 3.51 (d, J=2.8 Hz, 2H), 3.45-3.37 (m, 2H), 3.21 (br s, 4H), 3.07-2.88 (m, 2H), 2.73-2.59 (m, 2H), 1.96-1.56 (m, 12H), 1.50 (d, J=11.1 Hz, 2H). LCMS (ESI, m/z): 586.2 [M+H]$^+$.

Example 16: 1,1,1,3,3,3-Hexafluoropropan-2-yl 1-(2-(4-(dimethylcarbamoyl)piperidin-1-yl)-4-(trifluoromethyl)benzyl)-1,8-diazaspiro[4.5]decane-8-carboxylate

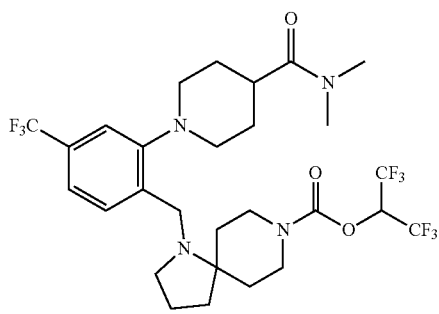 [SMILES: CN(C)C(=O)C1CCN(c2cc(C(F)(F)F)ccc2CN2CCCC23CCN(C(=O)OC(C(F)(F)F)C(F)(F)F)CC3)CC1]

Step 1: Preparation of 1-(2-formyl-5-(trifluoromethyl)phenyl)-N,N-dimethylpiperidine-4-carboxamide

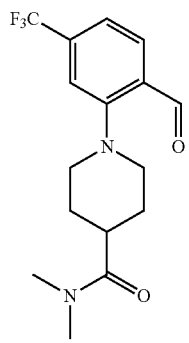

A sealed tube was charged with 2-fluoro-4-(trifluoromethyl)benzaldehyde (520 mg, 2.71 mmol), N,N-dimethylpiperidine-4-carboxamide (507 mg, 73.2 mmol), and potassium carbonate (1.2 g, 8.66 mmol). DMA (4 mL) was added and the mixture was stirred at 140° C. for 20 h. The reaction was cooled to rt, then diluted with EtOAc (200 mL). The organic layer was washed with brine (3×) and with sat. NH$_4$Cl (1×). The organic layer was dried over Na$_2$SO$_4$, filtered and concentrated to yield a solid. The solid was purified by flash column chromatography to afford 1-(2-formyl-5-(trifluoromethyl)phenyl)-N,N-dimethylpiperidine-4-carboxamide as a yellow solid (489 mg, 55% yield). $^1$H NMR (400 MHz, Chloroform-d) δ 10.31 (s, 1H), 7.90 (s, 1H), 7.40-7.32 (m, 2H), 3.47-3.38 (m, 2H), 3.12 (s, 3H), 3.08-2.96 (m, 5H), 2.80-2.66 (m, 1H), 2.19-2.05 (m, 2H), 1.96-1.85 (m, 2H).

Step 2: Preparation of tert-butyl 1-(2-(4-(dimethylcarbamoyl)piperidin-1-yl)-4-(trifluoromethyl)benzyl)-1,8-diazaspiro[4.5]decane-8-carboxylate

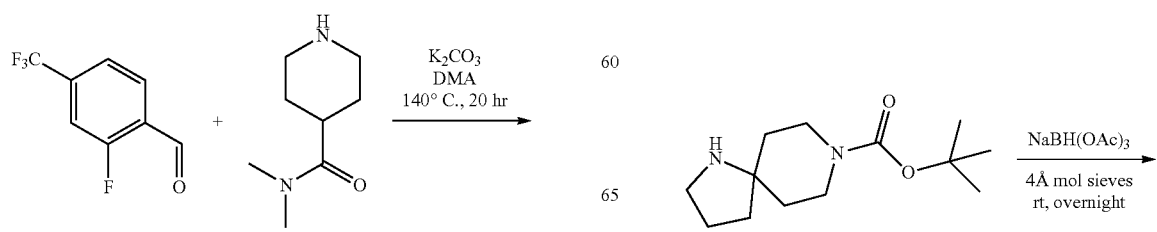

89

-continued

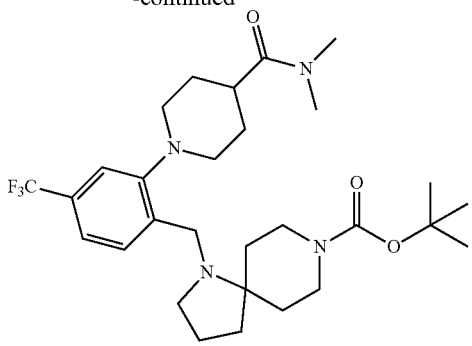

A vial equipped was charged with 1-(2-formyl-5-(trifluoromethyl)phenyl)-N,N-dimethylpiperidine-4-carboxamide (124 mg, 0.379 mmol) and tert-butyl 1,8-diazaspiro[4.5]decane-8-carboxylate (109 mg, 0.455 mmol). DCM (5 mL) was added and the mixture was stirred until dissolved at rt. 4 Å Molecular sieves (100 mg) were added and the vial was purged with $N_2$ and stirred at rt for 2 h. NaBH(OAc)$_3$ (88 mg, 0.417 mmol) was added. The reaction was allowed to stir at rt overnight. The reaction was filtered over Celite and rinsed with MeOH, then concentrated and taken up in EtOAc. The organic layer was washed with saturated NaHCO$_3$ (3×), dried over Na$_2$SO$_4$ and concentrated to yield an oil. The oil was purified by flash column chromatography to afford tert-butyl 1-(2-(4-(dimethylcarbamoyl)piperidin-1-yl)-4-(trifluoromethyl)benzyl)-1,8-diazaspiro[4.5]decane-8-carboxylate (128 mg, 61% yield). $^1$H NMR (400 MHz, Chloroform-d) δ 7.79-7.69 (m, 1H), 7.34-7.24 (m, 2H), 4.23-4.03 (m, 2H), 3.75 (s, 2H), 3.18-3.09 (m, 5H), 2.99 (s, 3H), 2.90-2.55 (m, 7H), 2.10-1.97 (m, 4H), 1.87-1.59 (m, 8H), 1.47 (s, 9H).

Step 3: Preparation of 1,1,1,3,3,3-hexafluoropropan-2-yl 1-(2-(4-(dimethylcarbamoyl)piperidin-1-yl)-4-(trifluoromethyl)benzyl)-1,8-diazaspiro[4.5]decane-8-carboxylate

90

A vial was charged with tert-butyl 1-(2-(4-(dimethylcarbamoyl)piperidin-1-yl)-4-(trifluoromethyl)benzyl)-1,8-diazaspiro[4.5]decane-8-carboxylate (128 mg, 0.232 mmol). DCM (3 mL) was added and the mixture stirred at 0° C. for 10 min. 4 N HCl in dioxane was added dropwise via syringe (0.347 mL, 1.39 mmol). The mixture stirred at rt overnight. MeOH was added and the mixture was concentrated to yield a solid. The solid was dissolved in DCM (3 mL) and DIEA (0.2 mL), and stirred at rt. A separate vial was charged with triphosgene (241 mg, 0.814 mmol). To this vial was added DCM (3 mL). The mixture was then purged with $N_2$ and stirred at rt for 5 min. The vial was cooled to 0° C. and HFIP was added (444 mg, 2.64 mmol), followed by DIEA (525 mg, 4.07 mmol). The mixture was allowed to stir at rt for 45 min. At that time, the contents of the first vial were transferred to the HFIP mixture, dropwise via syringe, and the solution was stirred at rt overnight. The mixture was diluted with DCM, washed with sat. NaHCO$_3$ (3×), dried over Na$_2$SO$_4$, and concentrated to yield a residue. The residue was purified by flash column chromatography and preparative HPLC to afford 1,1,1,3,3,3-hexafluoropropan-2-yl 1-(2-(4-(dimethylcarbamoyl)piperidin-1-yl)-4-(trifluoromethyl)benzyl)-1,8-diazaspiro[4.5]decane-8-carboxylate as a clear oil (61 mg, 20% yield). $^1$H NMR (400 MHz, Chloroform-d) δ 7.73-7.66 (m, 1H), 7.33-7.29 (m, 1H), 7.28-7.24 (m, 1H), 5.84-5.72 (m, 1H), 4.30-4.13 (m, 2H), 3.75-3.63 (m, 2H), 3.21-3.09 (m, 5H), 3.08-2.92 (m, 5H), 2.80-2.59 (m, 5H), 2.11-1.97 (m, 2H), 1.91-1.62 (m, 8H), 1.57-1.46 (m, 2H). LCMS (ESI, m/z): 647.3 [M+H]$^+$.

Example 17: 1,1,1,3,3,3-Hexafluoropropan-2-yl 2-(4-chloro-2-(pyrrolidin-1-yl)benzyl)-2,8-diazaspiro[4.5]decane-8-carboxylate

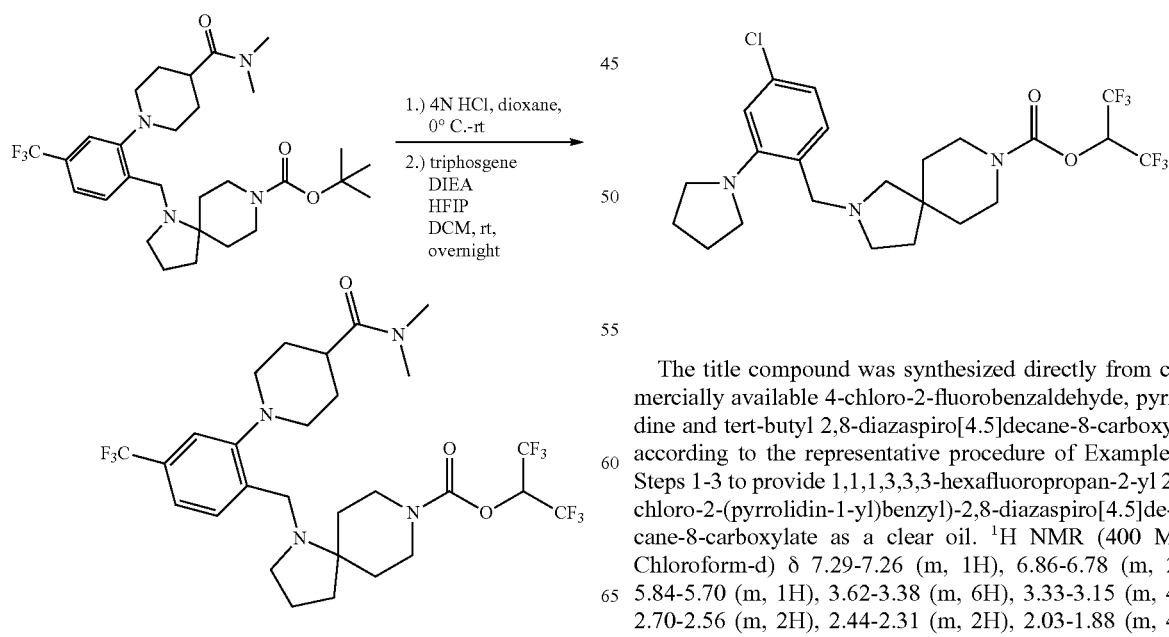

The title compound was synthesized directly from commercially available 4-chloro-2-fluorobenzaldehyde, pyrrolidine and tert-butyl 2,8-diazaspiro[4.5]decane-8-carboxylate according to the representative procedure of Example 16, Steps 1-3 to provide 1,1,1,3,3,3-hexafluoropropan-2-yl 2-(4-chloro-2-(pyrrolidin-1-yl)benzyl)-2,8-diazaspiro[4.5]decane-8-carboxylate as a clear oil. $^1$H NMR (400 MHz, Chloroform-d) δ 7.29-7.26 (m, 1H), 6.86-6.78 (m, 2H), 5.84-5.70 (m, 1H), 3.62-3.38 (m, 6H), 3.33-3.15 (m, 4H), 2.70-2.56 (m, 2H), 2.44-2.31 (m, 2H), 2.03-1.88 (m, 4H), 1.75-1.53 (m, 7H). LCMS (ESI, m/z): 528.2 [M+H]$^+$.

Example 18: 1,1,1,3,3,3-Hexafluoropropan-2-yl 2-(2-(tetrahydro-1H-furo[3,4-c]pyrrol-5(3H)-yl)-6-(trifluoromethyl)benzyl)-2,8-diazaspiro[4.5]decane-8-carboxylate

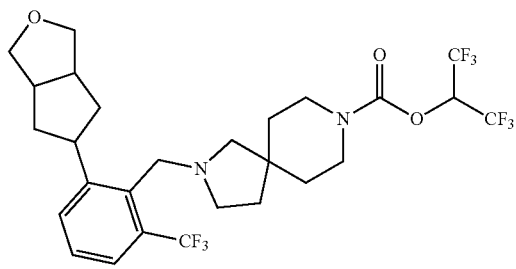 [SMILES: O=C(OC(C(F)(F)F)C(F)(F)F)N1CCC2(CCN(Cc3c(C4CC5COCC5C4)cccc3C(F)(F)F)C2)CC1]

The title compound was synthesized directly from commercially available 4-trifluoromethyl-2-fluorobenzaldehyde, and hexahydro-1H-furo[3,4-c]pyrrole and tert-butyl 2,8-diazaspiro[4.5]decane-8-carboxylate according to the representative procedure of Example 16, Steps 1-3 to provide 1,1,1,3,3,3-hexafluoropropan-2-yl 2-(2-(tetrahydro-1H-furo[3,4-c]pyrrol-5 (3H)-yl)-6-(trifluoromethyl)benzyl)-2,8-diazaspiro[4.5]decane-8-carboxylate as a clear oil. $^1$H NMR (400 MHz, Chloroform-d) δ 7.43 (dd, J=6.4, 2.6 Hz, 1H), 7.33 (d, J=6.7 Hz, 2H), 5.76 (hept, J=6.3 Hz, 1H), 4.11-4.02 (m, 2H), 3.85 (s, 2H), 3.65 (dd, J=8.5, 3.9 Hz, 2H), 3.55-3.45 (m, 2H), 3.42 (dt, J=13.0, 6.1 Hz, 2H), 3.10 (dd, J=8.7, 5.6 Hz, 2H), 2.94 (d, J=8.1 Hz, 4H), 2.53 (q, J=6.7 Hz, 2H), 2.35 (q, J=8.8 Hz, 2H), 1.55 (dt, J=11.7, 6.1 Hz, 6H).

Example 19: 1,1,1,3,3,3-Hexafluoropropan-2-yl 1-(4-chloro-2-(4-(2-fluoroethyl)piperazin-1-yl)benzyl)-1,8-diazaspiro[4.5]decane-8-carboxylate

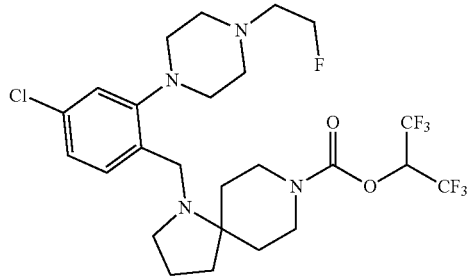 [SMILES: O=C(OC(C(F)(F)F)C(F)(F)F)N1CCC2(CCCN2Cc2ccc(Cl)cc2N2CCN(CCF)CC2)CC1]

Step 1: Preparation of tert-butyl 4-(5-chloro-2-formylphenyl)piperazine-1-carboxylate

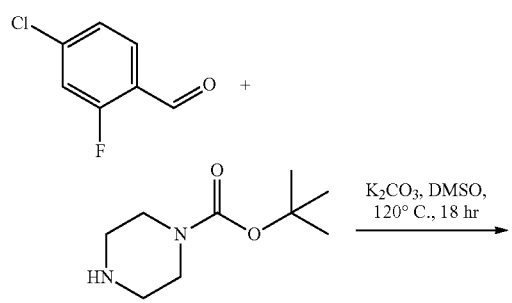

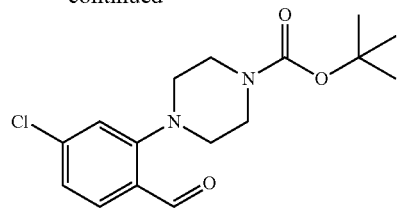

The title compound was prepared from commercially available 4-chloro-2-fluorobenzaldehyde and tert-butyl piperazine-1-carboxylate according to the representative procedure of Example 16, Step 1, with the exception that DMSO and 120° C. were used, and yielded tert-butyl 4-(5-chloro-2-formylphenyl)piperazine-1-carboxylate as a yellow solid. $^1$H NMR (400 MHz, Chloroform-d) δ 10.25 (s, 1H), 7.77 (d, J=8.3 Hz, 1H), 7.18-7.05 (m, 2H), 3.69-3.61 (m, 4H), 3.09-3.02 (m, 4H), 1.51 (s, 9H). LCMS (ESI, m/z): 586.2 [M+H]$^+$.

Step 2: Preparation of 1,1,1,3,3,3-hexafluoropropan-2-yl 1-(2-(4-(tert-butoxycarbonyl)piperazin-1-yl)-4-chlorobenzyl)-1,8-diazaspiro[4.5]decane-8-carboxylate

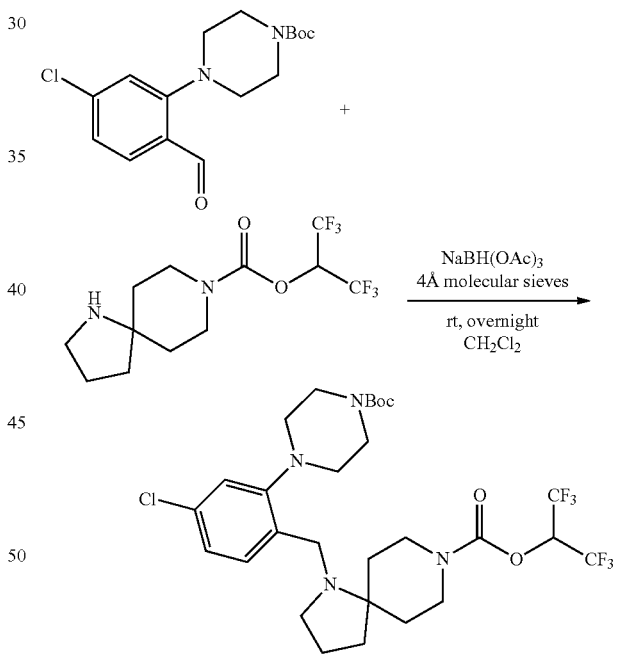

A vial was charged with 1,1,1,3,3,3-hexafluoropropan-2-yl 1,8-diazaspiro[4.5]decane-8-carboxylate (300 mg, 0.900 mmol), prepared as described in Example 1, Steps 1-2, and DCM (5 mL). Molecular sieves (300 mg) and tert-butyl 4-(5-chloro-2-formyl-phenyl)piperazine-1-carboxylate (276 mg, 0.850 mmol) were added and the reaction was stirred at rt for 10 min. NaBH(OAc)$_3$ (240 mg, 1.14 mmol) was added and the reaction was stirred for 18 h. The reaction was poured into brine (30 mL) and extracted with DCM (3×50 mL). The combined organic layers were dried over anhydrous Na$_2$SO$_4$, filtered, and concentrated. The resulting oil was purified on a silica column (0 to 40% EtOAc in hexane)

to yield 1,1,1,3,3,3-hexafluoropropan-2-yl 1-(2-(4-(tert-butoxycarbonyl)piperazin-1-yl)-4-chlorobenzyl)-1,8-diazaspiro[4.5]decane-8-carboxylate (388 mg, 0.603 mmol, 67% yield) as a clear oil. $^1$H NMR (400 MHz, Chloroform-d) δ 7.43 (d, J=8.2 Hz, 1H), 7.03 (dd, J=8.2, 2.0 Hz, 1H), 7.00 (d, J=2.0 Hz, 1H), 5.77 (hept, J=6.2 Hz, 1H), 4.20 (t, J=15.9 Hz, 2H), 3.62 (s, 2H), 3.55 (s, 4H), 3.06-2.89 (m, 2H), 2.83 (s, 4H), 2.65 (t, J=6.6 Hz, 2H), 1.89-1.63 (m, 6H), 1.54-1.42 (m, 11H). LCMS (ESI, m/z): 643 [M+H]$^+$.

Step 3: Preparation of 1,1,1,3,3,3-hexafluoropropan-2-yl 1-(4-chloro-2-(piperazin-1-yl)benzyl)-1,8-diazaspiro[4.5]decane-8-carboxylate

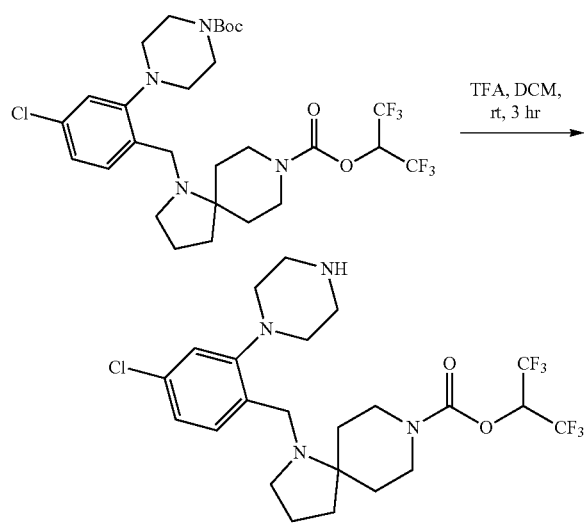

A vial was charged with 1,1,1,3,3,3-hexafluoropropan-2-yl 1-(2-(4-(tert-butoxycarbonyl)piperazin-1-yl)-4-chlorobenzyl)-1,8-diazaspiro[4.5]decane-8-carboxylate (388 mg, 0.600 mmol) and DCM (16 mL). TFA (4 mL) was added and the reaction was stirred at rt for 3 h. The reaction mixture was concentrated, diluted in DCM (50 mL), poured into sat. Na$_2$CO$_3$ (40 mL) and extracted with DCM (3×50 mL). The combined organic layers were dried over anhydrous Na$_2$SO$_4$, filtered, and concentrated to yield 1,1,1,3,3,3-hexafluoropropan-2-yl 1-(4-chloro-2-(piperazin-1-yl)benzyl)-1,8-diazaspiro[4.5]decane-8-carboxylate (300 mg, 0.552 mmol, 92% yield) which was used without further purification. LCMS (ESI, m/z): 543.2 [M+H]$^+$.

Step 4: Preparation of 1,1,1,3,3,3-hexafluoropropan-2-yl 1-(4-chloro-2-(4-(2-fluoroethyl)piperazin-1-yl)benzyl)-1,8-diazaspiro[4.5]decane-8-carboxylate

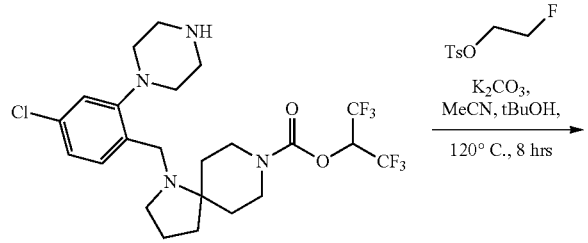

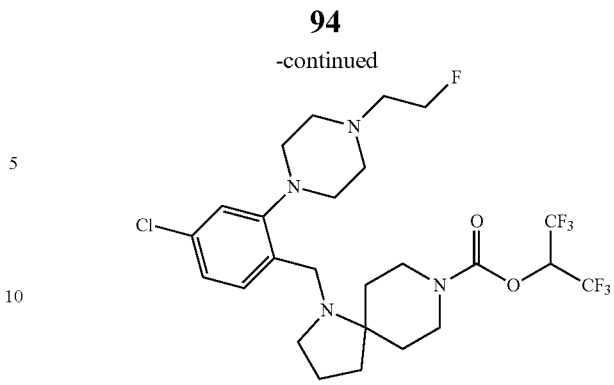

A thick walled tube was charged with 1,1,1,3,3,3-hexafluoropropan-2-yl 1-(4-chloro-2-(piperazin-1-yl)benzyl)-1,8-diazaspiro[4.5]decane-8-carboxylate (60 mg, 0.110 mmol), potassium carbonate (61 mg, 0.440 mmol), 2-fluoroethyl 4-methylbenzenesulfonate (24 mg, 0.110 mmol) in MeCN (3.6 mL) and tert-butanol (8.4 mL). The reaction was heated to 120° C. for 8 h. The reaction mixture was poured into sat. Na$_2$CO$_3$ (30 mL) and extracted with DCM (3×50 mL). The combined organic layers were dried over anhydrous Na$_2$SO$_4$, filtered, and concentrated. The resulting oil was purified on a silica column to give 1,1,1,3,3,3-hexafluoropropan-2-yl 1-(4-chloro-2-(4-(2-fluoroethyl)piperazin-1-yl)benzyl)-1,8-diazaspiro[4.5]decane-8-carboxylate (45 mg, 0.076 mmol, 69% yield) as a clear oil. $^1$H NMR (400 MHz, Chloroform-d) δ 7.48-7.41 (m, 1H), 7.04 (dd, J=6.4, 2.1 Hz, 2H), 5.79 (hept, J=6.2 Hz, 1H), 4.74-4.66 (m, 1H), 4.62-4.54 (m, 1H), 4.29-4.16 (m, 2H), 3.61 (s, 2H), 3.08-2.92 (m, 6H), 2.87-2.80 (m, 1H), 2.80-2.59 (m, 7H), 1.90-1.66 (m, 6H), 1.48 (t, J=10.4 Hz, 2H). LCMS (ESI, m/z): 589.2 [M+H]$^+$.

Example 20: 1,1,1,3,3,3-Hexafluoropropan-2-yl 1-(2-(4-(2-fluoroethyl)piperazin-1-yl)-4-(trifluoromethyl)benzyl)-1,8-diazaspiro[4.5]decane-8-carboxylate

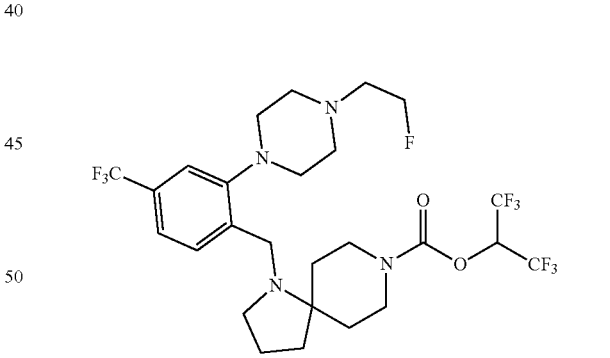

The title compound was synthesized directly from 1,1,1,3,3,3-hexafluoropropan-2-yl 1,8-diazaspiro[4.5]decane-8-carboxylate and tert-butyl 4-(2-formyl-5-(trifluoromethyl)phenyl)piperazine-1-carboxylate according to the representative procedure of Example 19, Steps 1-4 and yielded 1,1,1,3,3,3-hexafluoropropan-2-yl 1-(2-(4-(2-fluoroethyl)piperazin-1-yl)-4-(trifluoromethyl)benzyl)-1,8-diazaspiro[4.5]decane-8-carboxylate as an orange oil. $^1$H NMR (400 MHz, Chloroform-d) δ 7.65 (d, J=8.3 Hz, 1H), 7.32 (d, J=6.1 Hz, 2H), 5.79 (hept, J=6.3 Hz, 1H), 4.74-4.67 (m, 1H), 4.63-4.55 (m, 1H), 4.30-4.17 (m, 2H), 3.69 (s, 2H), 3.09-2.93 (m, 6H), 2.89-2.64 (m, 8H), 1.91-1.66 (m, 6H), 1.51 (t, J=10.6 Hz, 2H). LCMS (ESI, m/z): 623.2 [M+H]$^+$.

Example 21: 1,1,1,3,3,3-Hexafluoropropan-2-yl 2-(4-chloro-2-morpholinobenzyl)-2,8-diazaspiro[4.5]decane-8-carboxylate

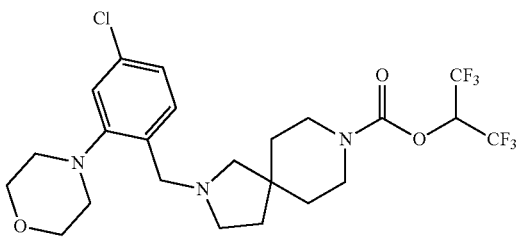 [SMILES: O=C(OC(C(F)(F)F)C(F)(F)F)N1CCC2(CCN(Cc3ccc(Cl)cc3N3CCOCC3)C2)CC1]

The title compound was synthesized directly from 4-chloro-2-morpholinobenzaldehyde (prepared from commercially available 4-chloro-2-fluorobenzaldehyde and morpholine according to the representative procedure of Example 16, Step 1) and 1,1,1,3,3,3-hexafluoropropan-2-yl 2,8-diazaspiro[4.5]decane-8-carboxylate (prepared from commercially available tert-butyl 2,8-diazaspiro[4.5]decane-2-carboxylate according to the representative procedure of Example 1, Step 2) according to the representative procedure of Example 1, Step 3 to afford 1,1,1,3,3,3-hexafluoropropan-2-yl 2-(4-chloro-2-morpholinobenzyl)-2,8-diazaspiro[4.5]decane-8-carboxylate as a clear oil. $^1$H NMR (400 MHz, Chloroform-d) δ 7.37-7.31 (m, 1H), 7.08-7.02 (m, 2H), 5.84-5.70 (m, 1H), 3.92-3.83 (m, 4H), 3.65-3.52 (m, 4H), 3.51-3.38 (m, 2H), 3.06-2.95 (m, 4H), 2.71-2.58 (m, 2H), 2.47-2.38 (m, 2H), 1.73-1.51 (m, 8H). LCMS (ESI, m/z): 544.3 [M+H]$^+$.

Example 22: 1,1,1,3,3,3-Hexafluoropropan-2-yl 2-(2-morpholino-4-(trifluoromethyl)benzyl)-2,8-diazaspiro[4.5]decane-8-carboxylate

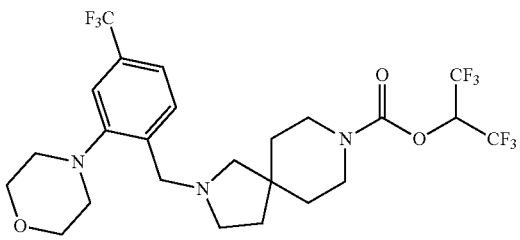 [SMILES: O=C(OC(C(F)(F)F)C(F)(F)F)N1CCC2(CCN(Cc3ccc(C(F)(F)F)cc3N3CCOCC3)C2)CC1]

The title compound was synthesized directly from 2-morpholino-4-(trifluoromethyl)benzaldehyde (prepared from commercially available 2-fluoro-4-(trifluoromethyl)benzaldehyde and morpholine according to the representative procedure of Example 16, Step 1) and 1,1,1,3,3,3-hexafluoropropan-2-yl 2,8-diazaspiro[4.5]decane-8-carboxylate (prepared from commercially available tert-butyl 2,8-diazaspiro[4.5]decane-2-carboxylate according to the representative procedure of Example 1, Step 2) according to the representative procedure of Example 1, Step 3 to afford 1,1,1,3,3,3-hexafluoropropan-2-yl 2-(2-morpholino-4-(trifluoromethyl)benzyl)-2,8-diazaspiro[4.5]decane-8-carboxylate as a clear oil. $^1$H NMR (400 MHz, Chloroform-d) δ 7.61-7.52 (m, 1H), 7.36-7.31 (m, 1H), 7.29-7.28 (m, 1H), 5.82-5.71 (m, 1H), 3.94-3.82 (m, 4H), 3.74-3.64 (m, 2H), 3.61-3.50 (m, 2H), 3.50-3.39 (m, 2H), 3.08-2.98 (m, 4H), 2.73-2.60 (m, 2H), 2.50-2.40 (m, 2H), 1.75-1.54 (m, 8H). LCMS (ESI, m/z): 578.2 [M+H]$^+$.

Example 23: 1,1,1,3,3,3-Hexafluoropropan-2-yl 2-(2-(piperidin-1-yl)-4-(trifluoromethyl)benzyl)-2,8-diazaspiro[4.5]decane-8-carboxylate

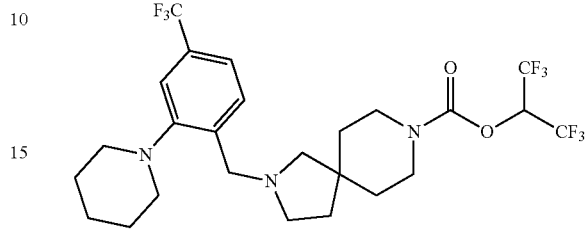

The title compound was synthesized directly from 2-(piperidin-1-yl)-4-(trifluoromethyl)benzaldehyde (prepared from commercially available 2-fluoro-4-(trifluoromethyl)benzaldehyde and piperidine according to the representative procedure of Example 16, Step 1) and 1,1,1,3,3,3-hexafluoropropan-2-yl 2,8-diazaspiro[4.5]decane-8-carboxylate (prepared from commercially available tert-butyl 2,8-diazaspiro[4.5]decane-2-carboxylate according to the representative procedure of Example 1, Step 2) according to the representative procedure of Example 1, Step 3 to afford 1,1,1,3,3,3-hexafluoropropan-2-yl 2-(2-(piperidin-1-yl)-4-(trifluoromethyl)benzyl)-2,8-diazaspiro[4.5]decane-8-carboxylate as a clear oil. $^1$H NMR (400 MHz, Chloroform-d) δ 7.59-7.54 (m, 1H), 7.31-7.25 (m, 2H), 5.83-5.73 (m, 1H), 3.68 (s, 2H), 3.59-3.42 (m, 4H), 2.97-2.88 (m, 4H), 2.72-2.63 (m, 2H), 2.52-2.41 (m, 2H), 1.79-1.68 (m, 6H), 1.66-1.58 (m, 6H). LCMS (ESI, m/z): 576.2 [M+H]$^+$.

Example 24: 1,1,1,3,3,3-Hexafluoropropan-2-yl 2-(4-chloro-2-(piperidin-1-yl)benzyl)-2,8-diazaspiro[4.5]decane-8-carboxylate

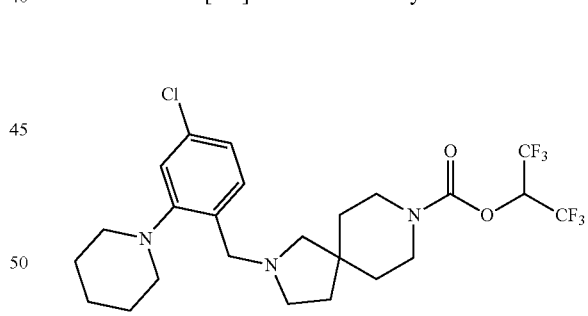

The title compound was synthesized directly from 4-chloro-2-(piperidin-1-yl)benzaldehyde (prepared from commercially available 4-chloro-2-fluorobenzaldehyde and piperidine according to the representative procedure of Example 16, Step 1) and 1,1,1,3,3,3-hexafluoropropan-2-yl 2,8-diazaspiro[4.5]decane-8-carboxylate (prepared from commercially available tert-butyl 2,8-diazaspiro[4.5]decane-2-carboxylate according to the representative procedure of Example 1, Step 2) according to the representative procedure of Example 1, Step 3 to afford 1,1,1,3,3,3-hexafluoropropan-2-yl 2-(4-chloro-2-(piperidin-1-yl)benzyl)-2,8-diazaspiro[4.5]decane-8-carboxylate as a clear oil. $^1$H NMR (400 MHz, Chloroform-d) δ 7.37-7.31 (m, 1H), 7.06-6.97 (m, 2H), 5.84-5.72 (m, 1H), 3.65-3.41 (m, 6H), 2.95-2.84 (m, 4H), 2.71-2.58 (m, 2H), 2.50-2.39 (m, 2H), 1.81-1.41 (m, 12H). LCMS (ESI, m/z): 542.2 [M+H]⁺.

Example 25: 1,1,1,3,3,3-Hexafluoropropan-2-yl 2-(4-chloro-2-(tetrahydro-1H-furo[3,4-c]pyrrol-5(3H)-yl)benzyl)-2,8-diazaspiro[4.5]decane-8-carboxylate

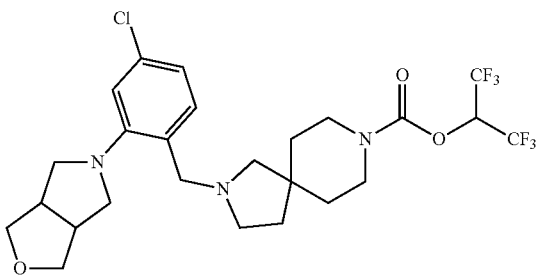 [SMILES: O=C(OC(C(F)(F)F)C(F)(F)F)N1CCC2(CCN(Cc3ccc(Cl)cc3N3CC4COCC4C3)C2)CC1]

The title compound was synthesized directly from 4-chloro-2-(tetrahydro-1H-furo[3,4-c]pyrrol-5(3H)-yl)benzaldehyde (prepared from commercially available 4-chloro-2-fluorobenzaldehyde and hexahydro-1H-furo[3,4-c]pyrrole according to the representative procedure of Example 16, Step 1) and 1,1,1,3,3,3-hexafluoropropan-2-yl 2,8-diazaspiro[4.5]decane-8-carboxylate (prepared from commercially available tert-butyl 2,8-diazaspiro[4.5]decane-2-carboxylate according to the representative procedure of Example 1, Step 2) according to the representative procedure of Example 1, Step 3 to afford 1,1,1,3,3,3-hexafluoropropan-2-yl 2-(4-chloro-2-(tetrahydro-1H-furo[3,4-c]pyrrol-5(3H)-yl)benzyl)-2,8-diazaspiro[4.5]decane-8-carboxylate as a clear oil. ¹H NMR (400 MHz, Chloroform-d) δ 7.34 (s, 1H), 7.01-6.96 (m, 2H), 5.83-5.71 (m, 1H), 4.12-4.03 (m, 2H), 3.65-3.50 (m, 6H), 3.50-3.38 (m, 2H), 3.12-3.03 (m, 4H), 2.99-2.86 (m, J=4.6 Hz, 2H), 2.68-2.57 (m, 2H), 2.44-2.35 (m, 2H), 1.73-1.64 (m, 2H), 1.64-1.56 (m, 4H). LCMS (ESI, m/z): 570.3 [M+H]⁺.

Example 26: 1,1,1,3,3,3-Hexafluoropropan-2-yl 2-(2-(tetrahydro-1H-furo[3,4-c]pyrrol-5(3H)-yl)-4-(trifluoromethyl)benzyl)-2,8-diazaspiro[4.5]decane-8-carboxylate

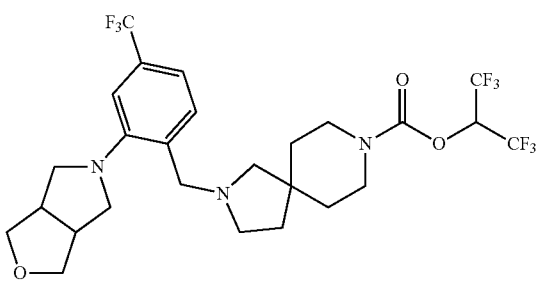 [SMILES: O=C(OC(C(F)(F)F)C(F)(F)F)N1CCC2(CCN(Cc3ccc(C(F)(F)F)cc3N3CC4COCC4C3)C2)CC1]

The title compound was synthesized directly from 2-(tetrahydro-1H-furo[3,4-c]pyrrol-5(3H)-yl)-4-(trifluoromethyl)benzaldehyde (prepared from commercially available 2-fluoro-4-(trifluoromethyl)benzaldehyde and hexahydro-1H-furo[3,4-c]pyrrole according to the representative procedure of Example 16, Step 1) and 1,1,1,3,3,3-hexafluoropropan-2-yl 2,8-diazaspiro[4.5]decane-8-carboxylate (prepared from commercially available tert-butyl 2,8-diazaspiro[4.5]decane-2-carboxylate according to the representative procedure of Example 1, Step 2) according to the representative procedure of Example 1, Step 3 to afford 1,1,1,3,3,3-hexafluoropropan-2-yl 2-(2-(tetrahydro-1H-furo[3,4-c]pyrrol-5(3H)-yl)-4-(trifluoromethyl)benzyl)-2,8-diazaspiro[4.5]decane-8-carboxylate as a clear oil. ¹H NMR (400 MHz, Chloroform-d) δ 7.61-7.51 (m, 1H), 7.31-7.17 (m, 2H), 5.84-5.69 (m, 1H), 4.14-4.02 (m, 2H), 3.73-3.61 (m, 4H), 3.61-3.51 (m, 2H), 3.51-3.39 (m, 2H), 3.20-3.04 (m, 4H), 3.03-2.89 (m, 2H), 2.73-2.59 (m, 2H), 2.48-2.36 (m, 2H), 1.75-1.56 (m, 6H). LCMS (ESI, m/z): 604.3 [M+H]⁺.

Example 27: 1,1,1,3,3,3-Hexafluoropropan-2-yl 1-(3-(2-fluoroethoxy)benzyl)-1,8-diazaspiro[4.5]decane-8-carboxylate

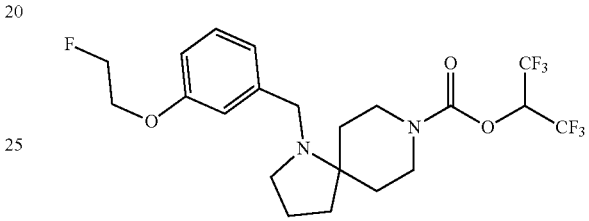

Step 1: Preparation of 1,1,1,3,3,3-hexafluoropropan-2-yl 1-(3-hydroxybenzyl)-1,8-diazaspiro[4.5]decane-8-carboxylate

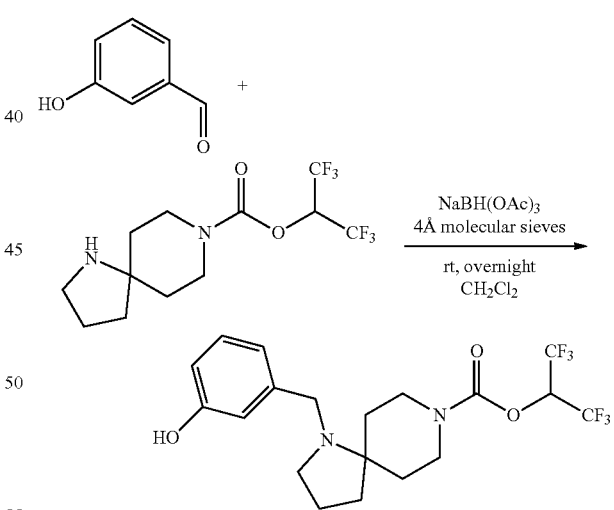

A vial was charged with 1,1,1,3,3,3-hexafluoropropan-2-yl 1,8-diazaspiro[4.5]decane-8-carboxylate (100 mg, 0.300 mmol, prepared according to Example 1, Steps 1-2), and DCM (2 mL). 3-Hydroxybenzaldehyde (36 mg, 0.300 mmol) and molecular sieves were added and the reaction mixture was stirred at rt for 30 min. NaBH(OAc)₃ (94 mg, 0.450 mmol) was added and the reaction was stirred at rt for 18 h. The reaction mixture was poured into brine (30 mL) and extracted with DCM (3×50 mL). The combined organic layers were dried over anhydrous Na₂SO₄, filtered, and concentrated. The resulting oil was purified on a silica column (0 to 20% EtOAc in hexane) to yield 1,1,1,3,3,3-hexafluoropropan-2-yl 1-(3-hydroxybenzyl)-1,8-diazaspiro[4.5]decane-8-carboxylate as a white solid. $^1$H NMR (400 MHz, Chloroform-d) δ 7.13 (t, J=7.8 Hz, 1H), 6.85 (d, J=7.6 Hz, 1H), 6.77 (s, 1H), 6.64 (dd, J=8.0, 2.4 Hz, 1H), 6.23 (br s, 1H), 5.80 (hept, J=6.2 Hz, 1H), 4.29-4.17 (m, 2H), 3.52 (d, J=2.7 Hz, 2H), 3.08-2.91 (m, 2H), 2.71 (t, J=6.9 Hz, 2H), 1.77 (dddt, J=31.4, 17.7, 13.2, 6.3 Hz, 6H), 1.50 (s, 2H). LCMS (ESI, m/z): 441.1 [M+H]$^+$.

Step 2: Preparation of 1,1,1,3,3,3-hexafluoropropan-2-yl 1-(3-(2-fluoroethoxy)benzyl)-1,8-diazaspiro[4.5]decane-8-carboxylate

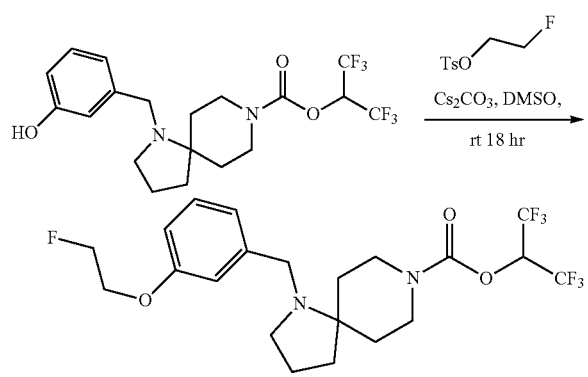

A vial was charged with 1,1,1,3,3,3-hexafluoropropan-2-yl 1-(3-hydroxybenzyl)-1,8-diazaspiro[4.5]decane-8-carboxylate (40 mg, 0.090 mmol), cesium carbonate (57 mg, 0.180 mmol) and DMSO (0.50 mL). 2-Fluoroethyl 4-methylbenzenesulfonate (19 mg, 0.090 mmol) was added and the reaction was stirred at rt for 18 h. The reaction was poured into EtOAc (100 mL) and washed with sat. Na$_2$CO$_3$ (3×25 mL). The organic layer was dried over anhydrous Na$_2$SO$_4$, filtered, and concentrated. The resulting oil was purified on a silica column with a gradient elution (EtOAc in hexane) to yield 1,1,1,3,3,3-hexafluoropropan-2-yl 1-(3-(2-fluoroethoxy)benzyl)-1,8-diazaspiro[4.5]decane-8-carboxylate (13 mg, 0.025 mmol, 28% yield). $^1$H NMR (400 MHz, Chloroform-d) δ 7.24 (t, J=7.8 Hz, 1H), 6.95 (d, J=8.3 Hz, 2H), 6.85-6.77 (m, 1H), 5.80 (hept, J=6.3 Hz, 1H), 4.87-4.80 (m, 1H), 4.75-4.68 (m, 1H), 4.30-4.16 (m, 4H), 3.59 (s, 2H), 3.00 (dtd, J=22.8, 13.3, 2.5 Hz, 2H), 2.77-2.66 (m, 2H), 1.90-1.66 (m, 6H), 1.56-1.46 (m, 2H). LCMS (ESI, m/z): 487.1 [M+H]$^+$.

Example 28: 1,1,1,3,3,3-Hexafluoropropan-2-yl 1-(4-chloro-3-(2-fluoroethoxy)benzyl)-1,8-diazaspiro[4.5]decane-8-carboxylate

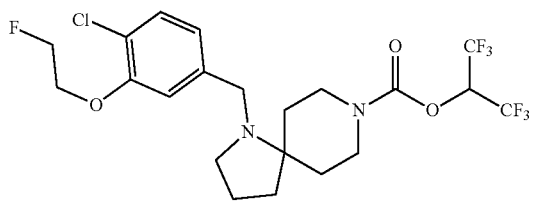 [SMILES: O=C(OC(C(F)(F)F)C(F)(F)F)N1CCC2(CCCN2Cc2ccc(Cl)c(OCCF)c2)CC1]

Step 1: Preparation of 4-chloro-3-(2-fluoroethoxy)benzaldehyde

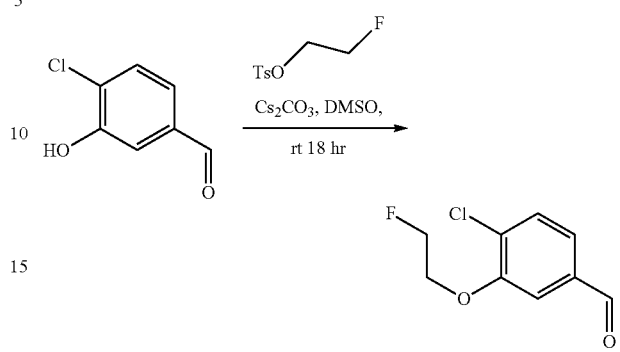

A vial was charged with cesium carbonate (211 mg, 0.650 mmol) and DMSO (2 mL), and the reaction was stirred for 5 min at rt prior to addition of 2-fluoroethyl 4-methylbenzenesulfonate (71 mg, 0.330 mmol). The reaction mixture was stirred at rt for 18 h. The resulting solution was poured into EtOAc (150 mL) and washed with sat sodium carbonate (3×50 mL). The organics were dried over anhydrous sodium sulfate, filtered, and concentrated under reduced pressure. The resulting oil was chromatographed on a silica column to afford [2,2,2-trifluoro-1-(trifluoromethyl)ethyl] 1-[[4-chloro-3-(2-fluoroethoxy)phenyl]methyl]-1,8-diazaspiro[4.5]decane-8-carboxylate (10 mg, 0.017 mmol, 22% yield). $^1$H NMR (400 MHz, Chloroform-d) δ 9.95 (s, 1H), 7.62-7.54 (m, 1H), 7.49-7.41 (m, 2H), 4.95-4.87 (m, 1H), 4.83-4.75 (m, 1H), 4.45-4.31 (m, 2H).

Step 2: Preparation of 1,1,1,3,3,3-hexafluoropropan-2-yl 1-(4-chloro-3-(2-fluoroethoxy)benzyl)-1,8-diazaspiro[4.5]decane-8-carboxylate

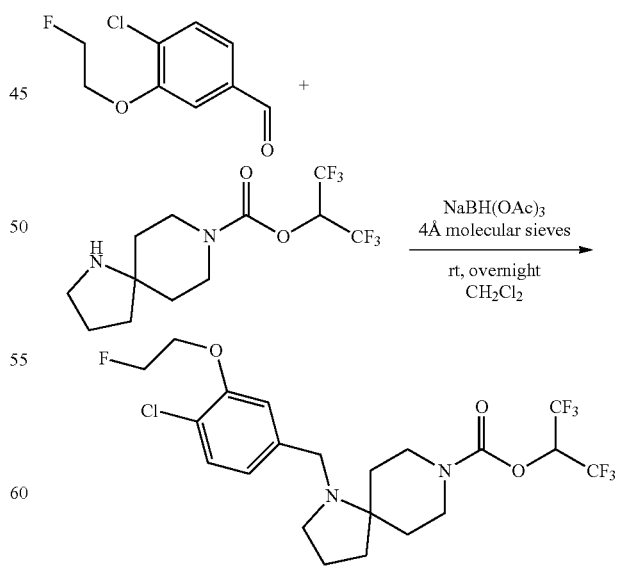

A vial was charged with 4-chloro-3-(2-fluoroethoxy)benzaldehyde (39 mg, 0.190 mmol), 1,1,1,3,3,3-hexafluoropropan-2-yl 1,8-diazaspiro[4.5]decane-8-carboxylate (64 mg, 0.190 mmol), DCM (1 mL) and molecular sieves. After stirring at rt for 5 min, NaBH(OAc)$_3$ (48 mg, 0.230 mmol) was added and the reaction was stirred at rt overnight. The reaction mixture was poured into brine (30 mL) and extracted with DCM (3×50 ml). The combined organic layers were dried over anhydrous Na$_2$SO$_4$, filtered, and concentrated. The resulting oil was purified on a silica column with a gradient first using hexane/acetone and second using a silica column with DCM/MeOH and yielded 1,1,1,3,3,3-hexafluoropropan-2-yl 1-(4-chloro-3-(2-fluoroethoxy)benzyl)-1,8-diazaspiro[4.5]decane-8-carboxylate (64 mg, 0.120 mmol, 62% yield) as a clear oil. $^1$H NMR (400 MHz, Chloroform-d) δ 7.28 (dd, J=8.0, 1.4 Hz, 1H), 6.95 (s, 1H), 6.89 (d, J=8.1 Hz, 1H), 5.85-5.70 (m, 1H), 4.89-4.82 (m, 1H), 4.78-4.70 (m, 1H), 4.35-4.15 (m, 4H), 3.55 (s, 2H), 2.98 (dt, J=24.9, 12.7 Hz, 2H), 2.66 (t, J=6.4 Hz, 2H), 1.89-1.69 (m, 6H), 1.52-1.47 (m, 2H). LCMS (ESI, m/z): 521.1 [M+H]$^+$.

Example 29: 1,1,1,3,3,3-Hexafluoropropan-2-yl 1-(4-fluoro-3-(2-fluoroethoxy)benzyl)-1,8-diazaspiro[4.5]decane-8-carboxylate

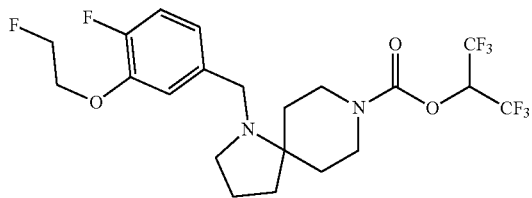 [SMILES: O=C(OC(C(F)(F)F)C(F)(F)F)N1CCC2(CCCN2Cc2ccc(F)c(OCCF)c2)CC1]

The title compound was synthesized directly from 1,1,1,3,3,3-hexafluoropropan-2-yl 1,8-diazaspiro[4.5]decane-8-carboxylate and 4-fluoro-3-hydroxybenzaldehyde according to the representative procedure of Example 28, Steps 1-2 and yielded 1,1,1,3,3,3-hexafluoropropan-2-yl 1-(4-fluoro-3-(2-fluoroethoxy)benzyl)-1,8-diazaspiro[4.5]decane-8-carboxylate as a clear oil. $^1$H NMR (400 MHz, Chloroform-d) δ 7.13-6.91 (m, 2H), 6.88 (dq, J=6.2, 2.2 Hz, 1H), 5.90-5.67 (m, 1H), 4.94-4.63 (m, 2H), 4.44-4.10 (m, 4H), 3.54 (s, 2H), 3.00 (dt, J=25.1, 13.1 Hz, 2H), 2.67 (t, J=6.1 Hz, 2H), 1.76 (dtt, J=35.9, 13.0, 5.4 Hz, 6H), 1.59-1.41 (m, 2H). LCMS (ESI, m/z): 505.1 [M+H]$^+$.

Example 30: 1,1,1,3,3,3-Hexafluoropropan-2-yl 1-(4-chloro-2-(2-fluoroethoxy)benzyl)-1,8-diazaspiro[4.5]decane-8-carboxylate

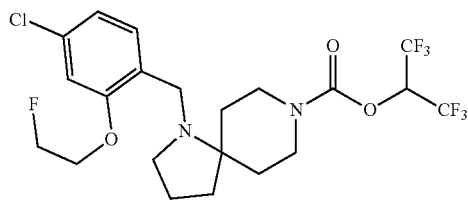 [SMILES: O=C(OC(C(F)(F)F)C(F)(F)F)N1CCC2(CCCN2Cc2ccc(Cl)cc2OCCF)CC1]

The title compound was synthesized directly from 1,1,1,3,3,3-hexafluoropropan-2-yl 1,8-diazaspiro[4.5]decane-8-carboxylate and 4-chloro-2-hydroxybenzaldehyde according to the representative procedure of Example 28, Steps 1-2 and yielded 1,1,1,3,3,3-hexafluoropropan-2-yl 1-(4-chloro-2-(2-fluoroethoxy)benzyl)-1,8-diazaspiro[4.5]decane-8-carboxylate as a clear oil. $^1$H NMR (400 MHz, Chloroform-d) δ 7.22-7.15 (m, 1H), 6.85 (dd, J=8.1, 1.9 Hz, 1H), 6.73 (s, 1H), 5.70 (hept, J=6.3 Hz, 1H), 4.77-4.70 (m, 1H), 4.65-4.58 (m, 1H), 4.19-4.05 (m, 4H), 3.58-3.43 (m, 2H), 2.89 (dtd, J=21.7, 13.3, 2.4 Hz, 2H), 2.69-2.61 (m, 2H), 1.74-1.68 (m, 5H), 1.44-1.34 (m, 2H). LCMS (ESI, m/z): 521.1 [M+H]$^+$.

Example 31: 1,1,1,3,3,3-Hexafluoropropan-2-yl 1-(4-(2-fluoroethoxy)benzyl)-1,8-diazaspiro[4.5]decane-8-carboxylate

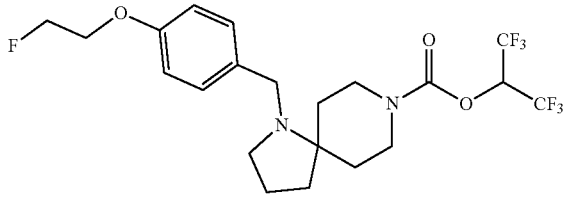 [SMILES: O=C(OC(C(F)(F)F)C(F)(F)F)N1CCC2(CCCN2Cc2ccc(OCCF)cc2)CC1]

The title compound was synthesized directly from 1,1,1,3,3,3-hexafluoropropan-2-yl 1,8-diazaspiro[4.5]decane-8-carboxylate and 4-(2-fluoroethoxy)benzaldehyde according to the representative procedure of Example 28, Steps 1-2 and yielded 1,1,1,3,3,3-hexafluoropropan-2-yl 1-(4-(2-fluoroethoxy)benzyl)-1,8-diazaspiro[4.5]decane-8-carboxylate as a clear oil. $^1$H NMR (400 MHz, Chloroform-d) δ 7.24 (d, J=8.4 Hz, 2H), 6.89 (d, J=8.6 Hz, 2H), 5.80 (p, J=6.2 Hz, 1H), 4.83 (ddd, J=4.3, 3.0, 1.3 Hz, 1H), 4.74-4.67 (m, 1H), 4.29-4.13 (m, 4H), 3.60-3.48 (m, 2H), 3.08-2.91 (m, 2H), 2.68 (t, J=6.7 Hz, 2H), 1.80 (ddq, J=22.9, 9.8, 5.9, 4.6 Hz, 6H), 1.60-1.40 (m, 2H). LCMS (ESI, m/z): 487.1 [M+H]$^+$.

Example 32: 1,1,1,3,3,3-Hexafluoropropan-2-yl 1-(4-chloro-3-ethoxybenzyl)-1,8-diazaspiro[4.5]decane-8-carboxylate

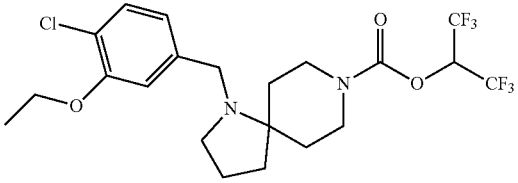 [SMILES: CCOc1cc(CN2CCCC23CCN(C(=O)OC(C(F)(F)F)C(F)(F)F)CC3)ccc1Cl]

The title compound was synthesized directly from 1,1,1,3,3,3-hexafluoropropan-2-yl 1,8-diazaspiro[4.5]decane-8-carboxylate, ethyl iodide, and 4-chloro-3-hydroxybenzaldehyde according to the representative procedure of Example 28, Steps 1-2 and yielded 1,1,1,3,3,3-hexafluoropropan-2-yl 1-(4-chloro-3-ethoxybenzyl)-1,8-diazaspiro[4.5]decane-8-carboxylate as a clear oil. $^1$H NMR (400 MHz, Chloroform-d) δ 7.31-7.22 (m, 1H), 6.92 (s, 1H), 6.84 (d, J=8.0 Hz, 1H), 5.79 (hept, J=6.2 Hz, 1H), 4.30-4.16 (m, 2H), 4.12 (q, J=7.0 Hz, 2H), 3.56 (s, 2H), 3.08-2.91 (m, 2H), 2.68 (t, J=6.6 Hz, 2H), 1.96-1.64 (m, 6H), 1.56-1.42 (m, 5H). LCMS (ESI, m/z): 503.2 [M+H]$^+$.

Example 33: 1,1,1,3,3,3-Hexafluoropropan-2-yl 1-(3-chloro-5-morpholinobenzyl)-1,8-diazaspiro[4.5]decane-8-carboxylate

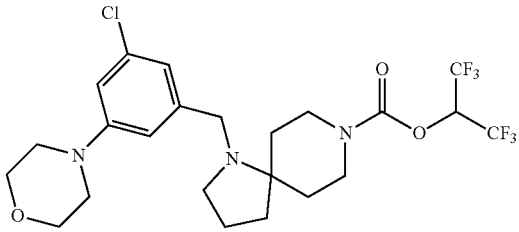 [SMILES: O=C(OC(C(F)(F)F)C(F)(F)F)N1CCC2(CCCN2Cc2cc(Cl)cc(N3CCOCC3)c2)CC1]

Step 1: Preparation of tert-butyl 1-(3-bromo-5-chlorobenzyl)-1,8-diazaspiro[4.5]decane-8-carboxylate

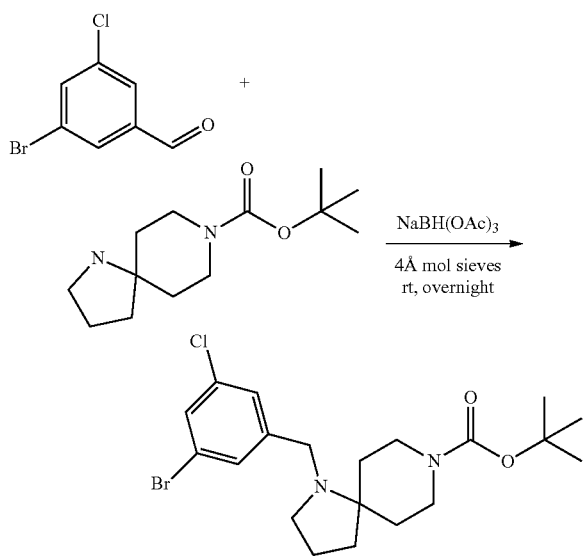

A vial was charged with 3-bromo-5-chlorobenzaldehyde (207 mg, 0.943 mmol). The solid was dissolved in DCM (5 mL) and stirred at rt. tert-Butyl 1,8-diazaspiro[4.5]decane-8-carboxylate (300 mg, 1.08 mmol) was added followed by 4 Å molecular sieves (300 mg). The vial was purged with $N_2$ and stirred at rt for 2 h. NaBH(OAc)$_3$ (219 mg, 1.03 mmol) was added and the reaction was allowed to stir at rt overnight. The reaction mixture was filtered over Celite and rinsed with MeOH. The mixture was concentrated, taken up in EtOAc, washed with sat. NaHCO$_3$, dried over Na$_2$SO$_4$ and concentrated to yield an oil. The oil was purified by flash column chromatography to afford tert-butyl 1-(3-bromo-5-chlorobenzyl)-1,8-diazaspiro[4.5]decane-8-carboxylate (254 mg, 60% yield). $^1$H NMR (400 MHz, Chloroform-d) δ 7.38-7.35 (m, 2H), 7.26-7.24 (m, 1H), 4.26-4.07 (m, 2H), 3.57-3.49 (m, 2H), 2.85-2.71 (m, 2H), 2.68-2.61 (m, 2H), 1.85-1.74 (m, 4H), 1.65-1.57 (m, 2H), 1.47 (s, 9H), 1.43-1.35 (m, 2H). LCMS (ESI, m/z): 451.2 [M+H]$^+$.

Step 2: Preparation of tert-butyl 1-(3-chloro-5-morpholinobenzyl)-1,8-diazaspiro[4.5]decane-8-carboxylate

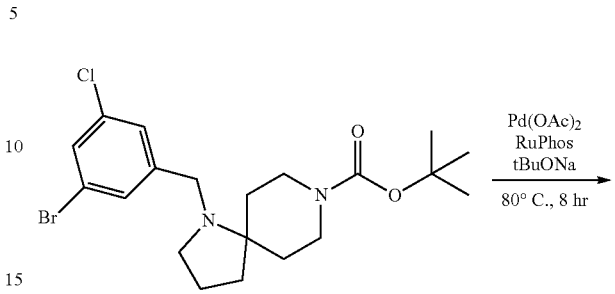

A vial was charged with tert-butyl 1-(3-bromo-5-chlorobenzyl)-1,8-diazaspiro[4.5]decane-8-carboxylate (129 mg, 0.291 mmol). To this vial was added Pd(OAc)$_2$ (7 mg, 0.029 mmol), RuPhos (54 mg, 0.117 mmol), and t-BuONa (42 mg, 0.438 mmol). The vial was then flushed with $N_2$ and evacuated 3 times. Morpholine (28 mg, 0.321 mmol) was added to the vial, followed by anhydrous THF (3 mL). The resulting stirred mixture was heated at 80° C. for 8 h. The reaction was then cooled to rt whereupon H$_2$O (5 mL) was added. The reaction mixture was extracted with EtOAc (3×10 mL) and the combined organic layers were dried over Na$_2$SO$_4$, filtered and concentrated to yield an oil. The oil was purified by flash column chromatography to afford tert-butyl 1-(3-chloro-5-morpholinobenzyl)-1,8-diazaspiro[4.5]decane-8-carboxylate (45 mg, 34% yield). $^1$H NMR (400 MHz, Chloroform-d) δ 6.73-6.64 (m, 1H), 6.62-6.55 (m, 2H), 4.01 (s, 2H), 3.76-3.68 (m, 4H), 3.43-3.29 (m, 2H), 3.08-2.93 (m, 4H), 2.72-2.45 (m, 4H), 1.75-1.57 (m, 4H), 1.56-1.43 (m, 2H), 1.37-1.29 (m, 9H), 1.29-1.19 (m, 2H).

Step 3: Preparation of 1,1,1,3,3,3-hexafluoropropan-2-yl 1-(3-chloro-5-morpholinobenzyl)-1,8-diazaspiro[4.5]decane-8-carboxylate

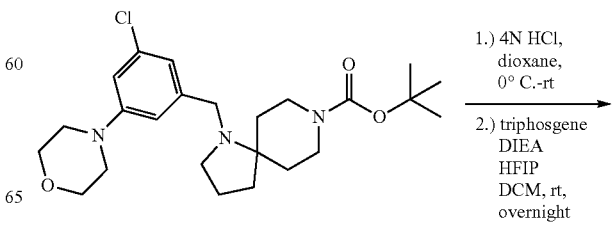

-continued

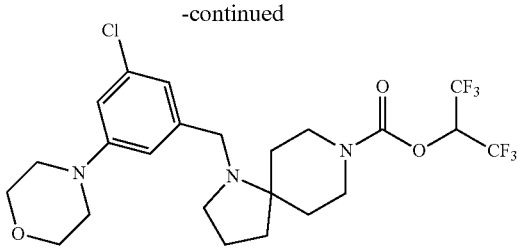

A vial was charged with tert-butyl 1-(3-chloro-5-morpholinobenzyl)-1,8-diazaspiro[4.5]decane-8-carboxylate (45 mg, 0.100 mmol). DCM (3 mL) was added and the mixture was stirred at 0° C. for 10 min. 4 N HCl in dioxane was added dropwise via syringe (0.150 mL, 0.600 mmol). The mixture was stirred at rt overnight. MeOH was added, and the mixture was concentrated to yield a solid. The solid was dissolved in DCM (3 mL), DIEA (0.2 mL) was added, and the reaction was stirred at rt. A separate vial was charged with triphosgene (87 mg, 0.295 mmol). To this vial was added DCM (3 mL). The mixture was then purged with $N_2$ and stirred at rt for 5 min. The vial was cooled to 0° C. and HFIP was added (0.118 mL, 0.959 mmol), followed by DIEA (0.257 mL, 1.47 mmol). The mixture was allowed to stir at rt for 45 min. At that time, the contents of the first vial were transferred to the HFIP mixture dropwise via syringe, and the solution was stirred at rt overnight. The mixture was diluted with DCM, washed with sat. $NaHCO_3$ (3×), dried over $Na_2SO_4$, and concentrated to yield a residue. The residue was purified by flash column chromatography and preparative HPLC to afford 1,1,1,3,3,3-hexafluoropropan-2-yl 1-(3-chloro-5-morpholinobenzyl)-1,8-diazaspiro[4.5]decane-8-carboxylate (15 mg, 18% yield). $^1$H NMR (400 MHz, Chloroform-d) δ 6.76 (s, 1H), 6.66 (s, 2H), 5.76-5.61 (m, 1H), 4.25-4.07 (m, 2H), 3.86-3.69 (m, 4H), 3.51-3.38 (m, 2H), 3.15-3.03 (m, 4H), 3.02-2.81 (m, 2H), 2.70-2.52 (m, 2H), 1.85-1.51 (m, 6H), 1.47-1.32 (m, 2H). LCMS (ESI, m/z): 544.2 [M+H]$^+$.

Example 34: 1,1,1,3,3,3-Hexafluoropropan-2-yl 1-(3-chloro-5-(pyrrolidin-1-yl)benzyl)-1,8-diazaspiro[4.5]decane-8-carboxylate

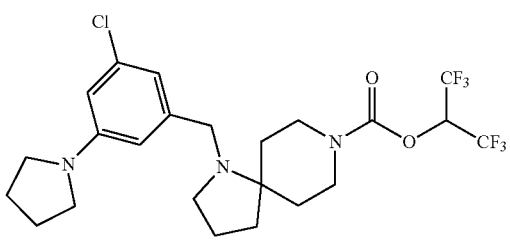

The title compound was synthesized directly from pyrrolidine according to the representative procedure of Example 33, Steps 1-3 to provide 1,1,1,3,3,3-hexafluoropropan-2-yl 1-(3-chloro-5-(pyrrolidin-1-yl)benzyl)-1,8-diazaspiro[4.5]decane-8-carboxylate as a clear oil. $^1$H NMR (400 MHz, Chloroform-d) δ 6.68-6.62 (m, 1H), 6.45-6.34 (m, 2H), 5.85-5.72 (m, 1H), 4.30-4.15 (m, 2H), 3.57-3.46 (m, 2H), 3.32-3.23 (m, 4H), 3.10-2.91 (m, 2H), 2.79-2.65 (m, 2H), 2.08-1.94 (m, 4H), 1.88-1.69 (m, 6H), 1.50 (ddt, J=13.2, 7.7, 2.3 Hz, 2H). LCMS (ESI, m/z): 528.2 [M+H]$^+$.

Example 35: 1,1,1,3,3,3-Hexafluoropropan-2-yl 1-(3-morpholino-5-(trifluoromethyl)benzyl)-1,8-diazaspiro[4.5]decane-8-carboxylate

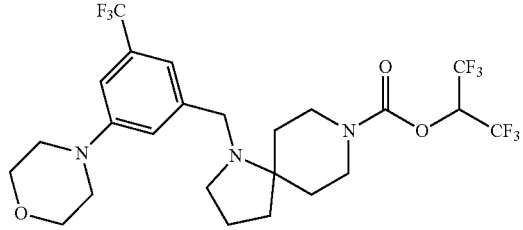 [SMILES: O=C(OC(C(F)(F)F)C(F)(F)F)N1CCC2(CCCN2Cc2cc(N3CCOCC3)cc(C(F)(F)F)c2)CC1]

The title compound was synthesized directly from commercially available 3-bromo-5-(trifluoromethyl)benzaldehyde according to the representative procedure of Example 33, Steps 1-3 to provide 1,1,1,3,3,3-hexafluoropropan-2-yl 1-(3-morpholino-5-(trifluoromethyl)benzyl)-1,8-diazaspiro[4.5]decane-8-carboxylate as a clear oil. $^1$H NMR (400 MHz, Chloroform-d) δ 7.03-6.86 (m, 3H), 5.75-5.62 (m, 1H), 4.24-4.08 (m, 2H), 3.84-3.76 (m, 4H), 3.51 (s, 2H), 3.12 (s, 4H), 3.00-2.82 (m, 2H), 2.65-2.54 (m, 2H), 1.81-1.60 (m, 6H), 1.47-1.37 (m, 2H). LCMS (ESI, m/z): 578.2 [M+H]$^+$.

Example 36: 1,1,1,3,3,3-Hexafluoropropan-2-yl 1-(3-(pyrrolidin-1-yl)-5-(trifluoromethyl)benzyl)-1,8-diazaspiro[4.5]decane-8-carboxylate

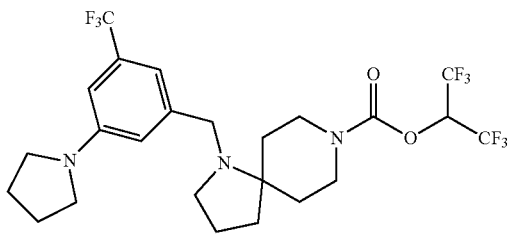 [SMILES: O=C(OC(C(F)(F)F)C(F)(F)F)N1CCC2(CCCN2Cc2cc(N3CCCC3)cc(C(F)(F)F)c2)CC1]

The title compound was synthesized directly from commercially available 3-bromo-5-(trifluoromethyl)benzaldehyde and pyrrolidine according to the representative procedure of Example 33, Steps 1-3 to provide 1,1,1,3,3,3-hexafluoropropan-2-yl 1-(3-(pyrrolidin-1-yl)-5-(trifluoromethyl)benzyl)-1,8-diazaspiro[4.5]decane-8-carboxylate as a clear oil. $^1$H NMR (400 MHz, Chloroform-d) δ 6.78 (s, 1H), 6.54 (d, 2H), 5.77-5.65 (m, 1H), 4.22-4.05 (m, 2H), 3.50 (s, 2H), 3.29-3.17 (m, 4H), 3.01-2.82 (m, 2H), 2.70-2.58 (m, 2H), 2.02-1.90 (m, 4H), 1.83-1.57 (m, 6H), 1.49-1.35 (m, 2H). LCMS (ESI, m/z): 562.2 [M+H]$^+$.

Example 37: 1,1,1,3,3,3-Hexafluoropropan-2-yl 1-(3-morpholino-5-(trifluoromethoxy)benzyl)-1,8-diazaspiro[4.5]decane-8-carboxylate

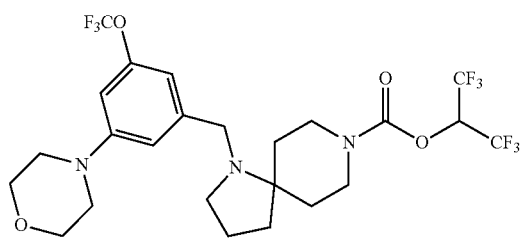 [SMILES: O=C(OC(C(F)(F)F)C(F)(F)F)N1CCC2(CCCN2Cc2cc(OC(F)(F)F)cc(N3CCOCC3)c2)CC1]

The title compound was synthesized directly from commercially available 3-bromo-5-(trifluoromethoxy)benzaldehyde according to the representative procedure of Example 33, Steps 1-3 to provide 1,1,1,3,3,3-hexafluoropropan-2-yl 1-(3-morpholino-5-(trifluoromethoxy)benzyl)-1,8-diazaspiro[4.5]decane-8-carboxylate as a clear oil. ¹H NMR (400 MHz, Chloroform-d) δ 6.84-6.70 (m, 2H), 6.59 (s, 1H), 5.86-5.71 (m, 1H), 4.33-4.16 (m, 2H), 3.94-3.80 (m, 4H), 3.57 (s, 2H), 3.18 (s, 4H), 3.09-2.91 (m, 2H), 2.77-2.65 (m, 2H), 1.90-1.75 (m, 4H), 1.75-1.67 (m, 2H), 1.55-1.45 (m, 2H). LCMS (ESI, m/z): 594.2 [M+H]⁺.

Example 38: 1,1,1,3,3,3-Hexafluoropropan-2-yl 1-(3-chloro-5-(tetrahydro-1H-furo[3,4-c]pyrrol-5 (3H)-yl)benzyl)-1,8-diazaspiro[4.5]decane-8-carboxylate

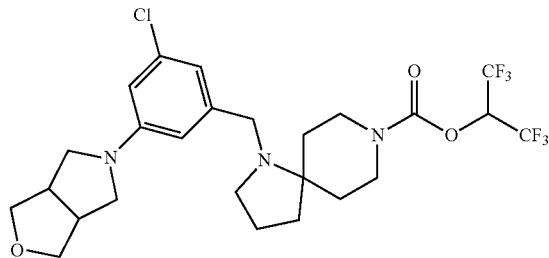 [SMILES: O=C(OC(C(F)(F)F)C(F)(F)F)N1CCC2(CCCN2Cc2cc(Cl)cc(N3CC4COCC4C3)c2)CC1]

The title compound was synthesized directly from commercially available hexahydro-1H-furo[3,4-c]pyrrole according to the representative procedure of Example 33, Steps 1-3 to provide 1,1,1,3,3,3-hexafluoropropan-2-yl 1-(3-chloro-5-(tetrahydro-1H-furo[3,4-c]pyrrol-5(3H)-yl)benzyl)-1,8-diazaspiro[4.5]decane-8-carboxylate as a clear oil. ¹H NMR (400 MHz, Chloroform-d) δ 6.71 (s, 1H), 6.47 (d, 2H), 5.83-5.73 (m, 1H), 4.30-4.15 (m, 2H), 4.06-3.96 (m, 2H), 3.74-3.65 (m, 2H), 3.58-3.48 (m, 2H), 3.49-3.40 (m, 2H), 3.28-3.19 (m, 2H), 3.13-2.91 (m, 4H), 2.76-2.64 (m, 2H), 1.92-1.62 (m, 6H), 1.55-1.42 (m, 2H). LCMS (ESI, m/z): 570.3 [M+H]⁺.

Example 39: 1,1,1,3,3,3-Hexafluoropropan-2-yl 1-(3-chloro-5-(4-fluoropiperidin-1-yl)benzyl)-1,8-diazaspiro[4.5]decane-8-carboxylate

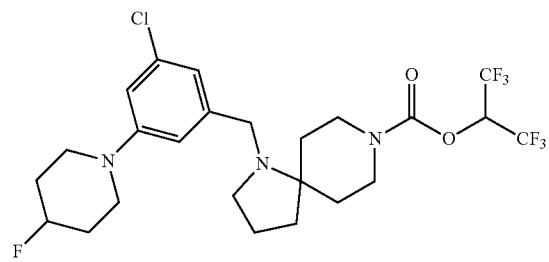

The title compound was synthesized directly from commercially available 4-fluoropiperidine hydrochloride according to the representative procedure of Example 33, Steps 1-3 to provide 1,1,1,3,3,3-hexafluoropropan-2-yl 1-(3-chloro-5-(4-fluoropiperidin-1-yl)benzyl)-1,8-diazaspiro[4.5]decane-8-carboxylate as a clear oil. ¹H NMR (400 MHz, Chloroform-d) δ 6.72 (s, 1H), 6.68 (m, 2H), 5.74-5.63 (m, 1H), 4.84-4.58 (m, 1H), 4.23-4.07 (m, 2H), 3.49-3.37 (m, 2H), 3.33-3.23 (m, 2H), 3.17-3.05 (m, 2H), 3.00-2.82 (m, 2H), 2.66-2.55 (m, 2H), 2.00-1.82 (m, 4H), 1.79-1.66 (m, 4H), 1.66-1.59 (m, 2H), 1.47-1.35 (m, 2H). LCMS (ESI, m/z): 560.3 [M+H]⁺.

Example 40: 1,1,1,3,3,3-Hexafluoropropan-2-yl 1-(3-chloro-5-(4-(methylsulfonyl)piperazin-1-yl) benzyl)-1,8-diazaspiro[4.5]decane-8-carboxylate

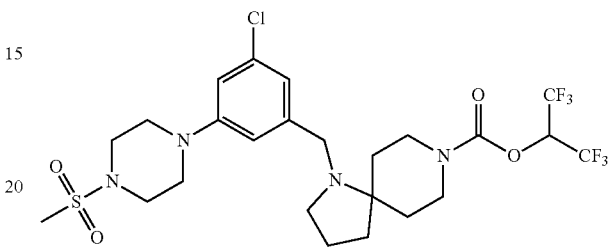

The title compound was synthesized directly from commercially available 1-(methylsulfonyl)piperazine according to the representative procedure of Example 33, Steps 1-3 to provide 1,1,1,3,3,3-hexafluoropropan-2-yl 1-(3-chloro-5-(4-(methylsulfonyl)piperazin-1-yl)benzyl)-1,8-diazaspiro[4.5]decane-8-carboxylate as a clear oil. ¹H NMR (400 MHz, Chloroform-d) δ 6.92-6.84 (m, 1H), 6.81-6.73 (m, 2H), 5.82-5.70 (m, 1H), 4.30-4.14 (m, 2H), 3.59-3.47 (m, 2H), 3.43-3.35 (m, 4H), 3.33-3.25 (m, 4H), 3.08-2.90 (m, 2H), 2.85 (s, 3H), 2.73-2.62 (m, 2H), 1.91-1.77 (m, 4H), 1.71-1.62 (m, 2H), 1.54-1.44 (m, 2H). LCMS (ESI, m/z): 621.3 [M+H]⁺.

Example 41: 1,1,1,3,3,3-Hexafluoropropan-2-yl 1-(3-(4-cyclopropylpiperazin-1-yl)-5-(trifluoromethyl)benzyl)-1,8-diazaspiro[4.5]decane-8-carboxylate

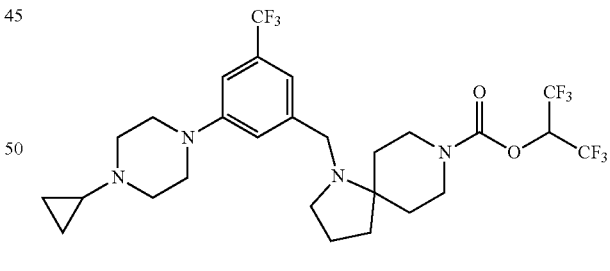

The title compound was synthesized directly from commercially available 1-cyclopropylpiperazine and 3-bromo-5-(trifluoromethyl)benzaldehyde according to the representative procedure of Example 33, Steps 1-3 to provide 1,1,1,3,3,3-hexafluoropropan-2-yl 1-(3-(4-cyclopropylpiperazin-1-yl)-5-(trifluoromethyl)benzyl)-1,8-diazaspiro[4.5]decane-8-carboxylate as a clear oil. ¹H NMR (400 MHz, Chloroform-d) δ 7.09-7.02 (m, 2H), 6.99 (s, 1H), 5.78 (hept, J=6.3 Hz, 1H), 4.31-4.14 (m, 2H), 3.66-3.52 (m, 2H), 3.25-3.17 (m, 4H), 3.08-2.91 (m, 2H), 2.85-2.75 (m, 4H), 2.75-2.62 (m, 2H), 1.95-1.67 (m, 7H), 1.57-1.46 (m, 2H), 0.56-0.44 (m, 4H). LCMS (ESI, m/z): 617.2 [M+H]⁺.

Example 42: 1,1,1,3,3,3-Hexafluoropropan-2-yl 1-(3-(1,1-dioxidothiomorpholino)-5-(trifluoromethyl)benzyl)-1,8-diazaspiro[4.5]decane-8-carboxylate

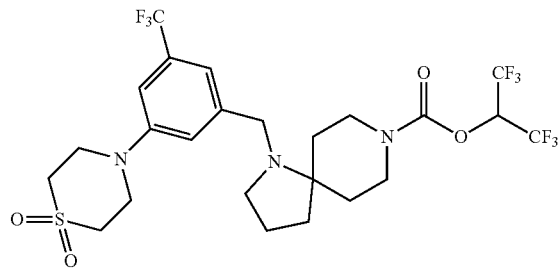 [SMILES: O=C(OC(C(F)(F)F)C(F)(F)F)N1CCC2(CCCN2Cc2cc(N3CCS(=O)(=O)CC3)cc(C(F)(F)F)c2)CC1]

The title compound was synthesized directly from commercially available thiomorpholine 1,1-dioxide and 3-bromo-5-(trifluoromethyl)benzaldehyde according to the representative procedure of Example 33, Steps 1-3 to provide 1,1,1,3,3,3-hexafluoropropan-2-yl 1-(3-(1,1-dioxidothiomorpholino)-5-(trifluoromethyl)benzyl)-1,8-diazaspiro[4.5]decane-8-carboxylate as a clear oil. $^1$H NMR (400 MHz, Chloroform-d) δ 7.06 (s, 1H), 6.97 (s, 1H), 6.90 (s, 1H), 5.75-5.62 (m, 1H), 4.22-4.07 (m, 2H), 3.86-3.74 (m, 4H), 3.58-3.47 (m, 2H), 3.11-3.01 (m, 4H), 3.01-2.82 (m, 2H), 2.64-2.53 (m, 2H), 1.85-1.69 (m, 4H), 1.61-1.54 (m, 2H), 1.48-1.35 (m, 2H). LCMS (ESI, m/z): 626.2 [M+H]$^+$.

Example 43: 1,1,1,3,3,3-Hexafluoropropan-2-yl 1-(3-(4-(methylsulfonyl)piperazin-1-yl)-5-(trifluoromethyl)benzyl)-1,8-diazaspiro[4.5]decane-8-carboxylate

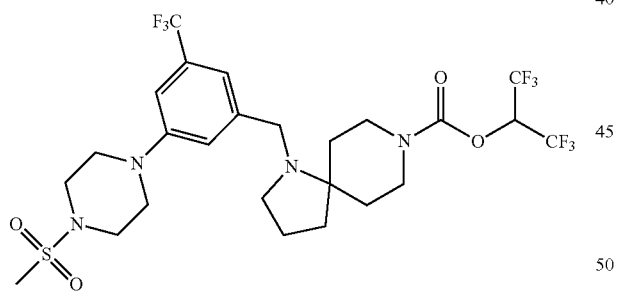

The title compound was synthesized directly from commercially available 1-(methyl sulfonyl)piperazine and 3-bromo-5-(trifluoromethyl)benzaldehyde according to the representative procedure of Example 33, Steps 1-3 to provide 1,1,1,3,3,3-hexafluoropropan-2-yl 1-(3-(4-(methylsulfonyl)piperazin-1-yl)-5-(trifluoromethyl)benzyl)-1,8-diazaspiro[4.5]decane-8-carboxylate as clear oil. $^1$H NMR (400 MHz, Chloroform-d) δ 7.13 (s, 1H), 7.06 (s, 1H), 7.01 (s, 1H), 5.83-5.72 (m, 1H), 4.30-4.15 (m, 2H), 3.67-3.56 (m, 2H), 3.45-3.37 (m, 4H), 3.37-3.31 (m, 4H), 3.10-2.92 (m, 2H), 2.88-2.81 (m, 3H), 2.73-2.63 (m, 2H), 1.94-1.76 (m, 4H), 1.76-1.65 (m, 2H), 1.55-1.47 (m, 2H). LCMS (ESI, m/z): 655.2 [M+H]$^+$.

Example 44: 1,1,1,3,3,3-Hexafluoropropan-2-yl 1-(3-(trifluoromethyl)-5-(4-(trifluoromethyl)piperidin-1-yl)benzyl)-1,8-diazaspiro[4.5]decane-8-carboxylate

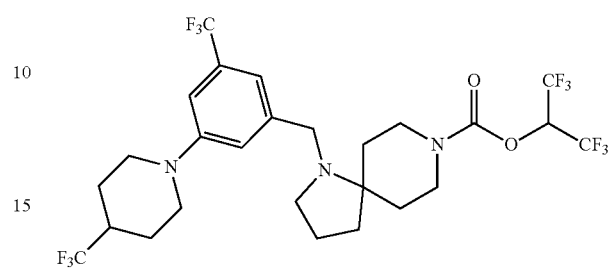

The title compound was synthesized directly from commercially available 4-(trifluoromethyl)piperidine hydrochloride and 3-bromo-5-(trifluoromethyl)benzaldehyde according to the representative procedure of Example 33, Steps 1-3 to provide 1,1,1,3,3,3-hexafluoropropan-2-yl 1-(3-(trifluoromethyl)-5-(4-(trifluoromethyl)piperidin-1-yl)benzyl)-1,8-diazaspiro[4.5]decane-8-carboxylate as a clear oil. $^1$H NMR (400 MHz, Chloroform-d) δ 7.02-6.87 (m, 3H), 5.75-5.62 (m, 1H), 4.22-4.05 (m, 2H), 3.78-3.63 (m, 2H), 3.57-3.44 (m, 2H), 3.02-2.84 (m, 2H), 2.74-2.54 (m, 4H), 2.20-2.03 (m, 1H), 2.01-1.87 (m, 2H), 1.83-1.51 (m, 7H), 1.46-1.34 (m, 2H). LCMS (ESI, m/z): 644.2 [M+H]$^+$.

Example 45: 1,1,1,3,3,3-Hexafluoropropan-2-yl 1-(3-(4-fluoropiperidin-1-yl)-5-(trifluoromethyl)benzyl)-1,8-diazaspiro[4.5]decane-8-carboxylate

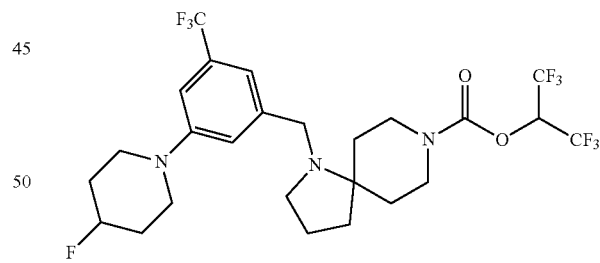

The title compound was synthesized directly from commercially available 4-fluoropiperidine hydrochloride and 3-bromo-5-(trifluoromethyl)benzaldehyde according to the representative procedure of Example 33, Steps 1-3 to provide 1,1,1,3,3,3-hexafluoropropan-2-yl 1-(3-(4-fluoropiperidin-1-yl)-5-(trifluoromethyl)benzyl)-1,8-diazaspiro[4.5]decane-8-carboxylate as a clear oil. $^1$H NMR (400 MHz, Chloroform-d) δ 7.06 (s, 2H), 7.02 (s, 1H), 5.84-5.72 (m, 1H), 4.98-4.73 (m, 1H), 4.33-4.17 (m, 2H), 3.60 (s, 2H), 3.48-3.36 (m, 2H), 3.31-3.22 (m, 2H), 3.10-2.91 (m, 2H), 2.74-2.63 (m, 2H), 2.13-1.95 (m, 4H), 1.91-1.69 (m, 6H), 1.58-1.44 (m, 2H). LCMS (ESI, m/z): 594.3 [M+H]$^+$.

Example 46: 1,1,1,3,3,3-Hexafluoropropan-2-yl 1-(3-(tetrahydro-1H-furo[3,4-c]pyrrol-5(3H)-yl)-5-(trifluoromethyl)benzyl)-1,8-diazaspiro[4.5]decane-8-carboxylate

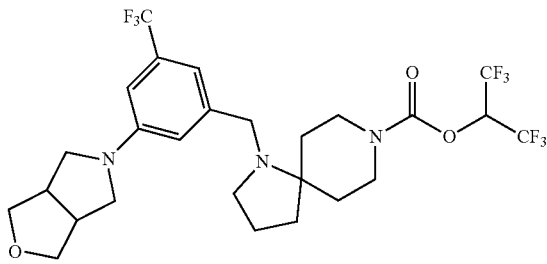 [SMILES: O=C(OC(C(F)(F)F)C(F)(F)F)N1CCC2(CCCN2Cc2cc(N3CC4COCC4C3)cc(C(F)(F)F)c2)CC1]

The title compound was synthesized directly from commercially available hexahydro-1H-furo[3,4-c]pyrrole and 3-bromo-5-(trifluoromethyl)benzaldehyde according to the representative procedure of Example 33, Steps 1-3 to provide 1,1,1,3,3,3-hexafluoropropan-2-yl 1-(3-(tetrahydro-1H-furo[3,4-c]pyrrol-5(3H)-yl)-5-(trifluoromethyl)benzyl)-1,8-diazaspiro[4.5]decane-8-carboxylate as a clear oil. $^1$H NMR (400 MHz, Chloroform-d) δ 6.85 (s, 1H), 6.66-6.56 (m, 2H), 5.74-5.62 (m, 1H), 4.21-4.05 (m, 2H), 3.97-3.86 (m, 2H), 3.67-3.56 (m, 2H), 3.55-3.43 (m, 2H), 3.44-3.32 (m, 2H), 3.24-3.14 (m, 2H), 3.05-2.80 (m, 4H), 2.65-2.51 (m, 2H), 1.81-1.67 (m, 4H), 1.68-1.59 (m, 2H), 1.46-1.36 (m, 2H). LCMS (ESI, m/z): 604.2 [M+H]$^+$.

Example 47: 1,1,1,3,3,3-Hexafluoropropan-2-yl 1-(3-(azetidin-1-yl)-5-(trifluoromethyl)benzyl)-1,8-diazaspiro[4.5]decane-8-carboxylate

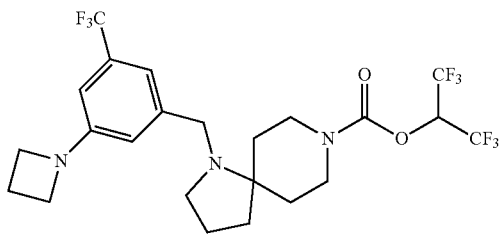 [SMILES: O=C(OC(C(F)(F)F)C(F)(F)F)N1CCC2(CCCN2Cc2cc(N3CCC3)cc(C(F)(F)F)c2)CC1]

The title compound was synthesized directly from commercially available azetidine and 3-bromo-5-(trifluoromethyl)benzaldehyde according to the representative procedure of Example 16, Step 1 and Example 1, Steps 2-3 to provide 1,1,1,3,3,3-hexafluoropropan-2-yl 1-(3-(azetidin-1-yl)-5-(trifluoromethyl)benzyl)-1,8-diazaspiro[4.5]decane-8-carboxylate as a clear oil. $^1$H NMR (400 MHz, Chloroform-d) δ 6.84 (s, 1H), 6.42 (s, 2H), 5.74-5.60 (m, 1H), 4.21-4.06 (m, 2H), 3.89-3.76 (m, 4H), 3.53-3.39 (m, 2H), 3.01-2.80 (m, 2H), 2.65-2.53 (m, 2H), 2.37-2.24 (m, 2H), 1.84-1.59 (m, 6H), 1.45-1.35 (m, 2H). LCMS (ESI, m/z): 548.2 [M+H]$^+$.

Example 48: 1,1,1,3,3,3-Hexafluoropropan-2-yl 2-(4-chlorobenzyl)-3,3-dimethyl-2,8-diazaspiro[4.5]decane-8-carboxylate

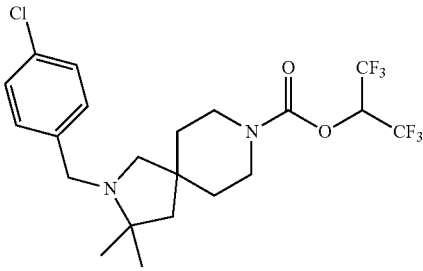 [SMILES: CC1(C)CC2(CCN(C(=O)OC(C(F)(F)F)C(F)(F)F)CC2)CN1Cc1ccc(Cl)cc1]

Step 1: Preparation of 1-(4-methoxybenzyl)piperidine-4-carbonitrile

A flask was charged with 4-methoxybenzaldehyde (2.5 g, 18.1 mmol), piperidine-4-carbonitrile (2.0 g, 18.2 mmol), DCM (50 mL), and molecular sieves (4 g). After stirring at rt for 30 min, NaBH(OAc)$_3$ (5.75 g, 27.2 mmol) was added and the reaction was stirred at rt for 18 h. The reaction was diluted in DCM (200 mL) and washed with aqueous sat. Na$_2$CO$_3$ (2×100 mL). The organic layer was dried over anhydrous Na$_2$SO$_4$, filtered, and concentrated. The resulting oil was purified on a silica column (0 to 5% MeOH in DCM) to yield 1-(4-methoxybenzyl)piperidine-4-carbonitrile (4100 mg, 17.8 mmol, 98% yield) as a clear oil. $^1$H NMR (400 MHz, Chloroform-d) δ 7.31-7.19 (m, 2H), 6.87 (dd, J=8.7, 1.3 Hz, 2H), 3.82 (s, 3H), 3.46 (s, 2H), 2.66 (br s, 3H), 2.32 (br s, 2H), 2.00-1.81 (m, 5H). LCMS (ESI, m/z): 231.2 [M+H]$^+$.

Step 2: Preparation of 1-(4-methoxybenzyl)-4-(2-methylallyl)piperidine-4-carbonitrile

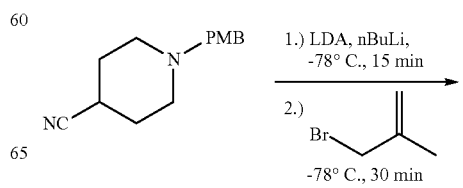

-continued

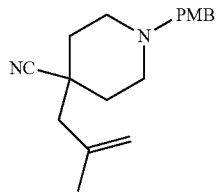

A flask was charged with THF (20 mL) and DIPEA (3.2 mL, 23.1 mmol) and cooled to −78° C. The solution was treated with n-butyllithium (9.0 mL, 21.4 mmol) and stirred at −78° C. for 15 min. A separate flask was charged with 1-(4-methoxybenzyl)piperidine-4-carbonitrile and THF (40 mL) and cooled to −78° C. LDA solution was added via syringe to the cyanopiperidine at −78° C. The solution became yellow and was stirred at −78° C. for 15 min. 3-Bromo-2-methyl-prop-1-ene (3.6 mL, 35.6 mmol) in THF (10 mL) was added dropwise to the cyanopiperidine solution at −78° C. The reaction was stirred at −78° C. for 30 min. The reaction mixture was poured into brine and EtOAc (100 mL). The organic layer was washed with brine (2×75 mL), dried over anhydrous Na$_2$SO$_4$, filtered, and concentrated. The resulting oil was purified on a silica column (0 to 5% MeOH in DCM) to yield 1-(4-methoxybenzyl)-4-(2-methylallyl)piperidine-4-carbonitrile (3700 mg, 13.0 mmol, 73% yield) as a white solid. $^1$H NMR (400 MHz, Chloroform-d) δ 7.23 (d, J=8.0 Hz, 2H), 6.91-6.83 (m, 2H), 5.01-4.95 (m, 1H), 4.88-4.83 (m, 1H), 3.82 (s, 3H), 3.49 (s, 2H), 2.87 (d, J=12.3 Hz, 2H), 2.37-2.26 (m, 4H), 1.97-1.89 (m, 5H), 1.64-1.52 (m, 2H). LCMS (ESI, m/z): 285.1 [M+H]$^+$.

Step 3: Preparation of (1-(4-methoxybenzyl)-4-(2-methylallyl)piperidin-4-yl)methanamine

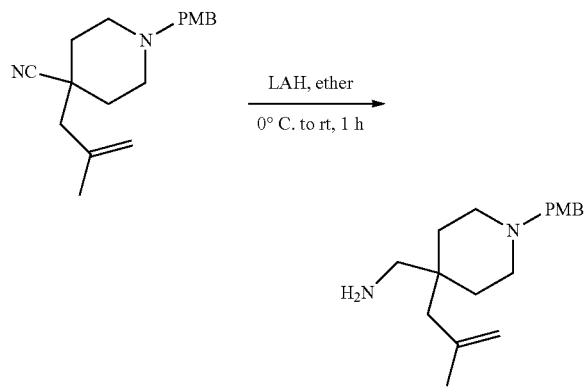

A flask was charged with 1-(4-methoxybenzyl)-4-(2-methylallyl)piperidine-4-carbonitrile (560 mg, 1.97 mmol) and diethyl ether (10 mL). The reaction mixture was cooled to 0° C. and LAH (2.4 M in THF, 3.3 mL, 7.88 mmol) was added dropwise. The reaction stirred for 5 min at 0° C. and then at rt for 1 h. The solution was cooled to 0° C. and H$_2$O (250 μL) was added followed by 10% aq. NaOH (280 μL) and additional H$_2$O (840 μL). The reaction was allowed to warm to rt and stirred for 2 h. The solids were filtered and washed with ether (2×20 mL). The filtrate was concentrated to yield (1-(4-methoxybenzyl)-4-(2-methylallyl)piperidin-4-yl)methanamine (560 mg, 1.94 mmol, 98% yield) as a clear oil that was used without further purification. $^1$H NMR (400 MHz, Chloroform-d) δ 7.28-7.20 (m, 3H), 6.91-6.82 (m, 3H), 4.89 (dd, J=2.3, 1.4 Hz, 1H), 4.73-4.67 (m, 1H), 3.82 (s, 3H), 3.47 (d, J=9.3 Hz, 2H), 2.63 (s, 2H), 2.41 (dh, J=22.7, 5.7 Hz, 4H), 2.08 (s, 2H), 1.80 (s, 3H), 1.50 (q, J=9.7, 7.4 Hz, 4H). LCMS (ESI, m/z): 289.2 [M+H]$^+$.

Step 4: Preparation of N-(4-chlorobenzyl)-1-(1-(4-methoxybenzyl)-4-(2-methylallyl)piperidin-4-yl)methanamine

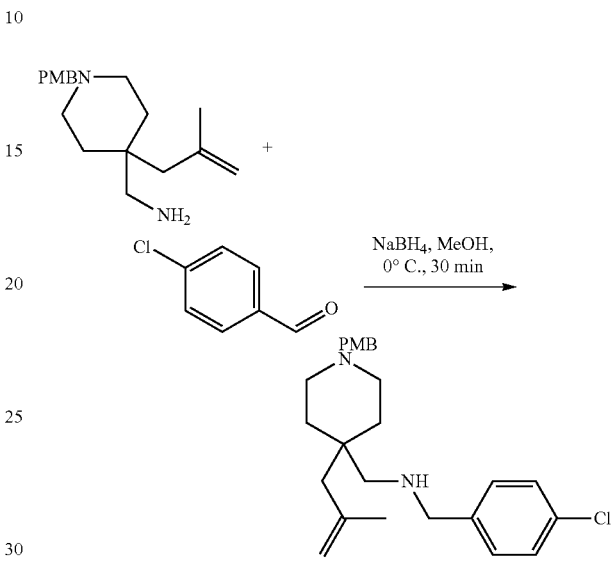

A flask was charged with molecular sieves (1 g), (1-(4-methoxybenzyl)-4-(2-methylallyl)piperidin-4-yl)methanamine (288 mg, 1.0 mmol) and MeOH (20 mL). 4-Chlorobenzaldehyde (140.5 mg, 1 mmol) was added and the reaction mixture was stirred for 1 h. The reaction was filtered and concentrated and resuspended in MeOH (20 mL) and cooled to 0° C. Sodium borohydride (100 mg, 2.70 mmol) was added and the reaction mixture was stirred at 0° C. for 30 min. The reaction mixture was then quenched at 0° C. with 1 N HCl (5 ml) and sat. Na$_2$CO$_3$ (30 mL), and the solution was extracted with DCM (3×75 mL). The combined organic layers were dried over anhydrous Na$_2$SO$_4$, filtered, and concentrated. The resulting oil was purified on a silica column (0 to 10% NH$_3$ (2M MeOHic) in DCM) to yield N-(4-chlorobenzyl)-1-(1-(4-methoxybenzyl)-4-(2-methylallyl)piperidin-4-yl)methanamine (358 mg, 0.867 mmol, 87% yield) as a clear oil. $^1$H NMR (400 MHz, Chloroform-d) δ 7.34-7.20 (m, 6H), 6.90-6.83 (m, 2H), 4.86 (s, 1H), 4.67 (s, 1H), 3.82 (d, J=1.5 Hz, 3H), 3.73 (s, 2H), 3.44 (s, 2H), 2.51-2.40 (m, 4H), 2.34-2.28 (m, 2H), 2.13 (s, 2H), 1.78 (s, 3H), 1.54 (s, 4H). LCMS (ESI, m/z): 413.3 [M+H]$^+$.

Step 5: Preparation of 2-(4-chlorobenzyl)-8-(4-methoxybenzyl)-3,3-dimethyl-2,8-diazaspiro[4.5]decane

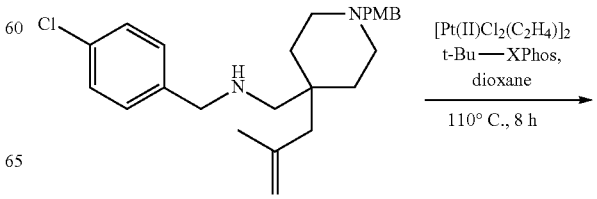

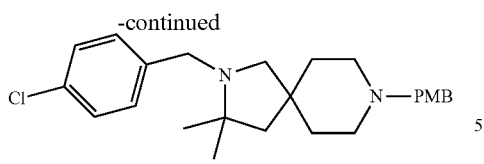

A vial was charged with N-(4-chlorobenzyl)-1-(1-(4-methoxybenzyl)-4-(2-methylallyl)piperidin-4-yl)methanamine (220 mg, 0.530 mmol) and 1,4-dioxane (5 mL). Nitrogen was bubbled through the solution for 10 min. [Pt(II)Cl$_2$(C$_2$H$_4$)]$_2$ (34 mg, 0.110 mmol) and tBuXPhos (54 mg, 0.130 mmol) were added and the reaction was heated to 110° C. for 8 h. The reaction mixture was poured into EtOAc (150 mL) and washed with aq. Na$_2$CO$_3$ (2×50 mL). The organic layer was dried over anhydrous Na$_2$SO$_4$, filtered, and concentrated. The resulting oil was purified on a silica column (0 to 5% NH$_3$ (2M methanolic in DCM) to yield 2-(4-chlorobenzyl)-8-(4-methoxybenzyl)-3,3-dimethyl-2,8-diazaspiro[4.5]decane (119 mg, 0.288 mmol, 54% yield) as a white clear oil. $^1$H NMR (400 MHz, Chloroform-d) δ 7.33-7.25 (m, 4H), 7.25-7.13 (m, 2H), 6.89-6.82 (m, 2H), 3.81 (s, 3H), 3.48 (s, 2H), 3.38 (s, 2H), 2.49-2.18 (m, 6H), 1.57 (s, 6H), 1.10 (d, J=1.5 Hz, 6H). LCMS (ESI, m/z): 413.3 [M+H]$^+$.

Step 6: Preparation of 1,1,1,3,3,3-hexafluoropropan-2-yl 2-(4-chlorobenzyl)-3,3-dimethyl-2,8-diazaspiro[4.5]decane-8-carboxylate

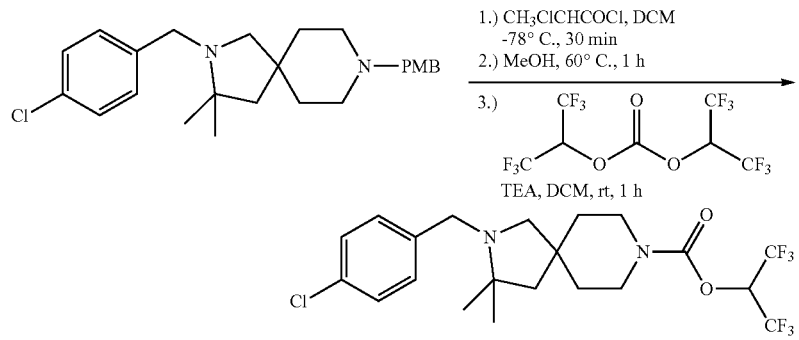

A solution of 1-chloroethyl chloroformate (0.02 mL, 0.170 mmol) in DCM (1 mL) was added dropwise to a solution of 2-(4-chlorobenzyl)-8-(4-methoxybenzyl)-3,3-dimethyl-2,8-diazaspiro[4.5]decane (48 mg, 0.120 mmol) in DCM (1 mL) at 0° C. The reaction was stirred at 0° C. for 20 min and concentrated. The crude material was resuspended in MeOH (5 mL) and heated to 60° C. for 1 h. The reaction mixture was concentrated, and DCM (3 mL) and TEA (100 µL) were added to the residue. The mixture was cooled to 0° C. Bis(1,1,1,3,3,3-hexafluoropropan-2-yl) carbonate (0.09 mL, 0.120 mmol) was added and the reaction mixture was stirred at rt for 1 h. The reaction was quenched with MeOH (0.5 mL) and concentrated. The resulting oil was purified on a silica column (0 to 30% EtOAc in hexanes) to yield 1,1,1,3,3,3-hexafluoropropan-2-yl 2-(4-chlorobenzyl)-3,3-dimethyl-2,8-diazaspiro[4.5]decane-8-carboxylate (22 mg, 0.045 mmol, 39% yield) as a clear oil. $^1$H NMR (400 MHz, Chloroform-d) δ 7.39-7.13 (m, 4H), 5.75 (hept, J=6.3, 1.5 Hz, 1H), 3.63-3.29 (m, 6H), 2.59-2.36 (m, 2H), 1.73-1.51 (m, 6H), 1.25-1.06 (m, 6H). LCMS (ESI, m/z): 487.2 [M+H]$^+$.

Example 49: 1,1,1,3,3,3-Hexafluoropropan-2-yl 2-(4-chloro-2-methoxybenzyl)-3,3-dimethyl-2,8-diazaspiro[4.5]decane-8-carboxylate

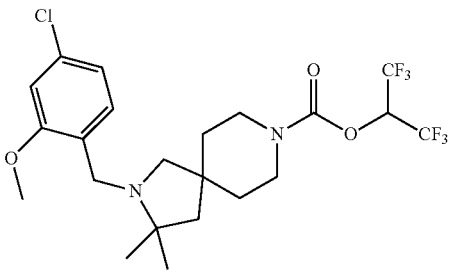 [SMILES: COc1cc(Cl)ccc1CN1CC2(CCN(C(=O)OC(C(F)(F)F)C(F)(F)F)CC2)CC1(C)C]

The title compound was prepared from (1-(4-methoxybenzyl)-4-(2-methylallyl)piperidin-4-yl)methanamine and 4-chloro-2-methoxybenzaldehyde according to the representative procedure of Example 48, Steps 4-6 and yielded 1,1,1,3,3,3-hexafluoropropan-2-yl 2-(4-chloro-2-methoxybenzyl)-3,3-dimethyl-2,8-diazaspiro[4.5]decane-8-carboxylate. $^1$H NMR (400 MHz, Chloroform-d) δ 7.38 (d, J=7.9 Hz, 1H), 6.93 (dt, J=8.1, 2.1 Hz, 1H), 6.84 (t, J=2.2 Hz, 1H), 5.84-5.69 (m, 1H), 3.86-3.80 (m, 3H), 3.53-3.37 (m, 6H), 2.60-2.47 (m, 2H), 1.72-1.53 (m, 6H), 1.13 (s, 6H). LCMS (ESI, m/z): 517.1 [M+H]$^+$.

Example 50: 1,1,1,3,3,3-Hexafluoropropan-2-yl 2-(4-chloro-2-morpholinobenzyl)-3,3-dimethyl-2,8-diazaspiro[4.5]decane-8-carboxylate

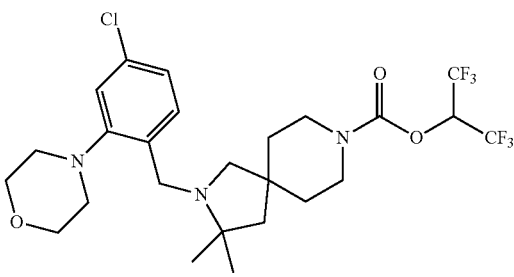 [SMILES: CC1(C)CC2(CCN(C(=O)OC(C(F)(F)F)C(F)(F)F)CC2)CN1Cc1ccc(Cl)cc1N1CCOCC1]

The title compound was prepared from (1-(4-methoxybenzyl)-4-(2-methylallyl)piperidin-4-yl)methanamine and 4-chloro-2-morpholinobenzaldehyde according to the representative procedure of Example 48, Steps 4-6 and yielded 1,1,1,3,3,3-hexafluoropropan-2-yl 2-(4-chloro-2-morpholinobenzyl)-3,3-dimethyl-2,8-diazaspiro[4.5]decane-8-carboxylate as a clear oil. ¹H NMR (400 MHz, Chloroform-d) δ 7.37 (d, J=8.1 Hz, 1H), 7.00-6.91 (m, 2H), 5.66 (dd, J=6.3 Hz, 1H), 3.76 (t, J=4.5 Hz, 4H), 3.47 (s, 2H), 3.39-3.31 (m, 4H), 2.86 (q, J=3.7 Hz, 4H), 2.39 (s, 2H), 1.55 (s, 2H), 1.53-1.43 (m, 4H), 1.06 (d, J=2.3 Hz, 6H). LCMS (ESI, m/z): 572.1 [M+H]⁺.

Example 51: 1,1,1,3,3,3-Hexafluoropropan-2-yl 3,3-dimethyl-2-(2-morpholino-4-(trifluoromethyl)benzyl)-2,8-diazaspiro[4.5]decane-8-carboxylate

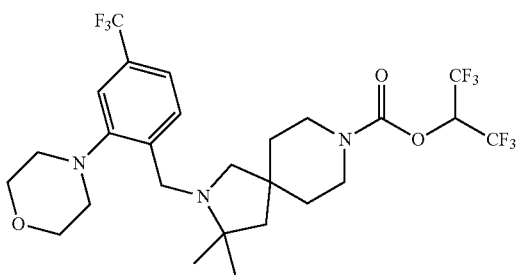 [SMILES: CC1(C)CC2(CCN(C(=O)OC(C(F)(F)F)C(F)(F)F)CC2)CN1Cc1ccc(C(F)(F)F)cc1N1CCOCC1]

Step 1: Preparation of N-(4-methoxybenzyl)-1-(1-(4-methoxybenzyl)-4-(2-methylallyl)piperidin-4-yl)methanamine

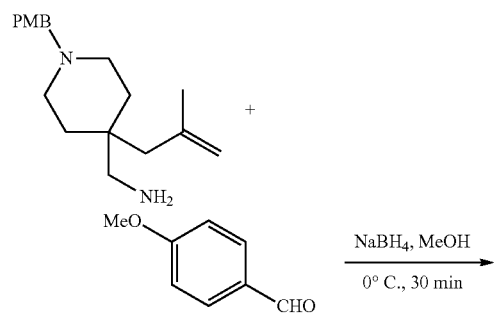

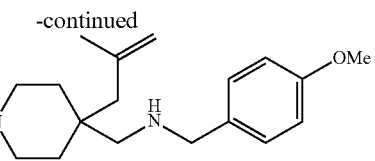

The title compound was prepared from (1-(4-methoxybenzyl)-4-(2-methylallyl)piperidin-4-yl)methanamine and 4-methoxybenzaldehyde according to the representative procedure of Example 48, Step 4 and yielded N-(4-methoxybenzyl)-1-(1-(4-methoxybenzyl)-4-(2-methylallyl)piperidin-4-yl)methanamine. LCMS (ESI, m/z): 409.1 [M+H]⁺.

Step 2: Preparation of 2,8-bis(4-methoxybenzyl)-3,3-dimethyl-2,8-diazaspiro[4.5]decane

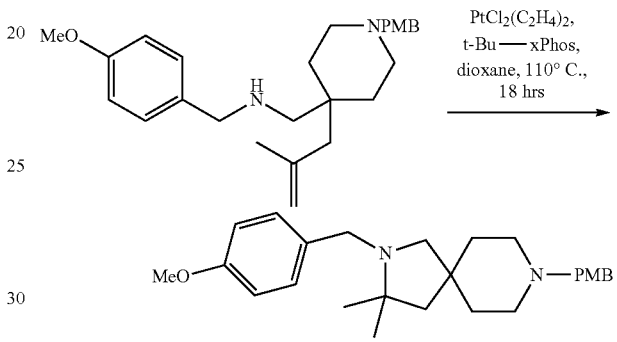

The title compound was prepared from N-(4-methoxybenzyl)-1-(1-(4-methoxybenzyl)-4-(2-methylallyl)piperidin-4-yl)methanamine according to the representative procedure of Example 48, Step 5, except an 18 h reaction time was used. The reaction gave 2,8-bis(4-methoxybenzyl)-3,3-dimethyl-2,8-diazaspiro[4.5]decane. ¹H NMR (400 MHz, Chloroform-d) δ 7.26 (d, J=8.4 Hz, 2H), 6.86 (d, J=8.5 Hz, 2H), 5.75 (hept, J=6.3 Hz, 1H), 3.83 (s, 3H), 3.54-3.36 (m, 6H), 2.48 (s, 2H), 1.66-1.53 (m, 8H), 1.14 (d, J=3.1 Hz, 6H). LCMS (ESI, m/z): 409.2 [M+H]⁺.

Step 3: Preparation of 1,1,1,3,3,3-hexafluoropropan-2-yl 2-(4-methoxybenzyl)-3,3-dimethyl-2,8-diazaspiro[4.5]decane-8-carboxylate

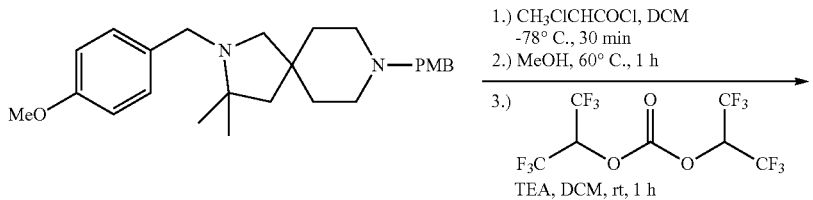

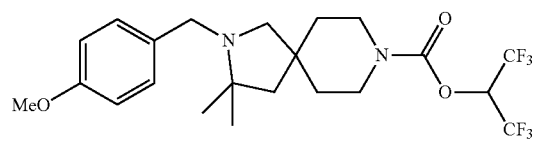

119

The title compound was prepared from 2,8-bis(4-methoxybenzyl)-3,3-dimethyl-2,8-diazaspiro[4.5]decane according to the representative procedure of Example 48, Step 6 and yielded 1,1,1,3,3,3-hexafluoropropan-2-yl 2-(4-methoxybenzyl)-3,3-dimethyl-2,8-diazaspiro[4.5]decane-8-carboxylate as a clear oil. $^1$H NMR (400 MHz, Chloroform-d) δ 7.26 (s, 2H), 6.93-6.83 (m, 2H), 5.77 (hept, J=6.3 Hz, 1H), 3.83 (s, 3H), 3.56-3.34 (m, 6H), 2.49 (d, J=1.6 Hz, 2H), 1.65 (s, 2H), 1.59 (dt, J=10.3, 5.5 Hz, 4H), 1.15 (d, J=3.2 Hz, 6H). LCMS (ESI, m/z): 483.1 [M+H]$^+$.

Step 4: Preparation of 1,1,1,3,3,3-hexafluoropropan-2-yl 3,3-dimethyl-2,8-diazaspiro[4.5]decane-8-carboxylate

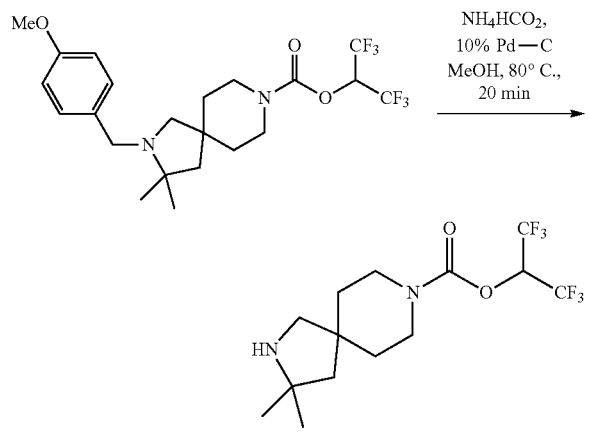

A flask was charged with 1,1,1,3,3,3-hexafluoropropan-2-yl 2-(4-methoxybenzyl)-3,3-dimethyl-2,8-diazaspiro[4.5]decane-8-carboxylate (590 mg, 1.22 mmol), MeOH (20 mL), ammonium formate (385 mg, 6.11 mmol), and 10% palladium on carbon (250 mg, 0.060 mmol). The reaction was heated to 80° C. for 20 min. The reaction mixture was filtered, concentrated, diluted in DCM, washed with sat. Na$_2$CO$_3$ and extracted with DCM (3×). The combined organic layers were dried over anhydrous Na$_2$SO$_4$, filtered, and concentrated. The resulting oil was purified on a silica column (0 to 100% acetone in hexane) to yield 1,1,1,3,3,3-hexafluoropropan-2-yl 3,3-dimethyl-2,8-diazaspiro[4.5]decane-8-carboxylate (400 mg, 1.10 mmol, 90% yield) as a clear oil. $^1$H NMR (400 MHz, Chloroform-d) δ 5.73 (hept, J=6.2 Hz, 1H), 3.59-3.48 (m, 2H), 3.44-3.32 (m, 2H), 2.83 (s, 2H), 1.84 (br s, 1H), 1.63-1.43 (m, 6H), 1.17 (s, 6H). LCMS (ESI, m/z): 363.1 [M+H]$^+$.

Step 5: Preparation of 4-(trifluoromethyl)-2-morpholinobenzaldehyde

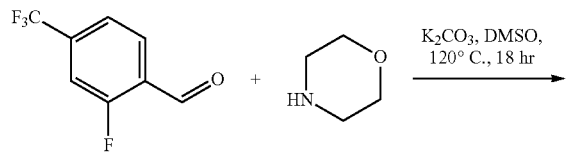

120

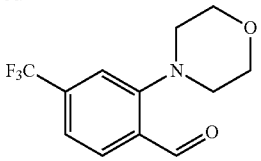

The title compound was prepared from 4-(trifluoromethyl)-2-fluorobenzaldehyde and morpholine according to the representative procedure of Example 16, Step 1, with the exception that DMSO and 120° C. were used, and yielded 4-(trifluoromethyl)-2-morpholinobenzaldehyde as a yellow solid. $^1$H NMR (400 MHz, Chloroform-d) δ 10.21 (s, 1H), 7.73 (d, J=8.3 Hz, 1H), 7.20-6.96 (m, 2H), 4.11-3.77 (m, 4H), 3.17-2.96 (m, 4H). LCMS (ESI, m/z): 226.0 [M+H]$^+$.

Step 6: Preparation of 1,1,1,3,3,3-hexafluoropropan-2-yl 3,3-dimethyl-2-(2-morpholino-4-(trifluoromethyl)benzyl)-2,8-diazaspiro[4.5]decane-8-carboxylate

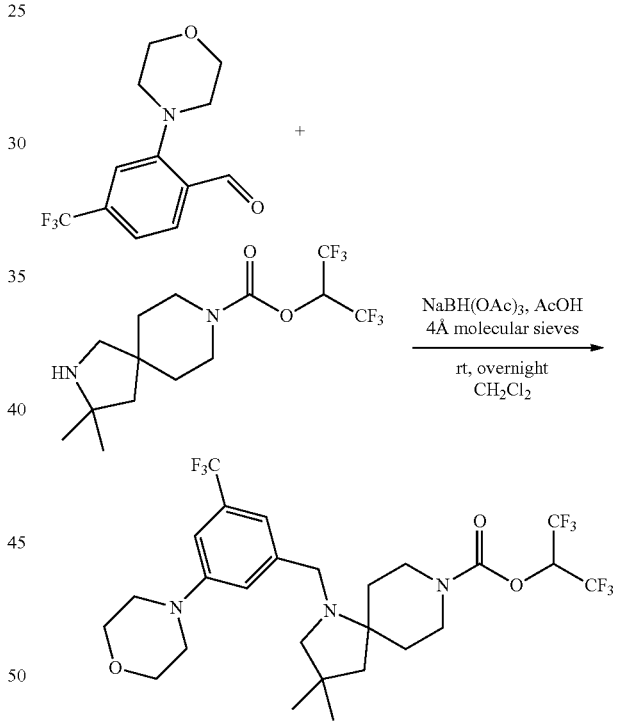

A vial was charged with 2-morpholino-4-(trifluoromethyl)benzaldehyde (42 mg, 0.170 mmol), 1,1,1,3,3,3-hexafluoropropan-2-yl 3,3-dimethyl-2,8-diazaspiro[4.5]decane-8-carboxylate, and DCM (2 mL). Molecular sieves (500 mg) and acetic acid (7 mg, 0.110 mmol) were added and the reaction mixture was stirred for 30 min. NaBH(OAc)$_3$ (35 mg, 0.170 mmol) was added and the mixture was stirred overnight at rt. The mixture was poured into brine (30 mL) and extracted with DCM (2×50 mL). The combined organic layers were dried over anhydrous Na$_2$SO$_4$, filtered, and concentrated. The resulting oil was purified on a silica column (0 to 50% EtOAc in hexane) to yield 1,1,1,3,3,3-hexafluoropropan-2-yl 3,3-dimethyl-2-(2-morpholino-4-(trifluoromethyl)benzyl)-2,8-diazaspiro[4.5]decane-8-carboxylate (45 mg, 0.072 mmol, 66% yield) as a white solid. $^1$H NMR (400 MHz, Chloroform-d) δ 7.67 (d, J=8.0 Hz, 1H), 7.36-7.25 (m, 2H), 5.81-5.67 (m, 2H), 3.87 (t, J=3.7 Hz, 4H), 3.63 (s, 2H), 3.47-3.41 (m, 4H), 3.00-2.94 (m, 4H), 2.49 (s, 2H), 1.72-1.64 (m, 2H), 1.64-1.54 (m, 4H), 1.16 (s, 6H). LCMS (ESI, m/z): 606.1 [M+H]$^+$.

Example 52: 1,1,1,3,3,3-Hexafluoropropan-2-yl 2-(2-(8-oxa-2-azaspiro[4.5]decan-2-yl)-4-(trifluoromethyl)benzyl)-3,3-dimethyl-2,8-diazaspiro[4.5]decane-8-carboxylate

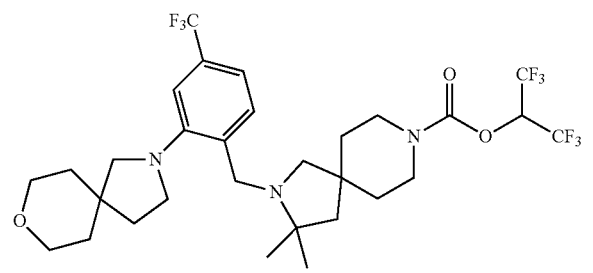 [SMILES: CC1(C)CC2(CCN(C(=O)OC(C(F)(F)F)C(F)(F)F)CC2)CN1Cc1ccc(C(F)(F)F)cc1N1CCC2(CCOCC2)C1]

The title compound was prepared from 1,1,1,3,3,3-hexafluoropropan-2-yl 3,3-dimethyl-2,8-diazaspiro[4.5]decane-8-carboxylate, and 2-fluoro-4-(trifluoromethyl)benzaldehyde according to the representative procedure of Example 51, Steps 5-6 and yielded 1,1,1,3,3,3-hexafluoropropan-2-yl 2-(2-(8-oxa-2-azaspiro[4.5]decan-2-yl)-4-(trifluoromethyl)benzyl)-3,3-dimethyl-2,8-diazaspiro[4.5]decane-8-carboxylate as a clear oil. $^1$H NMR (400 MHz, Chloroform-d) δ 7.68 (d, J=8.0 Hz, 1H), 7.16 (d, J=8.0 Hz, 1H), 7.10 (s, 1H), 5.74 (hept, J=6.3 Hz, 1H), 3.71 (h, J=7.5 Hz, 4H), 3.55 (s, 2H), 3.44 (qt, J=13.7, 7.0 Hz, 4H), 3.27 (td, J=6.7, 4.5 Hz, 2H), 3.07 (s, 2H), 2.47-2.41 (m, 2H), 1.85 (t, J=7.0 Hz, 2H), 1.77-1.66 (m, 5H), 1.59 (dt, J=10.5, 5.7 Hz, 5H), 1.15 (d, J=2.2 Hz, 6H). LCMS (ESI, m/z): 660.1 [M+H]$^+$.

Example 53: 1,1,1,3,3,3-Hexafluoropropan-2-yl 2-(2-(4-(methoxycarbonyl)piperidin-1-yl)-4-(trifluoromethyl)benzyl)-3,3-dimethyl-2,8-diazaspiro[4.5]decane-8-carboxylate

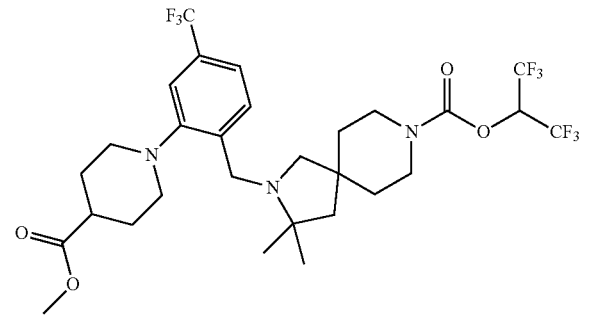 [SMILES: COC(=O)C1CCN(c2cc(C(F)(F)F)ccc2CN2CC3(CCN(C(=O)OC(C(F)(F)F)C(F)(F)F)CC3)CC2(C)C)CC1]

The title compound was prepared from 1,1,1,3,3,3-hexafluoropropan-2-yl 3,3-dimethyl-2,8-diazaspiro[4.5]decane-8-carboxylate, methyl piperidine-4-carboxylate, and 2-fluoro-4-(trifluoromethyl)benzaldehyde according to the representative procedure of Example 51, Steps 5-6 and yielded 1,1,1,3,3,3-hexafluoropropan-2-yl 2-(2-(4-(methoxycarbonyl)piperidin-1-yl)-4-(trifluoromethyl)benzyl)-3,3-dimethyl-2,8-diazaspiro[4.5]decane-8-carboxylate as a white solid. $^1$H NMR (400 MHz, Chloroform-d) δ 7.70 (d, J=8.0 Hz, 1H), 7.35-7.28 (m, 1H), 7.26 (s, 1H), 5.76 (hept, J=5.9 Hz, 1H), 3.74 (d, J=1.3 Hz, 3H), 3.61 (s, 2H), 3.45 (s, 4H), 3.16 (d, J=11.6 Hz, 2H), 2.73 (q, J=10.7 Hz, 2H), 2.48 (s, 3H), 2.05 (d, J=12.2 Hz, 2H), 2.00-1.86 (m, 2H), 1.72-1.51 (m, 6H), 1.17 (s, 6H). LCMS (ESI, m/z): 662.1 [M+H]$^+$.

Example 54: 1,1,1,3,3,3-Hexafluoropropan-2-yl 2-(3-chloro-2-morpholinobenzyl)-3,3-dimethyl-2,8-diazaspiro[4.5]decane-8-carboxylate

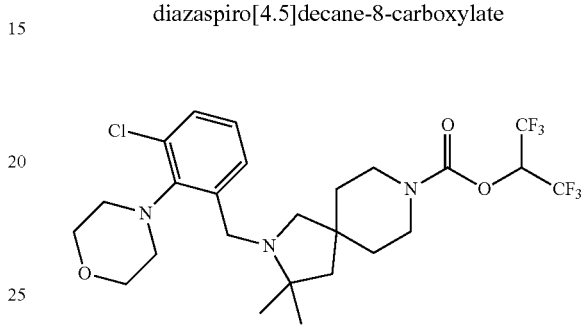

The title compound was prepared from 1,1,1,3,3,3-hexafluoropropan-2-yl 3,3-dimethyl-2,8-diazaspiro[4.5]decane-8-carboxylate, morpholine, and 2-fluoro-3-chlorobenzaldehyde according to the representative procedure of Example 51, Steps 5-6 and yielded 1,1,1,3,3,3-hexafluoropropan-2-yl 2-(3-chloro-2-morpholinobenzyl)-3,3-dimethyl-2,8-diazaspiro[4.5]decane-8-carboxylate as a light yellow solid. $^1$H NMR (400 MHz, Chloroform-d) δ 7.43 (dd, J=7.6, 1.7 Hz, 1H), 7.20 (dd, J=7.9, 1.7 Hz, 1H), 7.08 (t, J=7.8 Hz, 1H), 5.73 (hept, J=6.3 Hz, 1H), 3.88 (dt, J=10.7, 3.0 Hz, 2H), 3.79-3.58 (m, 6H), 3.43 (dt, J=7.7, 4.0 Hz, 4H), 2.78-2.70 (m, 2H), 2.54-2.42 (m, 2H), 1.67-1.63 (m, 2H), 1.64-1.53 (m, 4H), 1.14 (d, J=2.1 Hz, 6H). LCMS (ESI, m/z): 572.1 [M+H]$^+$.

Example 55: 1,1,1,3,3,3-Hexafluoropropan-2-yl 3,3-dimethyl-2-(2-(tetrahydro-1H-furo[3,4-c] pyrrol-5(3H)-yl)-4-(trifluoromethyl)benzyl)-2,8-diazaspiro[4.5]decane-8-carboxylate

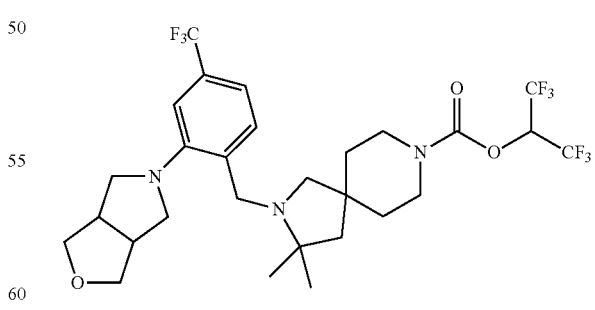

The title compound was prepared from 1,1,1,3,3,3-hexafluoropropan-2-yl 3,3-dimethyl-2,8-diazaspiro[4.5]decane-8-carboxylate, hexahydro-1H-furo[3,4-c]pyrrole, and 2-fluoro-4-(trifluoromethyl)benzaldehyde according to the representative procedure of Example 51, Steps 5-6 and yielded 1,1,1,3,3,3-hexafluoropropan-2-yl 3,3-dimethyl-2-

(2-(tetrahydro-1H-furo[3,4-c]pyrrol-5(3H)-yl)-4-(trifluoromethyl)benzyl)-2,8-diazaspiro[4.5]decane-8-carboxylate as a white solid. ¹H NMR (400 MHz, Chloroform-d) δ 7.74 (d, J=8.0 Hz, 1H), 7.33-7.20 (m, 2H), 5.75 (hept, J=6.3 Hz, 1H), 4.07 (dd, J=8.7, 6.3 Hz, 2H), 3.67-3.60 (m, 2H), 3.59 (s, 2H), 3.55-3.36 (m, 4H), 3.20-3.09 (m, 2H), 3.02-2.93 (m, 4H), 2.46 (s, 2H), 1.68 (s, 2H), 1.62 (dt, J=10.9, 5.7 Hz, 4H), 1.17 (d, J=2.4 Hz, 6H). LCMS (ESI, m/z): 632 [M+H]⁺.

Example 56: 1,1,1,3,3,3-Hexafluoropropan-2-yl 2-(2-(8-oxa-2-azaspiro[4.5]decan-2-yl)-6-(trifluoromethyl)benzyl)-3,3-dimethyl-2,8-diazaspiro[4.5]decane-8-carboxylate

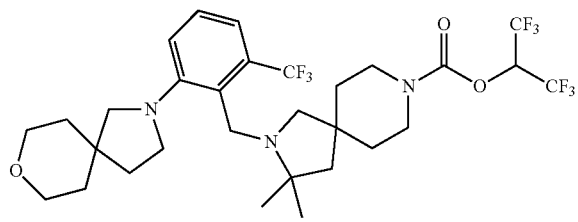 [SMILES: CC1(C)CC2(CCN(C(=O)OC(C(F)(F)F)C(F)(F)F)CC2)CN1Cc1c(N2CCC3(CCOCC3)C2)cccc1C(F)(F)F]

The title compound was prepared from 1,1,1,3,3,3-hexafluoropropan-2-yl 3,3-dimethyl-2,8-diazaspiro[4.5]decane-8-carboxylate, 8-oxa-2-azaspiro[4.5]decane, and 2-fluoro-6-(trifluoromethyl)benzaldehyde according to the representative procedure of Example 51, Steps 5-6 with the following modifications to Step 6: a vial was charged with 2-(8-oxa-2-azaspiro[4.5]decan-2-yl)-6-(trifluoromethyl)benzaldehyde (100 mg, 0.320 mmol) and 1,1,1,3,3,3-hexafluoropropan-2-yl 3,3-dimethyl-2,8-diazaspiro[4.5]decane-8-carboxylate (80 mg, 0.220 mmol) and DCM (2.0 mL). Molecular sieves (500 mg) and acetic acid (15 mg, 0.250 mmol) were added and the reaction was stirred for 30 min. NaBH(OAc)₃ (50 mg, 0.240 mmol) was added and the mixture was stirred overnight at rt. More 2-(8-oxa-2-azaspiro[4.5]decan-2-yl)-6-(trifluoromethyl)benzaldehyde (100 mg, 0.320 mmol) and NaBH(OAc)₃ (50 mg, 0.240 mmol) were added and the mixture was stirred an additional 24 h. The mixture was poured into brine (30 mL) and extracted with DCM (2×50 mL). The combined organic layers were dried over anhydrous Na₂SO₄, filtered, and concentrated. The resulting oil was purified on a silica column (0 to 50% EtOAc in hexane) to yield 1,1,1,3,3,3-hexafluoropropan-2-yl 2-(2-(8-oxa-2-azaspiro[4.5]decan-2-yl)-6-(trifluoromethyl)benzyl)-3,3-dimethyl-2,8-diazaspiro[4.5]decane-8-carboxylate (10 mg, 0.014 mmol, 7% yield) as a light yellow solid. ¹H NMR (400 MHz, Chloroform-d) δ 7.31-7.05 (m, 3H), 5.63 (hept, J=6.1 Hz, 1H), 3.75 (s, 2H), 3.70-3.50 (m, J=4.2 Hz, 4H), 3.26 (s, 4H), 3.08 (td, J=7.1, 3.2 Hz, 2H), 2.96-2.80 (m, 2H), 1.77 (t, J=6.9 Hz, 2H), 1.65-1.57 (m, 4H), 1.51 (s, 2H), 1.45 (s, 2H), 1.38 (dt, J=11.3, 6.1 Hz, 4H), 0.98 (s, 6H). LCMS (ESI, m/z): 660.1 [M+H]⁺.

Example 57: 1,1,1,3,3,3-Hexafluoropropan-2-yl 3,3-dimethyl-2-(2-(tetrahydro-1H-furo[3,4-c]pyrrol-5(3H)-yl)-6-(trifluoromethyl)benzyl)-2,8-diazaspiro[4.5]decane-8-carboxylate

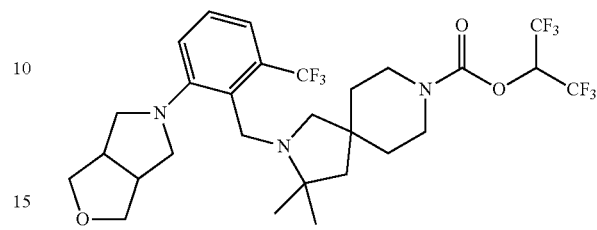

The title compound was prepared from 1,1,1,3,3,3-hexafluoropropan-2-yl 3,3-dimethyl-2,8-diazaspiro[4.5]decane-8-carboxylate, hexahydro-1H-furo[3,4-c]pyrrole, and 2-fluoro-6-(trifluoromethyl)benzaldehyde according to the representative procedure of Example 56, yielding 1,1,1,3,3,3-hexafluoropropan-2-yl 3,3-dimethyl-2-(2-(tetrahydro-1H-furo[3,4-c]pyrrol-5(3H)-yl)-6-(trifluoromethyl)benzyl)-2,8-diazaspiro[4.5]decane-8-carboxylate as a white solid. ¹H NMR (400 MHz, Chloroform-d) δ 7.43 (dd, J=5.1, 4.0 Hz, 1H), 7.35-7.27 (m, 2H), 5.74 (hept, J=6.1 Hz, 1H), 4.13-4.01 (m, 1H), 3.89 (s, 2H), 3.74-3.58 (m, 2H), 3.49-3.24 (m, 4H), 3.21-3.02 (m, 3H), 3.02-2.81 (m, 5H), 2.32 (s, 2H), 1.56 (s, 2H), 1.54-1.40 (m, 5H), 1.10 (s, 6H). LCMS (ESI, m/z): 632 [M+H]⁺.

Example 58: 1,1,1,3,3,3-Hexafluoropropan-2-yl 2-(3-(pyrrolidin-1-yl)benzyl)-2,8-diazaspiro[4.5]decane-8-carboxylate

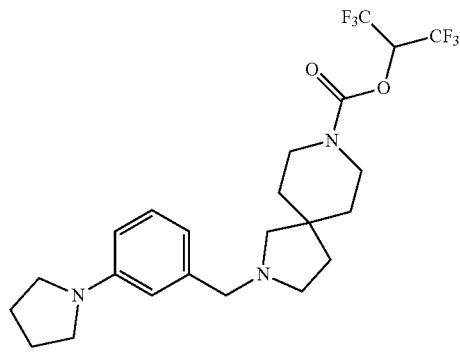 [SMILES: O=C(OC(C(F)(F)F)C(F)(F)F)N1CCC2(CCN(Cc3cccc(N4CCCC4)c3)C2)CC1]

The title compound was synthesized directly from commercially available 3-(pyrrolidin-1-yl)benzaldehyde and commercially available tert-butyl 2,8-diazaspiro[4.5]decane-2-carboxylate according to the representative procedure of Example 1, Steps 1-3 to provide 1,1,1,3,3,3-hexafluoropropan-2-yl 2-(3-(pyrrolidin-1-yl)benzyl)-2,8-diazaspiro[4.5]decane-8-carboxylate as a clear oil. ¹H NMR (400 MHz, Chloroform-d) δ 7.23-7.11 (m, 1H), 6.68-6.46 (m, 3H), 5.84-5.68 (m, 1H), 3.64-3.41 (m, 6H), 3.36-3.24 (m, 4H), 2.75-2.60 (m, 2H), 2.49-2.36 (m, 2H), 2.07-1.95 (m, 4H), 1.72-1.66 (m, 2H), 1.66-1.57 (m, 4H). LCMS (ESI, m/z): 494.2 [M+H]⁺.

Example 59: 1,1,1,3,3,3-Hexafluoropropan-2-yl 2-(2-(pyrrolidin-1-yl)-6-(trifluoromethyl)benzyl)-2,8-diazaspiro[4.5]decane-8-carboxylate

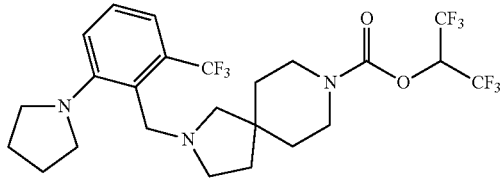 [SMILES: O=C(OC(C(F)(F)F)C(F)(F)F)N1CCC2(CCN(Cc3c(N4CCCC4)cccc3C(F)(F)F)C2)CC1]

Step 1: Preparation of 2-(pyrrolidin-1-yl)-6-(trifluoromethyl)benzaldehyde

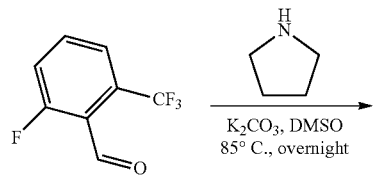

A flask was charged with 2-fluoro-6-(trifluoromethyl)benzaldehyde (6.00 g, 31.2 mmol, 1.00 equiv), pyrrolidine (3.33 g, 46.8 mmol, 1.50 equiv), potassium carbonate (10.8 g, 78.1 mmol, 2.50 equiv), and DMSO (50 mL) under nitrogen. The resulting solution was stirred overnight at 85° C. and diluted with H$_2$O (20 mL). The resulting solution was extracted with EtOAc (3×50 mL) and the organic layers were combined, washed with H$_2$O (2×20 mL), dried over anhydrous Na$_2$SO$_4$, filtered and concentrated. The residue was purified on a silica gel column (9:91 EtOAc/petroleum ether) to provide 5.98 g (79% yield) of 2-(pyrrolidin-1-yl)-6-(trifluoromethyl)benzaldehyde as a yellow oil. LCMS (ESI, m/z): 244 [M+H]$^+$.

Step 2: Preparation of tert-butyl 2-(2-(pyrrolidin-1-yl)-6-(trifluoromethyl)benzyl)-2,8-diazaspiro[4.5]decane-8-carboxylate

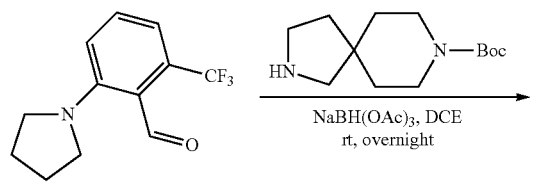

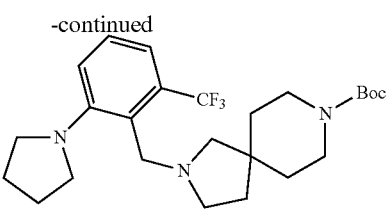

A flask was charged with 2-(pyrrolidin-1-yl)-6-(trifluoromethyl)benzaldehyde (200 mg, 0.820 mmol, 1.00 equiv), tert-butyl 2,8-diazaspiro[4.5]decane-8-carboxylate (198 mg, 0.820 mmol, 1.00 equiv), and DCE (10 mL). The resulting solution was stirred for 30 min at rt and NaBH(OAc)$_3$ (523 mg, 2.47 mmol, 3.00 equiv) was added. The resulting solution was stirred overnight at rt and quenched with H$_2$O (10 mL). The resulting solution was extracted with DCM (3×15 mL) and the organic layers were combined, washed with brine (15 mL), dried over anhydrous Na$_2$SO$_4$, filtered and concentrated. The residue was purified on a silica gel column (1:1 EtOAc/petroleum ether) to provide 230 mg (60% yield) of tert-butyl 2-(2-(pyrrolidin-1-yl)-6-(trifluoromethyl)benzyl)-2,8-diazaspiro[4.5]decane-8-carboxylate as a colorless oil. LCMS (ESI, m/z): 468 [M+H]$^+$.

Step 3: Preparation of 2-(2-(pyrrolidin-1-yl)-6-(trifluoromethyl)benzyl)-2,8-diazaspiro[4.5]decane

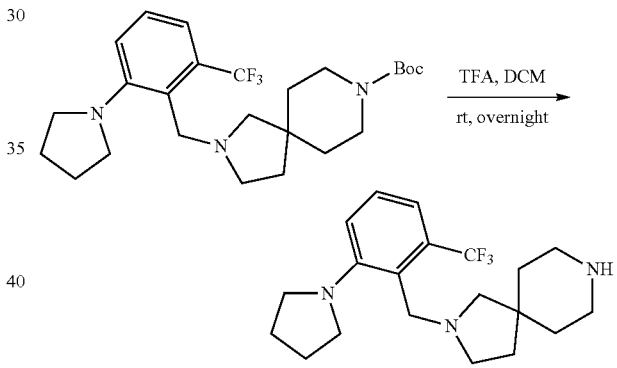

A flask was charged with tert-butyl 2-(2-(pyrrolidin-1-yl)-6-(trifluoromethyl)benzyl)-2,8-diazaspiro[4.5]decane-8-carboxylate (230 mg, 0.490 mmol, 1.00 equiv), and DCM (8 mL). TFA (1 mL) was added at 0° C. The resulting solution was stirred overnight at rt and concentrated to provide 260 mg (crude) of 2-(2-(pyrrolidin-1-yl)-6-(trifluoromethyl)benzyl)-2,8-diazaspiro[4.5]decane as a yellow oil. LCMS (ESI, m/z): 368 [M+H]$^+$.

Step 4: Preparation of 1,1,1,3,3,3-hexafluoropropan-2-yl 2-(2-(pyrrolidin-1-yl)-6-(trifluoromethyl)benzyl)-2,8-diazaspiro[4.5]decane-8-carboxylate

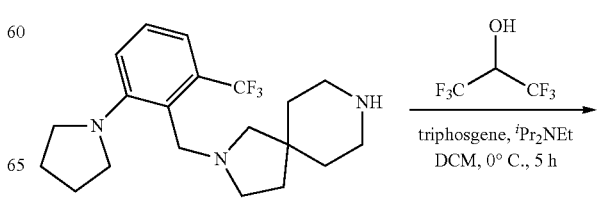

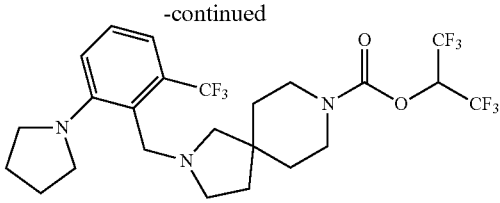

A flask was charged with triphosgene (51.0 mg, 0.170 mmol, 0.17 equiv), and DCM (10 mL) under nitrogen. HFIP (166 mg, 0.990 mmol, 1.00 equiv) was added at 0° C., followed by DIEA (509 mg, 3.94 mmol, 3.99 equiv). The resulting solution was stirred for 1 h at 0° C., after which 2-(2-(pyrrolidin-1-yl)-6-(trifluoromethyl)benzyl)-2,8-diazaspiro[4.5]decane (181 mg, 0.490 mmol, 0.50 equiv) was added. The resulting solution was stirred for 5 h at 0° C. and concentrated. The crude product was purified by preparative HPLC to provide 24.0 mg (4% yield) of 1,1,1,3,3,3-hexafluoropropan-2-yl 2-(2-(pyrrolidin-1-yl)-6-(trifluoromethyl)benzyl)-2,8-diazaspiro[4.5]decane-8-carboxylate as a white solid. $^1$H NMR (300 MHz, Chloroform-d) δ 7.14-7.38 (m, 3H), 5.67-5.80 (m, 1H), 3.79 (s, 2H), 3.36-3.49 (m, 4H), 3.13 (br, 4H), 2.46-2.51 (t, J=6.8 Hz, 2H), 2.27 (s, 2H), 1.92 (br, 4H), 1.52-1.57 (m, 6H). LCMS (ESI, m/z): 562 [M+H]$^+$.

Example 60: 1,1,1,3,3,3-Hexafluoropropan-2-yl 1-(2-chlorobenzyl)-1,8-diazaspiro[4.5]decane-8-carboxylate

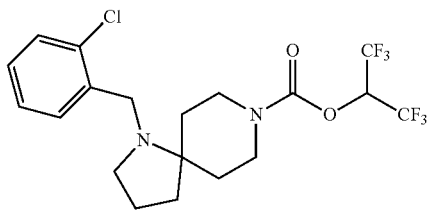 [SMILES: O=C(OC(C(F)(F)F)C(F)(F)F)N1CCC2(CCCN2Cc2ccccc2Cl)CC1]

Step 1: Preparation of tert-butyl 1-(2-chlorobenzyl)-1,8-diazaspiro[4.5]decane-8-carboxylate

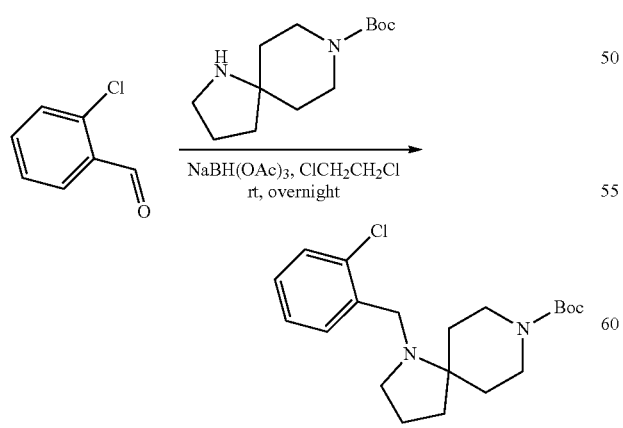

A flask was charged with 2-chlorobenzaldehyde (1.00, 7.11 mmol, 1.00 equiv), tert-butyl 1,8-diazaspiro[4.5]decane-8-carboxylate (2.00 g, 8.32 mmol, 1.20 equiv), and DCE (20 mL). The mixture was stirred for 1 h at rt. NaBH(OAc)$_3$ (4.50 g, 21.2 mmol, 3.00 equiv) was added. The resulting solution was stirred overnight at rt and then diluted with H$_2$O (20 mL). The resulting mixture was extracted with DCM (3×20 mL). The organic layers were combined, washed with brine (1x 100 mL), dried over anhydrous Na$_2$SO$_4$, filtered and concentrated. The residue was purified on a silica gel column with EtOAc/petroleum ether (50/50) to provide 1.90 g (73% yield) of tert-butyl 1-(2-chlorobenzyl)-1,8-diazaspiro[4.5]decane-8-carboxylate as a colorless oil. LCMS (ESI, m/z): 365 [M+H]$^+$.

Step 2: Preparation of 1-(2-chlorobenzyl)-1,8-diazaspiro[4.5]decane

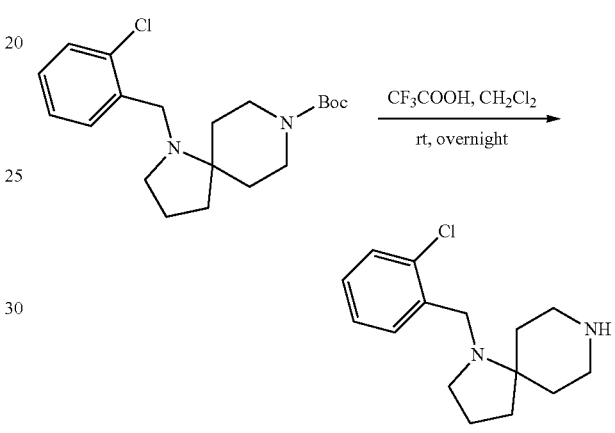

A flask was charged with tert-butyl 1-(2-chlorobenzyl)-1,8-diazaspiro[4.5]decane-8-carboxylate (470 mg, 1.29 mmol, 1.00 equiv), TFA (4 mL), and DCM (10 mL). The resulting solution was stirred overnight at rt and concentrated to yield 300 mg (88% yield) of 1-(2-chlorobenzyl)-1,8-diazaspiro[4.5]decane as a yellow oil. LCMS (ESI, m/z): 265 [M+H]$^+$.

Step 3: Preparation of 1,1,1,3,3,3-hexafluoropropan-2-yl 1-(2-chlorobenzyl)-1,8-diazaspiro[4.5]decane-8-carboxylate

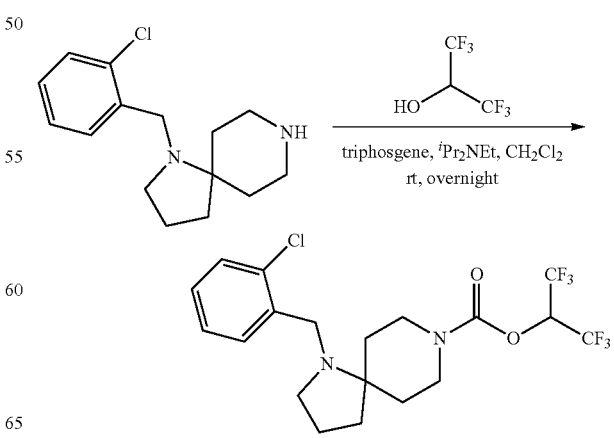

A flask was charged with triphosgene (149 mg, 0.500 mmol, 0.70 equiv), and DCM (15 mL). HFIP (240 mg, 1.43 mmol, 2.00 equiv) and DIEA (740 mg, 5.73 mmol, 8.00 equiv) were added at 0° C. The mixture was stirred for 2 h at rt, after which 1-(2-chlorobenzyl)-1,8-diazaspiro[4.5]decane (190 mg, 0.720 mmol, 1.00 equiv) was added. The resulting solution was stirred overnight at rt, and diluted with H₂O (10 mL). The resulting mixture was extracted with DCM (3×10 mL). The organic layers were combined, washed with brine (1×50 mL), dried over anhydrous Na₂SO₄, filtered and concentrated. The crude product was purified by preparative HPLC to give 114.9 mg (35% yield) of 1,1,1,3,3,3-hexafluoropropan-2-yl 1-(2-chlorobenzyl)-1,8-diazaspiro[4.5]decane-8-carboxylate as a white solid. ¹H NMR (300 MHz, Chloroform-d) δ 7.42-7.59 (m, 1H), 7.32-7.34 (m, 1H), 7.06-7.24 (m, 2H), 5.70-5.83 (m, 1H), 4.21 (t, J=12.4 Hz, 2H), 3.92 (s, 2H), 2.91-3.05 (m, 2H), 2.63-2.76 (m, 2H), 1.72-1.82 (m, 6H), 1.49-1.58 (m, 2H). LCMS (ESI, m/z): 459 [M+H]⁺.

Example 61: 1,1,1,3,3,3-Hexafluoropropan-2-yl 1-(3-chlorobenzyl)-1,8-diazaspiro[4.5]decane-8-carboxylate

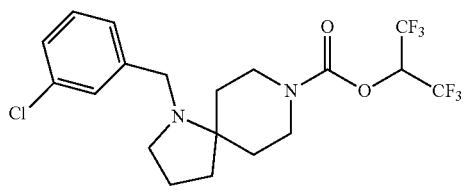 [SMILES: O=C(OC(C(F)(F)F)C(F)(F)F)N1CCC2(CCCN2Cc2cccc(Cl)c2)CC1]

The title compound was synthesized directly from commercially available 3-chlorobenzaldehyde according to the representative procedure of Example 60 to provide 1,1,1,3,3,3-hexafluoropropan-2-yl 1-(3-chlorobenzyl)-1,8-diazaspiro[4.5]decane-8-carboxylate as a colorless oil. ¹H NMR (300 MHz, Chloroform-d) δ 7.32 (s, 1H), 7.16-7.28 (m, 3H), 5.70-5.83 (m, 1H), 4.16-4.26 (m, 2H), 3.51-3.60 (m, 2H), 2.90-3.05 (m, 2H), 2.64-2.76 (m, 2H), 1.64-1.87 (m, 6H), 1.43-1.47 (m, 2H). LCMS (ESI, m/z): 459 [M+H]⁺.

Example 62: 1,1,1,3,3,3-Hexafluoropropan-2-yl 1-(4-chlorobenzyl)-1,8-diazaspiro[4.5]decane-8-carboxylate

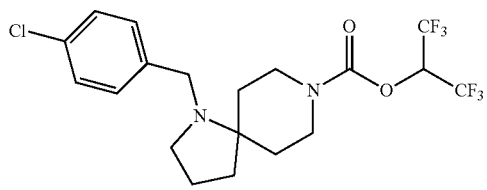 [SMILES: O=C(OC(C(F)(F)F)C(F)(F)F)N1CCC2(CCCN2Cc2ccc(Cl)cc2)CC1]

The title compound was synthesized directly from commercially available 4-chlorobenzaldehyde according to the representative procedure of Example 60 to provide 1,1,1,3,3,3-hexafluoropropan-2-yl 1-(4-chlorobenzyl)-1,8-diazaspiro[4.5]decane-8-carboxylate as a white solid. ¹H NMR (300 MHz, Chloroform-d) δ 7.25 (d, J=2.7 Hz, 4H), 5.69-5.82 (m, 1H), 4.17-4.33 (m, 2H), 3.55 (s, 2H), 2.91-3.05 (m, 2H), 2.64-2.66 (m, 2H), 1.60-1.99 (m, 6H), 1.46-1.50 (m, 2H). LCMS (ESI, m/z): 459 [M+H]⁺.

Example 63: 1,1,1,3,3,3-Hexafluoropropan-2-yl 1-benzyl-1,8-diazaspiro[4.5]decane-8-carboxylate

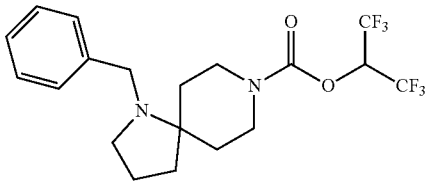 [SMILES: O=C(OC(C(F)(F)F)C(F)(F)F)N1CCC2(CCCN2Cc2ccccc2)CC1]

The title compound was synthesized directly from commercially available benzaldehyde according to the representative procedure of Example 60 to provide 1,1,1,3,3,3-hexafluoropropan-2-yl 1-benzyl-1,8-diazaspiro[4.5]decane-8-carboxylate as a white solid. ¹H NMR (300 MHz, Chloroform-d) δ 7.22-7.31 (m, 5H), 5.70-5.82 (m, 1H), 4.21 (t, J=13.0 Hz, 2H), 3.58 (s, 2H), 2.91-3.05 (m, 2H), 2.68-2.70 (m, 2H), 1.69-1.80 (m, 6H), 1.47-1.51 (m, 2H). LCMS (ESI, m/z): 425 [M+H]⁺.

Example 64: 1,1,1,3,3,3-Hexafluoropropan-2-yl 2-(3-chloro-2-(4,4-difluoropiperidin-1-yl)benzyl)-2,8-diazaspiro[4.5]decane-8-carboxylate

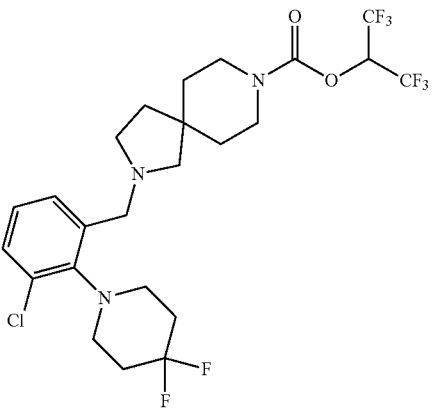 [SMILES: O=C(OC(C(F)(F)F)C(F)(F)F)N1CCC2(CCN(Cc3cccc(Cl)c3N3CCC(F)(F)CC3)C2)CC1]

Step 1: Preparation of 3-chloro-2-(4-hydroxypiperidin-1-yl)benzaldehyde

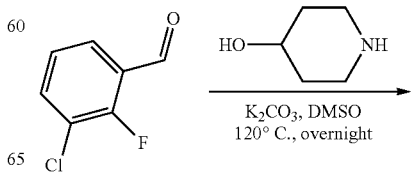

-continued

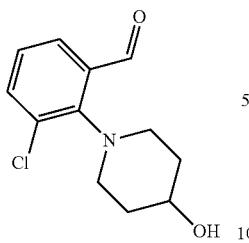

A flask was charged with 3-chloro-2-fluorobenzaldehyde (3.00 g, 18.9 mmol, 1.00 equiv), piperidin-4-ol (2.86 g, 28.3 mmol, 1.49 equiv), potassium carbonate (7.81 g, 56.5 mmol, 2.99 equiv), and DMSO (30 mL) under nitrogen. The resulting solution was stirred overnight at 120° C. and diluted with H$_2$O (15 mL). The resulting solution was extracted with EtOAc (3×30 mL) and the organic layers were combined, dried over anhydrous Na$_2$SO$_4$, filtered and concentrated. The residue was purified on a silica gel column (27:63 EtOAc/petroleum ether) to provide 3.20 g (71% yield) of 3-chloro-2-(4-hydroxypiperidin-1-yl)benzaldehyde as a yellow oil. LCMS (ESI, m/z): 240 [M+H]$^+$.

Step 2: Preparation of tert-butyl 2-(3-chloro-2-(4-hydroxypiperidin-1-yl)benzyl)-2,8-diazaspiro[4.5]decane-8-carboxylate

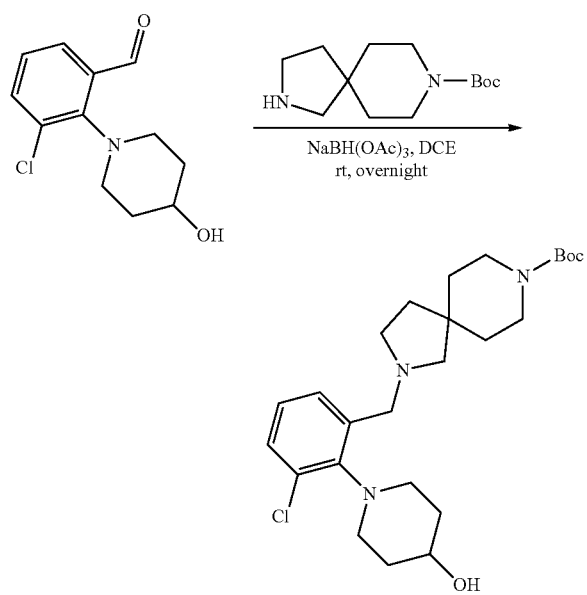

A flask was charged with 3-chloro-2-(4-hydroxypiperidin-1-yl)benzaldehyde (1.00 g, 4.17 mmol, 1.00 equiv), tert-butyl 2,8-diazaspiro[4.5]decane-8-carboxylate (1.00 g, 4.16 mmol, 1.00 equiv), and DCE (20 mL). The resulting solution was stirred for 30 min at rt and NaBH(OAc)$_3$ (2.65 g, 12.5 mmol, 3.00 equiv) was added. The resulting solution was stirred overnight at rt and quenched with H$_2$O (15 mL). The mixture was extracted with DCM (3×20 mL) and the organic layers were combined, dried over anhydrous Na$_2$SO$_4$, filtered and concentrated. The residue was purified on a silica gel column (30:70 EtOAc/petroleum ether) to provide 760 mg (39% yield) of tert-butyl 2-(3-chloro-2-(4-hydroxypiperidin-1-yl)benzyl)-2,8-diazaspiro[4.5]decane-8-carboxylate as a yellow oil. LCMS (ESI, m/z): 464 [M+H]$^+$.

Step 3: Preparation of tert-butyl 2-(3-chloro-2-(4-oxopiperidin-1-yl)benzyl)-2,8-diazaspiro[4.5]decane-8-carboxylate

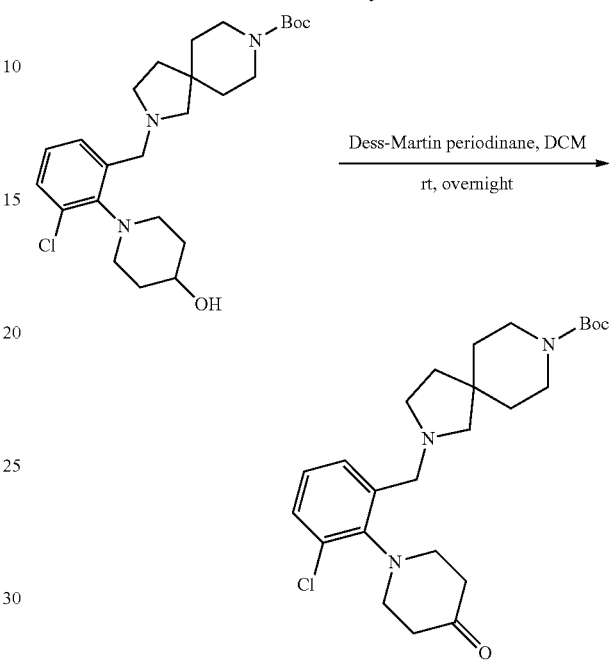

A flask was charged with tert-butyl 2-(3-chloro-2-(4-hydroxypiperidin-1-yl)benzyl)-2,8-diazaspiro[4.5]decane-8-carboxylate (760 mg, 1.64 mmol, 1.00 equiv), (1,1,1-triacetoxy)-1,1-dihydro-1,2-benziodoxol-3(1H)-one (1.04 g, 2.45 mmol, 1.50 equiv), and DCM (20 mL). The resulting solution was stirred overnight at rt and quenched with H$_2$O (15 mL). The mixture was extracted with DCM (3×20 mL) and the organic layers were combined, dried over anhydrous Na$_2$SO$_4$, filtered and concentrated. The residue was purified on a silica gel column (45:55 EtOAc/petroleum ether) to provide 280 mg (37% yield) of tert-butyl 2-(3-chloro-2-(4-oxopiperidin-1-yl)benzyl)-2,8-diazaspiro[4.5]decane-8-carboxylate as a yellow oil. LCMS (ESI, m/z): 462 [M+H]$^+$.

Step 4: Preparation of tert-butyl 2-(3-chloro-2-(4,4-difluoropiperidin-1-yl)benzyl)-2,8-diazaspiro[4.5]decane-8-carboxylate

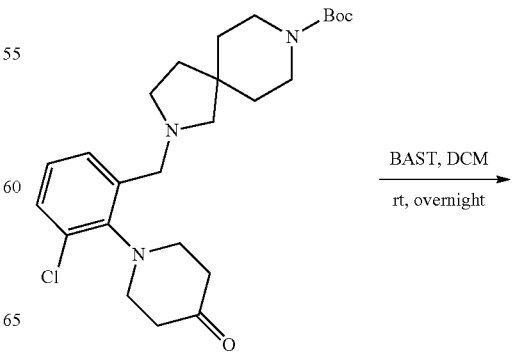

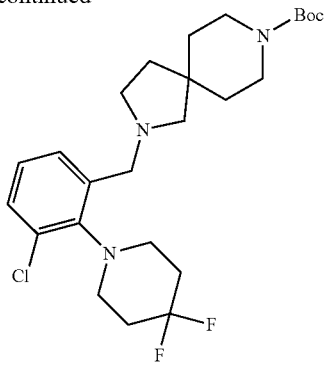

A flask was charged with tert-butyl 2-(3-chloro-2-(4-oxopiperidin-1-yl)benzyl)-2,8-diazaspiro[4.5]decane-8-carboxylate (280 mg, 0.610 mmol, 1.00 equiv) and DCM (10 mL) under nitrogen. Bis(2-methoxyethyl)aminosulfur trifluoride (403 mg, 1.82 mmol, 3.01 equiv) was added at 0° C. The resulting solution was stirred overnight at rt and quenched with H$_2$O (10 mL). The mixture was extracted with DCM (3×15 mL) and the organic layers were combined, dried over anhydrous Na$_2$SO$_4$, filtered and concentrated. The crude product was purified by preparative HPLC to provide 70.0 mg (24% yield) of tert-butyl 2-(3-chloro-2-(4,4-difluoropiperidin-1-yl)benzyl)-2,8-diazaspiro[4.5]decane-8-carboxylate as a yellow oil. LCMS (ESI, m/z): 484 [M+H]$^+$.

Step 5: Preparation of 2-(3-chloro-2-(4,4-difluoropiperidin-1-yl)benzyl)-2,8-diazaspiro[4.5]decane

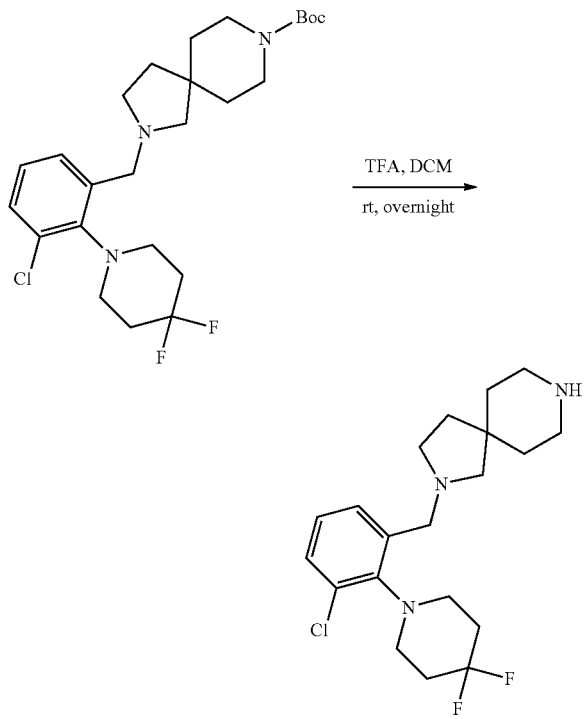

A flask was charged with tert-butyl 2-(3-chloro-2-(4,4-difluoropiperidin-1-yl)benzyl)-2,8-diazaspiro[4.5]decane-8-carboxylate (70.0 mg, 0.140 mmol, 1.00 equiv), DCM (5 mL), and TFA (1 mL). The resulting solution was stirred overnight at rt and concentrated to provide 50.0 mg (90% yield) of 2-(3-chloro-2-(4,4-difluoropiperidin-1-yl)benzyl)-2,8-diazaspiro[4.5]decane as a yellow oil. LCMS (ESI, m/z): 384 [M+H]$^+$.

Step 6: Preparation of 1,1,1,3,3,3-hexafluoropropan-2-yl 2-(3-chloro-2-(4,4-difluoropiperidin-1-yl)benzyl)-2,8-diazaspiro[4.5]decane-8-carboxylate

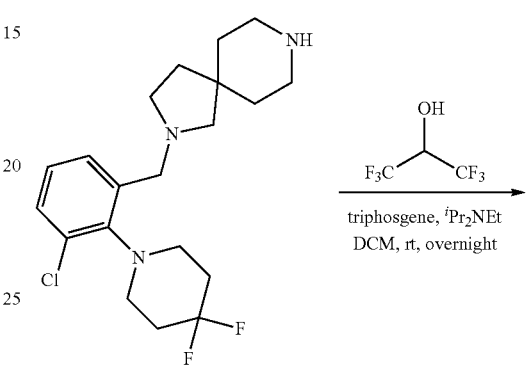

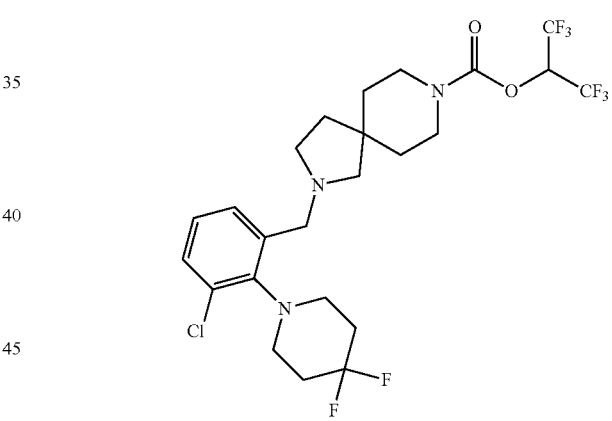

A flask was charged with triphosgene (27.0 mg, 0.0900 mmol, 0.70 equiv) and DCM (10 mL). HFIP (44.0 mg, 0.260 mmol, 2.01 equiv) was added at 0° C., followed by DIEA (50.0 mg, 0.390 mmol, 2.97 equiv). The resulting solution was stirred for 1 h at 0° C. and 2-(3-chloro-2-(4,4-difluoropiperidin-1-yl)benzyl)-2,8-diazaspiro[4.5]decane (50.0 mg, 0.130 mmol, 1.00 equiv) was added. The resulting solution was stirred overnight at rt and concentrated. The crude product was purified by preparative HPLC to provide 37.5 mg (50% yield) of 1,1,1,3,3,3-hexafluoropropan-2-yl 2-(3-chloro-2-(4,4-difluoropiperidin-1-yl)benzyl)-2,8-diazaspiro[4.5]decane-8-carboxylate as a yellow oil. $^1$H NMR (300 MHz, Chloroform-d) δ 7.24-7.28 (m, 2H), 7.06 (t, J=7.8 Hz, 1H), 5.68-5.81 (m, 1H), 3.37-3.64 (m, 8H), 3.00-3.04 (m, 2H), 2.58 (br, 2H), 2.39 (br, 2H), 1.94-2.25 (m, 4H), 1.58-1.66 (m, 6H). LCMS (ESI, m/z): 578 [M+H]$^+$.

Example 65: 1,1,1,3,3,3-Hexafluoropropan-2-yl 2-(3-chloro-2-(4-fluoropiperidin-1-yl)benzyl)-2,8-diazaspiro[4.5]decane-8-carboxylate

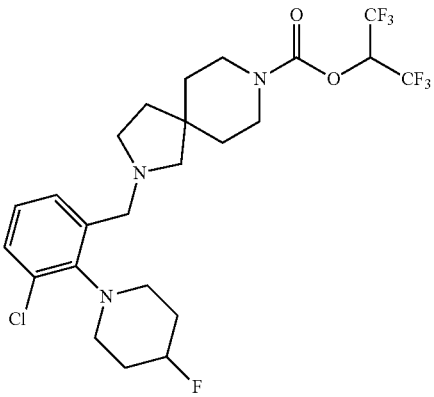 [SMILES: O=C(OC(C(F)(F)F)C(F)(F)F)N1CCC2(CCN(Cc3cccc(Cl)c3N3CCC(F)CC3)C2)CC1]

The title compound was synthesized directly from commercially available 3-chloro-2-fluorobenzaldehyde and 4-fluoropiperidine according to the representative procedure of Example 64, Steps 1, 2, 5, and 6 to provide 1,1,1,3,3,3-hexafluoropropan-2-yl 2-(3-chloro-2-(4-fluoropiperidin-1-yl)benzyl)-2,8-diazaspiro[4.5]decane-8-carboxylate as a yellow oil. $^1$H NMR (300 MHz, Chloroform-d) δ 7.21-7.24 (m, 2H), 7.04 (t, J=7.6 Hz, 1H), 5.70-5.79 (m, 1H), 4.60-4.80 (m, 1H), 3.33-3.66 (m, 8H), 3.01-3.06 (m, 1H), 2.75-2.80 (m, 1H), 2.60 (br, 2H), 2.41 (br, 2H), 1.80-2.12 (m, 4H), 1.58-1.68 (m, 6H). LCMS (ESI, m/z): 560 [M+H]$^+$.

Example 66: 1,1,1,3,3,3-Hexafluoropropan-2-yl 1-(2-(pyrrolidin-1-yl)-4-(trifluoromethyl)benzyl)-1,8-diazaspiro[4.5]decane-8-carboxylate

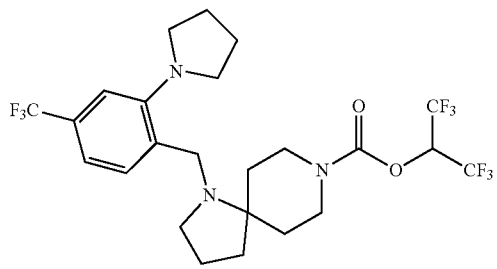 [SMILES: O=C(OC(C(F)(F)F)C(F)(F)F)N1CCC2(CCCN2Cc2ccc(C(F)(F)F)cc2N2CCCC2)CC1]

Step 1: Preparation of 2-(pyrrolidin-1-yl)-4-(trifluoromethyl)benzaldehyde

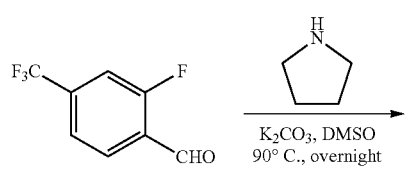

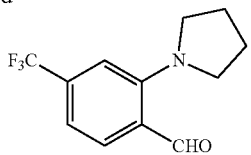

A flask was charged with 2-fluoro-4-(trifluoromethyl)benzaldehyde (6.00 g, 31.2 mmol, 1.00 equiv), pyrrolidine (3.30 g, 46.4 mmol, 1.50 equiv), potassium carbonate (12.9 g, 93.3 mmol, 3.00 equiv), and DMSO (50 mL) under nitrogen. The resulting solution was stirred overnight at 90° C. and diluted with H$_2$O (20 mL). The mixture was extracted with DCM (3×50 mL) and the organic layers were combined, washed with brine (3×10 mL), dried over anhydrous Na$_2$SO$_4$, filtered and concentrated. The residue was purified on a silica gel column (1:20 EtOAc/petroleum ether) to provide 6.00 g (79% yield) of 2-(pyrrolidin-1-yl)-4-(trifluoromethyl)benzaldehyde as a yellow oil. LCMS (ESI, m/z): 244 [M+H]$^+$.

Step 2: Preparation of tert-butyl 1-(2-(pyrrolidin-1-yl)-4-(trifluoromethyl)benzyl)-1,8-diazaspiro[4.5]decane-8-carboxylate

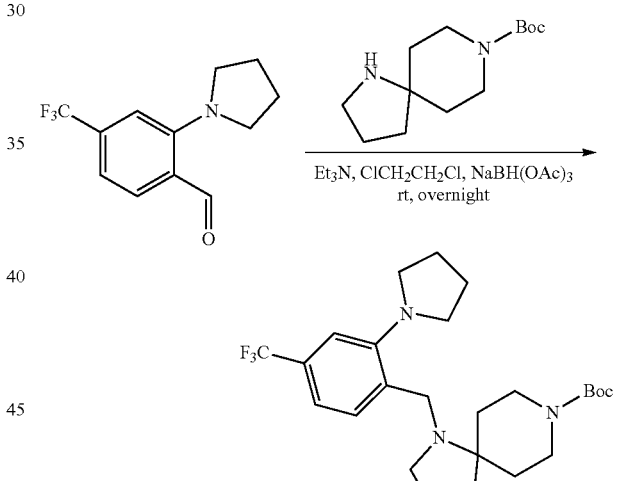

A flask was charged with tert-butyl 1,8-diazaspiro[4.5]decane-8-carboxylate (500 mg, 2.08 mmol, 1.00 equiv), DCE (10 mL), TEA (630 mg, 6.23 mmol, 3.00 equiv), and 2-(pyrrolidin-1-yl)-4-(trifluoromethyl)benzaldehyde (505 mg, 2.08 mmol, 1.00 equiv). The resulting solution was stirred for 1 h at rt. NaBH(OAc)$_3$ (1.32 mg, 6.24 mmol, 3.00 equiv) was added. The resulting solution was stirred overnight at rt and diluted with H$_2$O (20 mL). The mixture was extracted with DCM (3×30 mL) and the organic layers were combined, washed with brine (3×10 mL), dried over anhydrous Na$_2$SO$_4$, filtered and concentrated. The residue was purified on a silica gel column (3:7 EtOAc/petroleum ether) to provide 770 mg (79% yield) of tert-butyl 1-(2-(pyrrolidin-1-yl)-4-(trifluoromethyl)benzyl)-1,8-diazaspiro[4.5]decane-8-carboxylate as a yellow oil. LCMS (ESI, m/z): 468 [M+H]$^+$.

Step 3: Preparation of 1-(2-(pyrrolidin-1-yl)-4-(trifluoromethyl)benzyl)-1,8-diazaspiro[4.5]decane

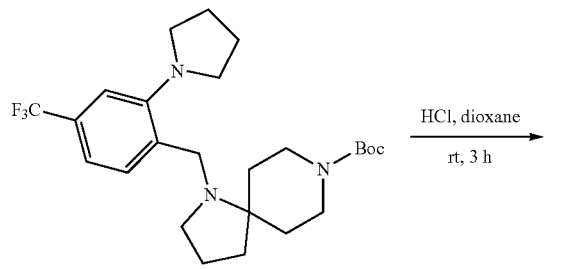

A flask was charged with tert-butyl 1-(2-(pyrrolidin-1-yl)-4-(trifluoromethyl)benzyl)-1,8-diazaspiro[4.5]decane-8-carboxylate (770 mg, 1.65 mmol, 1.00 equiv), 1,4-dioxane (15 mL), and hydrochloric acid (3 mL). The resulting solution was stirred for 3 h at rt and concentrated to provide 600 mg (99% yield) of 1-(2-(pyrrolidin-1-yl)-4-(trifluoromethyl)benzyl)-1,8-diazaspiro[4.5]decane as a yellow oil. LCMS (ESI, m/z): 368 [M+H]$^+$.

Step 4: Preparation of 1,1,1,3,3,3-hexafluoropropan-2-yl 1-(2-(pyrrolidin-1-yl)-4-(trifluoromethyl)benzyl)-1,8-diazaspiro[4.5]decane-8-carboxylate

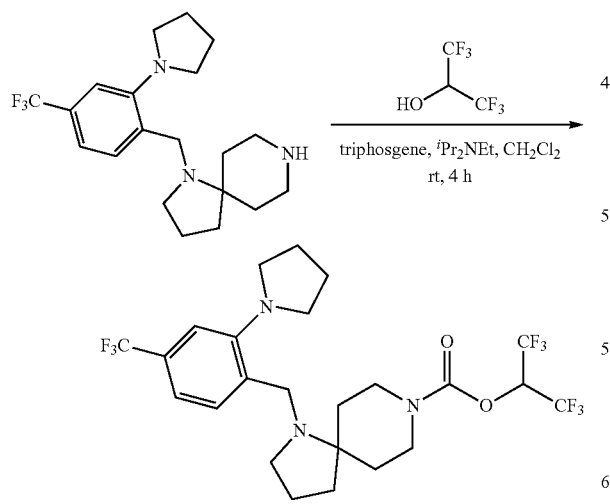

A flask was charged with triphosgene (85.0 mg, 0.290 mmol, 0.70 equiv), and DCM (10 mL). HFIP (138 mg, 0.820 mmol, 2.00 equiv) was added at 0° C., followed by DIEA (264 mg, 2.04 mmol, 5.00 equiv). The resulting solution was stirred for 2 h at rt. 1-(2-(Pyrrolidin-1-yl)-4-(trifluoromethyl)benzyl)-1,8-diazaspiro[4.5]decane (150 mg, 0.410 mmol, 1.00 equiv) was added. The resulting solution was stirred 2 h at rt and concentrated. The crude product was purified by preparative HPLC to provide 84.9 mg (37% yield) of 1,1,1,3,3,3-hexafluoropropan-2-yl 1-(2-(pyrrolidin-1-yl)-4-(trifluoromethyl)benzyl)-1,8-diazaspiro[4.5]decane-8-carboxylate as a light yellow oil. $^1$H NMR (300 MHz, Chloroform-d) δ 7.67 (d, J=7.8 Hz, 1H), 7.12-7.42 (m, 2H), 5.70-5.82 (m, 1H), 4.16-4.30 (m, 2H), 3.63 (s, 2H), 3.14-3.18 (m, 4H), 2.92-3.06 (m, 2H), 2.61-2.65 (m, 2H), 1.91-2.07 (m, 4H), 1.68-1.88 (m, 6H), 1.45-1.60 (m, 2H). LCMS (ESI, m/z): 562 [M+H]$^+$.

Example 67: 1,1,1,3,3,3-Hexafluoropropan-2-yl 1-(2-morpholino-4-(trifluoromethyl)benzyl)-1,8-diazaspiro[4.5]decane-8-carboxylate

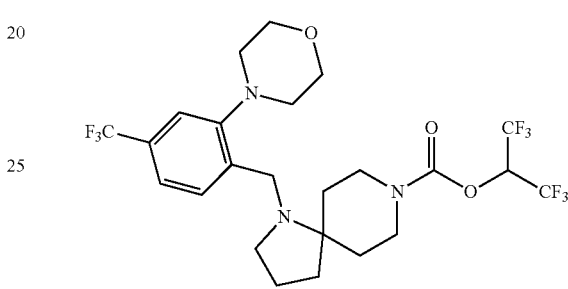

The title compound was synthesized directly from commercially available morpholine according to the representative procedure of Example 66 to provide 1,1,1,3,3,3-hexafluoropropan-2-yl 1-(2-morpholino-4-(trifluoromethyl)benzyl)-1,8-diazaspiro[4.5]decane-8-carboxylate as a light yellow oil. $^1$H NMR (300 MHz, Chloroform-d) δ 7.62 (d, J=8.7 Hz, 1H), 7.26-7.58 (m, 2H), 5.70-5.82 (m, 1H), 4.17-4.32 (m, 2H), 3.85 (t, J=9.0 Hz, 4H), 3.70 (s, 2H), 2.91-3.00 (m, 6H), 2.59-2.68 (m, 2H), 1.60-2.01 (m, 6H), 1.26-1.56 (m, 2H). LCMS (ESI, m/z): 578 [M+H]$^+$.

Example 68: 1,1,1,3,3,3-Hexafluoropropan-2-yl 1-((1-methyl-1,2,3,4-tetrahydroquinolin-7-yl)methyl)-1,8-diazaspiro[4.5]decane-8-carboxylate

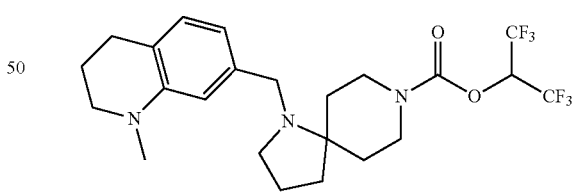

Step 1: Preparation of 7-bromo-1-methyl-1,2,3,4-tetrahydroquinoline

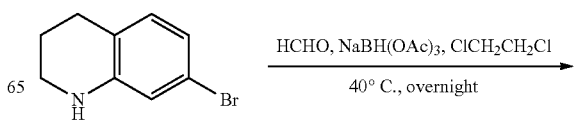

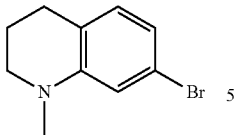

A flask was charged with 7-bromo-1,2,3,4-tetrahydroquinoline (2.50 g, 11.8 mmol, 1.00 equiv), paraformaldehyde (1.10 g, 35.4 mmol, 3.00 equiv), and DCE (30 mL). The resulting solution was stirred for 1 h at rt. NaBH(OAc)$_3$ (7.50 g, 35.4 mmol, 3.00 equiv) was added, and the solution was stirred overnight at 40° C. Water (20 mL) was added, and the mixture was extracted with DCM (3×30 mL); the organic layers were combined, washed with brine (3×10 mL), dried over anhydrous Na$_2$SO$_4$, filtered, and concentrated. The residue was purified on a silica gel column (1:5 EtOAc/petroleum ether) to provide (67% yield) of 7-bromo-1-methyl-1,2,3,4-tetrahydroquinoline as a yellow oil. LCMS (ESI, m/z): 226 [M+H]$^+$.

Step 2: Preparation of 1-methyl-1,2,3,4-tetrahydroquinoline-7-carbaldehyde

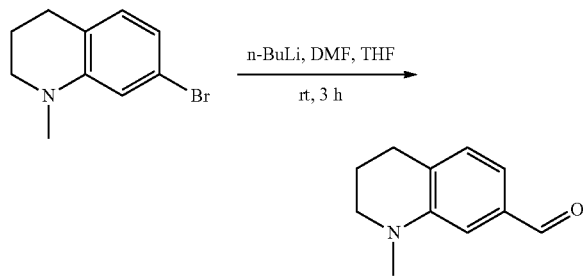

A flask was charged with 7-bromo-1-methyl-1,2,3,4-tetrahydroquinoline (800 mg, 3.54 mmol, 1.00 equiv) and THF (10 mL) under nitrogen. n-Butyllithium (2.5 M in THF, 1.6 mL, 3.92 mmol, 1.10 equiv) was added dropwise at −78° C. The resulting solution was stirred for 30 min at −78° C., after which DMF (1.04 g, 14.2 mmol, 4.00 equiv) was added. The resulting solution was stirred for 30 min at −78° C. and then for 2 h at rt. The resulting mixture was diluted with H$_2$O (20 mL), and the mixture was extracted with DCM (3×30 mL). The organic layers were combined, washed with H$_2$O (3×10 mL), dried over anhydrous Na$_2$SO$_4$, filtered, and concentrated. The residue was purified on a silica gel column (2:23 EtOAc/petroleum ether) to provide 283 mg (46% yield) of 1-methyl-1,2,3,4-tetrahydroquinoline-7-carbaldehyde as a light yellow oil. LCMS (ESI, m/z): 176 [M+H]$^+$.

Step 3: Preparation of tert-butyl 1-((1-methyl-1,2,3,4-tetrahydroquinolin-7-yl)methyl)-1,8-diazaspiro[4.5]decane-8-carboxylate

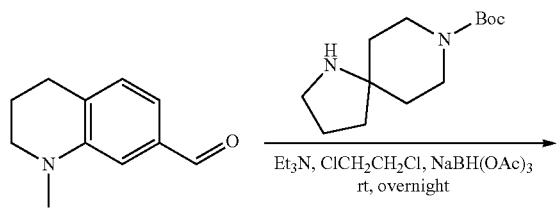

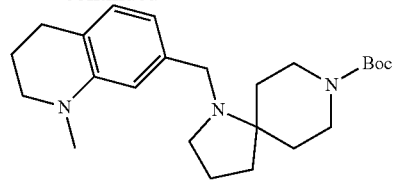

A flask was charged with tert-butyl 1,8-diazaspiro[4.5]decane-8-carboxylate (160 mg, 0.670 mmol, 1.00 equiv), DCE (5 mL), TEA (203 mg, 2.01 mmol, 3.00 equiv), and 1-methyl-1,2,3,4-tetrahydroquinoline-7-carbaldehyde (120 mg, 0.680 mmol, 1.03 equiv). The resulting solution was stirred for 1 h at rt. NaBH(OAc)$_3$ (426 mg, 2.01 mmol, 3.00 equiv) was added, and the resulting solution was stirred overnight at rt before diluting with H$_2$O (20 mL). The mixture was extracted with DCM (3×30 mL) and the organic layers were combined, washed with brine (3×10 mL), dried over anhydrous Na$_2$SO$_4$, filtered and concentrated. The residue was purified on a silica gel column (EtOAc/petroleum ether) to provide 200 mg (75% yield) of tert-butyl 1-((1-methyl-1,2,3,4-tetrahydroquinolin-7-yl)methyl)-1,8-diazaspiro[4.5]decane-8-carboxylate as a light yellow oil. LCMS (ESI, m/z): 400 [M+H]$^+$.

Step 4: Preparation of 1-((1-methyl-1,2,3,4-tetrahydroquinolin-7-yl)methyl)-1,8-diazaspiro[4.5]decane

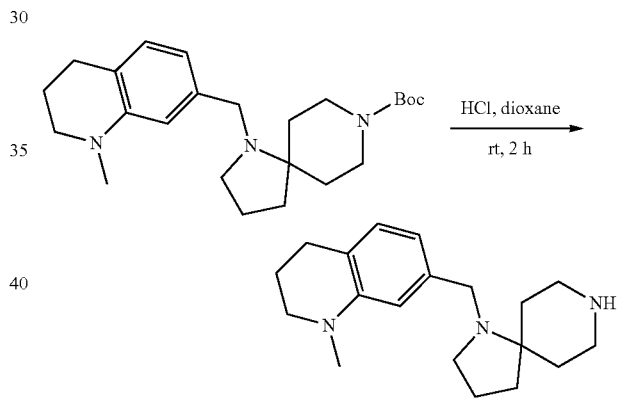

A flask was charged with tert-butyl 1-((1-methyl-1,2,3,4-tetrahydroquinolin-7-yl)methyl)-1,8-diazaspiro[4.5]decane-8-carboxylate (200 mg, 0.500 mmol, 1.00 equiv), 1,4-dioxane (10 mL), and hydrochloric acid (2 mL). The resulting solution was stirred for 2 h at rt and concentrated to provide 150 mg (100% yield) of 1-((1-methyl-1,2,3,4-tetrahydroquinolin-7-yl)methyl)-1,8-diazaspiro[4.5]decane as a light yellow oil. LCMS (ESI, m/z): 300 [M+H]$^+$.

Step 5: Preparation of 1,1,1,3,3,3-hexafluoropropan-2-yl 1-((1-methyl-1,2,3,4-tetrahydroquinolin-7-yl)methyl)-1,8-diazaspiro[4.5]decane-8-carboxylate

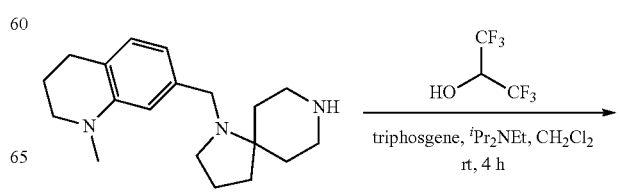

-continued

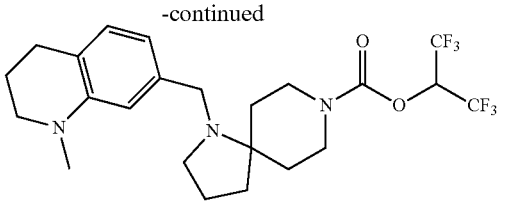

A flask was charged with triphosgene (104 mg, 0.350 mmol, 0.70 equiv), and DCM (10 mL). HFIP (168 mg, 1.00 mmol, 2.00 equiv) was added dropwise at 0° C., followed by DIEA (323 mg, 2.50 mmol, 4.99 equiv). The resulting solution stirred for 2 h at rt. 1-((1-Methyl-1,2,3,4-tetrahydroquinolin-7-yl)methyl)-1,8-diazaspiro[4.5]decane (150 mg, 0.500 mmol, 1.00 equiv) was added. The resulting solution was stirred for 2 h at rt and concentrated. The crude product was purified by preparative HPLC to provide 124.0 mg (50% yield) of 1,1,1,3,3,3-hexafluoropropan-2-yl 1-((1-methyl-1,2,3,4-tetrahydroquinolin-7-yl)methyl)-1,8-diazaspiro[4.5]decane-8-carboxylate as a light yellow oil. $^1$H NMR (300 MHz, Chloroform-d) δ 6.87 (d, J=7.5 Hz, 1H), 6.54-6.56 (m, 2H), 5.71-5.82 (m, 1H), 4.15-4.24 (m, 2H), 3.50 (s, 2H), 3.18-3.22 (m, 2H), 2.88-3.22 (m, 5H), 2.65-2.76 (m, 4H), 1.92-2.00 (m, 2H), 1.59-1.79 (m, 6H), 1.26-1.49 (m, 2H). LCMS (ESI, m/z): 494 [M+H]$^+$.

Example 69: 1,1,1,3,3,3-Hexafluoropropan-2-yl 1-(3-morpholinobenzyl)-1,8-diazaspiro[4.5]decane-8-carboxylate

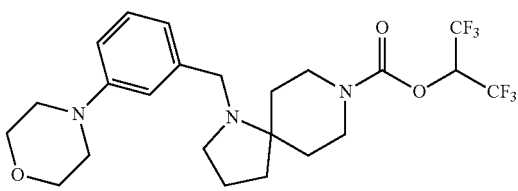 [SMILES: O=C(OC(C(F)(F)F)C(F)(F)F)N1CCC2(CCCN2Cc2cccc(N3CCOCC3)c2)CC1]

The title compound was synthesized directly from 3-morpholinobenzaldehyde according to the representative procedure of Example 60 to provide 1,1,1,3,3,3-hexafluoropropan-2-yl 1-(3-morpholinobenzyl)-1,8-diazaspiro[4.5]decane-8-carboxylate as a light yellow oil. $^1$H NMR (300 MHz, Chloroform-d) δ 7.18-7.23 (m, 1H), 6.76-6.91 (m, 3H), 5.69-5.80 (m, 1H), 4.16-4.25 (m, 2H), 3.85-3.94 (m, 4H), 3.50-3.60 (m, 2H), 3.14-3.29 (m, 4H), 2.91-3.05 (m, 2H), 2.66-2.71 (m, 2H), 1.62-1.86 (m, 6H), 1.46-1.56 (m, 2H). LCMS (ESI, m/z): 510 [M+H]$^+$.

Example 70: 1,1,1,3,3,3-Hexafluoropropan-2-yl 2-((1-acetyl-1,2,3,4-tetrahydroquinolin-8-yl)methyl)-2,8-diazaspiro[4.5]decane-8-carboxylate

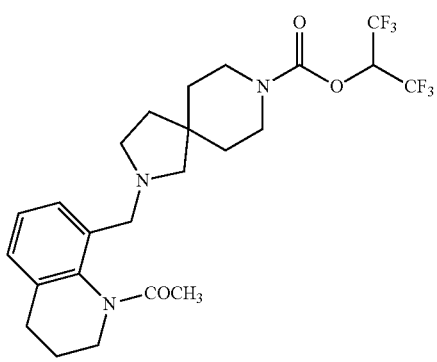 [SMILES: CC(=O)N1CCCc2cccc(CN3CCC4(CCN(C(=O)OC(C(F)(F)F)C(F)(F)F)CC4)C3)c21]

Step 1: Preparation of tert-butyl 2-(1,2,3,4-tetrahydroquinolin-8-ylmethyl)-2,8-diazaspiro[4.5]decane-8-carboxylate

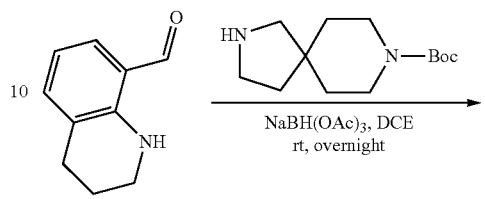

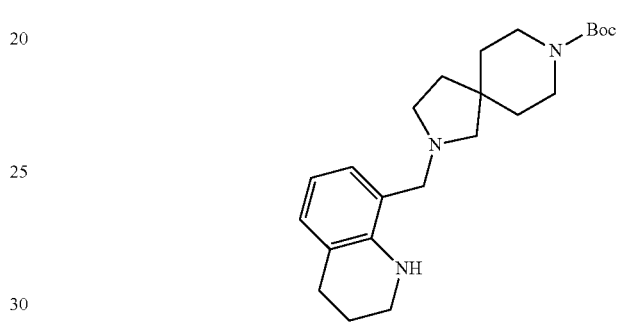

A flask was charged with 1,2,3,4-tetrahydroquinoline-8-carbaldehyde (1.00 g, 6.20 mmol, 1.00 equiv), tert-butyl 2,8-diazaspiro[4.5]decane-8-carboxylate (1.64 g, 6.82 mmol, 1.10 equiv), and DCE (25 mL). The resulting solution was stirred for 1 h at rt, and NaBH(OAc)$_3$ (3.95 g, 18.6 mmol, 3.00 equiv) was added. The resulting solution was stirred overnight at rt and quenched with H$_2$O (15 mL) before extracting with DCM (3×20 mL). The organic layers were combined, dried over anhydrous Na$_2$SO$_4$, filtered, and concentrated. The residue was purified on a silica gel column with EtOAc/petroleum ether (22/78) to provide 1.17 g (49% yield) of tert-butyl 2-(1,2,3,4-tetrahydroquinolin-8-ylmethyl)-2,8-diazaspiro[4.5]decane-8-carboxylate as a yellow oil. LCMS (ESI, m/z): 386 [M+H]$^+$.

Step 2: Preparation of tert-butyl 2-((1-acetyl-1,2,3,4-tetrahydroquinolin-8-yl)methyl)-2,8-diazaspiro[4.5]decane-8-carboxylate

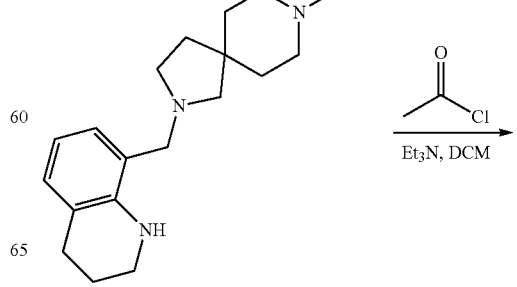

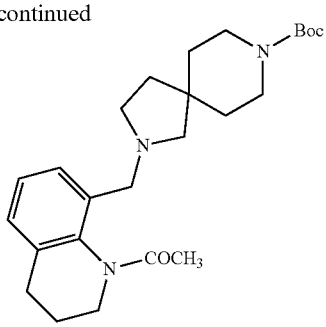

A flask was charged with tert-butyl 2-(1,2,3,4-tetrahydroquinolin-8-ylmethyl)-2,8-diazaspiro[4.5]decane-8-carboxylate (500 mg, 1.30 mmol, 1.00 equiv), acetyl chloride (152 mg, 1.94 mmol, 1.49 equiv), DCM (10 mL), and TEA (392 mg, 3.87 mmol, 2.99 equiv). The resulting solution was stirred overnight at rt and quenched with H₂O (10 mL). The resulting solution was extracted with DCM (3×15 mL) and the organic layers were combined, dried over anhydrous Na₂SO₄, filtered and concentrated. The residue was purified on a silica gel column (85:15 EtOAc/petroleum ether) to provide 410 mg (74% yield) of tert-butyl 2-((1-acetyl-1,2,3,4-tetrahydroquinolin-8-yl)methyl)-2,8-diazaspiro[4.5]decane-8-carboxylate as a yellow oil. LCMS (ESI, m/z): 428 [M+H]⁺.

Step 3: Preparation of 1-(8-((2,8-diazaspiro[4.5]decan-2-yl)methyl)-3,4-dihydroquinolin-1(2H)-yl)ethan-1-one

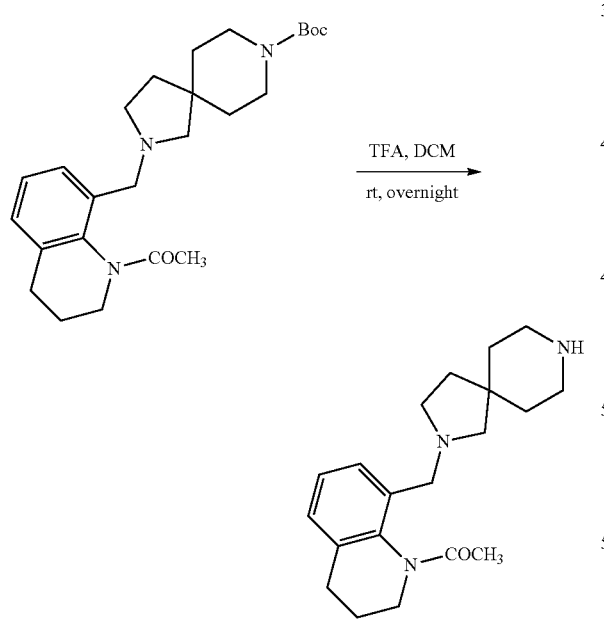

A flask was charged with tert-butyl 2-((1-acetyl-1,2,3,4-tetrahydroquinolin-8-yl)methyl)-2,8-diazaspiro[4.5]decane-8-carboxylate (410 mg, 0.960 mmol, 1.00 equiv), DCM (9 mL), and TFA (1.5 mL). The resulting solution was stirred overnight at rt and concentrated to provide 300 mg (96% yield) of 1-(8-((2,8-diazaspiro[4.5]decan-2-yl)methyl)-3,4-dihydroquinolin-1(2H)-yl)ethan-1-one as a yellow oil. LCMS (ESI, m/z): 328 [M+H]⁺.

Step 4: Preparation of 1,1,1,3,3,3-hexafluoropropan-2-yl 2-((1-acetyl-1,2,3,4-tetrahydroquinolin-8-yl)methyl)-2,8-diazaspiro[4.5]decane-8-carboxylate

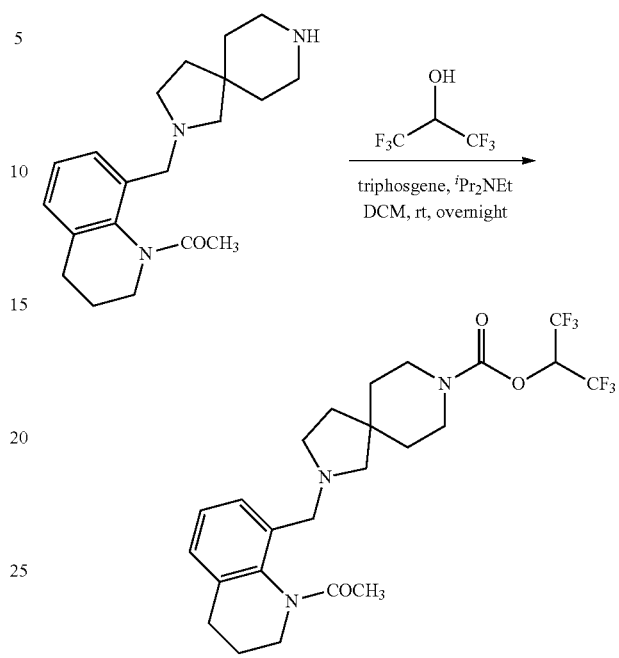

A flask was charged with triphosgene (95.0 mg, 0.320 mmol, 0.70 equiv) and DCM (10 mL). HFIP (154 mg, 0.920 mmol, 2.00 equiv) was added at 0° C., followed by DIEA (178 mg, 1.38 mmol, 3.01 equiv). The resulting solution was stirred for 2 h at rt and 1-(8-((2,8-diazaspiro[4.5]decan-2-yl)methyl)-3,4-dihydroquinolin-1(2H)-yl)ethan-1-one (150 mg, 0.460 mmol, 1.00 equiv) was added. The resulting solution was stirred overnight at rt and concentrated. The crude product was purified by preparative HPLC to provide 62.0 mg (26% yield) of 1,1,1,3,3,3-hexafluoropropan-2-yl 2-((1-acetyl-1,2,3,4-tetrahydroquinolin-8-yl)methyl)-2,8-diazaspiro[4.5]decane-8-carboxylate as a yellow oil. ¹H NMR (300 MHz, Chloroform-d) δ 7.30-7.33 (m, 1H), 7.09-7.14 (m, 2H), 6.21-6.34 (m, 1H), 3.89-4.91 (m, 1H), 3.16-3.48 (m, 8H), 2.62 (br, 2H), 2.32 (br, 2H), 1.78-2.12 (m, 5H), 1.49-1.61 (m, 7H). LCMS (ESI, m/z): 522 [M+H]⁺.

Example 71: 1,1,1,3,3,3-Hexafluoropropan-2-yl 2-((1-ethyl-1,2,3,4-tetrahydroquinolin-8-yl)methyl)-2,8-diazaspiro[4.5]decane-8-carboxylate

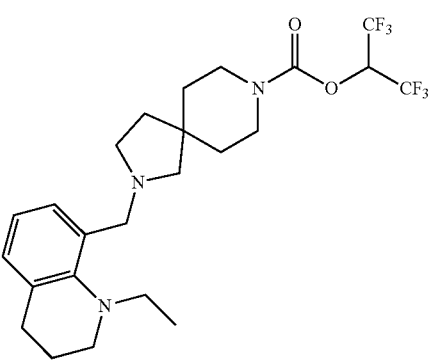 [SMILES: CCN1CCCc2cccc(CN3CCC4(CCN(C(=O)OC(C(F)(F)F)C(F)(F)F)CC4)C3)c21]

Step 1: Preparation of tert-butyl 2-(1,2,3,4-tetrahydroquinolin-8-ylmethyl)-2,8-diazaspiro[4.5]decane-8-carboxylate

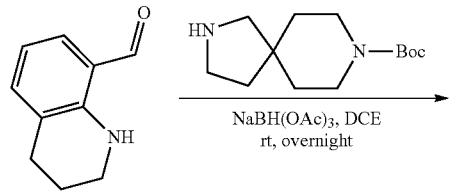

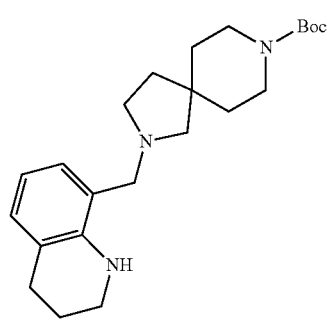

A flask was charged with 1,2,3,4-tetrahydroquinoline-8-carbaldehyde (1.00 g, 6.20 mmol, 1.00 equiv), tert-butyl 2,8-diazaspiro[4.5]decane-8-carboxylate (1.64 g, 6.82 mmol, 1.10 equiv), and DCE (25 mL). The resulting solution was stirred for 1 h at rt and NaBH(OAc)$_3$ (3.95 g, 18.6 mmol, 3.00 equiv) was added. The resulting solution was stirred overnight at rt and quenched with H$_2$O (15 mL) and extracted with DCM (3×20 mL). The combined organic layers were dried over anhydrous Na$_2$SO$_4$, filtered, and concentrated. The residue was purified on a silica gel column (22:78 EtOAc/petroleum ether) to provide 1.17 g (49% yield) of tert-butyl 2-(1,2,3,4-tetrahydroquinolin-8-ylmethyl)-2,8-diazaspiro[4.5]decane-8-carboxylate as a yellow oil. LCMS (ESI, m/z): 386 [M+H]$^+$.

Step 2: Preparation of tert-butyl 2-((1-ethyl-1,2,3,4-tetrahydroquinolin-8-yl)methyl)-2,8-diazaspiro[4.5]decane-8-carboxylate

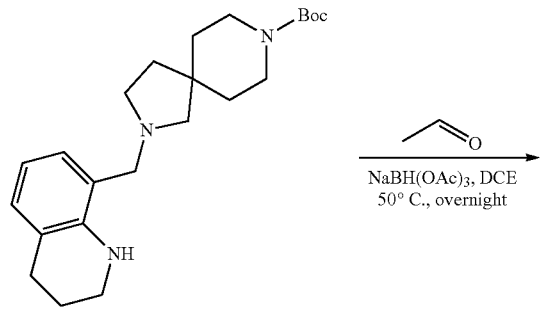

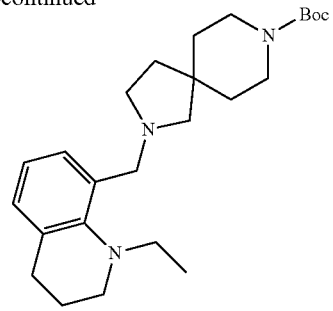

A flask was charged with tert-butyl 2-(1,2,3,4-tetrahydroquinolin-8-ylmethyl)-2,8-diazaspiro[4.5]decane-8-carboxylate (500 mg, 1.30 mmol, 1.00 equiv), acetaldehyde (171 mg, 3.88 mmol, 2.99 equiv), and DCE (10 mL). The resulting solution was stirred for 1 h at rt and NaBH(OAc)$_3$ (824 mg, 3.89 mmol, 3.00 equiv) was added. The resulting solution was stirred overnight at 50° C. and quenched with H$_2$O (10 mL). The resulting solution was extracted with DCM (3×15 mL) and the combined organic layers were dried over anhydrous Na$_2$SO$_4$, filtered, and concentrated. The residue was purified on a silica gel column (85:15 EtOAc/petroleum ether) to provide 230 mg (43% yield) of tert-butyl 2-((1-ethyl-1,2,3,4-tetrahydroquinolin-8-yl)methyl)-2,8-diazaspiro[4.5]decane-8-carboxylate as a yellow oil. LCMS (ESI, m/z): 414 [M+H]$^+$.

Step 3: Preparation of 2-((1-ethyl-1,2,3,4-tetrahydroquinolin-8-yl)methyl)-2,8-diazaspiro[4.5]decane

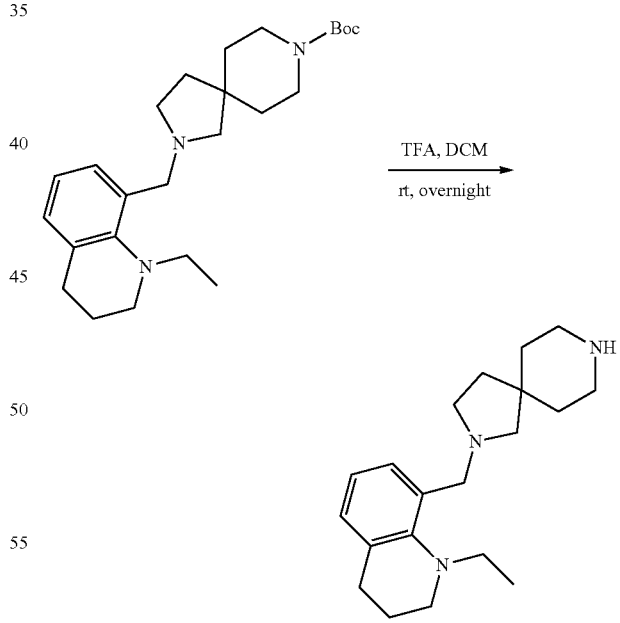

A flask was charged with tert-butyl 2-((1-ethyl-1,2,3,4-tetrahydroquinolin-8-yl)methyl)-2,8-diazaspiro[4.5]decane-8-carboxylate (230 mg, 0.560 mmol, 1.00 equiv), DCM (6 mL), and TFA (1 mL). The resulting solution was stirred overnight at rt and concentrated to provide 170 mg (98% yield) of 2-((1-ethyl-1,2,3,4-tetrahydroquinolin-8-yl)methyl)-2,8-diazaspiro[4.5]decane as a yellow oil. LCMS (ESI, m/z): 314 [M+H]$^+$.

Step 4: Preparation of 1,1,1,3,3,3-hexafluoropropan-2-yl 2-((1-ethyl-1,2,3,4-tetrahydroquinolin-8-yl)methyl)-2,8-diazaspiro[4.5]decane-8-carboxylate

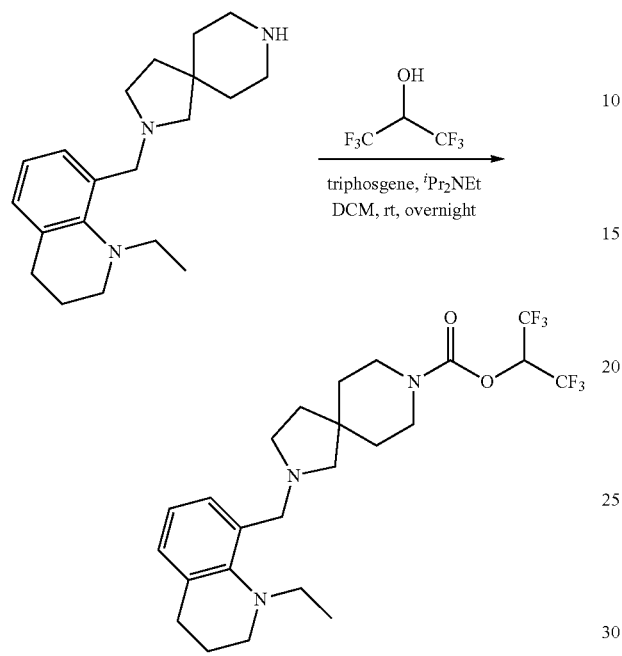

A flask was charged with triphosgene (56.0 mg, 0.190 mmol, 0.70 equiv) and DCM (10 mL). HFIP (91.0 mg, 0.540 mmol, 2.00 equiv) was added at 0° C., followed by DIEA (105 mg, 0.810 mmol, 3.00 equiv). The resulting solution was stirred for 1 h at 0° C. and 2-((1-ethyl-1,2,3,4-tetrahydroquinolin-8-yl)methyl)-2,8-diazaspiro[4.5]decane (85.0 mg, 0.270 mmol, 1.00 equiv) was added. The resulting solution was stirred overnight at rt and concentrated. The crude product was purified by preparative HPLC to provide 51.7 mg (38% yield) of 1,1,1,3,3,3-hexafluoropropan-2-yl 2-((1-ethyl-1,2,3,4-tetrahydroquinolin-8-yl)methyl)-2,8-diazaspiro[4.5]decane-8-carboxylate as a yellow oil. $^1$H NMR (300 MHz, Chloroform-d) δ 7.23-7.26 (m, 1H), 6.84-6.95 (m, 2H), 5.68-5.81 (m, 1H), 3.42-3.56 (m, 6H), 2.94-3.07 (m, 4H), 2.66-2.82 (m, 4H), 2.45 (br, 2H), 1.75-1.83 (m, 2H), 1.58-1.68 (m, 6H), 1.21 (t, J=6.0 Hz, 3H). LCMS (ESI, m/z): 508 [M+H]$^+$.

Example 72: 1,1,1,3,3,3-Hexafluoropropan-2-yl 2-(2-(pyrrolidin-1-yl)-4-(trifluoromethyl)benzyl)-2,8-diazaspiro[4.5]decane-8-carboxylate

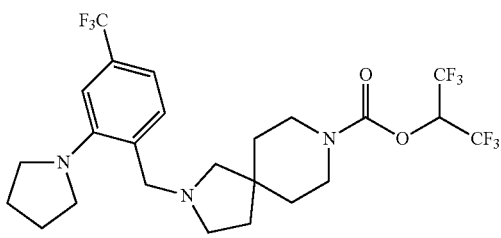 [SMILES: O=C(OC(C(F)(F)F)C(F)(F)F)N1CCC2(CCN(Cc3ccc(C(F)(F)F)cc3N3CCCC3)C2)CC1]

The title compound was synthesized directly from commercially available 2-fluoro-4-(trifluoromethyl)benzaldehyde and pyrrolidine in Step 1 and tert-butyl 2,8-diazaspiro[4.5]decane-8-carboxylate in Step 2 according to the representative procedure of Example 66 to provide 1,1,1,3,3,3-hexafluoropropan-2-yl 2-(2-(pyrrolidin-1-yl)-4-(trifluoromethyl)benzyl)-2,8-diazaspiro[4.5]decane-8-carboxylate as a yellow oil. $^1$H NMR (300 MHz, Chloroform-d) δ 7.47-7.50 (m, 1H), 7.06-7.17 (m, 2H), 5.68-5.78 (m, 1H), 3.33-3.72 (m, 6H), 3.25 (br, 4H), 2.63 (br, 2H), 2.40 (br, 2H), 1.94 (br, 4H), 1.62-1.67 (m, 6H). LCMS (ESI, m/z): 562 [M+H]$^+$.

Example 73: 1,1,1,3,3,3-Hexafluoropropan-2-yl 1-(2-(8-oxa-3-azabicyclo[3.2.1]octan-3-yl)-4-(trifluoromethyl)benzyl)-1,8-diazaspiro[4.5]decane-8-carboxylate

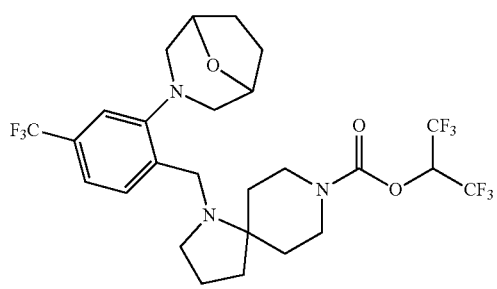 [SMILES: O=C(OC(C(F)(F)F)C(F)(F)F)N1CCC2(CCCN2Cc2ccc(C(F)(F)F)cc2N2CC3CCC(C2)O3)CC1]

The title compound was synthesized directly from commercially available 2-fluoro-4-(trifluoromethyl)benzaldehyde and 8-oxa-3-azabicyclo[3.2.1]octane in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(8-oxa-3-azabicyclo[3.2.1]octan-3-yl)-4-(trifluoromethyl)benzyl)-1,8-diazaspiro[4.5]decane-8-carboxylate as a white solid. $^1$H NMR (300 MHz, Chloroform-d) δ 7.69 (d, J=9.0 Hz, 1H), 7.26-7.33 (m, 2H), 5.70-5.82 (m, 1H), 4.42 (br, 2H), 4.18-4.32 (m, 2H), 3.73 (s, 2H), 2.93-3.18 (m, 4H), 2.62-2.71 (m, 4H), 1.89-2.10 (m, 4H), 1.63-1.84 (m, 6H), 1.49-1.58 (m, 2H). LCMS (ESI, m/z): 604 [M+H]$^+$.

Example 74: 1,1,1,3,3,3-Hexafluoropropan-2-yl 1-(4-chloro-2-(piperidin-1-yl)benzyl)-1,8-diazaspiro[4.5]decane-8-carboxylate

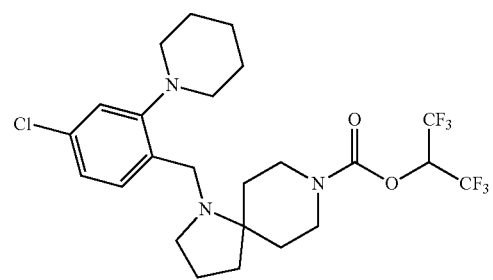 [SMILES: O=C(OC(C(F)(F)F)C(F)(F)F)N1CCC2(CCCN2Cc2ccc(Cl)cc2N2CCCCC2)CC1]

The title compound was synthesized directly from commercially available 4-chloro-2-fluorobenzaldehyde and piperidine in Step 1 and tert-butyl 1,8-diazaspiro[4.5]decane- 8-carboxylate in Step 2 according to the representative procedure of Example 66 to provide 1,1,1,3,3,3-hexafluoropropan-2-yl 1-(4-chloro-2-(piperidin-1-yl)benzyl)-1,8-diazaspiro[4.5]decane-8-carboxylate as an off-white solid. $^1$H NMR (300 MHz, Chloroform-d) δ 7.42 (d, J=9.0 Hz, 1H), 6.97-7.00 (m, 2H), 5.70-5.82 (m, 1H), 4.15-4.24 (m, 2H), 3.59 (s, 2H), 2.91-3.04 (m, 2H), 2.64-2.80 (m, 6H), 1.65-1.79 (m, 10H), 1.48-1.57 (m, 4H). LCMS (ESI, m/z): 542 [M+H]$^+$.

Example 75: 1,1,1,3,3,3-Hexafluoropropan-2-yl 1-(2-(8-oxa-3-azabicyclo[3.2.1]octan-3-yl)-4-chlorobenzyl)-1,8-diazaspiro[4.5]decane-8-carboxylate

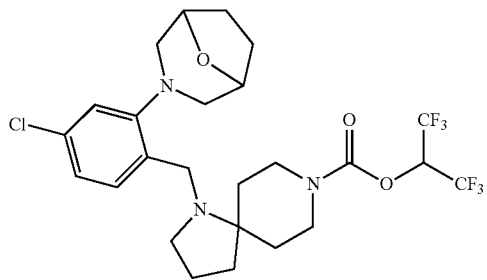 [SMILES: O=C(OC(C(F)(F)F)C(F)(F)F)N1CCC2(CCCN2Cc2ccc(Cl)cc2N2CC3CCC(C2)O3)CC1]

The title compound was synthesized directly from commercially available 4-chloro-2-fluorobenzaldehyde and 8-oxa-3-azabicyclo[3.2.1]octane in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(8-oxa-3-azabicyclo[3.2.1]octan-3-yl)-4-chlorobenzyl)-1,8-diazaspiro[4.5]decane-8-carboxylate as a white solid. $^1$H NMR (300 MHz, Chloroform-d) δ 7.48 (d, J=9.0 Hz, 1H), 7.03-7.06 (m, 2H), 5.70-5.80 (m, 1H), 4.40 (br, 2H), 4.17-4.24 (m, 2H), 3.70 (s, 2H), 2.92-3.06 (m, 4H), 2.61-2.69 (m, 4H), 1.94-2.10 (m, 4H), 1.61-1.90 (m, 6H), 1.41-1.58 (m, 2H). LCMS (ESI, m/z): 570 [M+H]$^+$.

Example 76: 1,1,1,3,3,3-Hexafluoropropan-2-yl 1-(4-chloro-2-(pyrrolidin-1-yl)benzyl)-1,8-diazaspiro[4.5]decane-8-carboxylate

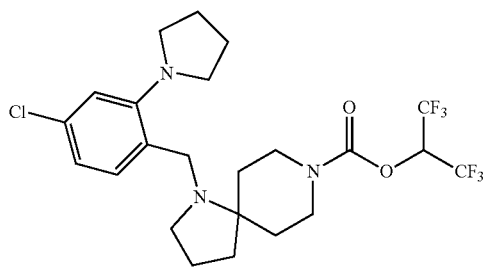 [SMILES: O=C(OC(C(F)(F)F)C(F)(F)F)N1CCC2(CCCN2Cc2ccc(Cl)cc2N2CCCC2)CC1]

The title compound was synthesized directly from commercially available 4-chloro-2-fluorobenzaldehyde and pyrrolidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(pyrrolidin-1-yl)benzyl)-1,8-diazaspiro[4.5]decane-8-carboxylate as a light yellow solid. $^1$H NMR (300 MHz, Chloroform-d) δ 7.46 (d, J=8.4 Hz, 1H), 6.85-6.91 (m, 2H), 5.70-5.82 (m, 1H), 4.15-4.24 (m, 2H), 3.56 (s, 2H), 2.92-3.14 (m, 6H), 2.63-2.65 (m, 2H), 1.80-1.97 (m, 4H), 1.65-1.78 (m, 6H), 1.40-1.55 (m, 2H). LCMS (ESI, m/z): 528 [M+H]$^+$.

Example 77: 1,1,1,3,3,3-Hexafluoropropan-2-yl 1-(4-chloro-2-morpholinobenzyl)-1,8-diazaspiro[4.5] decane-8-carboxylate

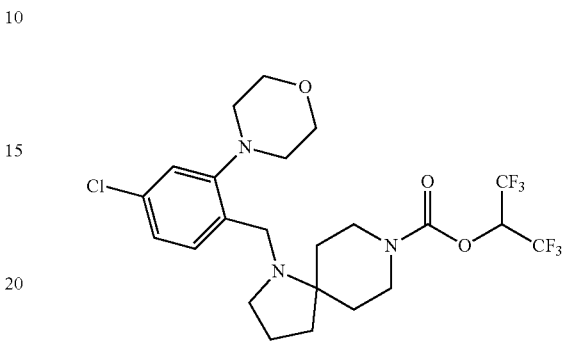

The title compound was synthesized directly from commercially available 4-chloro-2-fluorobenzaldehyde and morpholine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-morpholinobenzyl)-1,8-diazaspiro[4.5]decane-8-carboxylate as a white solid. $^1$H NMR (300 MHz, Chloroform-d) δ 7.43 (d, J=8.4 Hz, 1H), 7.03-7.09 (m, 2H), 5.70-5.82 (m, 1H), 4.17-4.25 (m, 2H), 3.81-3.84 (m, 4H), 3.62 (s, 2H), 2.88-3.05 (m, 6H), 2.63-2.72 (m, 2H), 1.66-1.85 (m, 6H), 1.44-1.56 (m, 2H). LCMS (ESI, m/z): 544 [M+H]$^+$.

Example 78: 1,1,1,3,3,3-Hexafluoropropan-2-yl 1-(2-(piperidin-1-yl)-4-(trifluoromethyl)benzyl)-1,8-diazaspiro[4.5]decane-8-carboxylate

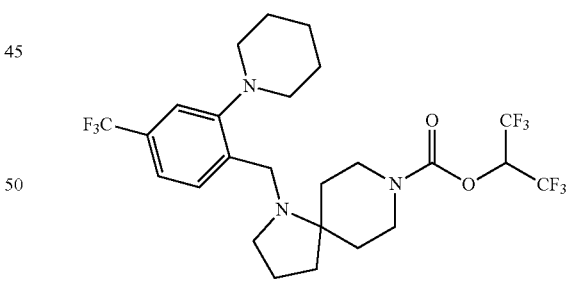

The title compound was synthesized directly from commercially available 2-fluoro-4-(trifluoromethyl)benzaldehyde and piperidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(piperidin-1-yl)-4-(trifluoromethyl)benzyl)-1,8-diazaspiro[4.5]decane-8-carboxylate as a yellow solid. $^1$H NMR (300 MHz, Chloroform-d) δ 7.62 (d, J=8.4 Hz, 1H), 7.25-7.27 (m, 2H), 5.70-5.83 (m, 1H), 4.17-4.25 (m, 2H), 3.67 (s, 2H), 2.92-3.05 (m, 2H), 2.81-2.84 (m, 4H), 2.60-2.69 (m, 2H), 1.69-1.86 (m, 10H), 1.45-1.58 (m, 4H). LCMS (ESI, m/z): 576 [M+H]$^+$.

Example 79: 1,1,1,3,3,3-Hexafluoropropan-2-yl 1-(2-chloro-3-morpholinobenzyl)-1,8-diazaspiro[4.5]decane-8-carboxylate

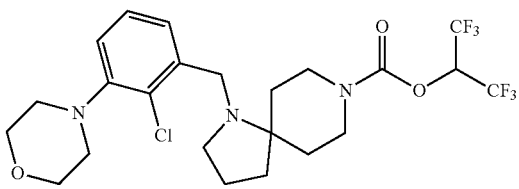 [SMILES: O=C(OC(C(F)(F)F)C(F)(F)F)N1CCC2(CCCN2Cc2cccc(N3CCOCC3)c2Cl)CC1]

Step 1: Preparation of tert-butyl 1-(3-bromo-2-chlorobenzyl)-1,8-diazaspiro[4.5]decane-8-carboxylate

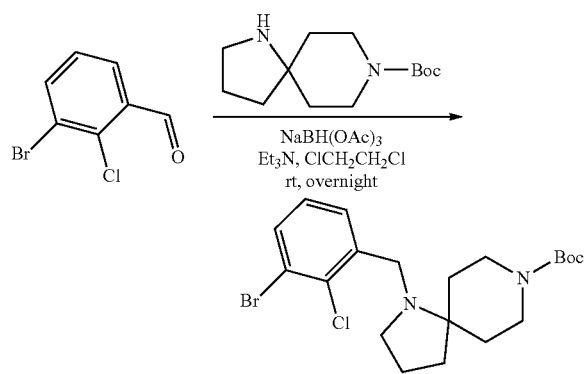

A flask was charged with 3-bromo-2-chlorobenzaldehyde (2.18 g, 9.93 mmol, 1.00 equiv) in DCE (20 mL), tert-butyl 1,8-diazaspiro[4.5]decane-8-carboxylate (3.60 g, 15.0 mmol, 1.51 equiv), and TEA (3.03 g, 30.0 mmol, 3.02 equiv); the resulting solution was stirred for 30 min at rt. NaBH(OAc)$_3$ (6.36 g, 30.0 mmol, 3.02 equiv) was added, after which the solution was stirred overnight at rt. The reaction was then quenched with H$_2$O (10 mL) and extracted with DCM (3×10 mL). The combined organic layers were washed with brine (2×10 mL), dried over anhydrous Na$_2$SO$_4$, filtered, and concentrated. The residue was purified on a silica gel column (20:1 DCM/MeOH) to yield 3.00 g (68% yield) of tert-butyl 1-(3-bromo-2-chlorobenzyl)-1,8-diazaspiro[4.5]decane-8-carboxylate as a light yellow solid. LCMS (ESI, m/z): 445 [M+H]$^+$.

Step 2: Preparation of tert-butyl 1-(2-chloro-3-morpholinobenzyl)-1,8-diazaspiro[4.5]decane-8-carboxylate

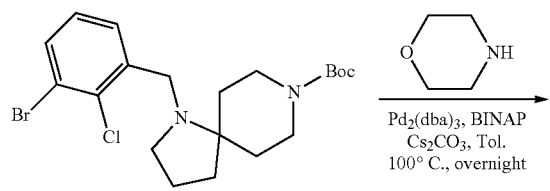

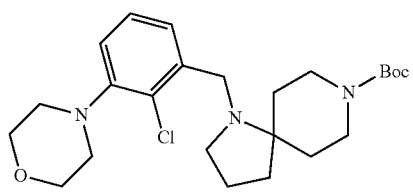

A flask was charged with tert-butyl 1-(3-bromo-2-chlorobenzyl)-1,8-diazaspiro[4.5]decane-8-carboxylate (800 mg, 1.80 mmol, 1.00 equiv) in toluene (20 mL), morpholine (235 mg, 2.70 mmol, 1.50 equiv), tris(dibenzylideneacetone)dipalladium (82.5 mg, 0.0900 mmol, 0.05 equiv), 2,2'-bis(diphenylphosphino)-1,1'-binaphthyl (168 mg, 0.270 mmol, 0.15 equiv), and cesium carbonate (881 mg, 2.70 mmol, 1.50 equiv) under nitrogen. The resulting solution was stirred overnight at 100° C. The reaction was then quenched with H$_2$O (20 mL). The resulting solution was extracted with EtOAc (3×20 mL) and the organic layers were combined, washed with brine (2×20 mL), dried over Na$_2$SO$_4$, filtered and concentrated. The residue was purified on a silica gel column (1:4 EtOAc/petroleum ether) to provide 650 mg (80% yield) of tert-butyl 1-(2-chloro-3-morpholinobenzyl)-1,8-diazaspiro[4.5]decane-8-carboxylate as a yellow oil. LCMS (ESI, m/z): 450 [M+H]$^+$.

Step 3: Preparation of 4-(3-((1,8-diazaspiro[4.5]decan-1-yl)methyl)-2-chlorophenyl)morpholine

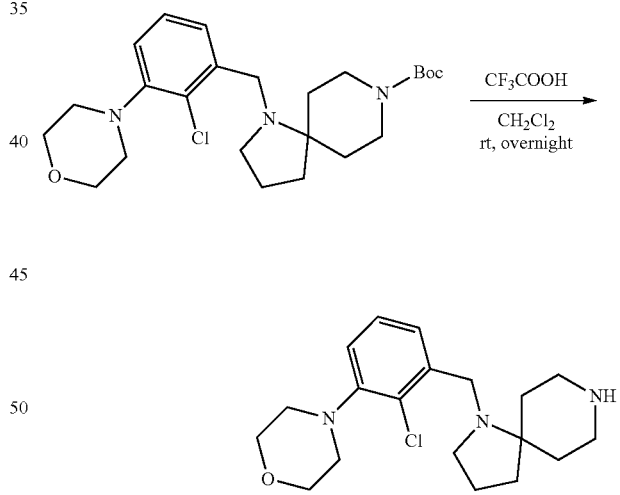

A flask was charged with tert-butyl 1-(2-chloro-3-morpholinobenzyl)-1,8-diazaspiro[4.5]decane-8-carboxylate (650 mg, 1.44 mmol, 1.00 equiv), DCM (10 mL), and TFA (2.5 mL). The resulting solution was stirred overnight at rt and then concentrated to provide 500 mg (99% yield) of 4-(3-((1,8-diazaspiro[4.5]decan-1-yl)methyl)-2-chlorophenyl)morpholine as a yellow oil. LCMS (ESI, m/z): 350 [M+H]$^+$.

Step 4: Preparation of 1,1,1,3,3,3-hexafluoropropan-2-yl 1-(2-chloro-3-morpholinobenzyl)-1,8-diazaspiro[4.5]decane-8-carboxylate

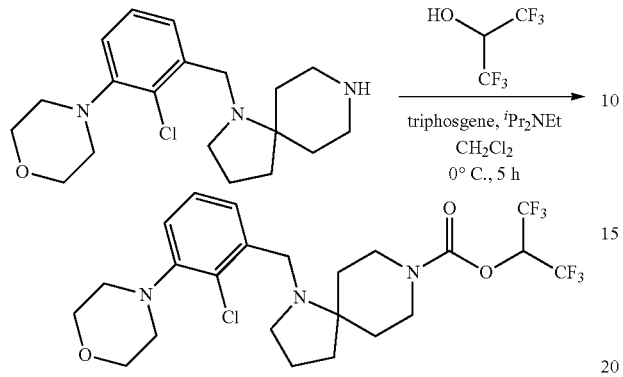

A flask was charged with triphosgene (74.5 mg, 0.250 mmol, 0.35 equiv) in DCM (5 mL) and HFIP (181 mg, 1.08 mmol, 1.51 equiv) under nitrogen. DIEA (277 mg, 2.15 mmol, 3.01 equiv) was added dropwise at 0° C. The resulting solution was stirred for 2 h at 0° C. A solution of 4-(3-((1,8-diazaspiro[4.5]decan-1-yl)methyl)-2-chlorophenyl)morpholine (250 mg, 0.710 mmol, 1.00 equiv) in DCM (5 mL) was added dropwise at 0° C. The resulting solution was stirred for 3 h at 0° C. and then quenched with $H_2O$ (10 mL). The mixture was extracted with DCM (3×10 mL) and the organic layers were combined, washed with brine (2×10 mL), dried over anhydrous $Na_2SO_4$, filtered and concentrated. The crude product was purified by preparative HPLC to give 163.9 mg (42% yield) of 1,1,1,3,3,3-hexafluoropropan-2-yl 1-(2-chloro-3-morpholinobenzyl)-1,8-diazaspiro[4.5]decane-8-carboxylate as a yellow solid. $^1$H NMR (300 MHz, Chloroform-d) δ 7.18-7.27 (m, 2H), 6.94-6.98 (m, 1H), 5.71-5.83 (m, 1H), 4.18-4.34 (m, 2H), 3.88-3.94 (m, 4H), 3.73 (s, 2H), 2.92-3.06 (m, 6H), 2.75-2.77 (m, 2H), 1.72-1.88 (m, 6H), 1.52-1.58 (m, 2H). LCMS (ESI, m/z): 544 [M+H]$^+$.

Example 80: 1,1,1,3,3,3-Hexafluoropropan-2-yl 1-(2-chloro-3-(piperidin-1-yl)benzyl)-1,8-diazaspiro[4.5]decane-8-carboxylate

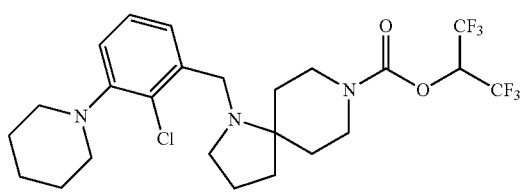 [SMILES: O=C(OC(C(F)(F)F)C(F)(F)F)N1CCC2(CCCN2Cc2cccc(N3CCCCC3)c2Cl)CC1]

The title compound was synthesized directly from commercially available piperidine in Step 2 according to the representative procedure of Example 79 to provide 1,1,1,3,3,3-hexafluoropropan-2-yl 1-(2-chloro-3-(piperidin-1-yl)benzyl)-1,8-diazaspiro[4.5]decane-8-carboxylate as a yellow oil. $^1$H NMR (400 MHz, Chloroform-d) δ 7.13-7.18 (m, 2H), 6.93-6.97 (m, 1H), 5.72-5.81 (m, 1H), 4.16-4.24 (m, 2H), 3.71 (s, 2H), 2.94-3.03 (m, 6H), 2.72-2.75 (m, 2H), 1.71-1.85 (m, 10H), 1.47-1.64 (m, 4H). LCMS (ESI, m/z): 542 [M+H]$^+$.

Example 81: 1,1,1,3,3,3-Hexafluoropropan-2-yl 1-(2-chloro-3-(pyrrolidin-1-yl)benzyl)-1,8-diazaspiro[4.5]decane-8-carboxylate

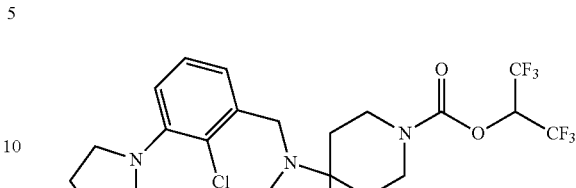

The title compound was synthesized directly from commercially available pyrrolidine in Step 2 according to the representative procedure of Example 79 to provide 1,1,1,3,3-hexafluoropropan-2-yl 1-(2-chloro-3-(pyrrolidin-1-yl)benzyl)-1,8-diazaspiro[4.5]decane-8-carboxylate as a yellow oil. $^1$H NMR (300 MHz, Chloroform-d) δ 7.02-7.14 (m, 2H), 6.85-6.91 (m, 1H), 5.70-5.82 (m, 1H), 4.16-4.24 (m, 2H), 3.72 (s, 2H), 3.30-3.34 (m, 4H), 2.91-3.09 (m, 2H), 2.76-2.78 (m, 2H), 1.89-1.98 (m, 4H), 1.65-1.82 (m, 6H), 1.39-1.56 (m, 2H). LCMS (ESI, m/z): 528 [M+H]$^+$.

Example 82: 1,1,1,3,3,3-Hexafluoropropan-2-yl 1-(3-(8-oxa-3-azabicyclo[3.2.1]octan-3-yl)-2-chlorobenzyl)-1,8-diazaspiro[4.5]decane-8-carboxylate

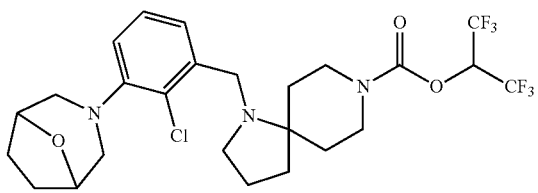 [SMILES: O=C(OC(C(F)(F)F)C(F)(F)F)N1CCC2(CCCN2Cc2cccc(N3CC4CCC(C3)O4)c2Cl)CC1]

The title compound was synthesized directly from commercially available 8-oxa-3-azabicyclo[3.2.1]octane in Step 2 according to the representative procedure of Example 79 to provide 1,1,1,3,3,3-hexafluoropropan-2-yl 1-(3-(8-oxa-3-azabicyclo[3.2.1]octan-3-yl)-2-chlorobenzyl)-1,8-diazaspiro[4.5]decane-8-carboxylate as a white solid. $^1$H NMR (300 MHz, Chloroform-d) δ 7.14-7.19 (m, 2H), 6.94-6.98 (m, 1H), 5.72-5.80 (m, 1H), 4.39-4.40 (m, 2H), 4.16-4.25 (m, 2H), 3.70 (s, 2H), 2.91-3.02 (m, 6H), 2.75-2.77 (m, 2H), 2.24-2.30 (m, 2H), 1.91-2.02 (m, 2H), 1.71-1.88 (m, 6H), 1.51-1.60 (m, 2H). LCMS (ESI, m/z): 570 [M+H]$^+$.

Example 83: 1,1,1,3,3,3-Hexafluoropropan-2-yl 1-(2-methyl-3-morpholinobenzyl)-1,8-diazaspiro[4.5]decane-8-carboxylate

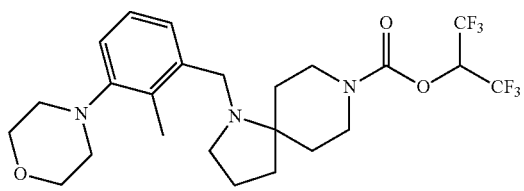 [SMILES: Cc1c(CN2CCCC23CCN(C(=O)OC(C(F)(F)F)C(F)(F)F)CC3)cccc1N1CCCCC1]

The title compound was synthesized directly from commercially available 3-bromo-2-methylbenzaldehyde in Step 1 and morpholine in Step 2 according to the representative procedure of Example 79 to provide 1,1,1,3,3,3-hexafluoropropan-2-yl 1-(2-methyl-3-morpholinobenzyl)-1,8-diazaspiro[4.5]decane-8-carboxylate as a yellow solid. ¹H NMR (300 MHz, Chloroform-d) δ 7.06-7.15 (m, 2H), 6.96 (d, J=7.8 Hz, 1H), 5.72-5.81 (m, 1H), 4.17-4.25 (m, 2H), 3.84-3.87 (m, 4H), 3.57 (s, 2H), 2.86-3.05 (m, 6H), 2.64-2.68 (m, 2H), 2.31 (s, 3H), 1.72-1.83 (m, 6H), 1.47-1.57 (m, 2H). LCMS (ESI, m/z): 524 [M+H]⁺.

Example 84: 1,1,1,3,3,3-Hexafluoropropan-2-yl 1-(2-methyl-3-(piperidin-1-yl)benzyl)-1,8-diazaspiro[4.5]decane-8-carboxylate

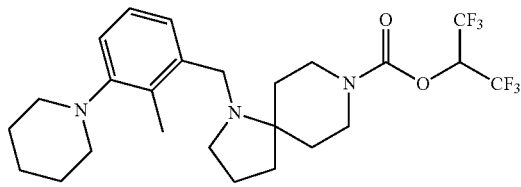

The title compound was synthesized directly from commercially available 3-bromo-2-methylbenzaldehyde in Step 1 and piperidine in Step 2 according to the representative procedure of Example 79 to provide 1,1,1,3,3,3-hexafluoropropan-2-yl 1-(2-methyl-3-(piperidin-1-yl)benzyl)-1,8-diazaspiro[4.5]decane-8-carboxylate as a white solid. ¹H NMR (300 MHz, Chloroform-d) δ 7.07-7.12 (m, 1H), 7.00-7.02 (m, 1H), 6.92-6.95 (m, 1H), 5.72-5.81 (m, 1H), 4.16-4.24 (m, 2H), 3.56 (s, 2H), 2.91-3.04 (m, 2H), 2.80 (br, 4H), 2.64-2.68 (m, 2H), 2.29 (s, 3H), 1.67-1.86 (m, 10H), 1.47-1.56 (m, 4H). LCMS (ESI, m/z): 522 [M+H]⁺.

Example 85: 1,1,1,3,3,3-Hexafluoropropan-2-yl 1-(2-methyl-3-(pyrrolidin-1-yl)benzyl)-1,8-diazaspiro[4.5]decane-8-carboxylate

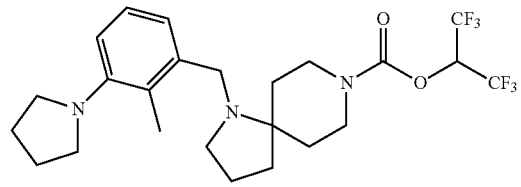 [SMILES: Cc1c(CN2CCCC23CCN(C(=O)OC(C(F)(F)F)C(F)(F)F)CC3)cccc1N1CCCC1]

The title compound was synthesized directly from commercially available 3-bromo-2-methylbenzaldehyde in Step 1 and pyrrolidine in Step 2 according to the representative procedure of Example 79 to provide 1,1,1,3,3,3-hexafluoropropan-2-yl 1-(2-methyl-3-(pyrrolidin-1-yl)benzyl)-1,8-diazaspiro[4.5]decane-8-carboxylate as a white solid. ¹H NMR (300 MHz, Chloroform-d) δ 7.04-7.09 (m, 1H), 6.90-6.96 (m, 2H), 5.72-5.81 (m, 1H), 4.16-4.25 (m, 2H), 3.58 (s, 2H), 2.91-3.10 (m, 6H), 2.64-2.69 (m, 2H), 2.27 (s, 3H), 1.71-1.96 (m, 10H), 1.51-1.56 (m, 2H). LCMS (ESI, m/z): 508 [M+H]⁺.

Example 86: 1,1,1,3,3,3-Hexafluoropropan-2-yl 1-(3-(8-oxa-3-azabicyclo[3.2.1]octan-3-yl)-2-methylbenzyl)-1,8-diazaspiro[4.5]decane-8-carboxylate

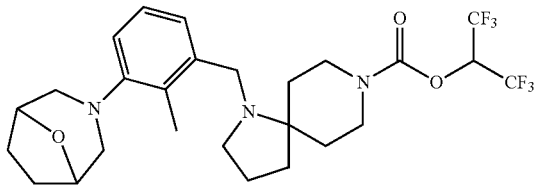 [SMILES: Cc1c(CN2CCCC23CCN(C(=O)OC(C(F)(F)F)C(F)(F)F)CC3)cccc1N1CC2CCC(C1)O2]

The title compound was synthesized directly from commercially available 3-bromo-2-methylbenzaldehyde in Step 1 and 8-oxa-3-azabicyclo[3.2.1]octane in Step 2 according to the representative procedure of Example 79 to provide 1,1,1,3,3,3-hexafluoropropan-2-yl 1-(3-(8-oxa-3-azabicyclo[3.2.1]octan-3-yl)-2-methylbenzyl)-1,8-diazaspiro[4.5]decane-8-carboxylate as an off-white solid. ¹H NMR (300 MHz, Chloroform-d) δ 7.00-7.19 (m, 3H), 5.74-5.81 (m, 1H), 4.40 (br, 2H), 4.16-4.25 (m, 2H), 3.56 (s, 2H), 2.91-3.05 (m, 4H), 2.64-2.74 (m, 4H), 2.33 (s, 3H), 2.14-2.21 (m, 2H), 1.94-2.11 (m, 2H), 1.70-1.85 (m, 6H), 1.49-1.56 (m, 2H). LCMS (ESI, m/z): 550 [M+H]⁺.

Example 87: 1,1,1,3,3,3-Hexafluoropropan-2-yl 1-(2-(4-ethylpiperazin-1-yl)-4-(trifluoromethyl)benzyl)-1,8-diazaspiro[4.5]decane-8-carboxylate

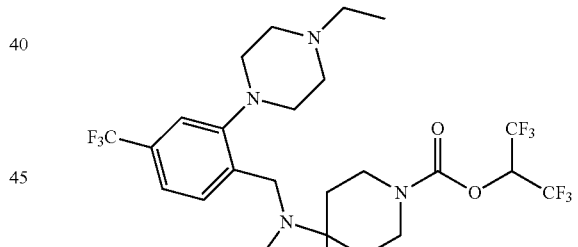

The title compound was synthesized directly from commercially available 2-fluoro-4-(trifluoromethyl)benzaldehyde and 1-ethylpiperazine in Step 1 and tert-butyl 1,8-diazaspiro[4.5]decane-8-carboxylate in Step 2 according to the representative procedure of Example 79 to provide 1,1,1,3,3,3-hexafluoropropan-2-yl 1-(2-(4-ethylpiperazin-1-yl)-4-(trifluoromethyl)benzyl)-1,8-diazaspiro[4.5]decane-8-carboxylate as a yellow oil. ¹H NMR (300 MHz, Chloroform-d) δ 7.63 (d, J=8.1 Hz, 1H), 7.29-7.40 (m, 2H), 5.70-5.83 (m, 1H), 4.17-4.26 (m, 2H), 3.67 (s, 2H), 2.92-3.24 (m, 6H), 2.43-2.85 (m, 8H), 1.74-1.87 (m, 6H), 1.44-1.53 (m, 2H), 1.05-1.25 (m, 3H). LCMS (ESI, m/z): 605 [M+H]⁺.

Example 88: 1,1,1,3,3,3-Hexafluoropropan-2-yl 1-(2-(4-acetylpiperazin-1-yl)-4-(trifluoromethyl)benzyl)-1,8-diazaspiro[4.5]decane-8-carboxylate

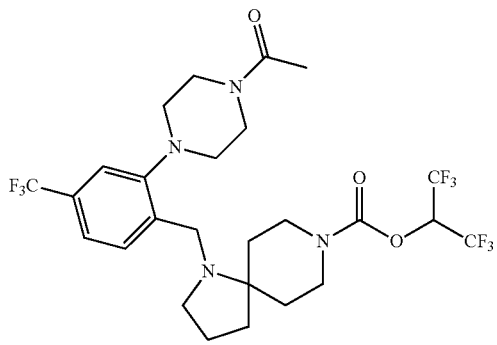 [SMILES: CC(=O)N1CCN(c2cc(C(F)(F)F)ccc2CN2CCCC23CCN(C(=O)OC(C(F)(F)F)C(F)(F)F)CC3)CC1]

The title compound was synthesized directly from commercially available 2-fluoro-4-(trifluoromethyl)benzaldehyde and 1-(piperazin-1-yl)ethan-1-one in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-acetylpiperazin-1-yl)-4-(trifluoromethyl)benzyl)-1,8-diazaspiro[4.5]decane-8-carboxylate as a light yellow oil. $^1$H NMR (300 MHz, Chloroform-d) δ 7.65 (d, J=8.1 Hz, 1H), 7.34 (d, J=8.4 Hz, 1H), 7.26 (s, 1H), 5.72-5.80 (m, 1H), 4.17-4.26 (m, 2H), 3.71-3.76 (m, 4H), 3.60-3.63 (m, 2H), 2.89-3.06 (m, 6H), 2.64-2.69 (m, 2H), 2.15 (s, 3H), 1.66-1.88 (m, 6H), 1.47-1.51 (m, 2H). LCMS (ESI, m/z): 619 [M+H]$^+$.

Example 89: 1,1,1,3,3,3-Hexafluoropropan-2-yl 1-(2-(4-(methylsulfonyl)piperazin-1-yl)-4-(trifluoromethyl)benzyl)-1,8-diazaspiro[4.5]decane-8-carboxylate

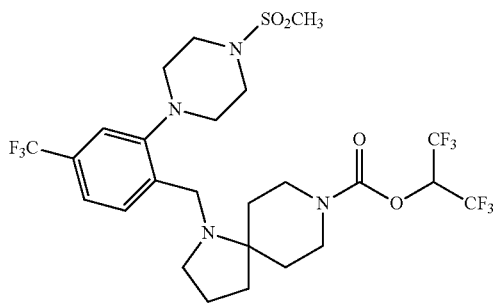 [SMILES: CS(=O)(=O)N1CCN(c2cc(C(F)(F)F)ccc2CN2CCCC23CCN(C(=O)OC(C(F)(F)F)C(F)(F)F)CC3)CC1]

The title compound was synthesized directly from commercially available 2-fluoro-4-(trifluoromethyl)benzaldehyde and 1-methanesulfonylpiperazine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-(methylsulfonyl)piperazin-1-yl)-4-(trifluoromethyl)benzyl)-1,8-diazaspiro[4.5]decane-8-carboxylate as a white solid. $^1$H NMR (300 MHz, Chloroform-d) δ 7.66 (d, J=8.1 Hz, 1H), 7.30-7.37 (m, 2H), 5.72-5.80 (m, 1H), 4.17-4.26 (m, 2H), 3.68 (s, 2H), 3.38-3.41 (m, 4H), 2.87-3.10 (m, 9H), 2.66-2.68 (m, 2H), 1.64-1.88 (m, 6H), 1.51-1.55 (m, 2H). LCMS (ESI, m/z): 655 [M+H]$^+$.

Example 90: 1,1,1,3,3,3-Hexafluoropropan-2-yl 1-(2-(4,4-difluoropiperidin-1-yl)-4-(trifluoromethyl)benzyl)-1,8-diazaspiro[4.5]decane-8-carboxylate

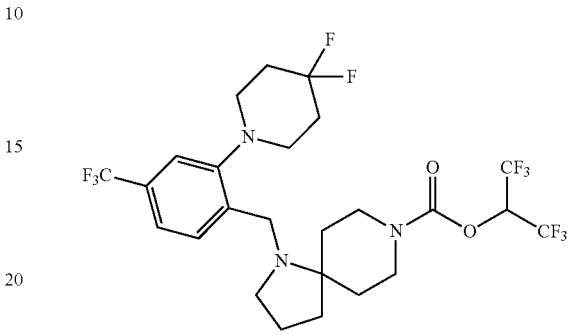

The title compound was synthesized directly from commercially available 2-fluoro-4-(trifluoromethyl)benzaldehyde and 4,4-difluoropiperidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4,4-difluoropiperidin-1-yl)-4-(trifluoromethyl)benzyl)-1,8-diazaspiro[4.5]decane-8-carboxylate as a light yellow semi-solid. $^1$H NMR (300 MHz, Chloroform-d) δ 7.62 (d, J=10.8 Hz, 1H), 7.30-7.34 (m, 2H), 5.70-5.82 (m, 1H), 4.18-4.26 (m, 2H), 3.68 (s, 2H), 2.92-3.04 (m, 6H), 2.60-2.68 (m, 2H), 2.07-2.20 (m, 4H), 1.63-1.88 (m, 6H), 1.48-1.59 (m, 2H). LCMS (ESI, m/z): 612 [M+H]$^+$.

Example 91: 1,1,1,3,3,3-Hexafluoropropan-2-yl 1-(2-(4-fluoropiperidin-1-yl)-4-(trifluoromethyl)benzyl)-1,8-diazaspiro[4.5]decane-8-carboxylate

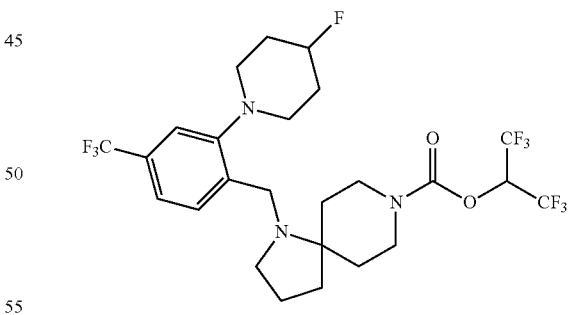

The title compound was synthesized directly from commercially available 2-fluoro-4-(trifluoromethyl)benzaldehyde and 4-fluoropiperidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-fluoropiperidin-1-yl)-4-(trifluoromethyl)benzyl)-1,8-diazaspiro[4.5]decane-8-carboxylate as a light yellow semi-solid. $^1$H NMR (300 MHz, Chloroform-d) δ 7.62 (d, J=9.0 Hz, 1H), 7.29-7.31 (m, 2H), 5.72-5.80 (m, 1H), 4.72-4.90 (m, 1H), 4.16-4.26 (m, 2H), 3.68 (s, 2H), 2.83-3.11 (m, 4H), 2.79-2.81 (m, 2H), 2.64-2.68 (m, 2H), 1.96-2.09 (m, 4H), 1.64-1.86 (m, 6H), 1.45-1.55 (m, 2H). LCMS (ESI, m/z): 594 [M+H]+.

Example 92: 1,1,1,3,3,3-Hexafluoropropan-2-yl 1-(2-(1,1-dioxidothiomorpholino)-4-(trifluoromethyl)benzyl)-1,8-diazaspiro[4.5]decane-8-carboxylate

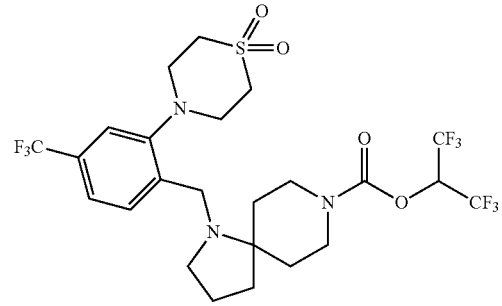 [SMILES: O=C(OC(C(F)(F)F)C(F)(F)F)N1CCC2(CCCN2Cc2ccc(C(F)(F)F)cc2N2CCS(=O)(=O)CC2)CC1]

Step 1: Preparation of 2-thiomorpholino-4-(trifluoromethyl)benzaldehyde

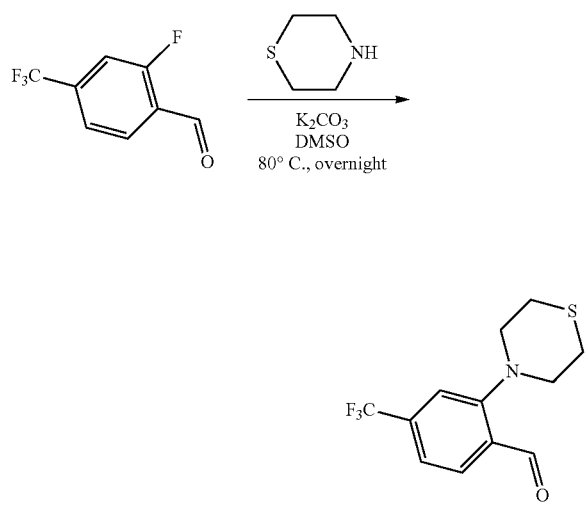 [SMILES: O=Cc1ccc(C(F)(F)F)cc1F ; C1CSCCN1 ; O=Cc1ccc(C(F)(F)F)cc1N1CCSCC1]

A flask was charged with 2-fluoro-4-(trifluoromethyl)benzaldehyde (300 mg, 1.56 mmol, 1.00 equiv) in DMSO (10 mL), thiomorpholine (241 mg, 2.34 mmol, 1.49 equiv), and potassium carbonate (647 mg, 4.69 mmol, 3.01 equiv) under nitrogen. The resulting solution was stirred overnight at 80° C. and then quenched with H2O (10 mL). The resulting solution was extracted with EtOAc (3×10 mL) and the organic layers were combined, washed with brine (2×10 mL), dried over Na2SO4, filtered and concentrated. The residue was purified on a silica gel column (1:4 EtOAc/petroleum ether) to provide 210 mg (49% yield) of 2-thiomorpholino-4-(trifluoromethyl)benzaldehyde as a light-yellow solid. LCMS (ESI, m/z): 276 [M+H]+.

Step 2: Preparation of tert-butyl 1-(2-thiomorpholino-4-(trifluoromethyl)benzyl)-1,8-diazaspiro[4.5]decane-8-carboxylate

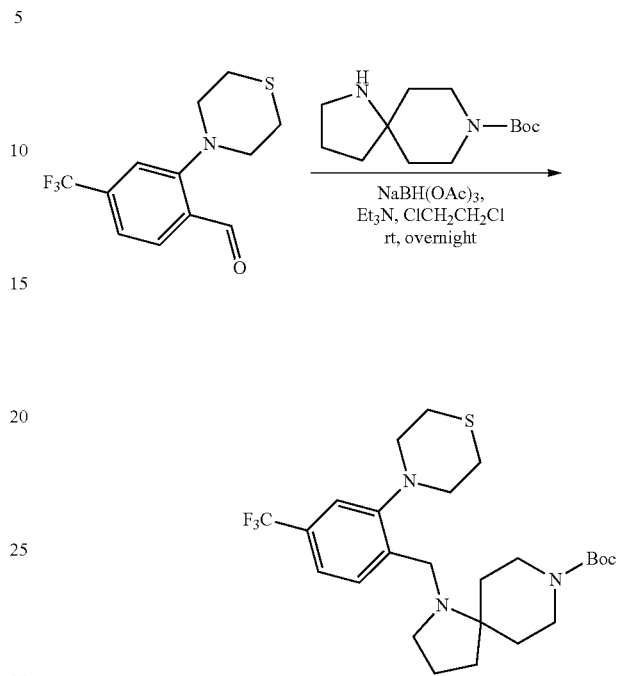

A flask was charged with 2-thiomorpholino-4-(trifluoromethyl)benzaldehyde (210 mg, 0.760 mmol, 1.00 equiv) in DCE (10 mL), tert-butyl 1,8-diazaspiro[4.5]decane-8-carboxylate (275 mg, 1.14 mmol, 1.50 equiv), and TEA (231 mg, 2.29 mmol, 3.00 equiv), and the resulting solution was stirred for 30 min at rt. NaBH(OAc)3 (486 mg, 2.29 mmol, 3.01 equiv) was added, after which the mixture was stirred overnight at rt. The reaction was then quenched with H2O (10 mL) and extracted with DCM (3×10 mL). The combined organic layers were washed with brine (2×10 mL), dried over anhydrous Na2SO4, filtered and concentrated. The residue was purified on a silica gel column (20:1 DCM/MeOH) to yield 350 mg (92% yield) of tert-butyl 1-(2-thiomorpholino-4-(trifluoromethyl)benzyl)-1,8-diazaspiro[4.5]decane-8-carboxylate as a yellow oil. LCMS (ESI, m/z): 500 [M+H]+.

Step 3: Preparation of tert-butyl 1-(2-(1,1-dioxidothiomorpholino)-4-(trifluoromethyl)benzyl)-1,8-diazaspiro[4.5]decane-8-carboxylate

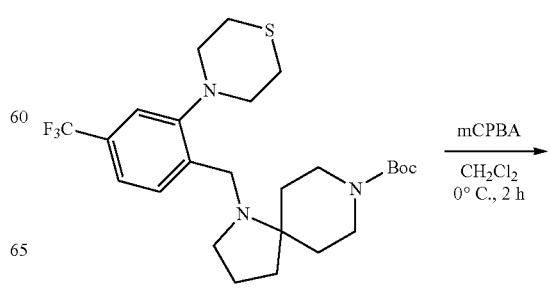

-continued

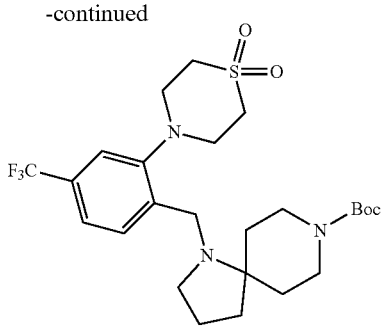

A flask was charged with tert-butyl 1-(2-thiomorpholino-4-(trifluoromethyl)benzyl)-1,8-diazaspiro[4.5]decane-8-carboxylate (350 mg, 0.700 mmol, 1.00 equiv) in DCM (10 mL), and 3-chlorobenzoperoxoic acid (241 mg, 1.40 mmol, 1.99 equiv). The resulting solution was stirred for 2 h at 0° C. The reaction was then quenched with H₂O (10 mL) and extracted with DCM (3×10 mL). The combined organic layers were washed with brine (2×10 mL), dried over anhydrous Na₂SO₄, filtered, and concentrated. The residue was purified on a silica gel column (1:1 DCM/MeOH) to yield 300 mg (81% yield) of tert-butyl 1-(2-(1,1-dioxidothiomorpholino)-4-(trifluoromethyl)benzyl)-1,8-diazaspiro[4.5]decane-8-carboxylate as a white solid. LCMS (ESI, m/z): 532 [M+H]⁺.

Step 4: Preparation of 4-(2-((1,8-diazaspiro[4.5]decan-1-yl)methyl)-5-(trifluoromethyl)phenyl)thiomorpholine 1,1-dioxide

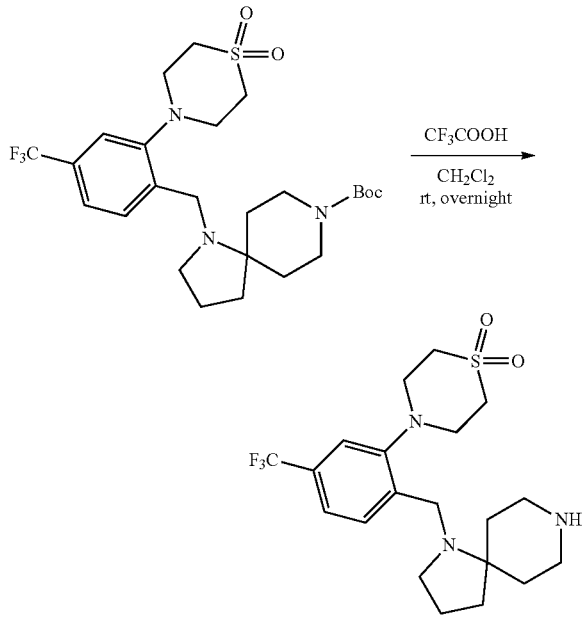

A flask was charged with tert-butyl 1-(2-(1,1-dioxidothiomorpholino)-4-(trifluoromethyl)benzyl)-1,8-diazaspiro[4.5]decane-8-carboxylate (300 mg, 0.560 mmol, 1.00 equiv) in DCM (10 mL), and TFA (2.5 mL). The resulting solution was stirred overnight at rt and then concentrated to yield 240 mg (99% yield) of 4-(2-((1,8-diazaspiro[4.5]decan-1-yl)methyl)-5-(trifluoromethyl)phenyl)thiomorpholine 1,1-dioxide as a yellow oil. LCMS (ESI, m/z): 432 [M+H]⁺.

Step 5: Preparation of 1,1,1,3,3,3-hexafluoropropan-2-yl 1-(2-(1,1-dioxidothiomorpholino)-4-(trifluoromethyl)benzyl)-1,8-diazaspiro[4.5]decane-8-carboxylate

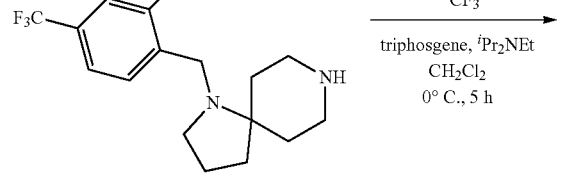

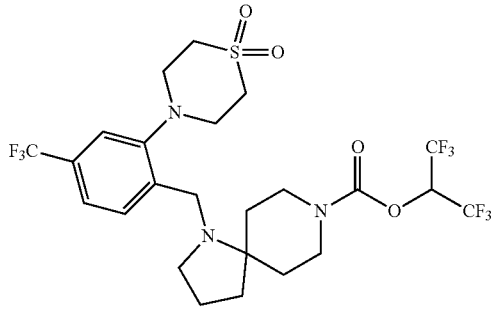

A flask was charged with triphosgene (29.0 mg, 0.100 mmol, 0.35 equiv) in DCM (5 mL) and HFIP (70.0 mg, 0.420 mmol, 1.50 equiv) under nitrogen. DIEA (108 mg, 0.840 mmol, 3.01 equiv) was added dropwise at 0° C. The resulting solution was stirred for 2 h at 0° C. A solution of 4-(2-((1,8-diazaspiro[4.5]decan-1-yl)methyl)-5-(trifluoromethyl)phenyl)thiomorpholine 1,1-dioxide (120 mg, 0.280 mmol, 1.00 equiv) in DCM (5 mL) was added dropwise at 0° C. The resulting solution was stirred for 3 h at 0° C. and then quenched with H₂O (10 mL). The mixture was extracted with DCM (3×10 mL) and the organic layers were combined, washed with brine (2×10 mL), dried over anhydrous Na₂SO₄, filtered and concentrated. The crude product was purified by preparative HPLC to give 62.4 mg (36% yield) of 1,1,1,3,3,3-hexafluoropropan-2-yl 1-(2-(1,1-dioxidothiomorpholino)-4-(trifluoromethyl)benzyl)-1,8-diazaspiro[4.5]decane-8-carboxylate as a white solid. ¹H NMR (300 MHz, Chloroform-d) δ 7.64 (d, J=7.8 Hz, 1H), 7.38-7.42 (m, 2H), 5.72-5.84 (m, 1H), 5.36-5.42 (m, 1H), 4.96 (br, 1H), 3.92-3.98 (m, 4H), 3.60-3.75 (m, 4H), 3.11-3.17 (m, 2H), 2.92-3.02 (m, 4H), 2.76-2.81 (m, 2H), 2.10 (br, 4H), 1.72-1.82 (m, 2H). LCMS (ESI, m/z): 626 [M+H]⁺.

Example 93: 1,1,1,3,3,3-Hexafluoropropan-2-yl 1-(2-(4-acetamidopiperidin-1-yl)-4-(trifluoromethyl)benzyl)-1,8-diazaspiro[4.5]decane-8-carboxylate

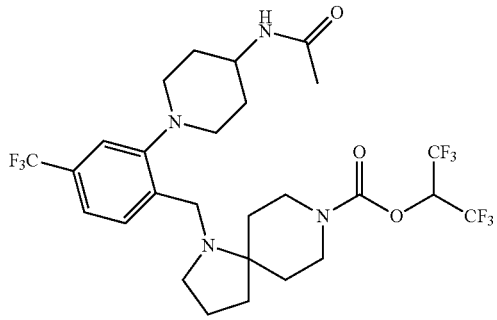 [SMILES: CC(=O)NC1CCN(c2cc(C(F)(F)F)ccc2CN2CCCC23CCN(C(=O)OC(C(F)(F)F)C(F)(F)F)CC3)CC1]

The title compound was synthesized directly from commercially available 2-fluoro-4-(trifluoromethyl)benzaldehyde and N-(piperidin-4-yl)acetamide in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-acetamidopiperidin-1-yl)-4-(trifluoromethyl)benzyl)-1,8-diazaspiro[4.5]decane-8-carboxylate as a white solid. $^1$H NMR (300 MHz, Chloroform-d) δ 7.59 (d, J=7.8 Hz, 1H), 7.26-7.30 (m, 2H), 5.72-5.80 (m, 1H), 5.45-5.48 (m, 1H), 4.17-4.26 (m, 2H), 3.91-4.01 (m, 1H), 3.58-3.73 (m, 2H), 2.92-3.09 (m, 4H), 2.80-2.84 (m, 2H), 2.67-2.76 (m, 2H), 2.01-2.07 (m, 5H), 1.62-1.87 (m, 10H). LCMS (ESI, m/z): 633 [M+H]$^+$.

Example 94: 1,1,1,3,3,3-Hexafluoropropan-2-yl 1-(2-(4-(methylsulfonamido)piperidin-1-yl)-4-(trifluoromethyl)benzyl)-1,8-diazaspiro[4.5]decane-8-carboxylate

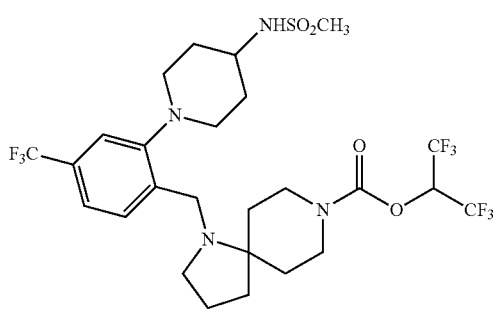

The title compound was synthesized directly from commercially available 2-fluoro-4-(trifluoromethyl)benzaldehyde and N-(piperidin-4-yl)methanesulfonamide in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-(methyl sulfonamido)piperidin-1-yl)-4-(trifluoromethyl)benzyl)-1,8-diazaspiro[4.5]decane-8-carboxylate as a light yellow solid. $^1$H NMR (300 MHz, Chloroform-d) δ 7.62 (d, J=8.1 Hz, 1H), 7.29-7.32 (m, 2H), 5.74-5.83 (m, 1H), 4.45-4.47 (m, 1H), 4.18-4.26 (m, 2H), 3.46-3.74 (m, 3H), 2.92-3.07 (m, 7H), 2.68-2.84 (m, 4H), 2.11-2.14 (m, 2H), 1.65-1.87 (m, 8H), 1.46-1.51 (m, 2H). LCMS (ESI, m/z): 669 [M+H]$^+$.

Example 95: 1,1,1,3,3,3-Hexafluoropropan-2-yl 1-(2-(azepan-1-yl)-4-(trifluoromethyl)benzyl)-1,8-diazaspiro[4.5]decane-8-carboxylate

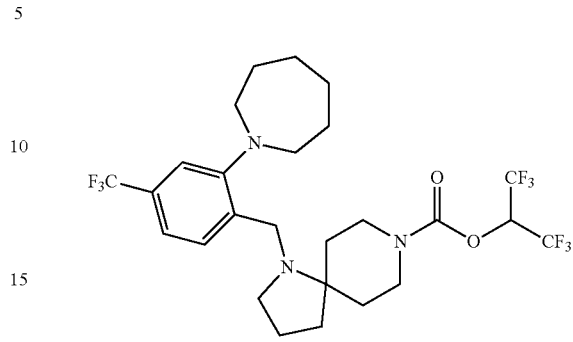

The title compound was synthesized directly from commercially available 2-fluoro-4-(trifluoromethyl)benzaldehyde and azepane in Step 1 and tert-butyl 1,8-diazaspiro[4.5]decane-8-carboxylate in Step 2 according to the representative procedure of Example 66 to provide 1,1,1,3,3-hexafluoropropan-2-yl 1-(2-(azepan-1-yl)-4-(trifluoromethyl)benzyl)-1,8-diazaspiro[4.5]decane-8-carboxylate as a light yellow solid. $^1$H NMR (300 MHz, Chloroform-d) δ 7.63 (d, J=8.1 Hz, 1H), 7.30 (s, 1H), 7.22-7.25 (m, 1H), 5.72-5.80 (m, 1H), 4.16-4.25 (m, 2H), 3.70 (s, 2H), 2.92-3.06 (m, 6H), 2.65-2.70 (m, 2H), 1.64-1.88 (m, 14H), 1.49-1.52 (m, 2H). LCMS (ESI, m/z): 590 [M+H]$^+$.

Example 96: 1,1,1,3,3,3-Hexafluoropropan-2-yl 1-(2-(azetidin-1-yl)-4-(trifluoromethyl)benzyl)-1,8-diazaspiro[4.5]decane-8-carboxylate

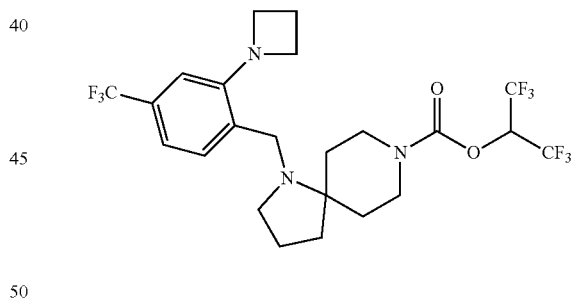

The title compound was synthesized directly from commercially available 2-fluoro-4-(trifluoromethyl)benzaldehyde and azetidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(azetidin-1-yl)-4-(trifluoromethyl)benzyl)-1,8-diazaspiro[4.5]decane-8-carboxylate as a yellow oil. $^1$H NMR (300 MHz, Chloroform-d) δ 7.58 (d, J=8.1 Hz, 1H), 7.04-7.07 (m, 1H), 6.68 (s, 1H), 5.69-5.82 (m, 1H), 4.15-4.24 (m, 2H), 3.90-3.95 (m, 4H), 3.53 (s, 2H), 2.92-3.05 (m, 2H), 2.66-2.68 (m, 2H), 2.27-2.37 (m, 2H), 1.84-1.89 (m, 4H), 1.61-1.77 (m, 2H), 1.44-1.51 (m, 2H). LCMS (ESI, m/z): 548 [M+H]$^+$.

Example 97: 1,1,1,3,3,3-Hexafluoropropan-2-yl 1-(2-(tetrahydro-1H-furo[3,4-c]pyrrol-5(3H)-yl)-4-(trifluoromethyl)benzyl)-1,8-diazaspiro[4.5]decane-8-carboxylate

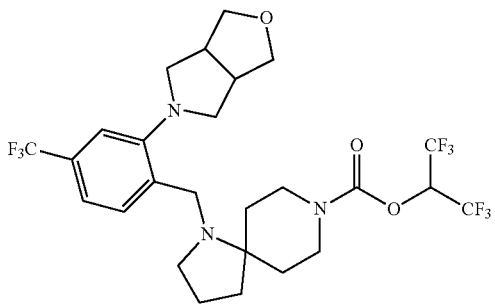 [SMILES: O=C(OC(C(F)(F)F)C(F)(F)F)N1CCC2(CCCN2Cc2ccc(C(F)(F)F)cc2N2CC3COCC3C2)CC1]

The title compound was synthesized directly from commercially available 2-fluoro-4-(trifluoromethyl)benzaldehyde and hexahydro-1H-furo[3,4-c]pyrrole in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(tetrahydro-1H-furo[3,4-c]pyrrol-5(3H)-yl)-4-(trifluoromethyl)benzyl)-1,8-diazaspiro[4.5]decane-8-carboxylate as a yellow solid. $^1$H NMR (300 MHz, Chloroform-d) δ 7.69 (d, J=8.1 Hz, 1H), 7.22-7.25 (m, 2H), 5.70-5.83 (m, 1H), 4.16-4.25 (m, 2H), 4.00-4.04 (m, 2H), 3.60-3.65 (m, 4H), 3.14 (br, 2H), 2.89-3.06 (m, 6H), 2.60-2.64 (m, 2H), 1.78-1.89 (m, 4H), 1.62-1.75 (m, 2H), 1.53-1.58 (m, 2H). LCMS (ESI, m/z): 604 [M+H]$^+$.

Example 98: 1,1,1,3,3,3-Hexafluoropropan-2-yl 1-(4-chloro-2-(4-ethylpiperazin-1-yl)benzyl)-1,8-diazaspiro[4.5]decane-8-carboxylate

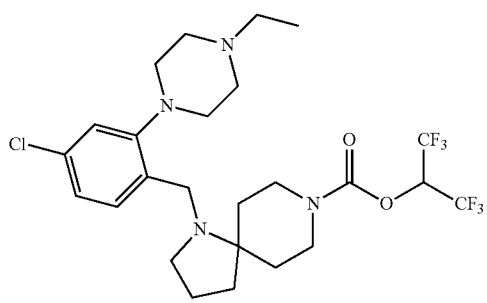 [SMILES: CCN1CCN(c2cc(Cl)ccc2CN2CCCC23CCN(C(=O)OC(C(F)(F)F)C(F)(F)F)CC3)CC1]

The title compound was synthesized directly from commercially available 4-chloro-2-fluorobenzaldehyde and 1-ethylpiperazine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(4-ethylpiperazin-1-yl)benzyl)-1,8-diazaspiro[4.5]decane-8-carboxylate as a yellow oil. $^1$H NMR (300 MHz, Chloroform-d) δ 7.42 (d, J=8.1 Hz, 1H), 7.00-7.03 (m, 2H), 5.70-5.83 (m, 1H), 4.16-4.25 (m, 2H), 3.60 (s, 2H), 2.93-3.05 (m, 6H), 2.47-2.68 (m, 8H), 1.67-1.85 (m, 6H), 1.48 (br, 2H), 1.23 (t, J=8.1 Hz, 3H). LCMS (ESI, m/z): 571 [M+H]$^+$.

Example 99: 1,1,1,3,3,3-Hexafluoropropan-2-yl 1-(2-(4-acetylpiperazin-1-yl)-4-chlorobenzyl)-1,8-diazaspiro[4.5]decane-8-carboxylate

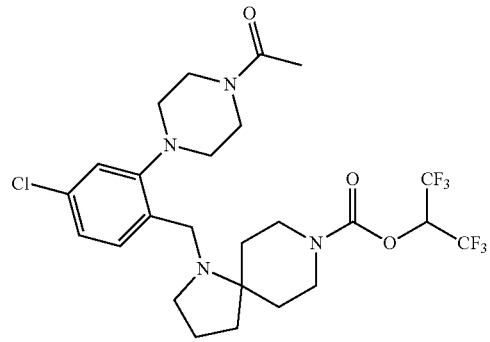 [SMILES: CC(=O)N1CCN(c2cc(Cl)ccc2CN2CCCC23CCN(C(=O)OC(C(F)(F)F)C(F)(F)F)CC3)CC1]

The title compound was synthesized directly from commercially available 4-chloro-2-fluorobenzaldehyde and 1-(piperazin-1-yl)ethan-1-one in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-acetylpiperazin-1-yl)-4-chlorobenzyl)-1,8-diazaspiro[4.5]decane-8-carboxylate as a light yellow solid. $^1$H NMR (300 MHz, Chloroform-d) δ 7.43 (d, J=8.4 Hz, 1H), 7.00-7.07 (m, 2H), 5.72-5.81 (m, 1H), 4.16-4.25 (m, 2H), 3.74 (br, 2H), 3.57-3.63 (m, 4H), 2.87-3.05 (m, 6H), 2.63-2.68 (m, 2H), 2.14 (s, 3H), 1.67-1.86 (m, 6H), 1.45-1.49 (m, 2H). LCMS (ESI, m/z): 585 [M+H]$^+$.

Example 100: 1,1,1,3,3,3-Hexafluoropropan-2-yl 1-(4-chloro-2-(4-(methylsulfonyl)piperazin-1-yl)benzyl)-1,8-diazaspiro[4.5]decane-8-carboxylate

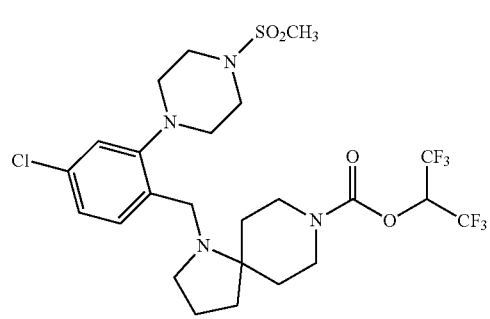 [SMILES: CS(=O)(=O)N1CCN(c2cc(Cl)ccc2CN2CCCC23CCN(C(=O)OC(C(F)(F)F)C(F)(F)F)CC3)CC1]

The title compound was synthesized directly from commercially available 4-chloro-2-fluorobenzaldehyde and 1-methanesulfonylpiperazine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(4-(methylsulfonyl)piperazin-1-yl)benzyl)-1,8-diazaspiro[4.5]decane-8-carboxylate as a light yellow solid. $^1$H NMR (300 MHz, Chloroform-d) δ 7.44 (d, J=8.4 Hz, 1H), 7.04-7.08 (m, 2H), 5.72-5.80 (m, 1H), 4.16-4.25 (m, 2H), 3.60 (br, 2H), 3.35-3.38 (m, 4H), 2.91-3.09 (m, 6H), 2.86 (s, 3H), 2.65-2.67 (m, 2H), 1.65-1.86 (m, 6H), 1.44-1.48 (m, 2H). LCMS (ESI, m/z): 621 [M+H]$^+$.

Example 101: 1,1,1,3,3,3-Hexafluoropropan-2-yl 1-(4-chloro-2-(4,4-difluoropiperidin-1-yl)benzyl)-1,8-diazaspiro[4.5]decane-8-carboxylate

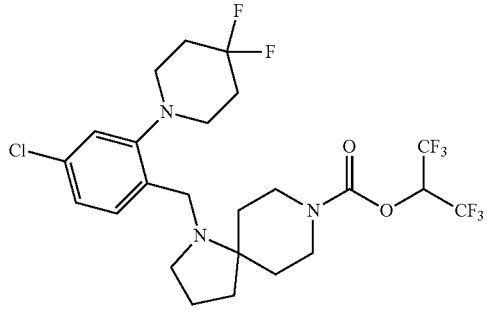 [SMILES: O=C(OC(C(F)(F)F)C(F)(F)F)N1CCC2(CCCN2Cc2ccc(Cl)cc2N2CCC(F)(F)CC2)CC1]

The title compound was synthesized directly from commercially available 4-chloro-2-fluorobenzaldehyde and 4,4-difluoropiperidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(4,4-difluoropiperidin-1-yl)benzyl)-1,8-diazaspiro[4.5]decane-8-carboxylate as an off-white solid. $^1$H NMR (300 MHz, Chloroform-d) δ 7.44 (d, J=8.7 Hz, 1H), 7.04-7.07 (m, 2H), 5.70-5.82 (m, 1H), 4.16-4.25 (m, 2H), 3.60 (s, 2H), 2.91-3.05 (m, 6H), 2.62-2.67 (m, 2H), 2.01-2.18 (m, 4H), 1.64-1.86 (m, 6H), 1.38-1.62 (m, 2H). LCMS (ESI, m/z): 578 [M+H]$^+$.

Example 102: 1,1,1,3,3,3-Hexafluoropropan-2-yl 1-(4-chloro-2-(4-fluoropiperidin-1-yl)benzyl)-1,8-diazaspiro[4.5]decane-8-carboxylate

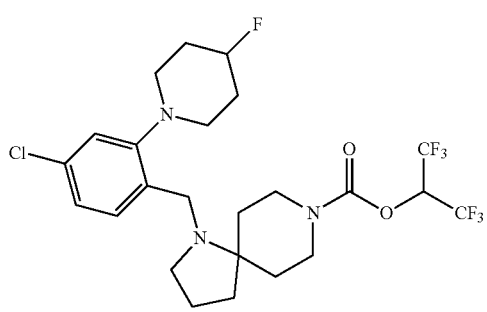 [SMILES: O=C(OC(C(F)(F)F)C(F)(F)F)N1CCC2(CCCN2Cc2ccc(Cl)cc2N2CCC(F)CC2)CC1]

The title compound was synthesized directly from commercially available 4-chloro-2-fluorobenzaldehyde and 4-fluoropiperidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(4-fluoropiperidin-1-yl)benzyl)-1,8-diazaspiro[4.5]decane-8-carboxylate as a light yellow solid. $^1$H NMR (300 MHz, Chloroform-d) δ 7.42 (d, J=9.0 Hz, 1H), 7.00-7.03 (m, 2H), 5.72-5.80 (m, 1H), 4.70-4.89 (m, 1H), 4.16-4.24 (m, 2H), 3.60 (s, 2H), 2.91-3.07 (m, 4H), 2.63-2.80 (m, 4H), 1.94-2.07 (m, 4H), 1.65-1.83 (m, 6H), 1.45-1.56 (m, 2H). LCMS (ESI, m/z): 560 [M+H]$^+$.

Example 103: 1,1,1,3,3,3-Hexafluoropropan-2-yl 1-(4-chloro-2-(1,1-dioxidothiomorpholino)benzyl)-1,8-diazaspiro[4.5]decane-8-carboxylate

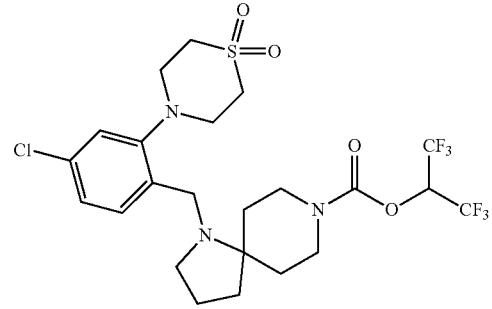 [SMILES: O=C(OC(C(F)(F)F)C(F)(F)F)N1CCC2(CCCN2Cc2ccc(Cl)cc2N2CCS(=O)(=O)CC2)CC1]

The title compound was synthesized from commercially available 4-chloro-2-fluorobenzaldehyde according to the representative procedure of Example 92 to provide 1,1,1,3,3,3-hexafluoropropan-2-yl 1-(2-(1,1-dioxidothiomorpholino)-4-(trifluoromethyl)benzyl)-1,8-diazaspiro[4.5]decane-8-carboxylate as a white solid. $^1$H NMR (300 MHz, Chloroform-d) δ 7.42 (d, J=8.1 Hz, 1H), 7.10-7.16 (m, 2H), 5.72-5.84 (m, 1H), 5.36-5.40 (m, 1H), 4.92 (br, 1H), 3.98 (br, 2H), 3.85 (s, 2H), 3.59-3.71 (m, 4H), 3.11-3.15 (m, 2H), 2.91-2.98 (m, 4H), 2.73-2.77 (m, 2H), 2.08-2.10 (m, 4H), 1.70-1.80 (m, 2H). LCMS (ESI, m/z): 592 [M+H]$^+$.

Example 104: 1,1,1,3,3,3-Hexafluoropropan-2-yl 1-(2-(4-acetamidopiperidin-1-yl)-4-chlorobenzyl)-1,8-diazaspiro[4.5]decane-8-carboxylate

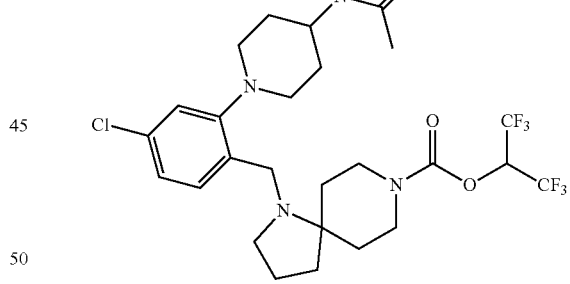

The title compound was synthesized directly from commercially available 4-chloro-2-fluorobenzaldehyde and N-(piperidin-4-yl)acetamide in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(4-acetamidopiperidin-1-yl)-4-chlorobenzyl)-1,8-diazaspiro[4.5]decane-8-carboxylate as a light yellow solid. $^1$H NMR (300 MHz, Chloroform-d) δ 7.38 (d, J=8.7 Hz, 1H), 7.00-7.02 (m, 2H), 5.72-5.80 (m, 1H), 5.52-5.54 (m, 1H), 4.16-4.25 (m, 2H), 3.88-3.98 (m, 1H), 3.50-3.66 (m, 2H), 2.91-3.08 (m, 4H), 2.69-2.78 (m, 4H), 2.00-2.09 (m, 5H), 1.66-1.88 (m, 6H), 1.42-1.61 (m, 4H). LCMS (ESI, m/z): 599 [M+H]$^+$.

Example 105: 1,1,1,3,3,3-Hexafluoropropan-2-yl 1-(4-chloro-2-(4-(methylsulfonamido)piperidin-1-yl)benzyl)-1,8-diazaspiro[4.5]decane-8-carboxylate

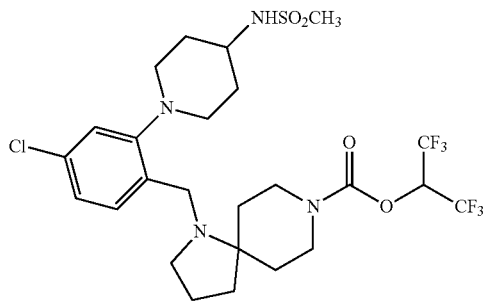

The title compound was synthesized directly from commercially available 4-chloro-2-fluorobenzaldehyde and N-(piperidin-4-yl)methanesulfonamide in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(4-(methyl sulfonamido)piperidin-1-yl)benzyl)-1,8-diazaspiro[4.5]decane-8-carboxylate as a white solid. $^1$H NMR (300 MHz, Chloroform-d) δ 7.40 (d, J=8.1 Hz, 1H), 7.00-7.05 (m, 2H), 5.74-5.83 (m, 1H), 4.39-4.41 (m, 1H), 4.17-4.25 (m, 2H), 3.62-3.66 (m, 1H), 3.43-3.52 (m, 2H), 2.91-3.05 (m, 7H), 2.64-2.79 (m, 4H), 2.08-2.12 (m, 2H), 1.63-1.89 (m, 8H), 1.40-1.48 (m, 2H). LCMS (ESI, m/z): 635 [M+H]$^+$.

Example 106: 1,1,1,3,3,3-Hexafluoropropan-2-yl 1-(2-(azepan-1-yl)-4-chlorobenzyl)-1,8-diazaspiro[4.5]decane-8-carboxylate

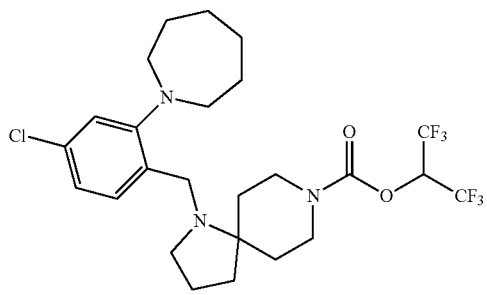 [SMILES: O=C(OC(C(F)(F)F)C(F)(F)F)N1CCC2(CCCN2Cc2ccc(Cl)cc2N2CCCCCC2)CC1]

The title compound was synthesized directly from commercially available 4-chloro-2-fluorobenzaldehyde and azepane in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(azepan-1-yl)-4-chlorobenzyl)-1,8-diazaspiro[4.5]decane-8-carboxylate as a yellow oil. $^1$H NMR (300 MHz, Chloroform-d) δ 7.43 (d, J=8.4 Hz, 1H), 6.95-7.04 (m, 2H), 5.72-5.80 (m, 1H), 4.16-4.24 (m, 2H), 3.63 (s, 2H), 2.91-3.02 (m, 6H), 2.65-2.69 (m, 2H), 1.72-1.86 (m, 14H), 1.46-1.50 (m, 2H). LCMS (ESI, m/z): 556 [M+H]$^+$.

Example 107: 1,1,1,3,3,3-Hexafluoropropan-2-yl 1-(2-(azetidin-1-yl)-4-chlorobenzyl)-1,8-diazaspiro[4.5]decane-8-carboxylate

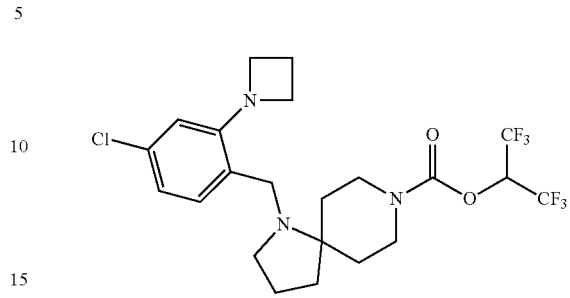

The title compound was synthesized directly from commercially available 4-chloro-2-fluorobenzaldehyde and azetidine in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(2-(azetidin-1-yl)-4-chlorobenzyl)-1,8-diazaspiro[4.5]decane-8-carboxylate as a light yellow solid. $^1$H NMR (300 MHz, Chloroform-d) δ 7.37 (d, J=8.1 Hz, 1H), 6.76-6.79 (m, 1H), 6.45 (d, J=1.8 Hz, 1H), 5.69-5.82 (m, 1H), 4.14-4.23 (m, 2H), 3.86-3.91 (m, 4H), 3.46 (s, 2H), 2.91-3.04 (m, 2H), 2.63-2.67 (m, 2H), 2.24-2.34 (m, 2H), 1.75-1.87 (m, 4H), 1.60-1.69 (m, 2H), 1.50-1.57 (m, 2H). LCMS (ESI, m/z): 514 [M+H]$^+$.

Example 108: 1,1,1,3,3,3-Hexafluoropropan-2-yl 1-(4-chloro-2-(tetrahydro-1H-furo[3,4-c]pyrrol-5(3H)-yl)benzyl)-1,8-diazaspiro[4.5]decane-8-carboxylate

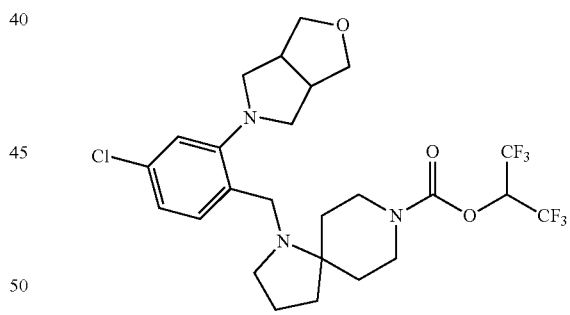

The title compound was synthesized directly from commercially available 4-chloro-2-fluorobenzaldehyde and hexahydro-1H-furo[3,4-c]pyrrole in Step 1 and tert-butyl 1,8-diazaspiro[4.5]decane-8-carboxylate in Step 2 according to the representative procedure of Example 66 to provide 1,1,1,3,3,3-hexafluoropropan-2-yl 1-(4-chloro-2-(tetrahydro-1H-furo[3,4-c]pyrrol-5(3H)-yl)benzyl)-1,8-diazaspiro[4.5]decane-8-carboxylate as a white solid. $^1$H NMR (300 MHz, Chloroform-d) δ 7.48 (d, J=8.1 Hz, 1H), 6.97-7.00 (m, 2H), 5.70-5.82 (m, 1H), 4.15-4.24 (m, 2H), 3.99-4.03 (m, 2H), 3.58-3.61 (m, 4H), 2.86-3.09 (m, 8H), 2.59-2.63 (m, 2H), 1.63-1.86 (m, 6H), 1.46-1.50 (m, 2H). LCMS (ESI, m/z): 570 [M+H]$^+$.

Example 109: 1,1,1,3,3,3-Hexafluoropropan-2-yl 1-(3-(3-oxa-8-azabicyclo[3.2.1]octan-8-yl)-2-chlorobenzyl)-1,8-diazaspiro[4.5]decane-8-carboxylate

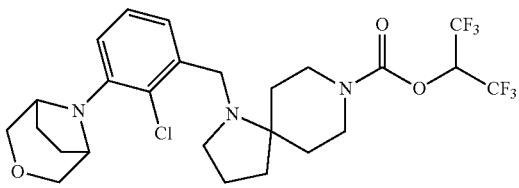 [SMILES: O=C(OC(C(F)(F)F)C(F)(F)F)N1CCC2(CCCN2Cc2cccc(N3C4CCC3COC4)c2Cl)CC1]

The title compound was synthesized directly from commercially available 3-bromo-2-chlorobenzaldehyde in Step 1 and 3-oxa-8-azabicyclo[3.2.1]octane in Step 2 according to the representative procedure of Example 79 to provide 1,1,1,3,3,3-hexafluoropropan-2-yl 1-(3-(3-oxa-8-azabicyclo[3.2.1]octan-8-yl)-2-chlorobenzyl)-1,8-diazaspiro[4.5]decane-8-carboxylate as a white solid. $^1$H NMR (300 MHz, Chloroform-d) δ 7.09-7.14 (m, 2H), 6.77-6.80 (m, 1H), 5.70-5.82 (m, 1H), 4.16-4.25 (m, 2H), 3.93-4.02 (m, 2H), 3.82 (2H), 3.65-3.71 (m, 4H), 2.91-3.05 (m, 2H), 2.75-2.77 (m, 2H), 1.94-2.12 (m, 4H), 1.71-1.82 (m, 6H), 1.52-1.58 (m, 2H). LCMS (ESI, m/z): 570 [M+H]$^+$.

Example 110: 1,1,1,3,3,3-Hexafluoropropan-2-yl 1-(2-chloro-3-(4-fluoropiperidin-1-yl)benzyl)-1,8-diazaspiro[4.5]decane-8-carboxylate

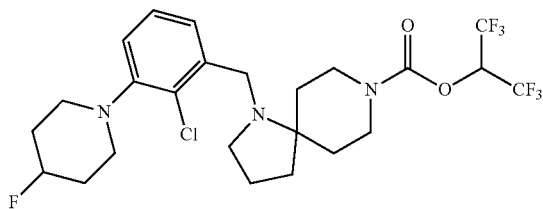 [SMILES: O=C(OC(C(F)(F)F)C(F)(F)F)N1CCC2(CCCN2Cc2cccc(N3CCC(F)CC3)c2Cl)CC1]

The title compound was synthesized directly from commercially available 3-bromo-2-chlorobenzaldehyde in Step 1 and 4-fluoropiperidine in Step 2 according to the representative procedure of Example 79 to provide 1,1,1,3,3,3-hexafluoropropan-2-yl 1-(2-chloro-3-(4-fluoropiperidin-1-yl)benzyl)-1,8-diazaspiro[4.5]decane-8-carboxylate as a white solid. $^1$H NMR (300 MHz, Chloroform-d) δ 7.14-7.18 (m, 2H), 6.95-6.98 (m, 1H), 5.70-5.82 (m, 1H), 4.72-4.93 (m, 1H), 4.16-4.24 (m, 2H), 3.72 (s, 2H), 3.12-3.18 (m, 2H), 2.92-3.05 (m, 4H), 2.74-2.76 (m, 2H), 1.96-2.17 (m, 4H), 1.71-1.82 (m, 6H), 1.52-1.56 (m, 2H). LCMS (ESI, m/z): 560 [M+H]$^+$.

Example 111: 1,1,1,3,3,3-Hexafluoropropan-2-yl 1-(2-chloro-3-(4,4-difluoropiperidin-1-yl)benzyl)-1,8-diazaspiro[4.5]decane-8-carboxylate

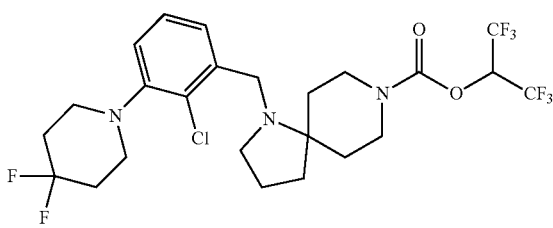 [SMILES: O=C(OC(C(F)(F)F)C(F)(F)F)N1CCC2(CCCN2Cc2cccc(N3CCC(F)(F)CC3)c2Cl)CC1]

The title compound was synthesized directly from commercially available 3-bromo-2-chlorobenzaldehyde in Step 1 and 4,4-difluoropiperidine in Step 2 according to the representative procedure of Example 79 to provide 1,1,1,3,3,3-hexafluoropropan-2-yl 1-(2-chloro-3-(4,4-difluoropiperidin-1-yl)benzyl)-1,8-diazaspiro[4.5]decane-8-carboxylate as a white solid. $^1$H NMR (300 MHz, Chloroform-d) δ 7.15-7.21 (m, 2H), 6.95-6.98 (m, 1H), 5.70-5.82 (m, 1H), 4.17-4.25 (m, 2H), 3.72 (s, 2H), 2.91-3.13 (m, 6H), 2.74-2.76 (m, 2H), 2.10-2.23 (m, 4H), 1.69-1.87 (m, 6H), 1.52-1.57 (m, 2H). LCMS (ESI, m/z): 578 [M+H]$^+$.

Example 112: 1,1,1,3,3,3-Hexafluoropropan-2-yl 1-(2-chloro-3-(tetrahydro-1H-furo[3,4-c]pyrrol-5(3H)-yl)benzyl)-1,8-diazaspiro[4.5]decane-8-carboxylate

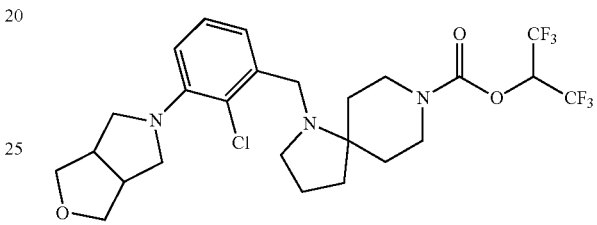

The title compound was synthesized directly from commercially available 3-bromo-2-chlorobenzaldehyde in Step 1 and hexahydro-1H-furo[3,4-c]pyrrole in Step 2 according to the representative procedure of Example 79 to provide 1,1,1,3,3,3-hexafluoropropan-2-yl 1-(2-chloro-3-(tetrahydro-1H-furo[3,4-c]pyrrol-5(3H)-yl)benzyl)-1,8-diazaspiro[4.5]decane-8-carboxylate as a white solid. $^1$H NMR (300 MHz, Chloroform-d) δ 7.14-7.22 (m, 2H), 6.90-6.95 (m, 1H), 5.70-5.82 (m, 1H), 4.16-4.24 (m, 2H), 3.95-4.05 (m, 2H), 3.63-3.71 (m, 4H), 3.12-3.23 (m, 4H), 2.87-3.05 (m, 4H), 2.75-2.77 (m, 2H), 1.71-1.82 (m, 6H), 1.51-1.58 (m, 2H). LCMS (ESI, m/z): 570 [M+H]$^+$.

Example 113: 1,1,1,3,3,3-Hexafluoropropan-2-yl 1-(2-chloro-3-(4-(methylsulfonyl)piperazin-1-yl)benzyl)-1,8-diazaspiro[4.5]decane-8-carboxylate

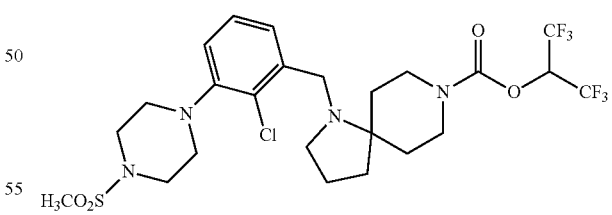

The title compound was synthesized directly from commercially available 3-bromo-2-chlorobenzaldehyde in Step 1 and 1-methanesulfonylpiperazine in Step 2 according to the representative procedure of Example 79 to provide 1,1,1,3,3,3-hexafluoropropan-2-yl 1-(2-chloro-3-(4-(methylsulfonyl)piperazin-1-yl)benzyl)-1,8-diazaspiro[4.5]decane-8-carboxylate as a light yellow solid. $^1$H NMR (300 MHz, Chloroform-d) δ 7.18-7.25 (m, 2H), 6.94-6.97 (m, 1H), 5.70-5.82 (m, 1H), 4.16-4.24 (m, 2H), 3.72 (s, 2H), 3.40-3.43 (m, 4H), 3.11-3.14 (m, 4H), 2.91-3.07 (m, 2H),

Example 114: 1,1,1,3,3,3-Hexafluoropropan-2-yl 1-(3-(4-acetylpiperazin-1-yl)-2-chlorobenzyl)-1,8-diazaspiro[4.5]decane-8-carboxylate

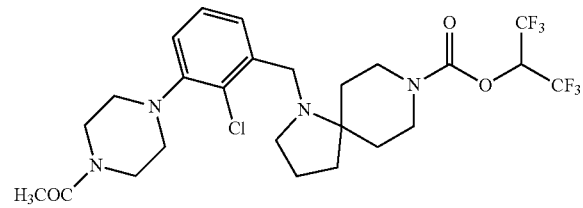

The title compound was synthesized directly from commercially available 3-bromo-2-chlorobenzaldehyde in Step 1 and 1-(piperazin-1-yl)ethan-1-one in Step 2 according to the representative procedure of Example 79 to provide 1,1,1,3,3,3-hexafluoropropan-2-yl 1-(3-(4-acetylpiperazin-1-yl)-2-chlorobenzyl)-1,8-diazaspiro[4.5]decane-8-carboxylate as a white solid. $^1$H NMR (300 MHz, Chloroform-d) δ 7.16-7.23 (m, 2H), 6.91-6.94 (m, 1H), 5.70-5.83 (m, 1H), 4.17-4.25 (m, 2H), 3.72-3.80 (m, 4H), 3.62-3.65 (m, 2H), 2.91-3.03 (m, 6H), 2.75-2.76 (m, 2H), 2.14 (s, 3H), 1.73-1.93 (m, 6H), 1.45-1.55 (m, 2H). LCMS (ESI, m/z): 585 [M+H]$^+$.

Example 115: 1,1,1,3,3,3-Hexafluoropropan-2-yl 1-(2-chloro-3-(4-cyclopropylpiperazin-1-yl)benzyl)-1,8-diazaspiro[4.5]decane-8-carboxylate

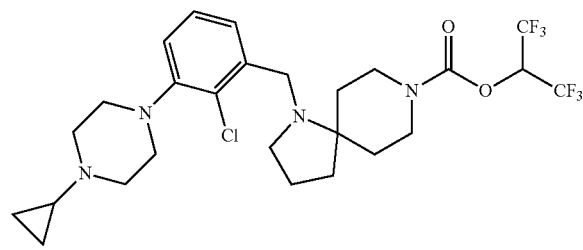 [SMILES: O=C(OC(C(F)(F)F)C(F)(F)F)N1CCC2(CCCN2Cc2cccc(N3CCN(C4CC4)CC3)c2Cl)CC1]

The title compound was synthesized directly from commercially available 3-bromo-2-chlorobenzaldehyde in Step 1 and 1-cyclopropylpiperazine in Step 2 according to the representative procedure of Example 79 to provide 1,1,1,3,3,3-hexafluoropropan-2-yl 1-(2-chloro-3-(4-cyclopropylpiperazin-1-yl)benzyl)-1,8-diazaspiro[4.5]decane-8-carboxylate as a light yellow solid. $^1$H NMR (300 MHz, Chloroform-d) δ 7.14-7.18 (m, 2H), 6.92-6.97 (m, 1H), 5.70-5.82 (m, 1H), 4.16-4.25 (m, 2H), 3.72 (s, 2H), 2.74-3.03 (m, 12H), 1.71-1.82 (m, 7H), 1.44-1.56 (m, 2H), 0.41-0.50 (m, 4H). LCMS (ESI, m/z): 583 [M+H]$^+$.

Example 116: 1,1,1,3,3,3-Hexafluoropropan-2-yl 1-(2-chloro-3-(4-ethylpiperazin-1-yl)benzyl)-1,8-diazaspiro[4.5]decane-8-carboxylate

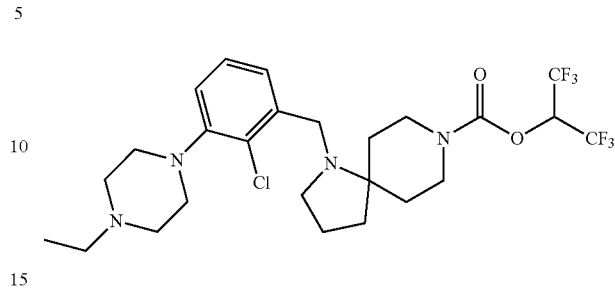

The title compound was synthesized directly from commercially available 3-bromo-2-chlorobenzaldehyde in Step 1 and 1-ethylpiperazine in Step 2 according to the representative procedure of Example 79 to provide 1,1,1,3,3,3-hexafluoropropan-2-yl 1-(2-chloro-3-(4-ethylpiperazin-1-yl)benzyl)-1,8-diazaspiro[4.5]decane-8-carboxylate as a yellow semi-solid. $^1$H NMR (300 MHz, Chloroform-d) δ 7.15-7.22 (m, 2H), 6.95-7.00 (m, 1H), 5.70-5.80 (m, 1H), 4.16-4.24 (m, 2H), 3.71 (s, 2H), 2.91-3.10 (m, 6H), 2.68-2.76 (m, 6H), 2.49-2.56 (m, 2H), 1.71-1.82 (m, 6H), 1.44-1.58 (m, 2H), 1.15 (t, J=7.2 Hz, 3H). LCMS (ESI, m/z): 571 [M+H]$^+$.

Example 117: 1,1,1,3,3,3-Hexafluoropropan-2-yl 1-(2-chloro-3-(8-oxa-2-azaspiro[4.5]decan-2-yl)benzyl)-1,8-diazaspiro[4.5]decane-8-carboxylate

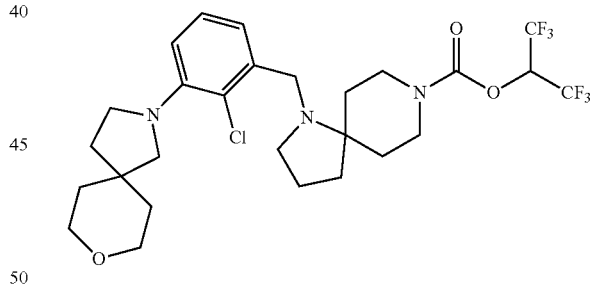

The title compound was synthesized directly from commercially available 3-bromo-2-chlorobenzaldehyde in Step 1 and 8-oxa-2-azaspiro[4.5]decane in Step 2 according to the representative procedure of Example 79 to provide 1,1,1,3,3,3-hexafluoropropan-2-yl 1-(2-chloro-3-(8-oxa-2-azaspiro[4.5]decan-2-yl)benzyl)-1,8-diazaspiro[4.5]decane-8-carboxylate as a yellow oil. $^1$H NMR (300 MHz, Chloroform-d) δ 7.03-7.14 (m, 2H), 6.83-6.85 (m, 1H), 5.72-5.80 (m, 1H), 4.16-4.24 (m, 2H), 3.62-3.77 (m, 6H), 3.38-3.43 (m, 2H), 3.22 (s, 2H), 2.91-3.05 (m, 2H), 2.76-2.78 (m, 2H), 1.65-1.86 (m, 12H), 1.44-1.58 (m, 2H). LCMS (ESI, m/z): 598 [M+H]$^+$.

---

2.85 (s, 3H), 2.74-2.76 (m, 2H), 1.70-1.88 (m, 6H), 1.52-1.58 (m, 2H). LCMS (ESI, m/z): 621 [M+H]$^+$.

Example 118: 1-(5-Chloro-2-((8-(((1,1,1,3,3,3-hexafluoropropan-2-yl)oxy)carbonyl)-2,8-diazaspiro[4.5]decan-2-yl)methyl)phenyl)piperidine-4-carboxylic acid

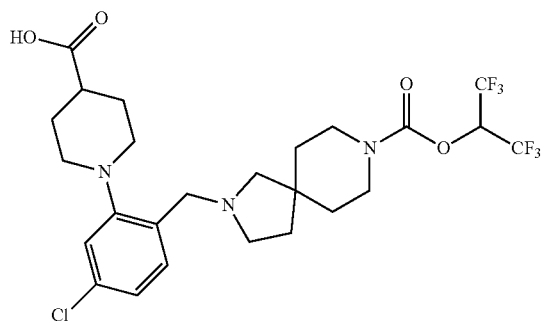

Step 1: Preparation of ethyl 1-(5-chloro-2-formylphenyl)piperidine-4-carboxylate

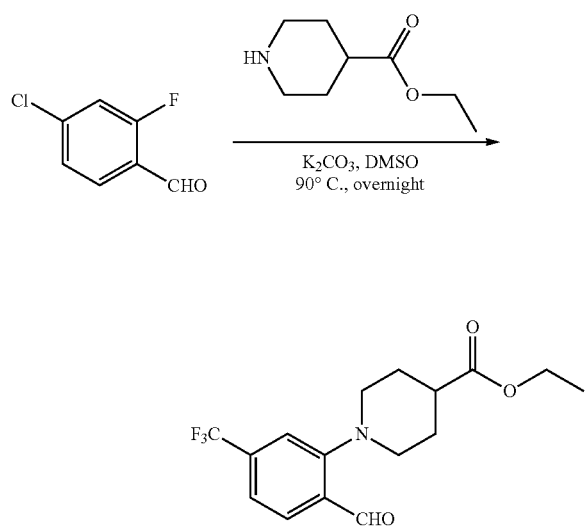 [SMILES: O=Cc1ccc(Cl)cc1F ; CCOC(=O)C1CCNCC1 ; CCOC(=O)C1CCN(c2cc(C(F)(F)F)ccc2C=O)CC1]

A flask was charged with 4-chloro-2-fluorobenzaldehyde (2.40 g, 15.1 mmol, 1.00 equiv), ethyl piperidine-4-carboxylate (2.60 g, 16.5 mmol, 1.20 equiv), potassium carbonate (6.20 g, 44.9 mmol, 3.00 equiv), and DMSO (25 mL). The resulting solution was stirred overnight at 90° C. and then diluted with $H_2O$ (20 mL). The mixture was extracted with DCM (3×50 mL), and the organic layers were combined, washed with brine (3×50 mL), dried over anhydrous $Na_2SO_4$, filtered, and concentrated. The residue was purified on a silica gel column (2:8 EtOAc/petroleum ether) to provide 4.00 g (89% yield) of ethyl 1-(5-chloro-2-formylphenyl) piperidine-4-carboxylate as a yellow oil. LCMS (ESI, m/z): 296 [M+H]⁺.

Step 2: Preparation of tert-butyl 2-(2-(4-(ethoxycarbonyl)piperidin-1-yl)-4-(trifluoromethyl)benzyl)-2,8-diazaspiro[4.5]decane-8-carboxylate

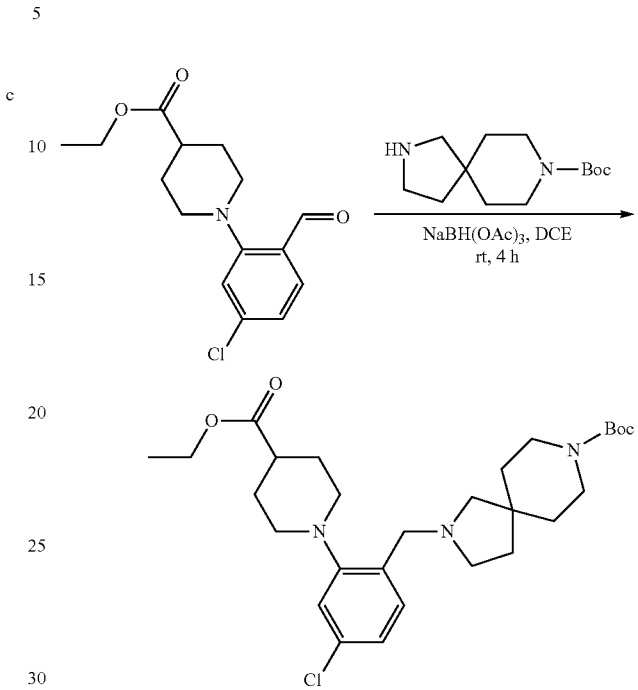

A flask was charged with ethyl 1-(5-chloro-2-formylphenyl)piperidine-4-carboxylate (1.33 g, 4.50 mmol, 1.00 equiv), tert-butyl 2,8-diazaspiro[4.5]decane-8-carboxylate (1.18 g, 4.91 mmol, 1.10 equiv), and DCE (10 mL). The resulting solution was stirred for 1 h at rt and then NaBH(OAc)₃ (2.86 g, 13.5 mmol, 3.00 equiv) was added. The resulting solution was stirred for 3 h at rt and diluted with $H_2O$ (20 mL). The mixture was extracted with DCM (3×50 mL) and the organic layers were combined, washed with brine (3×50 mL), dried over anhydrous $Na_2SO_4$, filtered and concentrated. The residue was purified on a silica gel column (3:7 EtOAc/petroleum ether) to provide 1.54 g (66% yield) of tert-butyl 2-(2-(4-(ethoxycarbonyl)piperidin-1-yl)-4-(trifluoromethyl)benzyl)-2,8-diazaspiro[4.5]decane-8-carboxylate as a colorless oil. LCMS (ESI, m/z): 520 [M+H]⁺.

Step 3: Preparation of 1-(2-((8-(tert-butoxycarbonyl)-2,8-diazaspiro[4.5]decan-2-yl)methyl)-5-(trifluoromethyl)phenyl)piperidine-4-carboxylic acid

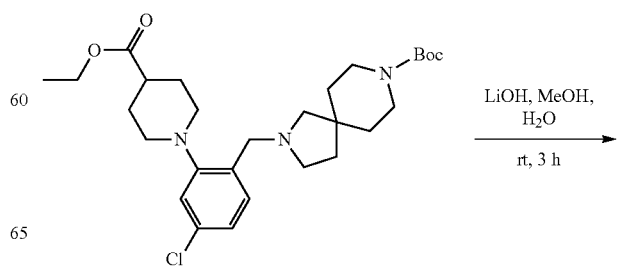

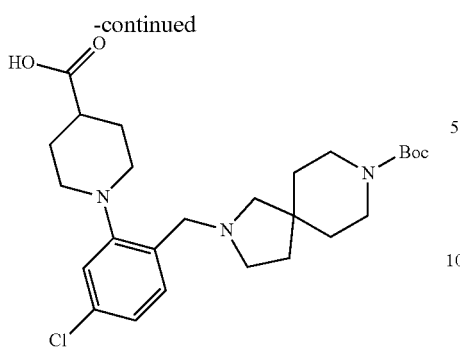

A flask was charged with tert-butyl 2-(2-(4-(ethoxycarbonyl)piperidin-1-yl)-4-(trifluoromethyl)benzyl)-2,8-diazaspiro[4.5]decane-8-carboxylate (1.54 g, 2.96 mmol, 1.00 equiv), MeOH (10 mL), H$_2$O (5 mL), and lithium hydroxide (0.356 g, 14.9 mmol, 5.00 equiv). The resulting solution was stirred for 3 h at rt. The pH value of the solution was adjusted to 7 with hydrochloric acid (1 M, 1.5 mL). The mixture was extracted with DCM (3×50 mL) and the organic layers were combined, washed with brine (3×50 mL), dried over anhydrous Na$_2$SO$_4$, filtered and concentrated to provide 0.978 g (67% yield) of 1-(2-((8-(tert-butoxycarbonyl)-2,8-diazaspiro[4.5]decan-2-yl)methyl)-5-(trifluoromethyl)phenyl)piperidine-4-carboxylic acid as a light yellow solid. LCMS (ESI, m/z): 492 [M+H]$^+$.

Step 4: Preparation of 1-(2-((2,8-diazaspiro[4.5]decan-2-yl)methyl)-5-(trifluoromethyl)phenyl)piperidine-4-carboxylic acid

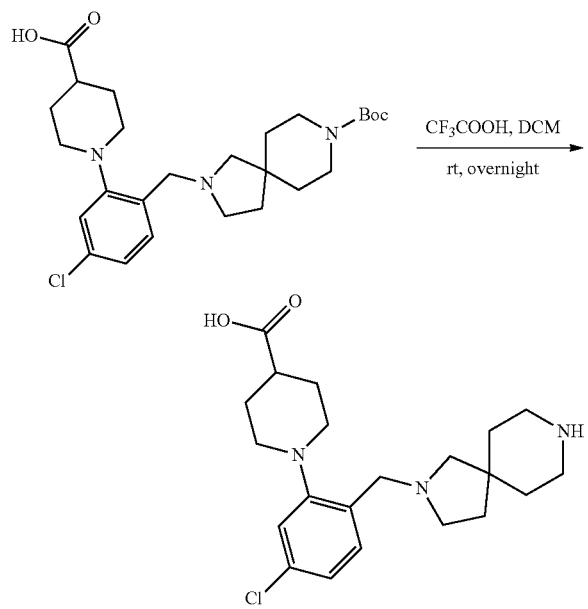

A flask was charged with 1-(2-((8-(tert-butoxycarbonyl)-2,8-diazaspiro[4.5]decan-2-yl)methyl)-5-(trifluoromethyl)phenyl)piperidine-4-carboxylic acid (246 mg, 0.470 mmol, 1.00 equiv), DCM (7 mL), and TFA (1 mL). The resulting solution was stirred overnight at rt and concentrated to provide 196 mg (98% yield) of 1-(2-((2,8-diazaspiro[4.5]decan-2-yl)methyl)-5-(trifluoromethyl)phenyl)piperidine-4-carboxylic acid as a light yellow solid. LCMS (ESI, m/z): 392 [M+H]$^+$.

Step 5: Preparation of 1-(5-chloro-2-((8-(((1,1,1,3,3,3-hexafluoropropan-2-yl)oxy)carbonyl)-2,8-diazaspiro[4.5]decan-2-yl)methyl)phenyl)piperidine-4-carboxylic acid

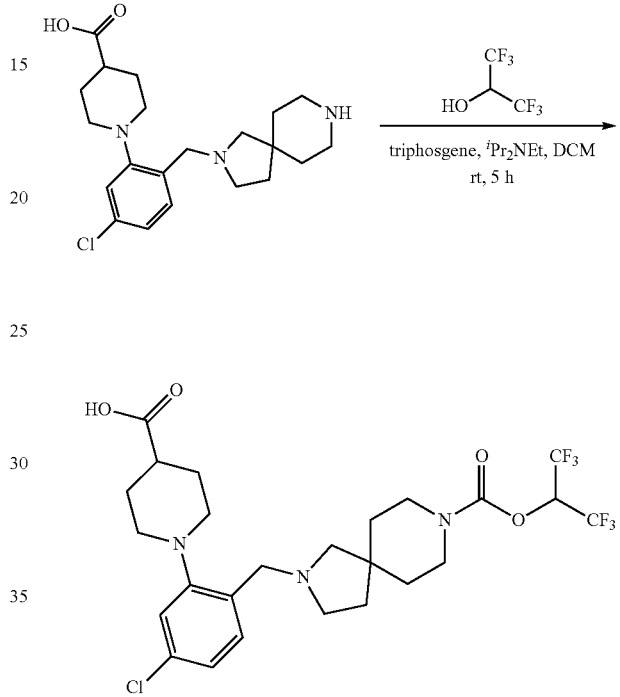

A flask was charged with triphosgene (59.4 mg, 0.201 mmol, 0.400 equiv) and DCM (5 mL). HFIP (100 mg, 0.603 mmol, 1.20 equiv) and DIEA (194 mg, 1.50 mmol, 3.00 equiv) were each added dropwise at 0° C. The resulting solution was stirred for 2 h at rt. 1-(2-((2,8-Diazaspiro[4.5]decan-2-yl)methyl)-5-(trifluoromethyl)phenyl)piperidine-4-carboxylic acid (196 mg, 0.462 mmol, 1.00 equiv) was added, and the mixture was stirred for 3 h at rt before diluting with H$_2$O (20 mL). The mixture was extracted with DCM (3×30 mL), and the organic layers were combined, washed with brine (3×30 mL), dried over anhydrous Na$_2$SO$_4$, filtered, and concentrated. The crude product was purified by preparative HPLC to provide 55.5 mg (21% yield) of 1-(5-chloro-2-((8-(((1,1,1,3,3,3-hexafluoropropan-2-yl)oxy)carbonyl)-2,8-diazaspiro[4.5]decan-2-yl)methyl)phenyl)piperidine-4-carboxylic acid as a light yellow solid. $^1$H NMR (400 MHz, Chloroform-d) δ 7.27-7.38 (m, 1H), 7.05 (br, 2H), 5.67-5.76 (m, 1H), 3.50-3.60 (m, 4H), 3.29 (d, J=10.4 Hz, 2H), 3.17 (br, 2H), 2.69-2.72 (m, 7H), 2.05 (d, J=10.4 Hz, 2H), 1.88-1.96 (m, 2H), 1.76-1.82 (m, 2H), 1.61 (br, 4H). LCMS (ESI, m/z): 586 [M+H]$^+$.

Example 119: 1-(2-((8-(((1,1,1,3,3,3-Hexafluoropropan-2-yl)oxy)carbonyl)-2,8-diazaspiro[4.5]decan-2-yl)methyl)-5-(trifluoromethyl)phenyl)piperidine-4-carboxylic acid

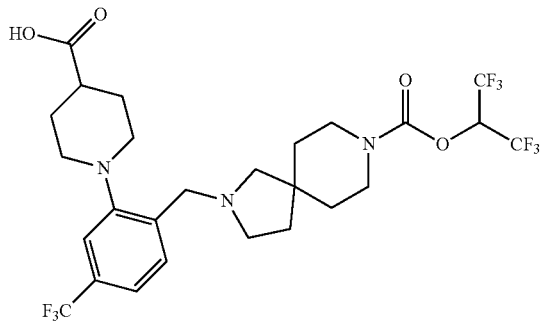 [SMILES: O=C(O)C1CCN(c2cc(C(F)(F)F)ccc2CN2CCC3(CCN(C(=O)OC(C(F)(F)F)C(F)(F)F)CC3)C2)CC1]

The title compound was synthesized directly from commercially available 2-fluoro-4-(trifluoromethyl)benzaldehyde according to the representative procedure of Example 118 to provide 1-(2-((8-(((1,1,1,3,3,3-hexafluoropropan-2-yl)oxy)carbonyl)-2,8-diazaspiro[4.5]decan-2-yl)methyl)-5-(trifluoromethyl)phenyl)piperidine-4-carboxylic acid as a white solid. $^1$H NMR (300 MHz, Chloroform-d) δ 7.58 (br, 1H), 7.29-7.49 (m, 2H), 5.69-5.78 (m, 1H), 3.57-3.80 (m, 2H), 3.35-3.57 (m, 4H), 3.19-3.35 (m, 2H), 2.66-2.79 (m, 4H), 2.40-2.55 (m, 3H), 1.87-2.09 (m, 4H), 1.62-1.81 (m, 2H), 1.60-1.72 (m, 4H). LCMS (ESI, m/z): 620 [M+H]$^+$.

Example 120: 1-(5-Chloro-2-((8-(((1,1,1,3,3,3-hexafluoropropan-2-yl)oxy)carbonyl)-1,8-diazaspiro[4.5]decan-1-yl)methyl)phenyl)piperidine-4-carboxylic acid

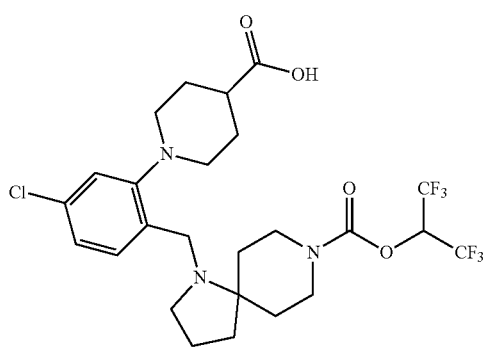 [SMILES: O=C(O)C1CCN(c2cc(Cl)ccc2CN2CCCC23CCN(C(=O)OC(C(F)(F)F)C(F)(F)F)CC3)CC1]

The title compound was synthesized directly from commercially available 4-chloro-2-fluorobenzaldehyde according to the representative procedure of Example 118 to provide 1-(5-chloro-2-((8-(((1,1,1,3,3,3-hexafluoropropan-2-yl)oxy)carbonyl)-1,8-diazaspiro[4.5]decan-1-yl)methyl)phenyl)piperidine-4-carboxylic acid as a white solid. $^1$H NMR (300 MHz, Chloroform-d) δ 7.43 (br, 1H), 6.91-7.08 (m, 2H), 5.69-5.80 (m, 1H), 4.16-4.36 (m, 2H), 3.61 (br, 2H), 2.91-3.08 (m, 4H), 2.52-2.72 (m, 4H), 2.43-2.50 (m, 1H), 1.95-2.07 (m, 2H), 1.67-1.94 (m, 8H), 1.37-1.67 (m, 2H). LCMS (ESI, m/z): 586 [M+H]$^+$.

Example 121: 1-(2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)piperidine-4-carboxylic acid

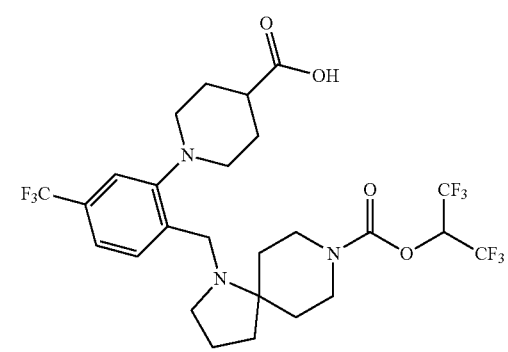 [SMILES: O=C(O)C1CCN(c2cc(C(F)(F)F)ccc2CN2CCCC23CCN(C(=O)OC(C(F)(F)F)C(F)(F)F)CC3)CC1]

The title compound was synthesized directly from commercially available 2-fluoro-4-(trifluoromethyl)benzaldehyde according to the representative procedure of Example 118 to provide 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)piperidine-4-carboxylic acid as a white solid. $^1$H NMR (300 MHz, Chloroform-d) δ 7.60-7.64 (m, 1H), 7.26-7.37 (m, 2H), 5.70-5.82 (m, 1H), 4.16-4.26 (m, 2H), 3.67 (br, 2H), 3.07-3.11 (m, 2H), 2.96-3.01 (m, 2H), 2.55-2.77 (m, 4H), 2.46-2.55 (m, 1H), 2.05-2.09 (m, 2H), 1.90-1.98 (m, 2H), 1.70-1.82 (m, 6H), 1.38-1.66 (m, 2H). LCMS (ESI, m/z): 620 [M+H]$^+$.

Example 122: 1-(3-Chloro-5-((8-(((1,1,1,3,3,3-hexafluoropropan-2-yl)oxy)carbonyl)-1,8-diazaspiro[4.5]decan-1-yl)methyl)phenyl)piperidine-4-carboxylic acid

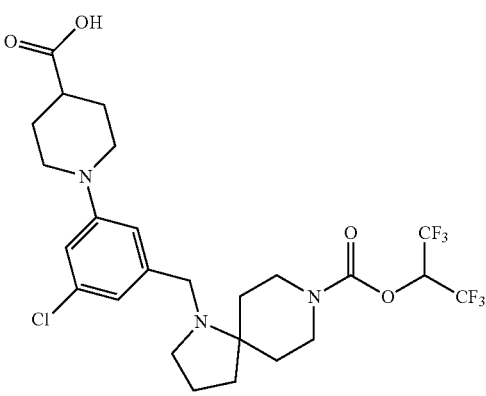 [SMILES: O=C(O)C1CCN(c2cc(Cl)cc(CN3CCCC34CCN(C(=O)OC(C(F)(F)F)C(F)(F)F)CC4)c2)CC1]

Step 1: Preparation of tert-butyl 1-(3-bromo-5-chlorobenzyl)-1,8-diazaspiro[4.5]decane-8-carboxylate

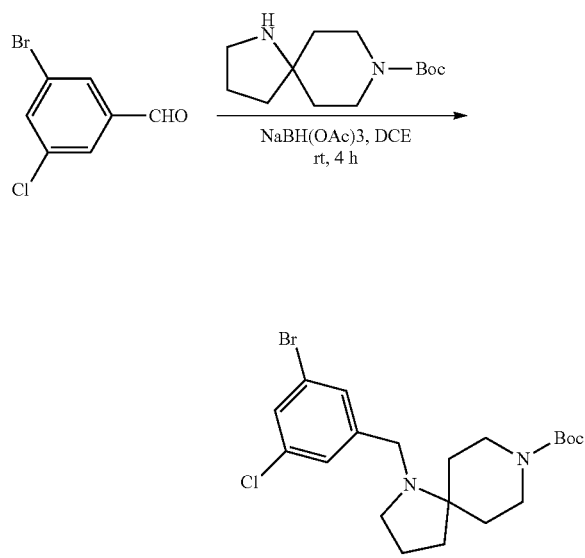

A flask was charged with 3-bromo-5-chlorobenzaldehyde (1.09 g, 4.97 mmol, 1.00 equiv), tert-butyl 1,8-diazaspiro[4.5]decane-8-carboxylate (1.32 g, 5.49 mmol, 1.10 equiv), and DCE (10 mL). The resulting solution was stirred for 1 h at rt. NaBH(OAc)$_3$ (3.18 g, 15.0 mmol, 3.00 equiv) was added, and the reaction was stirred for 3 h at rt before diluting with H$_2$O (20 mL). The mixture was extracted with DCM (3×50 mL) and the organic layers were combined, washed with brine (3×50 mL), dried over anhydrous Na$_2$SO$_4$, filtered, and concentrated. The residue was purified on a silica gel column (3:7 EtOAc/petroleum ether) to provide 1.00 g (45% yield) of tert-butyl 1-(3-bromo-5-chlorobenzyl)-1,8-diazaspiro[4.5]decane-8-carboxylate as a colorless oil. LCMS (ESI, m/z): 443 [M+H]$^+$.

Step 2: Preparation of tert-butyl 1-(3-chloro-5-(4-(ethoxycarbonyl)piperidin-1-yl)benzyl)-1,8-diazaspiro[4.5]decane-8-carboxylate

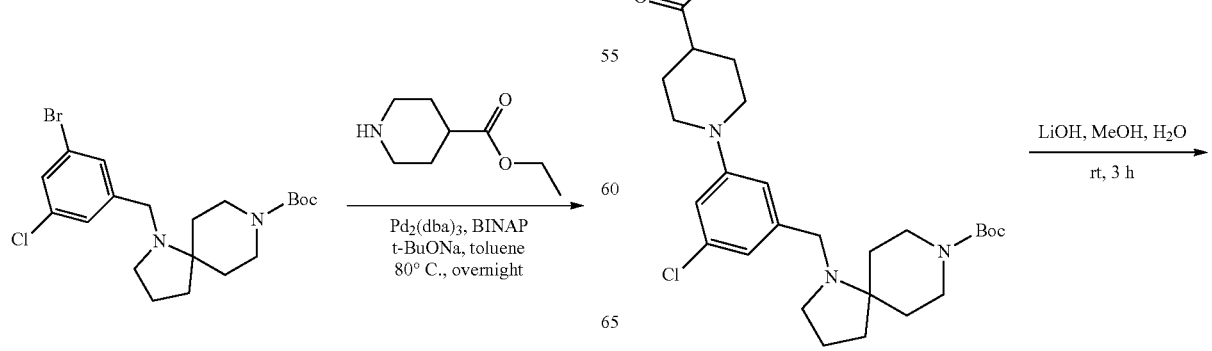

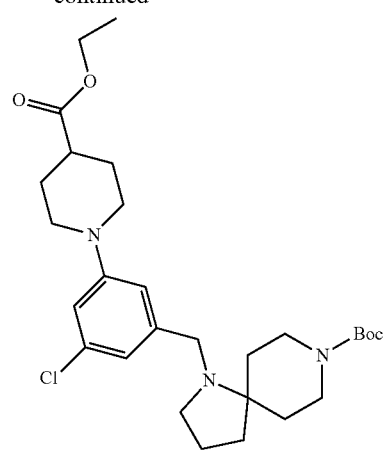

A flask purged and maintained with an inert atmosphere of nitrogen was charged with tert-butyl 1-(3-bromo-5-chlorobenzyl)-1,8-diazaspiro[4.5]decane-8-carboxylate (1.02 g, 2.25 mmol, 1.00 equiv), ethyl piperidine-4-carboxylate (0.531 g, 3.38 mmol, 1.50 equiv), tris(dibenzylideneacetone)dipalladium (0.103 g, 0.112 mmol, 0.05 equiv), 2,2'-bis(diphenylphosphino)-1,1'-binaphthyl (0.210 g, 0.341 mmol, 0.15 equiv), sodium tert-butoxide (0.324 g, 3.38 mmol, 1.50 equiv), and toluene (15 mL). The resulting solution was stirred overnight at 80° C. and diluted with H$_2$O (20 mL). The mixture was extracted with DCM (3×50 mL) and the organic layers were combined, washed with brine (3×50 mL), dried over anhydrous Na$_2$SO$_4$, filtered, and concentrated. The residue was purified on a silica gel column (2:8 EtOAc/petroleum ether) to provide 0.511 g (44% yield) of tert-butyl 1-(3-chloro-5-(4-(ethoxycarbonyl)piperidin-1-yl)benzyl)-1,8-diazaspiro[4.5]decane-8-carboxylate as a yellow oil. LCMS (ESI, m/z): 520 [M+H]$^+$.

Step 3: Preparation of 1-(3-((8-(tert-butoxycarbonyl)-1,8-diazaspiro[4.5]decan-1-yl)methyl)-5-chlorophenyl)piperidine-4-carboxylic acid

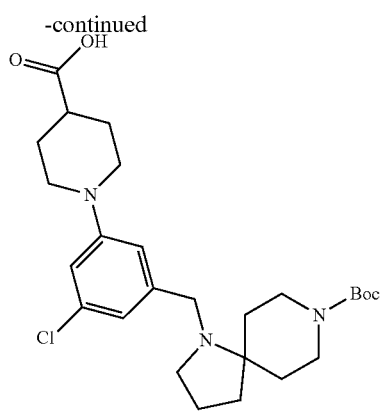

A flask was charged with tert-butyl 1-(3-chloro-5-(4-(ethoxycarbonyl)piperidin-1-yl)benzyl)-1,8-diazaspiro[4.5]decane-8-carboxylate (511 mg, 0.982 mmol, 1.00 equiv), lithium hydroxide (117 mg, 4.89 mmol, 5.00 equiv), MeOH (10 mL), and H₂O (5 mL). The resulting solution was stirred for 3 h at rt. The pH value of the solution was adjusted to 7 with hydrochloric acid (1 M, 1.5 mL). The mixture was extracted with DCM (3×50 mL) and the organic layers were combined, washed with brine (3×50 mL), dried over anhydrous Na₂SO₄, filtered, and concentrated to provide 330 mg (68% yield) of 1-(3-((8-(tert-butoxycarbonyl)-1,8-diazaspiro[4.5]decan-1-yl)methyl)-5-chlorophenyl)piperidine-4-carboxylic acid as a yellow oil. LCMS (ESI, m/z): 492 [M+H]⁺.

Step 4: Preparation of 1-(3-((1,8-diazaspiro[4.5]decan-1-yl)methyl)-5-chlorophenyl)piperidine-4-carboxylic acid

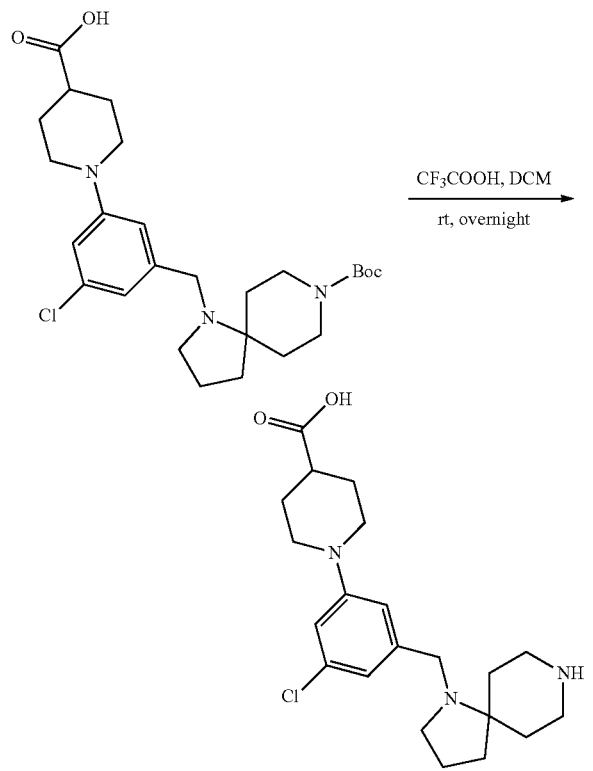

A flask was charged with 1-(3-((8-(tert-butoxycarbonyl)-1,8-diazaspiro[4.5]decan-1-yl)methyl)-5-chlorophenyl)piperidine-4-carboxylic acid (330 mg, 0.631 mmol, 1.00 equiv), TFA (1 mL), and DCM (5 mL). The resulting solution was stirred overnight at rt and concentrated to provide 262 mg (98% yield) of 1-(3-((1,8-diazaspiro[4.5]decan-1-yl)methyl)-5-chlorophenyl)piperidine-4-carboxylic acid as a yellow oil. LCMS (ESI, m/z): 392 [M+H]⁺.

Step 5: Preparation of 1-(3-chloro-5-((8-(((1,1,1,3,3,3-hexafluoropropan-2-yl)oxy)carbonyl)-1,8-diazaspiro[4.5]decan-1-yl)methyl)phenyl)piperidine-4-carboxylic acid

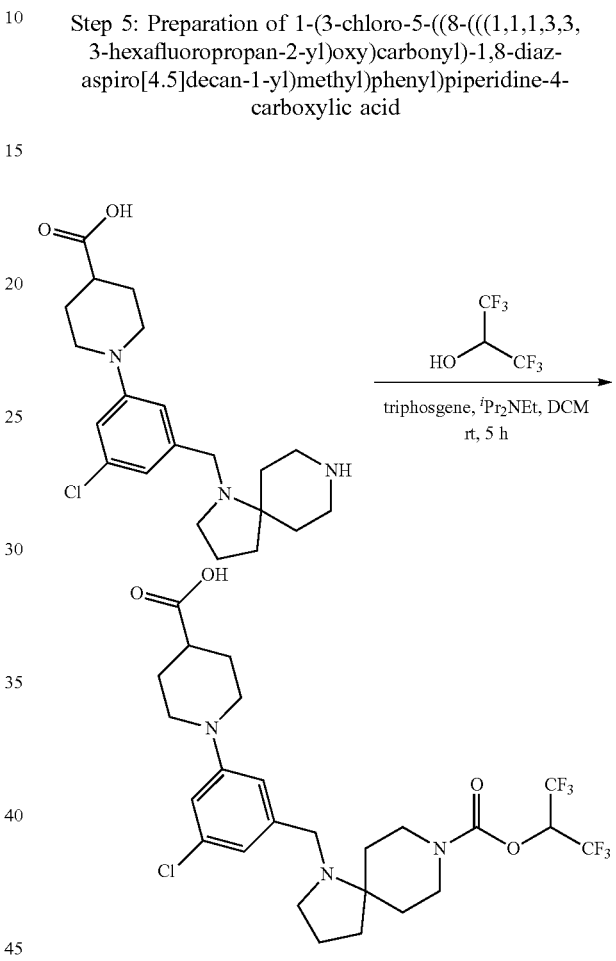

A flask was charged with triphosgene (78.4 mg, 0.262 mmol, 0.400 equiv), and DCM (5 mL). HFIP (135 mg, 0.802 mmol, 1.20 equiv) and DIEA (260 mg, 2.01 mmol, 3.00 equiv) were each added dropwise at 0° C. The resulting solution was stirred for 2 h at rt. 1-(3-((1,8-Diazaspiro[4.5]decan-1-yl)methyl)-5-chlorophenyl)piperidine-4-carboxylic acid (262 mg, 0.621 mmol, 1.00 equiv) was added, and the reaction was stirred for 3 h at rt before diluting with H₂O (20 mL). The mixture was extracted with DCM (3×50 mL) and the organic layers were combined, washed with brine (3×50 mL), dried over anhydrous Na₂SO₄, filtered, and concentrated. The crude product was purified by preparative HPLC to provide 14.3 mg (4% yield) of 1-(3-chloro-5-((8-(((1,1,1,3,3,3-hexafluoropropan-2-yl)oxy)carbonyl)-1,8-diazaspiro[4.5]decan-1-yl)methyl)phenyl)piperidine-4-carboxylic acid as a white solid. ¹H NMR (300 MHz, Chloroform-d) δ 6.76 (br, 3H), 5.71-5.79 (m, 1H), 4.13-4.25 (m, 2H), 3.60-3.73 (m, 2H), 3.48-3.60 (m, 2H), 2.90-3.05 (m, 2H), 2.71-2.90 (m, 4H), 2.43-2.56 (m, 1H), 2.03-2.07 (m, 2H), 1.70-1.92 (m, 8H), 1.40-1.70 (m, 2H). LCMS (ESI, m/z): 586 [M+H]⁺.

Example 123: 1-(3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)piperidine-4-carboxylic acid

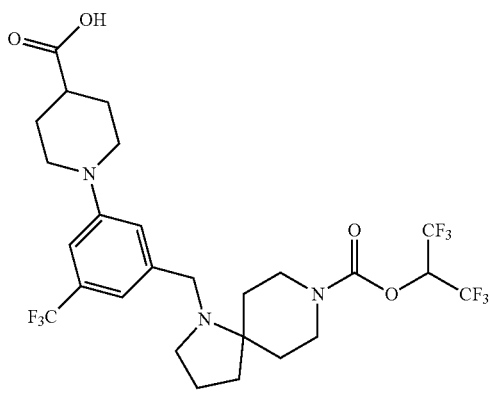 [SMILES: O=C(O)C1CCN(c2cc(CN3CCCC34CCN(C(=O)OC(C(F)(F)F)C(F)(F)F)CC4)cc(C(F)(F)F)c2)CC1]

The title compound was synthesized directly from commercially available 3-bromo-5-(trifluoromethyl)benzaldehyde according to the representative procedure of Example 122 to provide 1-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)piperidine-4-carboxylic acid as a white solid. $^1$H NMR (300 MHz, Chloroform-d) δ 6.91-7.07 (br, 3H), 5.71-5.79 (m, 1H), 4.19-4.23 (m, 2H), 3.41-3.87 (m, 4H), 2.82-3.06 (m, 4H), 2.58-2.82 (m, 2H), 2.48-2.58 (m, 1H), 2.04-2.92 (m, 2H), 2.66-2.96 (m, 8H), 1.44-1.76 (m, 2H). LCMS (ESI, m/z): 620 [M+H]$^+$.

Example 124: 1,1,1,3,3,3-Hexafluoropropan-2-yl 1-(4-chloro-3-methylbenzyl)-1,8-diazaspiro[4.5]decane-8-carboxylate

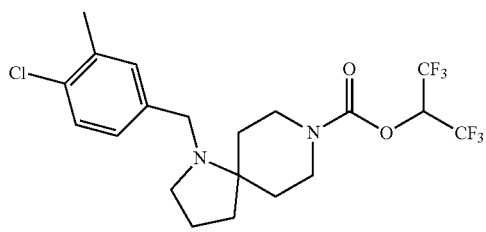 [SMILES: Cc1cc(CN2CCCC23CCN(C(=O)OC(C(F)(F)F)C(F)(F)F)CC3)ccc1Cl]

Step 1: Preparation of 1-tert-butyl 8-(1,1,1,3,3,3-hexafluoropropan-2-yl) 1,8-diazaspiro[4.5]decane-1,8-dicarboxylate

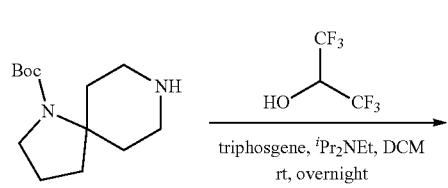

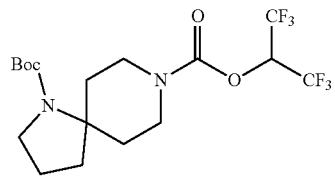

A flask was charged with triphosgene (2.60 g, 8.75 mmol, 0.70 equiv) and DCM (40 mL). HFIP (4.20 g, 25.0 mmol, 2.00 equiv) and DIEA (4.84 g, 37.5 mmol, 3.00 equiv) were each added dropwise at 0° C. The mixture was stirred for 1 h at rt. tert-Butyl 1,8-diazaspiro[4.5]decane-1-carboxylate (3.00 g, 12.5 mmol, 1.00 equiv) was added, and the reaction was stirred overnight at rt before diluting with H$_2$O (80 mL). The resulting solution was extracted with DCM (2×100 mL) and the organic layers were combined, dried over anhydrous Na$_2$SO$_4$, filtered, and concentrated. The residue was purified on a silica gel column (1:3 EtOAc/petroleum ether) to provide 1.80 g (33% yield) of 1-tert-butyl 8-(1,1,1,3,3,3-hexafluoropropan-2-yl) 1,8-diazaspiro[4.5]decane-1,8-dicarboxylate as a white solid. LCMS (ESI, m/z): 435 [M+H]$^+$.

Step 2: Preparation of 1,1,1,3,3,3-hexafluoropropan-2-yl 1,8-diazaspiro[4.5]decane-8-carboxylate

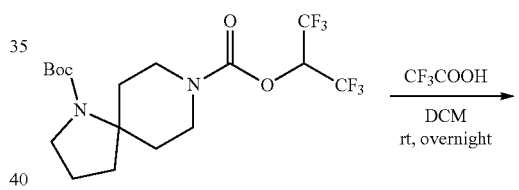

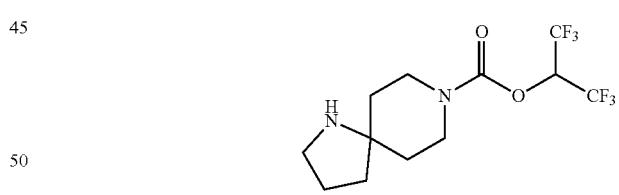

A flask was charged with 1-tert-butyl 8-(1,1,1,3,3,3-hexafluoropropan-2-yl) 1,8-diazaspiro[4.5]decane-1,8-dicarboxylate (1.00 g, 2.30 mmol, 1.00 equiv), DCM (15 mL), and TFA (3.0 mL). The resulting solution was stirred overnight at rt and concentrated to provide 769 mg (crude) of 1,1,1,3,3,3-hexafluoropropan-2-yl 1,8-diazaspiro[4.5]decane-8-carboxylate as a light yellow oil. LCMS (ESI, m/z): 335 [M+H]$^+$.

Step 3: Preparation of 1,1,1,3,3,3-hexafluoropropan-2-yl 1-(4-chloro-3-methylbenzyl)-1,8-diazaspiro[4.5]decane-8-carboxylate

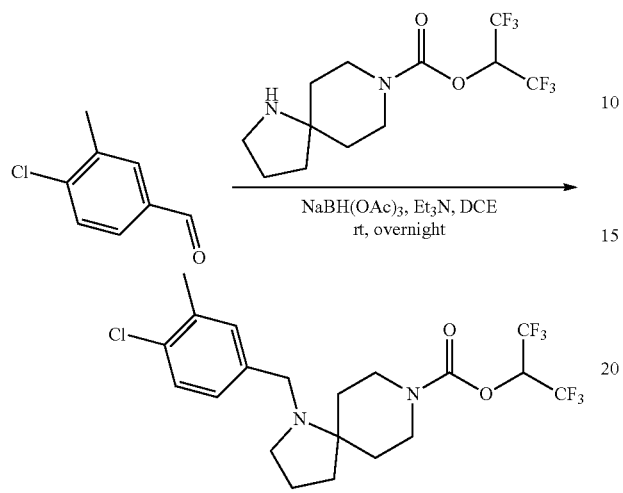

A flask was charged with 1,1,1,3,3,3-hexafluoropropan-2-yl 1,8-diazaspiro[4.5]decane-8-carboxylate (160 mg, 0.480 mmol, 1.00 equiv), DCE (10 mL), 4-chloro-3-methylbenzaldehyde (74.0 mg, 0.480 mmol, 1.00 equiv), and TEA (145 mg, 1.43 mmol, 3.00 equiv). The mixture was stirred for 1 h at rt. NaBH(OAc)$_3$ (305 mg, 1.44 mmol, 3.00 equiv) was added, and the reaction was stirred overnight at rt before diluting with H$_2$O (30 mL). The resulting solution was extracted with DCM (2×50 mL), and the organic layers were combined, dried over anhydrous Na$_2$SO$_4$, filtered, and concentrated. The crude product was purified by preparative HPLC to provide 81.9 mg (36% yield) of 1,1,1,3,3,3-hexafluoropropan-2-yl 1-(4-chloro-3-methylbenzyl)-1,8-diazaspiro[4.5]decane-8-carboxylate as a white solid. $^1$H NMR (300 MHz, Chloroform-d) δ 7.23 (s, 1H), 7.14 (s, 1H), 7.06 (d, J=7.8 Hz, 1H), 5.72-5.80 (m, 1H), 4.16-4.25 (m, 2H), 3.51 (s, 2H), 2.91-3.04 (m, 2H), 2.65 (t, J=6.4 Hz, 2H), 2.35 (s, 3H), 1.65-1.86 (m, 6H), 1.45-1.49 (m, 2H). LCMS (ESI, m/z): 473 [M+H]$^+$.

Example 125: 1,1,1,3,3,3-Hexafluoropropan-2-yl 1-(3-chloro-4-methylbenzyl)-1,8-diazaspiro[4.5]decane-8-carboxylate

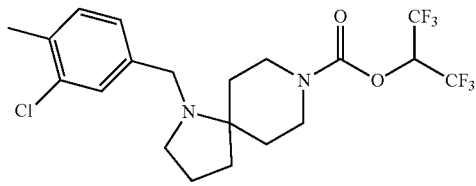 [SMILES: Cc1ccc(CN2CCCC23CCN(C(=O)OC(C(F)(F)F)C(F)(F)F)CC3)cc1Cl]

The title compound was synthesized directly from commercially available 3-chloro-4-methylbenzaldehyde in Step 3 according to the representative procedure of Example 124 to provide 1,1,1,3,3,3-hexafluoropropan-2-yl 1-(3-chloro-4-methylbenzyl)-1,8-diazaspiro[4.5]decane-8-carboxylate as a white solid. $^1$H NMR (300 MHz, Chloroform-d) δ 7.29 (s, 1H), 7.06-7.15 (m, 2H), 5.71-5.80 (m, 1H), 4.16-4.25 (m, 2H), 3.52 (s, 2H), 2.91-3.04 (m, 2H), 2.66-2.68 (m, 2H), 2.34 (s, 3H), 1.65-1.80 (m, 6H), 1.46-1.50 (m, 2H). LCMS (ESI, m/z): 473 [M+H]$^+$.

Example 126: 1,1,1,3,3,3-Hexafluoropropan-2-yl 1-(2,3-dihydro-1,4-benzodioxin-6-ylmethyl)-1,8-diazaspiro[4.5]decane-8-carboxylate

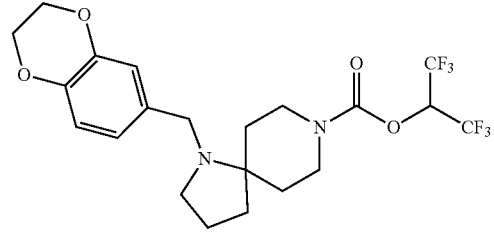 [SMILES: O=C(OC(C(F)(F)F)C(F)(F)F)N1CCC2(CCCN2Cc2ccc3c(c2)OCCO3)CC1]

The title compound was synthesized directly from commercially available 2,3-dihydro-1,4-benzodioxine-6-carbaldehyde in Step 3 according to the representative procedure of Example 124 to provide 1,1,1,3,3,3-hexafluoropropan-2-yl 1-(2,3-dihydro-1,4-benzodioxin-6-ylmethyl)-1,8-diazaspiro[4.5]decane-8-carboxylate as a yellow oil. $^1$H NMR (300 MHz, Chloroform-d) δ 6.74-6.84 (m, 3H), 5.71-5.80 (m, 1H), 4.24 (s, 4H), 4.15-4.20 (m, 2H), 3.47 (s, 2H), 2.90-3.04 (m, 2H), 2.67-2.69 (m, 2H), 1.65-1.79 (m, 6H), 1.44-1.48 (m, 2H). LCMS (ESI, m/z): 483 [M+H]$^+$.

Example 127: 1,1,1,3,3,3-Hexafluoropropan-2-yl 1-(3-chloro-4-morpholinobenzyl)-1,8-diazaspiro[4.5]decane-8-carboxylate

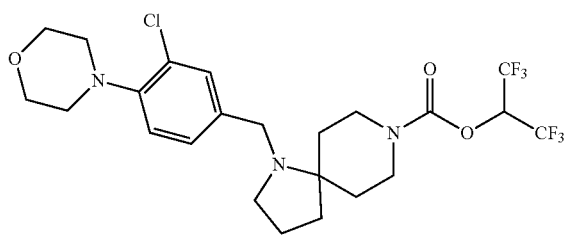 [SMILES: O=C(OC(C(F)(F)F)C(F)(F)F)N1CCC2(CCCN2Cc2ccc(N3CCOCC3)c(Cl)c2)CC1]

The title compound was synthesized directly from 3-chloro-4-morpholinobenzaldehyde (synthesized as described in Step 1 of Example 59) in Step 3 according to the representative procedure of Example 124 to provide 1,1,1,3,3,3-hexafluoropropan-2-yl 1-(3-chloro-4-morpholinobenzyl)-1,8-diazaspiro[4.5]decane-8-carboxylate as a white solid. $^1$H NMR (300 MHz, Chloroform-d) δ 7.33 (s, 1H), 7.14 (d, J=8.1 Hz, 1H), 6.96 (d, J=8.4 Hz, 1H), 5.69-5.82 (m, 1H), 4.16-4.24 (m, 2H), 3.86-3.89 (m, 4H), 3.51 (s, 2H), 2.91-3.05 (m, 6H), 2.66 (t, J=6.0 Hz, 2H), 1.65-1.80 (m, 6H), 1.45-1.50 (m, 2H). LCMS (ESI, m/z): 544 [M+H]$^+$.

Example 128: 1,1,1,3,3,3-Hexafluoropropan-2-yl 1-(3-chloro-4-(pyrrolidin-1-yl)benzyl)-1,8-diazaspiro[4.5]decane-8-carboxylate

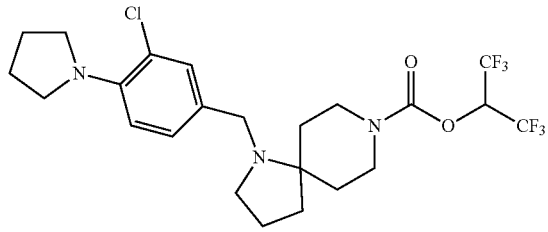 [SMILES: O=C(OC(C(F)(F)F)C(F)(F)F)N1CCC2(CCCN2Cc2ccc(N3CCCC3)c(Cl)c2)CC1]

The title compound was synthesized directly from 3-chloro-4-(pyrrolidin-1-yl)benzaldehyde (synthesized as described in Step 1 of Example 59) in Step 3 according to the representative procedure of Example 124 to provide 1,1,1,3,3,3-hexafluoropropan-2-yl 1-(3-chloro-4-(pyrrolidin-1-yl)benzyl)-1,8-diazaspiro[4.5]decane-8-carboxylate as a yellow oil. $^1$H NMR (300 MHz, Chloroform-d) δ 7.24 (s, 1H), 7.03-7.06 (m, 1H), 6.83 (d, J=8.1 Hz, 1H), 5.69-5.82 (m, 1H), 4.16-4.24 (m, 2H), 3.47 (s, 2H), 3.34 (t, J=6.3 Hz, 4H), 2.90-3.04 (m, 2H), 2.66-2.68 (m, 2H) 1.88-1.98 (m, 4H), 1.66-1.79 (m, 6H), 1.47-1.58 (m, 2H). LCMS (ESI, m/z): 528 [M+H]$^+$.

Example 129: 1,1,1,3,3,3-Hexafluoropropan-2-yl 1-(4-morpholino-3-(trifluoromethyl)benzyl)-1,8-diazaspiro[4.5]decane-8-carboxylate

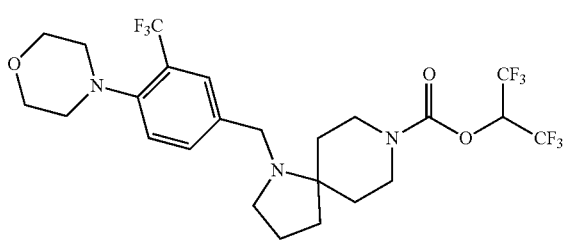 [SMILES: O=C(OC(C(F)(F)F)C(F)(F)F)N1CCC2(CCCN2Cc2ccc(N3CCOCC3)c(C(F)(F)F)c2)CC1]

The title compound was synthesized directly from 4-morpholino-3-(trifluoromethyl)benzaldehyde (synthesized as described in Step 1 of Example 59) in Step 3 according to the representative procedure of Example 124 to provide 1,1,1,3,3,3-hexafluoropropan-2-yl 1-(4-morpholino-3-(trifluoromethyl)benzyl)-1,8-diazaspiro[4.5]decane-8-carboxylate as a yellow oil. $^1$H NMR (300 MHz, Chloroform-d) δ 7.55 (s, 1H), 7.46 (d, J=8.1 Hz, 1H), 7.30 (d, J=8.1 Hz, 1H), 5.69-5.82 (m, 1H), 4.17-4.26 (m, 2H), 3.81-3.84 (m, 4H), 3.58 (s, 2H), 2.83-3.05 (m, 6H), 2.66-2.68 (m, 2H), 1.64-1.82 (m, 6H), 1.47-1.51 (m, 2H). LCMS (ESI, m/z): 578 [M+H]$^+$.

Example 130: 1,1,1,3,3,3-Hexafluoropropan-2-yl 1-(4-(pyrrolidin-1-yl)-3-(trifluoromethyl)benzyl)-1,8-diazaspiro[4.5]decane-8-carboxylate

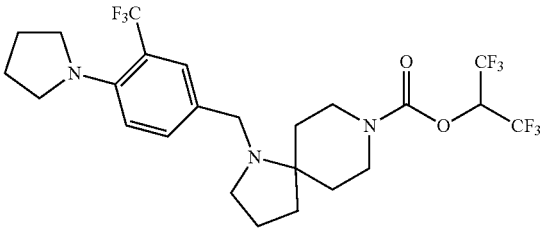

The title compound was synthesized directly from 4-(pyrrolidin-1-yl)-3-(trifluoromethyl)benzaldehyde (synthesized as described in Step 1 of Example 59) in Step 3 according to the representative procedure of Example 124 to provide 1,1,1,3,3,3-hexafluoropropan-2-yl 1-(4-(pyrrolidin-1-yl)-3-(trifluoromethyl)benzyl)-1,8-diazaspiro[4.5]decane-8-carboxylate as a light yellow oil. $^1$H NMR (300 MHz, Chloroform-d) δ 7.47 (s, 1H), 7.28-7.31 (m, 1H), 6.94 (d, J=8.7 Hz, 1H), 5.69-5.82 (m, 1H), 4.17-4.25 (m, 2H), 3.51 (s, 2H), 3.29 (br, 4H), 2.91-3.05 (m, 2H), 2.66 (br, 2H) 1.89-1.90 (m, 4H), 1.72-1.80 (m, 6H), 1.46-1.50 (m, 2H). LCMS (ESI, m/z): 562 [M+H]$^+$.

Example 131: 1,1,1,3,3,3-Hexafluoropropan-2-yl 1-(4-chloro-3-morpholinobenzyl)-1,8-diazaspiro[4.5]decane-8-carboxylate

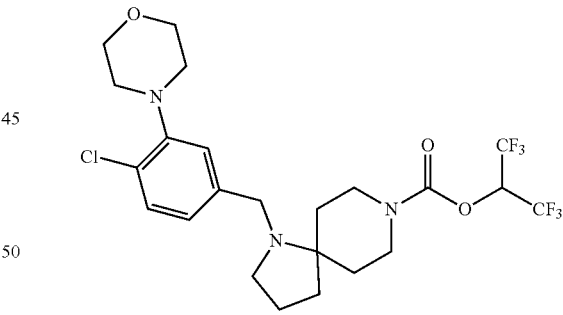

The title compound was synthesized directly from 4-chloro-3-morpholinobenzaldehyde (synthesized as described in Step 2 of Example 79) in Step 3 according to the representative procedure of Example 124 to provide 1,1,1,3,3,3-hexafluoropropan-2-yl 1-(4-chloro-3-morpholinobenzyl)-1,8-diazaspiro[4.5]decane-8-carboxylate as a white solid. $^1$H NMR (300 MHz, Chloroform-d) δ 7.30 (s, 1H), 6.91-7.00 (m, 2H), 5.71-5.81 (m, 1H), 4.17-4.21 (m, 2H), 3.86-3.89 (m, 4H), 3.54 (s, 2H), 2.82-3.05 (m, 6H), 2.66 (br, 2H), 1.41-1.81 (m, 8H). LCMS (ESI, m/z): 544 [M+H]$^+$.

Example 132: 1,1,1,3,3,3-Hexafluoropropan-2-yl 1-(4-chloro-3-(pyrrolidin-1-yl)benzyl)-1,8-diazaspiro[4.5]decane-8-carboxylate

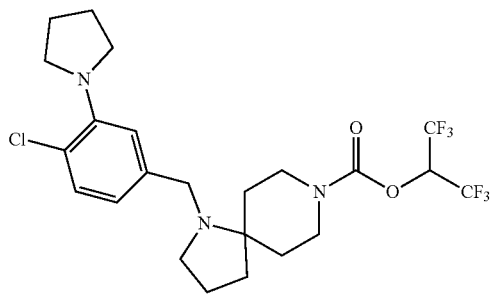 [SMILES: O=C(OC(C(F)(F)F)C(F)(F)F)N1CCC2(CCCN2Cc2ccc(Cl)c(N3CCCC3)c2)CC1]

The title compound was synthesized directly from 4-chloro-3-(pyrrolidin-1-yl)benzaldehyde (synthesized as described in Step 2 of Example 79) in Step 3 according to the representative procedure of Example 124 to provide 1,1,1,3,3,3-hexafluoropropan-2-yl 1-(4-chloro-3-(pyrrolidin-1-yl)benzyl)-1,8-diazaspiro[4.5]decane-8-carboxylate as a yellow oil. $^1$H NMR (300 MHz, Chloroform-d) δ 6.20 (d, J=8.1 Hz, 1H), 6.82 (s, 1H), 6.72-6.75 (m, 1H), 5.69-5.82 (m, 1H), 4.16-4.25 (m, 2H), 3.51 (s, 2H), 3.37 (t, J=6.3 Hz, 4H), 2.91-3.04 (m, 2H), 2.66-2.70 (m, 2H) 1.88-1.99 (m, 4H), 1.66-1.80 (m, 6H), 1.45-1.50 (m, 2H). LCMS (ESI, m/z): 528 [M+H]$^+$.

Example 133: 1,1,1,3,3,3-Hexafluoropropan-2-yl 1-(3-morpholino-4-(trifluoromethyl)benzyl)-1,8-diazaspiro[4.5]decane-8-carboxylate

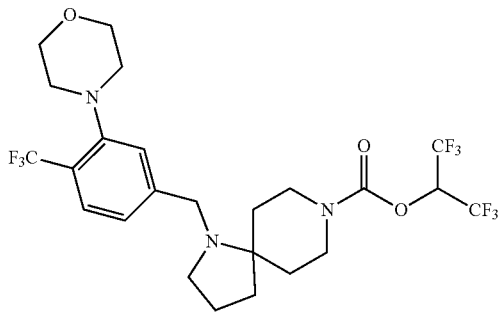 [SMILES: O=C(OC(C(F)(F)F)C(F)(F)F)N1CCC2(CCCN2Cc2ccc(C(F)(F)F)c(N3CCOCC3)c2)CC1]

The title compound was synthesized directly from 3-morpholino-4-(trifluoromethyl)benzaldehyde (synthesized as described in Step 2 of Example 79) in Step 3 according to the representative procedure of Example 124 to provide 1,1,1,3,3,3-hexafluoropropan-2-yl 1-(3-morpholino-4-(trifluoromethyl)benzyl)-1,8-diazaspiro[4.5]decane-8-carboxylate as an off-white solid. $^1$H NMR (300 MHz, Chloroform-d) δ 7.55 (d, J=7.8 Hz, 1H), 7.31 (s, 1H), 7.18 (d, J=7.8 Hz, 1H), 5.69-5.80 (m, 1H), 4.18-4.26 (m, 2H), 3.82-3.84 (m, 4H), 3.62 (s, 2H), 2.92-3.06 (m, 6H), 2.67-2.69 (m, 2H), 1.56-1.92 (m, 8H). LCMS (ESI, m/z): [M+H]$^+$.

Example 134: 1,1,1,3,3,3-Hexafluoropropan-2-yl 1-(3-(pyrrolidin-1-yl)-4-(trifluoromethyl)benzyl)-1,8-diazaspiro[4.5]decane-8-carboxylate

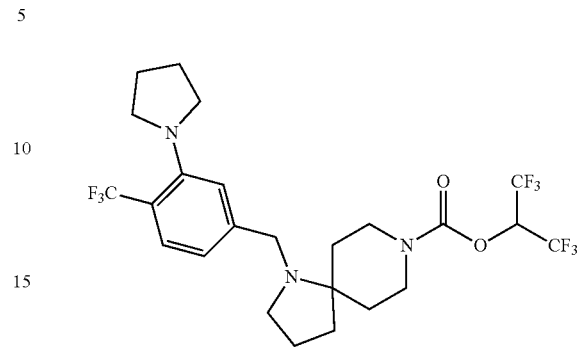

The title compound was synthesized directly from 3-(pyrrolidin-1-yl)-4-(trifluoromethyl)benzaldehyde (synthesized as described in Step 2 of Example 79) in Step 3 according to the representative procedure of Example 124 to provide 1,1,1,3,3,3-hexafluoropropan-2-yl 1-(3-(pyrrolidin-1-yl)-4-(trifluoromethyl)benzyl)-1,8-diazaspiro[4.5]decane-8-carboxylate as a light yellow oil. $^1$H NMR (300 MHz, Chloroform-d) δ 7.49 (d, J=8.1 Hz, 1H), 6.92 (s, 1H), 6.80 (d, J=8.1 Hz, 1H), 5.69-5.80 (m, 1H), 4.17-4.25 (m, 2H), 3.56 (s, 2H), 3.32 (s, 4H), 2.91-3.05 (m, 2H), 2.70-2.72 (m, 2H), 1.88-2.00 (m, 4H), 1.65-1.81 (m, 6H), 1.41-1.50 (m, 2H). LCMS (ESI, m/z): 562 [M+H]$^+$.

Example 135: 1,1,1,3,3,3-Hexafluoropropan-2-yl 2-(4-chloro-3-methylbenzyl)-2,8-diazaspiro[4.5]decane-8-carboxylate

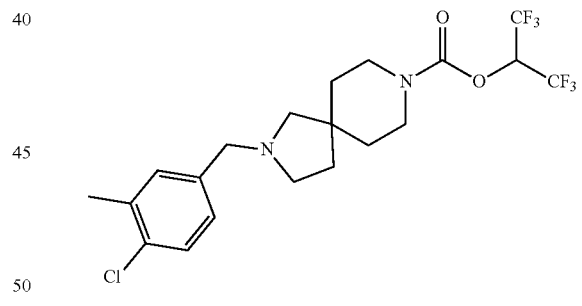

The title compound was synthesized directly from commercially available 4-chloro-3-methylbenzaldehyde and tert-butyl 2,8-diazaspiro[4.5]decane-8-carboxylate according to the representative procedure of Example 60 to provide 1,1,1,3,3,3-hexafluoropropan-2-yl 2-(4-chloro-3-methylbenzyl)-2,8-diazaspiro[4.5]decane-8-carboxylate as a yellow oil. $^1$H NMR (300 MHz, Chloroform-d) δ 7.27 (d, J=8.1 Hz, 1H), 7.08 (d, J=8.1 Hz, 1H), 7.18 (s, 1H), 5.70-5.78 (m, 1H), 3.39-3.55 (m, 6H), 2.61 (br, 2H), 2.38 (br, 2H), 2.36 (s, 3H), 1.68 (t, J=6.8 Hz, 2H), 1.57-1.63 (m, 4H). LCMS (ESI, m z): 473 [M+H]$^+$.

Example 136: 1,1,1,3,3,3-Hexafluoropropan-2-yl 2-(3-chloro-4-methylbenzyl)-2,8-diazaspiro[4.5]decane-8-carboxylate

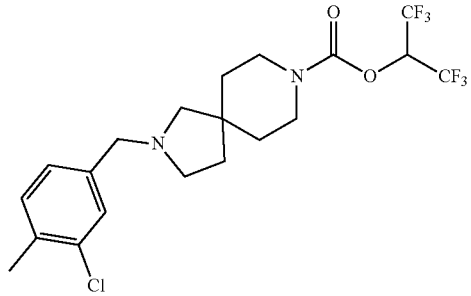 [SMILES: Cc1ccc(CN2CCC3(CCN(C(=O)OC(C(F)(F)F)C(F)(F)F)CC3)C2)cc1Cl]

The title compound was synthesized directly from commercially available 3-chloro-4-methylbenzaldehyde and tert-butyl 2,8-diazaspiro[4.5]decane-8-carboxylate according to the representative procedure of Example 60 to provide 1,1,1,3,3,3-hexafluoropropan-2-yl 2-(3-chloro-4-methylbenzyl)-2,8-diazaspiro[4.5]decane-8-carboxylate as a yellow oil. $^1$H NMR (300 MHz, Chloroform-d) δ 7.30 (s, 1H), 7.10-7.18 (m, 2H), 5.70-5.78 (m, 1H), 3.39-3.54 (m, 6H), 2.62 (br, 2H), 2.40 (br, 2H), 2.35 (s, 3H), 1.68 (t, J=6.9 Hz, 2H), 1.57-1.63 (m, 4H). LCMS (ESI, m/z): 473 [M+H]$^+$.

Example 137: 1,1,1,3,3,3-Hexafluoropropan-2-yl 2-((2,3-dihydrobenzo[b][1,4]dioxin-6-yl)methyl)-2,8-diazaspiro[4.5]decane-8-carboxylate

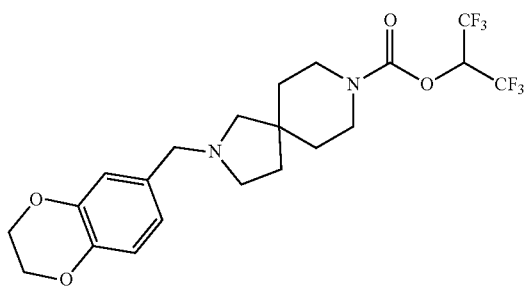 [SMILES: O=C(OC(C(F)(F)F)C(F)(F)F)N1CCC2(CCN(Cc3ccc4c(c3)OCCO4)C2)CC1]

The title compound was synthesized directly from commercially available 2,3-dihydro-1,4-benzodioxine-6-carbaldehyde and tert-butyl 2,8-diazaspiro[4.5]decane-8-carboxylate according to the representative procedure of Example 60 to provide 1,1,1,3,3,3-hexafluoropropan-2-yl 2-((2,3-dihydrobenzo[b][1,4]dioxin-6-yl)methyl)-2,8-diazaspiro[4.5]decane-8-carboxylate as a yellow solid. $^1$H NMR (300 MHz, Chloroform-d) δ 6.75-6.83 (m, 3H), 5.70-5.79 (m, 1H), 4.25 (s, 4H), 3.39-3.54 (m, 6H), 2.58-2.63 (m, 2H), 2.34-2.41 (m, 2H), 1.56-1.68 (m, 6H). LCMS (ESI, m/z): 483 [M+H]$^+$.

Example 138: 1,1,1,3,3,3-Hexafluoropropan-2-yl 2-(3-chloro-4-morpholinobenzyl)-2,8-diazaspiro[4.5]decane-8-carboxylate

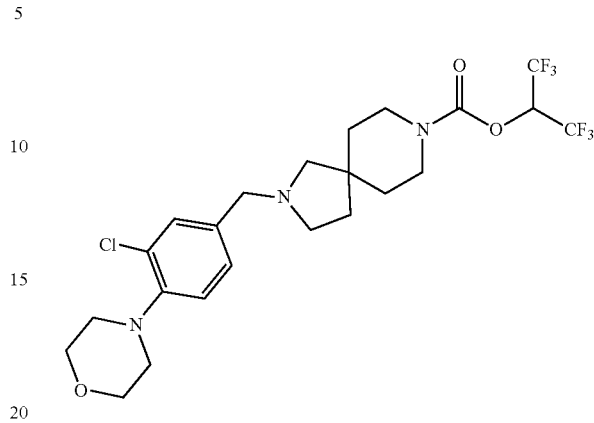

The title compound was synthesized directly from 3-chloro-4-morpholinobenzaldehyde (synthesized as described in Step 1 of Example 59) and tert-butyl 2,8-diazaspiro[4.5]decane-8-carboxylate according to the representative procedure of Example 60 to provide 1,1,1,3,3,3-hexafluoropropan-2-yl 2-(3-chloro-4-morpholinobenzyl)-2,8-diazaspiro[4.5]decane-8-carboxylate as a yellow oil. $^1$H NMR (300 MHz, Chloroform-d) δ 7.34 (s, 1H), 7.16-7.18 (m, 1H), 7.00 (d, J=7.8 Hz, 1H), 5.70-5.78 (m, 1H), 3.88 (t, J=4.5 Hz, 4H), 3.32-3.56 (m, 6H), 3.05 (t, J=4.5 Hz, 4H), 2.61 (br, 2H), 2.39 (br, 2H), 1.59-1.81 (m, 6H). LCMS (ESI, m/z): 544 [M+H]$^+$.

Example 139: 1,1,1,3,3,3-Hexafluoropropan-2-yl 2-(3-chloro-4-(pyrrolidin-1-yl)benzyl)-2,8-diazaspiro[4.5]decane-8-carboxylate

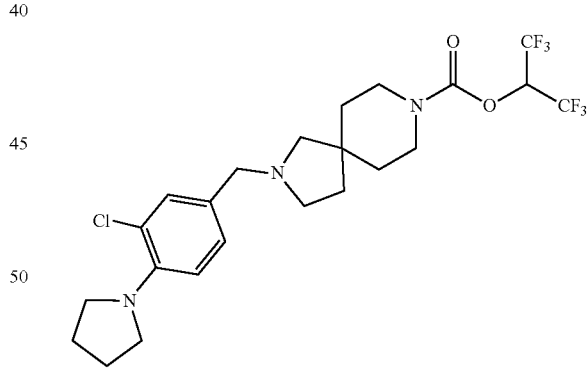

The title compound was synthesized directly from 3-chloro-4-(pyrrolidin-1-yl)benzaldehyde (synthesized as described in Step 1 of Example 59) and tert-butyl 2,8-diazaspiro[4.5]decane-8-carboxylate according to the representative procedure of Example 60 to provide 1,1,1,3,3,3-hexafluoropropan-2-yl 2-(3-chloro-4-(pyrrolidin-1-yl)benzyl)-2,8-diazaspiro[4.5]decane-8-carboxylate as a yellow oil. $^1$H NMR (300 MHz, Chloroform-d) δ 7.25 (s, 1H), 7.09 (d, J=7.8 Hz, 1H), 6.83 (d, J=8.4 Hz, 1H), 5.68-5.80 (m, 1H), 3.41-3.61 (m, 6H), 3.36 (t, J=6.4 Hz, 4H), 2.62 (br, 2H), 2.40 (br, 2H), 1.89-1.98 (m, 4H), 1.61-1.70 (m, 6H). LCMS (ESI, m/z): 528 [M+H]$^+$.

Example 140: 1,1,1,3,3,3-Hexafluoropropan-2-yl 2-(4-morpholino-3-(trifluoromethyl)benzyl)-2,8-diazaspiro[4.5]decane-8-carboxylate

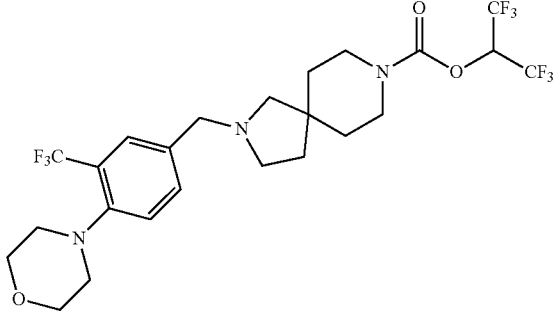 [SMILES: O=C(OC(C(F)(F)F)C(F)(F)F)N1CCC2(CCN(Cc3ccc(N4CCOCC4)c(C(F)(F)F)c3)C2)CC1]

The title compound was synthesized directly from 4-morpholino-3-(trifluoromethyl)benzaldehyde (synthesized as described in Step 1 of Example 59) and tert-butyl 2,8-diazaspiro[4.5]decane-8-carboxylate according to the representative procedure of Example 60 to provide 1,1,1,3,3,3-hexafluoropropan-2-yl 2-(4-morpholino-3-(trifluoromethyl)benzyl)-2,8-diazaspiro[4.5]decane-8-carboxylate as a colorless oil. $^1$H NMR (300 MHz, Chloroform-d) δ 7.57 (s, 1H), 7.49 (br, 1H), 7.31 (d, J=8.1 Hz, 1H), 5.68-5.81 (m, 1H), 3.83 (t, J=4.5 Hz, 4H), 3.40-3.60 (m, 6H), 2.92 (t, J=4.5 Hz, 4H), 2.78 (br, 2H), 2.40 (br, 2H), 1.60-1.70 (m, 6H). LCMS (ESI, m/z): 578 [M+H]$^+$.

Example 141: 1,1,1,3,3,3-Hexafluoropropan-2-yl 2-(4-(pyrrolidin-1-yl)-3-(trifluoromethyl)benzyl)-2,8-diazaspiro[4.5]decane-8-carboxylate

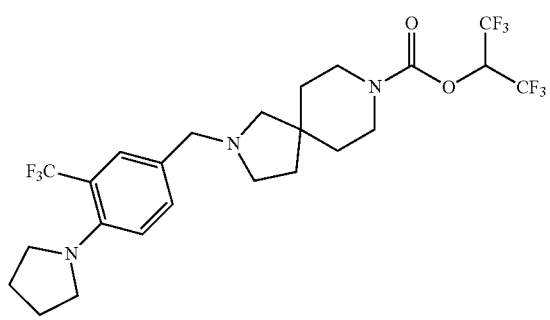 [SMILES: O=C(OC(C(F)(F)F)C(F)(F)F)N1CCC2(CCN(Cc3ccc(N4CCCC4)c(C(F)(F)F)c3)C2)CC1]

The title compound was synthesized directly from 4-(pyrrolidin-1-yl)-3-(trifluoromethyl)benzaldehyde (synthesized as described in Step 1 of Example 59) and tert-butyl 2,8-diazaspiro[4.5]decane-8-carboxylate according to the representative procedure of Example 60 to provide 1,1,1,3,3,3-hexafluoropropan-2-yl 2-(4-(pyrrolidin-1-yl)-3-(trifluoromethyl)benzyl)-2,8-diazaspiro[4.5]decane-8-carboxylate as pink oil. $^1$H NMR (300 MHz, Chloroform-d) δ 7.56 (s, 1H), 7.36-7.37 (m, 1H), 6.94 (d, J=8.7 Hz, 1H), 5.68-5.80 (m, 1H), 3.39-3.57 (m, 6H), 3.32 (t, J=4.5 Hz, 4H), 2.67 (br, 2H), 2.43 (br, 2H), 1.88-1.97 (m, 4H), 1.71 (br, 2H), 1.60-1.62 (m, 4H). LCMS (ESI, m/z): 562 [M+H]$^+$.

Example 142: 1,1,1,3,3,3-Hexafluoropropan-2-yl 1-((1-acetyl-1,2,3,4-tetrahydroquinolin-8-yl)methyl)-1,8-diazaspiro[4.5]decane-8-carboxylate

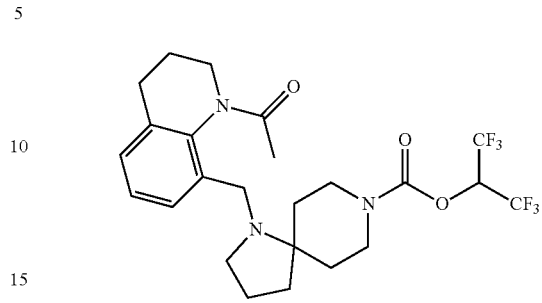

Step 1: Preparation of 1-tert-butyl 8-(1,1,1,3,3,3-hexafluoropropan-2-yl) 1,8-diazaspiro[4.5]decane-1,8-dicarboxylate

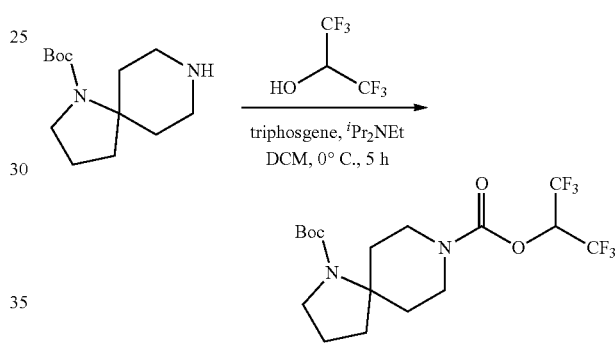

A flask was charged with triphosgene (2.46 g, 8.29 mmol, 0.50 equiv), DCM (100 mL) and HFIP (4.21 g, 24.9 mmol, 1.50 equiv). DIEA (6.45 g, 49.7 mmol, 3.00 equiv) was added dropwise at 0° C. The reaction mixture was stirred for 2 h at 0° C. tert-Butyl 1,8-diazaspiro[4.5]decane-1-carboxylate (4.01 g, 16.6 mmol, 1.00 equiv) was added, and the reaction was stirred for 3 h at 0° C. before quenching with H$_2$O (50 mL). The mixture was extracted with DCM (3×50 mL) and the organic layers were combined, washed with H$_2$O (3×100 mL), dried over anhydrous Na$_2$SO$_4$, filtered, and concentrated. The residue was purified on a silica gel column (1:2 EtOAc/petroleum ether) to provide 4.34 g (60% yield) of 1-tert-butyl 8-(1,1,1,3,3,3-hexafluoropropan-2-yl) 1,8-diazaspiro[4.5]decane-1,8-dicarboxylate as a white solid. LCMS (ESI, m/z): 435 [M+H]$^+$.

Step 2: Preparation of 1,1,1,3,3,3-hexafluoropropan-2-yl 1,8-diazaspiro[4.5]decane-8-carboxylate

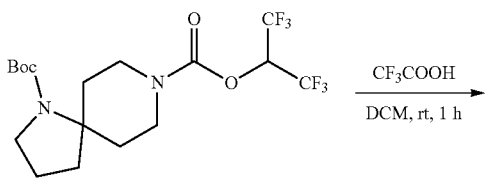

-continued

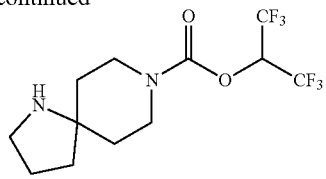

A flask was charged with 1-tert-butyl 8-(1,1,1,3,3,3-hexafluoropropan-2-yl) 1,8-diazaspiro[4.5]decane-1,8-dicarboxylate (4.34 g, 9.99 mmol, 1.00 equiv), DCM (20 mL), and TFA (10 mL). The resulting solution was stirred for 1 h at rt and concentrated to provide 3.34 g (crude) of 1,1,1,3,3,3-hexafluoropropan-2-yl 1,8-diazaspiro[4.5]decane-8-carboxylate as a yellow oil. LCMS (ESI, m/z): 335 [M+H]$^+$.

Step 3: Preparation of 1,1,1,3,3,3-hexafluoropropan-2-yl 1-((1,2,3,4-tetrahydroquinolin-8-yl)methyl)-1,8-diazaspiro[4.5]decane-8-carboxylate

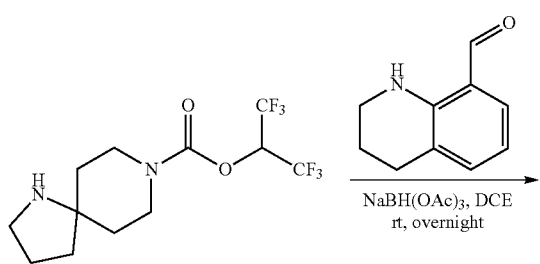

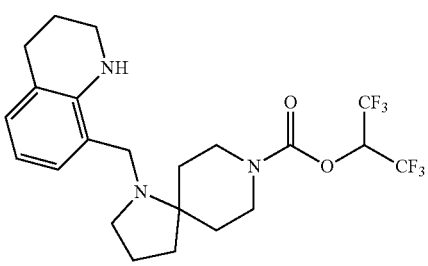 [SMILES: CC(=O)N1CCCc2cccc(CN3CCCC34CCN(C(=O)OC(C(F)(F)F)C(F)(F)F)CC4)c21]

A flask was charged with 1,2,3,4-tetrahydroquinoline-8-carbaldehyde (161 mg, 1.01 mmol, 1.00 equiv), 1,1,1,3,3,3-hexafluoropropan-2-yl 1,8-diazaspiro[4.5]decane-8-carboxylate (400 mg, 1.20 mmol, 1.20 equiv), DCE (10 mL) and NaBH(OAc)$_3$ (424 mg, 2.02 mmol, 2.00 equiv). The resulting solution was stirred overnight at rt and diluted with DCM (50 mL). The mixture was washed with H$_2$O (3×50 mL), dried over anhydrous Na$_2$SO$_4$, filtered, and concentrated. The residue was purified on a silica gel column (1:2 EtOAc/petroleum ether) to provide 240 mg (50% yield) of 1,1,1,3,3,3-hexafluoropropan-2-yl 1-((1,2,3,4-tetrahydroquinolin-8-yl)methyl)-1,8-diazaspiro[4.5]decane-8-carboxylate as a yellow oil. LCMS (ESI, m/z): 480 [M+H]$^+$.

Step 4: Preparation of 1,1,1,3,3,3-hexafluoropropan-2-yl 1-((1-acetyl-1,2,3,4-tetrahydroquinolin-8-yl)methyl)-1,8-diazaspiro[4.5]decane-8-carboxylate

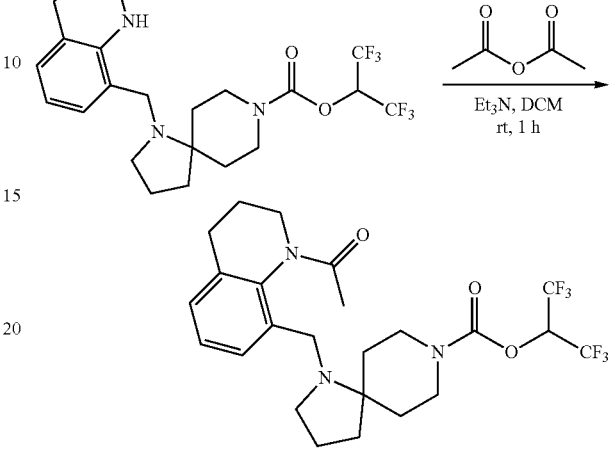

A flask was charged with 1,1,1,3,3,3-hexafluoropropan-2-yl 1-((1,2,3,4-tetrahydroquinolin-8-yl)methyl)-1,8-diazaspiro[4.5]decane-8-carboxylate (133 mg, 0.281 mmol, 1.00 equiv), DCM (20 mL), and TEA (56.1 mg, 0.556 mmol, 2.00 equiv). Acetyl acetate (42.6 mg, 0.421 mmol, 1.50 equiv) was added at rt. The resulting solution was stirred for 1 h at rt and diluted with DCM (20 mL). The mixture was washed with H$_2$O (3×20 mL), dried over anhydrous Na$_2$SO$_4$, filtered, and concentrated. The residue was purified by preparative HPLC to provide 39.5 mg (27% yield) of 1,1,1,3,3,3-hexafluoropropan-2-yl 1-((1-acetyl-1,2,3,4-tetrahydroquinolin-8-yl)methyl)-1,8-diazaspiro[4.5]decane-8-carboxylate as an off-white solid. $^1$H NMR (300 MHz, Chloroform-d) δ 7.39 (d, J=7.1 Hz, 1H), 6.96-7.23 (m, 2H), 5.71-5.77 (m, 1H), 4.71-4.87 (m, 1H), 4.10-4.31 (m, 2H), 3.45-3.68 (m, 2H), 2.83-3.05 (m, 2H), 2.58-2.81 (m, 3H), 2.35-2.55 (m, 2H), 2.12-2.34 (m, 2H), 1.81-2.01 (m, 4H), 1.63-1.80 (m, 4H), 1.27-1.63 (m, 3H). LCMS (ESI, m/z): 522 [M+H]$^+$.

Example 143: 1,1,1,3,3,3-Hexafluoropropan-2-yl 1-((1-methanesulfonyl-1,2,3,4-tetrahydroquinolin-8-yl)methyl)-1,8-diazaspiro[4.5]decane-8-carboxylate

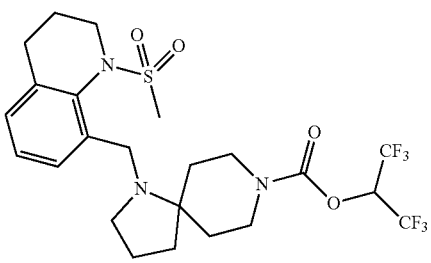 [SMILES: CS(=O)(=O)N1CCCc2cccc(CN3CCCC34CCN(C(=O)OC(C(F)(F)F)C(F)(F)F)CC4)c21]

A flask was charged with 1,1,1,3,3,3-hexafluoropropan-2-yl 1-(1,2,3,4-tetrahydroquinolin-8-ylmethyl)-1,8-diazaspiro[4.5]decane-8-carboxylate (from Example 142, Step 3, 133 mg, 0.278 mmol, 1.00 equiv), DCM (20 mL), and TEA (56.2 mg, 0.556 mmol, 2.00 equiv). Methanesulfonyl chloride (48.1 mg, 0.420 mmol, 1.50 equiv) was added at rt. The resulting solution was stirred for 1 h at rt and diluted with DCM (20 mL). The mixture was washed with H₂O (3×20 mL), dried over anhydrous Na₂SO₄, filtered, and concentrated. The residue was purified by preparative HPLC to provide 36.4 mg (24% yield) of 1,1,1,3,3,3-hexafluoropropan-2-yl 1-((1-methanesulfonyl-1,2,3,4-tetrahydroquinolin-8-yl)methyl)-1,8-diazaspiro[4.5]decane-8-carboxylate as a yellow oil. ¹H NMR (300 MHz, Chloroform-d) δ 7.53 (d, J=7.7 Hz, 1H), 7.22 (t, J=7.5 Hz, 1H), 7.04 (d, J=7.4 Hz, 1H), 5.69-5.82 (m, 1H), 4.01-4.31 (m, 3H), 3.70-3.89 (m, 2H), 3.21-3.35 (m, 1H), 2.87-3.11 (m, 5H), 2.75-2.86 (m, 2H), 2.61-2.75 (m, 1H), 2.35-2.56 (m, 2H), 1.65-2.03 (m, 7H), 1.40-1.51 (m, 2H). LCMS (ESI, m/z): 558 [M+H]⁺.

Example 144: 1,1,1,3,3,3-Hexafluoropropan-2-yl 1-((2-ethyl-1,2,3,4-tetrahydroisoquinolin-8-yl)methyl)-1,8-diazaspiro[4.5]decane-8-carboxylate

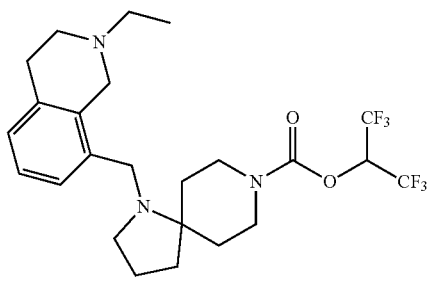 [SMILES: CCN1CCc2cccc(CN3CCCC34CCN(C(=O)OC(C(F)(F)F)C(F)(F)F)CC4)c2C1]

Step 1: Preparation of tert-butyl 8-formyl-1,2,3,4-tetrahydroisoquinoline-2-carboxylate

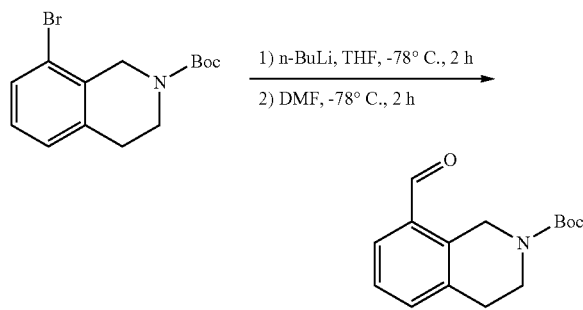

A flask was charged with tert-butyl 8-bromo-1,2,3,4-tetrahydroisoquinoline-2-carboxylate (3.11 g, 9.93 mmol, 1.00 equiv) and THF (50 mL) under nitrogen. The reaction mixture was cooled to −78° C. and n-butyllithium (2.5 M in hexane, 6 mL, 15.1 mmol, 1.50 equiv) was added dropwise. The reaction mixture was stirred at −78° C. for 2 h, then DMF (1.46 g, 19.9 mmol, 2.00 equiv) was added dropwise. The resulting solution was stirred for 2 h at −78° C., quenched with aq. NH₄Cl (10 mL) and diluted with EtOAc (100 mL). The mixture was washed with H₂O (3×100 mL), dried over anhydrous Na₂SO₄, filtered, and concentrated. The residue was purified on a silica gel column (1:5 EtOAc/petroleum ether) to provide 1.81 g (69% yield) of tert-butyl 8-formyl-1,2,3,4-tetrahydroisoquinoline-2-carboxylate as a yellow solid. LCMS (ESI, m/z): 262 [M+H]⁺.

Step 2: Preparation of 1,1,1,3,3,3-hexafluoropropan-2-yl 1-((2-(tert-butoxycarbonyl)-1,2,3,4-tetrahydroisoquinolin-8-yl)methyl)-1,8-diazaspiro[4.5]decane-8-carboxylate

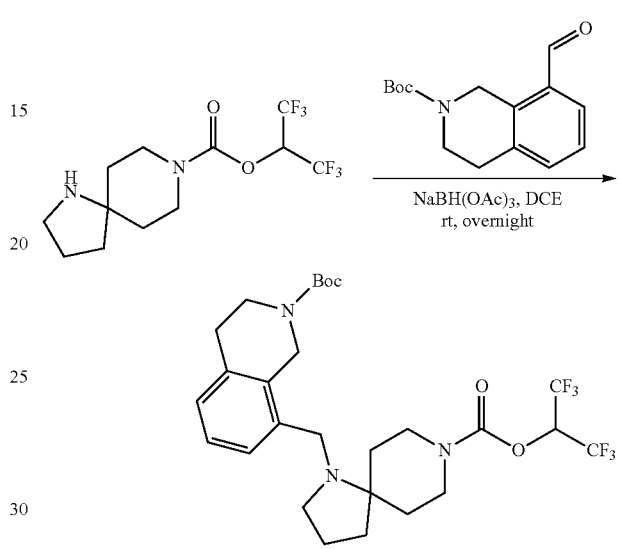

A flask was charged with tert-butyl 8-formyl-1,2,3,4-tetrahydroisoquinoline-2-carboxylate (1.81 g, 6.89 mmol, 1.00 equiv), 1,1,1,3,3,3-hexafluoropropan-2-yl 1,8-diazaspiro[4.5]decane-8-carboxylate (2.71 g, 8.08 mmol, 1.20 equiv), DCE (50 mL), and NaBH(OAc)₃ (4.41 g, 20.7 mmol, 3.00 equiv). The resulting solution was stirred overnight at rt and diluted with DCM (50 mL). The mixture was washed with H₂O (3×50 mL), dried over anhydrous Na₂SO₄, filtered, and concentrated. The residue was purified on a silica gel column (1:1 EtOAc/petroleum ether) to provide 500 mg (13% yield) of 1,1,1,3,3,3-hexafluoropropan-2-yl 1-((2-(tert-butoxycarbonyl)-1,2,3,4-tetrahydroisoquinolin-8-yl)methyl)-1,8-diazaspiro[4.5]decane-8-carboxylate as a yellow solid. LCMS (ESI, m/z): 580 [M+H]⁺.

Step 3: Preparation of 1,1,1,3,3,3-hexafluoropropan-2-yl 1-((1,2,3,4-tetrahydroisoquinolin-8-yl)methyl)-1,8-diazaspiro[4.5]decane-8-carboxylate

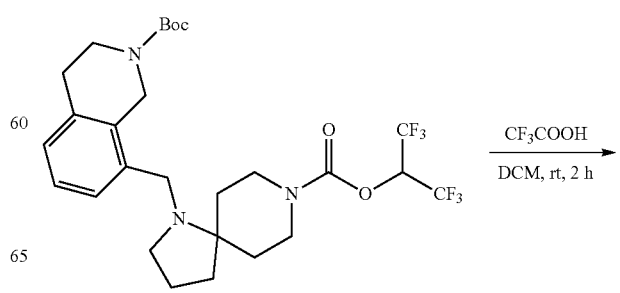

-continued

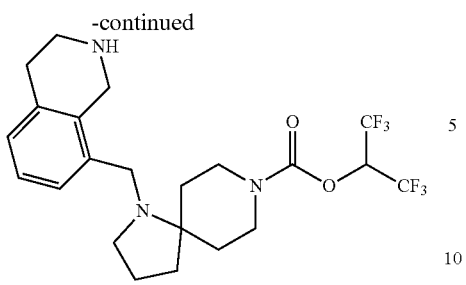

A flask was charged with 1,1,1,3,3,3-hexafluoropropan-2-yl 1-((2-(tert-butoxycarbonyl)-1,2,3,4-tetrahydroisoquinolin-8-yl)methyl)-1,8-diazaspiro[4.5]decane-8-carboxylate (500 mg, 0.860 mmol, 1.00 equiv), DCM (10 mL) and TFA (5 mL). The resulting solution was stirred for 2 h at rt and concentrated to provide 414 mg (crude) of 1,1,1,3,3,3-hexafluoropropan-2-yl 1-((1,2,3,4-tetrahydroisoquinolin-8-yl)methyl)-1,8-diazaspiro[4.5]decane-8-carboxylate as a yellow oil. LCMS (ESI, m/z): 480 [M+H]$^+$.

Step 4: Preparation of 1,1,1,3,3,3-hexafluoropropan-2-yl 1-((2-ethyl-1,2,3,4-tetrahydroisoquinolin-8-yl)methyl)-1,8-diazaspiro[4.5]decane-8-carboxylate

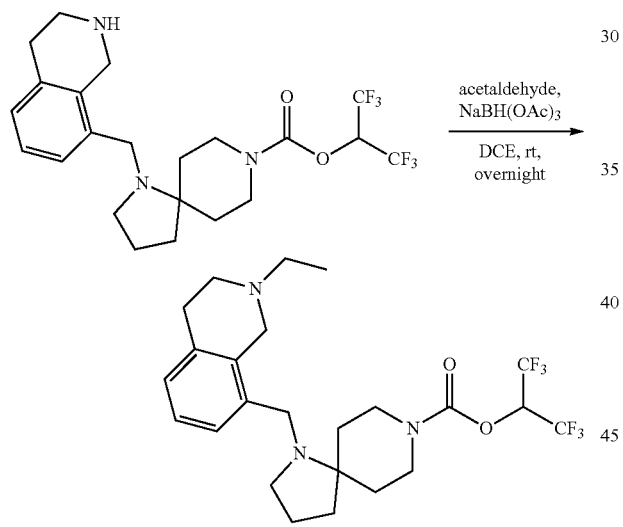

A flask was charged with 1,1,1,3,3,3-hexafluoropropan-2-yl 1-((1,2,3,4-tetrahydroisoquinolin-8-yl)methyl)-1,8-diazaspiro[4.5]decane-8-carboxylate (165 mg, 0.340 mmol, 1.00 equiv), acetaldehyde (76.2 mg, 1.73 mmol, 5.00 equiv), DCE (20 mL), and NaBH(OAc)$_3$ (212 mg, 1.02 mmol, 3.00 equiv). The resulting solution was stirred overnight at rt and diluted with DCM (20 mL). The mixture was washed with H$_2$O (3×20 mL), dried over anhydrous Na$_2$SO$_4$, filtered, and concentrated. The residue was purified by preparative HPLC to provide 52.3 mg (30% yield) of 1,1,1,3,3,3-hexafluoropropan-2-yl 1-((2-ethyl-1,2,3,4-tetrahydroisoquinolin-8-yl)methyl)-1,8-diazaspiro[4.5]decane-8-carboxylate as a white solid. $^1$H NMR (300 MHz, Chloroform-d) δ 7.05-7.12 (m, 2H), 6.99-7.04 (m, 1H), 5.70-5.83 (m, 1H), 4.21 (t, J=12.6 Hz, 2H), 3.78 (s, 2H), 3.52 (s, 2H), 2.86-3.04 (m, 4H), 2.75 (s, 2H), 2.55-2.70 (m, 4H), 1.65-1.90 (m, 6H), 1.41-1.55 (m, 2H), 1.20-1.24 (m, 3H). LCMS (ESI, m/z): 508 [M+H]$^+$.

Example 145: 1,1,1,3,3,3-Hexafluoropropan-2-yl 1-((2-acetyl-1,2,3,4-tetrahydroisoquinolin-8-yl)methyl)-1,8-diazaspiro[4.5]decane-8-carboxylate

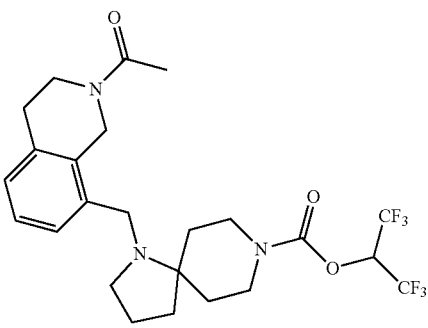 [SMILES: CC(=O)N1CCc2cccc(CN3CCCC34CCN(C(=O)OC(C(F)(F)F)C(F)(F)F)CC4)c2C1]

A flask was charged with 1,1,1,3,3,3-hexafluoropropan-2-yl 1-((1,2,3,4-tetrahydroisoquinolin-8-yl)methyl)-1,8-diazaspiro[4.5]decane-8-carboxylate (from Example 144, Step 3, 138 mg, 0.290 mmol, 1.00 equiv), DCM (20 mL) and TEA (88.1 mg, 0.870 mmol, 3.00 equiv). Acetyl acetate (59.1 mg, 0.580 mmol, 2.00 equiv) was added at rt at rt. The resulting solution was stirred for 2 h at rt and diluted with DCM (20 mL). The mixture was washed with H$_2$O (3×20 mL), dried over anhydrous Na$_2$SO$_4$, filtered, and concentrated. The residue was purified by preparative HPLC to provide 112.9 mg (75% yield) of 1,1,1,3,3,3-hexafluoropropan-2-yl 1-((2-acetyl-1,2,3,4-tetrahydroisoquinolin-8-yl)methyl)-1,8-diazaspiro[4.5]decane-8-carboxylate as a yellow oil. $^1$H NMR (300 MHz, Chloroform-d) δ 7.03-7.27 (m, 3H), 5.73-5.82 (m, 1H), 4.77-4.91 (m, 2H), 4.24 (t, J=12.6 Hz, 2H), 3.81 (t, J=6.0 Hz, 1H), 3.52-3.74 (m, 3H), 2.80-3.12 (m, 4H), 2.62 (q, J=6.7 Hz, 2H), 2.17 (s, 3H), 1.65-1.93 (m, 6H), 1.42-1.65 (m, 2H). LCMS (ESI, m/z): 522 [M+H]$^+$.

Example 146: 1,1,1,3,3,3-Hexafluoropropan-2-yl 1-((2-methanesulfonyl-1,2,3,4-tetrahydroisoquinolin-8-yl)methyl)-1,8-diazaspiro[4.5]decane-8-carboxylate

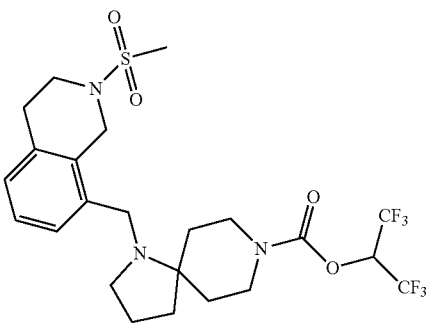 [SMILES: CS(=O)(=O)N1CCc2cccc(CN3CCCC34CCN(C(=O)OC(C(F)(F)F)C(F)(F)F)CC4)c2C1]

A flask was charged with 1,1,1,3,3,3-hexafluoropropan-2-yl 1-((1,2,3,4-tetrahydroisoquinolin-8-yl)methyl)-1,8-diazaspiro[4.5]decane-8-carboxylate (from Example 144, Step 3, 138 mg, 0.290 mmol, 1.00 equiv), DCM (20 mL) and TEA (88.1 mg, 0.871 mmol, 3.00 equiv). Methanesulfonyl chloride (66.2 mg, 0.590 mmol, 2.00 equiv) was added at rt. The resulting solution was stirred for 2 h and diluted with DCM (20 mL). The mixture was washed with H$_2$O (3×20 mL), dried over anhydrous Na₂SO₄, filtered, and concentrated. The residue was purified by preparative HPLC to provide 65.8 mg (41% yield) of 1,1,1,3,3,3-hexafluoropropan-2-yl 1-((2-methanesulfonyl-1,2,3,4-tetrahydroisoquinolin-8-yl)methyl)-1,8-diazaspiro[4.5]decane-8-carboxylate as an off-white solid. ¹H NMR (300 MHz, Chloroform-d) δ 7.11-7.17 (m, 2H), 7.03-7.10 (m, 1H), 5.71-5.85 (m, 1H), 4.64 (s, 2H), 4.24 (t, J=11.4 Hz, 2H), 3.51-3.58 (m, 4H), 2.89-3.11 (m, 4H), 2.81 (s, 3H), 2.58 (t, J=6.9 Hz, 2H), 1.65-1.89 (m, 6H), 1.56 (s, 2H). LCMS (ESI, m/z): 558 [M+H]⁺.

Example 147: 1,1,1,3,3,3-Hexafluoropropan-2-yl 1-((2-isopropyl-1,2,3,4-tetrahydroisoquinolin-8-yl)methyl)-1,8-diazaspiro[4.5]decane-8-carboxylate

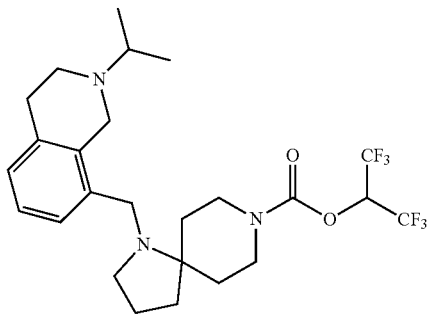 [SMILES: CC(C)N1CCc2cccc(CN3CCCC34CCN(C(=O)OC(C(F)(F)F)C(F)(F)F)CC4)c2C1]

The title compound was synthesized using acetone in Step 4 according to the representative procedure of Example 144 to provide 1,1,1,3,3,3-hexafluoropropan-2-yl 1-((2-isopropyl-1,2,3,4-tetrahydroisoquinolin-8-yl)methyl)-1,8-diazaspiro[4.5]decane-8-carboxylate formate as a yellow oil. ¹H NMR (400 MHz, Chloroform-d) δ 8.37 (s, 1H), 7.61-8.32 (br, 1H), 7.05-7.21 (m, 3H), 5.71-5.85 (m, 1H), 4.42 (s, 2H), 4.25 (t, J=14.4 Hz, 2H), 3.62 (s, 3H), 3.33 (s, 2H), 3.19 (s, 2H), 2.85-3.10 (m, 2H), 2.57 (t, J=6.7 Hz, 2H), 1.62-1.95 (m, 6H), 1.28-1.61 (m, 8H). LCMS (ESI, m/z): 522 [M+H]⁺.

Example 148: 1,1,1,3,3,3-Hexafluoropropan-2-yl 1-((2-cyclopropyl-1,2,3,4-tetrahydroisoquinolin-8-yl)methyl)-1,8-diazaspiro[4.5]decane-8-carboxylate

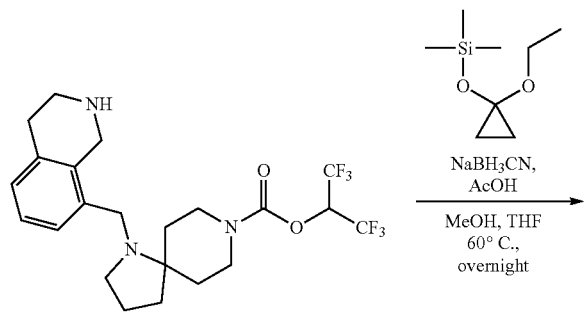

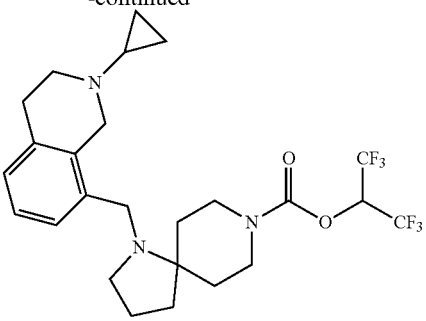

A flask was charged with 1,1,1,3,3,3-hexafluoropropan-2-yl 1-((1,2,3,4-tetrahydroisoquinolin-8-yl)methyl)-1,8-diazaspiro[4.5]decane-8-carboxylate (from Example 144, Step 3, 165 mg, 0.340 mmol, 1.00 equiv), MeOH (10 mL), THF (10 mL), (1-ethoxycyclopropoxy)trimethylsilane (174 mg, 1.01 mmol, 3.00 equiv), acetic acid (80.1 mg, 1.33 mmol, 4.00 equiv) and sodium cyanoborohydride (63.2 mg, 1.01 mmol, 3.00 equiv). The resulting solution was stirred overnight at 60° C. and diluted with DCM (50 mL). The mixture was washed with H₂O (3×50 mL), dried over anhydrous Na₂SO₄, filtered, and concentrated. The residue was purified by preparative HPLC to provide 72.6 mg (41% yield) of 1,1,1,3,3,3-hexafluoropropan-2-yl 1-((2-cyclopropyl-1,2,3,4-tetrahydroisoquinolin-8-yl)methyl)-1,8-diazaspiro[4.5]decane-8-carboxylate as a yellow oil. ¹H NMR (400 MHz, Chloroform-d) δ 7.05-7.12 (m, 2H), 7.00 (d, J=6.8 Hz, 1H), 5.70-5.81 (m, 1H), 4.22 (t, J=16.8 Hz, 2H), 3.97 (s, 2H), 3.54 (s, 2H), 2.85-3.11 (m, 6H), 2.61 (t, J=6.8 Hz, 2H), 1.65-1.97 (m, 7H), 1.40-1.56 (m, 2H) 0.45-0.78 (m, 4H). LCMS (ESI, m/z): 520 [M+H]⁺.

Example 149: 1,1,1,3,3,3-Hexafluoropropan-2-yl 1-((2-(2-methylpropyl)-1,2,3,4-tetrahydroisoquinolin-8-yl)methyl)-1,8-diazaspiro[4.5]decane-8-carboxylate

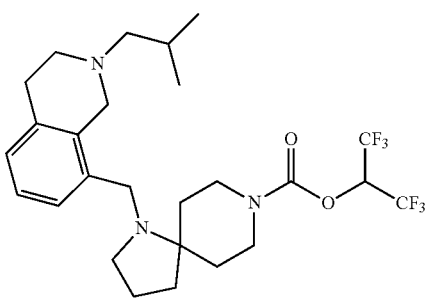 [SMILES: CC(C)CN1CCc2cccc(CN3CCCC34CCN(C(=O)OC(C(F)(F)F)C(F)(F)F)CC4)c2C1]

The title compound was synthesized using 2-methylpropanal in Step 4 according to the representative procedure of Example 144 to provide 1,1,1,3,3,3-hexafluoropropan-2-yl 1-((2-(2-methylpropyl)-1,2,3,4-tetrahydroisoquinolin-8-yl)methyl)-1,8-diazaspiro[4.5]decane-8-carboxylate as an off-white solid. ¹H NMR (300 MHz, Chloroform-d) δ 7.03-7.15 (m, 2H), 6.95-7.03 (m, 1H), 5.71-5.85 (m, 1H), 4.20 (t, J=13.0 Hz, 2H), 3.67 (s, 2H), 3.51 (s, 2H), 2.85-3.09 (m, 4H), 2.55-2.76 (m, 4H), 2.29 (s, 2H), 1.89-2.03 (m, 1H), 1.67-1.83 (m, 6H), 1.40-1.52 (m, 2H), 0.95 (d, J=7.0 Hz, 6H). LCMS (ESI, m/z): 536 [M+H]⁺.

Example 150: 1,1,1,3,3,3-Hexafluoropropan-2-yl 1-(3-ethyl-4-fluorobenzyl)-1,8-diazaspiro[4.5]decane-8-carboxylate

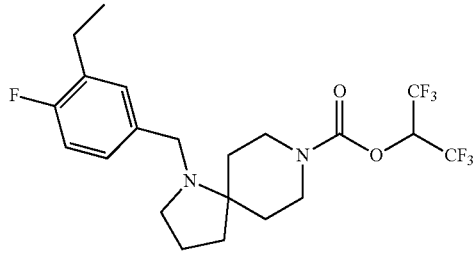 [SMILES: CCc1cc(CN2CCCC23CCN(C(=O)OC(C(F)(F)F)C(F)(F)F)CC3)ccc1F]

Step 1: Synthesis of 1-tert-butyl 8-(1,1,1,3,3,3-hexafluoropropan-2-yl) 1,8-diazaspiro[4.5]decane-1,8-dicarboxylate

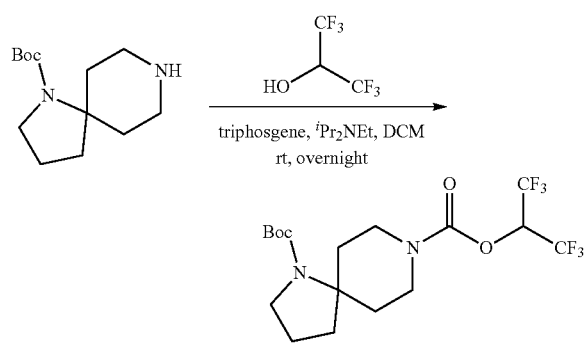

A flask was charged with triphosgene (2.60 g, 8.75 mmol, 0.70 equiv), and DCM (40 mL). HFIP (4.20 g, 25.0 mmol, 2.00 equiv) and DIPEA (4.84 g, 37.5 mmol, 3.00 equiv) were each added dropwise at 0° C. The mixture was stirred for 1 h at rt. tert-Butyl 1,8-diazaspiro[4.5]decane-1-carboxylate (3.00 g, 12.5 mmol, 1.00 equiv) was added, and the reaction was stirred overnight at rt before quenching with water (80 mL). The resulting solution was extracted with DCM (2×100 mL) and the organic layers were combined, dried over anhydrous sodium sulfate, filtered, and concentrated. The residue was chromatographed on a silica gel column with EtOAc/petroleum ether (1/3) to provide 1.80 g (33% yield) of 1-tert-butyl 8-(1,1,1,3,3,3-hexafluoropropan-2-yl) 1,8-diazaspiro[4.5]decane-1,8-dicarboxylate as a white solid. LCMS (ESI, m/z): 435 [M+H]$^+$.

Step 2: Synthesis of 1,1,1,3,3,3-hexafluoropropan-2-yl 1,8-diazaspiro[4.5]decane-8-carboxylate

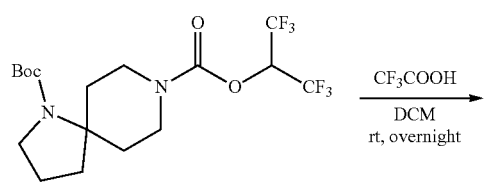

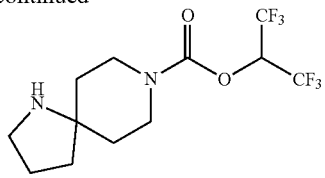

A flask was charged with 1-tert-butyl 8-(1,1,1,3,3,3-hexafluoropropan-2-yl) 1,8-diazaspiro[4.5]decane-1,8-dicarboxylate (1.00 g, 2.30 mmol, 1.00 equiv), DCM (15 mL), and TFA (3 mL). The resulting solution was stirred overnight at rt and concentrated to provide 769 mg (crude) of 1,1,1,3,3,3-hexafluoropropan-2-yl 1,8-diazaspiro[4.5]decane-8-carboxylate as a light yellow oil. LCMS (ESI, m/z): 335 [M+H]$^+$.

Step 3: Synthesis of 3-ethyl-4-fluorobenzaldehyde

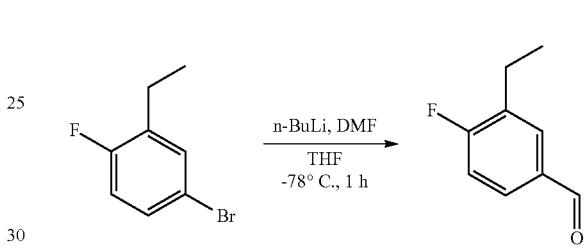

A flask was charged with 4-bromo-2-ethyl-1-fluorobenzene (2.00 g, 9.85 mmol, 1.00 equiv), and THF (25 mL) under nitrogen. The mixture was cooled to −78° C. n-Butyllithium (2.5 M in hexane, 4.80 mL, 11.8 mmol, 1.20 equiv) was added dropwise at −78° C. The mixture was stirred for 1 h at −78° C. and DMF (2.17 g, 29.6 mmol, 3.00 equiv) was added. The resulting solution was stirred for 1 h at −78° C. and quenched with saturated NH$_4$Cl solution (30 mL). The resulting solution was extracted with EtOAc (2×100 mL) and the organic layers were combined, dried over anhydrous sodium sulfate, filtered, and concentrated. The residue was chromatographed on a silica gel column with EtOAc/petroleum ether (1/9) to provide 1.20 g (80% yield) of 3-ethyl-4-fluorobenzaldehyde as a light yellow oil. $^1$H NMR (300 MHz, Chloroform-d) δ 9.94 (s, 1H), 7.71-7.82 (m, 2H), 7.16 (t, J=8.8 Hz, 1H), 2.68-2.78 (m, 2H), 1.28 (t, J=6.4 Hz, 3H).

Step 4: Synthesis of 1,1,1,3,3,3-hexafluoropropan-2-yl 1-(3-ethyl-4-fluorobenzyl)-1,8-diazaspiro[4.5]decane-8-carboxylate

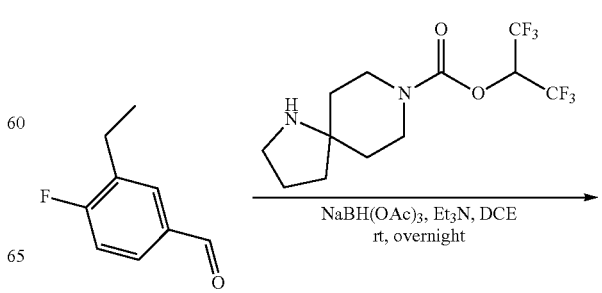

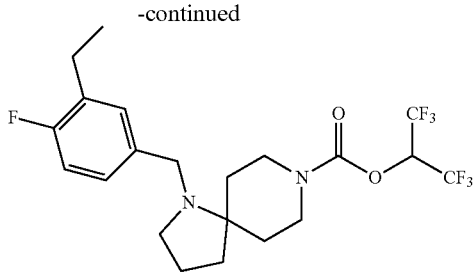

A flask was charged with 3-ethyl-4-fluorobenzaldehyde (68.0 mg, 0.450 mmol, 1.00 equiv), DCE (10 mL), 1,1,1,3,3,3-hexafluoropropan-2-yl 1,8-diazaspiro[4.5]decane-8-carboxylate (150 mg, 0.450 mmol, 1.00 equiv), and TEA (136 mg, 1.34 mmol, 3.00 equiv). The mixture was stirred for 1 h at rt. Sodium triacetoxyborohydride (286 mg, 1.35 mmol, 3.00 equiv) was added, and the reaction was stirred overnight at rt before quenching with water (30 mL). The resulting solution was extracted with DCM (2×50 mL) and the organic layers were combined, dried over anhydrous sodium sulfate, filtered, and concentrated. The crude product was purified by preparative HPLC to give 78.9 mg (38% yield) of 1,1,1,3,3,3-hexafluoropropan-2-yl 1-(3-ethyl-4-fluorobenzyl)-1,8-diazaspiro[4.5]decane-8-carboxylate as a light yellow oil. $^1$H NMR (400 MHz, DMSO-$d_6$) δ 7.17 (d, J=5.6 Hz, 1H), 7.10-7.15 (m, 1H), 7.03 (t, J=5.0 Hz, 1H), 6.52-6.57 (m, 2H), 4.16-4.25 (m, 2H), 3.51 (s, 2H), 2.98-3.11 (m, 2H), 2.51-2.62 (m, 4H), 1.77-1.80 (m, 2H), 1.56-1.71 (m, 4H), 1.48 (d, J=12.8 Hz, 2H), 1.16 (t, J=7.6 Hz, 3H). LCMS (ESI, m/z): 471 [M+H]$^+$.

Example 151: 1,1,1,3,3,3-Hexafluoropropan-2-yl 1-((1,3-dihydroisobenzofuran-5-yl)methyl)-1,8-diazaspiro[4.5]decane-8-carboxylate

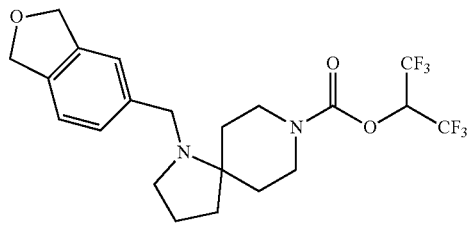 [SMILES: O=C(OC(C(F)(F)F)C(F)(F)F)N1CCC2(CCCN2Cc2ccc3c(c2)COC3)CC1]

Step 1: Synthesis of (4-bromo-1,2-phenylene)dimethanol

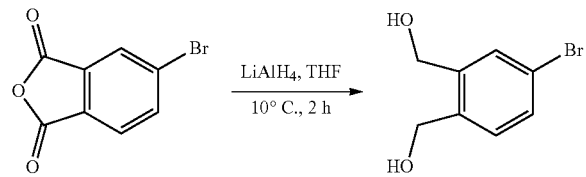

A flask was charged with 5-bromoisobenzofuran-1,3-dione (8.00 g, 35.2 mmol, 1.00 equiv), and THF (100 mL). LAH (2.69 g, 70.9 mmol, 2.00 equiv) was added at 0° C. The resulting solution was stirred for 2 h at 10° C. and quenched with EtOAc (50 mL) and diluted with water (100 mL). The pH value of the solution was adjusted to 3 with 1 M HCl. The resulting solution was extracted with EtOAc (2×100 mL) and the organic layers were combined, dried over anhydrous sodium sulfate, filtered, and concentrated. The residue was chromatographed on a silica gel column with EtOAc/petroleum ether (1/2) to provide 4.00 g (52% yield) of (4-bromo-1,2-phenylene)dimethanol as a white solid. $^1$H NMR (300 MHz, Chloroform-d) δ 7.66-7.70 (m, 1H), 7.43-7.47 (m, 1H), 7.23 (d, J=7.8 Hz, 1H), 4.71 (s, 4H), 2.62 (br, 2H).

Step 2: Synthesis of (5-bromo-2-(chloromethyl)phenyl)methanol

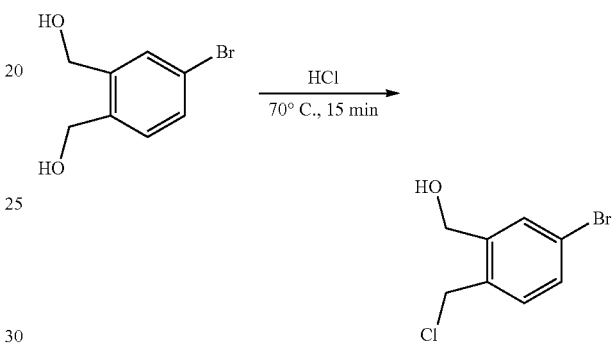

A flask was charged with (4-bromo-1,2-phenylene)dimethanol (4.00 g, 18.4 mmol, 1.00 equiv) and hydrochloric acid (25 mL). The resulting solution was stirred for 15 min at 70° C. and quenched with water (50 mL). The mixture was extracted with EtOAc (2×80 mL) and the organic layers were combined, dried over anhydrous sodium sulfate, filtered, and concentrated. The residue was chromatographed on a silica gel column with EtOAc/petroleum ether (1/8) to provide 2.70 g (62% yield) of (5-bromo-2-(chloromethyl)phenyl)methanol as an off-white solid. $^1$H NMR (300 MHz, DMSO-$d_6$) δ 7.64-7.66 (m, 1H), 7.45-7.49 (m, 1H), 7.36 (d, J=8.1 Hz, 1H), 5.40-5.45 (m, 1H), 4.78 (s, 2H), 4.66 (d, J=4.5 Hz, 2H).

Step 3: Synthesis 5-bromo-1,3-dihydroisobenzofuran

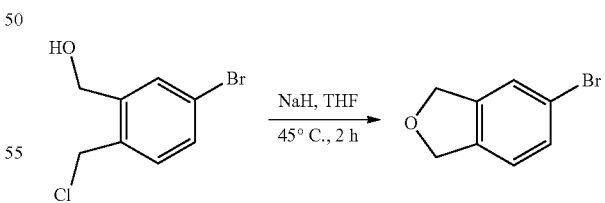

A flask was charged with (5-bromo-2-(chloromethyl)phenyl)methanol (2.50 g, 10.7 mmol, 1.00 equiv), and THF (40 mL). Sodium hydride (60% in mineral oil, 856 mg, 21.4 mmol, 2.00 equiv) was added at 0° C. The reaction mixture was stirred for 2 h at 45° C. and quenched with water (80 mL). The resulting solution was extracted with EtOAc (2×100 mL) and the organic layers were combined, dried over anhydrous sodium sulfate, filtered, and concentrated. The residue was chromatographed on a silica gel column with EtOAc/petroleum ether (7/93) to provide 1.90 g (90% yield) of 5-bromo-1,3-dihydroisobenzofuran as an off-white solid. $^1$H NMR (300 MHz, DMSO-$d_6$) δ 7.54 (s, 1H), 7.45 (d, J=8.1 Hz, 1H), 7.28 (d, J=8.1 Hz, 1H), 4.95-4.98 (m, 1H).

Step 4: Synthesis of 1,3-dihydroisobenzofuran-5-carbaldehyde

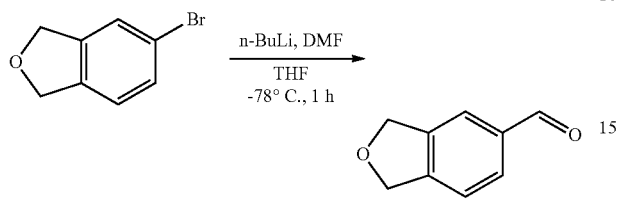

A flask was charged with 5-bromo-1,3-dihydroisobenzofuran (1.60 g, 8.08 mmol, 1.00 equiv), and THF (25 mL) under nitrogen. n-Butyllithium (2.5 M in hexane, 3.90 mL, 9.70 mmol, 1.20 equiv) was added dropwise at −78° C. The mixture was stirred at −78° C. for 1 h and DMF (1.77 g, 24.2 mmol, 3.00 equiv) was added. The resulting solution was stirred for 1 h at −78° C. and quenched with saturated NH$_4$Cl solution (50 mL). The resulting solution was extracted with EtOAc (2×80 mL) and the organic layers were combined, dried over anhydrous sodium sulfate, filtered and concentrated. The residue was chromatographed on a silica gel column with EtOAc/petroleum ether (1/9) to provide 900 mg (76% yield) of 1,3-dihydroisobenzofuran-5-carbaldehyde as a white solid. $^1$H NMR (300 MHz, Chloroform-d) δ 10.0 (s, 1H), 7.77-7.82 (m, 2H), 7.40 (d, J=7.5 Hz, 1H), 5.16 (s, 4H).

Step 5: Synthesis of 1,1,1,3,3,3-hexafluoropropan-2-yl 1-((1,3-dihydroisobenzofuran-5-yl)methyl)-1,8-diazaspiro[4.5]decane-8-carboxylate

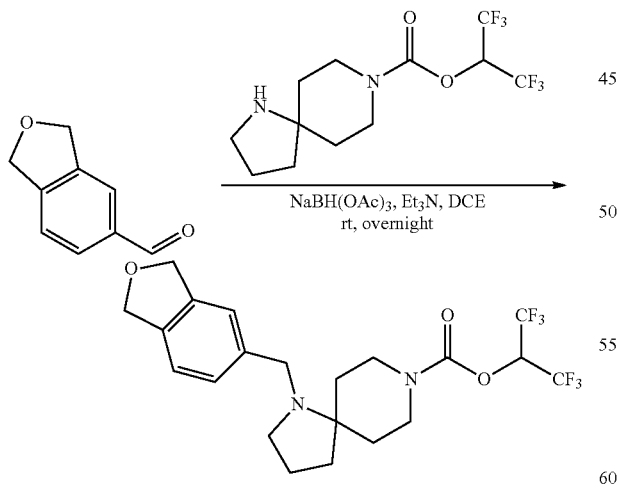

A flask was charged with 1,3-dihydroisobenzofuran-5-carbaldehyde (66.0 mg, 0.450 mmol, 1.00 equiv), DCE (10 mL), 1,1,1,3,3,3-hexafluoropropan-2-yl 1,8-diazaspiro[4.5]decane-8-carboxylate (150 mg, 0.450 mmol, 1.00 equiv), and TEA (136 mg, 1.34 mmol, 3.00 equiv). The mixture was stirred for 1 h at rt. Sodium triacetoxyborohydride (286 mg, 1.35 mmol, 3.00 equiv) was added, and the reaction was stirred overnight at rt before quenching with water (30 mL). The resulting solution was extracted with DCM (2×50 mL) and the organic layers were combined, dried over anhydrous sodium sulfate, filtered, and concentrated. The crude product was purified by preparative HPLC to give 127.1 mg (61% yield) of 1,1,1,3,3,3-hexafluoropropan-2-yl 1-((1,3-dihydroisobenzofuran-5-yl)methyl)-1,8-diazaspiro[4.5]decane-8-carboxylate as a light yellow oil. $^1$H NMR (400 MHz, DMSO-$d_6$) δ 7.16-7.22 (m, 3H), 6.53-6.60 (m, 1H), 4.97 (s, 4H), 3.97-4.06 (m, 2H), 3.55 (s, 2H), 2.98-3.33 (m, 2H), 2.57 (t, J=6.8 Hz, 2H), 1.77-1.81 (m, 2H), 1.58-1.71 (m, 4H), 1.41-1.42 (m, 2H). LCMS (ESI, m/z): 467 [M+H]$^+$.

Example 152: 1,1,1,3,3,3-Hexafluoropropan-2-yl 2-(3-ethyl-4-fluorobenzyl)-2,8-diazaspiro[4.5]decane-8-carboxylate

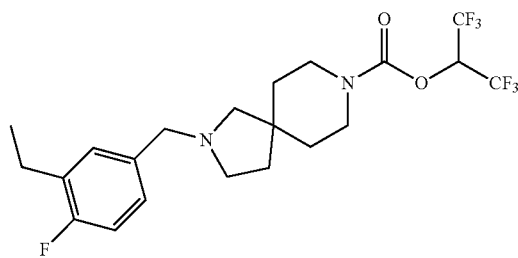 [SMILES: CCc1cc(CN2CCC3(CCN(C(=O)OC(C(F)(F)F)C(F)(F)F)CC3)C2)ccc1F]

The title compound was synthesized according to the representative procedure of Example 150 using 3-ethyl-4-fluorobenzaldehyde and tert-butyl 2,8-diazaspiro[4.5]decane-2-carboxylate. Purification resulted in 85.9 mg of 1,1,1,3,3,3-hexafluoropropan-2-yl 2-(3-ethyl-4-fluorobenzyl)-2,8-diazaspiro[4.5]decane-8-carboxylate as a light yellow oil. $^1$H NMR (400 MHz, DMSO-$d_6$) δ 7.19-7.22 (m, 1H), 7.12-7.16 (m, 1H), 7.03-7.08 (m, 1H), 6.52-6.58 (m, 1H), 3.41-3.50 (m, 4H), 3.33-3.39 (m, 2H), 2.58-2.64 (m, 2H), 2.52-2.53 (m, 2H), 3.34 (s, 2H), 1.60 (t, J=7.0 Hz, 2H), 1.46-1.52 (m, 4H), 1.16 (t, J=7.6 Hz, 3H). LCMS (ESI, m/z): 471 [M+H]$^+$.

Example 153: 1,1,1,3,3,3-Hexafluoropropan-2-yl 2-((1,3-dihydroisobenzofuran-5-yl)methyl)-2,8-diazaspiro[4.5]decane-8-carboxylate

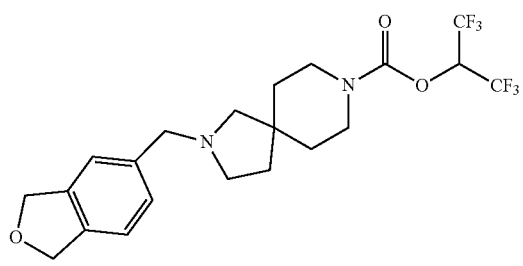 [SMILES: O=C(OC(C(F)(F)F)C(F)(F)F)N1CCC2(CCN(Cc3ccc4c(c3)COC4)C2)CC1]

The title compound was synthesized according to the representative procedure of Example 151 using 1,3-dihydroisobenzofuran-5-carbaldehyde and tert-butyl 2,8-diazaspiro[4.5]decane-2-carboxylate. Purification resulted in 160.3 mg of 1,1,1,3,3,3-hexafluoropropan-2-yl 2-((1,3-dihydroisobenzofuran-5-yl)methyl)-2,8-diazaspiro[4.5]decane- 8-carboxylate as a light yellow oil. ¹H NMR (300 MHz, Chloroform-d) δ 7.16-7.22 (m, 3H), 5.70-5.79 (m, 1H), 5.10 (s, 4H), 3.58-3.60 (m, 2H), 3.39-3.54 (m, 4H), 2.59-2.64 (m, 2H), 2.36-2.43 (m, 2H), 1.68 (t, J=6.9 Hz, 2H), 1.56-1.63 (m, 4H). LCMS (ESI, m/z): 467 [M+H]⁺.

Example 154: 1,1,1,3,3,3-Hexafluoropropan-2-yl 2-(4-chloro-3-morpholinobenzyl)-2,8-diazaspiro[4.5]decane-8-carboxylate

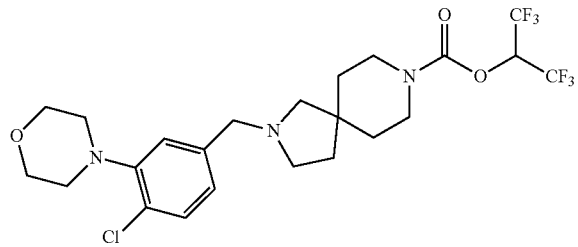 [SMILES: O=C(OC(C(F)(F)F)C(F)(F)F)N1CCC2(CCN(Cc3ccc(Cl)c(N4CCOCC4)c3)C2)CC1]

Step 1: Synthesis of 4-chloro-3-morpholinobenzaldehyde

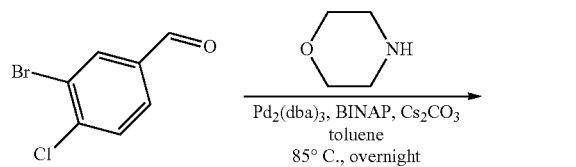

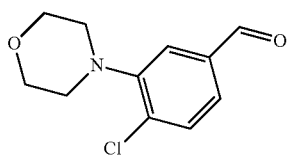

A flask was charged with 3-bromo-4-chlorobenzaldehyde (2.00 g, 9.11 mmol, 1.00 equiv), tris(dibenzylideneacetone)dipalladium (0.420 g, 0.460 mmol, 0.05 equiv), cesium carbonate (8.97 g, 27.5 mmol, 3.00 equiv), 2,2'-bis(diphenylphosphino)-1,1'-binaphthyl (0.856 g, 1.37 mmol, 0.15 equiv), morpholine (1.20 g, 13.8 mmol, 1.50 equiv), and toluene (40 mL) under nitrogen. The reaction mixture was stirred overnight at 85° C. and quenched with water (100 mL). The resulting solution was extracted with EtOAc (2×150 mL) and the organic layers were combined, dried over anhydrous sodium sulfate, filtered, and concentrated. The residue was chromatographed on a silica gel column with EtOAc/petroleum ether (1/8) to provide 1.60 g (78% yield) of 4-chloro-3-morpholinobenzaldehyde as a yellow oil. LCMS (ESI, m/z): 226 [M+H]⁺.

Step 2: Synthesis of 1,1,1,3,3,3-hexafluoropropan-2-yl 2-(4-chloro-3-morpholinobenzyl)-2,8-diazaspiro[4.5]decane-8-carboxylate

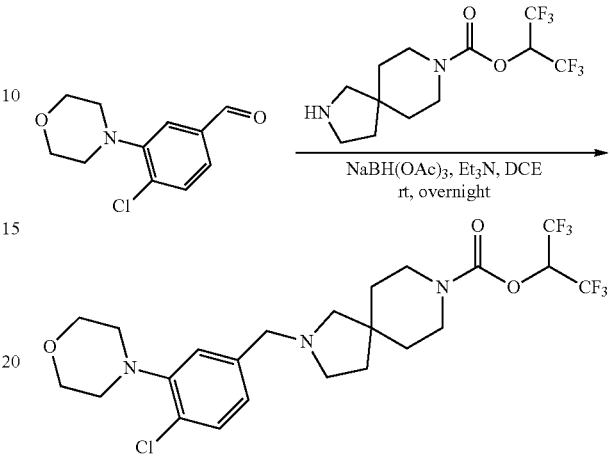

A flask was charged with 4-chloro-3-morpholinobenzaldehyde (101 mg, 0.450 mmol, 1.00 equiv), DCE (10 mL), TEA (136 mg, 1.34 mmol, 3.00 equiv), and 1,1,1,3,3,3-hexafluoropropan-2-yl 2,8-diazaspiro[4.5]decane-8-carboxylate (150 mg, 0.450 mmol, 1.00 equiv). The mixture was stirred for 1 h at rt. Sodium triacetoxyborohydride (286 mg, 1.35 mmol, 3.00 equiv) was added, and the reaction was stirred overnight at rt before quenching with water (30 mL). The resulting solution was extracted with DCM (2×50 mL) and the organic layers were combined, dried over anhydrous sodium sulfate, filtered, and concentrated. The crude product was purified by preparative HPLC to give 199.1 mg (82% yield) of 1,1,1,3,3,3-hexafluoropropan-2-yl 2-(4-chloro-3-morpholinobenzyl)-2,8-diazaspiro[4.5]decane-8-carboxylate as a yellow oil. ¹H NMR (300 MHz, Chloroform-d) δ 7.29 (d, J=7.8 Hz, 1H), 7.01 (br, 1H), 6.94 (d, J=7.8 Hz, 1H), 5.68-5.81 (m, 1H), 3.88 (t, J=4.5 Hz, 4H), 3.39-3.62 (m, 6H), 3.08 (t, J=4.6 Hz, 4H), 2.62 (br, 2H), 2.37 (br, 2H), 1.59-1.70 (m, 6H). LCMS (ESI, m/z): 544 [M+H]⁺.

Example 155: 1,1,1,3,3,3-Hexafluoropropan-2-yl 2-(4-chloro-3-(pyrrolidin-1-yl)benzyl)-2,8-diazaspiro[4.5]decane-8-carboxylate

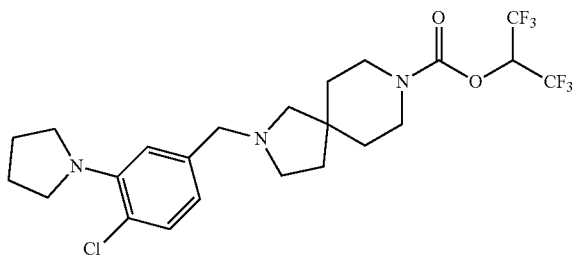 [SMILES: O=C(OC(C(F)(F)F)C(F)(F)F)N1CCC2(CCN(Cc3ccc(Cl)c(N4CCCC4)c3)C2)CC1]

The title compound was synthesized according to the representative procedure of Example 154 using pyrrolidine in Step 1. Purification resulted in 179.5 mg of 1,1,1,3,3,3-hexafluoropropan-2-yl 2-(4-chloro-3-(pyrrolidin-1-yl)benzyl)-2,8-diazaspiro[4.5]decane-8-carboxylate as a yellow oil. ¹H NMR (300 MHz, Chloroform-d) δ 7.21 (d, J=8.1 Hz, 1H), 6.86 (br, 1H), 6.70-6.73 (m, 1H), 5.68-5.81 (m, 1H), 3.44-3.55 (m, 6H), 3.36-3.40 (m, 4H), 2.62 (br, 2H), 2.38 (br, 2H), 1.89-2.00 (m, 4H), 1.61-1.68 (m, 6H). LCMS (ESI, m/z): 528 [M+H]⁺.

Example 156: 1,1,1,3,3,3-Hexafluoropropan-2-yl 2-(3-morpholino-4-(trifluoromethyl)benzyl)-2,8-diazaspiro[4.5]decane-8-carboxylate

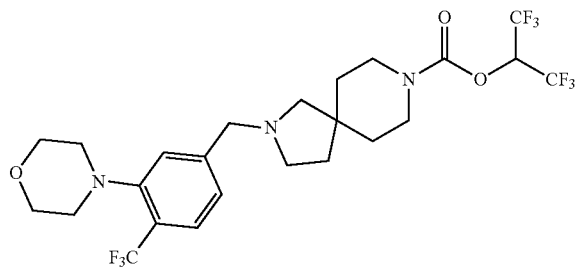 [SMILES: O=C(OC(C(F)(F)F)C(F)(F)F)N1CCC2(CCN(Cc3ccc(C(F)(F)F)c(N4CCOCC4)c3)C2)CC1]

The title compound was synthesized according to the representative procedure of Example 154 using 3-bromo-4-(trifluoromethyl)benzaldehyde and morpholine in Step 1. Purification resulted in 174.5 mg of 1,1,1,3,3,3-hexafluoropropan-2-yl 2-(3-morpholino-4-(trifluoromethyl)benzyl)-2,8-diazaspiro[4.5]decane-8-carboxylate as a yellow solid. ¹H NMR (300 MHz, Chloroform-d) δ 7.55-7.58 (m, 1H), 7.33 (s, 1H), 7.16-7.18 (m, 1H), 5.70-5.78 (m, 1H), 3.84 (t, J=4.4 Hz, 4H), 3.42-3.70 (m, 6H), 2.93 (br, 4H), 2.61-2.66 (m, 2H), 2.38 (br, 2H), 1.49-1.72 (m, 6H). LCMS (ESI, m/z): 578 [M+H]⁺.

Example 157: 1,1,1,3,3,3-Hexafluoropropan-2-yl 2-(3-(pyrrolidin-1-yl)-4-(trifluoromethyl)benzyl)-2,8-diazaspiro[4.5]decane-8-carboxylate

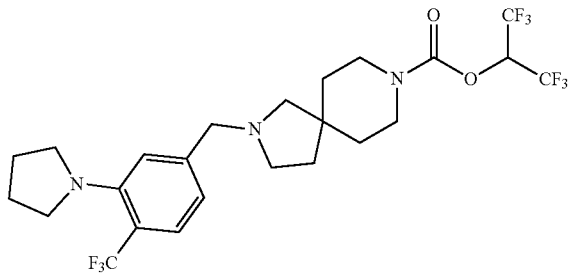 [SMILES: O=C(OC(C(F)(F)F)C(F)(F)F)N1CCC2(CCN(Cc3ccc(C(F)(F)F)c(N4CCCC4)c3)C2)CC1]

The title compound was synthesized according to the representative procedure of Example 154 using 3-bromo-4-(trifluoromethyl)benzaldehyde and pyrrolidine in Step 1. Purification resulted in 91.5 mg of 1,1,1,3,3,3-hexafluoropropan-2-yl 2-(3-(pyrrolidin-1-yl)-4-(trifluoromethyl)benzyl)-2,8-diazaspiro[4.5]decane-8-carboxylate as a yellow oil. ¹H NMR (400 MHz, Chloroform-d) δ 7.52 (d, J=8.4 Hz, 1H), 6.97 (br, 1H), 6.81 (d, J=8.0 Hz, 1H), 5.72-5.80 (m, 1H), 3.45-3.70 (m, 6H), 3.36 (br, 4H), 2.66 (br, 2H), 2.42 (br, 2H), 1.97 (br, 4H), 1.62-1.71 (m, 6H). LCMS (ESI, m/z): 562 [M+H]⁺.

Example 158: 1,1,1,3,3,3-Hexafluoropropan-2-yl 1-((1-ethyl-1,2,3,4-tetrahydroquinolin-8-yl)methyl)-1,8-diazaspiro[4.5]decane-8-carboxylate

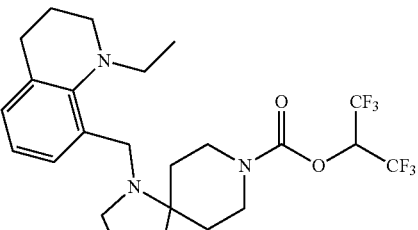

Step 1: Synthesis of 1,1,1,3,3,3-hexafluoropropan-2-yl 1-((1,2,3,4-tetrahydroquinolin-8-yl)methyl)-1,8-diazaspiro[4.5]decane-8-carboxylate

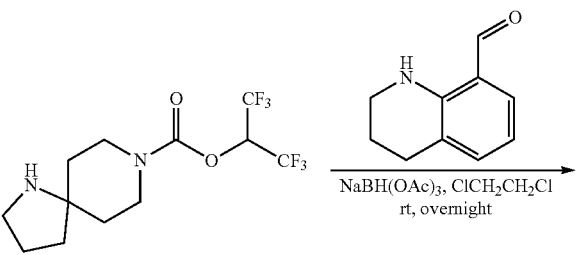

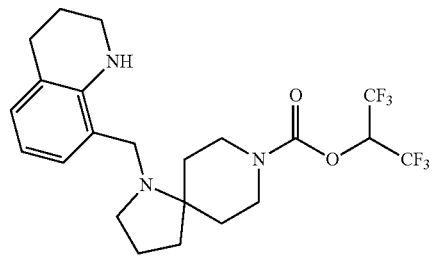

A flask was charged with 1,2,3,4-tetrahydroquinoline-8-carbaldehyde (161 mg, 1.01 mmol, 1.00 equiv), 1,1,1,3,3,3-hexafluoropropan-2-yl 1,8-diazaspiro[4.5]decane-8-carboxylate (400 mg, 1.20 mmol, 1.20 equiv), DCE (10 mL) and sodium triacetoxyborohydride (424 mg, 2.02 mmol, 2.00 equiv). The resulting solution was stirred overnight at rt and quenched with water (20 mL). The mixture was extracted with DCM (3×20 mL) and the organic layers were combined, washed with water (3×100 mL), dried over anhydrous sodium sulfate, filtered, and concentrated. The residue was chromatographed on a silica gel column with EtOAc/petroleum ether (1/2) to provide 240 mg (50% yield) of 1,1,1,3,3,3-hexafluoropropan-2-yl 1-((1,2,3,4-tetrahydroquinolin-8-yl)methyl)-1,8-diazaspiro[4.5]decane-8-carboxylate as a yellow oil. LCMS (ESI, m/z): 480 [M+H]⁺.

Step 2: Synthesis of 1,1,1,3,3,3-hexafluoropropan-2-yl 1-((1-ethyl-1,2,3,4-tetrahydroquinolin-8-yl)methyl)-1,8-diazaspiro[4.5]decane-8-carboxylate

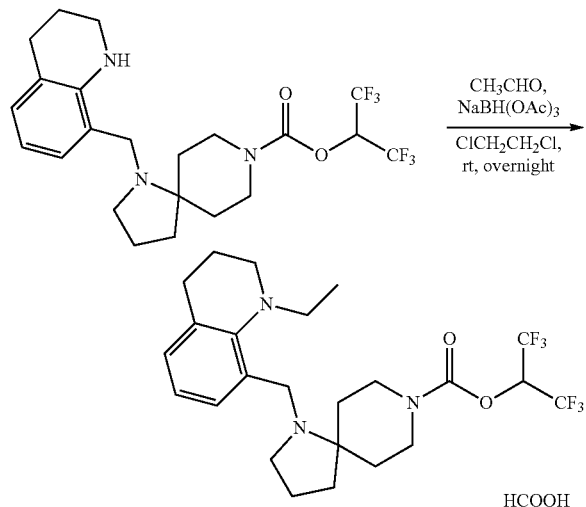

A flask was charged with 1,1,1,3,3,3-hexafluoropropan-2-yl 1-((1,2,3,4-tetrahydroquinolin-8-yl)methyl)-1,8-diazaspiro[4.5]decane-8-carboxylate (240 mg, 0.50 mmol, 1.00 equiv), acetaldehyde (110 mg, 5.00 equiv), DCE (10 mL) and sodium triacetoxyborohydride (318 mg, 1.50 mmol, 3.00 equiv). The resulting solution was stirred overnight at rt and quenched with water (20 mL). The mixture was extracted with DCM (3×20 mL) and the organic layers were combined, washed with water (3×100 mL), dried over anhydrous sodium sulfate, filtered, and concentrated. The residue was purified by preparative HPLC to give 75.7 mg (27% yield) of 1,1,1,3,3,3-hexafluoropropan-2-yl 1-((1-ethyl-1,2,3,4-tetrahydroquinolin-8-yl)methyl)-1,8-diazaspiro[4.5]decane-8-carboxylate formic acid salt as a yellow solid. $^1$H NMR (400 MHz, Chloroform-d) δ 11.11 (s, 1H), 8.42 (s, 1H), 7.53 (d, J=6.8 Hz, 1H), 6.95-7.03 (m, 2H), 5.71-5.77 (m, 1H), 4.16-4.27 (m, 2H), 4.06 (s, 2H), 3.22 (s, 2H), 2.95-3.22 (m, 4H), 2.75-2.81 (m, 4H), 2.12 (d, J=6.8 Hz, 2H), 1.91-2.09 (m, 4H), 1.74-1.90 (m, 4H), 1.22 (t, J=6.8 Hz, 3H). LCMS (ESI, m/z): 508 [M+H−HCOOH]$^+$.

Example 159: 1,1,1,3,3,3-Hexafluoropropan-2-yl 2-((2-ethyl-1,2,3,4-tetrahydroisoquinolin-8-yl)methyl)-2,8-diazaspiro[4.5]decane-8-carboxylate

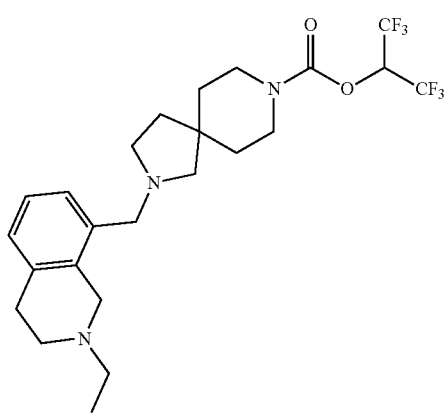 [SMILES: CCN1CCc2cccc(CN3CCC4(CCN(C(=O)OC(C(F)(F)F)C(F)(F)F)CC4)C3)c2C1]

Step 1: Synthesis of tert-butyl 8-formyl-3,4-dihydroisoquinoline-2(1H)-carboxylate

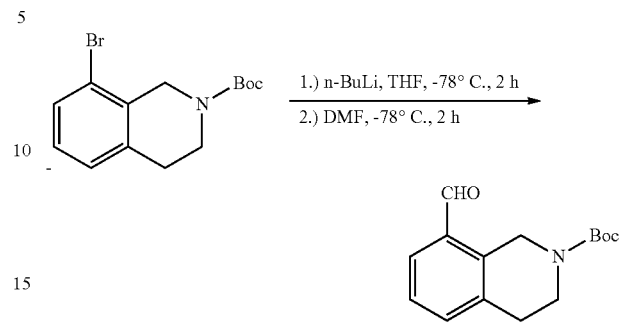

A 3-necked flask was charged with tert-butyl 8-bromo-3,4-dihydroisoquinoline-2(1H)-carboxylate (3.11 g, 9.93 mmol, 1.00 equiv) and THF (50 mL) under nitrogen. The reaction mixture was cooled to −78° C. and n-butyllithium (2.5 M in hexane, 6 mL, 15.1 mmol, 1.50 equiv) was added dropwise. The reaction mixture was stirred at −78° C. for 2 h, and DMF (1.46 g, 19.9 mmol, 2.00 equiv) was added dropwise. The resulting solution was stirred for 2 h at −78° C., quenched with aqueous ammonium chloride (10 mL) and diluted with EtOAc (100 mL). The resulting mixture was washed with water (3×100 mL), dried over anhydrous sodium sulfate, filtered, and concentrated. The residue was chromatographed on a silica gel column with EtOAc/petroleum ether (1/5) to provide 1.81 g (69% yield) of tert-butyl 8-formyl-3,4-dihydroisoquinoline-2(1H)-carboxylate as a yellow solid. LCMS (ESI, m/z): 262 [M+H]$^+$.

Step 2: Synthesis of 1,1,1,3,3,3-hexafluoropropan-2-yl 2-((2-(tert-butoxycarbonyl)-1,2,3,4-tetrahydroisoquinolin-8-yl)methyl)-2,8-diazaspiro[4.5]decane-8-carboxylate

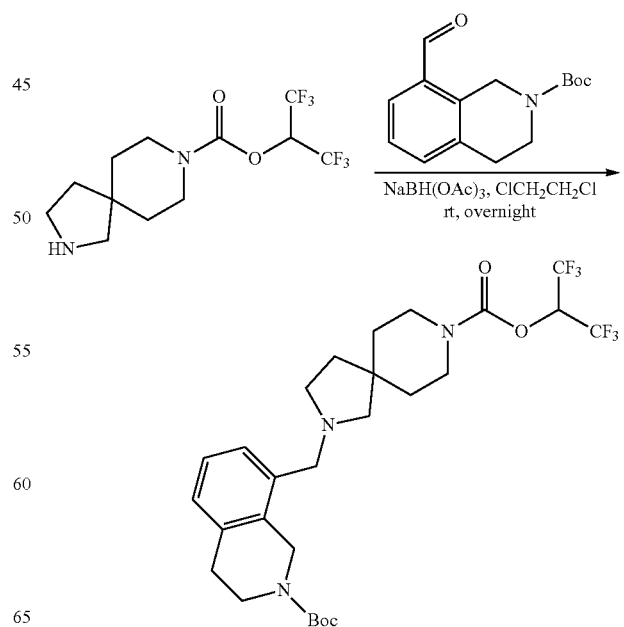

A flask was charged with tert-butyl 8-formyl-3,4-dihydroisoquinoline-2(1H)-carboxylate (1.38 g, 5.28 mmol, 1.00 equiv), DCE (20 mL), 1,1,1,3,3,3-hexafluoropropan-2-yl 2,8-diazaspiro[4.5]decane-8-carboxylate (1.77 g, 5.30 mmol, 1.00 equiv) and sodium triacetoxyborohydride (2.25 g, 10.6 mmol, 2.00 equiv). The resulting solution was stirred overnight at rt and diluted with DCM (100 mL). The mixture was washed with water (3×100 mL), dried over anhydrous sodium sulfate, filtered and concentrated. The residue was chromatographed on a silica gel column with EtOAc/petroleum ether (1/2) to provide 2.20 g (65% yield) of tert-butyl 8-((8-(((1,1,1,3,3,3-hexafluoropropan-2-yloxy)carbonyl)-2,8-diazaspiro[4.5]decan-2-yl)methyl)-3,4-dihydroisoquinoline-2(1H)-carboxylate as a yellow oil. LCMS (ESI, m/z): 580 [M+H]⁺.

Step 3: Synthesis of 1,1,1,3,3,3-hexafluoropropan-2-yl 2-((1,2,3,4-tetrahydroisoquinolin-8-yl)methyl)-2,8-diazaspiro[4.5]decane-8-carboxylate Step 4: Synthesis of 1,1,1,3,3,3-hexafluoropropan-2-yl 2-((2-ethyl-1,2,3,4-tetrahydroisoquinolin-8-yl)methyl)-2,8-diazaspiro[4.5]decane-8-carboxylate

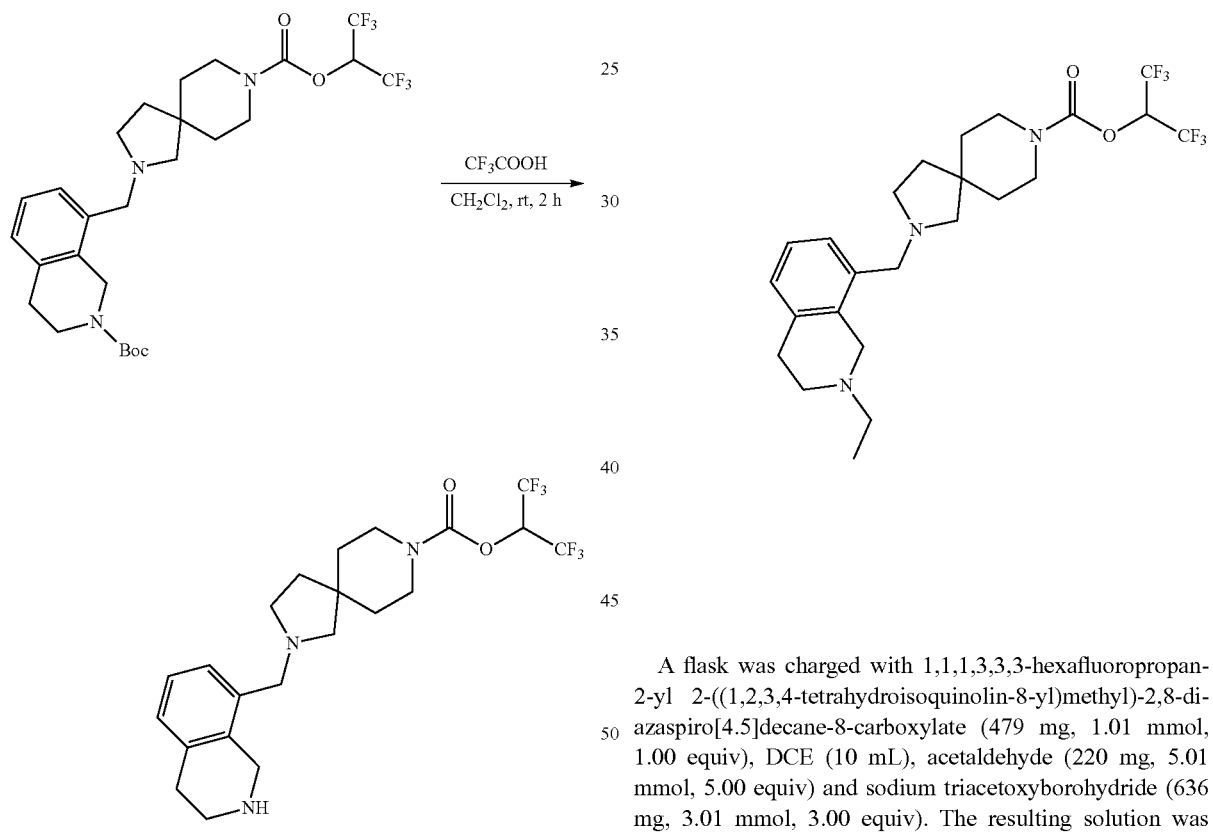

A flask was charged with tert-butyl 8-((8-(((1,1,1,3,3,3-hexafluoropropan-2-yloxy)carbonyl)-2,8-diazaspiro[4.5]decan-2-yl)methyl)-3,4-dihydroisoquinoline-2(1H)-carboxylate (2.20 g, 3.80 mmol, 1.00 equiv), DCM (20 mL), and TFA (10 mL). The resulting solution was stirred for 2 h at rt and concentrated to provide 3.00 g (crude) of 1,1,1,3,3,3-hexafluoropropan-2-yl 2-((1,2,3,4-tetrahydroisoquinolin-8-yl)methyl)-2,8-diazaspiro[4.5]decane-8-carboxylate as a yellow oil. LCMS (ESI, m/z): 480 [M+H]⁺.

A flask was charged with 1,1,1,3,3,3-hexafluoropropan-2-yl 2-((1,2,3,4-tetrahydroisoquinolin-8-yl)methyl)-2,8-diazaspiro[4.5]decane-8-carboxylate (479 mg, 1.01 mmol, 1.00 equiv), DCE (10 mL), acetaldehyde (220 mg, 5.01 mmol, 5.00 equiv) and sodium triacetoxyborohydride (636 mg, 3.01 mmol, 3.00 equiv). The resulting solution was stirred overnight at rt and diluted with DCM (50 mL). The resulting solution was washed with water (3×50 mL), dried over anhydrous sodium sulfate, filtered, and concentrated. The residue was purified by preparative HPLC to give 123 mg (24% yield) of 1,1,1,3,3,3-hexafluoropropan-2-yl 2-((2-ethyl-1,2,3,4-tetrahydroisoquinolin-8-yl)methyl)-2,8-diazaspiro[4.5]decane-8-carboxylate as a yellow oil. ¹H NMR (400 MHz, Chloroform-d) δ 7.00-7.12 (m, 3H), 5.71-5.78 (m, 1H), 3.69-3.92 (br, 2H), 3.32-3.59 (m, 6H), 2.97 (s, 2H), 2.60-2.91 (m, 4H), 2.57 (t, J=6.0 Hz, 2H), 2.37 (s, 2H), 1.50-1.69 (m, 6H), 1.25 (s, 3H). LCMS (ESI, m/z): 508 [M+H]⁺.

Example 160: 1,1,1,3,3,3-Hexafluoropropan-2-yl 2-((2-acetyl-1,2,3,4-tetrahydroisoquinolin-8-yl)methyl)-2,8-diazaspiro[4.5]decane-8-carboxylate

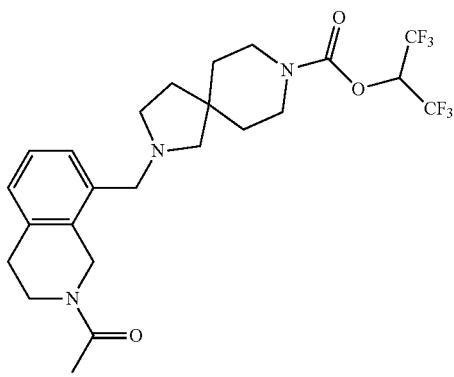 [SMILES: CC(=O)N1CCc2cccc(CN3CCC4(CCN(C(=O)OC(C(F)(F)F)C(F)(F)F)CC4)C3)c2C1]

A flask was charged with 1,1,1,3,3,3-hexafluoropropan-2-yl 2-((1,2,3,4-tetrahydroisoquinolin-8-yl)methyl)-2,8-diazaspiro[4.5]decane-8-carboxylate (240 mg, 0.501 mmol, 1.00 equiv), DCM (10 mL) and TEA (150 mg, 1.48 mmol, 3.00 equiv). Acetic anhydride (102 mg, 1.01 mmol, 2.00 equiv) was added dropwise. The reaction mixture was stirred for 2 h at rt and diluted with DCM (50 mL). The resulting solution was washed with water (3×50 mL), dried over anhydrous sodium sulfate, filtered, and concentrated. The residue was purified by preparative HPLC to give 154.1 mg (59% yield) of 1,1,1,3,3,3-hexafluoropropan-2-yl 2-((2-acetyl-1,2,3,4-tetrahydroisoquinolin-8-yl)methyl)-2,8-diazaspiro[4.5]decane-8-carboxylate as a yellow solid. $^1$H NMR (400 MHz, Chloroform-d) δ 7.02-7.21 (m, 3H), 5.71-5.77 (m, 1H), 4.75-4.87 (m, 2H), 3.64-3.87 (m, 2H), 3.46-3.64 (m, 4H), 3.32-3.48 (m, 2H), 3.81-3.98 (m, 2H), 2.51-2.68 (br, 2H), 2.29-2.47 (m, 2H), 2.18 (s, 3H), 1.52-1.71 (m, 6H). LCMS (ESI, m/z): 522 [M+H]$^+$.

Example 161: 1,1,1,3,3,3-hexafluoropropan-2-yl 2-((2-(methylsulfonyl)-1,2,3,4-tetrahydroisoquinolin-8-yl)methyl)-2,8-diazaspiro[4.5]decane-8-carboxylate

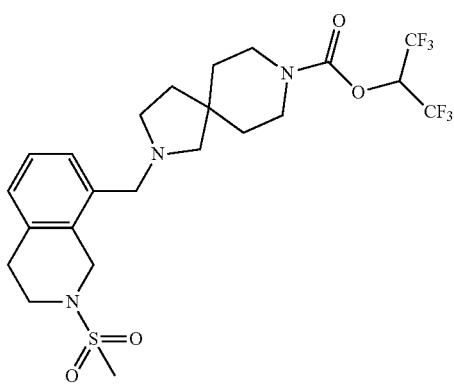 [SMILES: CS(=O)(=O)N1CCc2cccc(CN3CCC4(CCN(C(=O)OC(C(F)(F)F)C(F)(F)F)CC4)C3)c2C1]

A flask was charged with 1,1,1,3,3,3-Hexafluoropropan-2-yl 2-((1,2,3,4-tetrahydroisoquinolin-8-yl)methyl)-2,8-diazaspiro[4.5]decane-8-carboxylate (240 mg, 0.501 mmol, 1.00 equiv), DCM (10 mL), TEA (150 mg, 1.48 mmol, 3.00 equiv) and methanesulfonyl chloride (115 mg, 1.01 mmol, 2.00 equiv). The resulting solution was stirred for 2 h at rt and diluted with DCM (50 mL). The resulting mixture was washed with water (3×50 mL), dried over anhydrous sodium sulfate, filtered, and concentrated. The residue was purified by preparative HPLC to give 171.1 mg (61% yield) of 1,1,1,3,3,3-hexafluoropropan-2-yl 2-((2-(methylsulfonyl)-1,2,3,4-tetrahydroisoquinolin-8-yl)methyl)-2,8-diazaspiro[4.5]decane-8-carboxylate as an off-white solid. $^1$H NMR (400 MHz, Chloroform-d) δ 7.01-7.19 (m, 3H), 5.71-5.77 (m, 1H), 4.62 (s, 2H), 3.50-3.59 (m, 6H), 3.35-3.46 (m, 2H), 2.94-3.06 (m, 2H), 2.82 (s, 3H), 2.46-2.64 (m, 2H), 2.25-2.46 (m, 2H), 1.49-1.71 (m, 6H). LCMS (ESI, m/z): 558 [M+H]$^+$.

Example 162: 1,1,1,3,3,3-Hexafluoropropan-2-yl 2-((2-isopropyl-1,2,3,4-tetrahydroisoquinolin-8-yl)methyl)-2,8-diazaspiro[4.5]decane-8-carboxylate

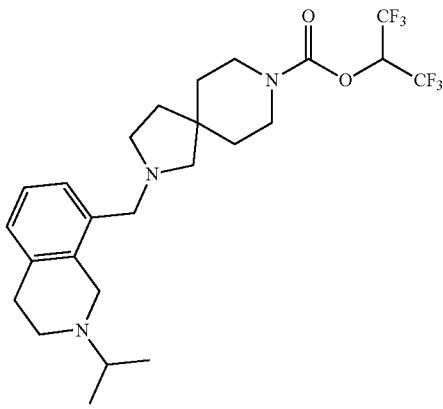 [SMILES: CC(C)N1CCc2cccc(CN3CCC4(CCN(C(=O)OC(C(F)(F)F)C(F)(F)F)CC4)C3)c2C1]

The title compound was synthesized according to the representative procedure of Example 159 using 1,1,1,3,3,3-hexafluoropropan-2-yl 2-((1,2,3,4-tetrahydroisoquinolin-8-yl)methyl)-2,8-diazaspiro[4.5]decane-8-carboxylate and acetone in Step 4. Purification resulted in 88.2 mg of 1,1,1,3,3,3-hexafluoropropan-2-yl 2-((2-isopropyl-1,2,3,4-tetrahydroisoquinolin-8-yl)methyl)-2,8-diazaspiro[4.5]decane-8-carboxylate as a yellow oil. $^1$H NMR (400 MHz, Chloroform-d) δ 6.98-7.12 (m, 3H), 5.73-5.82 (m, 1H), 3.86 (s, 2H), 3.36-3.59 (m, 6H), 2.89-2.97 (m, 3H), 2.78 (t, J=6.0 Hz, 2H), 2.58 (t, J=7.0 Hz, 2H), 2.41 (s, 2H), 1.51-1.71 (m, 6H), 1.28 (d, J=6.0 Hz, 6H). LCMS (ESI, m/z): 522 [M+H]$^+$.

Example 163: 1,1,1,3,3,3-Hexafluoropropan-2-yl 2-((2-cyclopropyl-1,2,3,4-tetrahydroisoquinolin-8-yl)methyl)-2,8-diazaspiro[4.5]decane-8-carboxylate

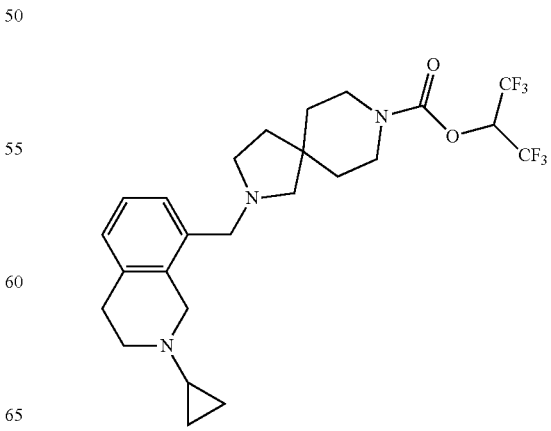

A flask was charged with 1,1,1,3,3,3-hexafluoropropan-2-yl 2-(1,2,3,4-tetrahydroisoquinolin-8-ylmethyl)-2,8-diazaspiro[4.5]decane-8-carboxylate (479 mg, 1.01 mmol, 1.00 equiv), MeOH (20 mL), THF (20 mL), (1-ethoxycyclopropoxy)trimethylsilane (522 mg, 2.99 mmol, 3.00 equiv), acetic acid (240 mg, 4.01 mmol, 4.00 equiv) and sodium cyanoborohydride (190 mg, 3.01 mmol, 3.00 equiv). The resulting solution was stirred overnight at 60° C. and quenched with water (50 mL). The mixture was extracted with DCM (3×50 mL) and the organic layers were combined, washed with water (3×100 mL), dried over anhydrous sodium sulfate, filtered, and concentrated. The residue was purified by preparative HPLC to give 78.8 mg (15% yield) of 1,1,1,3,3,3-hexafluoropropan-2-yl 2-((2-cyclopropyl-1,2,3,4-tetrahydroisoquinolin-8-yl)methyl)-2,8-diazaspiro[4.5]decane-8-carboxylate as a yellow oil. $^1$H NMR (400 MHz, Chloroform-d) δ 6.98-7.12 (m, 3H), 5.73-5.82 (m, 1H), 3.91 (s, 2H), 3.36-3.62 (m, 6H), 2.94 (s, 4H), 2.61 (s, 2H), 2.43 (s, 2H), 1.86 (s, 1H), 1.51-1.75 (m, 6H), 0.58 (s, 4H). LCMS (ESI, m/z): 520 [M+H]$^+$.

Example 164: 1,1,1,3,3,3-Hexafluoropropan-2-yl 2-((2-isobutyl-1,2,3,4-tetrahydroisoquinolin-8-yl)methyl)-2,8-diazaspiro[4.5]decane-8-carboxylate

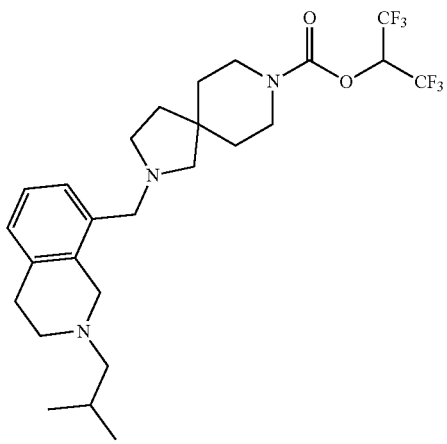 [SMILES: CC(C)CN1CCc2cccc(CN3CCC4(CCN(C(=O)OC(C(F)(F)F)C(F)(F)F)CC4)C3)c2C1]

The title compound was synthesized according to the representative procedure of Example 159 using 1,1,1,3,3,3-hexafluoropropan-2-yl 2-((1,2,3,4-tetrahydroisoquinolin-8-yl)methyl)-2,8-diazaspiro[4.5]decane-8-carboxylate and 2-methylpropanal in Step 4. Purification resulted in 345.8 mg of 1,1,1,3,3,3-hexafluoropropan-2-yl 2-((2-isobutyl-1,2,3,4-tetrahydroisoquinolin-8-yl)methyl)-2,8-diazaspiro[4.5]decane-8-carboxylate as a white solid. $^1$H NMR (400 MHz, Chloroform-d) δ 6.98-7.15 (m, 3H), 5.71-5.82 (m, 1H), 3.70 (s, 2H), 3.36-3.59 (m, 6H), 2.95 (s, 2H), 2.71 (s, 2H), 2.60 (t, J=7.0 Hz, 2H), 2.21-2.48 (m, 4H), 1.95 (s, 1H), 1.51-1.72 (m, 6H), 0.78-1.15 (m, 6H). LCMS (ESI, m/z): 536 [M+H]$^+$.

Example 165: 1,1,1,3,3,3-Hexafluoropropan-2-yl 1-(2-(1-methylpiperidin-4-yloxy)-4-(trifluoromethyl)benzyl)-1,8-diazaspiro[4.5]decane-8-carboxylate

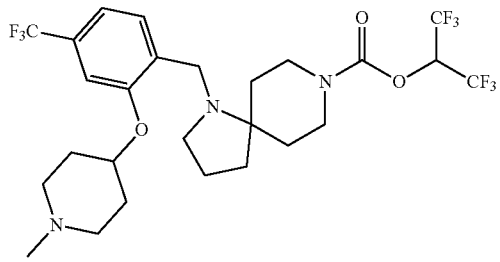 [SMILES: CN1CCC(Oc2cc(C(F)(F)F)ccc2CN2CCCC23CCN(C(=O)OC(C(F)(F)F)C(F)(F)F)CC3)CC1]

Step 1: Synthesis of 1-methylpiperidin-4-yl methanesulfonate

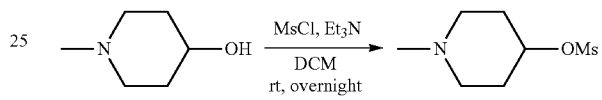

A flask was charged with 1-methylpiperidin-4-ol (2.00 g, 17.4 mmol, 1.00 equiv), TEA (5.27 g, 52.1 mmol, 3.00 equiv), and DCM (30 mL). Methanesulfonyl chloride (2.97 g, 26.1 mmol, 1.50 equiv) was added at 0° C. The resulting solution was stirred overnight at rt and quenched with H$_2$O (50 mL). The mixture was extracted with DCM (3×70 mL) and the organic layers were combined, washed with brine (100 mL), dried over anhydrous sodium sulfate, filtered, and concentrated to provide 2.60 g (77% yield) of 1-methylpiperidin-4-yl methanesulfonate as a light yellow oil. LCMS (ESI, m/z): 194 [M+H]$^+$.

Step 2: Synthesis of 2-hydroxy-4-(trifluoromethyl)benzaldehyde

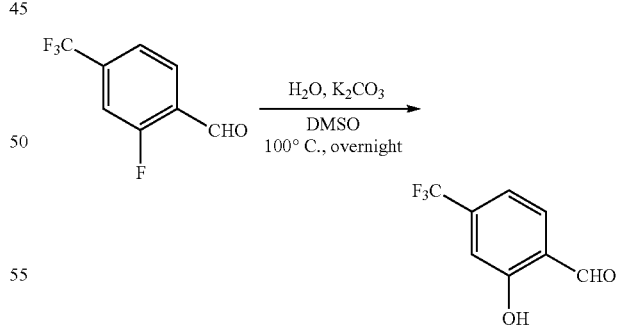

A flask was charged with 2-fluoro-4-(trifluoromethyl)benzaldehyde (5.00 g, 26.0 mmol, 1.00 equiv), water (5 mL), potassium carbonate (10.8 g, 78.1 mmol, 3.00 equiv), and DMSO (50 mL) under nitrogen. The resulting solution was stirred overnight at 100° C. and quenched with H$_2$O (70 mL). The mixture was extracted with DCM (3×100 mL) and the organic layers were combined, washed with brine (200 mL), dried over anhydrous sodium sulfate, filtered, and concentrated. The residue was chromatographed on a silica gel column with EtOAc/petroleum ether (6/94) to provide 3.07 g (62% yield) of 2-hydroxy-4-(trifluoromethyl)benzaldehyde as a yellow oil.

Step 3: Synthesis of tert-butyl 1-(2-hydroxy-4-(trifluoromethyl)benzyl)-1,8-diazaspiro[4.5]decane-8-carboxylate

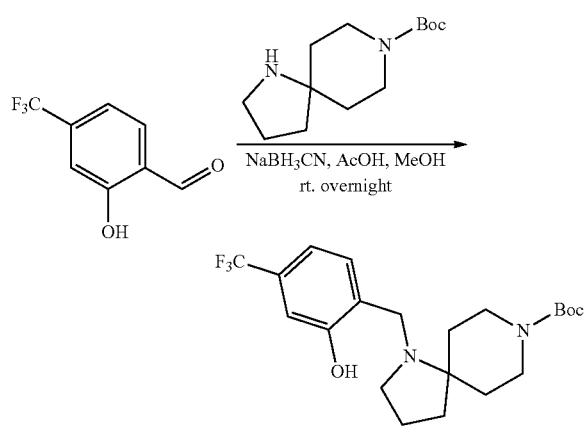

A flask was charged with 2-hydroxy-4-(trifluoromethyl)benzaldehyde (1.00 g, 5.26 mmol, 1.00 equiv), tert-butyl 1,8-diazaspiro[4.5]decane-8-carboxylate (1.89 g, 7.86 mmol, 1.50 equiv), acetic acid (0.948 g, 15.8 mmol, 3.00 equiv), and MeOH (30 mL). The mixture was stirred for 1 h at rt. Sodium cyanoborohydride (0.995 g, 15.8 mmol, 3.00 equiv) was added, and the reaction was stirred overnight at rt before quenching with H₂O (50 mL). The mixture was extracted with DCM (3×70 mL) and the organic layers were combined, washed with brine (100 mL), dried over anhydrous sodium sulfate, filtered, and concentrated. The residue was chromatographed on a silica gel column with EtOAc/petroleum ether (14/86) to provide 1.60 g (73% yield) of tert-butyl 1-(2-hydroxy-4-(trifluoromethyl)benzyl)-1,8-diazaspiro[4.5]decane-8-carboxylate as a yellow solid. LCMS (ESI, m/z): 415 [M+H]⁺.

Step 4: Synthesis of tert-butyl 1-(2-(1-methylpiperidin-4-yloxy)-4-(trifluoromethyl)benzyl)-1,8-diazaspiro[4.5]decane-8-carboxylate

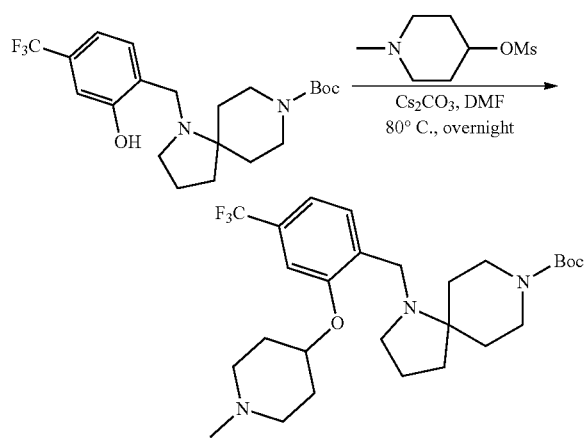

A flask was charged with tert-butyl 1-(2-hydroxy-4-(trifluoromethyl)benzyl)-1,8-diazaspiro[4.5]decane-8-carboxylate (200 mg, 0.483 mmol, 1.00 equiv), 1-methylpiperidin-4-yl methanesulfonate (280 mg, 1.45 mmol, 3.00 equiv), cesium carbonate (630 mg, 1.93 mmol, 4.00 equiv), and DMF (10 mL). The resulting solution was stirred overnight at 80° C. and quenched with H₂O (20 mL). The mixture was extracted with DCM (3×50 mL) and the organic layers were combined, washed with brine (100 mL), dried over anhydrous sodium sulfate, filtered, and concentrated. The residue was chromatographed on a silica gel column with MeOH/DCM (7/93) to provide 220 mg (89% yield) of tert-butyl 1-(2-(1-methylpiperidin-4-yloxy)-4-(trifluoromethyl)benzyl)-1,8-diazaspiro[4.5]decane-8-carboxylate as a light yellow oil. LCMS (ESI, m/z): 512 [M+H]⁺.

Step 5: Synthesis of 1-(2-(1-methylpiperidin-4-yloxy)-4-(trifluoromethyl)benzyl)-1,8-diazaspiro[4.5]decane

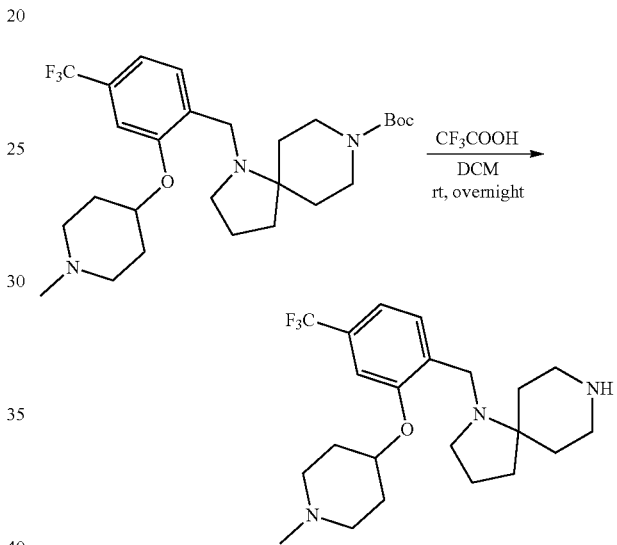

A flask was charged with tert-butyl 1-(2-(1-methylpiperidin-4-yloxy)-4-(trifluoromethyl)benzyl)-1,8-diazaspiro[4.5]decane-8-carboxylate (220 mg, 0.430 mmol, 1.00 equiv), DCM (5 mL), and TFA (1 mL). The resulting solution was stirred overnight at rt and concentrated to provide 300 mg (crude) of 1-(2-(1-methylpiperidin-4-yloxy)-4-(trifluoromethyl)benzyl)-1,8-diazaspiro[4.5]decane as a light yellow solid. LCMS (ESI, m/z): 412 [M+H]⁺.

Step 6: Synthesis of 1,1,1,3,3,3-hexafluoropropan-2-yl 1-(2-(1-methylpiperidin-4-yloxy)-4-(trifluoromethyl)benzyl)-1,8-diazaspiro[4.5]decane-8-carboxylate

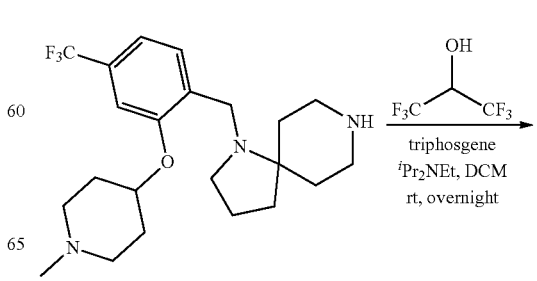

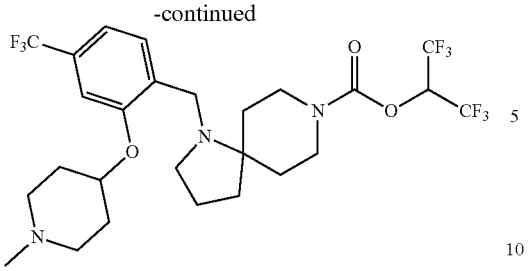

A flask was charged with triphosgene (89.4 mg, 0.301 mmol, 0.70 equiv), and DCM (10 mL). HFIP (144 mg, 0.860 mmol, 2.00 equiv) was added at 0° C., followed by DIEA (222 mg, 1.72 mmol, 4.00 equiv). The mixture was stirred for 2 h at rt. 1-(2-(1-Methylpiperidin-4-yloxy)-4-(trifluoromethyl)benzyl)-1,8-diazaspiro[4.5]decane (177 mg, 0.430 mmol, 1.00 equiv) was added, and the reaction was stirred overnight at rt before quenching with H₂O (10 mL). The mixture was extracted with DCM (3×30 mL) and the organic layers were combined, washed with brine (30 mL), dried over anhydrous sodium sulfate, filtered, and concentrated. The crude product was purified by preparative HPLC to give 54.0 mg (21% yield) of 1,1,1,3,3,3-hexafluoropropan-2-yl 1-(2-(1-methylpiperidin-4-yloxy)-4-(trifluoromethyl)benzyl)-1,8-diazaspiro[4.5]decane-8-carboxylate as a yellow solid. ¹H NMR (300 MHz, Chloroform-d) δ 7.52 (d, J=7.8 Hz, 1H), 7.19 (d, J=8.4 Hz, 1H), 7.05 (s, 1H), 5.73-5.86 (m, 1H), 4.46 (br, 1H), 4.20-4.29 (m, 2H), 3.67 (s, 2H), 2.94-3.08 (m, 2H), 2.76-2.78 (m, 4H), 2.38-2.44 (m, 5H), 2.10 (br, 2H), 1.64-1.94 (m, 8H), 1.48-1.55 (m, 2H). LCMS (ESI, m/z): 606 [M+H]⁺.

Example 166: 1,1,1,3,3,3-Hexafluoropropan-2-yl 1-(3-(1-methylpiperidin-4-yloxy)-5-(trifluoromethyl)benzyl)-1,8-diazaspiro[4.5]decane-8-carboxylate

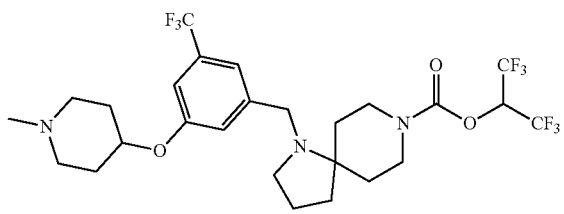 [SMILES: CN1CCC(Oc2cc(CN3CCCC34CCN(C(=O)OC(C(F)(F)F)C(F)(F)F)CC4)cc(C(F)(F)F)c2)CC1]

The title compound was synthesized according to the representative procedure of Example 165 using 3-hydroxy-5-(trifluoromethyl)benzaldehyde as the starting material in Step 3. Purification resulted in 28.9 mg of 1,1,1,3,3,3-hexafluoropropan-2-yl 1-(3-(1-methylpiperidin-4-yloxy)-5-(trifluoromethyl)benzyl)-1,8-diazaspiro[4.5]decane-8-carboxylate as a light yellow solid. ¹H NMR (300 MHz, Chloroform-d) δ 7.15 (s, 1H), 7.04 (s, 1H), 6.98 (s, 1H), 5.71-5.79 (m, 1H), 4.44 (br, 1H), 4.17-4.25 (m, 2H), 3.60 (s, 2H), 2.91-3.05 (m, 2H), 2.82 (br, 2H), 2.51-2.69 (m, 4H), 2.45 (s, 3H), 2.14 (br, 2H), 1.63-2.00 (m, 8H), 1.48-1.51 (m, 2H). LCMS (ESI, m/z): 606 [M+H]⁺.

Example 167: 1,1,1,3,3,3-Hexafluoropropan-2-yl 1-(2-(2-oxo-2-(pyrrolidin-1-yl)ethoxy)-4-(trifluoromethyl)benzyl)-1,8-diazaspiro[4.5]decane-8-carboxylate

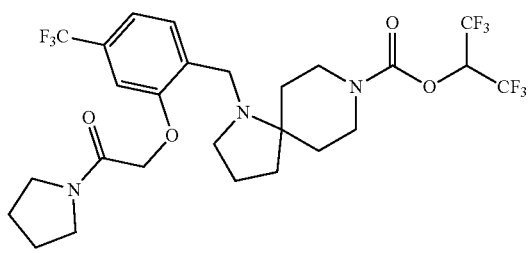 [SMILES: O=C(COc1cc(C(F)(F)F)ccc1CN1CCCC12CCN(C(=O)OC(C(F)(F)F)C(F)(F)F)CC2)N1CCCC1]

Step 1: Synthesis of 2-chloro-1-(pyrrolidin-1-yl)ethanone

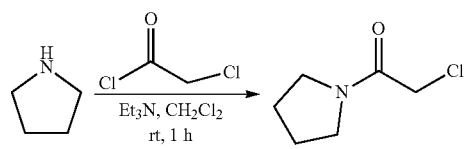

A flask was charged with pyrrolidine (0.500 g, 7.03 mmol, 1.00 equiv), DCM (20 mL), and TEA (2.13 g, 21.1 mmol, 3.00 equiv). 2-Chloroacetyl chloride (1.18 g, 10.4 mmol, 1.50 equiv) was added at 0° C. The resulting solution was stirred for 1 h at rt and concentrated. The residue was chromatographed on a silica gel column with EtOAc/petroleum ether (1/3) to provide 0.902 g (87% yield) of 2-chloro-1-(pyrrolidin-1-yl)ethanone as a yellow solid. LCMS (ESI, m/z): 148 [M+H]⁺.

Step 2: Synthesis of tert-butyl 1-(2-(2-oxo-2-(pyrrolidin-1-yl)ethoxy)-4-(trifluoromethyl)benzyl)-1,8-diazaspiro[4.5]decane-8-carboxylate

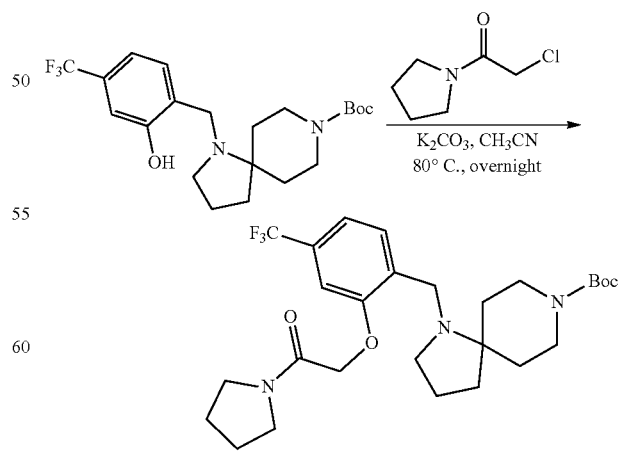

A flask was charged with tert-butyl 1-(2-hydroxy-4-(trifluoromethyl)benzyl)-1,8-diazaspiro[4.5]decane-8-carboxylate (200 mg, 0.480 mmol, 1.00 equiv), 2-chloro-1-(pyrrolidin-1-yl)ethan-1-one (213 mg, 1.44 mmol, 3.00 equiv), potassium carbonate (200 mg, 1.45 mmol, 3.00 equiv), and MeCN (10 mL). The resulting solution was stirred overnight at 80° C. and quenched with H$_2$O (10 mL). The mixture was extracted with DCM (3×30 mL) and the organic layers were combined, washed with brine (30 mL), dried over anhydrous sodium sulfate, filtered, and concentrated. The residue was chromatographed on a silica gel column with EtOAc/petroleum ether (75/25) to provide 220 mg (87% yield) of tert-butyl 1-(2-(2-oxo-2-(pyrrolidin-1-yl)ethoxy)-4-(trifluoromethyl)benzyl)-1,8-diazaspiro[4.5]decane-8-carboxylate as a light yellow oil. LCMS (ESI, m/z): 526 [M+H]$^+$.

Step 3: Synthesis of 1,1,1,3,3,3-hexafluoropropan-2-yl 1-(2-(2-oxo-2-(pyrrolidin-1-yl)ethoxy)-4-(trifluoromethyl)benzyl)-1,8-diazaspiro[4.5]decane-8-carboxylate

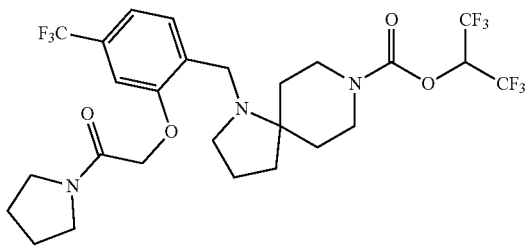 [SMILES: O=C(COc1cc(C(F)(F)F)ccc1CN1CCCC12CCN(C(=O)OC(C(F)(F)F)C(F)(F)F)CC2)N1CCCC1]

The title compound was synthesized according to the representative procedure of Example 167 using tert-butyl 1-(2-(2-oxo-2-(pyrrolidin-1-yl)ethoxy)-4-(trifluoromethyl)benzyl)-1,8-diazaspiro[4.5]decane-8-carboxylate as the starting material to yield 1,1,1,3,3,3-hexafluoropropan-2-yl 1-(2-(2-oxo-2-(pyrrolidin-1-yl)ethoxy)-4-(trifluoromethyl)benzyl)-1,8-diazaspiro[4.5]decane-8-carboxylate as a white solid. $^1$H NMR (300 MHz, Chloroform-d) δ 7.55 (d, J=7.8 Hz, 1H), 7.23-7.29 (m, 1H), 7.04 (s, 1H), 5.72-5.85 (m, 1H), 4.76 (s, 2H), 4.19-4.26 (m, 2H), 3.75 (s, 2H), 3.51-3.60 (m, 4H), 2.93-3.07 (m, 2H), 2.77 (br, 2H), 2.00-2.07 (m, 2H), 1.70-1.99 (m, 8H), 1.45-1.52 (m, 2H). LCMS (ESI, m/z): 620 [M+H]$^+$.

Example 168: 1,1,1,3,3,3-Hexafluoropropan-2-yl 1-(3-(2-oxo-2-(pyrrolidin-1-yl)ethoxy)-5-(trifluoromethyl)benzyl)-1,8-diazaspiro[4.5]decane-8-carboxylate

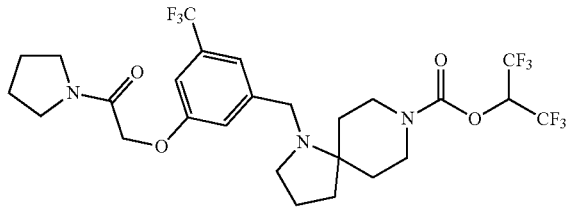 [SMILES: O=C(COc1cc(CN2CCCC23CCN(C(=O)OC(C(F)(F)F)C(F)(F)F)CC3)cc(C(F)(F)F)c1)N1CCCC1]

The title compound was synthesized according to the representative procedure of Example 167 using 3-hydroxy-5-(trifluoromethyl)benzaldehyde as the starting material. Purification resulted in 61.5 mg of 1,1,1,3,3,3-hexafluoropropan-2-yl 1-(3-(2-oxo-2-(pyrrolidin-1-yl)ethoxy)-5-(trifluoromethyl)benzyl)-1,8-diazaspiro[4.5]decane-8-carboxylate as a light yellow solid. $^1$H NMR (300 MHz, Chloroform-d) δ 7.27 (br, 2H), 7.03 (br, 1H), 5.70-5.82 (m, 1H), 4.66 (br, 2H), 4.19-4.26 (m, 2H), 3.63 (br, 2H), 3.51-3.57 (m, 4H), 2.92-3.06 (m, 2H), 2.68 (br, 2H), 1.98-2.08 (m, 2H), 1.68-1.96 (m, 8H), 1.53 (br, 2H). LCMS (ESI, m/z): 620 [M+H]$^+$.

Example 169: 1,1,1,3,3,3-Hexafluoropropan-2-yl 1-(2-(tetrahydro-2H-pyran-4-yloxy)-4-(trifluoromethyl)benzyl)-1,8-diazaspiro[4.5]decane-8-carboxylate

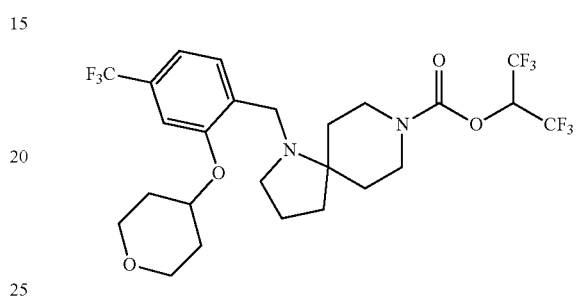

The title compound was synthesized according to the representative procedure of Example 165 using 4-bromotetrahydro-2H-pyran in Step 4. Purification resulted in 37.4 mg of 1,1,1,3,3,3-hexafluoropropan-2-yl 1-(2-(tetrahydro-2H-pyran-4-yloxy)-4-(trifluoromethyl)benzyl)-1,8-diazaspiro[4.5]decane-8-carboxylate as a light yellow semi-solid. $^1$H NMR (300 MHz, Chloroform-d) δ 7.49 (d, J=7.8 Hz, 1H), 7.17 (d, J=8.1 Hz, 1H), 7.03 (s, 1H), 5.72-5.83 (m, 1H), 4.53-4.61 (m, 1H), 4.17-4.25 (m, 2H), 3.94-4.02 (m, 2H), 3.57-3.65 (m, 4H), 2.91-3.05 (m, 2H), 2.73-2.75 (m, 2H), 2.04-2.07 (m, 2H), 1.68-1.86 (m, 8H), 1.40-1.55 (m, 2H). LCMS (ESI, m/z): 593 [M+H]$^+$.

Example 170: 1,1,1,3,3,3-Hexafluoropropan-2-yl 1-(3-(tetrahydro-2H-pyran-4-yloxy)-5-(trifluoromethyl)benzyl)-1,8-diazaspiro[4.5]decane-8-carboxylate

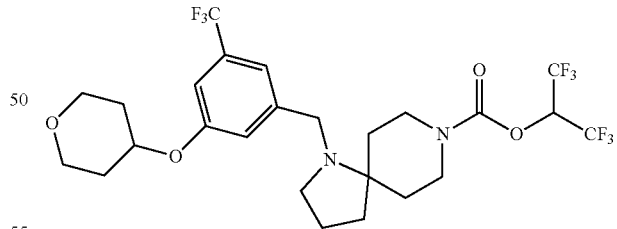

The title compound was synthesized according to the representative procedure of Example 166 using 4-bromotetrahydro-2H-pyran as the starting material. Purification resulted in 16.4 mg of 1,1,1,3,3,3-hexafluoropropan-2-yl 1-(3-(tetrahydro-2H-pyran-4-yloxy)-5-(trifluoromethyl)benzyl)-1,8-diazaspiro[4.5]decane-8-carboxylate as a light yellow solid. $^1$H NMR (300 MHz, Chloroform-d) δ 7.15 (s, 1H), 7.05 (s, 1H), 6.99 (s, 1H), 5.71-5.79 (m, 1H), 4.53 (br, 1H), 4.17-4.26 (m, 2H), 3.95-4.02 (m, 2H), 3.51-3.72 (m, 4H), 2.91-3.06 (m, 2H), 2.67-2.69 (m, 2H), 2.01-2.06 (m, 2H), 1.48-1.82 (m, 10H). LCMS (ESI, m/z): 593 [M+H]$^+$.

Example 171: 1,1,1,3,3,3-Hexafluoropropan-2-yl 1-(2-(benzo[d]thiazol-2-yloxy)-4-(trifluoromethyl)benzyl)-1,8-diazaspiro[4.5]decane-8-carboxylate

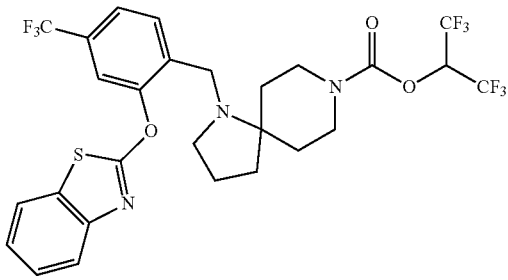 [SMILES: O=C(OC(C(F)(F)F)C(F)(F)F)N1CCC2(CCCN2Cc2ccc(C(F)(F)F)cc2Oc2nc3ccccc3s2)CC1]

The title compound was synthesized according to the representative procedure of Example 165 using 2-chlorobenzo[d]thiazole in Step 4. Purification resulted in 122.8 mg of 1,1,1,3,3,3-hexafluoropropan-2-yl 1-(2-(benzo[d]thiazol-2-yloxy)-4-(trifluoromethyl)benzyl)-1,8-diazaspiro[4.5]decane-8-carboxylate as a light yellow semi-solid. $^1$H NMR (300 MHz, Chloroform-d) δ 7.65-7.81 (m, 4H), 7.56 (d, J=8.1 Hz, 1H), 7.44 (t, J=7.5 Hz, 1H), 7.33 (t, J=7.5 Hz, 1H), 5.68-5.80 (m, 1H), 4.16-4.38 (m, 2H), 3.75 (s, 2H), 2.89-3.02 (m, 2H), 2.72 (br, 2H), 1.69-1.75 (m, 6H), 1.44-1.48 (m, 2H). LCMS (ESI, m/z): 642 [M+H]$^+$.

Example 172: 1,1,1,3,3,3-Hexafluoropropan-2-yl 1-(3-(benzo[d]thiazol-2-yloxy)-5-(trifluoromethyl)benzyl)-1,8-diazaspiro[4.5]decane-8-carboxylate

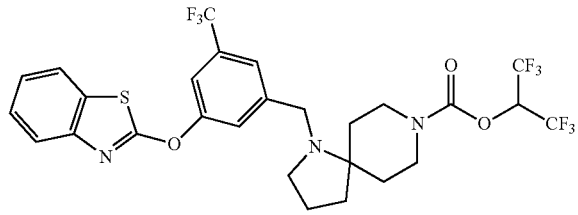 [SMILES: O=C(OC(C(F)(F)F)C(F)(F)F)N1CCC2(CCCN2Cc2cc(Oc3nc4ccccc4s3)cc(C(F)(F)F)c2)CC1]

The title compound was synthesized according to the representative procedure of Example 166 using 2-chlorobenzo[d]thiazole as the starting material. Purification resulted in 79.9 mg of 1,1,1,3,3,3-hexafluoropropan-2-yl 1-(3-(benzo[d]thiazol-2-yloxy)-5-(trifluoromethyl)benzyl)-1,8-diazaspiro[4.5]decane-8-carboxylate as a light yellow oil. $^1$H NMR (300 MHz, Chloroform-d) δ 7.70-7.76 (m, 2H), 7.52-7.59 (m, 3H), 7.40-7.46 (m, 1H), 7.29-7.35 (m, 1H), 5.70-5.82 (m, 1H), 4.19-4.28 (m, 2H), 3.72 (br, 2H), 2.92-3.06 (m, 2H), 2.74 (br, 2H), 1.60-1.86 (m, 6H), 1.54 (br, 2H). LCMS (ESI, m/z): 642 [M+H]$^+$.

Example 173: 1,1,1,3,3,3-Hexafluoropropan-2-yl 1-(2-(pyridin-3-yloxy)-4-(trifluoromethyl)benzyl)-1,8-diazaspiro[4.5]decane-8-carboxylate

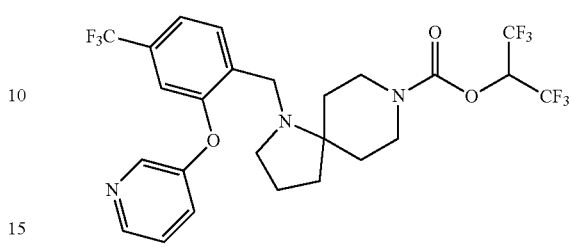

Step 1: Synthesis of tert-butyl 1-(2-(pyridin-3-yloxy)-4-(trifluoromethyl)benzyl)-1,8-diazaspiro[4.5]decane-8-carboxylate

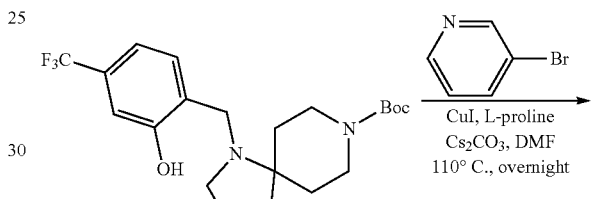

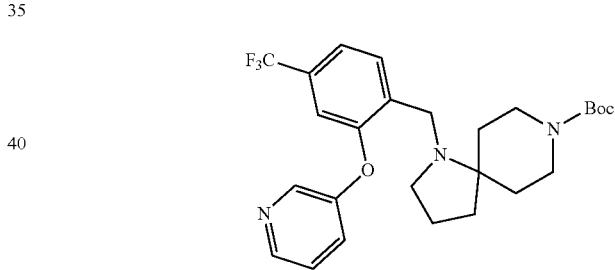

A flask was charged with tert-butyl 1-(2-hydroxy-4-(trifluoromethyl)benzyl)-1,8-diazaspiro[4.5]decane-8-carboxylate (200 mg, 0.480 mmol, 1.00 equiv), 3-bromopyridine (228 mg, 1.44 mmol, 3.00 equiv), copper(I) iodide (18.5 mg, 0.100 mmol, 0.20 equiv), L-proline (22.4 mg, 0.193 mmol, 0.40 equiv), cesium carbonate (346 mg, 1.06 mmol, 2.20 equiv), and DMF (6 mL) under nitrogen. The resulting solution was stirred overnight at 110° C. and quenched with H$_2$O (20 mL). The mixture was extracted with DCM (3×50 mL) and the organic layers were combined, washed with brine (50 mL), dried over anhydrous sodium sulfate, filtered, and concentrated. The residue was chromatographed on a silica gel column with DCM/MeOH (98/2) to provide 200 mg (84% yield) of tert-butyl 1-(2-(pyridin-3-yloxy)-4-(trifluoromethyl)benzyl)-1,8-diazaspiro[4.5]decane-8-carboxylate as a yellow oil. LCMS (ESI, m/z): 491 [M+H]$^+$.

Step 2: Synthesis of 1,1,1,3,3,3-hexafluoropropan-2-yl 1-(2-(pyridin-3-yloxy)-4-(trifluoromethyl)benzyl)-1,8-diazaspiro[4.5]decane-8-carboxylate

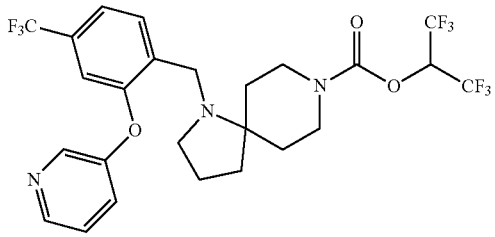 [SMILES: O=C(OC(C(F)(F)F)C(F)(F)F)N1CCC2(CCCN2Cc2ccc(C(F)(F)F)cc2Oc2cccnc2)CC1]

The title compound was synthesized according to the representative procedure of Example 165, Steps 5-6. Purification resulted in 60.2 mg of 1,1,1,3,3,3-hexafluoropropan-2-yl 1-(2-(pyridin-3-yloxy)-4-(trifluoromethyl)benzyl)-1,8-diazaspiro[4.5]decane-8-carboxylate as a yellow oil. $^1$H NMR (300 MHz, Chloroform-d) δ 8.02-8.34 (m, 2H), 7.74 (d, J=8.1 Hz, 1H), 7.39-7.54 (m, 3H), 7.21 (s, 1H), 6.06-6.19 (m, 1H), 4.12 (br, 2H), 3.75 (s, 2H), 2.94-3.18 (m, 2H), 2.75 (t, J=5.7 Hz, 2H), 1.63-1.81 (m, 6H), 1.32-1.41 (m, 2H). LCMS (ESI, m/z): 586 [M+H]$^+$.

Example 174: 1,1,1,3,3,3-Hexafluoropropan-2-yl 1-(3-(pyridin-3-yloxy)-5-(trifluoromethyl)benzyl)-1,8-diazaspiro[4.5]decane-8-carboxylate

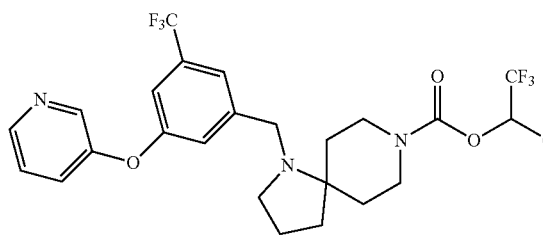

The title compound was synthesized according to the representative procedure of Example 166. Purification resulted in 104.0 mg of 1,1,1,3,3,3-hexafluoropropan-2-yl 1-(3-(pyridin-3-yloxy)-5-(trifluoromethyl)benzyl)-1,8-diazaspiro[4.5]decane-8-carboxylate as a yellow oil. $^1$H NMR (300 MHz, Chloroform-d) δ 8.42 (s, 2H), 7.53-7.61 (m, 3H), 7.10-7.26 (m, 2H), 5.69-5.79 (m, 1H), 4.16-4.38 (m, 2H), 3.63 (s, 2H), 2.90-3.04 (m, 2H), 2.67-2.69 (m, 2H), 1.82 (br, 4H), 1.49-1.73 (m, 4H). LCMS (ESI, m/z): 586 [M+H]$^+$.

Example 175: 1,1,1,3,3,3-Hexafluoropropan-2-yl 1-(2-((1,1-dioxidotetrahydro-2H-thiopyran-4-yl)oxy)-4-(trifluoromethyl)benzyl)-1,8-diazaspiro[4.5]decane-8-carboxylate

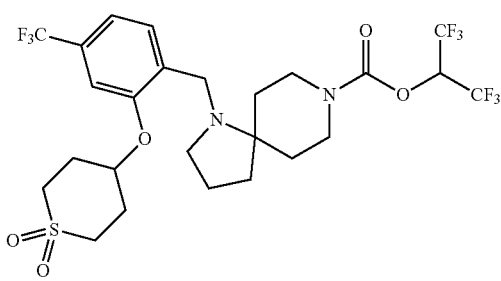 [SMILES: O=C(OC(C(F)(F)F)C(F)(F)F)N1CCC2(CCCN2Cc2ccc(C(F)(F)F)cc2OC2CCS(=O)(=O)CC2)CC1]

Step 1: Synthesis of 1,1-dioxidotetrahydro-2H-thiopyran-4-yl methanesulfonate

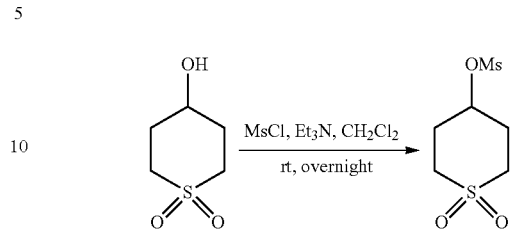

A flask was charged with 4-hydroxytetrahydro-2H-thiopyran 1,1-dioxide (3.50 g, 23.3 mmol, 1.00 equiv), methanesulfonyl chloride (5.30 g, 46.5 mmol, 2.00 equiv), TEA (7.10 g, 70.2 mmol, 3.00 equiv), and DCM (40 mL). The resulting solution was stirred overnight at rt and quenched with H$_2$O (40 mL). The resulting mixture was extracted with DCM (3×30 mL) and the organic layers were combined, washed with brine (200 mL), dried over anhydrous sodium sulfate, filtered, and concentrated. The residue was chromatographed on a silica gel column with EtOAc/petroleum ether (10/1) to provide 4.00 g (75% yield) of 1,1-dioxidotetrahydro-2H-thiopyran-4-yl methanesulfonate as a white solid.

Step 2: Synthesis of 1,1,1,3,3,3-hexafluoropropan-2-yl 1-(2-((1,1-dioxidotetrahydro-2H-thiopyran-4-yl)oxy)-4-(trifluoromethyl)benzyl)-1,8-diazaspiro[4.5]decane-8-carboxylate

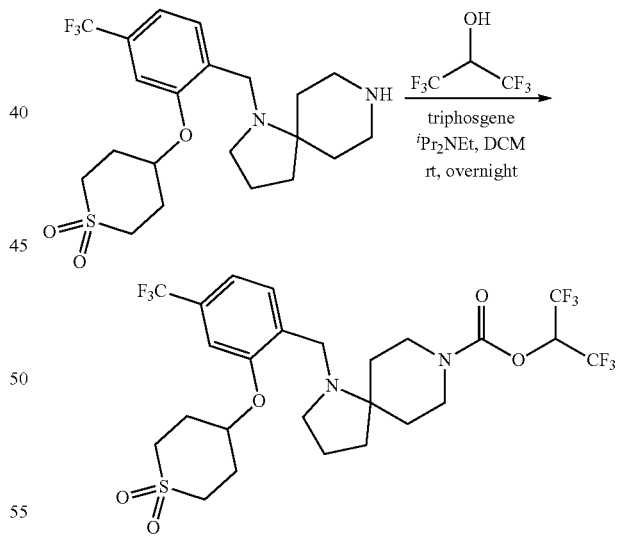

The title compound was synthesized according to the representative procedure of Example 165 using 1,1-dioxidotetrahydro-2H-thiopyran-4-yl methanesulfonate in Step 4. Purification resulted in 139.7 mg of 1,1,1,3,3,3-hexafluoropropan-2-yl 1-(2-((1,1-dioxidotetrahydro-2H-thiopyran-4-yl)oxy)-4-(trifluoromethyl)benzyl)-1,8-diazaspiro[4.5]decane-8-carboxylate as a white solid. $^1$H NMR (300 MHz, Chloroform-d) δ 7.58 (d, J=7.8 Hz, 1H), 7.29 (s, 1H), 7.06 (s, 1H), 5.73-5.85 (m, 1H), 4.78 (br, 1H), 4.21-4.30 (m, 2H), 3.70 (br, 2H), 3.38-3.41 (m, 2H), 2.95-3.09 (m, 4H), 2.71

(br, 2H), 2.40-2.64 (m, 4H), 1.73-2.04 (m, 6H), 1.54 (br, 2H). LCMS (ESI, m/z): 641 [M+H]+.

Example 176: 1,1,1,3,3,3-Hexafluoropropan-2-yl 1-(3-((1,1-dioxidotetrahydro-2H-thiopyran-4-yl)oxy)-5-(trifluoromethyl)benzyl)-1,8-diazaspiro[4.5]decane-8-carboxylate

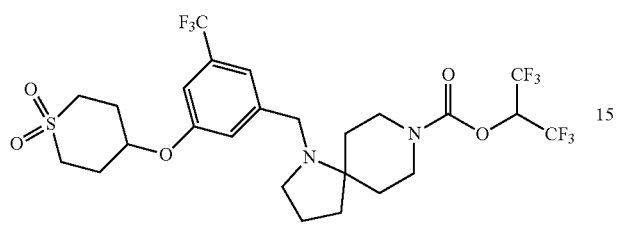

The title compound was synthesized according to the representative procedure of Example 166 using 1,1-dioxothian-4-yl methanesulfonate as the starting material. Purification resulted in 77.8 mg of 1,1,1,3,3,3-hexafluoropropan-2-yl 1-(3-((1,1-dioxidotetrahydro-2H-thiopyran-4-yl)oxy)-5-(trifluoromethyl)benzyl)-1,8-diazaspiro[4.5]decane-8-carboxylate as a light yellow solid. $^1$H NMR (300 MHz, Chloroform-d) δ 7.27 (s, 1H), 7.09 (s, 1H), 7.01 (s, 1H), 5.71-5.82 (m, 1H), 4.70 (br, 1H), 4.19-4.28 (m, 2H), 3.62 (br, 2H), 3.36-3.46 (m, 2H), 2.95-3.06 (m, 4H), 2.68 (br, 2H), 2.29-2.51 (m, 4H), 1.60-2.00 (m, 6H), 1.53 (br, 2H). LCMS (ESI, m/z): 641 [M+H]+.

Example 177: 1,1,1,3,3,3-Hexafluoropropan-2-yl 1-(3-methyl-4-(trifluoromethyl)benzyl)-1,8-diazaspiro[4.5]decane-8-carboxylate

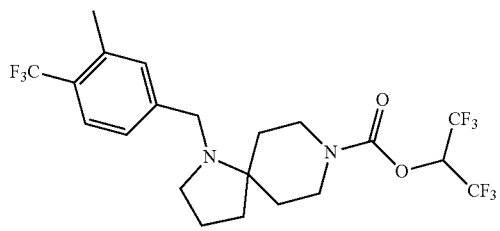 [SMILES: Cc1cc(CN2CCCC23CCN(C(=O)OC(C(F)(F)F)C(F)(F)F)CC3)ccc1C(F)(F)F]

The title compound was synthesized according to the representative procedure of Example 150 using 3-methyl-4-(trifluoromethyl)benzaldehyde and 1,1,1,3,3,3-hexafluoropropan-2-yl 1,8-diazaspiro[4.5]decane-8-carboxylate. Purification resulted in 101.5 mg (45% yield) of 1,1,1,3,3,3-hexafluoropropan-2-yl 1-(3-methyl-4-(trifluoromethyl)benzyl)-1,8-diazaspiro[4.5]decane-8-carboxylate as a white solid. $^1$H NMR (300 MHz, Chloroform-d) δ 7.52 (d, J=7.8 Hz, 1H), 7.21 (br, 2H), 5.69-5.82 (m, 1H), 4.18-4.26 (m, 2H), 3.58 (s, 2H), 2.92-3.05 (m, 2H), 2.66 (br, 2H), 2.46 (s, 3H), 1.66-1.82 (m, 6H), 1.48-1.51 (m, 2H). LCMS (ESI, m/z): 507 [M+H]+.

Example 178: 1,1,1,3,3,3-Hexafluoropropan-2-yl 1-(3-carbamoyl-4-(trifluoromethyl)benzyl)-1,8-diazaspiro[4.5]decane-8-carboxylate

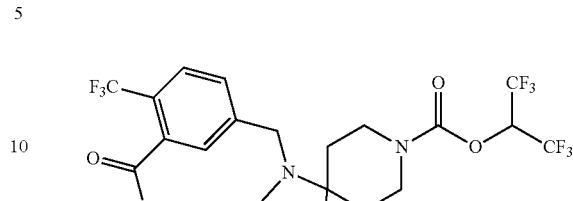

Step 1: Synthesis of methyl 5-formyl-2-(trifluoromethyl)benzoate

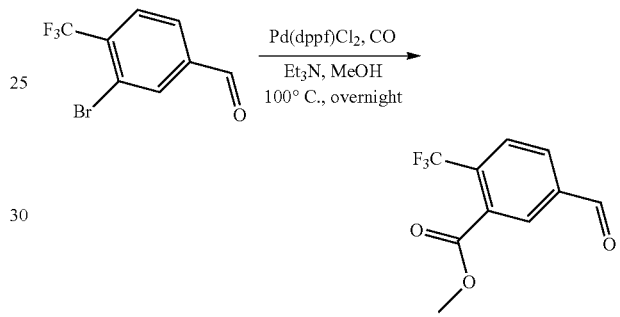

A flask was charged with 3-bromo-4-(trifluoromethyl)benzaldehyde (3.00 g, 11.9 mmol, 1.00 equiv), MeOH (50 mL), 1,1'-bis(diphenylphosphino)ferrocenepalladiumdichloride (870 mg, 1.19 mmol, 0.10 equiv), and TEA (3.61 g, 35.7 mmol, 3.00 equiv). Carbon monoxide (10 atm) was introduced, and the reaction was stirred overnight at 100° C. before quenching with water (50 mL). The resulting solution was extracted with EtOAc (2×80 mL) and the organic layers were combined, dried over anhydrous sodium sulfate, filtered, and concentrated. The residue was chromatographed on a silica gel column with EtOAc/petroleum ether (8/92) to provide 2.2 g (80% yield) of methyl 5-formyl-2-(trifluoromethyl)benzoate as an off-white semi-solid. $^1$H NMR (400 MHz, Chloroform-d) δ 10.1 (s, 1H), 8.31 (s, 1H), 8.12-8.15 (m, 1H), 7.97 (d, J=8.0 Hz, 1H), 4.00 (s, 3H).

Step 2: Synthesis of tert-butyl 1-(3-(methoxycarbonyl)-4-(trifluoromethyl)benzyl)-1,8-diazaspiro[4.5]decane-8-carboxylate

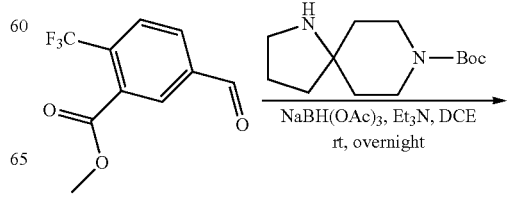

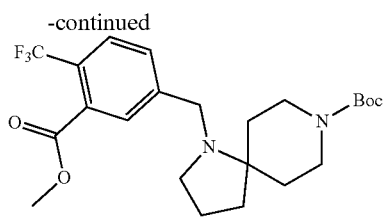

A flask was charged with methyl 5-formyl-2-(trifluoromethyl)benzoate (2.20 g, 9.48 mmol, 1.00 equiv), DCE (50 mL), and tert-butyl 1,8-diazaspiro[4.5]decane-8-carboxylate (2.27 g, 9.44 mmol, 1.00 equiv). The mixture was stirred for 1 h at rt. Sodium triacetoxyborohydride (6.02 g, 28.4 mmol, 3.00 equiv) was added, and the reaction was stirred overnight at rt before quenching with water (80 mL). The resulting solution was extracted with DCM (2×150 mL) and the organic layers were combined, dried over anhydrous sodium sulfate, filtered, and concentrated. The residue was chromatographed on a silica gel column with DCM/MeOH (96/4) to provide 3.1 g (72% yield) of tert-butyl 1-(3-(methoxycarbonyl)-4-(trifluoromethyl)benzyl)-1,8-diazaspiro[4.5]decane-8-carboxylate as a white solid. LCMS (ESI, m/z): 457 [M+H]⁺.

Step 3: Synthesis of 5-((8-(tert-butoxycarbonyl)-1,8-diazaspiro[4.5]decan-1-yl)methyl)-2-(trifluoromethyl)benzoic acid

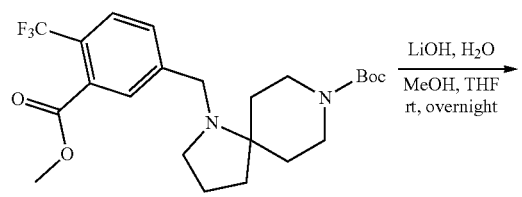

A flask was charged with tert-butyl 1-(3-(methoxycarbonyl)-4-(trifluoromethyl)benzyl)-1,8-diazaspiro[4.5]decane-8-carboxylate (1.50 g, 3.29 mmol, 1.00 equiv), THF (10 mL), MeOH (10 mL), water (20 mL), and lithium hydroxide (1.38 g, 32.9 mmol, 10.0 equiv). The resulting solution was stirred overnight at rt. The pH of the solution was adjusted to 5 with hydrochloric acid (1 M). The resulting solution was extracted with DCM (2×80 mL) and the organic layers were combined, dried over anhydrous sodium sulfate, filtered, and concentrated to yield 800 mg (55%) of 5-((8-(tert-butoxycarbonyl)-1,8-diazaspiro[4.5]decan-1-yl)methyl)-2-(trifluoromethyl)benzoic acid as a light yellow solid. LCMS (ESI, m/z): 443 [M+H]⁺.

Step 4: Synthesis of tert-butyl 1-(3-carbamoyl-4-(trifluoromethyl)benzyl)-1,8-diazaspiro[4.5]decane-8-carboxylate

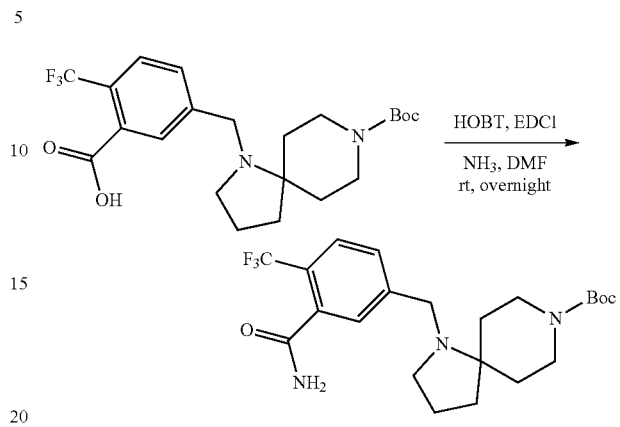

A flask was charged with 5-((8-(tert-butoxycarbonyl)-1,8-diazaspiro[4.5]decan-1-yl)methyl)-2-(trifluoromethyl)benzoic acid (600 mg, 1.36 mmol, 1.00 equiv), DMF (15 mL), 1-hydroxybenzotriazole (275 mg, 2.04 mmol, 1.50 equiv), and 3-(ethyliminomethyleneamino)-N,N-dimethylpropan-1-amine (392 mg, 2.04 mmol, 1.50 equiv). The resulting solution was stirred for 1 h at rt. A saturated solution of NH₃ in dioxane (2 mL) was added. The reaction mixture was stirred overnight at rt before quenching with water (30 mL). The resulting solution was extracted with EtOAc (2×50 mL) and the organic layers were combined, dried over anhydrous sodium sulfate, filtered and concentrated. The residue was chromatographed on a silica gel column with EtOAc/petroleum ether (4/1) to 120 mg (20% yield) of tert-butyl 1-(3-carbamoyl-4-(trifluoromethyl)benzyl)-1,8-diazaspiro[4.5]decane-8-carboxylate as a light yellow solid. LCMS (ESI, m/z): 442 [M+H]⁺.

Step 5. Synthesis of 5-(1,8-diazaspiro[4.5]decan-1-ylmethyl)-2-(trifluoromethyl)benzamide

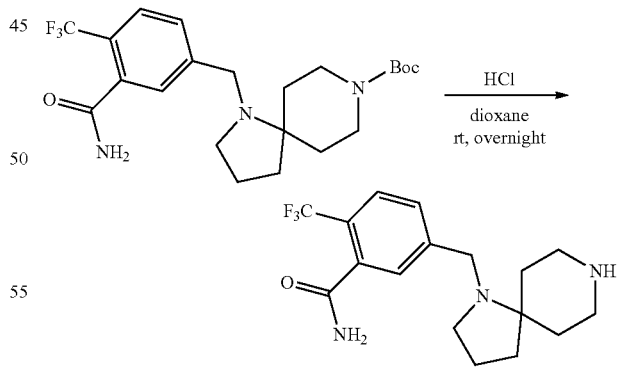

A flask was charged with tert-butyl 1-(3-carbamoyl-4-(trifluoromethyl)benzyl)-1,8-diazaspiro[4.5]decane-8-carboxylate (120 mg, 0.270 mmol, 1.00 equiv), dioxane (10 mL), and hydrochloric acid (2 mL). The resulting solution was stirred overnight at rt and concentrated to provide 90 mg (crude) of 5-(1,8-diazaspiro[4.5]decan-1-ylmethyl)-2-(trifluoromethyl)benzamide as a yellow oil. LCMS (ESI, m/z): 342 [M+H]⁺.

Step 6: Synthesis of 1,1,1,3,3,3-hexafluoropropan-2-yl 1-(3-carbamoyl-4-(trifluoromethyl)benzyl)-1,8-diazaspiro[4.5]decane-8-carboxylate

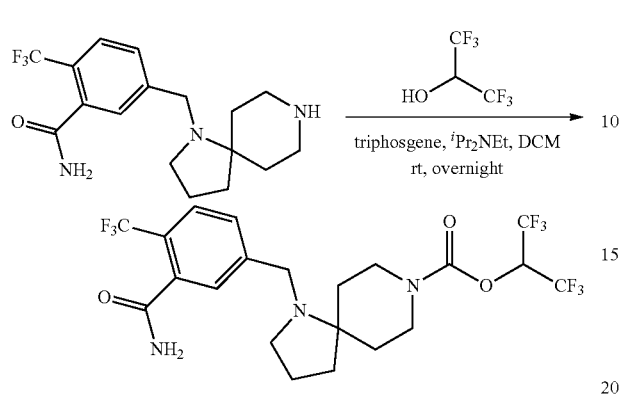

A flask was charged with triphosgene (20.0 mg, 0.070 mmol, 0.50 equiv), and DCM (10 mL). HFIP (44.0 mg, 0.260 mmol, 2.00 equiv) and DIPEA (51.0 mg, 0.390 mmol, 3.00 equiv) were each added dropwise at 0° C. The mixture was stirred for 1 h at rt. 5-(1,8-Diazaspiro[4.5]decan-1-ylmethyl)-2-(trifluoromethyl)benzamide (45.0 mg, 0.130 mmol, 1.00 equiv) was added, and the reaction was stirred overnight at rt before quenching with water (30 mL). The resulting solution was extracted with DCM (2×50 mL) and the organic layers were combined, dried over anhydrous sodium sulfate, filtered, and concentrated. The crude product was purified by preparative HPLC to yield 11.6 mg (16%) of 1,1,1,3,3,3-hexafluoropropan-2-yl 1-(3-carbamoyl-4-(trifluoromethyl)benzyl)-1,8-diazaspiro[4.5]decane-8-carboxylate as a white solid. $^1$H NMR (300 MHz, Chloroform-d) δ 7.61-7.66 (m, 2H), 7.48-7.51 (m, 1H), 5.64-5.81 (m, 3H), 4.20-4.28 (m, 2H), 3.69 (br, 2H), 2.85-3.07 (m, 2H), 2.69 (br, 2H), 1.40-1.85 (m, 8H). LCMS (ESI, m/z): 536 [M+H]$^+$.

Example 179: 5-((8-((1,1,1,3,3,3-Hexafluoropropan-2-yloxy)carbonyl)-1,8-diazaspiro[4.5]decan-1-yl)methyl)-2-(trifluoromethyl)benzoic acid

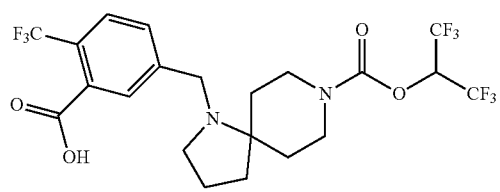 [SMILES: O=C(O)c1cc(CN2CCCC23CCN(C(=O)OC(C(F)(F)F)C(F)(F)F)CC3)ccc1C(F)(F)F]

The title compound was synthesized according to the representative procedure of Example 178, Steps 1-3 and 5. Purification resulted in 96.4 mg of 5-((8-((1,1,1,3,3,3-hexafluoropropan-2-yloxy)carbonyl)-1,8-diazaspiro[4.5]decan-1-yl)methyl)-2-(trifluoromethyl)benzoic acid as a white solid. $^1$H NMR (400 MHz, DMSO-d$_6$) δ 13.6 (br, 1H), 7.74 (d, J=8.0 Hz, 1H), 7.67 (s, 1H), 7.59 (d, J=8.4 Hz, 1H), 6.51-6.59 (m, 1H), 3.98-4.06 (m, 2H), 3.69 (s, 2H), 2.99-3.19 (m, 2H), 2.57-2.60 (m, 1H), 1.75-1.83 (m, 2H), 1.58-1.73 (m, 4H), 1.44-1.47 (m, 2H). LCMS (ESI, m/z): 537 [M+H]$^+$.

Example 180: 1,1,1,3,3,3-Hexafluoropropan-2-yl 1-(4-methyl-3-(trifluoromethyl)benzyl)-1,8-diazaspiro[4.5]decane-8-carboxylate

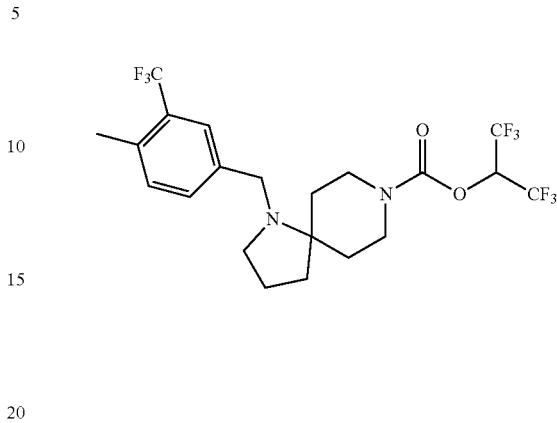

The title compound was synthesized according to the representative procedure of Example 150 using 1,1,1,3,3,3-hexafluoropropan-2-yl 1,8-diazaspiro[4.5]decane-8-carboxylate and 4-methyl-3-(trifluoromethyl)benzaldehyde. Purification resulted in 118.1 mg of 1,1,1,3,3,3-hexafluoropropan-2-yl 1-(4-methyl-3-(trifluoromethyl)benzyl)-1,8-diazaspiro[4.5]decane-8-carboxylate as a white solid. $^1$H NMR (300 MHz, Chloroform-d) δ 7.53 (s, 1H), 7.35 (d, J=7.8 Hz, 1H), 7.20 (d, J=7.8 Hz, 1H), 5.70-5.82 (m, 1H), 4.17-4.26 (m, 2H), 3.53-3.63 (m, 2H), 2.90-3.06 (m, 2H), 2.64 (t, J=6.4 Hz, 2H), 2.45 (s, 3H), 1.60-1.87 (m, 6H), 1.42-1.50 (m, 2H). LCMS (ESI, m/z): 507 [M+H]$^+$.

Example 181: 1,1,1,3,3,3-Hexafluoropropan-2-yl 1-(4-carbamoyl-3-(trifluoromethyl)benzyl)-1,8-diazaspiro[4.5]decane-8-carboxylate

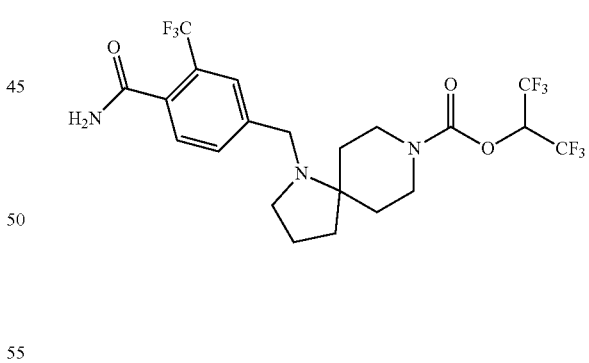

The title compound was synthesized according to the representative procedure of Example 178 using 4-bromo-3-(trifluoromethyl)benzaldehyde in Step 1. Purification resulted in 57.6 mg of 1,1,1,3,3,3-hexafluoropropan-2-yl 1-(4-carbamoyl-3-(trifluoromethyl)benzyl)-1,8-diazaspiro[4.5]decane-8-carboxylate as a white solid. $^1$H NMR (300 MHz, Chloroform-d) δ 7.67 (s, 1H), 7.56 (br, 2H), 5.69-5.96 (m, 3H), 4.19-4.27 (m, 2H), 3.68 (br, 2H), 2.92-3.06 (m, 2H), 2.66 (br, 2H), 1.85 (br, 4H), 1.66-1.74 (m, 2H), 1.55 (br, 2H). LCMS (ESI, m/z): 536 [M+H]$^+$.

Example 182: 4-((8-((1,1,1,3,3,3-Hexafluoropropan-2-yloxy)carbonyl)-1,8-diazaspiro[4.5]decan-1-yl)methyl)-2-(trifluoromethyl)benzoic acid

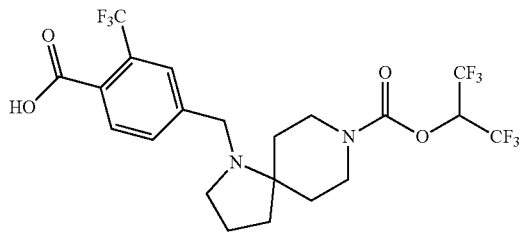 [SMILES: O=C(O)c1ccc(CN2CCCC23CCN(C(=O)OC(C(F)(F)F)C(F)(F)F)CC3)cc1C(F)(F)F]

The title compound was synthesized according to the representative procedure of Example 178, Steps 1-3, and 5 using 4-bromo-3-(trifluoromethyl)benzaldehyde as the starting material. Purification resulted in 59.6 mg of 4-((8-((1,1,1,3,3,3-hexafluoropropan-2-yloxy)carbonyl)-1,8-diazaspiro[4.5]decan-1-yl)methyl)-2-(trifluoromethyl)benzoic acid as a white solid. $^1$H NMR (300 MHz, DMSO-$d_6$) δ 7.60-7.99 (m, 3H), 6.47-6.58 (m, 1H), 3.97-4.06 (m, 2H), 3.68 (s, 2H), 2.97-3.16 (m, 2H), 2.56-2.60 (m, 2H), 1.56-1.81 (m, 6H), 1.42-1.48 (m, 2H). LCMS (ESI, m/z): 537 [M+H]$^+$.

Example 183: 1,1,1,3,3,3-Hexafluoropropan-2-yl 1-(3-chloro-4-(trifluoromethyl)benzyl)-1,8-diazaspiro[4.5]decane-8-carboxylate

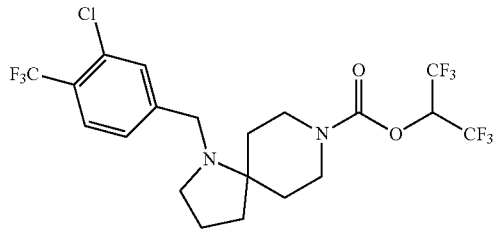 [SMILES: O=C(OC(C(F)(F)F)C(F)(F)F)N1CCC2(CCCN2Cc2ccc(C(F)(F)F)c(Cl)c2)CC1]

The title compound was synthesized according to the representative procedure of Example 150 using 1,1,1,3,3,3-hexafluoropropan-2-yl 1,8-diazaspiro[4.5]decane-8-carboxylate and 3-chloro-4-(trifluoromethyl)benzaldehyde. Purification resulted in 100.5 mg of 1,1,1,3,3,3-hexafluoropropan-2-yl 1-(3-chloro-4-(trifluoromethyl)benzyl)-1,8-diazaspiro[4.5]decane-8-carboxylate as a white solid. $^1$H NMR (300 MHz, Chloroform-d) δ 7.60 (d, J=8.1 Hz, 1H), 7.48 (s, 1H), 7.27-7.30 (m, 1H), 5.69-5.82 (m, 1H), 4.18-4.26 (m, 2H), 3.57-3.66 (m, 2H), 2.91-3.05 (m, 2H), 2.64-2.68 (m, 2H), 1.84 (br, 4H), 1.61-1.77 (m, 2H), 1.48-1.52 (m, 2H). LCMS (ESI, m/z): 527 [M+H]$^+$.

Example 184: 1,1,1,3,3,3-Hexafluoropropan-2-yl 1-(4-chloro-3-(trifluoromethyl)benzyl)-1,8-diazaspiro[4.5]decane-8-carboxylate

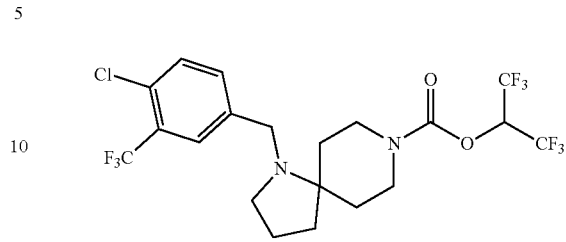

The title compound was synthesized according to the representative procedure of Example 150 using 1,1,1,3,3,3-hexafluoropropan-2-yl 1,8-diazaspiro[4.5]decane-8-carboxylate and 4-chloro-3-(trifluoromethyl)benzaldehyde. Purification resulted in 64.1 mg of 1,1,1,3,3,3-hexafluoropropan-2-yl 1-(4-chloro-3-(trifluoromethyl)benzyl)-1,8-diazaspiro[4.5]decane-8-carboxylate as a white solid. $^1$H NMR (300 MHz, Chloroform-d) δ 7.62 (s, 1H), 7.39-7.42 (m, 2H), 5.69-5.82 (m, 1H), 4.17-4.26 (m, 2H), 3.55-3.65 (m, 2H), 2.90-3.06 (m, 2H), 2.60 (t, J=6.4 Hz, 2H), 1.75-1.88 (m, 4H), 1.62-1.72 (m, 2H), 1.47-1.53 (m, 2H). LCMS (ESI, m/z): 527 [M+H]$^+$.

Example 185: 1,1,1,3,3,3Hhexafluoropropan-2-yl 2-(2-chloro-3-morpholinobenzyl)-3,3-dimethyl-2,8-diazaspiro[4.5]decane-8-carboxylate

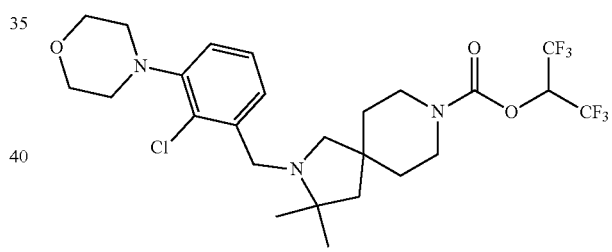

Step 1: Synthesis of 2-chloro-3-morpholinobenzaldehyde

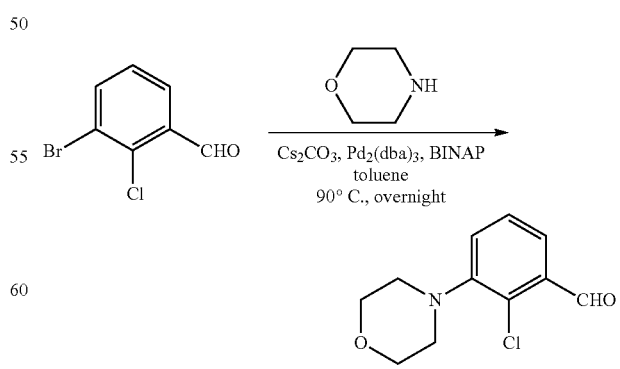

A flask was charged with 3-bromo-2-chlorobenzaldehyde (218 mg, 0.990 mmol, 1.00 equiv), toluene (8 mL), morpholine (104 mg, 1.19 mmol, 1.20 equiv), cesium carbonate (652 mg, 2.00 mmol, 2.00 equiv), tris(dibenzylideneacetone)dipalladium (52.0 mg, 0.050 mmol, 0.050 equiv) and 2,2'-bis(diphenylphosphino)-1,1'-binaphthyl (93.0 mg, 0.150 mmol, 0.150 equiv) under nitrogen. The reaction mixture was stirred overnight at 90° C. and quenched with water (40 mL). The resulting solution was extracted with DCM (3×80 mL) and the organic layers were combined, washed with water (3×20 mL), dried over anhydrous sodium sulfate, filtered, and concentrated. The residue was chromatographed on a silica gel column with EtOAc/petroleum ether (1/3) to afford 150 mg (67% yield) of 2-chloro-3-morpholinobenzaldehyde as a yellow solid. LCMS (ESI, m/z): 226 [M+H]$^+$.

Step 2: Synthesis of 1-(4-methoxybenzyl)piperidine-4-carbonitrile

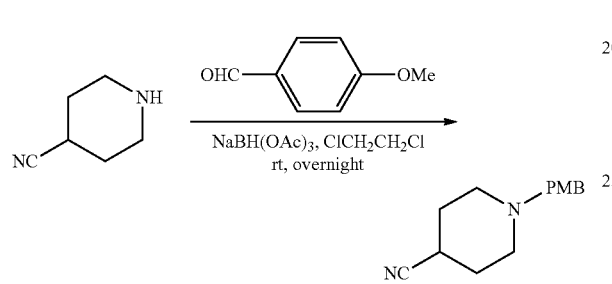

A flask was charged with piperidine-4-carbonitrile (5.00 g, 45.4 mmol, 1.00 equiv), DCE (50 mL) and 4-methoxybenzaldehyde (6.18 g, 45.4 mmol, 1.00 equiv). After 30 min, sodium triacetoxyborohydride (19.3 g, 91.1 mmol, 2.00 equiv) was added, and the reaction was stirred overnight at rt before quenching with water (40 mL). The mixture was extracted with DCM (3×80 mL) and the organic layers were combined, washed with water (3×20 mL), dried over anhydrous sodium sulfate, filtered, and concentrated. The residue was chromatographed on a silica gel column with DCM/MeOH (20/1) to provide 7.55 g (72% yield) of 1-(4-methoxybenzyl)piperidine-4-carbonitrile as a light yellow oil. LCMS (ESI, m/z): 231 [M+H]$^+$.

Step 3: Synthesis of 1-(4-methoxybenzyl)-4-(2-methylallyl)piperidine-4-carbonitrile

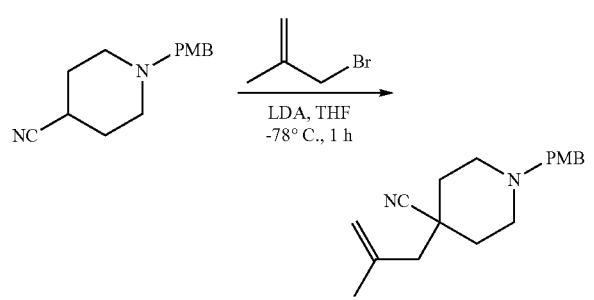

A 3-necked round-bottom flask was charged with 1-(4-methoxybenzyl)piperidine-4-carbonitrile (1.00 g, 4.34 mmol, 1.00 equiv) and THF (20 mL) under nitrogen. Lithium diisopropylamide (2.80 mL, 1.30 equiv, 2.0 M in THF) was added dropwise at −78° C. The solution was stirred for 30 min at −78° C., then 3-bromo-2-methylprop-1-ene (1.16 g, 8.59 mmol, 2.00 equiv) was added dropwise at −78° C. The resulting solution was stirred for 1 h at −78° C. and quenched with brine (20 mL). The resulting solution was extracted with EtOAc (2×80 mL) and the organic layers were combined, washed with brine (80 mL), dried over anhydrous sodium sulfate, filtered, and concentrated. The residue was chromatographed on a silica gel column with EtOAc/petroleum ether (1/2) to provide 790 mg (64% yield) of 1-(4-methoxybenzyl)-4-(2-methylallyl)piperidine-4-carbonitrile as a light yellow oil. LCMS (ESI, m/z): 285 [M+H]$^+$.

Step 4: Synthesis of (1-(4-methoxybenzyl)-4-(2-methylallyl)piperidin-4-yl)methanamine

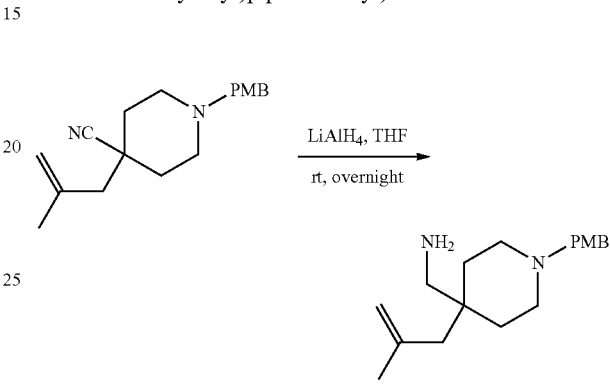

A flask was charged with 1-(4-methoxybenzyl)-4-(2-methylallyl)piperidine-4-carbonitrile (500 mg, 1.76 mmol, 1.00 equiv) and THF (10 mL). LAH (753 mg, 19.8 mmol, 4.00 equiv) was added in portions at 0° C. The resulting solution was stirred overnight at rt. The solution was cooled to 0° C. and water (753 mg) was added, followed by 15% aq. NaOH (2.26 g), followed by water (753 mg). The solids were filtered and washed with THF (2×20 mL). The filtrate was concentrated to provide 540 mg (crude) of (1-(4-methoxybenzyl)-4-(2-methylallyl)piperidin-4-yl)methanamine as a colorless oil. LCMS (ESI, m/z): 289 [M+H]$^+$.

Step 5: Synthesis of N-(4-methoxybenzyl)-1-(1-(4-methoxybenzyl)-4-(2-methylallyl)piperidin-4-yl)methanamine

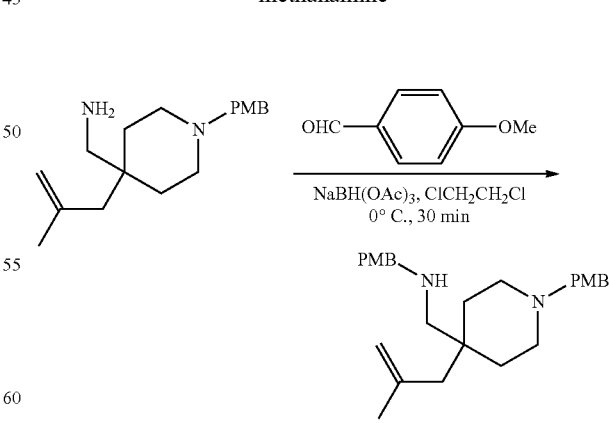

A flask was charged with 4-methoxybenzaldehyde (1.06 g, 7.79 mmol, 1.00 equiv), MeOH (20 mL) and (1-(4-methoxybenzyl)-4-(2-methylallyl)piperidin-4-yl)methanamine (500 mg, 1.73 mmol, 1.00 equiv). Sodium triacetoxyborohydride (178 mg, 4.71 mmol, 2.70 equiv) was added in portions at 0° C. The resulting solution was stirred for 30 min at 0° C., quenched with hydrogen chloride (5 mL, 1 moL/L), and diluted with saturated sodium carbonate (30 mL). The resulting solution was extracted with DCM (3×80 mL) and the organic layers were combined, washed with water (3×20 mL), dried over anhydrous sodium sulfate, filtered, and concentrated. The residue was chromatographed on a silica gel column with DCM/MeOH (10/1) to provide 600 mg (19%) of N-(4-methoxybenzyl)-1-(1-(4-methoxybenzyl)-4-(2-methylallyl)piperidin-4-yl)methanamine as a light yellow oil. LCMS (ESI, m/z): 409 [M+H]⁺.

Step 6: Synthesis of 2,8-bis(4-methoxybenzyl)-3,3-dimethyl-2,8-diazaspiro[4.5]decane

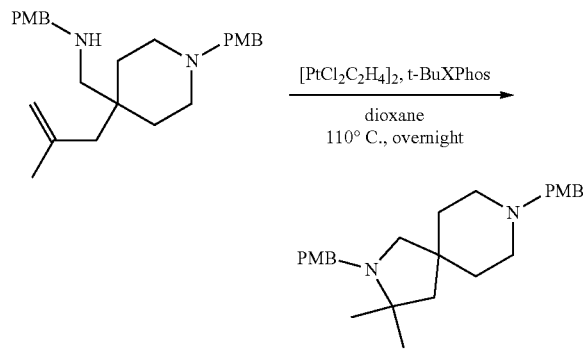

A 3-necked flask purged and maintained with an inert atmosphere of nitrogen, was charged with N-(4-methoxybenzyl)-1-(1-(4-methoxybenzyl)-4-(2-methylallyl)piperidin-4-yl)methanamine (4.56 g, 11.2 mmol, 1.00 equiv), dioxane (50 mL), [Pt(II)Cl$_2$(C$_2$H$_4$)]$_2$ (590 mg, 1.12 mmol, 0.100 equiv) and di-tert-butyl(2',4',6'-triisopropyl-[1,1'-biphenyl]-2-yl)phosphane (1.14 g, 2.69 mmol, 0.240 equiv). The resulting solution was stirred overnight at 110° C. and quenched with water (40 mL). The mixture was extracted with DCM (3×80 mL) and the organic layers were combined, washed with water (3×20 mL), dried over anhydrous sodium sulfate, filtered, and concentrated. The residue was chromatographed on a silica gel column with EtOAc/petroleum ether (4/1) to provide 2.71 g (59% yield) of 2,8-bis(4-methoxybenzyl)-3,3-dimethyl-2,8-diazaspiro[4.5]decane as a brown oil. LCMS (ESI, m/z): 409 [M+H]⁺.

Step 7: Synthesis of 2-(4-methoxybenzyl)-3,3-dimethyl-2,8-diazaspiro[4.5]decane

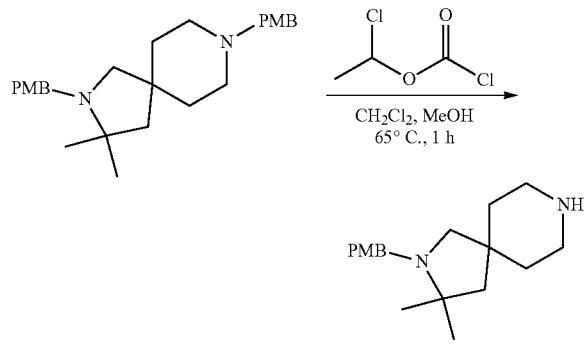

A flask was charged with 2,8-bis(4-methoxybenzyl)-3,3-dimethyl-2,8-diazaspiro[4.5]decane (1.48 g, 3.62 mmol, 1.00 equiv) and DCM (20 mL). 1-Chloroethyl chloroformate (721 mg, 5.04 mmol, 1.40 equiv) was added dropwise at 0° C. The resulting solution was stirred for 30 min at 0° C. and concentrated. MeOH (20 mL) was added, and the resulting solution was stirred for 1 h at 65° C. and concentrated to provide 1.08 g (crude) of 2-(4-methoxybenzyl)-3,3-dimethyl-2,8-diazaspiro[4.5]decane as an off-white solid. LCMS (ESI, m/z): 289 [M+H]⁺.

Step 8: Synthesis of 1,1,1,3,3,3-hexafluoropropan-2-yl 2-(4-methoxybenzyl)-3,3-dimethyl-2,8-diazaspiro[4.5]decane-8-carboxylate

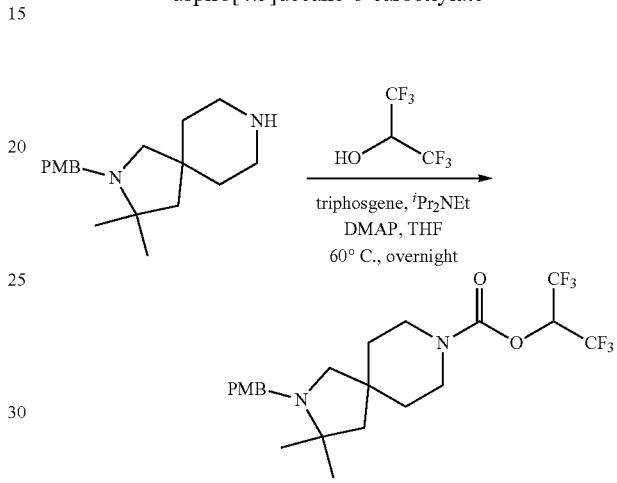

A flask was charged with triphosgene (206 mg, 0.690 mmol, 0.500 equiv), THF (10 mL) and HFIP (350 mg, 2.08 mmol, 1.50 equiv). DIPEA (573 mg, 4.43 mmol, 3.00 equiv) was added dropwise at 0° C. The resulting solution was stirred for 1 h at rt, after which 2-(4-methoxybenzyl)-3,3-dimethyl-2,8-diazaspiro[4.5]decane (400 mg, 1.39 mmol, 1.00 equiv) and DMAP (34.0 mg, 0.280 mmol, 0.200 equiv) were added. The reaction mixture was stirred overnight at 60° C. and quenched with water (40 mL). The resulting solution was extracted with DCM (3×80 mL) and the organic layers were combined, washed with water (3×20 mL), dried over anhydrous sodium sulfate, filtered, and concentrated. The residue was chromatographed on a silica gel column with EtOAc/petroleum ether (1/2) to provide 1.73 g (crude) of 1,1,1,3,3,3-hexafluoropropan-2-yl 2-(4-methoxybenzyl)-3,3-dimethyl-2,8-diazaspiro[4.5]decane-8-carboxylate as a light yellow oil. LCMS (ESI, m/z): 483 [M+H]⁺.

Step 9: Synthesis of 1,1,1,3,3,3-hexafluoropropan-2-yl 3,3-dimethyl-2,8-diazaspiro[4.5]decane-8-carboxylate

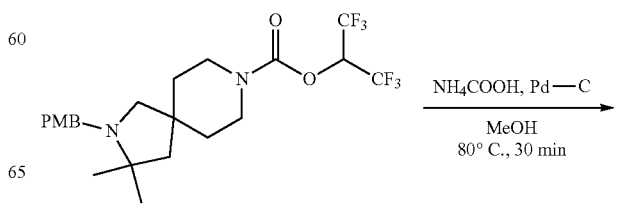

-continued

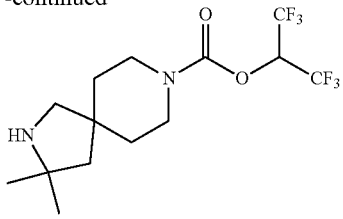

A flask was charged with 1,1,1,3,3,3-hexafluoropropan-2-yl 2-(4-methoxybenzyl)-3,3-dimethyl-2,8-diazaspiro[4.5]decane-8-carboxylate (1.20 g, 2.49 mmol, 1.00 equiv), MeOH (20 mL), ammonium formate (784 mg, 12.4 mmol, 5.00 equiv) and 10% palladium on carbon (1.00 g). The resulting solution was stirred for 30 min at 80° C. The solids were filtered and washed with MeOH (2×20 mL). The filtrate was concentrated to provide 1.0 g (crude) of 1,1,1,3,3,3-hexafluoropropan-2-yl 3,3-dimethyl-2,8-diazaspiro[4.5]decane-8-carboxylate as a light yellow oil. LCMS (ESI, m/z): 363 [M+H]+.

Step 10: Synthesis of 1,1,1,3,3,3-hexafluoropropan-2-yl 2-(2-chloro-3-morpholinobenzyl)-3,3-dimethyl-2,8-diazaspiro[4.5]decane-8-carboxylate

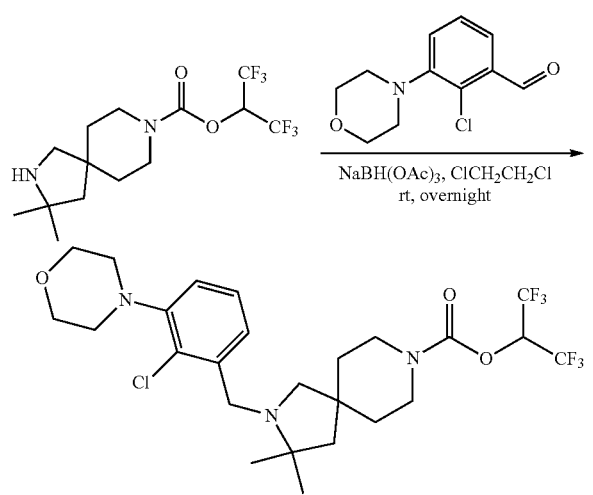

A flask was charged with 2-chloro-3-morpholinobenzaldehyde (62.0 mg, 0.270 mmol, 1.00 equiv), DCE (5 mL), 1,1,1,3,3,3-hexafluoropropan-2-yl 3,3-dimethyl-2,8-diazaspiro[4.5]decane-8-carboxylate (100 mg, 0.280 mmol, 1.00 equiv) and sodium triacetoxyborohydride (175 mg, 0.830 mmol, 3.00 equiv). The reaction mixture was stirred overnight at rt and quenched with water (40 mL). The resulting solution was extracted with DCM (3×80 mL) and the organic layers were combined, washed with water (3×20 mL), dried over anhydrous sodium sulfate, filtered, and concentrated. The residue was purified by preparative HPLC to yield 112.8 mg (72%) of 1,1,1,3,3,3-hexafluoropropan-2-yl 2-(2-chloro-3-morpholinobenzyl)-3,3-dimethyl-2,8-diazaspiro[4.5]decane-8-carboxylate as a colorless oil. 1H NMR (400 MHz, Chloroform-d) δ 7.21-7.30 (m, 2H), 6.91-6.99 (m, 1H), 5.73-5.79 (m, 1H), 3.91 (t, J=4.6 Hz, 4H), 3.67 (s, 2H), 3.42-3.50 (m, 4H), 3.05-3.10 (m, 4H), 2.58 (s, 2H), 1.60-1.67 (m, 6H), 1.65 (s, 6H). LCMS (ESI, m/z): 572 [M+H]+.

Example 186: 1,1,1,3,3,3-Hexafluoropropan-2-yl 2-(3-chloro-5-morpholinobenzyl)-3,3-dimethyl-2,8-diazaspiro[4.5]decane-8-carboxylate

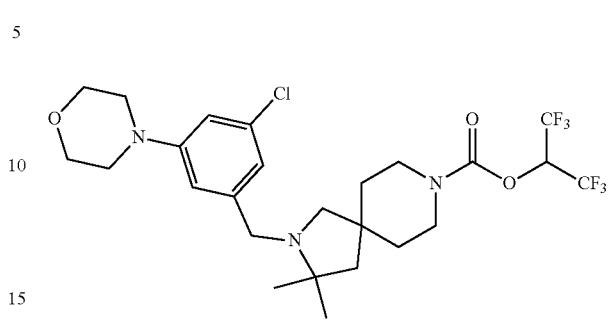

The title compound was synthesized according to the representative procedure of Example 185 using 3-bromo-5-chlorobenzaldehyde as the starting material in Step 1 and 1,1,1,3,3,3-hexafluoropropan-2-yl 3,3-dimethyl-2,8-diazaspiro[4.5]decane-8-carboxylate as the starting material in Step 10. Purification resulted in 84.2 mg (54% yield) of 1,1,1,3,3,3-hexafluoropropan-2-yl 2-(3-chloro-5-morpholinobenzyl)-3,3-dimethyl-2,8-diazaspiro[4.5]decane-8-carboxylate as a light yellow oil. 1H NMR (300 MHz, Chloroform-d) δ 6.85 (s, 1H), 6.74-6.78 (m, 2H), 5.70-5.78 (m, 1H), 3.86 (t, J=4.8 Hz, 4H), 3.39-3.51 (m, 6H), 3.15 (t, J=4.9 Hz, 4H), 2.49 (s, 2H), 1.55-1.64 (m, 6H), 1.12 (s, 6H). LCMS (ESI, m/z): 572 [M+H]+.

Example 187: 1,1,1,3,3,3-Hexafluoropropan-2-yl 2-(5-chloro-2-morpholinobenzyl)-3,3-dimethyl-2,8-diazaspiro[4.5]decane-8-carboxylate

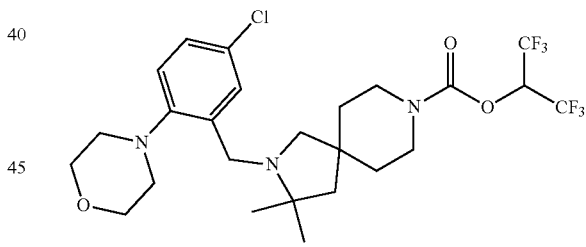

The title compound was synthesized according to the representative procedure of Example 185 using 2-bromo-5-chlorobenzaldehyde as the starting material in Step 1 and 1,1,1,3,3,3-hexafluoropropan-2-yl 3,3-dimethyl-2,8-diazaspiro[4.5]decane-8-carboxylate as the starting material in Step 10. Purification resulted in 88.7 mg of 1,1,1,3,3,3-hexafluoropropan-2-yl 2-(5-chloro-2-morpholinobenzyl)-3,3-dimethyl-2,8-diazaspiro[4.5]decane-8-carboxylate as a white solid. 1H NMR (400 MHz, Chloroform-d) δ 7.53 (d, J=2.4 Hz, 1H), 7.18-7.21 (m, 1H), 7.01 (d, J=8.4 Hz, 1H), 5.73-5.79 (m, 1H), 3.84-3.86 (m, 4H), 3.59 (s, 2H), 3.40-3.51 (m, 4H), 2.85-3.00 (m, 4H), 2.51 (s, 2H), 1.58-1.67 (m, 6H), 1.16 (s, 6H). LCMS (ESI, m/z): 572 [M+H]+.

Example 188: 1,1,1,3,3,3-Hexafluoropropan-2-yl 3,3-dimethyl-2-(3-morpholino-5-(trifluoromethyl)benzyl)-2,8-diazaspiro[4.5]decane-8-carboxylate

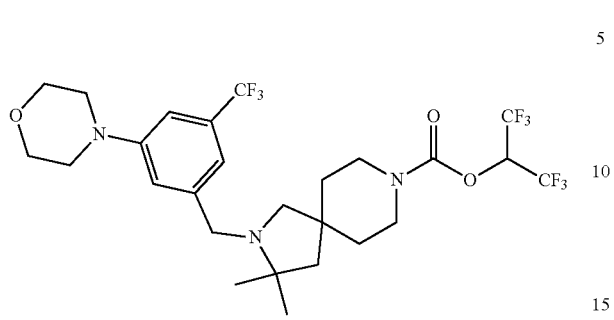

The title compound was synthesized according to the representative procedure of Example 185 using 3-bromo-5-(trifluoromethyl)benzaldehyde as the starting material in Step 1 and 1,1,1,3,3,3-hexafluoropropan-2-yl 3,3-dimethyl-2,8-diazaspiro[4.5]decane-8-carboxylate as the starting material in Step 10. Purification resulted in 92.8 mg of 1,1,1,3,3,3-hexafluoropropan-2-yl 3,3-dimethyl-2-(3-morpholino-5-(trifluoromethyl)benzyl)-2,8-diazaspiro[4.5]decane-8-carboxylate as a light yellow oil. $^1$H NMR (300 MHz, Chloroform-d) δ 7.12 (s, 1H), 7.07 (s, 1H), 6.98 (s, 1H), 5.70-5.78 (m, 1H), 3.88 (t, J=4.8 Hz, 4H), 3.36-3.54 (m, 6H), 3.20 (t, J=4.8 Hz, 4H), 2.49 (s, 2H), 1.55-1.66 (m, 6H), 1.14 (s, 6H). LCMS (ESI, m/z): 606 [M+H]$^+$.

Example 189: 1,1,1,3,3,3-Hexafluoropropan-2-yl 2-(3-chloro-2-(4-methylpiperazin-1-yl)benzyl)-3,3-dimethyl-2,8-diazaspiro[4.5]decane-8-carboxylate

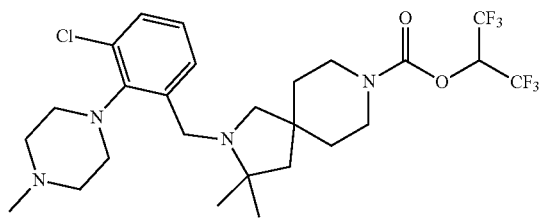 [SMILES: CN1CCN(c2c(Cl)cccc2CN2CC3(CCN(C(=O)OC(C(F)(F)F)C(F)(F)F)CC3)CC2(C)C)CC1]

The title compound was synthesized according to the representative procedure of Example 185 using 2-bromo-3-chlorobenzaldehyde and 1-methylpiperazine in Step 1 and 1,1,1,3,3,3-hexafluoropropan-2-yl 3,3-dimethyl-2,8-diazaspiro[4.5]decane-8-carboxylate in Step 10. Purification resulted in 86.0 mg of 1,1,1,3,3,3-hexafluoropropan-2-yl 2-(3-chloro-2-(4-methylpiperazin-1-yl)benzyl)-3,3-dimethyl-2,8-diazaspiro[4.5]decane-8-carboxylate as a yellow oil. $^1$H NMR (400 MHz, Chloroform-d) δ 7.45 (d, J=7.6 Hz, 1H), 7.21 (d, J=6.8 Hz, 1H), 7.09 (t, J=7.6 Hz, 1H), 5.72-5.78 (m, 1H), 3.61-3.67 (m, 4H), 3.40-3.51 (m, 4H), 2.76-2.90 (m, 5H), 2.30-2.55 (m, 6H), 1.58-1.66 (m, 6H), 1.16 (s, 6H). LCMS (ESI, m/z): 585 [M+H]$^+$.

Example 190: 1,1,1,3,3,3-Hexafluoropropan-2-yl 3,3-dimethyl-2-(2-morpholino-3-(trifluoromethoxy)benzyl)-2,8-diazaspiro[4.5]decane-8-carboxylate

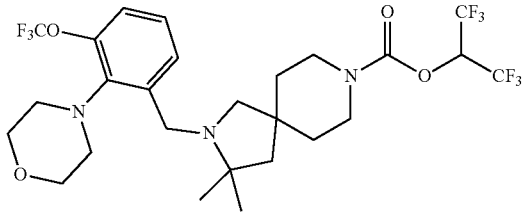 [SMILES: CC1(C)CC2(CCN(C(=O)OC(C(F)(F)F)C(F)(F)F)CC2)CN1Cc1cccc(OC(F)(F)F)c1N1CCOCC1]

Step 1: Synthesis of 2-morpholino-3-(trifluoromethoxy)benzaldehyde

A flask was charged with 2-fluoro-3-(trifluoromethoxy)benzaldehyde (208 mg, 1.00 mmol, 1.00 equiv), DMSO (5 mL), morpholine (174 mg, 2.00 mmol, 2.00 equiv) and potassium carbonate (414 mg, 3.00 mmol, 3.00 equiv) under nitrogen. The reaction mixture was stirred overnight at 80° C. and quenched with water (40 mL). The resulting solution was extracted with DCM (3×80 mL) and the organic layers were combined, washed with water (3×20 mL), dried over anhydrous sodium sulfate, filtered, and concentrated. The residue was chromatographed on a silica gel column with EtOAc/petroleum ether (1/5) to provide 50 mg (18% yield) of 2-morpholino-3-(trifluoromethoxy)benzaldehyde as a light yellow oil.

Step 2: Synthesis of 1,1,1,3,3,3-hexafluoropropan-2-yl 3,3-dimethyl-2-(2-morpholino-3-(trifluoromethoxy)benzyl)-2,8-diazaspiro[4.5]decane-8-carboxylate

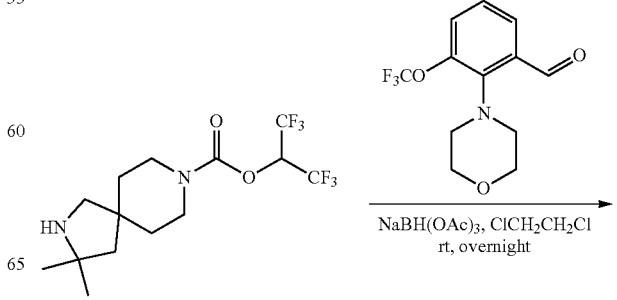

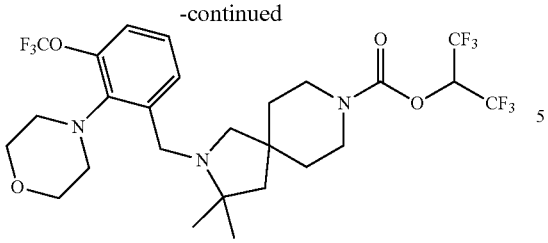

A flask was charged with 1,1,1,3,3,3-hexafluoropropan-2-yl 3,3-dimethyl-2,8-diazaspiro[4.5]decane-8-carboxylate (66.0 mg, 0.180 mmol, 1.00 equiv), and DCE (3 mL), 2-morpholino-3-(trifluoromethoxy)benzaldehyde (50.0 mg, 0.180 mmol, 1.00 equiv). The mixture was stirred for 1 h at rt, followed by addition of sodium triacetoxyborohydride (115 mg, 0.540 mmol, 3.00 equiv). The reaction mixture was stirred overnight at rt before quenching with water (40 mL). The resulting solution was extracted with DCM (3×80 mL) and the organic layers were combined, washed with water (3×20 mL), dried over anhydrous sodium sulfate, filtered, and concentrated. The residue was purified by preparative HPLC to give 8.1 mg (7% yield) of 1,1,1,3,3,3-hexafluoropropan-2-yl 3,3-dimethyl-2-(2-morpholino-3-(trifluoromethoxy)benzyl)-2,8-diazaspiro[4.5]decane-8-carboxylate as a colorless oil. $^1$H NMR (300 MHz, Chloroform-d) δ 7.44-7.47 (m, 1H), 7.09-7.17 (m, 2H), 5.69-5.77 (m, 1H), 3.67-3.90 (m, 6H), 3.20-3.50 (m, 6H), 2.60-3.00 (m, 2H), 2.48 (s, 2H), 1.56-1.65 (m, 6H), 1.14 (s, 6H). LCMS (ESI, m/z): 622 [M+H]$^+$.

Example 191: 1,1,1,3,3,3-Hexafluoropropan-2-yl 2-(2-fluoro-3-(morpholinomethyl)benzyl)-3,3-dimethyl-2,8-diazaspiro[4.5]decane-8-carboxylate

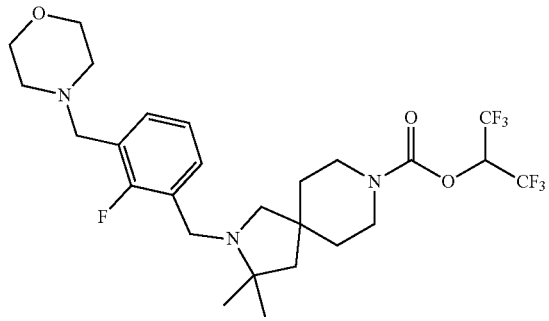 [SMILES: CC1(C)CC2(CCN(C(=O)OC(C(F)(F)F)C(F)(F)F)CC2)CN1Cc1cccc(CN2CCOCC2)c1F]

Step 1: Synthesis of 2-fluoro-3-(morpholinomethyl)benzaldehyde

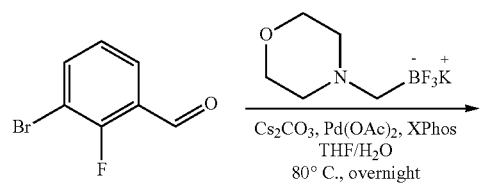

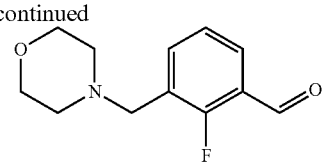

A flask was charged with 3-bromo-2-fluorobenzaldehyde (202 mg, 1.00 mmol, 1.00 equiv), THF (12 mL), water (3 mL), potassium (morpholin-4-yl)methyltrifluoroborate (248 mg, 1.20 mmol, 1.20 equiv), palladium acetate (7.00 mg, 0.030 mmol, 0.03 equiv), XPhos (29.0 mg, 0.0600 mmol, 0.06 equiv), and cesium carbonate (987 mg, 3.03 mmol, 3.00 equiv) under nitrogen. The reaction mixture was stirred overnight at 80° C. and quenched with water (40 mL). The resulting solution was extracted with DCM (3×80 mL) and the organic layers were combined, washed with water (3×20 mL), dried over anhydrous sodium sulfate, filtered, and concentrated. The residue was chromatographed on a silica gel column with EtOAc/petroleum ether (1/3) to provide 150 mg (68% yield) of 2-fluoro-3-(morpholinomethyl)benzaldehyde as a light yellow oil.

Step 2: Synthesis of 1,1,1,3,3,3-hexafluoropropan-2-yl 2-(2-fluoro-3-(morpholinomethyl)benzyl)-3,3-dimethyl-2,8-diazaspiro[4.5]decane-8-carboxylate

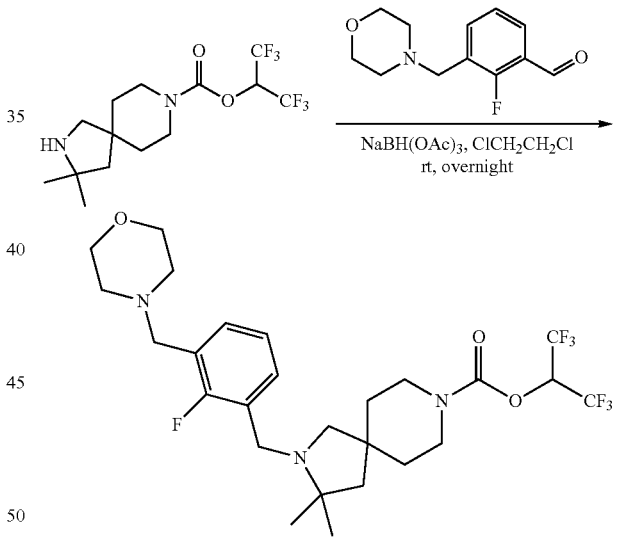

A flask was charged with 2-fluoro-3-(morpholinomethyl)benzaldehyde (49.0 mg, 0.220 mmol, 1.00 equiv), DCE (10 mL) and 1,1,1,3,3,3-hexafluoropropan-2-yl 3,3-dimethyl-2,8-diazaspiro[4.5]decane-8-carboxylate (80.0 mg, 0.220 mmol, 1.00 equiv). The mixture was stirred for 1 h at rt, followed by addition of sodium triacetoxyborohydride (141 mg, 0.670 mmol, 3.00 equiv). The reaction mixture was stirred overnight at rt before quenching with water (40 mL). The resulting solution was extracted with DCM (3×80 mL) and the organic layers were combined, washed with water (3×20 mL), dried over anhydrous sodium sulfate, filtered, and concentrated. The residue was purified by preparative HPLC to give 56.3 mg (45% yield) of 1,1,1,3,3,3-hexafluoropropan-2-yl 2-(2-fluoro-3-(morpholinomethyl)benzyl)-3,3-dimethyl-2,8-diazaspiro[4.5]decane-8-carboxylate as a light brown oil. ¹H NMR (300 MHz, Chloroform-d) δ 7.26-7.32 (m, 1H), 7.21-7.25 (m, 1H), 7.04-7.09 (m, 1H), 5.68-5.77 (m, 1H), 3.70-3.73 (m, 4H), 3.55-3.65 (m, 4H), 3.35-3.50 (m, 4H), 2.49-2.54 (m, 6H), 1.50-1.70 (m, 6H), 1.05-1.20 (s, 6H). LCMS (ESI, m/z): 570 [M+H]⁺.

Example 192: 1,1,1,3,3,3-Hexafluoropropan-2-yl 3,3-dimethyl-2-(5-(morpholinomethyl)-2-(trifluoromethoxy)benzyl)-2,8-diazaspiro[4.5]decane-8-carboxylate

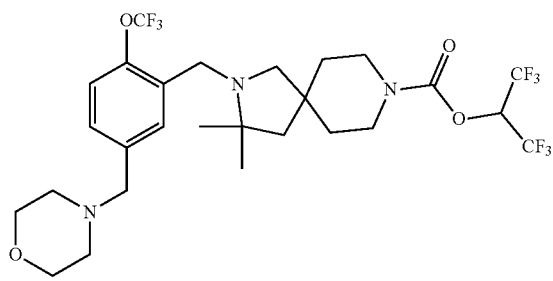 [SMILES: CC1(C)CC2(CCN(C(=O)OC(C(F)(F)F)C(F)(F)F)CC2)CN1Cc1cc(CN2CCOCC2)ccc1OC(F)(F)F]

Step 1: Synthesis of 4-(3-bromo-4-(trifluoromethoxy)benzyl)morpholine

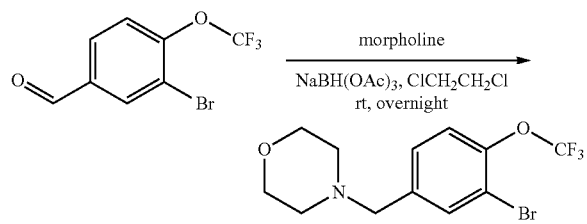

A flask was charged with 3-bromo-4-(trifluoromethoxy)benzaldehyde (804 mg, 2.99 mmol, 1.00 equiv), DCE (10 mL) and morpholine (261 mg, 3.00 mmol, 1.10 equiv). The resulting solution was stirred for 1 h at rt, followed by the addition of sodium triacetoxyborohydride (1.91 g, 9.01 mmol, 3.00 equiv). The mixture was stirred overnight at rt and quenched with water (40 mL). The resulting solution was extracted with DCM (3×40 mL) and the organic layers were combined, washed with water (3×20 mL), dried over anhydrous sodium sulfate, filtered, and concentrated. The residue was chromatographed on a silica gel column with EtOAc/petroleum ether (1/3) to provide 920 mg (91% yield) of 4-(3-bromo-4-(trifluoromethoxy)benzyl)morpholine as a colorless oil. LCMS (ESI, m/z): 340 [M+H]⁺.

Step 2: Synthesis of 5-(morpholinomethyl)-2-(trifluoromethoxy)benzaldehyde

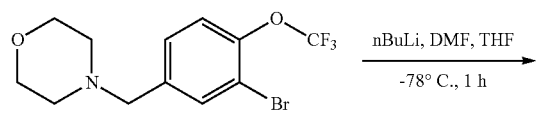

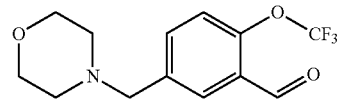

A 3-necked round-bottom flask was charged with 4-(3-bromo-4-(trifluoromethoxy)benzyl)morpholine (200 mg, 0.590 mmol, 1.00 equiv) and THF (5 mL) under nitrogen. Then n-butyllithium (0.501 mL, 2.0 M in hexane, 1.50 equiv) was added dropwise at −78° C. The resulting solution was stirred for 30 min at −78° C., and DMF (86.0 mg, 1.18 mmol, 2.00 equiv) was added. The resulting solution was stirred for 1 h at −78° C. and quenched with saturated ammonium chloride (20 mL). The mixture was extracted with DCM (3×50 mL) and the organic layers were combined, washed with water (3×20 mL), dried over anhydrous sodium sulfate, filtered, and concentrated. The residue was chromatographed on a silica gel column with EtOAc/petroleum ether (1/1) to provide 80.0 mg (47% yield) of 5-(morpholinomethyl)-2-(trifluoromethoxy)benzaldehyde as a light yellow oil. LCMS (ESI, m/z): 290 [M+H]⁺.

Step 3: Synthesis of 1,1,1,3,3,3-hexafluoropropan-2-yl 3,3-dimethyl-2-(5-(morpholinomethyl)-2-(trifluoromethoxy)benzyl)-2,8-diazaspiro[4.5]decane-8-carboxylate

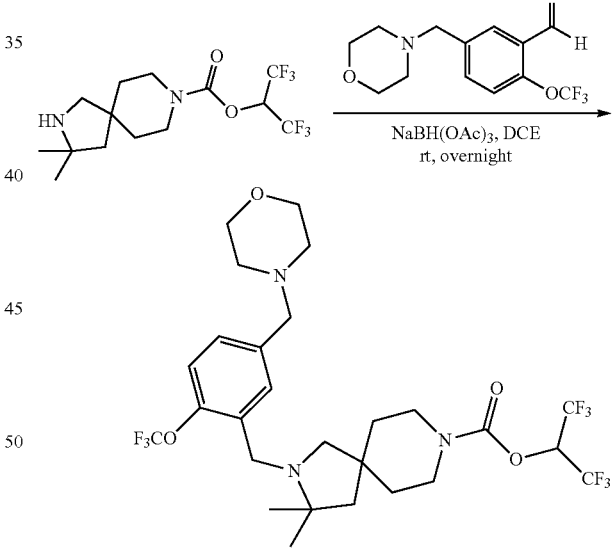

The title compound was synthesized according to the representative procedure of Example 185, Steps 2-10, using 5-(morpholinomethyl)-2-(trifluoromethoxy)benzaldehyde in Step 10 to afford 18.4 mg (10% yield) of 1,1,1,3,3,3-hexafluoropropan-2-yl 3,3-dimethyl-2-(5-(morpholinomethyl)-2-(trifluoromethoxy)benzyl)-2,8-diazaspiro[4.5]decane-8-carboxylate as a light yellow oil. ¹H NMR (300 MHz, Chloroform-d) δ 7.47 (s, 1H), 7.12-7.26 (m, 2H), 5.66-5.78 (m, 1H), 3.71-3.80 (m, 4H), 3.36-3.57 (m, 8H), 2.30-2.60 (m, 6H), 1.40-1.80 (m, 6H), 1.00-1.25 (m, 6H). LCMS (ESI, m/z): 636 [M+H]⁺.

Example 193: 1,1,1,3,3,3-Hexafluoropropan-2-yl 1-(2-(3-(methylsulfonyl)pyrrolidin-1-yl)-4-(trifluoromethyl)benzyl)-1,8-diazaspiro[4.5]decane-8-carboxylate

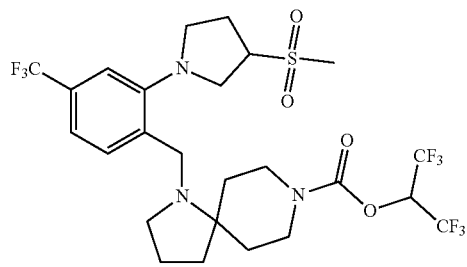 [SMILES: CS(=O)(=O)C1CCN(c2cc(C(F)(F)F)ccc2CN2CCCC23CCN(C(=O)OC(C(F)(F)F)C(F)(F)F)CC3)C1]

Step 1: Synthesis of sodium (2-fluoro-4-(trifluoromethyl)phenyl)(hydroxy)methanesulfonate

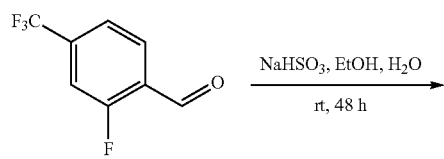

A flask was charged with 2-fluoro-4-(trifluoromethyl)benzaldehyde (2.00 g, 10.4 mmol, 1.00 equiv), EtOH (30 mL), saturated sodium bisulfite aqueous solution (2.5 mL), and water. The resulting solution was stirred for 48 h at rt and cooled to 0° C. and tert-butyl methyl ether was added. The solids were collected by filtration to provide 2.45 g (79% yield) of sodium (2-fluoro-4-(trifluoromethyl)phenyl)(hydroxy)methanesulfonate as a white solid. LCMS (ESI, m/z): 297 [M+H]⁺.

Step 2: Synthesis of 2-(3-(methylsulfonyl)pyrrolidin-1-yl)-4-(trifluoromethyl)benzaldehyde

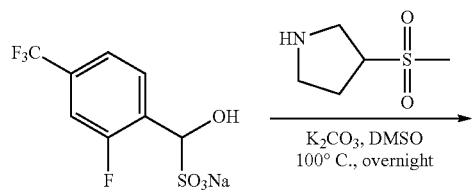

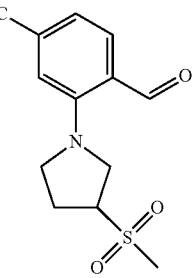

A flask was charged with sodium (2-fluoro-4-(trifluoromethyl)phenyl)(hydroxy)methanesulfonate (500 mg, 1.69 mmol, 1.00 equiv), 3-methanesulfonylpyrrolidine (378 mg, 2.53 mmol, 1.50 equiv), potassium carbonate (932 mg, 6.74 mmol, 4.00 equiv), and DMSO (5 mL) under nitrogen. The reaction mixture was stirred overnight at 100° C. before quenching with water (50 mL). The resulting solution was extracted with EtOAc (3×50 mL) and the organic layers were combined, washed with brine (50 mL), dried over anhydrous sodium sulfate, filtered and concentrated. The residue was chromatographed on a silica gel column to provide 190 mg (35% yield) of 2-(3-methanesulfonylpyrrolidin-1-yl)-4-(trifluoromethyl)benzaldehyde. LCMS (ESI, m/z): 322 [M+H]⁺.

Step 3: Synthesis of 1,1,1,3,3,3-hexafluoropropan-2-yl 1-(2-(3-(methylsulfonyl)pyrrolidin-1-yl)-4-(trifluoromethyl)benzyl)-1,8-diazaspiro[4.5]decane-8-carboxylate

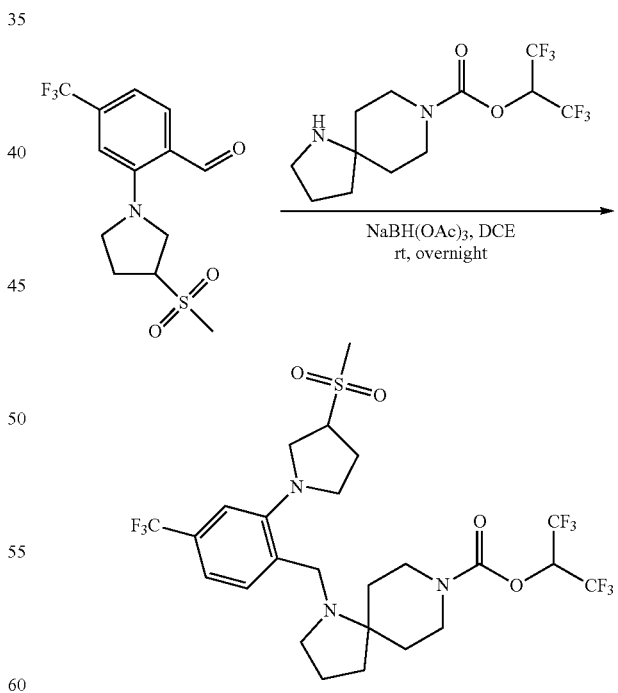

A flask was charged with 2-(3-methanesulfonylpyrrolidin-1-yl)-4-(trifluoromethyl)benzaldehyde (90.0 mg, 0.280 mmol, 1.00 equiv), 1,1,1,3,3,3-hexafluoropropan-2-yl 1,8-diazaspiro[4.5]decane-8-carboxylate (140 mg, 0.420 mmol, 1.50 equiv), and DCE (3 mL). The resulting solution was stirred for 1 h at rt prior to addition of sodium triacetoxyborohydride (238 mg, 1.12 mmol, 4.00 equiv). The reaction mixture was stirred overnight at rt and quenched with water (20 mL). The resulting mixture was extracted with DCM (3×20 mL) and the organic layers were combined, washed with brine (20 mL), dried over anhydrous sodium sulfate, filtered and concentrated. The residue was purified by preparative HPLC to yield 69.4 mg (39% yield) of 1,1,1,3,3,3-hexafluoropropan-2-yl 1-(2-(3-(methylsulfonyl)pyrrolidin-1-yl)-4-(trifluoromethyl)benzyl)-1,8-diazaspiro[4.5]decane-8-carboxylate. $^1$H NMR (300 MHz, Chloroform-d) δ 7.67-7.70 (m, 1H), 7.28-7.31 (m, 1H), 7.24 (br, 1H), 5.72-5.80 (m, 1H), 4.17-4.26 (m, 2H), 3.57-3.77 (m, 4H), 3.44-3.50 (m, 1H), 3.22-3.32 (m, 2H), 2.94-3.06 (m, 5H), 2.63-2.65 (m, 2H), 2.40-2.49 (m, 2H), 1.65-1.88 (m, 5H), 1.53-1.56 (m, 3H). LCMS (ESI, m/z): 640 [M+H]$^+$.

Example 194: 1-(3-Chloro-5-((8-(((1,1,1,3,3,3-hexafluoropropan-2-yl)oxy)carbonyl)-1,8-diazaspiro[4.5]decan-1-yl)methyl)benzyl)piperidine-4-carboxylic acid

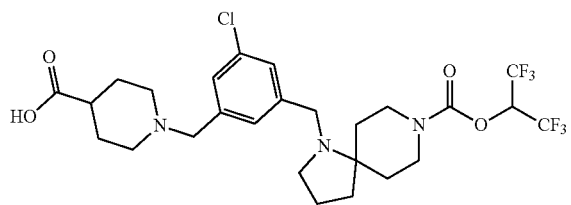 [SMILES: O=C(O)C1CCN(Cc2cc(Cl)cc(CN3CCCC34CCN(C(=O)OC(C(F)(F)F)C(F)(F)F)CC4)c2)CC1]

Step 1: Synthesis of potassium ((4-(tert-butoxycarbonyl)piperidin-1-yl)methyl)trifluoroborate

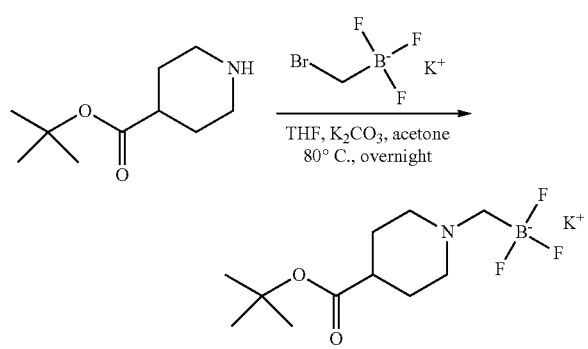

A flask was charged with tert-butyl piperidine-4-carboxylate (7.00 g, 37.8 mmol, 1.00 equiv), potassium (bromomethyl)trifluoroboranate (7.60 g, 37.8 mmol, 1.00 equiv), and THF (70 mL). The reaction mixture was stirred overnight at 80° C. and concentrated. Acetone (70 mL) and potassium carbonate (5.22 g, 37.8 mmol, 1.00 equiv) were added. The resulting solution was stirred for 1.5 h at rt before the solids were filtered. The filtrate was concentrated and then triturated with acetone/hexane to provide 6.50 g (56% yield) of potassium ((4-(tert-butoxycarbonyl)piperidin-1-yl)methyl)trifluoroborate as a yellow semi-solid. LCMS (ESI, m/z): 266 [M−K]$^-$.

Step 2: Synthesis of tert-butyl 1-(3-chloro-5-formylbenzyl)piperidine-4-carboxylate

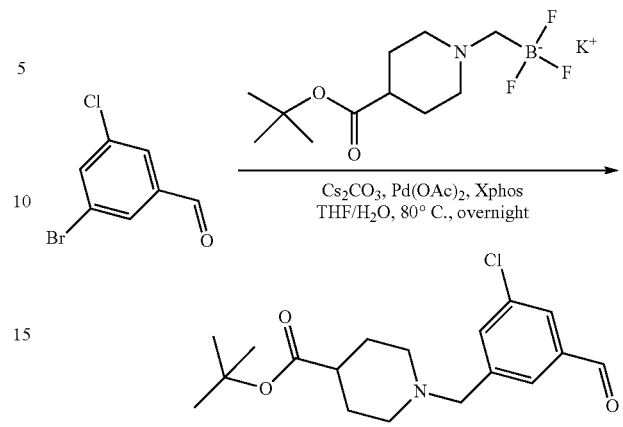

A flask was placed 3-bromo-5-chlorobenzaldehyde (431 mg, 1.96 mmol, 1.20 equiv), potassium ((4-(tert-butoxycarbonyl)piperidin-1-yl)methyl)trifluoroborate (500 mg, 1.64 mmol, 1.00 equiv), cesium carbonate (1.60 g, 4.91 mmol, 3.00 equiv), palladium acetate (11.1 mg, 0.0493 mmol, 0.03 equiv), XPhos (46.9 mg, 0.0983 mmol, 0.06 equiv), THF (8 mL), and water (2 mL) under nitrogen. The reaction mixture was stirred overnight at 80° C. and quenched with water (10 mL). The resulting solution was extracted with DCM (3×20 mL) and the organic layers were combined, washed with brine (2×5 mL), dried over anhydrous sodium sulfate, filtered and concentrated. The residue was chromatographed on a silica gel column to provide 260 mg (47% yield) of tert-butyl 1-(3-chloro-5-formylbenzyl)piperidine-4-carboxylate. LCMS (ESI, m/z): 338 [M+H]$^+$.

Step 3: Synthesis of 1,1,1,3,3,3-hexafluoropropan-2-yl 1-(3-((4-(tert-butoxycarbonyl)piperidin-1-yl)methyl)-5-chlorobenzyl)-1,8-diazaspiro[4.5]decane-8-carboxylate

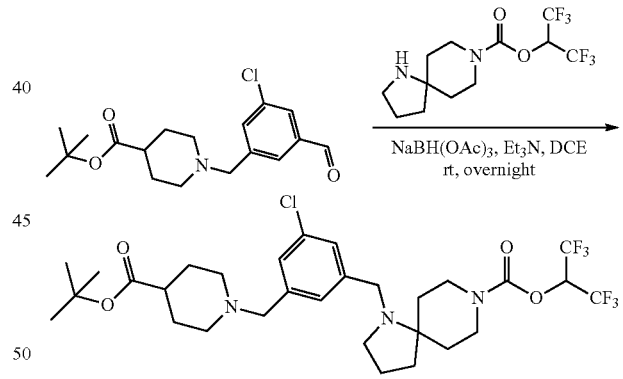

A flask was charged with tert-butyl 1-(3-chloro-5-formylbenzyl)piperidine-4-carboxylate (260 mg, 0.769 mmol, 1.50 equiv), 1,1,1,3,3,3-hexafluoropropan-2-yl 1,8-diazaspiro[4.5]decane-8-carboxylate (173 mg, 0.518 mmol, 1.00 equiv), TEA (157 mg, 1.55 mmol, 3.00 equiv), and DCE (5 mL). The reaction mixture was stirred for 30 min at rt prior to addition of sodium triacetoxyborohydride (329 mg, 1.55 mmol, 3.00 equiv). The resulting solution was stirred overnight at rt and quenched with water (5 mL). The mixture was extracted with DCM (3×10 mL) and the organic layers were combined, washed with brine (2×5 mL), dried over anhydrous sodium sulfate, filtered and concentrated. The residue was chromatographed on a silica gel column to provide 168 mg (49% yield) of 1,1,1,3,3,3-hexafluoropropan-2-yl 1-(3-((4-(tert-butoxycarbonyl)piperidin-1-yl)methyl)-5-chlorobenzyl)-1,8-diazaspiro[4.5]decane-8-carboxylate. LCMS (ESI, m/z): 656 [M+H]$^+$.

Step 4: Synthesis of 1-(3-chloro-5-((8-(((1,1,1,3,3,3-hexafluoropropan-2-yl)oxy)carbonyl)-1,8-diazaspiro[4.5]decan-1-yl)methyl)benzyl)piperidine-4-carboxylic acid

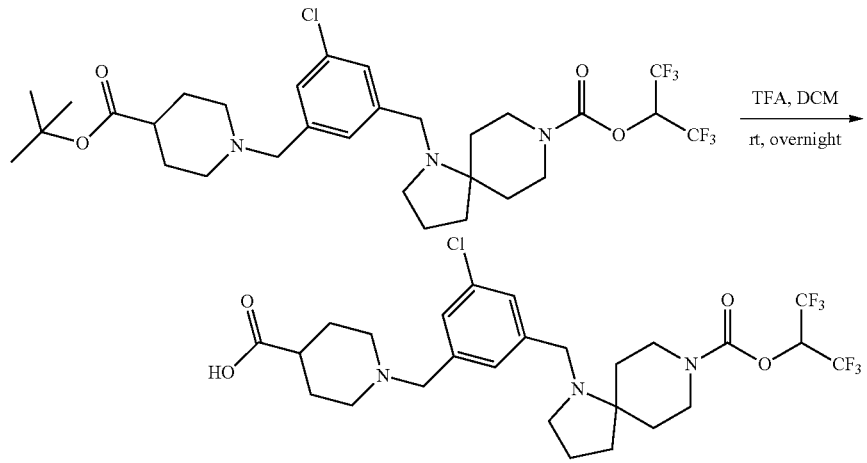

A flask was charged with 1,1,1,3,3,3-hexafluoropropan-2-yl 1-(3-((4-(tert-butoxycarbonyl)piperidin-1-yl)methyl)-5-chlorobenzyl)-1,8-diazaspiro[4.5]decane-8-carboxylate (168 mg, 0.256 mmol, 1.00 equiv), DCM (4 mL), and TFA (1 mL). The resulting solution was stirred overnight at rt and concentrated. The residue was diluted with sodium bicarbonate (20% aqueous, 5 mL), and the resulting solution was extracted with DCM (3×10 mL). Organic layers were combined, washed with brine (2×5 mL), dried over anhydrous sodium sulfate, filtered and concentrated. The residue was purified by preparative HPLC to afford 57.8 mg (38% yield) of 1-(3-chloro-5-((8-(((1,1,1,3,3,3-hexafluoropropan-2-yl)oxy)carbonyl)-1,8-diazaspiro[4.5]decan-1-yl)methyl)benzyl)piperidine-4-carboxylic acid as a white semi-solid. $^1$H NMR (300 MHz, Methanol-$d_4$) δ 7.36-7.39 (m, 3H), 6.10-6.14 (m, 1H), 4.16-4.20 (m, 2H), 3.98 (br, 2H), 3.66 (br, 2H), 3.04-3.32 (m, 4H), 2.65-2.74 (m, 4H), 2.32 (br, 1H), 1.73-2.03 (m, 10H), 1.53-1.58 (m, 2H). LCMS (ESI, m/z): 600 [M+H]$^+$.

Example 195: 4-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2-methylmorpholine-2-carboxylic acid

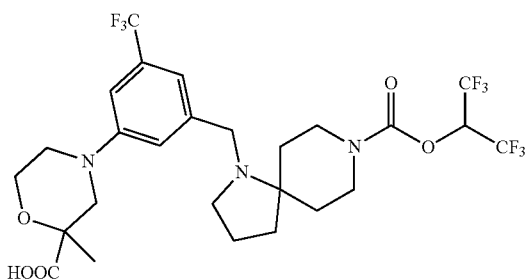 [SMILES: CC1(C(=O)O)CN(c2cc(CN3CCCC34CCN(C(=O)OC(C(F)(F)F)C(F)(F)F)CC4)cc(C(F)(F)F)c2)CCO1]

Step 1: Synthesis of 4-(tert-butyl) 2-ethyl 2-methylmorpholine-2,4-dicarboxylate

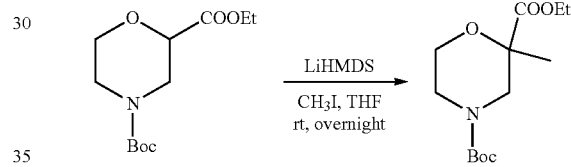

A flask was charged with 4-tert-butyl 2-ethyl morpholine-2,4-dicarboxylate (8.00 g, 31.0 mmol, 1.00 equiv) and THF (80 mL) under nitrogen. Lithium bis(trimethylsilyl)amide (93.0 mL, 93.0 mmol, 3.00 equiv, 1M in THF) was added dropwise over 1 h at −78° C. The mixture was stirred for 30 min at −78° C. and iodomethane (13.2 g, 93.0 mmol, 3.00 equiv) was added dropwise over 20 min. The reaction mixture was stirred overnight at rt and quenched with saturated NH$_4$Cl solution (50 ml). The resulting solution was extracted with EtOAc (2×80 mL) and the organic layers were combined, washed with brine (2×50 mL), dried over anhydrous sodium sulfate, filtered and concentrated. The residue was chromatographed on a silica gel column to provide 5.00 g (59% yield) of 4-(tert-butyl) 2-ethyl 2-methylmorpholine-2,4-dicarboxylate. LCMS (ESI, m/z): 274 [M+H]$^+$.

Step 2: Synthesis of ethyl 2-methylmorpholine-2-carboxylate

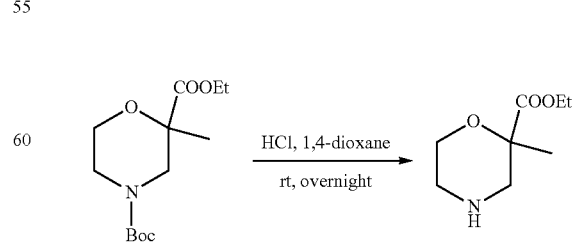

A flask was charged with 4-tert-butyl 2-ethyl 2-methylmorpholine-2,4-dicarboxylate (3.00 g, 11.0 mmol, 1.00 equiv), 1,4-dioxane (15 mL), and concentrated hydrochloric acid (4 mL). The resulting solution was stirred overnight at rt and concentrated to provide 2.50 g (crude) of ethyl 2-methylmorpholine-2-carboxylate. LCMS (ESI, m/z): 174 [M+H]+.

Step 3: Synthesis of ethyl 4-(3-formyl-5-(trifluoromethyl)phenyl)-2-methylmorpholine-2-carboxylate

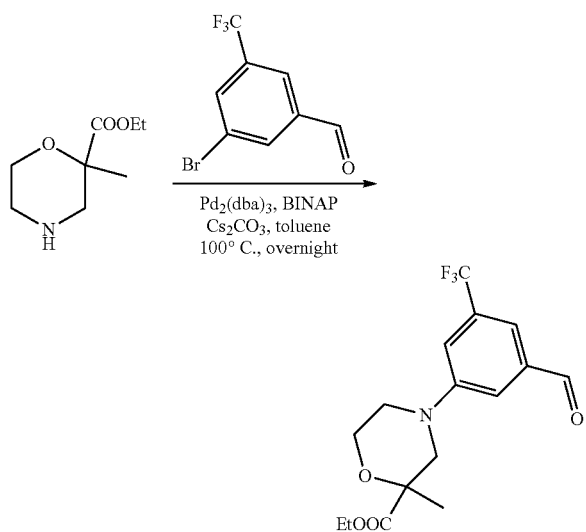

A flask was charged with 3-bromo-5-(trifluoromethyl) benzaldehyde (1.30 g, 5.16 mmol, 1.00 equiv), toluene (15 mL), ethyl 2-methylmorpholine-2-carboxylate (1.78 g, 10.3 mmol, 2.00 equiv), tris(dibenzylideneacetone)dipalladium (0.708 g, 0.774 mmol, 0.15 equiv), 2,2'-bis(diphenylphosphino)-1,1'-binaphthyl (1.44 g, 2.32 mmol, 0.45 equiv), and cesium carbonate (5.05 g, 15.5 mmol, 3.00 equiv) under nitrogen. The reaction mixture was stirred overnight at 100° C. and quenched with water (50 mL). The resulting mixture was extracted with DCM (2×80 mL) and the organic layers were combined, washed with brine (2×50 mL), dried over anhydrous sodium sulfate, filtered and concentrated. The residue was chromatographed on a silica gel column to provide 0.640 g (36% yield) of ethyl 4-(3-formyl-5-(trifluoromethyl)phenyl)-2-methylmorpholine-2-carboxylate. LCMS (ESI, m/z): 346 [M+H]+.

Step 4: Synthesis of ethyl 4-(3-((8-(tert-butoxycarbonyl)-1,8-diazaspiro[4.5]decan-1-yl)methyl)-5-(trifluoromethyl)phenyl)-2-methylmorpholine-2-carboxylate

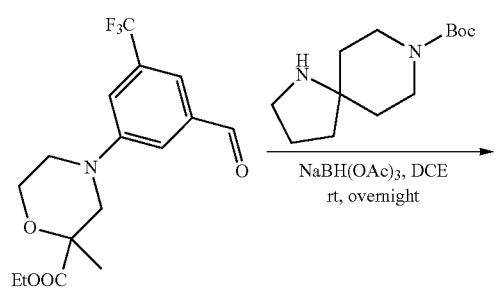

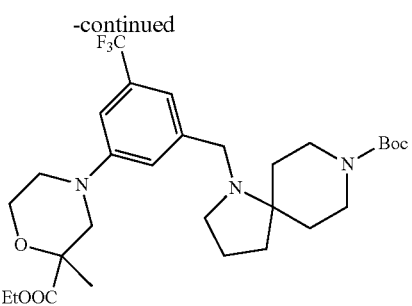

A flask was charged with ethyl 4-(3-formyl-5-(trifluoromethyl)phenyl)-2-methylmorpholine-2-carboxylate (0.840 g, 2.43 mmol, 1.00 equiv), DCE (20 mL), and tert-butyl 1,8-diazaspiro[4.5]decane-8-carboxylate (0.700 g, 2.91 mmol, 1.20 equiv). The mixture was stirred for 1 h at rt prior to the addition of sodium triacetoxyborohydride (1.55 g, 7.29 mmol, 3.00 equiv). The reaction mixture was stirred overnight at rt and quenched with water (50 mL). The resulting solution was extracted with DCM (2×80 mL) and the organic layers were combined, washed with brine (2×50 mL), dried over anhydrous sodium sulfate, filtered and concentrated. The residue was chromatographed on a silica gel column to provide 1.20 g (87% yield) of ethyl 4-(3-((8-(tert-butoxycarbonyl)-1,8-diazaspiro[4.5]decan-1-yl)methyl)-5-(trifluoromethyl)phenyl)-2-methylmorpholine-2-carboxylate. LCMS (ESI, m/z): 570 [M+H]+.

Step 5: Synthesis of 4-(3-((8-(tert-butoxycarbonyl)-1,8-diazaspiro[4.5]decan-1-yl)methyl)-5-(trifluoromethyl)phenyl)-2-methylmorpholine-2-carboxylic acid

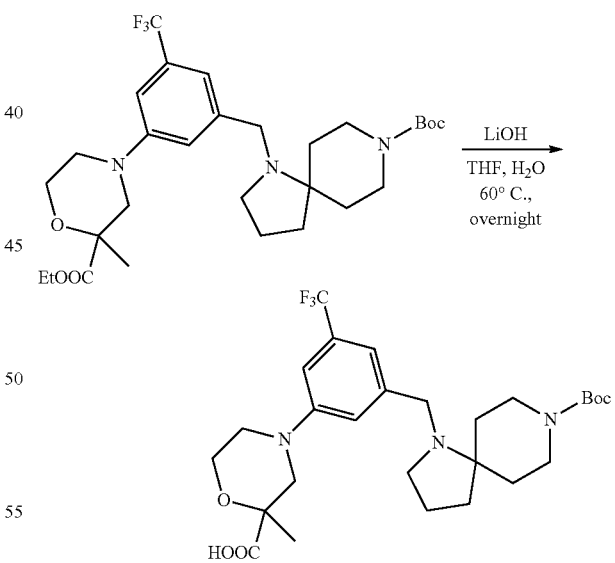

A flask was charged with ethyl 4-(3-((8-(tert-butoxycarbonyl)-1,8-diazaspiro[4.5]decan-1-yl)methyl)-5-(trifluoromethyl)phenyl)-2-methylmorpholine-2-carboxylate (1.20 g, 2.11 mmol, 1.00 equiv), THF (10 mL), water (10 mL), and lithium hydroxide (0.761 g, 31.7 mmol, 15.0 equiv). The reaction mixture was stirred overnight at 60° C. The pH value of the solution was adjusted to 5 with hydrochloric acid (1 M). The resulting solution was extracted with DCM (2×50 mL) and the organic layers were combined, washed with brine (2×30 mL), dried over anhydrous sodium sulfate, filtered and concentrated to provide 1.00 g (88% yield) of 4-(3-((8-(tert-butoxycarbonyl)-1,8-diazaspiro[4.5]decan-1-yl)methyl)-5-(trifluoromethyl)phenyl)-2-methylmorpholine-2-carboxylic acid. LCMS (ESI, m/z): 542 [M+H]$^+$.

Step 6: Synthesis of 4-(3-((1,8-diazaspiro[4.5]decan-1-yl)methyl)-5-(trifluoromethyl)phenyl)-2-methylmorpholine-2-carboxylic acid

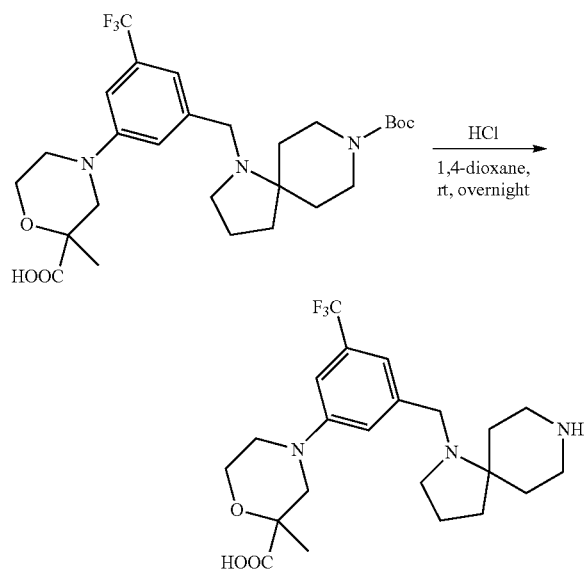

A flask was charged with 4-(3-((8-(tert-butoxycarbonyl)-1,8-diazaspiro[4.5]decan-1-yl)methyl)-5-(trifluoromethyl)phenyl)-2-methylmorpholine-2-carboxylic acid (1.00 g, 1.85 mmol, 1.00 equiv), 1,4-dioxane (10 mL), and concentrated hydrochloric acid (3 mL). The resulting solution was stirred overnight at rt and concentrated to provide 1.20 g (crude) of 4-(3-((1,8-diazaspiro[4.5]decan-1-yl)methyl)-5-(trifluoromethyl)phenyl)-2-methylmorpholine-2-carboxylic acid. LCMS (ESI, m/z): 442 [M+H]$^+$.

Step 7: Synthesis of 4-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2-methylmorpholine-2-carboxylic acid

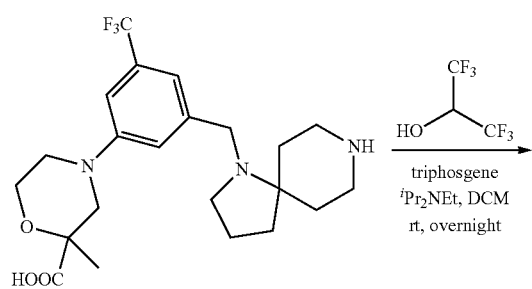

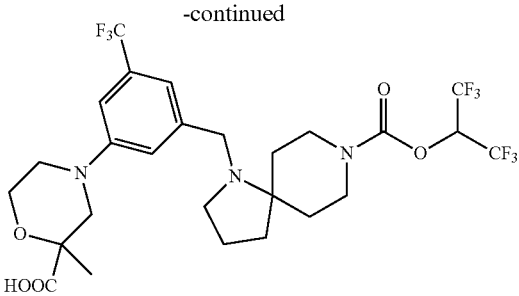

A flask was charged with triphosgene (377 mg, 1.27 mmol, 0.70 equiv), DCM (15 mL), and HFIP (608 mg, 3.62 mmol, 2.00 equiv). DIPEA (700 mg, 5.43 mmol, 3.00 equiv) was added at 0° C. The mixture was stirred for 1 h at rt. 4-(3-((1,8-Diazaspiro[4.5]decan-1-yl)methyl)-5-(trifluoromethyl)phenyl)-2-methylmorpholine-2-carboxylic acid (800 mg, 1.81 mmol, 1.00 equiv) was added. The reaction mixture was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was purified by preparative HPLC to afford 258.1 mg (22% yield) of 4-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2-methylmorpholine-2-carboxylic acid as a white solid. $^1$H NMR (300 MHz, Methanol-d$_4$) δ 7.24 (s, 1H), 7.12 (br, 2H), 6.13-6.17 (m, 1H), 4.06-4.23 (m, 4H), 3.93 (s, 2H), 3.80-3.84 (m, 1H), 3.32-3.35 (m, 1H), 2.70-3.15 (m, 6H), 1.93-2.10 (m, 6H), 1.68-1.73 (m, 2H), 1.39 (s, 3H). LCMS (ESI, m/z): 636 [M+H]$^+$.

Example 196: (S)-1-(3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)piperidine-2-carboxylic acid

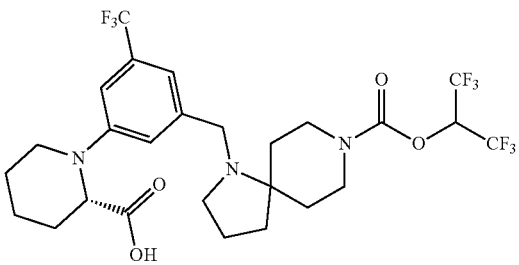 [SMILES: O=C(O)[C@@H]1CCCCN1c1cc(CN2CCCC23CCN(C(=O)OC(C(F)(F)F)C(F)(F)F)CC3)cc(C(F)(F)F)c1]

Step 1: Synthesis of tert-butyl 1-(3-bromo-5-(trifluoromethyl)benzyl)-1,8-diazaspiro[4.5]decane-8-carboxylate

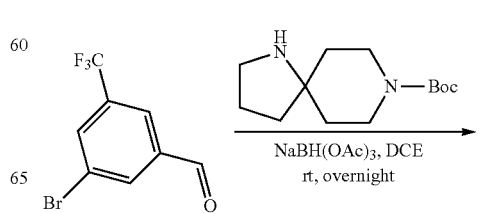

-continued

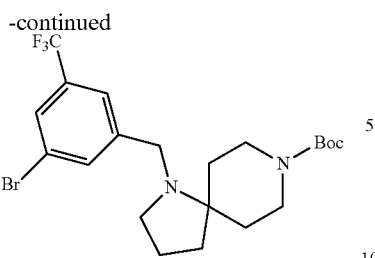

A flask was charged with 3-bromo-5-(trifluoromethyl)benzaldehyde (2.00 g, 7.94 mmol, 1.00 equiv), DCE (20 mL), and tert-butyl 1,8-diazaspiro[4.5]decane-8-carboxylate (1.90 g, 7.94 mmol, 1.00 equiv). The reaction mixture was stirred for 1 h at rt prior to addition of sodium triacetoxyborohydride (5.05 g, 23.8 mmol, 3.00 equiv). The resulting solution was stirred overnight at rt and quenched with water (30 mL). The mixture was extracted with DCM (2×50 mL) and the organic layers were combined, washed with brine (2×30 mL), dried over anhydrous sodium sulfate, filtered and concentrated. The residue was chromatographed on a silica gel column to provide 1.40 g (37% yield) of tert-butyl 1-(3-bromo-5-(trifluoromethyl)benzyl)-1,8-diazaspiro[4.5]decane-8-carboxylate. LCMS (ESI, m/z): 477 [M+H]⁺.

Step 2: Synthesis of (S)-1-(3-((8-(tert-butoxycarbonyl)-1,8-diazaspiro[4.5]decan-1-yl)methyl)-5-(trifluoromethyl)phenyl)piperidine-2-carboxylic acid

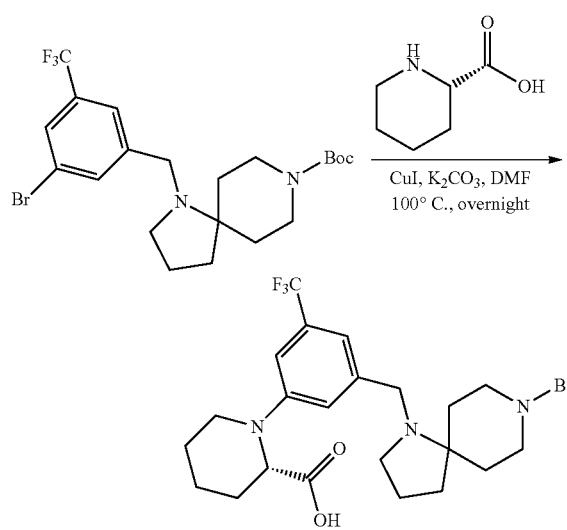

A flask was charged with tert-butyl 1-(3-bromo-5-(trifluoromethyl)benzyl)-1,8-diazaspiro[4.5]decane-8-carboxylate (600 mg, 1.26 mmol, 1.00 equiv), DMF (10 mL), (2S)-piperidine-2-carboxylic acid (325 mg, 2.52 mmol, 2.00 equiv), potassium carbonate (696 mg, 5.04 mmol, 4.00 equiv), and copper(I) iodide (48.0 mg, 0.252 mmol, 0.20 equiv) under nitrogen. The reaction mixture was stirred overnight at 100° C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column to provide 450 mg (68% yield) of (S)-1-(3-((8-(tert-butoxycarbonyl)-1,8-diazaspiro[4.5]decan-1-yl)methyl)-5-(trifluoromethyl)phenyl)piperidine-2-carboxylic acid. LCMS (ESI, m/z): 526 [M+H]⁺.

Step 3: Synthesis of (S)-1-(3-((8-(tert-butoxycarbonyl)-1,8-diazaspiro[4.5]decan-1-yl)methyl)-5-(trifluoromethyl)phenyl)piperidine-2-carboxylic acid

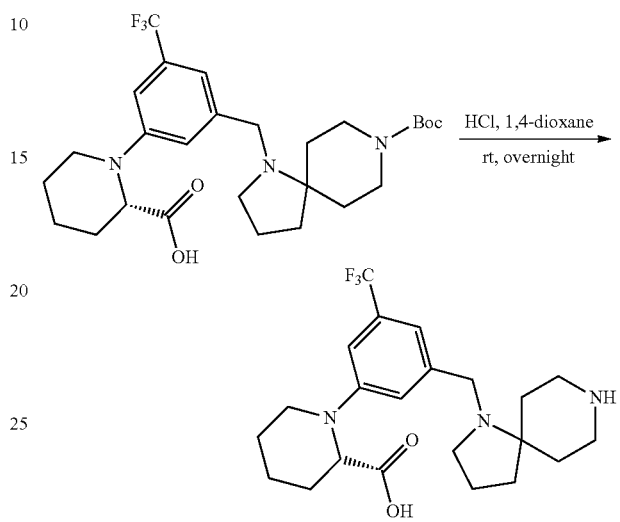

A flask was charged with (S)-1-(3-((8-(tert-butoxycarbonyl)-1,8-diazaspiro[4.5]decan-1-yl)methyl)-5-(trifluoromethyl)phenyl)piperidine-2-carboxylic acid (450 mg, 0.857 mmol, 1.00 equiv), 1,4-dioxane (10 mL), and concentrated hydrochloric acid (3 mL). The resulting solution was stirred overnight at rt and concentrated to provide 600 mg (crude) of (S)-1-(3-((8-(tert-butoxycarbonyl)-1,8-diazaspiro[4.5]decan-1-yl)methyl)-5-(trifluoromethyl)phenyl)piperidine-2-carboxylic acid. LCMS (ESI, m/z): 426 [M+H]⁺.

Step 4: Synthesis of (S)-1-(3-((1,8-diazaspiro[4.5]decan-1-yl)methyl)-5-(trifluoromethyl)phenyl)piperidine-2-carboxylic acid

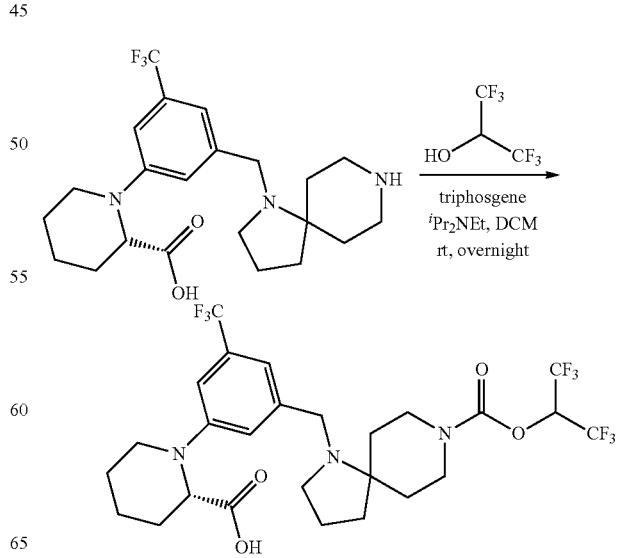

A flask was charged with triphosgene (171 mg, 0.577 mmol, 0.70 equiv), DCM (10 mL), and HFIP 277 mg, 1.65 mmol, 2.00 equiv). DIPEA (319 mg, 2.47 mmol, 3.00 equiv) was added at 0° C. and the mixture was stirred for 1 h at rt prior to addition of (S)-1-(3-((8-(tert-butoxycarbonyl)-1,8-diazaspiro[4.5]decan-1-yl)methyl)-5-(trifluoromethyl)phenyl)piperidine-2-carboxylic acid (350 mg, 0.824 mmol, 1.00 equiv). The reaction mixture was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was purified by preparative HPLC to afford 242.4 mg (48% yield) of (S)-1-(3-((1,8-diazaspiro[4.5]decan-1-yl)methyl)-5-(trifluoromethyl)phenyl)piperidine-2-carboxylic acid. $^1$H NMR (300 MHz, Methanol-$d_4$) δ 7.10-7.11 (m, 2H), 7.02 (s, 1H), 6.13-6.17 (m, 1H), 4.41 (br, 1H), 4.24 (br, 2H), 3.95 (s, 2H), 3.31-3.53 (m, 2H), 3.04-3.16 (m, 4H), 2.25 (br, 1H), 1.94-2.08 (m, 8H), 1.55-1.73 (m, 5H). LCMS (ESI, m/z): 620 [M+H]$^+$.

Example 197: 4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)morpholine-2-carboxylic acid

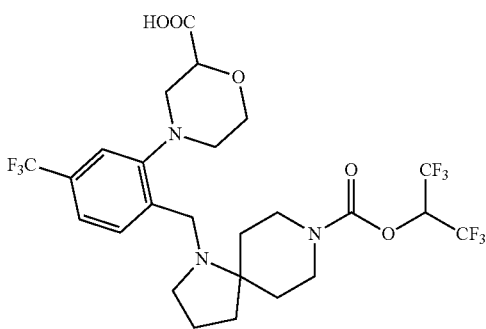 [SMILES: O=C(O)C1CN(c2cc(C(F)(F)F)ccc2CN2CCCC23CCN(C(=O)OC(C(F)(F)F)C(F)(F)F)CC3)CCO1]

Step 1: Synthesis of methyl 4-(2-formyl-5-(trifluoromethyl)phenyl)morpholine-2-carboxylate

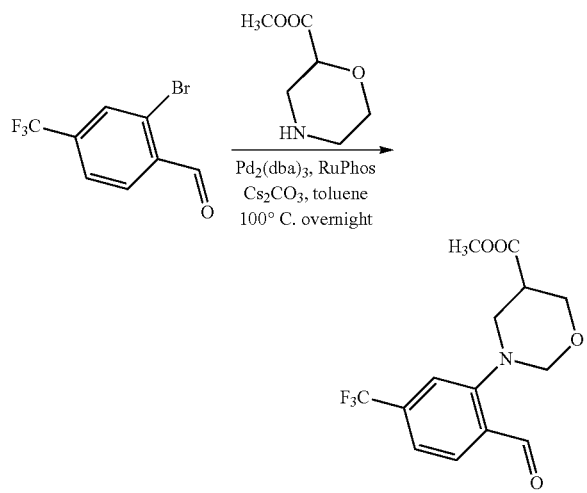

A flask was charged with 2-bromo-4-(trifluoromethyl)benzaldehyde (1.20 g, 4.74 mmol, 1.00 equiv), methyl morpholine-2-carboxylate (1.38 g, 9.51 mmol, 2.00 equiv), tris(dibenzylideneacetone)dipalladium (0.218 g, 0.240 mmol, 0.05 equiv), dicyclohexyl(2',6'-diisopropoxybiphenyl-2-yl)phosphine (0.445 g, 0.950 mmol, 0.20 equiv), cesium carbonate (4.66 g, 14.3 mmol, 3.00 equiv), and toluene (30 mL) under nitrogen. The reaction mixture was stirred overnight at 100° C. and then quenched with water (50 mL). The resulting solution was extracted with EtOAc (3×50 mL) and the organic layers were combined, washed with brine (3×100 mL), dried over anhydrous sodium sulfate, filtered and concentrated. The residue was chromatographed on a silica gel column to provide 0.432 g (25% yield) of methyl 4-(2-formyl-5-(trifluoromethyl)phenyl)morpholine-2-carboxylate. LCMS (ESI, m/z): 318 [M+H]$^+$.

Step 2: Synthesis of 4-(2-formyl-5-(trifluoromethyl)phenyl)morpholine-2-carboxylic acid

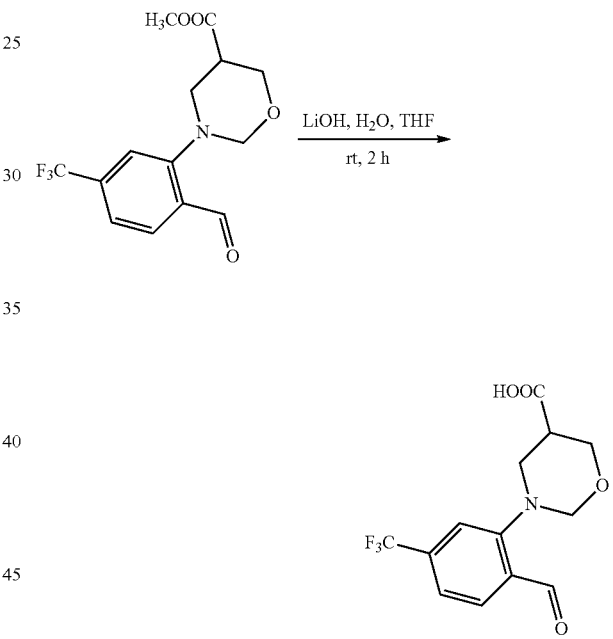

A flask was charged with methyl 4-(2-formyl-5-(trifluoromethyl)phenyl)morpholine-2-carboxylate (432 mg, 1.36 mmol, 1.00 equiv), THF (10 mL), lithium hydroxide (98.0 mg, 4.09 mmol, 3.00 equiv), and water (5 mL). The reaction mixture was stirred for 2 h at rt and quenched with water (5 mL). The pH of the solution was adjusted to 5 with hydrochloric acid (1M, 4 mL). The resulting solution was extracted with DCM (3×20 mL) and the organic layers were combined, washed with brine (2×20 mL), dried over anhydrous sodium sulfate, filtered and concentrated to provide 410 mg (99% yield) of 4-(2-formyl-5-(trifluoromethyl)phenyl)morpholine-2-carboxylic acid. LCMS (ESI, m/z): 304 [M+H]$^+$.

Step 3: Synthesis of 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)morpholine-2-carboxylic acid

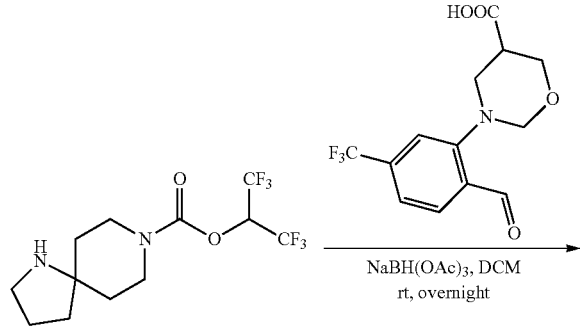

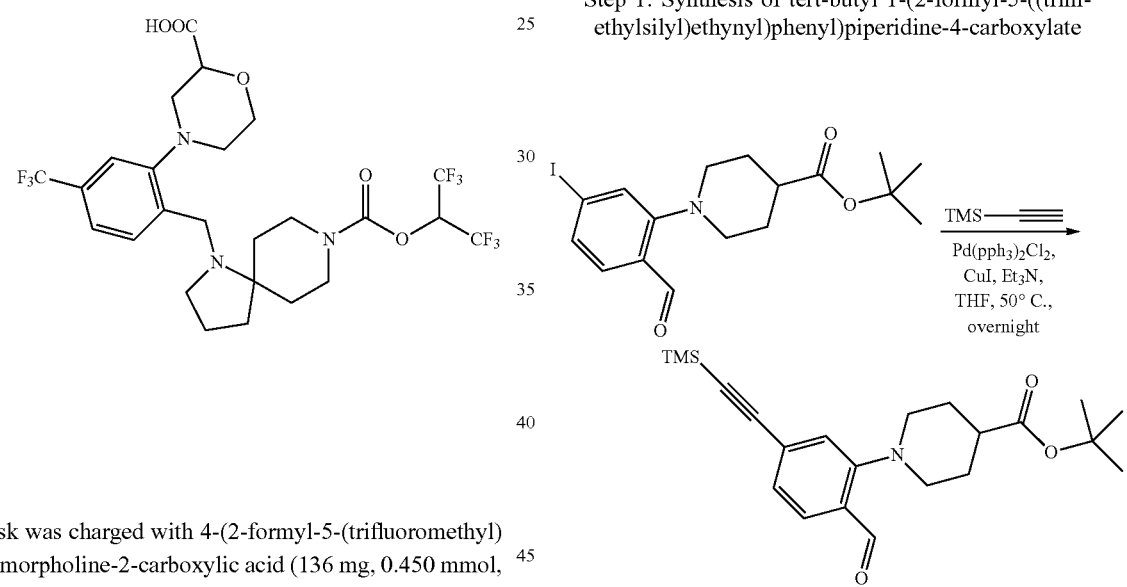

A flask was charged with 4-(2-formyl-5-(trifluoromethyl)phenyl)morpholine-2-carboxylic acid (136 mg, 0.450 mmol, 1.00 equiv), 1,1,1,3,3,3-hexafluoropropan-2-yl 1,8-diazaspiro[4.5]decane-8-carboxylate (180 mg, 0.540 mmol, 1.20 equiv), and DCM (20 mL). The mixture was stirred for 2 h at rt prior to addition of sodium triacetoxyborohydride (286 mg, 1.35 mmol, 3.00 equiv). The reaction mixture was stirred overnight at rt and quenched with water (20 mL). The resulting solution was extracted with DCM (3×20 mL) and the organic layers were combined, washed with brine (1×100 mL), dried over anhydrous sodium sulfate, filtered and concentrated. The crude residue was purified by preparative HPLC to afford 8.7 mg (3% yield) of 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)morpholine-2-carboxylic acid. $^1$H NMR (300 MHz, Methanol-$d_4$) δ 7.73-7.75 (m, 1H), 7.63 (s, 1H), 7.54-7.57 (m, 1H), 6.14-6.23 (m, 1H), 4.11-4.44 (m, 6H), 3.85 (br, 1H), 3.19 (br, 6H), 2.97 (br, 2H), 1.87-2.32 (br, 8H). LCMS (ESI, m/z): 622 [M+H]$^+$.

Example 198: 1-{5-Ethynyl-2-[(8-{[(1,1,1,3,3,3-hexafluoropropan-2-yl)oxy]carbonyl}-1,8-diazaspiro[4.5]decan-1-yl)methyl]phenyl}piperidine-4-carboxylic acid

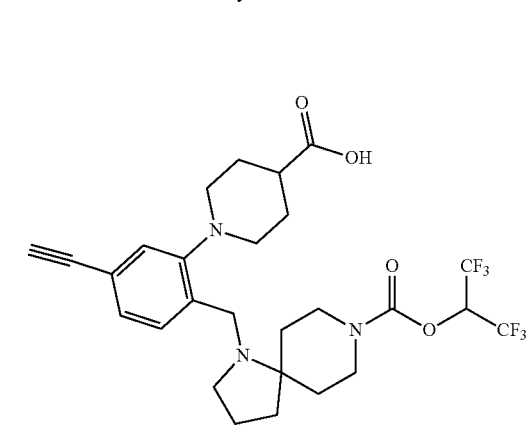

Step 1: Synthesis of tert-butyl 1-(2-formyl-5-((trimethylsilyl)ethynyl)phenyl)piperidine-4-carboxylate A 50-mL round-bottom flask was charged with tert-butyl 1-(2-formyl-5-iodophenyl)piperidine-4-carboxylate (660 mg, 1.59 mmol, 1.00 equiv), tetrahydrofuran (10 mL), ethynyltrimethylsilane (187 mg, 1.91 mmol, 1.20 equiv), bis(triphenylphosphine)palladium(II) chloride (22.3 mg, 0.0320 mmol, 0.02 equiv), copper(I) iodide (12.1 mg, 0.0640 mmol, 0.04 equiv), and triethylamine (321 mg, 3.18 mmol, 2.00 equiv) under nitrogen. The reaction mixture was stirred overnight at 50° C. and quenched with water (50 mL). The resulting solution was extracted with dichloromethane (3×50 mL) and the organic layers were combined, washed with brine (1×50 mL), dried over anhydrous sodium sulfate, filtered and concentrated under reduced pressure. The residue was chromatographed on a silica gel column to provide 580 mg (95% yield) of tert-butyl 1-(2-formyl-5-((trimethylsilyl)ethynyl)phenyl)piperidine-4-carboxylate. LCMS (ESI, m/z): 386 [M+H]$^+$.

Step 2: Synthesis of 1,1,1,3,3,3-hexafluoropropan-2-yl 1-(2-(4-(tert-butoxycarbonyl)piperidin-1-yl)-4-((trimethylsilyl)ethynyl)benzyl)-1,8-diazaspiro[4.5]decane-8-carboxylate

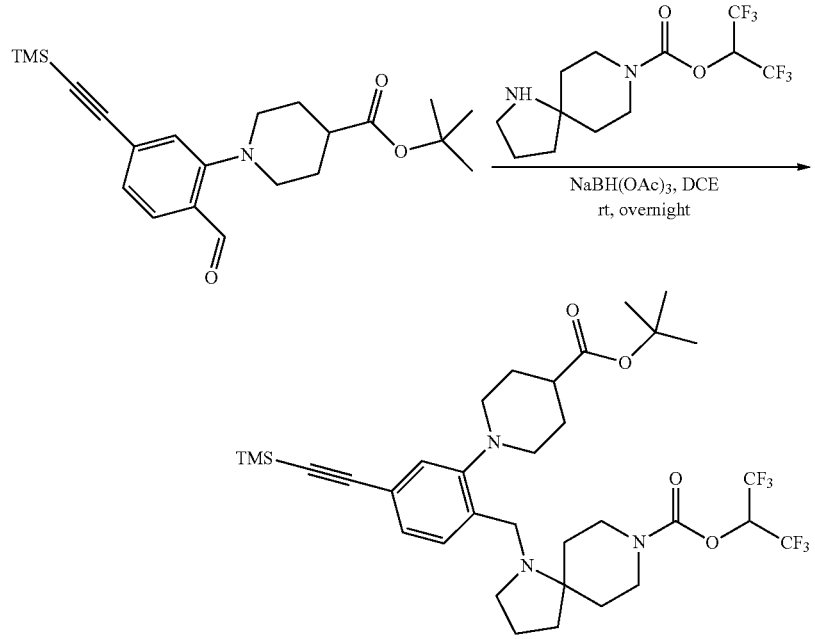

A 50-mL round-bottom flask was charged with tert-butyl 1-(2-formyl-5-((trimethylsilyl)ethynyl)phenyl)piperidine-4-carboxylate (180 mg, 0.468 mmol, 1.00 equiv), 1,1,1,3,3,3-hexafluoropropan-2-yl 1,8-diazaspiro[4.5]decane-8-carboxylate (234 mg, 0.701 mmol, 1.50 equiv), and 1,2-dichloroethane (5 mL). The resulting solution was stirred for 1.5 h at room temperature prior to addition of sodium triacetoxyborohydride (396 mg, 1.87 mmol, 4.00 equiv). The reaction mixture was stirred overnight at room temperature and then quenched with water (50 mL). The resulting solution was extracted with dichloromethane (3×50 mL) and the organic layers were combined, washed with brine (50 mL), dried over anhydrous sodium sulfate, filtered and concentrated under reduced pressure. The residue was chromatographed on a silica gel column to provide 317 mg (96% yield) of 1,1,1,3,3,3-hexafluoropropan-2-yl 1-(2-(4-(tert-butoxycarbonyl)piperidin-1-yl)-4-((trimethylsilyl)ethynyl)benzyl)-1,8-diazaspiro[4.5]decane-8-carboxylate. LCMS (ESI, m/z): 704 [M+H]$^+$.

Step 3: Synthesis of 1,1,1,3,3,3-hexafluoropropan-2-yl 1-(2-(4-(tert-butoxycarbonyl)piperidin-1-yl)-4-ethynylbenzyl)-1,8-diazaspiro[4.5]decane-8-carboxylate

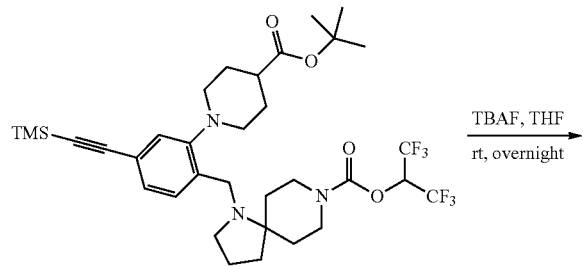

A 50-mL round-bottom flask was charged with 1,1,1,3,3,3-hexafluoropropan-2-yl 1-(2-(4-(tert-butoxycarbonyl)piperidin-1-yl)-4-((trimethylsilyl)ethynyl)benzyl)-1,8-diazaspiro[4.5]decane-8-carboxylate (277 mg, 0.394 mmol, 1.00 equiv), and tetrahydrofuran (5 mL). Tetrabutylammonium fluoride (1.97 mL, 1M in tetrahydrofuran, 1.97 mmol, 5.00 equiv) was added. The reaction mixture was stirred overnight at room temperature and concentrated under reduced pressure. The residue was chromatographed on a silica gel column to provide 170 mg (68% yield) of 1,1,1,3,3,3-hexafluoropropan-2-yl 1-(2-(4-(tert-butoxycarbonyl)piperidin-1-yl)-4-ethynylbenzyl)-1,8-diazaspiro[4.5]decane-8-carboxylate. LCMS (ESI, m/z): 632 [M+H]$^+$.

Step 4: Synthesis of 1-(5-ethynyl-2-((8-(((1,1,1,3,3,3-hexafluoropropan-2-yl)oxy)carbonyl)-1,8-diazaspiro[4.5]decan-1-yl)methyl)phenyl)piperidine-4-carboxylic acid

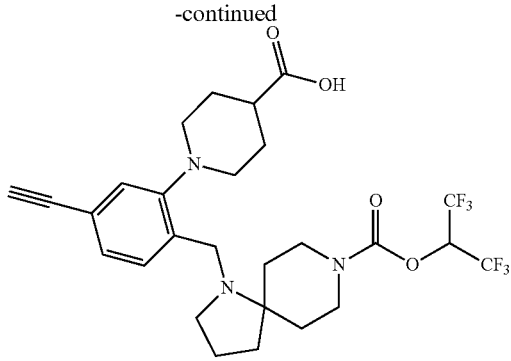

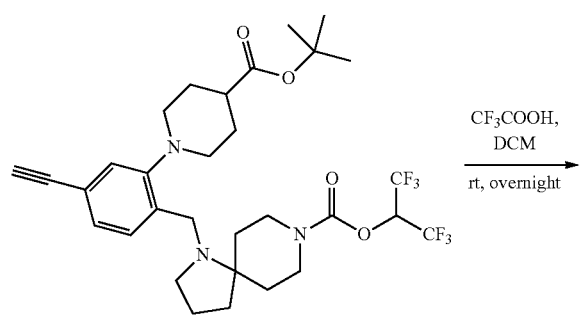

A 100-mL round-bottom flask was charged with 1,1,1,3,3,3-hexafluoropropan-2-yl 1-(2-(4-(tert-butoxycarbonyl)piperidin-1-yl)-4-ethynylbenzyl)-1,8-diazaspiro[4.5]decane-8-carboxylate (157 mg, 0.249 mmol, 1.00 equiv), dichloromethane (5 mL), and trifluoroacetic acid (2 mL). The resulting solution was stirred overnight at room temperature and then concentrated under reduced pressure. The crude product (250 mg) was purified by preparative HPLC to provide 76.7 mg (54% yield) of 1-(5-ethynyl-2-((8-(((1,1,1,3,3,3-hexafluoropropan-2-yl)oxy)carbonyl)-1,8-diazaspiro[4.5]decan-1-yl)methyl)phenyl)piperidine-4-carboxylic acid. $^1$H NMR (300 MHz, Methanol-$d_4$) δ 7.43-7.46 (m, 1H), 7.29-7.30 (m, 1H), 7.20-7.23 (m, 1H), 6.10-6.17 (m, 1H), 4.18-4.26 (m, 2H), 4.00 (br, 2H), 3.50 (s, 1H), 2.99-3.14 (m, 6H), 2.70-2.77 (m, 2H), 2.31-2.36 (m, 1H), 1.90-2.09 (m, 10H), 1.66-1.73 (m, 2H). LCMS (ESI, m/z): 576 [M+H]$^+$.

Examples 199-281 (Table 1) were prepared by similar procedures as described in Examples 1-198.

TABLE 1

| Ex | Structure | NMR ($^1$H NMR, 300 MHz or 400 MHz Methanol-d4) | MS [M + H]$^+$ |
|---|---|---|---|
| 199 | 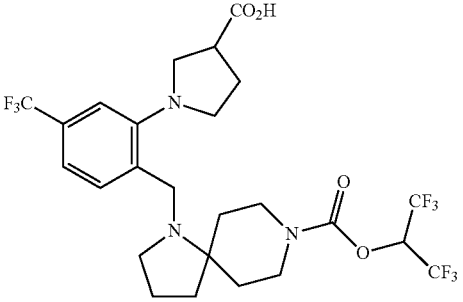 [SMILES: O=C(O)C1CCN(c2cc(C(F)(F)F)ccc2CN2CCCC23CCN(C(=O)OC(C(F)(F)F)C(F)(F)F)CC3)C1] | δ 7.70-7.73 (m, 1H), 7.17-7.22 (m, 2H), 6.10-6.19 (m, 1H), 4.19 (br, 2H), 3.78-3.80 (m, 2H), 3.40-3.48 (m, 2H), 3.14-3.29 (m, 2H), 3.03-3.06 (m, 3H), 2.67-2.75 (m, 2H), 2.21-2.23 (m, 2H), 1.81-1.97 (m, 6H), 1.57-1.62 (m, 2H). | 606 |
| 200 | 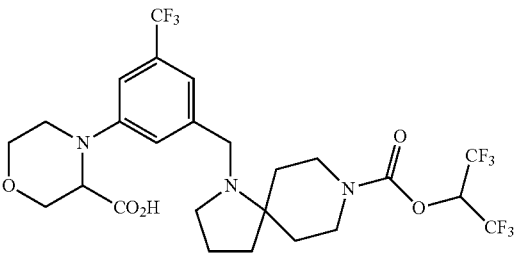 [SMILES: O=C(O)C1COCCN1c1cc(CN2CCCC23CCN(C(=O)OC(C(F)(F)F)C(F)(F)F)CC3)cc(C(F)(F)F)c1] | δ 7.07-7.12 (m, 3H), 6.10-6.23 (m, 1H), 4.40-4.44 (m, 1H), 4.19-4.28 (m, 3H), 3.91-4.05 (m, 3H), 3.80-3.88 (m, 1H), 3.65-3.79 (m, 1H), 3.48-3.63 (m, 1H), 3.39-3.50 (m, 1H), 3.05-3.21 (m, 4H), 1.82-2.17 (m, 6H), 1.71-1.74 (m, 2H). | 622 |

TABLE 1-continued

| Ex | Structure | NMR (¹H NMR, 300 MHz or 400 MHz Methanol-d4) | MS [M + H]⁺ |
|---|---|---|---|
| 201 | 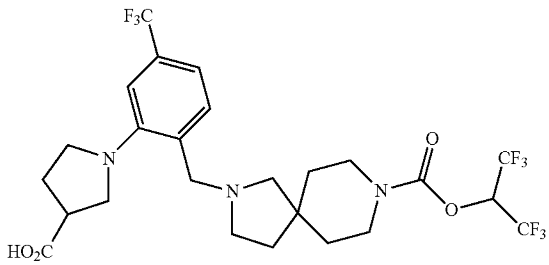 | δ 7.53-7.56 (m, 2H), 7.41-7.43 (m, 1H), 6.07-6.14 (m, 1H), 4.67-4.72 (m, 1H), 4.37-4.42 (m, 1H), 3.60-3.68 (m, 3H), 3.36-3.51 (m, 4H), 3.30-3.31 (m, 1H), 3.01-3.16 (m, 4H), 2.85-2.90 (m, 1H), 2.41-2.45 (m, 1H), 2.05-2.18 (m, 3H), 1.70-1.73 (m, 4H). | 606 |
| 202 | 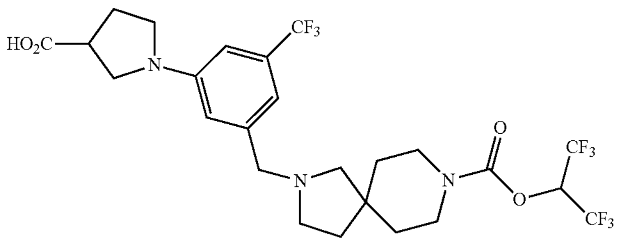 [SMILES: O=C(O)C1CCN(c2cc(CN3CCC4(CCN(C(=O)OC(C(F)(F)F)C(F)(F)F)CC4)C3)cc(C(F)(F)F)c2)C1] | δ 7.03 (br, 1H), 6.94 (s, 1H), 6.78 (s, 1H), 6.08-6.19 (m, 1H), 4.14-4.28 (m, 2H), 3.41-3.58 (m, 7H), 3.38 (s, 1H), 3.25-3.31 (m, 2H), 3.12-3.23 (m, 3H), 2.24-2.35 (m, 2H), 1.91-1.99 (m, 2H), 1.65 (br, 4H). | 606 |
| 203 | 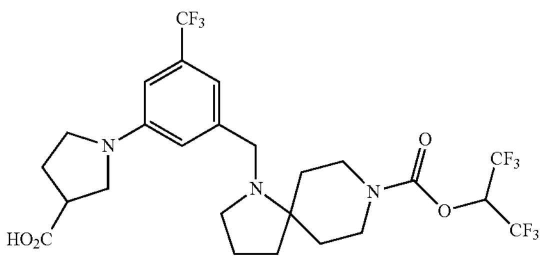 [SMILES: O=C(O)C1CCN(c2cc(CN3CCCC34CCN(C(=O)OC(C(F)(F)F)C(F)(F)F)CC4)cc(C(F)(F)F)c2)C1] | δ 6.92 (s, 1H), 6.84 (s, 1H), 6.70 (s, 1H), 6.09-6.22 (m, 1H), 4.13-4.32 (m, 2H), 3.90 (s, 2H), 3.53-3.55 (m, 2H), 3.39-3.44 (m, 2H), 3.08-3.20 (m, 3H), 2.90-3.03 (m, 2H), 2.25-2.29 (m, 2H), 2.02-2.09 (m, 2H), 1.82-1.97 (m, 4H), 1.62-1.72 (m, 2H). | 606 |
| 204 | 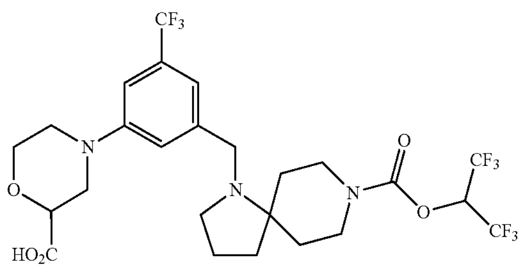 [SMILES: O=C(O)C1CN(c2cc(CN3CCCC34CCN(C(=O)OC(C(F)(F)F)C(F)(F)F)CC4)cc(C(F)(F)F)c2)CCO1] | δ 7.22 (s, 1H), 7.13 (s, 2H), 6.10-6.21 (m, 1H), 4.04-4.22 (m, 4H), 3.68-3.95 (m, 4H), 3.42-3.48 (m, 1H), 3.03-3.19 (m, 2H), 2.80-2.91 (m, 4H), 1.86-204 (m, 6H), 1.63-1.67 (m, 2H). | 622 |
| 205 | 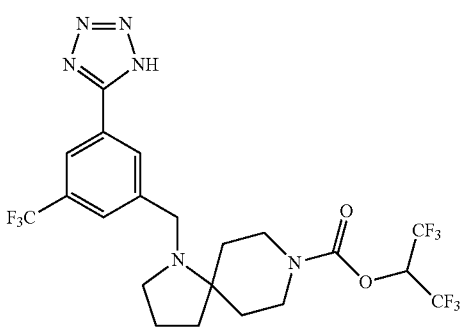 [SMILES: O=C(OC(C(F)(F)F)C(F)(F)F)N1CCC2(CCCN2Cc2cc(-c3nnn[nH]3)cc(C(F)(F)F)c2)CC1] | (Chloroform-d) δ 9.20 (br, 1H), 8.69 (s, 1H), 8.37 (s, 1H), 7.60 (s, 1H), 5.71-5.79 (m, 1H), 4.28-4.31 (m, 2H), 4.02-4.08 (m, 2H), 2.97-3.11 (m, 4H), 2.22-2.27 (m, 2H), 2.09-2.12 (m, 2H), 1.84-1.98 (m, 4H). | 561 |

TABLE 1-continued
| Ex | Structure | NMR (¹H NMR, 300 MHz or 400 MHz Methanol-d4) | MS [M + H]⁺ |
|---|---|---|---|
| 206 | 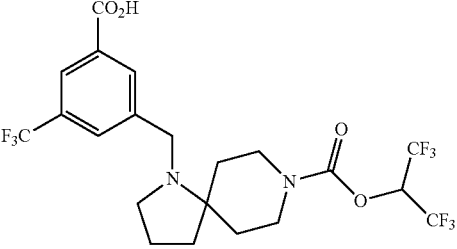 [SMILES: O=C(O)c1cc(CN2CCCC23CCN(C(=O)OC(C(F)(F)F)C(F)(F)F)CC3)cc(C(F)(F)F)c1] | (Chloroform-d) δ 8.65 (s, 1H), 8.25 (s, 1H), 7.65 (s, 1H), 5.70-5.85 (m, 1H), 4.25-4.35 (m, 2H), 3.88-3.90 (m, 2H), 2.85-3.15 (m, 4H), 2.15-2.30 (m, 2H), 1.85-2.15 (m, 6H). | 537 |
| 207 | 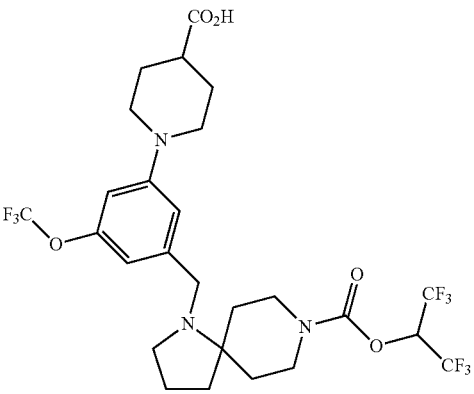 [SMILES: O=C(O)C1CCN(c2cc(CN3CCCC34CCN(C(=O)OC(C(F)(F)F)C(F)(F)F)CC4)cc(OC(F)(F)F)c2)CC1] | δ 6.95 (s, 1H), 6.78 (s, 2H), 6.10-6.20 (m, 1H), 4.19 (br, 2H), 3.60-3.81 (m, 4H), 2.98-3.18 (m, 2H), 2.77-2.91 (m, 4H), 2.35-2.49 (m, 1H), 1.95-2.09 (m, 4H), 1.71-1.90 (m, 6H), 1.53-1.67 (m, 2H). | 636 |
| 208 | 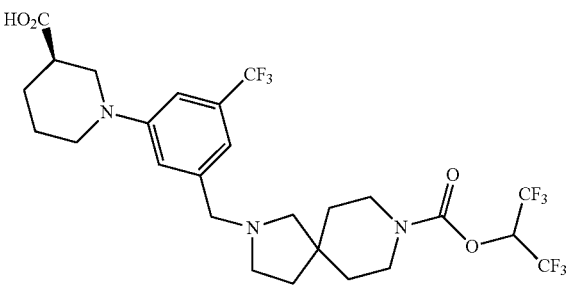 [SMILES: O=C(O)[C@@H]1CCCN(c2cc(CN3CCC4(CCN(C(=O)OC(C(F)(F)F)C(F)(F)F)CC4)C3)cc(C(F)(F)F)c2)C1] | (Chloroform-d) δ 7.36 (s, 1H), 7.07 (s, 1H), 6.88 (s, 1H), 5.69-5.78 (m, 1H), 3.93-3.98 (m, 1H), 3.74-3.88 (m, 2H), 3.42-3.55 (m, 5H), 3.08-3.14 (m, 1H), 2.73-2.97 (m, 5H), 2.56-2.60 (m, 1H), 2.03-2.05 (m, 1H), 1.75-1.85 (m, 3H), 1.62-1.78 (m, 6H). | 620 |
| 209 | 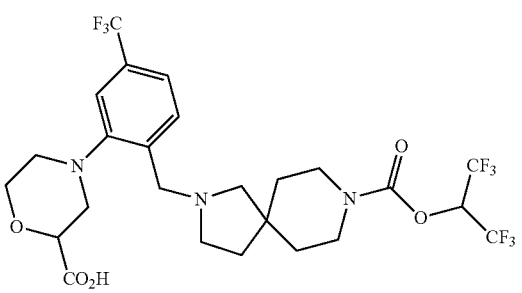 [SMILES: O=C(O)C1CN(c2cc(C(F)(F)F)ccc2CN2CCC3(CCN(C(=O)OC(C(F)(F)F)C(F)(F)F)CC3)C2)CCO1] | δ 7.67-7.70 (m, 2H), 7.56-7.58 (m, 1H), 6.10-6.19 (m, 1H), 4.38-4.53 (m, 2H), 4.22-4.24 (m, 1H), 3.80-3.84 (m, 1H), 3.80-3.84 (m, 1H), 3.39-3.66 (m, 6H), 3.19-3.27 (m, 3H), 3.06-3.12 (m, 2H), 2.92-2.96 (m, 1H), 2.08-2.10 (m, 2H), 1.76-1.78 (m, 4H). | 622 |

TABLE 1-continued

| Ex | Structure | NMR (¹H NMR, 300 MHz or 400 MHz Methanol-d4) | MS [M + H]⁺ |
|---|---|---|---|
| 210 | 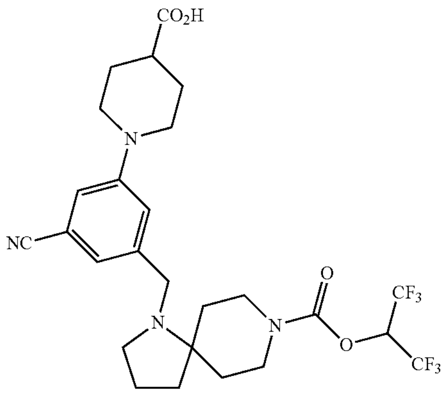 [SMILES: N#Cc1cc(CN2CCCC23CCN(C(=O)OC(C(F)(F)F)C(F)(F)F)CC3)cc(N2CCC(C(=O)O)CC2)c1] | δ 7.26 (s, 1H), 7.17 (s, 1H), 7.11 (s, 1H), 6.12-6.21 (m, 1H), 4.19-4.24 (m, 2H), 3.69-3.77 (m, 4H), 3.04-3.18 (m, 2H), 2.79-2.90 (m, 4H), 2.43-2.49 (m, 1H), 1.97-2.04 (m, 4H), 1.80-1.91 (m, 6H), 1.57-1.65 (m, 2H). | 577 |
| 211 | 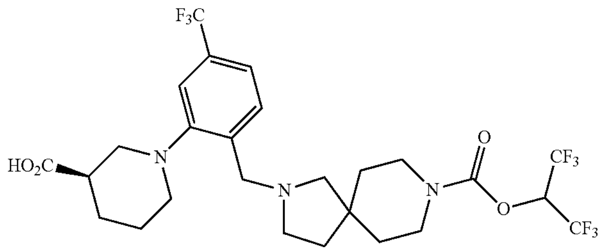 [SMILES: O=C(O)[C@@H]1CCCN(c2cc(C(F)(F)F)ccc2CN2CCC3(CCN(C(=O)OC(C(F)(F)F)C(F)(F)F)CC3)C2)C1] | δ 7.62-7.64 (m, 2H), 7.51-7.53 (m, 1H), 6.10-6.19 (m, 1H), 4.49 (br, 1H), 4.20-4.23 (m, 1H), 3.46-3.66 (m, 4H), 3.32-3.34 (m, 1H), 3.22-3.24 (m, 2H), 3.04-3.10 (m, 4H), 2.80-2.82 (m, 1H), 2.64 (br, 1H), 2.11-2.13 (m, 3H), 1.76-1.96 (m, 7H). | 620 |
| 212 | 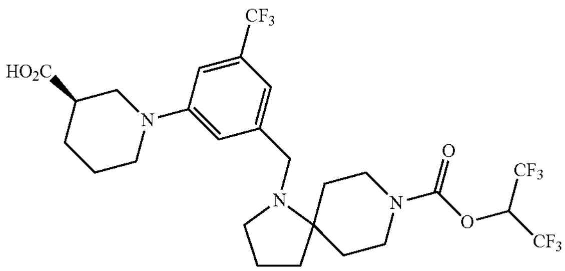 [SMILES: O=C(O)[C@@H]1CCCN(c2cc(CN3CCCC34CCN(C(=O)OC(C(F)(F)F)C(F)(F)F)CC4)cc(C(F)(F)F)c2)C1] | (Chloroform-d) δ 7.23 (br, 1H), 7.02 (s, 2H), 5.70-5.80 (m, 1H), 4.11-4.28 (m, 2H), 3.60-3.68 (m, 3H), 3.42-3.45 (m, 1H), 3.22-3.24 (m, 1H), 2.93-3.02 (m, 3H), 2.62-2.81 (m, 3H), 1.66-1.98 (m, 12H). | 620 |
| 213 | 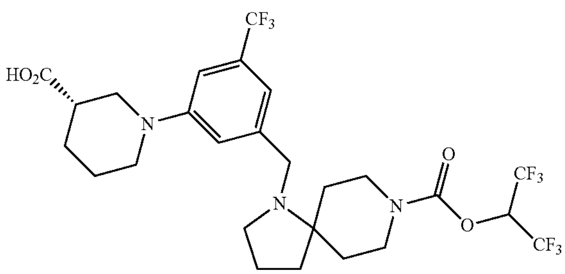 [SMILES: O=C(O)[C@H]1CCCN(c2cc(CN3CCCC34CCN(C(=O)OC(C(F)(F)F)C(F)(F)F)CC4)cc(C(F)(F)F)c2)C1] | (Chloroform-d) δ 7.36 (br, 1H), 7.05-7.16 (m, 2H), 5.72-5.78 (m, 1H), 4.14-4.39 (m, 2H), 3.48-3.72 (m, 4H), 3.30-3.39 (m, 1H), 2.66-3.00 (m, 6H), 1.50-2.14 (m, 12H). | 620 |
| 214 | 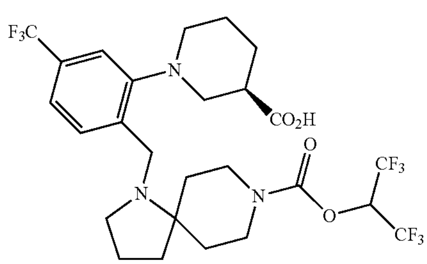 [SMILES: O=C(O)[C@@H]1CCCN(c2cc(C(F)(F)F)ccc2CN2CCCC23CCN(C(=O)OC(C(F)(F)F)C(F)(F)F)CC3)C1] | (Chloroform-d) δ 7.62 (br, 1H), 7.32-7.34 (m, 2H), 5.73-5.79 (m, 1H), 4.17-4.26 (m, 2H), 3.66-3.75 (m, 2H), 3.13-3.21 (m, 1H), 2.96-3.05 (m, 3H), 2.84-2.91 (m, 1H), 2.72-2.74 (m, 4H), 1.50-2.00 (m, 12 H). | 620 |

TABLE 1-continued

| Ex | Structure | NMR (¹H NMR, 300 MHz or 400 MHz Methanol-d4) | MS [M + H]⁺ |
|---|---|---|---|
| 215 | 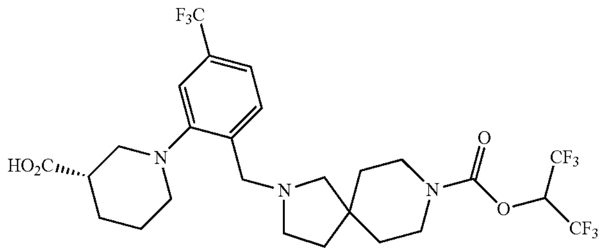 [SMILES: O=C(O)[C@H]1CCCN(c2cc(C(F)(F)F)ccc2CN2CCC3(CCN(C(=O)OC(C(F)(F)F)C(F)(F)F)CC3)C2)C1] | δ 7.62-7.67 (m, 2H), 7.53-7.56 (m, 1H), 6.10-6.18 (m, 1H), 4.54-4.58 (m, 1H), 4.24-4.28 (m, 1H), 3.33-3.64 (m, 6H), 3.17-3.30 (m, 2H), 3.06-3.10 (m, 3H), 2.75-2.82 (m, 1H), 2.66 (br, 1H), 2.11-2.29 (m, 3H), 1.76-1.96 (m, 7H). | 620 |
| 216 | 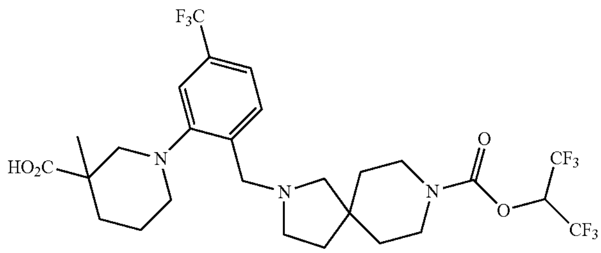 [SMILES: CC1(C(=O)O)CCCN(c2cc(C(F)(F)F)ccc2CN2CCC3(CCN(C(=O)OC(C(F)(F)F)C(F)(F)F)CC3)C2)C1] | δ 7.63-7.65 (m, 2H), 7.54-7.57 (m, 1H), 6.10-6.19 (m, 1H), 4.60-4.64 (m, 1H), 4.14-4.19 (m, 1H), 3.52-3.66 (m, 5H), 3.25-3.34 (m, 3H), 3.04-3.10 (m, 2H), 2.62-2.70 (m, 2H), 2.12-2.37 (m, 3H), 1.73-1.84 (m, 6H), 1.20-1.28 (m, 1H), 1.18 (s, 3H). | 634 |
| 217 | 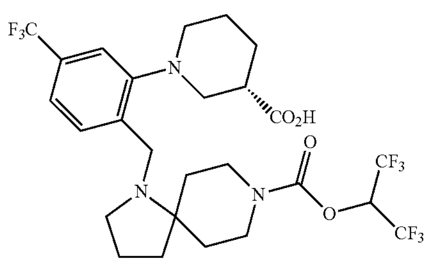 [SMILES: O=C(O)[C@H]1CCCN(c2cc(C(F)(F)F)ccc2CN2CCCC23CCN(C(=O)OC(C(F)(F)F)C(F)(F)F)CC3)C1] | δ 7.62-7.69 (m, 2H), 7.48-7.51 (m, 1H), 6.13-6.22 (m, 1H), 4.21-4.45 (m, 3H), 3.98-4.05 (m, 1H), 3.00-3.18 (m, 7H), 2.66-2.67 (m, 2H), 2.34-2.45 (m, 2H), 2.07-2.12 (m, 5H), 1.72-1.93 (m, 5H). | 620 |
| 218 | 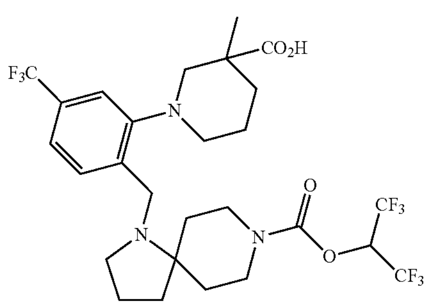 [SMILES: CC1(C(=O)O)CCCN(c2cc(C(F)(F)F)ccc2CN2CCCC23CCN(C(=O)OC(C(F)(F)F)C(F)(F)F)CC3)C1] | δ 7.73 (s, 1H), 7.67 (d, J = 8.1 Hz, 1H), 7.60 (d, J = 8.1 Hz, 1H), 6.11-6.19 (m, 1H), 4.63-4.68 (m, 1H), 4.31-4.36 (m, 1H), 3.95-4.02 (m, 1H), 3.81-3.85 (m, 1H), 3.34-3.65 (m, 8H), 3.09-3.13 (m 1H), 2.88-2.99 (m, 2H), 2.77-2.81 (m, 1H), 2.11-2.22 (m, 2H), 1.78-1.82 (m, 4H), 1.36 (s, 3H). | 636 |
| 219 | 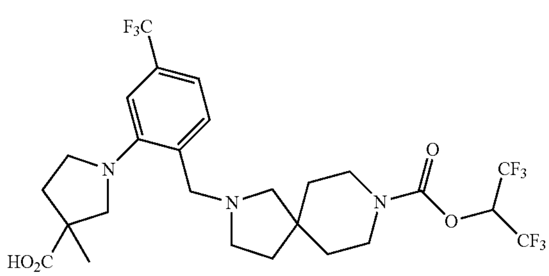 [SMILES: CC1(C(=O)O)CCN(c2cc(C(F)(F)F)ccc2CN2CCC3(CCN(C(=O)OC(C(F)(F)F)C(F)(F)F)CC3)C2)C1] | δ 7.49 (br, 2H), 7.35-7.38 (m, 1H), 6.06-6.14 (m, 1H), 4.64-4.86 (m, 1H), 4.36-4.59 (m, 1H), 3.59-3.73 (m, 3H), 3.38-3.44 (m, 4H), 3.16-3.30 (m, 2H), 2.90-3.03 (m, 2H), 2.63-2.66 (m, 1H), 2.34-2.44 (m, 1H), 2.04-2.17 (m, 2H), 1.85-1.99 (m, 1H), 1.70 (br, 4H), 1.35 (s, 3H). | 620 |

TABLE 1-continued
| Ex | Structure | NMR (¹H NMR, 300 MHz or 400 MHz Methanol-d4) | MS [M + H]⁺ |
|---|---|---|---|
| 220 | 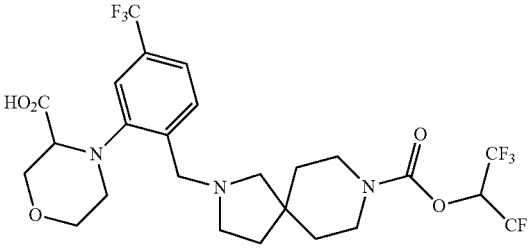 [SMILES: O=C(O)C1COCCN1c1cc(C(F)(F)F)ccc1CN1CCC2(CCN(C(=O)OC(C(F)(F)F)C(F)(F)F)CC2)C1] | (Chloroform-d) δ 7.68 (s, 1H), 7.46-7.49 (m, 1H), 7.38-7.40 (m, 1H), 5.69-5.77 (m, 1H), 4.65-4.69 (m, 1H), 4.33-4.38 (m, 1H), 4.09-4.13 (m, 1H), 3.92-4.00 (m, 1H), 3.62-3.78 (m, 3H), 3.24-3.58 (m, 6H), 2.86-3.02 (m, 3H), 2.69-2.73 (m, 1H), 1.84-2.18 (m, 3H), 1.62-1.78 (m, 3H). | 622 |
| 221 | 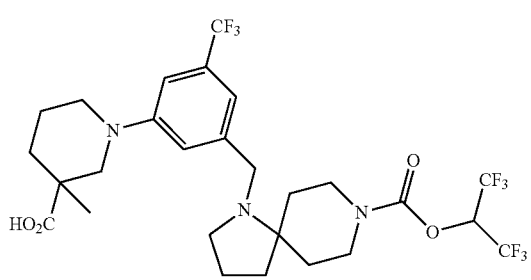 [SMILES: CC1(C(=O)O)CCCN(c2cc(CN3CCCC34CCN(C(=O)OC(C(F)(F)F)C(F)(F)F)CC4)cc(C(F)(F)F)c2)C1] | δ 7.20 (s, 1H), 7.03-7.08 (m, 2H), 6.11-6.15 (m, 1H), 4.17-4.19 (m, 2H), 3.85-3.89 (m, 1H), 3.71 (s, 2H), 3.36-3.40 (m, 1H), 3.05-3.12 (m, 2H), 2.77-2.93 (m, 3H), 2.68-2.71 (m, 1H), 2.14-2.20 (m, 1H), 1.91-1.99 (m, 2H), 1.68-1.88 (m, 6H), 1.55-1.61 (m, 2H), 1.29-1.38 (m, 1H), 1.21 (s, 3H). | 634 |
| 222 | 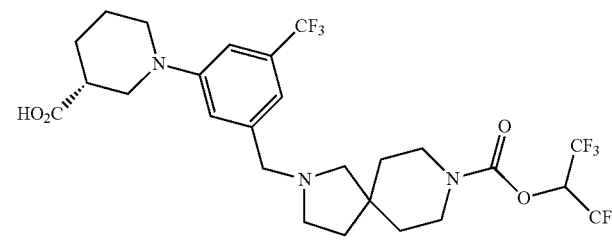 | (Chloroform-d) δ 7.28 (s, 1H), 7.14 (s, 1H), 7.08 (s, 1H), 6.09-6.13 (m, 1H), 3.96 (br, 2H), 3.81-3.85 (m, 1H), 3.46-3.64 (m, 5H), 2.85-3.09 (m, 6H), 2.53 (br, 1H), 2.03 (br, 1H), 1.85-1.89 (m, 3H), 1.64-1.66 (m, 6H). | 620 |
| 223 | 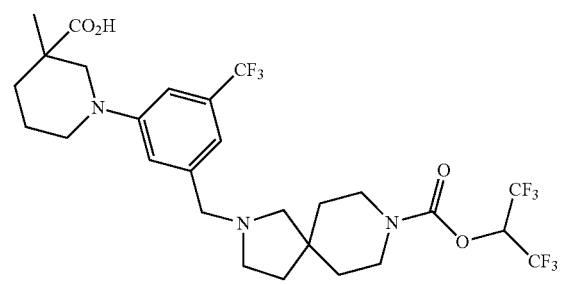 [SMILES: CC1(C(=O)O)CCCN(c2cc(CN3CCC4(CCN(C(=O)OC(C(F)(F)F)C(F)(F)F)CC4)C3)cc(C(F)(F)F)c2)C1] | δ 7.27 (s, 1H), 7.14 (s, 1H), 7.06 (s, 1H), 6.07-6.13 (m, 1H), 3.88-3.93 (m, 3H), 3.40-3.57 (m, 5H), 2.81-2.95 (m, 3H), 2.70-2.78 (m, 3H), 2.16-2.20 (m, 1H), 1.72-1.84 (m, 4H), 1.58-1.63 (m, 4H), 1.30-1.40 (m, 1H), 1.19 (s, 3H). | 634 |
| 224 | 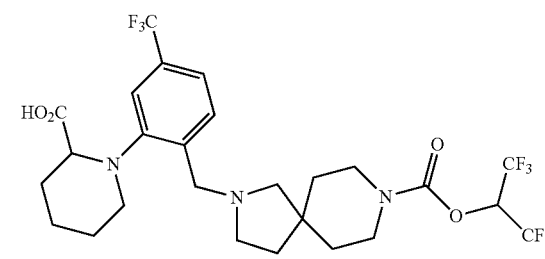 | δ 7.64-7.69 (m, 2H), 7.55 (d, J = 8.1 Hz, 1H), 6.12-6.20 (m, 1H), 4.77-4.81 (m, 1H), 3.93-3.97 (m, 1H), 3.72-3.81 (m, 3H), 3.62 (br, 1H), 3.34-3.50 (m, 3H), 3.21-3.28 (m, 2H), 2.99-3.03 (m, 1H), 2.58-2.67 (m, 1H), 1.90-2.22 (m, 4H), 1.51-1.89 (m, 8H). | 620 |
| 225 | 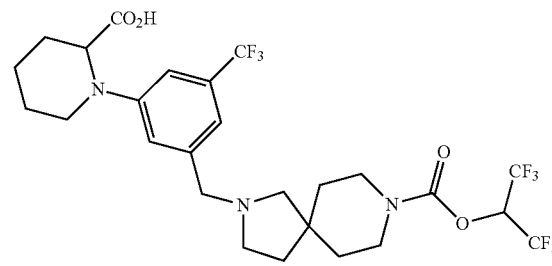 | δ 7.17-7.24 (m, 2H), 7.04 (s, 1H), 6.11-6.20 (m, 1H), 4.46 (br, 1H), 4.12-4.23 (m, 2H), 3.34-3.59 (m, 6H), 3.23-3.28 (m, 2H), 3.03-3.16 (m, 2H), 2.32-2.36 (m, 1H), 1.85-1.98 (m, 4H), 1.56-1.68 (m, 7H). | 620 |

TABLE 1-continued
| Ex | Structure | NMR (¹H NMR, 300 MHz or 400 MHz Methanol-d4) | MS [M + H]⁺ |
|---|---|---|---|
| 226 | 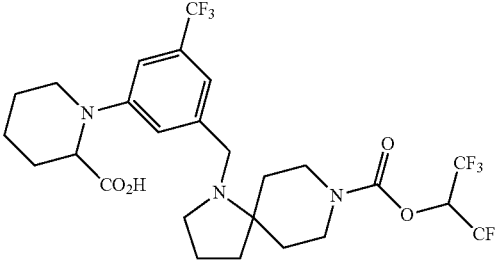 | δ 7.10-7.14 (m, 2H), 7.04 (s, 1H), 6.14-6.23 (m, 1H), 4.41-4.44 (m, 1H), 4.23-4.26 (m, 2H), 3.96 (s, 2H), 3.53-3.58 (m, 1H), 3.34-3.45 (m, 1H), 3.05-3.22 (m, 4H), 2.28-2.32 (m, 1H), 2.11-2.27 (m, 2H), 1.85-2.00 (m, 6H), 1.52-1.75 (m, 5H). | 620 |
| 227 | 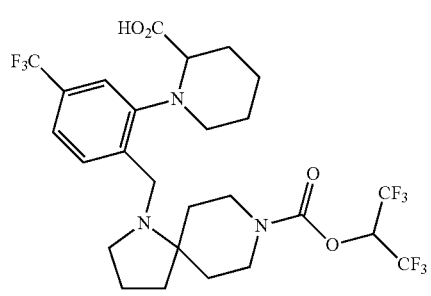 [SMILES: O=C(O)C1CCCCN1c1cc(C(F)(F)F)ccc1CN1CCCC12CCN(C(=O)OC(C(F)(F)F)C(F)(F)F)CC2] | δ 7.80 (s, 1H), 7.70-7.73 (m, 1H), 7.60-7.63 (m, 1H), 6.22-6.28 (m, 1H), 4.98 (s, 1H), 4.29-4.58 (m, 2H), 4.18-4.22 (m, 1H), 4.04-4.11 (m, 1H), 3.90-3.96 (m, 1H), 3.74-3.86 (m, 2H), 3.55-3.68 (m, 1H), 3.22-3.28 (m, 2H), 3.09-3.18 (m, 2H), 2.92-2.97 (m, 1H), 2.80-2.88 (m, 1H), 2.45-2.62 (m, 2H), 1.94-2.16 (m, 6H). | 622 |
| 228 | 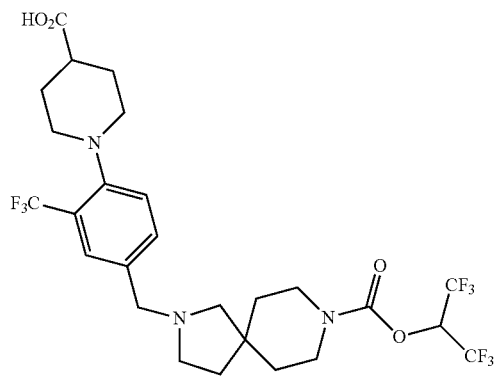 [SMILES: O=C(O)C1CCN(c2ccc(CN3CCC4(CCN(C(=O)OC(C(F)(F)F)C(F)(F)F)CC4)C3)cc2C(F)(F)F)CC1] | δ 7.69 (s, 1H), 7.60-7.63 (m, 1H), 7.44-7.47 (m, 1H), 6.07-6.16 (m, 1H), 3.89 (s, 2H), 3.41-3.61 (m, 4H), 3.03-3.06 (m, 2H), 2.91-2.94 (m, 2H), 2.75-2.89 (m, 4H), 2.31-2.40 (m, 1H), 1.80-1.98 (m, 6H), 1.62-1.66 (m, 4H). | 620 |
| 229 | 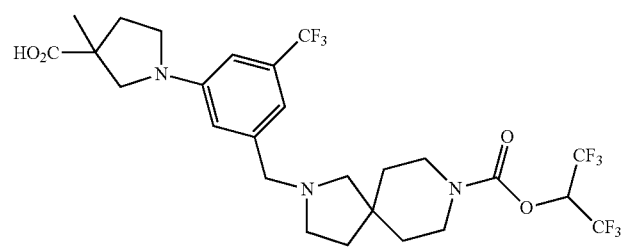 [SMILES: CC1(C(=O)O)CCN(c2cc(CN3CCC4(CCN(C(=O)OC(C(F)(F)F)C(F)(F)F)CC4)C3)cc(C(F)(F)F)c2)C1] | δ 6.94 (br, 2H), 6.75 (br, 1H), 6.10-6.19 (m, 1H), 4.11 (br, 2H), 3.84-3.87 (m, 1H), 3.41-3.63 (m, 6H), 3.14-3.18 (m, 3H), 3.02 (br, 2H), 2.49-2.57 (m, 1H), 1.90-1.97 (m, 3H), 1.68-1.70 (m, 4H), 1.41 (s, 3H). | 620 |
| 230 | 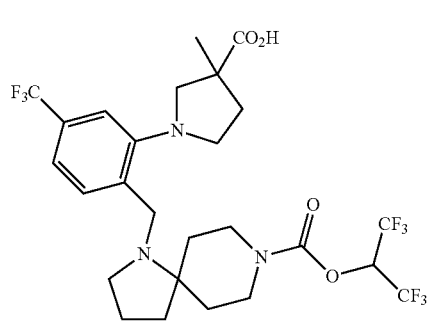 [SMILES: CC1(C(=O)O)CCN(c2cc(C(F)(F)F)ccc2CN2CCCC23CCN(C(=O)OC(C(F)(F)F)C(F)(F)F)CC3)C1] | δ 7.60-7.62 (m, 1H), 7.45 (s, 1H), 7.33-7.36 (m, 1H), 6.14-6.18 (m, 1H), 4.09-4.38 (m, 4H), 3.56-3.60 (m, 1H), 3.32-3.44 (m, 1H), 3.01-3.18 (m, 6H), 2.48-2.57 (m, 1H), 2.27-2.30 (m, 2H), 1.77-2.04 (m, 7H), 1.43 (s, 3H). | 620 |

TABLE 1-continued

| Ex | Structure | NMR (¹H NMR, 300 MHz or 400 MHz Methanol-d4) | MS [M + H]⁺ |
|---|---|---|---|
| 231 | 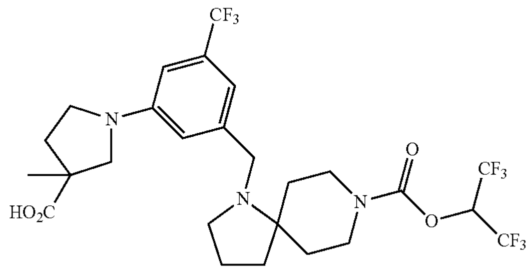 [SMILES: CC1(C(=O)O)CCN(c2cc(CN3CCCC34CCN(C(=O)OC(C(F)(F)F)C(F)(F)F)CC4)cc(C(F)(F)F)c2)C1] | δ 6.91 (s, 1H), 6.80 (s, 1H), 6.68 (s, 1H), 6.14-6.20 (m, 1H), 4.21-4.26 (m, 2H), 3.80-3.88 (m, 3H), 3.40-3.44 (m, 2H), 3.05-3.19 (m, 3H), 2.94-2.98 (m, 2H), 2.49-2.55 (m, 1H), 2.03-2.07 (m, 2H), 1.86-1.96 (m, 5H), 1.65-1.74 (m, 2H), 1.42 (s, 3H). | 620 |
| 232 | 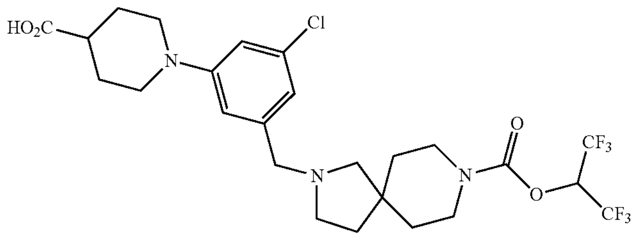 [SMILES: O=C(O)C1CCN(c2cc(Cl)cc(CN3CCC4(CCN(C(=O)OC(C(F)(F)F)C(F)(F)F)CC4)C3)c2)CC1] | δ 6.93 (s, 1H), 6.91 (s, 1H), 6.84 (s, 1H), 6.10-6.12 (m, 1H), 3.95 (s, 2H), 3.62-3.74 (m, 2H), 3.46-3.60 (m, 4H), 3.10-3.30 (m, 2H), 2.94 (s, 2H), 2.76-2.84 (m, 2H), 2.32-2.37 (m, 1H), 1.91-2.03 (m, 4H), 1.66-1.89 (m, 6H). | 586 |
| 233 | 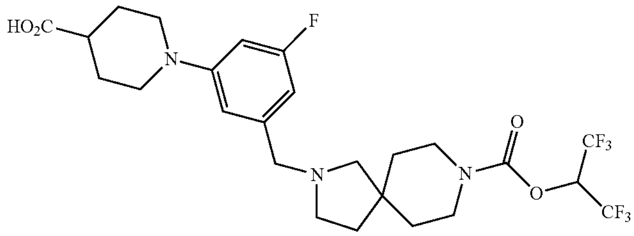 | δ 6.93 (s, 1H), 6.75-6.79 (m, 1H), 6.64-6.67 (m, 1H), 6.13-6.17 (m, 1H), 4.92 (s, 2H), 3.63-3.79 (m, 2H), 3.51-3.56 (m, 2H), 3.35-3.49 (m, 4H), 3.25-3.32 (m, 2H), 2.87-2.91 (m, 2H), 2.46-2.50 (m, 1H), 2.00-2.08 (m, 4H), 1.75-1.85 (m, 6H). | 570 |
| 234 | 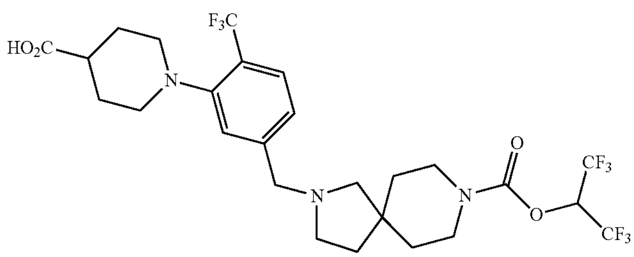 [SMILES: O=C(O)C1CCN(c2cc(CN3CCC4(CCN(C(=O)OC(C(F)(F)F)C(F)(F)F)CC4)C3)ccc2C(F)(F)F)CC1] | δ 7.60 (d, J = 8.1 Hz, 1H), 7.50 (s, 1H), 1.21 (d, J = 7.8 Hz, 1H), 6.07-6.15 (m, 1H), 3.84 (br, 2H), 3.43-3.60 (m, 4H), 3.04-3.08 (m, 2H), 2.67-2.84 (m, 6H), 2.36-2.43 (m, 1H), 1.82-2.00 (m, 6H), 1.61-1.68 (m, 4H). | 620 |
| 235 | 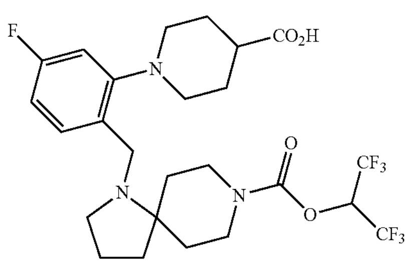 [SMILES: O=C(O)C1CCN(c2cc(F)ccc2CN2CCCC23CCN(C(=O)OC(C(F)(F)F)C(F)(F)F)CC3)CC1] | δ 7.49-7.52 (m, 1H), 7.07-7.12 (m, 1H), 6.92-6.99 (m, 1H), 6.18-6.22 (m, 1H), 4.21-4.29 (m, 4H), 3.31-3.33 (m, 2H), 3.09-3.29 (m, 4H), 2.74-2.82 (m, 2H), 2.41-2.42 (m, 1H), 2.02-2.24 (m, 8H), 1.82-1.94 (m, 4H). | 570 |
| 236 | 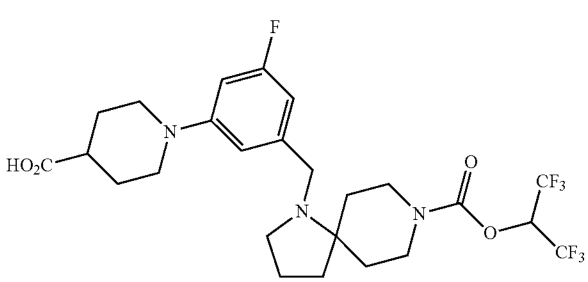 [SMILES: O=C(O)C1CCN(c2cc(F)cc(CN3CCCC34CCN(C(=O)OC(C(F)(F)F)C(F)(F)F)CC4)c2)CC1] | δ 6.63 (s, 1H), 6.54-6.60 (m, 2H), 6.13-6.19 (m, 1H), 4.22 (br, 2H), 3.70-3.74 (m, 4H), 3.08-3.34 (m, 2H), 2.77-2.93 (m, 4H), 2.39-2.40 (m, 1H), 1.77-2.04 (m, 10H), 1.61-1.65 (m, 2H). | 570 |

TABLE 1-continued
| Ex | Structure | NMR (¹H NMR, 300 MHz or 400 MHz Methanol-d4) | MS [M + H]⁺ |
|---|---|---|---|
| 237 | 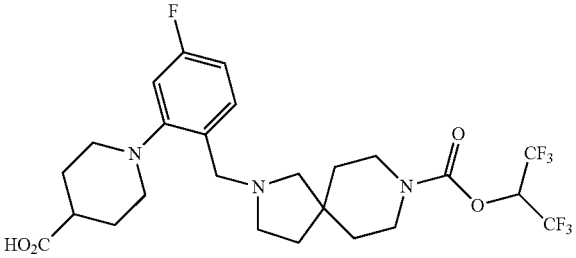 [SMILES: O=C(O)C1CCN(c2cc(F)ccc2CN2CCC3(CCN(C(=O)OC(C(F)(F)F)C(F)(F)F)CC3)C2)CC1] | δ 7.46-7.49 (m, 1H), 7.04-7.09 (m, 1H), 6.90-6.96 (m, 1H), 6.13-6.17 (m, 1H), 4.91 (s, 2H), 3.61-3.67 (m, 2H), 3.49-3.54 (m, 2H), 3.28-3.33 (m, 2H), 3.09-3.25 (m, 4H), 2.74-2.78 (m, 2H), 2.35-2.37 (m, 1H), 1.85-2.07 (m, 6H), 1.70 (br, 4H). | 570 |
| 238 | 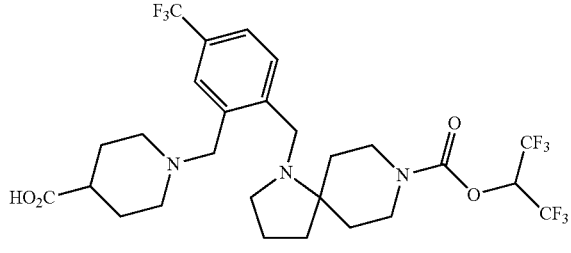 [SMILES: O=C(O)C1CCN(Cc2cc(C(F)(F)F)ccc2CN2CCCC23CCN(C(=O)OC(C(F)(F)F)C(F)(F)F)CC3)CC1] | δ 7.80 (s, 1H), 7.69-7.74 (m, 2H), 6.12-6.21 (m, 1H), 4.24-4.27 (m, 2H), 4.16 (br, 2H), 4.05 (br, 2H), 3.09-3.23 (m, 4H), 2.69-2.78 (m, 4H), 2.31-2.37 (m, 1H), 1.89-2.12 (m, 8H), 1.75 (br, 2H), 1.60-1.64 (m, 2H). | 634 |
| 239 | 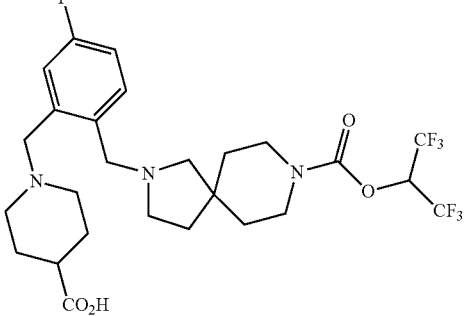 | δ 7.81 (s, 1H), 7.75-7.79 (m, 2H), 6.10-6.19 (m, 1H), 4.20-4.22 (m, 4H), 3.62-3.67 (m, 2H), 3.51-3.57 (m, 2H), 3.24-3.27 (m, 2H), 3.08-3.17 (m, 2H), 2.88-2.99 (m, 2H), 2.70-2.75 (m, 2H), 2.34-2.39 (m, 1H), 1.98-2.07 (m, 4H), 1.73 (br, 6H). | 634 |
| 240 | 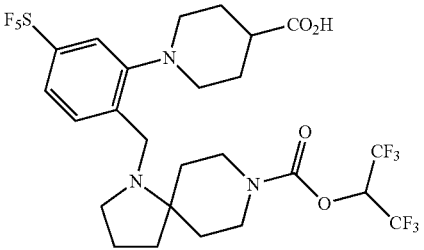 | δ 7.67-7.70 (m, 1H), 7.47-7.52 (m, 2H), 6.11-6.16 (m, 1H), 4.12-4.26 (m, 2H), 3.84 (s, 2H), 3.10-3.29 (m, 4H), 2.75-2.84 (m, 4H), 2.32-2.46 (m, 1H), 1.60-2.04 (m, 12H). | 678 |
| 241 | 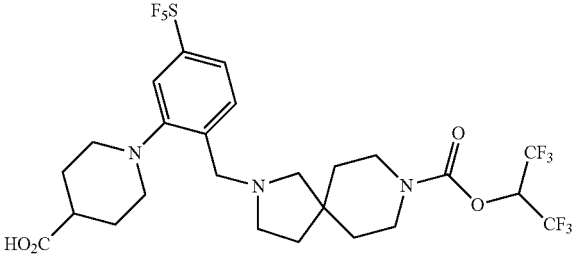 | δ 7.55-7.62 (m, 1H), 7.51-7.54 (m, 2H), 6.06-6.17 (m, 1H), 3.93 (s, 2H), 3.42-3.56 (m, 4H), 3.17-3.21 (m, 2H), 2.86-2.94 (m, 2H), 2.72-2.80 (m, 4H), 2.32-2.48 (m, 1H), 1.97-2.08 (m, 2H), 1.79-1.94 (m, 4H), 1.59-1.64 (m, 4H). | 678 |

TABLE 1-continued

| Ex | Structure | NMR (¹H NMR, 300 MHz or 400 MHz Methanol-d4) | MS [M + H]⁺ |
|---|---|---|---|
| 242 | 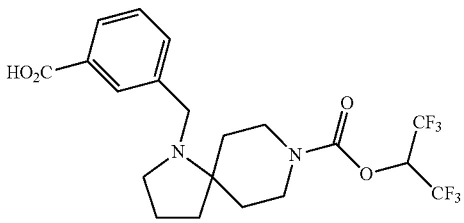 [SMILES: O=C(O)c1cccc(CN2CCCC23CCN(C(=O)OC(C(F)(F)F)C(F)(F)F)CC3)c1] | δ 8.04 (s, 1H), 7.92 (d, J = 7.6 Hz, 1H), 7.51 (d, J = 7.6 Hz, 1H), 7.40 (t, J = 7.6 Hz, 1H), 6.12-6.20 (m, 1H), 4.21-4.24 (m, 2H), 3.98 (s, 2H), 3.02-3.21 (m, 4H), 2.05-2.13 (m, 2H), 1.91-2.00 (m, 4H), 1.73-1.77 (m, 2H). | 469 |
| 243 | 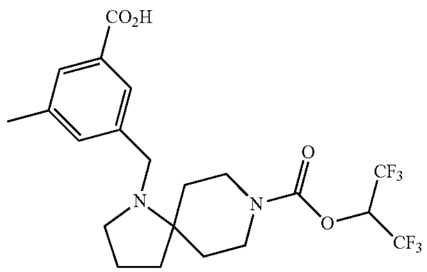 [SMILES: Cc1cc(CN2CCCC23CCN(C(=O)OC(C(F)(F)F)C(F)(F)F)CC3)cc(C(=O)O)c1] | δ 7.78-7.81 (m, 2H), 7.36 (s, 1H), 6.13-6.21 (m, 1H), 4.22-4.26 (m, 2H), 3.99 (s, 2H), 3.06-3.18 (m, 4H), 2.39 (s, 3H), 2.09-2.14 (m, 2H), 1.91-2.03 (m, 4H), 1.74-1.78 (m, 2H). | 483 |
| 244 | 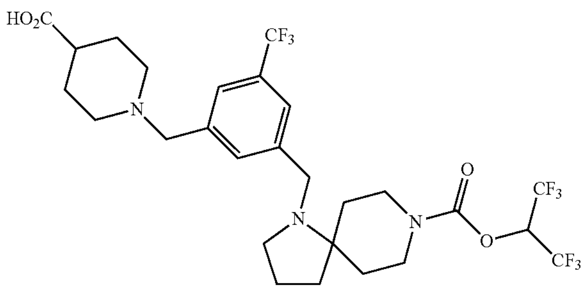 [SMILES: O=C(O)C1CCN(Cc2cc(CN3CCCC34CCN(C(=O)OC(C(F)(F)F)C(F)(F)F)CC4)cc(C(F)(F)F)c2)CC1] | δ 7.63-7.65 (m, 3H), 6.09-6.18 (m, 1H), 4.19-4.20 (m, 2H), 3.96 (br, 2H), 3.75 (br, 2H), 3.01-3.14 (m, 4H), 2.68-2.73 (m, 2H), 2.55-2.64 (m, 2H), 2.30-2.35 (m, 1H), 1.72-2.01 (m, 10H), 1.56-1.60 (m, 2H). | 634 |
| 245 | 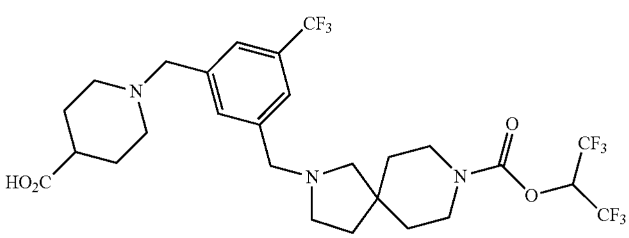 [SMILES: O=C(O)C1CCN(Cc2cc(CN3CCC4(CCN(C(=O)OC(C(F)(F)F)C(F)(F)F)CC4)C3)cc(C(F)(F)F)c2)CC1] | δ 7.68 (s, 3H), 6.07-6.13 (m, 1H), 3.80-3.90 (m, 4H), 3.42-3.60 (m, 4H), 3.05-3.09 (m, 2H), 2.75 (br, 2H), 2.46-2.59 (m, 4H), 2.28-2.32 (m, 1H), 1.95-1.99 (m, 2H), 1.75-1.86 (m, 4H), 1.61-1.63 (m, 4H). | 634 |
| 246 | 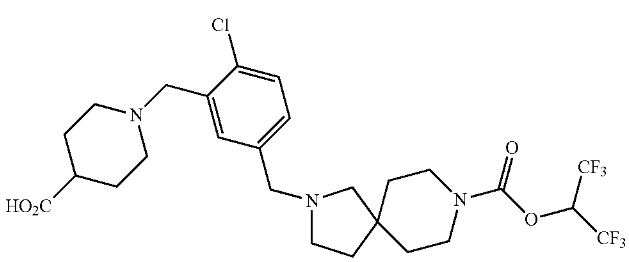 [SMILES: O=C(O)C1CCN(Cc2cc(CN3CCC4(CCN(C(=O)OC(C(F)(F)F)C(F)(F)F)CC4)C3)ccc2Cl)CC1] | δ 7.58 (s, 1H), 7.43 (d, J = 8.1 Hz, 1H), 7.33-7.36 (m, 1H), 6.07-6.13 (m, 1H), 3.92 (br, 2H), 3.78 (br, 2H), 3.42-3.59 (m, 4H), 3.09-3.13 (m, 2H), 2.82 (br, 2H), 2.49-2.64 (m, 4H), 2.26-2.31 (m, 1H), 1.94-1.98 (m, 2H), 1.82-1.87 (m, 4H), 1.77-1.79 (m, 4H). | 600 |

TABLE 1-continued
| Ex | Structure | NMR (¹H NMR, 300 MHz or 400 MHz Methanol-d4) | MS [M + H]+ |
|---|---|---|---|
| 247 | 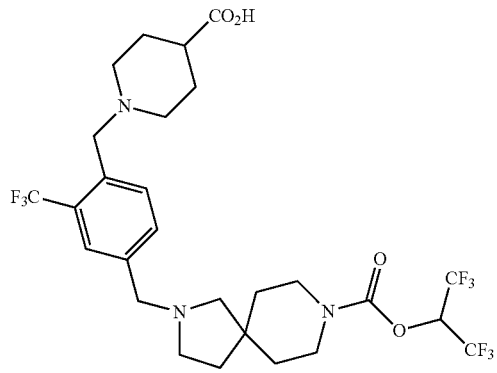 [SMILES: O=C(O)C1CCN(Cc2ccc(CN3CCC4(CCN(C(=O)OC(C(F)(F)F)C(F)(F)F)CC4)C3)cc2C(F)(F)F)CC1] | δ 7.83 (d, J = 7.8 Hz, 1H), 7.72 (s, 1H), 7.64 (d, J = 8.1 Hz, 1H), 6.07-6.16 (m, 1H), 3.86-3.89 (m, 2H), 3.73 (br, 2H), 3.41-3.60 (m, 4H), 2.86-2.94 (m, 4H), 2.68-2.72 (m, 2H), 2.19-2.26 (m, 3H), 1.63-1.96 (m, 10H). | 634 |
| 248 | 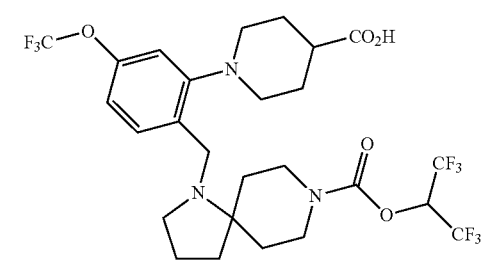 [SMILES: O=C(O)C1CCN(c2cc(OC(F)(F)F)ccc2CN2CCCC23CCN(C(=O)OC(C(F)(F)F)C(F)(F)F)CC3)CC1] | δ 7.58-7.59 (m, 1H), 7.02-7.08 (m, 2H), 6.10-6.23 (m, 1H), 4.22-4.26 (m, 2H), 3.98 (s, 2H), 2.94-3.32 (m, 6H), 2.71-2.79 (m, 2H), 2.35-2.44 (m, 1H), 1.83-2.09 (m, 10H), 1.67-1.72 (m, 2H). | 636 |
| 249 | 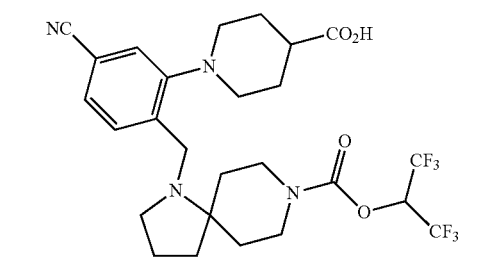 [SMILES: N#Cc1ccc(CN2CCCC23CCN(C(=O)OC(C(F)(F)F)C(F)(F)F)CC3)c(N2CCC(C(=O)O)CC2)c1] | δ 7.70-7.80 (m, 1H), 7.43-7.50 (m, 2H), 6.12-6.21 (m, 1H), 4.22-4.25 (m, 2H), 3.93 (s, 2H), 3.04-3.35 (m, 4H), 2.74-2.90 (m, 4H), 2.42-2.49 (m, 1H), 2.02-2.08 (m, 4H), 1.76-2.00 (m, 6H), 1.62-1.66 (m, 2H). | 577 |
| 250 | 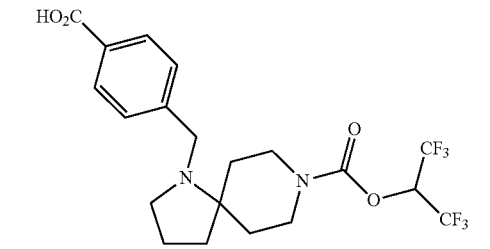 [SMILES: O=C(O)c1ccc(CN2CCCC23CCN(C(=O)OC(C(F)(F)F)C(F)(F)F)CC3)cc1] | δ 8.08-8.10 (m, 2H), 7.61-7.63 (m, 2H), 6.16-6.26 (m, 1H), 4.29-4.35 (m, 4H), 3.12-3.39 (m, 4H), 2.24-2.26 (m, 2H), 2.04-2.20 (m, 4H), 1.96-2.01 (m, 2H). | 469 |
| 251 | 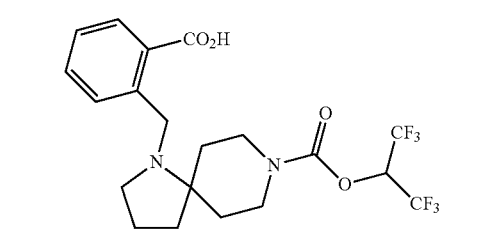 [SMILES: O=C(O)c1ccccc1CN1CCCC12CCN(C(=O)OC(C(F)(F)F)C(F)(F)F)CC2] | δ 7.96-8.01 (m, 1H), 7.48-7.54 (m, 3H), 6.15-6.24 (m, 1H), 3.98-4.32 (m, 4H), 3.15-3.40 (m, 4H), 2.30 (br, 2H), 2.06-2.22 (m, 4H), 1.95-1.99 (m, 2H). | 469 |

TABLE 1-continued

| Ex | Structure | NMR (¹H NMR, 300 MHz or 400 MHz Methanol-d4) | MS [M + H]⁺ |
|---|---|---|---|
| 252 | 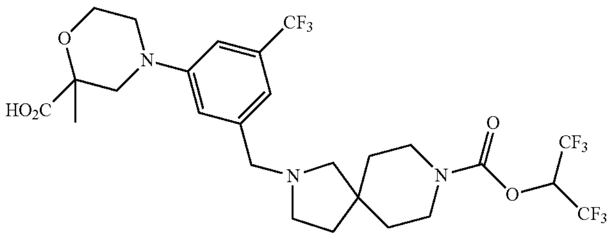 [SMILES: CC1(C(=O)O)CN(c2cc(CN3CCC4(CCN(C(=O)OC(C(F)(F)F)C(F)(F)F)CC4)C3)cc(C(F)(F)F)c2)CCO1] | δ 7.37 (br, 1H), 7.17-7.20 (m, 2H), 6.12-6.16 (m, 1H), 4.20 (br, 3H), 4.02-4.18 (m, 1H), 3.81-3.85 (m, 1H), 3.57-3.68 (m, 2H), 3.41-3.55 (m, 3H), 3.25 (br, 2H), 3.09 (s, 2H), 2.87-2.99 (m, 1H), 2.71-2.79 (m, 1H), 1.97 (t, J = 6.8 Hz, 2H), 1.70 (s, 4H), 1.41 (s, 3H). | 636 |
| 253 | 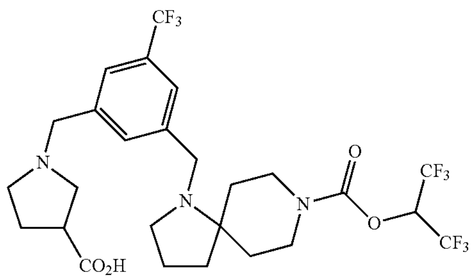 | δ 7.70-7.71 (m, 3H), 6.09-6.16 (m, 1H), 4.28-4.33 (m, 2H), 4.16-4.21 (m, 2H), 3.75-3.76 (m, 2H), 3.38-3.40 (m, 1H), 3.02-3.31 (m, 6H), 2.68-2.72 (m, 2H), 2.21-2.30 (m, 2H), 1.91-1.95 (m, 2H), 1.71-1.85 (m, 4H), 1.55-1.58 (m, 2H). | 620 |
| 254 | 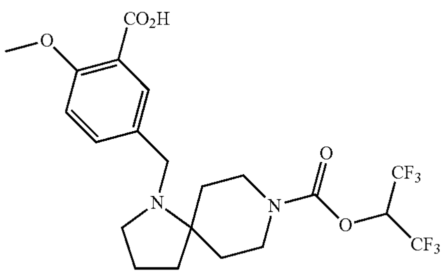 [SMILES: COc1ccc(CN2CCCC23CCN(C(=O)OC(C(F)(F)F)C(F)(F)F)CC3)cc1C(=O)O] | (Chloroform-d) δ 7.56-7.59 (m, 1H), 7.36-7.39 (m, 1H), 7.00-7.03 (m, 1H), 6.14-6.22 (m, 1H), 4.22-4.30 (m, 2H), 4.09 (s, 2H), 3.84 (s, 3H), 3.07-3.25 (m, 4H), 2.20-2.21 (m, 2H), 2.02-2.13 (m, 4H), 1.86-1.87 (m, 2H). | 499 |
| 255 | 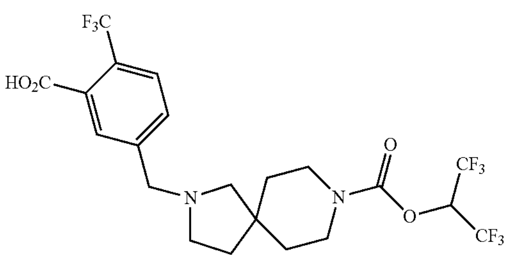 [SMILES: O=C(O)c1cc(CN2CCC3(CCN(C(=O)OC(C(F)(F)F)C(F)(F)F)CC3)C2)ccc1C(F)(F)F] | δ 7.91 (s, 1H), 7.70-7.73 (m, 1H), 7.56-7.59 (m, 1H), 6.08-6.20 (m, 1H), 4.45 (s, 2H), 3.56-3.57 (m, 4H), 3.43-3.47 (m, 2H), 3.30-3.34 (m, 2H), 2.05-2.10 (m, 2H), 1.77 (br, 4H). | 537 |
| 256 | 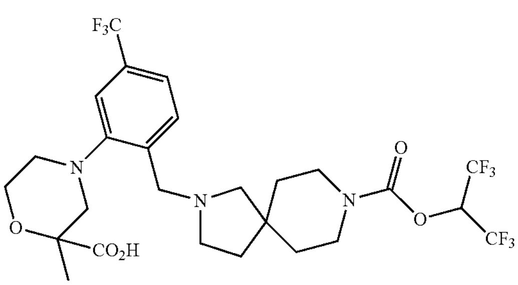 [SMILES: CC1(C(=O)O)CN(c2cc(C(F)(F)F)ccc2CN2CCC3(CCN(C(=O)OC(C(F)(F)F)C(F)(F)F)CC3)C2)CCO1] | δ 7.73 (s, 1H), 7.67 (d, J = 8.1 Hz, 1H), 7.60 (d, J = 8.1 Hz, 1H), 6.11-6.19 (m, 1H), 4.63-4.68 (m, 1H), 4.31-4.36 (m, 1H), 3.95-4.02 (m, 1H), 3.81-3.85 (m, 1H), 3.34-3.65 (m, 8H), 3.09-3.13 (m, 1H), 2.88-2.99 (m, 2H), 2.77-2.81 (m, 1H), 2.11-2.22 (m, 2H), 1.78-1.82 (m, 4H), 1.36 (s, 3H). | 636 |

TABLE 1-continued

| Ex | Structure | NMR (¹H NMR, 300 MHz or 400 MHz Methanol-d4) | MS [M + H]⁺ |
|---|---|---|---|
| 257 | 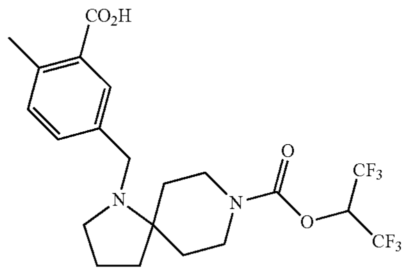 [SMILES: Cc1ccc(CN2CCCC23CCN(C(=O)OC(C(F)(F)F)C(F)(F)F)CC3)cc1C(=O)O] | δ 7.61-7.62 (m, 1H), 7.29-7.31 (m, 1H), 7.21-7.23 (m, 1H), 6.14-6.20 (m, 1H), 4.22-4.29 (m, 2H), 4.04 (s, 2H), 3.07-3.21 (m, 4H), 2.48 (s, 3H), 2.13-2.17 (m, 2H), 1.94-2.09 (m, 4H), 1.77-1.80 (m, 2H). | 483 |
| 258 | 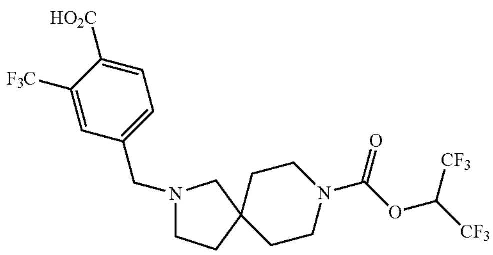 [SMILES: O=C(O)c1ccc(CN2CCC3(CCN(C(=O)OC(C(F)(F)F)C(F)(F)F)CC3)C2)cc1C(F)(F)F] | δ 7.76 (s, 1H), 7.64-7.66 (m, 1H), 7.56-7.58 (m, 1H), 6.08-6.16 (m, 1H), 4.17 (br, 2H), 3.55-3.63 (m, 2H), 3.41-3.54 (m, 2H), 3.12-3.19 (m, 2H), 2.96-3.03 (m, 2H), 1.94 (br, 2H), 1.66-1.68 (m, 4H). | 537 |
| 259 | 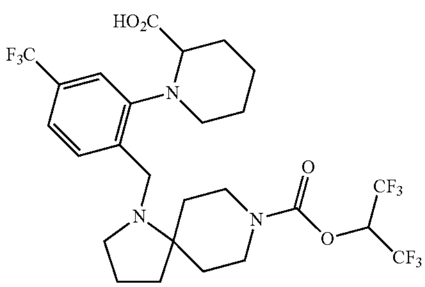 [SMILES: O=C(O)C1CCCCN1c1cc(C(F)(F)F)ccc1CN1CCCC12CCN(C(=O)OC(C(F)(F)F)C(F)(F)F)CC2] | δ 7.72 (s, 1H), 7.63-7.65 (m, 1H), 7.52-7.54 (m, 1H), 6.19-6.23 (m, 1H), 4.83-4.87 (m, 1H), 4.32-4.36 (m, 2H), 3.70-3.74 (m, 2H), 2.99-3.25 (m, 5H), 2.50-2.55 (m, 3H), 2.06-2.13 (m, 6H), 1.88-1.95 (m, 2H), 1.64-1.74 (m, 4H). | 620 |
| 260 | 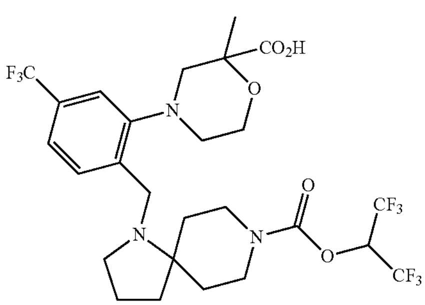 | δ 7.66-7.68 (m, 2H), 7.53-7.56 (m, 1H), 6.12-6.20 (m, 1H), 4.60 (br, 1H), 4.05-4.34 (m, 3H), 3.90-3.97 (m, 1H), 3.76-3.80 (m, 1H), 3.37-3.40 (m, 1H), 3.09-3.29 (m, 4H), 2.87-2.96 (m, 2H), 2.72-2.80 (m, 2H), 2.26-2.55 (m, 3H), 2.10 (br, 3H), 1.86 (br, 2H), 1.45 (s, 3H). | 636 |
| 261 | 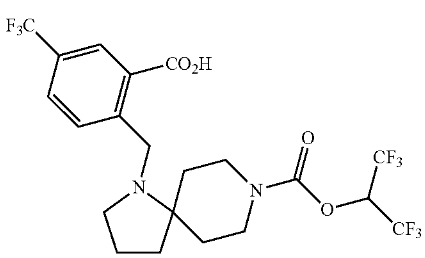 [SMILES: O=C(O)c1cc(C(F)(F)F)ccc1CN1CCCC12CCN(C(=O)OC(C(F)(F)F)C(F)(F)F)CC2] | δ 8.24 (s, 1H), 7.74-7.77 (m, 1H), 7.64-7.66 (m, 1H), 6.12-6.21 (m, 1H), 4.10-4.40 (m, 4H), 3.12-3.19 (m, 4H), 2.27 (br, 2H), 2.04-2.13 (m, 4H), 1.93-1.96 (m, 2H). | 537 |

TABLE 1-continued

| Ex | Structure | NMR (¹H NMR, 300 MHz or 400 MHz Methanol-d4) | MS [M + H]⁺ |
|---|---|---|---|
| 262 | 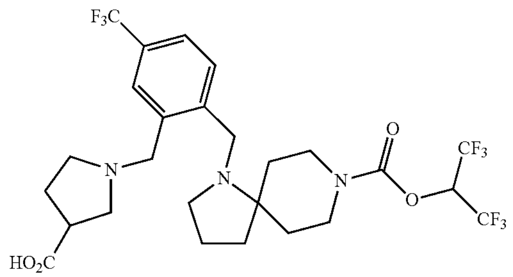 [SMILES: O=C(O)C1CCN(Cc2cc(C(F)(F)F)ccc2CN2CCCC23CCN(C(=O)OC(C(F)(F)F)C(F)(F)F)CC3)C1] | δ 7.89 (s, 1H), 7.71-7.76 (m, 2H), 6.18-6.22 (m, 1H), 4.28-4.34 (m, 4H), 4.10 (br, 2H), 3.34 (br. 1H), 3.04-3.22 (m, 6H), 2.81-2.83 (m, 2H), 1.78-2.30 (m, 9H), 1.64-1.69 (m, 1H). | 620 |
| 263 | 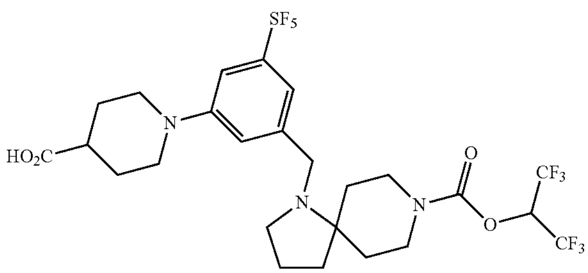 | δ 7.16-7.20 (m, 3H), 6.11-6.15 (m, 1H), 4.19 (br, 2H), 3.67-3.73 (m, 4H), 3.01-3.19 (m, 2H), 2.77-2.89 (m, 4H), 2.38-2.47 (m, 1H), 1.91-2.04 (m, 4H), 1.78-1.85 (m, 6H), 1.56-1.60 (m, 2H). | 678 |
| 264 | 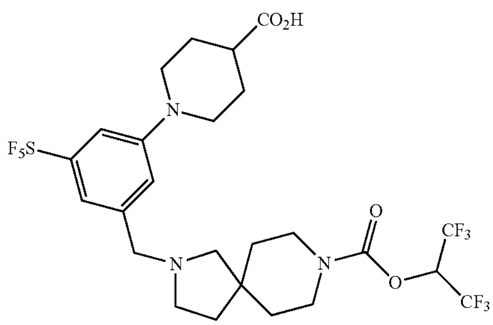 | δ 7.25 (s, 3H), 6.08-6.17 (m, 1H), 3.71-3.91 (m, 4H), 3.42-3.56 (m, 4H), 2.70-2.92 (m, 6H), 2.34-2.48 (m, 1H), 1.99-2.04 (m, 2H), 1.70-1.88 (m, 4H), 1.62-1.65 (m, 4H). | 678 |
| 265 | 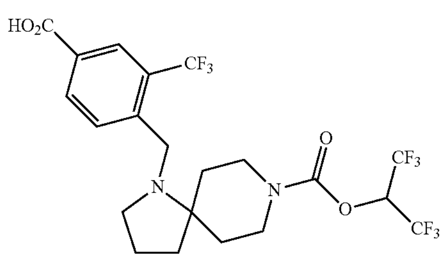 [SMILES: O=C(O)c1ccc(CN2CCCC23CCN(C(=O)OC(C(F)(F)F)C(F)(F)F)CC3)c(C(F)(F)F)c1] | δ 826 (s, 1H), 8.08 (d, J = 8.1 Hz, 1H), 7.93 (d, J = 8.1 Hz, 1H), 6.09-6.17 (m, 1H), 4.16-4.20 (m, 2H), 3.90 (s, 2H), 3.00-3.16 (m, 2H), 2.76-2.78 (m, 2H), 1.93-1.98 (m, 4H), 1.70-1.90 (m, 2H), 1.51-1.59 (m, 2H). | 537 |
| 266 | 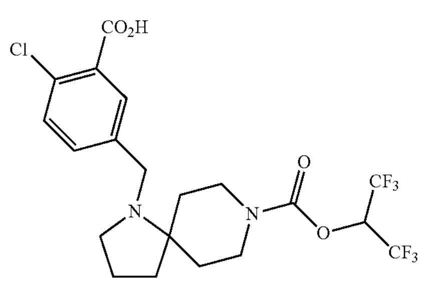 [SMILES: O=C(O)c1cc(CN2CCCC23CCN(C(=O)OC(C(F)(F)F)C(F)(F)F)CC3)ccc1Cl] | δ 7.61 (s, 1H), 7.34-7.44 (m, 2H), 6.16-6.20 (m, 1H), 4.25-4.28 (m, 2H), 4.17 (s, 2H), 3.12-3.32 (m, 4H), 2.02-2.25 (m, 6H), 1.85-1.89 (m, 2H). | 503 |

TABLE 1-continued

| Ex | Structure | NMR (¹H NMR, 300 MHz or 400 MHz Methanol-d4) | MS [M + H]⁺ |
|---|---|---|---|
| 267 | 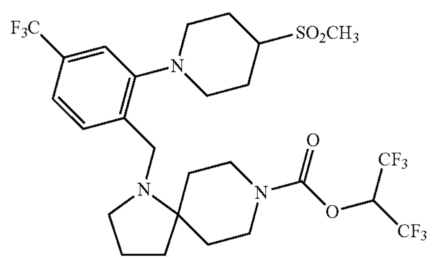 | (Chloroform-d) δ 7.68-7.70 (m, 1H), 7.32-7.34 (m, 1H), 7.25 (s, 1H), 5.72-5.80 (m, 1H), 4.18-4.26 (m, 2H), 3.66 (br, 2H), 3.23-3.27 (m, 2H), 2.92-3.06 (m, 6H), 2.69-2.79 (m, 2H), 2.61-2.65 (m, 2H), 2.23-2.27 (m, 2H), 1.98-2.11 (m, 2H), 1.70-1.82 (m, 5H), 1.50-1.68 (m, 3H). | 654 |
| 268 | 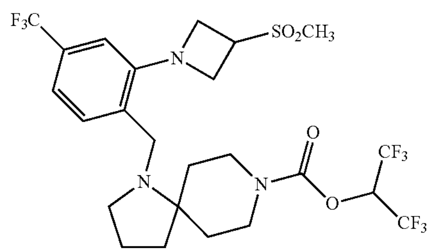 [SMILES: CS(=O)(=O)C1CN(c2cc(C(F)(F)F)ccc2CN2CCCC23CCN(C(=O)OC(C(F)(F)F)C(F)(F)F)CC3)C1] | (Chloroform-d) δ 7.61 (br, 1H), 7.15-7.17 (m, 1H), 6.74 (br, 1H), 5.71-5.79 (m, 1H), 4.17-4.30 (m, 6H), 4.06-4.12 (m, 1H), 3.56 (br, 2H), 2.92-3.06 (m, 5H), 2.66 (br, 2H), 1.85 (br, 3H), 1.55-1.64 (m, 5H). | 626 |
| 269 | 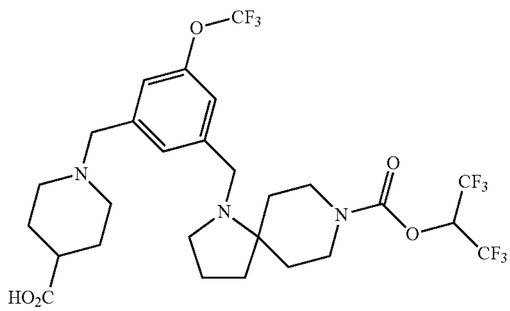 [SMILES: O=C(O)C1CCN(Cc2cc(CN3CCCC34CCN(C(=O)OC(C(F)(F)F)C(F)(F)F)CC4)cc(OC(F)(F)F)c2)CC1] | δ 7.43 (s, 1H), 7.29 (d, J = 12.4 Hz, 2H), 6.10-6.20 (m, 1H), 4.17-4.22 (m, 2H), 3.96 (br, 2H), 3.69-3.77 (m, 2H), 3.03-3.18 (m, 4H), 2.72-2.76 (m, 2H), 2.60-2.65 (m, 2H), 2.32-2.39 (m, 1H), 1.93-2.03 (m, 4H), 1.71-1.90 (m, 6H), 1.56-1.59 (m, 2H). | 650 |
| 270 | 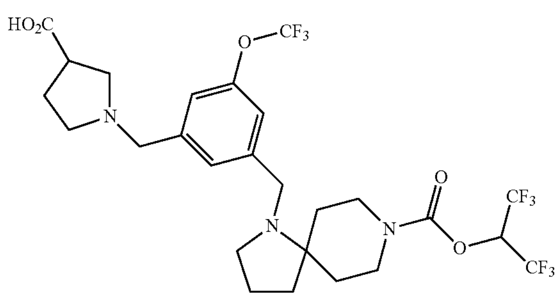 [SMILES: O=C(O)C1CCN(Cc2cc(CN3CCCC34CCN(C(=O)OC(C(F)(F)F)C(F)(F)F)CC4)cc(OC(F)(F)F)c2)C1] | δ 7.51 (s, 1H), 7.35 (s, 2H), 6.13-6.16 (m, 1H), 4.28-4.32 (m, 2H), 4.17-4.24 (m, 2H), 3.74 (br. 2H), 3.43-3.47 (m, 1H), 3.06-3.30 (m, 6H), 2.72-2.75 (m, 2H), 2.24-2.32 (m, 2H), 1.92-1.96 (m, 2H), 1.73-1.87 (m, 4H), 1.56-1.59 (m, 2H). | 636 |
| 271 | 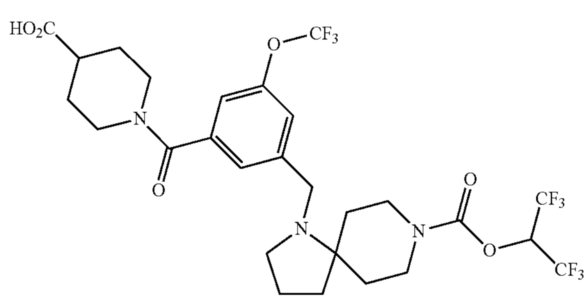 [SMILES: O=C(O)C1CCN(C(=O)c2cc(CN3CCCC34CCN(C(=O)OC(C(F)(F)F)C(F)(F)F)CC4)cc(OC(F)(F)F)c2)CC1] | δ 7.77 (s, 1H), 7.67 (s, 1H), 7.60 (s, 1H), 6.10-6.20 (m, 1H), 4.48-4.51 (m, 1H), 4.19-4.23 (m, 2H), 3.78-3.86 (m, 2H), 3.62-3.66 (m, 1H), 3.04-3.22 (m, 4H), 2.73-2.76 (m, 2H), 2.59-2.64 (m, 1H), 1.58-2.08 (m, 12H). | 648 |

TABLE 1-continued

| Ex | Structure | NMR (¹H NMR, 300 MHz or 400 MHz Methanol-d4) | MS [M + H]⁺ |
|---|---|---|---|
| 272 | 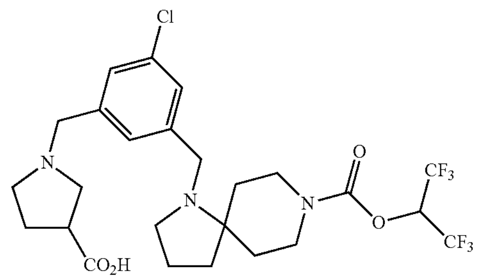 [SMILES: O=C(O)C1CCN(Cc2cc(Cl)cc(CN3CCCC34CCN(C(=O)OC(C(F)(F)F)C(F)(F)F)CC4)c2)C1] | δ 7.40-7.41 (m, 3H), 6.08-6.16 (m, 1H), 4.16-4.26 (m, 4H), 3.66 (br, 2H), 3.40-3.43 (m, 1H), 3.00-3.30 (m, 6H), 2.68-2.72 (m, 2H), 2.21-2.30 (m, 2H), 1.69-1.97 (m, 6H), 1.55-1.59 (m, 2H). | 586 |
| 273 | 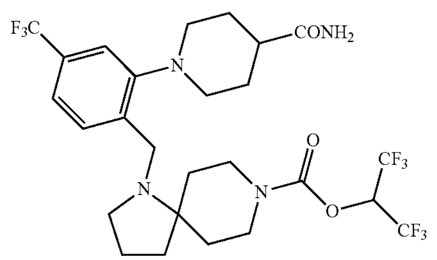 | (Chloroform-d) δ 7.65-7.66 (m, 1H), 7.27-7.31 (m, 2H), 5.70-5.83 (m, 1H), 5.47-5.53 (m, 2H), 4.17-4.25 (m, 2H), 3.66 (s, 2H), 2.92-3.15 (m, 4H), 2.62-2.69 (m, 4H), 2.26-2.27 (m, 1H), 1.67-1.94 (m, 10H), 1.48-1.52 (m, 2H). | 619 |
| 274 | 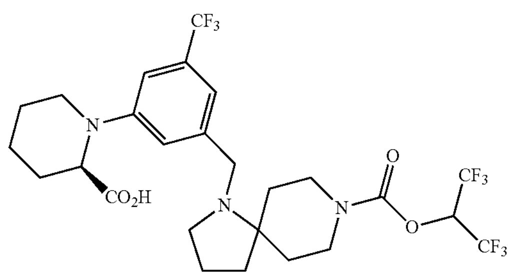 [SMILES: O=C(O)[C@H]1CCCCN1c1cc(CN2CCCC23CCN(C(=O)OC(C(F)(F)F)C(F)(F)F)CC3)cc(C(F)(F)F)c1] | δ 7.10 (br, 2H), 7.02 (s, 1H), 6.14-6.18 (m, 1H), 4.40 (br, 1H), 4.21-4.28 (m, 2H), 3.96 (s, 2H), 3.52 (br, 1H), 3.29-3.38 (m, 1H), 3.05-3.16 (m, 4H), 2.07-2.10 (m, 1H), 1.90-2.02 (m, 8H), 1.51-1.74 (m, 5H). | 620 |
| 275 | 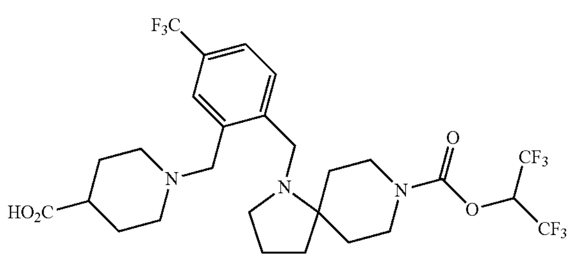 [SMILES: O=C(O)C1CCN(Cc2cc(C(F)(F)F)ccc2CN2CCCC23CCN(C(=O)OC(C(F)(F)F)C(F)(F)F)CC3)CC1] | (Chloroform-d) δ 7.61 (s, 1H), 7.44-7.57 (m, 2H), 5.70-5.83 (m, 1H), 5.49 (br, 2H), 4.17-4.26 (m, 2H), 3.71-3.82 (m, 2H), 3.57 (s, 2H), 2.84-3.06 (m, 4H), 2.64-2.64 (m, 2H), 2.01-2.02 (m, 3H), 1.73-1.89 (m, 10H), 1.42-1.52 (m, 2H). | 633 |
| 276 | 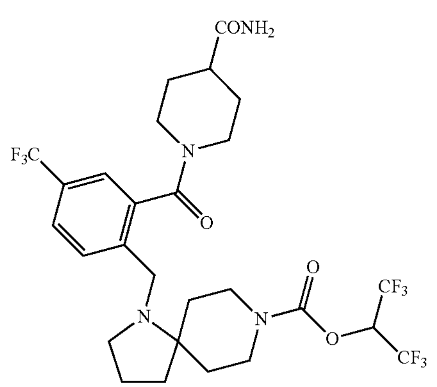 [SMILES: NC(=O)C1CCN(C(=O)c2cc(C(F)(F)F)ccc2CN2CCCC23CCN(C(=O)OC(C(F)(F)F)C(F)(F)F)CC3)CC1] | (Chloroform-d) δ 7.51-7.53 (m, 2H), 7.37-7.43 (m, 1H), 5.71-5.80 (m, 1H), 5.51 (br, 2H), 4.54-4.78 (m, 1H), 4.20 (br, 2H), 3.93-4.00 (m, 1H), 3.35-3.51 (m, 2H), 2.70-3.18 (m, 4H), 2.35-2.62 (m, 3H), 2.01 (s, 1H), 1.60-1.91 (m, 9H), 1.64 (br, 1H), 1.21-1.30 (m, 1H). | 647 |

TABLE 1-continued

| Ex | Structure | NMR ($^1$H NMR, 300 MHz or 400 MHz Methanol-d4) | MS [M + H]$^+$ |
|---|---|---|---|
| 277 | 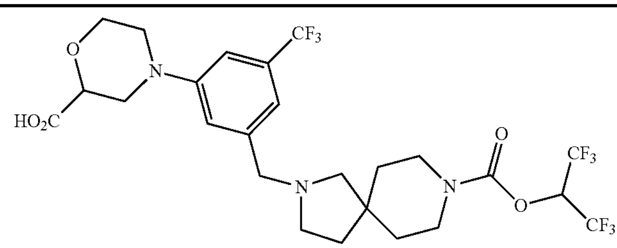 | δ 7.32 (s, 1H), 7.20-7.23 (m, 2H), 6.09-6.18 (m, 1H), 4.07-4.13 (m, 4H), 3.80-3.95 (m, 1H), 3.73-3.76 (m, 1H), 3.59-3.64 (m, 2H), 3.51-3.55 (m, 3H), 3.17 (br, 2H), 2.84-3.08 (m, 4H), 1.92-1.97 (m, 2H), 1.68-1.70 (m, 4H). | 622 |
| 278 | 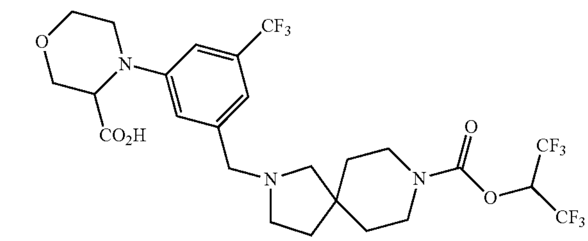 [SMILES: O=C(O)C1COCCN1c1cc(CN2CCC3(CCN(C(=O)OC(C(F)(F)F)C(F)(F)F)CC3)C2)cc(C(F)(F)F)c1] | δ 7.34 (br, 1H), 7.15 (s, 1H), 7.02 (s, 1H), 6.06-6.17 (m, 1H), 4.49-4.53 (m, 1H), 4.23-4.33 (m, 2H), 3.98-4.11 (m, 2H), 3.81-3.85 (m, 1H), 3.66-3.69 (m, 1H), 3.51 (br, 6H), 3.19-3.28 (m, 3H), 2.96-3.00 (m, 1H), 1.90-1.94 (m, 2H), 1.65-1.68 (m, 4H). | 622 |
| 279 | 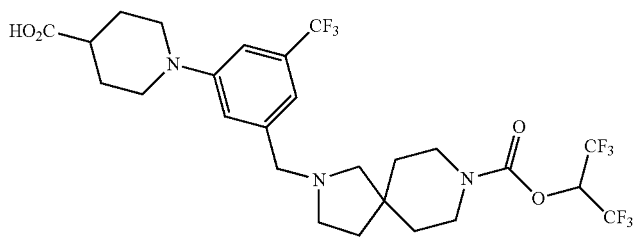 [SMILES: O=C(O)C1CCN(c2cc(CN3CCC4(CCN(C(=O)OC(C(F)(F)F)C(F)(F)F)CC4)C3)cc(C(F)(F)F)c2)CC1] | δ 7.32 (s, 1H), 7.12-7.14 (m, 2H), 6.08-6.17 (m, 1H), 4.00 (br, 2H), 3.76-3.80 (m, 2H), 3.43-3.62 (m, 4H), 3.05-3.07 (m, 2H), 2.81-2.92 (m, 4H), 2.34-2.41 (m, 1H), 1.93-2.06 (m, 2H), 1.74-1.91 (m, 4H), 1.61-1.72 (m, 4H). | 620 |
| 280 | 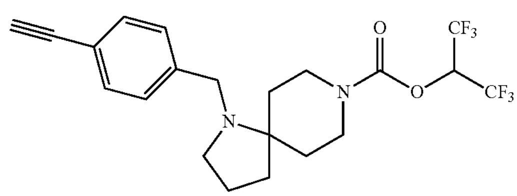 [SMILES: C#Cc1ccc(CN2CCCC23CCN(C(=O)OC(C(F)(F)F)C(F)(F)F)CC3)cc1] | (Chloroform-d) δ 7.42-7.44 (m, 2H), 7.26-7.28 (m, 2H), 5.71-5.80 (m, 1H), 4.17-4.25 (m, 2H), 3.58 (br, 2H), 2.91-3.05 (m, 3H), 2.64-2.66 (m, 2H), 1.66-1.80 (m, 6H), 1.43-1.50 (m, 2H). | 449 |
| 281 | 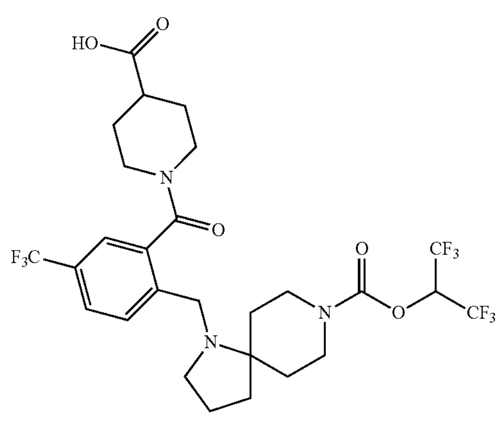 [SMILES: O=C(O)C1CCN(C(=O)c2cc(C(F)(F)F)ccc2CN2CCCC23CCN(C(=O)OC(C(F)(F)F)C(F)(F)F)CC3)CC1] | δ 7.60-7.68 (m, 2H), 7.52 (s, 1H), 6.08-6.16 (m, 1H), 4.34-4.60 (m, 1H), 3.96-4.17 (m, 3H), 3.36-3.39 (m, 2H), 2.82-3.20 (m, 4H), 2.59 (br, 3H), 2.01-2.11 (m, 2H), 1.33-1.87 (m, 10H). | 648 |

II. Biological Evaluation

Compounds are tested to assess their MAGL and serine hydrolase activity using the following in vitro and in vivo assays.

In Vitro Competitive Activity-Based Protein Profiling.

Proteomes (mouse brain membrane fraction or cell lysates) (50 μL, 1.0 mg/mL total protein concentration) were preincubated with varying concentrations of inhibitors at 37° C. After 30 min, FP-Rh (1.0 μL, 50 μM in DMSO) was added and the mixture was incubated for another 30 min at 37° C. Reactions were quenched with SDS loading buffer (50 μL-4X) and run on SDS-PAGE. Following gel imaging, serine hydrolase activity was determined by measuring fluorescent intensity of gel bands corresponding to MAGL, ABHD6 and FAAH using ImageJ 1.43 u software. Data from this assay is shown in Table 2 (% inhibition at 1 μM).

In Vitro Competitive Activity-Based Protein Profiling (Human).

Proteomes (human prefrontal cortex or cell membrane fractions) (50 μL, 1.0-2.0 mg/mL total protein concentration) were preincubated with varying concentrations of inhibitors at 37° C. After 30 min, FP-Rh or JW912 (1.0 μL, 50 μM in DMSO) was added and the mixture was incubated for another 30 min at room temperature. Reactions were quenched with SDS loading buffer (15 μL-4X) and run on SDS-PAGE. Following gel imaging, serine hydrolase activity was determined by measuring fluorescent intensity of gel bands corresponding to MAGL using ImageJ 1.49 k software.

Preparation of Mouse Brain Proteomes from Inhibitor Treated Mice.

Inhibitors were administered to wild-type C57Bl/6J by oral gavage in a vehicle, e.g. PEG400/Ethanol/PBS (7/2/1). Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44). Data from this assay is shown in Table 2 (% inhibition at 5 mg/kg).

Recombinant Expression of Human MAGL in HEK293T Cells.

hMAGL was expressed in HEK293T cells according to previously reported methods (see Niphakis, Long, and Blankman, J. L., et al. (2007) Chem. Biol. 14:1347-1356). Cell lysates were diluted with mock proteomes for use in competitive ABPP experiments.

TABLE 2

| Ex | MAGL $IC_{50}$ (mouse) | FAAH $IC_{50}$ (mouse) | ABHD6 $IC_{50}$ (mouse) | MAGL $IC_{50}$ (human) | MAGL % Inh 1 μM (mouse) | FAAH % Inh 1 μM (mouse) | ABHD6 % Inh 1 μM (mouse) | MAGL % Inh 5 mg/kg (mouse) | FAAH % Inh 5 mg/kg (mouse) | ABHD6 % Inh 5 mg/kg (mouse) |
|---|---|---|---|---|---|---|---|---|---|---|
| 1 | ** | * | * | | ### | # | # | | | |
| 2 | ** | * | * | | ### | # | # | | | |
| 3 | ** | * | * | | ### | # | # | | | |
| 4 | ** | * | * | | ### | # | # | ### | # | # |
| 5 | *** | * | * | | ### | # | # | ### | # | ## |
| 6 | ** | * | * | | | | | | | |
| 7 | *** | * | * | | | | | ### | ### | # |
| 8 | *** | * | * | | | | | ### | ## | ## |
| 9 | *** | * | * | | | | | ### | # | # |
| 10 | *** | * | * | | | | | ### | ## | # |
| 11 | ** | * | * | | ### | # | # | | | |
| 12 | ** | * | * | | ### | # | # | | | |
| 13 | ** | * | * | | ### | # | # | | | |
| 14 | ** | * | * | | ### | # | # | | | |
| 15 | ** | * | * | | ### | # | # | | | |
| 16 | *** | * | * | *** | ### | # | # | # | # | # |
| 17 | *** | * | * | | ### | # | ### | ## | # | # |
| 18 | *** | * | * | | ### | # | ## | ## | # | # |
| 19 | *** | * | * | | | | | ## | # | # |
| 20 | *** | * | * | *** | | | | ## | # | # |
| 21 | *** | * | ** | | ### | # | ### | ### | # | ## |
| 22 | *** | * | ** | | ### | # | ### | ### | # | # |
| 23 | *** | * | * | | ### | # | # | ## | # | # |
| 24 | *** | * | * | | ### | # | # | ### | # | # |
| 25 | *** | * | ** | | ### | # | ### | ## | # | # |
| 26 | *** | * | ** | | ### | # | ### | ## | # | # |
| 27 | ** | * | * | | | | | ### | # | # |
| 28 | *** | * | * | | | | | ### | # | # |
| 29 | *** | * | * | | ### | # | ### | ### | ## | ### |
| 30 | *** | * | * | | ### | # | # | ### | # | # |
| 31 | *** | * | * | | ### | # | # | ### | # | ## |
| 32 | *** | * | * | | ### | # | # | ### | # | # |
| 33 | *** | * | * | | ### | # | # | ### | ## | # |
| 34 | *** | * | * | | ### | # | # | ### | # | # |
| 35 | *** | * | * | | ### | # | # | ### | # | # |
| 36 | *** | * | * | | ### | # | # | ### | # | # |
| 37 | *** | * | * | | ### | # | # | ### | # | # |
| 38 | *** | * | * | | ### | ## | # | | | |
| 39 | *** | * | * | | ### | # | # | | | |
| 40 | *** | * | * | | ### | # | # | | | |
| 41 | *** | * | * | | ### | # | # | | | |
| 42 | *** | * | * | | ### | # | # | ### | # | # |
| 43 | *** | * | * | | ### | # | # | ## | # | # |
| 44 | ** | * | * | | | | | | | |
| 45 | *** | * | * | | | | | ## | # | # |
| 46 | *** | * | * | | | | | ### | # | # |
| 47 | *** | * | * | | ### | # | # | ### | # | # |
| 48 | *** | * | ** | | ### | # | ### | ### | # | ## |
| 49 | ** | * | * | | ### | # | # | | | |
| 50 | *** | * | * | | ### | # | ## | ## | # | # |
| 51 | *** | * | * | | ### | # | # | ## | # | # |
| 52 | *** | * | * | | ### | # | # | # | # | # |
| 53 | ** | * | * | *** | ### | # | # | | | |
| 54 | *** | * | * | | ### | # | # | ## | # | # |
| 55 | *** | * | * | | ### | # | # | | | |

TABLE 2-continued

| Ex | MAGL IC$_{50}$ (mouse) | FAAH IC$_{50}$ (mouse) | ABHD6 IC$_{50}$ (mouse) | MAGL IC$_{50}$ (human) | MAGL % Inh 1 μM (mouse) | FAAH % Inh 1 μM (mouse) | ABHD6 % Inh 1 μM (mouse) | MAGL % Inh 5 mg/kg (mouse) | FAAH % Inh 5 mg/kg (mouse) | ABHD6 % Inh 5 mg/kg (mouse) |
|---|---|---|---|---|---|---|---|---|---|---|
| 56 | ** | * | * |  | ## | # | # |  |  |  |
| 57 | ** | * | * |  | ### | # | # |  |  |  |
| 58 | ** | * | ** |  | ### | # | ### |  |  |  |
| 59 | ** | * | * |  | ### | # | # |  |  |  |
| 60 | *** | * | * |  | ### | # | # | ### | ## | # |
| 61 | *** | * | * |  | ### | ## | ## | ### | ### | # |
| 62 | *** | * | * |  | ### | # | # | ### | ## | ## |
| 63 | ** | * | * |  | ### | # | # |  |  |  |
| 64 | *** | * | * |  | ### | # | # | ## | # | # |
| 65 | *** | * | * |  | ### | # | ## | ## | # | ## |
| 66 | *** | * | * |  | ### | # | # | ## | # | # |
| 67 | *** | * | * |  | ### | # | # | ### | # | # |
| 68 | *** | * | * | *** | ### | # | # | ### | # | # |
| 69 | ** |  | * |  | ### | # | # |  |  |  |
| 70 | *** | * | ** |  | ### | # | ### | ### | # | ### |
| 71 | *** | * | * |  | ### | # | ## | ### | # | ## |
| 72 | *** | * | * |  | ### | # | # | ## | # | # |
| 73 | *** | * | * |  | ### | # | # | ## | # | # |
| 74 | *** | * | * |  | ### | # | ## | ## | # | # |
| 75 | *** | * | * |  | ### | # | # | ### | # | # |
| 76 | *** | * | * |  | ### | # | # | ### | # | # |
| 77 | *** | * | * |  | ### | # | # | ### | # | # |
| 78 | *** | * | * |  | ### | # | # | ## | # | # |
| 79 | *** | * | * |  | ### | # | # | ### | # | # |
| 80 | *** | * | * |  | ### | # | # | ### | ## | ## |
| 81 | *** | * | * |  | ### | # | # | ### | # | # |
| 82 | *** | * | * |  | ### | # | # | ### | # | # |
| 83 | *** | * | * |  | ### | # | # |  |  |  |
| 84 | ** | * | * |  | ### | # | # | ### | # | # |
| 85 | *** | * | * |  | ### | # | # | ### | # | # |
| 86 | *** | * | * |  | ### | # | # | ### | # | # |
| 87 | *** | * | * |  | ### | # | # | ## | # | # |
| 88 | *** | * | * |  | ### | # | # | ## | # | # |
| 89 | *** | * | * |  | ### | # | # | # | # | # |
| 90 | *** | * | * |  | ### | # | # | ## | # | # |
| 91 | *** | * | * |  | ### | # | # | ### | # | # |
| 92 | *** | * | ** |  | ### | # | ### |  |  |  |
| 93 | *** | * | * |  | ### | # | # | ### | # | # |
| 94 | *** | * | * |  | ### | # | # | # | # | # |
| 95 | ** | * | * |  | ## | # | # |  |  |  |
| 96 | *** | * | * |  | ### | # | # | ### | # | # |
| 97 | *** | * | * |  | ### | # | # | ### | # | # |
| 98 | ** | * | * |  | ### | # | # |  |  |  |
| 99 | *** | * | * |  | ### | # | # | ### | # | # |
| 100 | *** | * | * |  | ### | # | # | ### | # | # |
| 101 | *** | * | * |  | ### | # | # | ### | # | # |
| 102 | *** | * | * |  | ### | # | # | ### | # | # |
| 103 | ** | * | ** |  | ### | # | ### |  |  |  |
| 104 | *** | * | * |  | ### | ## | # | ## | # | # |
| 105 | *** | * | * |  | ### | # | # | # | # | # |
| 106 | ** | * | * |  | ### | # | # |  |  |  |
| 107 | *** | * | * |  | ### | # | # | ### | ## | # |
| 108 | *** | * | * |  | ### | # | # | ### | # | # |
| 109 | *** | * | * |  | ### | # | # |  |  |  |
| 110 | *** | * | * |  | ### | # | # |  |  |  |
| 111 | *** | * | * |  | ### | # | # |  |  |  |
| 112 | *** | * | * |  | ### | # | # |  |  |  |
| 113 | *** | * | * |  | ### | # | # |  |  |  |
| 114 | *** | * | * |  | ### | # | ## |  |  |  |
| 115 | ** | * | * |  | ### | # | # |  |  |  |
| 116 | *** | * | * |  | ### | # | # |  |  |  |
| 117 | ** | * | * |  | ### | # | # |  |  |  |
| 118 | * | * | * | ** | ## | # | # |  |  |  |
| 119 | *** | * | ** | *** | ### | # | ### | ### | # | ### |
| 120 | *** | * | * | *** | ### | # | # | ### | # | # |
| 121 | *** | * | * | *** | ### | # | # | ### | # | # |
| 122 | *** | * | * | *** | ### | # | # | ### | ## | ## |
| 123 | *** | * | * | *** | ### | # | # | ### | # | ## |
| 124 | *** | * | * |  | ### | # | # | ### | # | # |
| 125 | *** | * | * |  | ### | # | # | ### | # | # |
| 126 | *** | * | * |  | ### | # | ## |  |  |  |
| 127 | ** | * | * |  | ### | # | ## |  |  |  |
| 128 | *** | * | * |  | ### | # | # | ### | # | # |
| 129 | *** | * | * |  | ### | # | ## | ### | # | # |
| 130 | *** | * | * |  | ### | # | ## | ### | # | # |

TABLE 2-continued

| Ex | MAGL IC$_{50}$ (mouse) | FAAH IC$_{50}$ (mouse) | ABHD6 IC$_{50}$ (mouse) | MAGL IC$_{50}$ (human) | MAGL % Inh 1 μM (mouse) | FAAH % Inh 1 μM (mouse) | ABHD6 % Inh 1 μM (mouse) | MAGL % Inh 5 mg/kg (mouse) | FAAH % Inh 5 mg/kg (mouse) | ABHD6 % Inh 5 mg/kg (mouse) |
|---|---|---|---|---|---|---|---|---|---|---|
| 131 | *** | * | * |  | ### | # | # |  |  |  |
| 132 | *** | * | * |  | ### | # | # | ### | # | # |
| 133 | *** | * | * | *** | ### | # | # | ### | # | # |
| 134 | *** | * | * | *** | ### | # | # | ### | # | # |
| 135 | *** | * | ** |  | ### | # | ### |  |  |  |
| 136 | ** | * | ** |  | ### | # | ### |  |  |  |
| 137 | ** | * | *** |  | ### | # | ### |  |  |  |
| 138 | ** | * | *** |  | ### | # | ### |  |  |  |
| 139 | ** | * | ** |  | ### | # | ### |  |  |  |
| 140 | *** | * | ** |  | ### | # | ### |  |  |  |
| 141 | ** | * | ** |  | ### | # | ### |  |  |  |
| 142 | ** | * | * |  | ### | # | # |  |  |  |
| 143 | *** | * | * |  | ### | # | # |  |  |  |
| 144 | ** | * | * |  | ### | # | ## |  |  |  |
| 145 | *** | * | * |  | ### | # | # |  |  |  |
| 146 | *** | * | * |  | ### | # | ## | ### | # | ## |
| 147 | ** | * | * |  | ### | # | # |  |  |  |
| 148 | *** | * | * |  | ### | # | # |  |  |  |
| 149 | ** | * | * |  | ### | # | ## |  |  |  |
| 150 | *** | * | * |  | ### | # | # | ### | # | # |
| 151 | *** | * | * |  | ### | # | # | ### | ## | ## |
| 152 | *** | * | ** |  | ### | # | ### | ### | # | ### |
| 153 | ** | * | *** |  | ### | # | ### |  |  |  |
| 154 | *** | * | ** |  | ### | # | ### |  |  |  |
| 155 | *** | * | ** |  | ### | # | ### |  |  |  |
| 156 | *** | * | ** |  | ### | # | ### |  |  |  |
| 157 | *** | * | ** |  | ### | # | ### | ### | # | ## |
| 158 | ** | * | * |  | ### | # | # |  |  |  |
| 159 | *** | * | * |  | ### | # | ### |  |  |  |
| 160 | *** | * | *** |  | ### | # | ### |  |  |  |
| 161 | *** | * | *** |  | ### | # | ### |  |  |  |
| 162 | *** | * | ** |  | ### | # | ### |  |  |  |
| 163 | *** | * | ** |  | ### | # | ## |  |  |  |
| 164 | *** | * | ** |  | ### | # | ### |  |  |  |
| 165 | *** | * | * |  | ### | # | ## |  |  |  |
| 166 | *** | * | * |  | ### | # | # | # | # | # |
| 167 | *** | * | * |  | ### | # | ## |  |  |  |
| 168 | *** | * | * |  | ### | # | # | ## | # | # |
| 169 | *** | * | * |  | ### | # | ## |  |  |  |
| 170 | *** | * | * |  | ### | # | # | ## | # | # |
| 171 | ** | * | * |  | ### | # | # |  |  |  |
| 172 | *** | * | * |  | ### | # | # | # | # | # |
| 173 | *** | * | * |  | ### | # | ## | ## | # | # |
| 174 | *** | * | * |  | ### | # | ## | ## | # | # |
| 175 | *** | * | * |  | ### | # | # |  |  |  |
| 176 | *** | * | * |  | ### | # | # | ## | # | # |
| 177 | ** | * | * |  | ### | # | ## | ### | # | # |
| 178 | *** | * | * | *** | ### | # | ## |  |  |  |
| 179 | ** | * | * | *** | ### | # | # | ### | ## | # |
| 180 | *** | * | * |  | ### | # | # | ### | ## | ## |
| 181 | *** | * | ** |  | ### | # | ## |  |  |  |
| 182 | *** | * | * | ** | ### | # | # |  |  |  |
| 183 | *** | * | * |  | ### | # | ## | ### | # | # |
| 184 | *** | * | * |  | ### | # | # | ### | # | # |
| 185 | ** | * | ** |  | ### | # | ### |  |  |  |
| 186 | ** | * | ** |  | ### | # | ## |  |  |  |
| 187 | *** | * | ** |  | ### | # | ### |  |  |  |
| 188 | ** | * | ** |  | ### | # | ## |  |  |  |
| 189 | *** | * | ** |  | ### | # | ## | ## | # | # |
| 190 | *** | * | * |  | ### | # | # |  |  |  |
| 191 | ** | * | * |  | ### | # | ## |  |  |  |
| 192 | *** | * | ** |  | ### | # | ## |  |  |  |
| 193 |  |  |  | *** | ### | # | # | ## | # | # |
| 194 |  |  |  | *** | ### | # | # | ## | # | # |
| 195 | *** | * | * | *** | ### | # | # | # | # | # |
| 196 |  |  |  | *** | ### | # | # | ### | # | # |
| 197 | ** | * | * | *** | ### | # | ## | # | # | # |
| 198 |  |  |  | *** | ### | # | # |  |  |  |
| 199 | *** | * | * | *** | ### | # | ## | ## | # | # |
| 200 |  |  |  | *** | ### | # | # | ## | # | # |
| 201 |  |  |  | *** | ### | # | ### |  |  |  |
| 202 |  |  |  | *** | ### | # | ### |  |  |  |
| 203 |  |  |  | *** | ### | # | # |  |  |  |
| 204 |  |  |  | *** | ### | # | # |  |  |  |
| 205 |  |  |  | *** | ### | # | ## |  |  |  |

TABLE 2-continued

| Ex | MAGL IC$_{50}$ (mouse) | FAAH IC$_{50}$ (mouse) | ABHD6 IC$_{50}$ (mouse) | MAGL IC$_{50}$ (human) | MAGL % Inh 1 μM (mouse) | FAAH % Inh 1 μM (mouse) | ABHD6 % Inh 1 μM (mouse) | MAGL % Inh 5 mg/kg (mouse) | FAAH % Inh 5 mg/kg (mouse) | ABHD6 % Inh 5 mg/kg (mouse) |
|---|---|---|---|---|---|---|---|---|---|---|
| 206 | | | | *** | ### | # | ## | | | |
| 207 | | | | | ### | # | # | | | |
| 208 | | | | | ### | # | ### | | | |
| 209 | | | | *** | ### | # | ## | | | |
| 210 | | | | *** | ### | # | # | ### | # | ## |
| 211 | | | | *** | ### | # | # | ## | # | # |
| 212 | | | | | ### | # | # | | | |
| 213 | | | | | ### | # | # | | | |
| 214 | | | | *** | ### | # | # | ### | # | # |
| 215 | | | | *** | ### | # | ### | | | |
| 216 | | | | *** | ### | # | ## | ## | # | # |
| 217 | | | | *** | ### | # | # | ### | # | # |
| 218 | | | | *** | ### | # | # | ## | # | # |
| 219 | | | | *** | ### | # | ### | | | |
| 220 | | | | | ## | # | # | | | |
| 221 | | | | *** | ### | # | # | ### | # | # |
| 222 | | | | *** | ### | # | # | | | |
| 223 | | | | *** | ### | # | # | | | |
| 224 | | | | | ## | # | # | | | |
| 225 | | | | *** | ### | # | # | | | |
| 226 | | | | *** | ### | # | # | ### | # | # |
| 227 | | | | | # | # | # | | | |
| 228 | | | | *** | ### | # | ### | | | |
| 229 | | | | *** | ### | # | ### | | | |
| 230 | | | | *** | ### | # | # | ## | # | # |
| 231 | | | | *** | ### | # | # | | | |
| 232 | | | | *** | ### | # | ## | | | |
| 233 | | | | *** | ### | # | ## | | | |
| 234 | | | | *** | ### | # | ### | | | |
| 235 | | | | ** | ### | # | # | | | |
| 236 | | | | *** | ### | # | # | ### | # | # |
| 237 | | | | ** | ### | # | ## | | | |
| 238 | ** | * | * | *** | ### | # | # | ### | # | # |
| 239 | | | | *** | ### | # | # | | | |
| 240 | | | | *** | ### | # | # | ### | # | # |
| 241 | | | | *** | ### | # | ### | | | |
| 242 | | | | | ## | # | ## | | | |
| 243 | | | | ** | ### | # | # | | | |
| 244 | | | | *** | ### | # | # | ### | # | # |
| 245 | | | | *** | ### | # | ### | | | |
| 246 | | | | ** | ### | # | ## | | | |
| 247 | | | | *** | ### | # | ### | | | |
| 248 | | | | *** | ### | # | # | ### | # | # |
| 249 | | | | *** | ### | # | # | ## | # | # |
| 250 | | | | | ### | # | # | | | |
| 251 | | | | | ## | # | # | | | |
| 252 | | | | *** | ### | # | ### | | | |
| 253 | | | | *** | ### | # | # | ## | # | # |
| 254 | | | | | ## | # | # | | | |
| 255 | | | | ** | ### | # | ## | | | |
| 256 | | | | *** | ### | # | # | # | # | # |
| 257 | | | | | # | # | # | | | |
| 258 | | | | * | ### | # | ### | | | |
| 259 | | | | | # | # | # | | | |
| 260 | | | | ** | ### | # | # | | | |
| 261 | | | | *** | ## | # | # | | | |
| 262 | | | | *** | ### | # | # | ## | # | # |
| 263 | | | | *** | ### | # | ## | | | |
| 264 | | | | *** | ### | # | ### | | | |
| 265 | | | | *** | ### | # | ### | | | |
| 266 | | | | ** | ### | # | # | | | |
| 267 | | | | *** | ### | # | ### | # | # | # |
| 268 | | | | *** | ### | # | ## | ## | # | ## |
| 269 | | | | *** | ### | # | # | ## | # | # |
| 270 | | | | *** | ### | # | # | ## | # | # |
| 271 | | | | *** | ### | # | ## | | | |
| 272 | | | | *** | ### | # | # | ### | # | # |
| 273 | | | | | ### | # | ## | | | |
| 274 | | | | *** | ### | # | ## | ### | # | # |
| 275 | | | | *** | ### | # | ## | ### | # | # |
| 276 | | | | *** | ### | # | ## | | | |
| 277 | | | | *** | ### | # | ### | | | |
| 278 | | | | *** | ### | # | ### | | | |
| 279 | | | | *** | ### | # | ### | | | |
| 280 | | | | *** | ### | # | # | | | |

TABLE 2-continued

| Ex | MAGL IC$_{50}$ (mouse) | FAAH IC$_{50}$ (mouse) | ABHD6 IC$_{50}$ (mouse) | MAGL IC$_{50}$ (human) | MAGL % Inh 1 μM (mouse) | FAAH % Inh 1 μM (mouse) | ABHD6 % Inh 1 μM (mouse) | MAGL % Inh 5 mg/kg (mouse) | FAAH % Inh 5 mg/kg (mouse) | ABHD6 % Inh 5 mg/kg (mouse) |
|---|---|---|---|---|---|---|---|---|---|---|
| 281 | | | | *** | ### | # | ## | # | # | # |

\*\*\* is less than 100 nM;
\*\* is between 1000 and 100 nM;
\* is greater than 1000 nM
### is ≥ 75%;
## is equal to or greater than 25% but less than 75%;
# is < 25%

What is claimed is:

1. A method of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, functional dyspepsia, Persistent Motor Tic Disorder, Persistent Vocal Tic Disorder, attention deficit hyperactivity disorder (ADHD), obsessive-compulsive disorder (OCD), glaucoma, atopic dermatitis, pruritis, or Down's Syndrome in a patient, comprising administering to the patient a therapeutically effective amount of a compound of Formula (Ia):

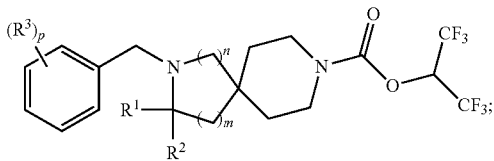

Formula (Ia)

wherein:
$R^1$ is H or $C_{1-6}$alkyl;
$R^2$ is H or $C_{1-6}$alkyl;
each $R^3$ is independently selected from $C_{1-6}$ alkyl, $C_{2-6}$ alkenyl, $C_{2-6}$ alkynyl, halogen, —CN, $C_{1-6}$haloalkyl, $C_{1-6}$aminoalkyl, heterocycloalkyl, —$C_{1-6}$alkyl(heterocycloalkyl), heteroaryl, —SF$_5$, —NR$^5$R$^6$, —CO$_2$R$^8$, —C(O)R$^8$, and —C(O)NR$^8$R$^9$, wherein heterocycloalkyl and —$C_{1-6}$alkyl(heterocycloalkyl) are optionally substituted with one or two R$^4$; or two adjacent R$^3$ form a heterocycloalkyl ring optionally substituted with one, two, or three R$^4$;
each $R^4$ is independently selected from $C_{1-6}$ alkyl, $C_{1-6}$ haloalkyl, $C_{3-8}$cycloalkyl, halogen, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
each $R^5$ and $R^6$ is independently selected from H, $C_{1-6}$ alkyl, $C_{1-6}$haloalkyl, $C_{1-6}$aminoalkyl, $C_{3-8}$cycloalkyl, —$C_{1-6}$ alkyl(heterocycloalkyl), —$C_{1-6}$ alkyl-C(O)(heterocycloalkyl), heterocycloalkyl, aryl, and heteroaryl; or R$^5$ and R$^6$, together with the nitrogen to which they are attached, form a heterocycloalkyl ring optionally substituted with one, two, or three R$^{10}$;
each $R^7$ is independently selected from H, $C_{1-6}$ alkyl, $C_{1-6}$haloalkyl, $C_{1-6}$aminoalkyl, $C_{3-8}$cycloalkyl, —$C_{1-6}$ alkyl(heterocycloalkyl), —$C_{1-6}$ alkyl-C(O)(heterocycloalkyl), heterocycloalkyl, aryl, and heteroaryl, wherein heterocycloalkyl, aryl, and heteroaryl are optionally substituted with one or two groups selected from oxo, $C_{1-6}$alkyl, $C_{1-6}$haloalkyl, CO$_2$H, and C(O)NH$_2$;
each $R^8$ and $R^9$ is independently selected from H, $C_{1-6}$ alkyl, $C_{1-6}$haloalkyl, $C_{3-8}$cycloalkyl, aryl, and heteroaryl; or R$^8$ and R$^9$, together with the nitrogen to which they are attached, form a heterocycloalkyl ring optionally substituted with one or two groups selected from $C_{1-6}$alkyl, $C_{1-6}$ haloalkyl, CO$_2$H, and C(O)NH$_2$;
each $R^{10}$ is independently selected from $C_{1-6}$ alkyl, $C_{3-8}$cycloalkyl, $C_{1-6}$ haloalkyl, halogen, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
p is 0, 1, 2, 3, 4, or 5;
n is 0 or 1; and
m is 1 or 2; provided that when n is 0, then m is 2; and when n is 1, then m is 1;
or a solvate, hydrate, tautomer, N-oxide, stereoisomer, or pharmaceutically acceptable salt thereof.

2. The method of claim 1, or a solvate, hydrate, tautomer, N-oxide, stereoisomer, or pharmaceutically acceptable salt thereof, wherein each R$^3$ is independently selected from $C_{1-6}$alkyl, $C_{2-6}$ alkynyl, halogen, —CN, $C_{1-6}$ haloalkyl, heterocycloalkyl, —$C_{1-6}$alkyl(heterocycloalkyl), heteroaryl, —SF$_5$, —NR$^5$R$^6$, —OR$^7$, —CO$_2$R$^8$, and —C(O)NR$^8$R$^9$.

3. The method of claim 1, or a solvate, hydrate, tautomer, N-oxide, stereoisomer, or pharmaceutically acceptable salt thereof, wherein R$^1$ and R$^2$ are both H.

4. The method of claim 1, or a solvate, hydrate, tautomer, N-oxide, stereoisomer, or pharmaceutically acceptable salt thereof, wherein R$^1$ and R$^2$ are both —CH$_3$.

5. The method of claim 1, or a solvate, hydrate, tautomer, N-oxide, stereoisomer, or pharmaceutically acceptable salt thereof, wherein each R$^3$ is independently selected from $C_{1-6}$alkyl, halogen, $C_{1-6}$ haloalkyl, —$C_{1-6}$alkyl(heterocycloalkyl), —NR$^5$R$^6$, —CO$_2$R$^8$, and —C(O)NR$^8$R$^9$.

6. The method of claim 5, or a solvate, hydrate, tautomer, N-oxide, stereoisomer, or pharmaceutically acceptable salt thereof, wherein each R$^3$ is independently selected from halogen, $C_{1-6}$haloalkyl, —NR$^5$R$^6$, and —OR$^7$.

7. The method of claim 5, or a solvate, hydrate, tautomer, N-oxide, stereoisomer, or pharmaceutically acceptable salt thereof, wherein R$^5$ and R$^6$, together with the nitrogen to which they are attached, form a heterocycloalkyl ring substituted with one or two R$^{10}$ independently selected from $C_{1-6}$alkyl, $C_{3-8}$cycloalkyl, $C_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$.

8. The method of claim 7, or a solvate, hydrate, tautomer, N-oxide, stereoisomer, or pharmaceutically acceptable salt thereof, wherein R$^5$ and R$^6$, together with the nitrogen to which they are attached, form a heterocycloalkyl ring substituted with one or two $R^{10}$ independently selected from $C_{1-6}$alkyl and —$CO_2H$.

9. The method of claim 5, or a solvate, hydrate, tautomer, N-oxide, stereoisomer, or pharmaceutically acceptable salt thereof, wherein $R^5$ and $R^6$, together with the nitrogen to which they are attached, form an unsubstituted heterocycloalkyl ring.

10. The method of claim 5, or a solvate, hydrate, tautomer, N-oxide, stereoisomer, or pharmaceutically acceptable salt thereof, wherein $R^5$ and $R^6$, together with the nitrogen to which they are attached, form a heterocycloalkyl ring, optionally substituted with one, two, or three $R^{10}$ selected from:

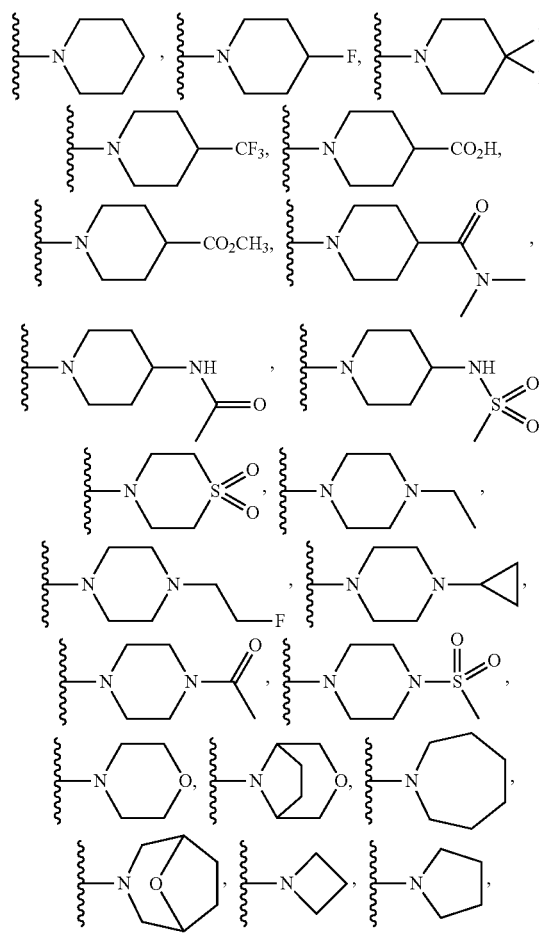

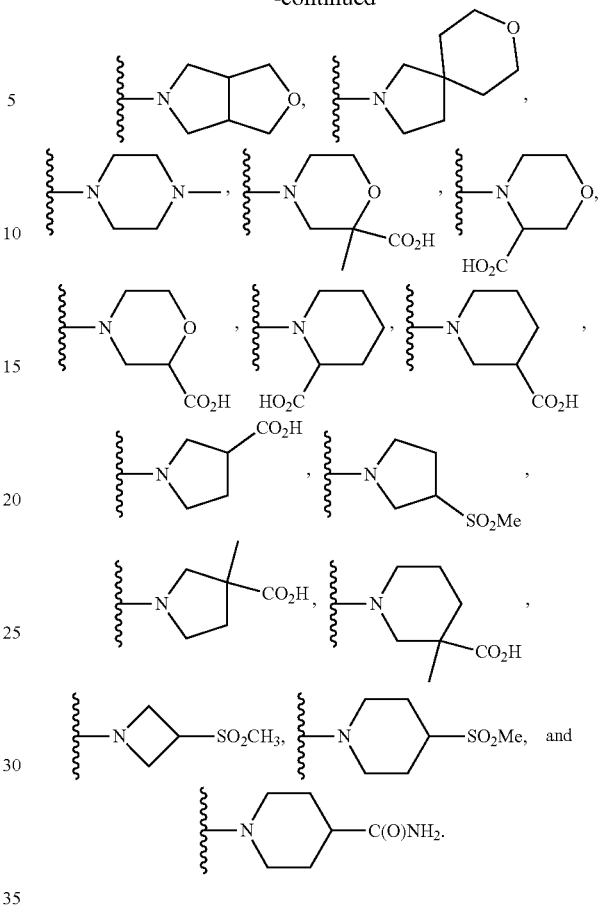

11. The method of claim 5, or a solvate, hydrate, tautomer, N-oxide, stereoisomer, or pharmaceutically acceptable salt thereof, wherein each $R^7$ is independently selected from $C_{1-6}$alkyl, $C_{1-6}$haloalkyl, $C_{1-6}$aminoalkyl, —$C_{1-6}$alkyl(heterocycloalkyl), —$C_{1-6}$alkyl-C(O)(heterocycloalkyl), heterocycloalkyl, and heteroaryl.

12. The method of claim 1, or a solvate, hydrate, tautomer, N-oxide, stereoisomer, or pharmaceutically acceptable salt thereof, wherein two adjacent $R^3$ form a heterocycloalkyl ring optionally substituted with one or two $R^4$.

13. The method of claim 1, wherein p is 2.

14. The method of claim 1, wherein p is 1.

15. The method of claim 1, wherein n is 0 and m is 2.

16. The method of claim 1, wherein n is 1 and m is 1.

* * * * *